US00RE43858E

(19) United States
(12) Reissued Patent
Kimura et al.

(10) Patent Number: US RE43,858 E
(45) Date of Reissued Patent: Dec. 11, 2012

(54) SUBSTITUTED CYCLOALKENE DERIVATIVE

(75) Inventors: Tomio Kimura, Tokyo (JP); Nobuyuki Ohkawa, Tokyo (JP); Takayoshi Nagasaki, Tokyo (JP); Atsuhiro Sugidachi, Tokyo (JP); Osamu Ando, Tokyo (JP)

(73) Assignee: Daiichi Sankyo Company, Limited, Tokyo (JP)

(21) Appl. No.: 13/224,745

(22) Filed: Sep. 2, 2011

Related U.S. Patent Documents

Reissue of:
(64) Patent No.: 7,935,835
Issued: May 3, 2011
Appl. No.: 12/066,813
PCT Filed: Sep. 13, 2006
PCT No.: PCT/JP2006/318103
§ 371 (c)(1),
(2), (4) Date: Jan. 8, 2009
PCT Pub. No.: WO2007/032362
PCT Pub. Date: Mar. 22, 2007

(30) Foreign Application Priority Data

Sep. 14, 2005 (JP) ..... 2005-267504

(51) Int. Cl.
*A61K 31/335* (2006.01)
*C07D 317/72* (2006.01)

(52) U.S. Cl. ..... 514/462; 549/341

(58) Field of Classification Search ..... None
See application file for complete search history.

(56) References Cited

U.S. PATENT DOCUMENTS

| | | | | |
|---|---|---|---|---|
| 4,497,954 | A * | 2/1985 | Banitt | 546/221 |
| 5,001,144 | A * | 3/1991 | Regan et al. | 514/436 |
| 5,635,529 | A * | 6/1997 | Dumic et al. | 514/452 |

FOREIGN PATENT DOCUMENTS

| | | | |
|---|---|---|---|
| EP | 1 310 248 | A1 | 5/2003 |
| EP | 2 039 681 | A1 | 3/2009 |
| JP | 2000-178246 | | 6/2000 |
| JP | 2001-114751 | A | 4/2001 |
| JP | 2004-002370 | A | 1/2004 |
| WO | 0041698 | A1 | 7/2000 |
| WO | 01/40498 | A1 | 6/2001 |

OTHER PUBLICATIONS

Yamada, Masami, et al. "Optically Active Cyclohexene Derivative as a New Antisepsis Agent: An Efficient Synthesis of Ethyl (6R)-6-[N-(2-Chloro-4-fluorophenyl)-sulfamoyl]cyclohex-1-ene-l-carboxylate (TAK-242)", Chem. Pharm. Bull. 54(1): 58-62 (2006).

Yamada, Masami, et al. "Discovery of Novel and Potent Small-Molecule Inhibitors of NO and Cytokine Production as Antisepsis Agents: Synthesis and Biological Activity of Alkyl 6-(N-Substituted sulfamoyl)cyclohex-1-ene-1-carboxylate", J. Med. Chem., 48(23): 7457-7467 (2005).

Iqbal et al., "Antithrombotic agents in the treatment of Severe Sepsis", Expert Opin. Emerging Drugs, (2002), vol. 7 (1): 111-139.

Hawkins et al., "Inhibition of Endotoxin Response by Synthetic TLR4 Antagonists", Current Topics in Medicinal Chemistry (2004), vol. 4, pp. 1147-1171.

Beutler, "Inferences, questions and possibilities in Toll-like receptor sinalling", Nature, Jul. 8, 2004, vol. 430, pp. 257-263.

Kakutani et al., "JTE-607, a novel inflammatory cytokine synthesis inhibitor without immunosuppression, protects from endotixin shock in mice", Inflammation Research (1999) vol. 48, pp. 461-468, Copyright Birkhauser Verlag, Basel.

Cook, Donald N. et al., "Toll-like receptors in the pathogenesus of human disease", Nature Immunology, Oct. 2004, vol. 5, No. 10, pp. 975-979.

* cited by examiner

*Primary Examiner* — Noble Jarrell
(74) *Attorney, Agent, or Firm* — Dorsey & Whitney LLP

(57) ABSTRACT

A compound of formula (I)

(I)

Wherein X, Y, ring A, ring B, l, m, $R^1$, $R^2$, $R^4$ and $R^5$ are as defined herein, to supress intracellular signal transduction or cell activation induced by endotoxin and to suppress cell responses due to the intracellular signal transduction and cell activation such as an excess generation of inflammatory mediators such as TNF-α, pharmacologically acceptable salts therefor, a preparation method therefor, and a medicament containing the aforementioned substituted cycloalkene derivative as an active ingredient which is superior in prophylaxis and/or treatment of diseases such as sepsis (septic shock, disseminated intravascular coagulation, multiple organ failure and the like), that are associated with intracellular signal transduction or cell activation induced by endotoxin and to cell responses to the intracellular signal transduction and cell activation.

45 Claims, No Drawings

SUBSTITUTED CYCLOALKENE DERIVATIVE

Matter enclosed in heavy brackets [ ] appears in the original patent but forms no part of this reissue specification; matter printed in italics indicates the additions made by reissue.

CROSS-REFERENCE TO RELATED APPLICATION

This Application is a Section 371 National Stage Application of International Application No. PCT/JP2006/318103, filed 13 Sep. 2006 and published as WO 2007/032362 A1 on 22 Mar. 2007, which claims the priority from the Japanese application 2005-267504, filed 14 Sep. 2005, the subject matter of which are hereby incorporated by reference in its entirety.

TECHNICAL FIELD

The present invention relates to a novel compound which has an action to suppress intracellular signal transduction or cell activation in various cells such as monocytes, macrophages and vascular endothelial cells, the intracellular signal transduction or cell activation being induced by endotoxin, and to suppress the generation of inflammatory mediators such as TNF-α due to the intracellular signal transduction and cell activation, and which is useful as a prophylactic and/or therapeutic agent for various diseases such as sepsis (septic shock, disseminated intravascular coagulation, multiple organ failure and the like), a production method therefor and a use thereof.

BACKGROUND ART

Sepsis is a systemic inflammatory response syndrome (SIRS) which occurs due to an excess inflammatory response of a biological body against bacterial infection, and is a disease which may result in death when it is accompanied by shock or organ failure. Since there are only a few agents that are effective against sepsis until now, it is considered to be a disease that is difficult to prevent and treat. However, since its fatality is high and the number of patients is large, development of therapeutic agents for it is particularly important (for example, refer to Non-patent document 1).

Endotoxin (lipopolysaccharide, LPS), which is a membrane component of bacteria, acts against cells such as monocytes, macrophages and vascular endothelial cells, induces an excess generation of various inflammatory mediators such as TNF-α and the like, causes sudden blood pressure reduction, blood coagulation disorders, cardiovascular disturbances and the like in addition to systemic inflammatory responses, and thus exhibits sepsis (for example, refer to Non-patent document 2). Lipid A, which corresponds to lipopolysaccharide and its partial structure, activates intracellular signal transduction via TLR4 (Toll-like receptor 4), which is a functional cell surface receptor, after binding with CD14 (for example, refer to Non-patent document 3). Accordingly, lipid A initiates various cell responses represented by the generation of inflammatory mediators. Therefore, it is considered that a substance which suppresses the intracellular signal transduction or cell activation induced by endotoxin, and various cell responses induced by intracellular signal transduction and cell activation, the various cell responses being represented by an excess generation of inflammatory mediators such as TNF-α, can be an effective prophylactic and therapeutic agent for sepsis (for example, refer to Non-patent document 3, Non-patent document 4, Patent document 1 and Patent document 2).

Intracellular signal transduction or cell activation induced by endotoxin, and various cell responses induced by the intracellular signal transduction and cell activation, the various cell responses being represented by an excess generation of inflammatory mediators such as TNF-α, lead to development and progress of various diseases such as ischemic brain disorder, arteriosclerosis, poor prognosis after coronary angioplasty, heart failure, diabetes, diabetic complication, joint inflammation, osteoporosis, osteopenia, autoimmune disease, tissue disorder and rejection after organ transplantation, bacterial infection, virus infection, gastritis, pancreatitis, nephritis, pneumonia, hepatitis and leukemia, in addition to the aforementioned sepsis (for example, Non-patent document 5 and Patent document 3).

Therefore, a substance which suppresses intracellular signal transduction or cell activation induced by endotoxin, and various cell responses induced by the intracellular signal transduction and cell activation such as an excess generation of inflammatory mediators such as TNF-α, is considered to be effective as a prophylactic and/or therapeutic agent for these various diseases, and thus the development of an excellent therapeutic agent has been desired.

[Non-patent Document 1] Iqbal et al., Expert Opin. Emerging Drugs, Vol. 7, page 111, 2002

[Non-patent Document 2] Hawkins et al., Current Topics in Medicinal Chemistry, Vol. 4, page 1147, 2004

[Non-patent Document 3] Beutler, Nature, Vol. 430, pages 257-263, 2004

[Non-patent Document 4] Kakutani et al., Inflammation Research, Vol. 48, page 461, 1999

[Non-patent Document 5] Donald N. Cook et al., Nature Immunology, Vol. 5, pages 975-979, 2004

[Patent Document 1] Japanese Patent Application (Kokai) No. 2000-178246

[Patent Document 2] Japanese Patent Application (Kokai) No. 2004-2370

[Patent Document 3] International Publication WO 00/41698 Pamphlet

DISCLOSURE OF THE INVENTION

Problems to be Solved by the Invention

As a result of conducting extensive studies on the pharmacological activity of various substituted cycloalkene derivatives for the purpose of developing a compound which has an activity to suppress intracellular signal transduction or cell activation in various cells such as monocytes, macrophages and vascular endothelial cells, the intracellular signal transduction or the cell activation being induced by endotoxin, and to suppress various cell responses induced by the intracellular signal transduction and cell activation, such as an excess generation of inflammatory mediators such as TNF-α, the inventors of the present invention found that a substituted cycloalkene derivative having a unique structure possesses an excellent suppressing effect against intracellular signal transduction or cell activation induced by endotoxin, and against cell responses induced by the intracellular signal transduction and cell activation, such as an excess generation of inflammatory mediators such as TNF-α, and found that it is useful as a prophylactic and/or therapeutic agent for various diseases such as sepsis which are associated with intracellular signal transduction or cell activation induced by endotoxin, and with cell responses induced by the intracellular signal transduction and the cell activation, thereby leading to completion of the present invention.

The present invention provides a substituted cycloalkene derivative which possesses an activity to suppress intracellular signal transduction or cell activation induced by endotoxin, and cell responses due to the intracellular signal transduction and cell activation such as an excess generation of inflammatory mediators such as TNF-α, pharmacologically acceptable salts thereof, a production method therefor, and a medicament containing the aforementioned substituted cycloalkene derivative as an active ingredient, which is excellent for prophylaxis and/or treatment of various diseases caused by intracellular signal transduction or cell activation induced by endotoxin, and caused by cell responses including an excess generation of inflammatory mediators such as TNF-α, the cell responses being induced by the intracellular signal transduction and cell activation.

Means for Solving the Problems

Accordingly, the present invention provides:

(1) A compound represented by the general formula (I):

(I)

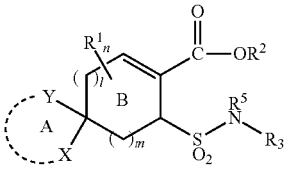

{wherein

X and Y represent a group in which X and Y together with the carbon atom of ring B to which they are bound form ring A, X and Y together represent a substituent of ring B, or X and Y each represents a hydrogen atom.

1) In the case where X and Y represent a group in which X and Y together with the carbon atom of ring B to which they are bound form ring A:

ring A represents a 3- to 7-membered heterocyclyl ring [in the heterocyclyl ring, X and Y, independently from each other, represent any one selected from a carbon atom, a group having the formula NR (R represents a hydrogen atom or a $C_1$-$C_6$ alkyl, $C_2$-$C_6$ alkenyl, $C_2$-$C_6$ alkynyl or $C_1$-$C_6$ alkanoyl group which may be substituted with a group selected from Substituent group α), an oxygen atom, a sulfur atom, a group having the formula SO and a group having the formula $SO_2$, the heterocyclyl ring may include an unsaturated bond, may form a fused ring or spiro ring with a 3- to 7-membered heterocyclyl ring or 3- to 7-membered cycloalkyl ring, and ring A, including the fused ring or spiro ring, may be substituted with the same or different 1 to 4 groups selected from the group consisting of an oxo group, a thioxo group, Substituent group α, a cyclopropyl a $C_1$-$C_6$ alkyl group, a $C_1$-$C_6$ alkyl group which may be substituted with 1 to 5 groups selected from Substituent group α, a $C_2$-$C_6$ alkenyl group which may be substituted with 1 to 5 groups selected from Substituent group α, and a $C_2$-$C_6$ alkynyl group which may be substituted with 1 to 5 groups selected from Substituent group α]

or a 3- to 7-membered cycloalkyl ring (the cycloalkyl ring may include an unsaturated bond, may form a fused ring or spiro ring with a 3- to 7-membered heterocyclyl ring or 3- to 7-membered cycloalkyl ring, and ring A, including the fused ring or spiro ring, may be substituted with the same or different 1 to 4 groups selected from the group consisting of Substituent group α, a cyclopropyl $C_1$-$C_6$ alkyl group, a $C_1$-$C_6$ alkyl group which may be substituted with 1 to 5 groups selected from Substituent group α, a $C_2$-$C_6$ alkenyl group which may be substituted with 1 to 5 groups selected from Substituent group α, and a $C_2$-$C_6$ alkynyl group which may be substituted with 1 to 5 groups selected from Substituent group α).

2) In the case where X and Y together represent a substituent of ring B:

X and Y represent an oxo group or a thioxo group.

l and m, independently from each other, represent an integer of 0 to 3, and l+m is 1 to 3.

$R^1$ represents an aliphatic hydrocarbon group which may be substituted with a group selected from Substituent group β and Substituent group γ (the aliphatic hydrocarbon group represents a $C_1$-$C_{20}$ alkyl group, $C_3$-$C_{10}$ cycloalkyl group, $C_4$-$C_{12}$ cycloalkylalkyl group, $C_3$-$C_6$ alkenyl group or $C_3$-$C_6$ alkynyl group), a phenyl group which may be substituted with a group selected from Substituent group δ, a group having the formula $OR^4$ ($R^4$ represents a hydrogen atom or an aliphatic hydrocarbon group which may be substituted with a group selected from Substituent group β and Substituent group γ, the aliphatic hydrocarbon group represents the same as aforementioned) or a halogen atom.

n represents an integer of 0 to 3.

$R^2$ represents a hydrogen atom, a $C_1$-$C_6$ alkyl group which may be substituted with a group selected from Substituent group β, a $C_2$-$C_6$ alkenyl group which may be substituted with a group selected from Substituent group β, or a $C_2$-$C_6$ alkynyl group which may be substituted with a group selected from Substituent group β.

$R^3$ represents a phenyl group which may be substituted with a group selected from Substituent group ϵ, or a 5- or 6-membered heteroaryl group which may be substituted with a group selected from Substituent group ϵ (the heteroaryl group includes 1 to 3 hetero atoms selected from a nitrogen atom, oxygen atom and sulfur atom).

$R^5$ represents a hydrogen atom, a $C_1$-$C_6$ alkyl group which may be substituted with a group selected from Substituent group β, a $C_2$-$C_6$ alkenyl group which may be substituted with a group selected from Substituent group β, or a $C_2$-$C_6$ alkynyl group which may be substituted with a group selected from Substituent group β.

Provided that in the case where $R^3$ is a phenyl group which may be substituted with a group selected from Substituent group ϵ, X and Y represent the aforementioned (1) or (2).

Substituent group α represents a hydroxy group, halogen atom, $C_1$-$C_6$ alkoxy group, halogeno $C_1$-$C_6$ alkoxy group, carboxy group, $C_1$-$C_6$ alkoxycarbonyl group;

carbamoyl group which may be substituted with a group selected from a $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenyl-carbonyl group; and a group having the formula $NR^6R^7$.

$R^6$ and $R^7$, independently from each other, represent a hydrogen atom, $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenylcarbonyl group, or together with the nitrogen atom to which they are bound form a heterocyclyl group.

Substituent group β represents an oxo group, hydroxy group, cyclopropyl group, $C_1$-$C_6$ alkoxy group, $C_1$-$C_6$ alkylthio group, nitro group, halogen atom, cyano group, carboxy group, $C_1$-$C_{10}$ alkoxy-carbonyl group, $C_1$-$C_6$ alkanoyl group, $C_2$-$C_4$ alkenyl-carbonyl group, $C_2$-$C_6$ alkanoyloxy group, $C_2$-$C_4$ alkenyl-carbonyloxy group;

carbamoyl group which may be substituted with a group selected from a $C_1$-$C_4$ alkyl group, phenyl group, $C_1$-$C_7$ acyl group and $C_1$-$C_4$ alkoxy-phenyl group;

thiocarbamoyl group which may be substituted with a $C_1$-$C_4$ alkyl group or phenyl group;

carbamoyloxy group which may be substituted with a $C_1$-$C_4$ alkyl group or phenyl group;

$C_1$-$C_6$ alkanoylamino group, $C_1$-$C_{10}$ alkoxy-carboxamide group, $C_1$-$C_{10}$ alkoxy-carbonyloxy group, and ureido group which may be substituted with a $C_1$-$C_4$ alkyl group or phenyl group.

Substituent group γ represents a heterocyclic group, $C_3$-$C_{10}$ cycloalkyloxy group, $C_6$-$C_{10}$ aryloxy group, $C_7$-$C_{19}$ aralkyloxy group, heterocyclyloxy group, $C_3$-$C_{10}$ cycloalkylthio group, $C_6$-$C_{10}$ arylthio group, $C_7$-$C_{19}$ aralkylthio group, heterocyclylthio group, heterocyclylsulfinyl group, heterocyclylsulfonyl group, $C_3$-$C_6$ cycloalkyloxy-carbonyl group, $C_6$-$C_{10}$ aryloxy-carbonyl group, $C_7$-$C_{19}$ aralkyloxy-carbonyl group, heterocyclyloxycarbonyl group, $C_6$-$C_{10}$ aryl-carbonyl group, $C_9$-$C_{10}$ aryl-carbonyloxy group, $C_6$-$C_{10}$ aryl-carbonylamino group, $C_6$-$C_{10}$ aryloxy-carboxamide group, $C_7$-$C_{19}$ aralkyloxy-carboxamide group, $C_6$-$C_{10}$ aryloxy-carbonyloxy group, $C_7$-$C_{19}$ aralkyloxy-carbonyloxy group, $C_3$-$C_{10}$ cycloalkyloxy-carbonyloxy group and $C_6$-$C_{10}$ aryl group which may be substituted with a group selected from Substituent group β.

Substituent group δ represents a hydroxy group, nitro group, cyano group, halogen atom, $C_1$-$C_6$ alkyl group, halogeno $C_1$-$C_6$ alkyl group, $C_1$-$C_6$ alkoxy group, halogeno $C_1$-$C_6$ alkoxy group, carboxy group, $C_1$-$C_6$ alkanoyl group, $C_1$-$C_6$ alkoxy-carbonyl group, $C_1$-$C_6$ alkanoylamino group, $C_1$-$C_6$ alkylthio group, carbamoyl group, $C_1$-$C_6$alkyl-carbamoyl group, $C_1$-$C_6$ alkoxy-carbonyl $C_1$-$C_6$ alkyl-carbamoyl group, 1,3-diacylguanidino $C_1$-$C_6$ alkyl group, a group having the formula $NR^6R^7$ ($R^6$ and $R^7$ are the same as $R^6$ and $R^7$ of Substituent group α), $C_3$-$C_6$ cycloalkyl group, $C_6$-$C_{10}$ aryl group and 5-membered heteroaryl group.

Substituent group ϵ represents a hydroxy group, nitro group, cyano group, halogen atom, $C_1$-$C_{14}$ alkyl group, cyclopropyl $C_1$-$C_{14}$ alkyl group, halogeno $C_1$-$C_{14}$ alkyl group, $C_1$-$C_{14}$ alkoxy group, halogeno $C_1$-$C_{14}$ alkoxy group, carboxy group, $C_1$-$C_{14}$ alkanoyl group, $C_1$-$C_{14}$ alkoxy-carbonyl group, $C_1$-$C_{14}$ alkanoylamino group, $C_1$-$C_{14}$ alkylthio group, carbamoyl group, $C_1$-$C_{14}$ alkyl-carbamoyl group, $C_1$-$C_{14}$ alkoxy-carbonyl $C_1$-$C_{14}$ alkyl-carbamoyl group, 1,3-diacylguanidino $C_1$-$C_{14}$ alkyl group, a group having the formula $NR^6R^7$ ($R^6$ and $R^7$ are the same as $R^6$ and $R^7$ of Substituent group α), $C_3$-$C_6$ cycloalkyl group, $C_6$-$C_{10}$ aryl group and 5-membered heteroaryl group} or a pharmacologically acceptable salt thereof, (2) The compound or pharmacologically acceptable salt thereof according to the aforementioned (1), wherein l is 0 and m is an integer of 1 to 3, (3) The compound or pharmacologically acceptable salt thereof according to the aforementioned (1), wherein l is 0 and m is 2, (4) The compound or pharmacologically acceptable salt thereof according to any one of the aforementioned (1) to (3), wherein X and Y together with the carbon atom of ring B form ring A, and ring A is a 3- to 7-membered heterocyclyl ring

[in the heterocyclyl ring, X and Y, independently from each other, represent any one selected from a carbon atom, a group having the formula NR (R represents a hydrogen atom or a $C_1$-$C_6$ alkyl, $C_2$-$C_6$ alkenyl, $C_2$-$C_6$ alkynyl or $C_1$-$C_6$ alkanoyl group which may be substituted with a group selected from Substituent group α), an oxygen atom, a sulfur atom, a group having the formula SO and a group having the formula $SO_2$, the heterocyclyl ring may form a fused ring or spiro ring with a 5- or 6-membered heterocyclyl ring (the heterocyclyl ring includes 1 or 2 oxygen and/or nitrogen atoms as hetero atoms) or 5- or 6-membered cycloalkyl ring, and ring A, including the fused ring or spiro ring, may be substituted with the same or different 1 to 4 groups selected from the group consisting of an oxo group, a thioxo group, Substituent group α, a cyclopropyl $C_1$-$C_6$ alkyl group and a $C_1$-$C_6$ alkyl group which may be substituted with 1 to 5 groups selected from Substituent group α]

or a 3- to 7-membered saturated cycloalkyl ring (the 3- to 7-membered saturated cycloalkyl ring may be substituted with 1 or 2 groups selected from the group consisting of a hydroxy group, hydroxymethyl group, 1,2-dihydroxyethyl group, 1,2,3-trihydroxypropyl group, 1,2,3,4-tetrahydroxybutyl group and acetylamino group), (5) The compound or pharmacologically acceptable salt thereof according to any one of the aforementioned (1) to (3), wherein X and Y represent a group in which X and Y together with the carbon atom of ring B form ring A, and ring A is a 3- to 7-membered heterocyclyl ring

[in the heterocyclyl ring, X and Y, independently from each other, represent any one selected from a carbon atom, an oxygen atom, a sulfur atom, a group having the formula SO and a group having the formula $SO_2$, the heterocyclyl ring may form a fused ring or spiro ring with a 5- or 6-membered heterocyclyl ring (the heterocyclyl ring includes 1 or 2 oxygen and/or nitrogen atoms as hetero atoms) or 5- or 6-membered cycloalkyl ring, and ring A, including the fused ring or spiro ring, may be substituted with the same or different 1 to 4 groups selected from the group consisting of an oxo group, a thioxo group, Substituent group α and a $C_1$-$C_6$ alkyl group which may be substituted with 1 to 4 groups selected from Substituent group α]

or a 3- to 5-membered saturated cycloalkyl ring (the 3- to 5-membered saturated cycloalkyl ring may be substituted with 1 or 2 groups selected from the group consisting of a hydroxymethyl group, 1,2-dihydroxyethyl group, 1,2,3-trihydroxypropyl group, 1,2,3,4-tetrahydroxybutyl group and acetylamino group), (6) The compound or pharmacologically acceptable salt thereof according to any one of the aforementioned (1) to (3), wherein X and Y represent a group in which X and Y together with the carbon atom of ring B form ring A, and ring A is a 3- to 7-membered heterocyclyl ring

[the 3- to 7-membered heterocyclyl ring is oxirane, oxolane, tetrahydrofuran, tetrahydropyran, 1,3-dioxolane, 1,3-dioxane, 1,3-dioxepane, 1,3-dithiolane, 1,3-dithiane, 1,1,3,3-tetraoxo-1,3-dithiolane, 1,3-oxathiolane, 1,3-oxathiane or 1,3-oxathiepane, these heterocyclyl rings may form a fused ring or spiro ring with a 5- or 6-membered heterocyclyl ring (the 5- or 6-membered heterocyclyl ring is tetrahydrofuran, tetrahydropyran, pyrrolidine, piperidine or 1,3-dioxane) or cyclohexyl ring, and ring A, including the fused ring or spiro ring, may be substituted with 1 or 2 groups selected from the group consisting of an oxo group, a thioxo group, Substituent group α (Substituent group α represents a hydroxy group and a group having the formula $NR^6R^7$, and $R^6$ and $R^7$, independently from each other, represent a hydrogen atom or $C_1$-$C_6$ alkanoyl group), a methyl group, an ethyl group and a $C_1$-$C_6$ alkyl group which is substituted with 1 to 4 hydroxy groups], or a cyclopropyl or cyclopentyl ring (the cyclopropyl or cyclopentyl ring may be substituted with 1 or 2 groups selected from the group consisting of a hydroxymethyl group, 1,2-dihydroxyethyl group, 1,2,3-trihydroxypropyl group, and 1,2,3,4-tetrahydroxybutyl group), (7) The compound or pharmacologically acceptable salt thereof according to any one of the aforementioned (1) to (3), wherein X and Y represent a group in which X and Y together with the carbon atom of ring B form ring A, and ring A is a 3- to 6-membered heterocyclyl ring {the heterocyclyl ring is oxirane, tetrahydrofuran, 1,3-dioxolane, 1,3-dioxane, 1,3-dithiolane, 1,3-dithiane, 1,3-oxathiolane, or 1,3-oxathiane, these heterocyclyl rings may form a fused ring or spiro ring with a 5- or 6-membered heterocyclyl ring (the 5- or 6-membered heterocyclyl ring is tetrahydrofuran, tetrahydropyran or 1,3-dioxane) or cyclohexyl ring, and ring A, including the fused ring and spiro ring, may be substituted with 1 or 2 groups selected from the group consisting of Substituent group α [Substituent group α represents a hydroxy group and a group having the formula $NR^6R^7$ ($R^6$ and $R^7$, independently from each other, represent a hydrogen atom or acetyl group)], a methyl group, an ethyl group, a hydroxymethyl group, a 1,2-dihydroxyethyl group, a 1,2,3-trihydroxypropyl group and a 1,2,3,4-tetrahydroxybutyl group}, (8) The compound or pharmacologically acceptable salt thereof according to any one of the aforementioned (1) to (7), wherein n is 0 or 1, and $R^1$ is a hydroxy group, halogen atom, $C_1$-$C_6$ alkyl group or $C_1$-$C_6$ alkoxy group, (9) The compound or pharmacologically acceptable salt thereof according to any one of the aforementioned (1) to (7), wherein n is 0 or 1, and $R^1$ is a fluorine atom or methyl group,

(10) The compound or pharmacologically acceptable salt thereof according to any one of the aforementioned (1) to (7), wherein n is 0,

(11) The compound or pharmacologically acceptable salt thereof according to any one of the aforementioned (1) to (10), wherein $R^2$ is a $C_1$-$C_6$ alkyl group,

(12) The compound or pharmacologically acceptable salt thereof according to any one of the aforementioned (1) to (10), wherein $R^2$ is a $C_1$-$C_4$ alkyl group,

(13) The compound or pharmacologically acceptable salt thereof according to any one of the aforementioned (1) to (10), wherein $R^2$ is an ethyl group,

(14) The compound or pharmacologically acceptable salt thereof according to any one of the aforementioned (1) to (13), wherein $R^3$ is a phenyl group which may be substituted with a group selected from Substituent group ϵ, or a pyrrolyl group which may be substituted with a group selected from Substituent group ϵ, and Substituent group ϵ is a halogen atom, $C_1$-$C_{14}$ alkyl group and halogeno $C_1$-$C_{14}$ alkyl group,

(15) The compound or pharmacologically acceptable salt thereof according to any one of the aforementioned (1) to (13), wherein $R^3$ is a phenyl group which may be substituted with a group selected from Substituent group ϵ, or a pyrrolyl group which may be substituted with a group selected from Substituent group ϵ, and Substituent group ϵ is a fluorine atom, chlorine atom, bromine atom, $C_3$-$C_8$ alkyl group and halogeno $C_4$-$C_8$ alkyl group,

(16) The compound or pharmacologically acceptable salt thereof according to any one of the aforementioned (1) to (13), wherein $R^3$ is a phenyl group which may be substituted with a group selected from Substituent group ϵ, and Substituent group ϵ is a fluorine atom, chlorine atom and $C_3$-$C_8$ alkyl group,

(17) The compound or pharmacologically acceptable salt thereof according to any one of the aforementioned (1) to (16), wherein $R^5$ is a hydrogen atom or $C_1$-$C_6$ alkyl group,

(18) The compound or pharmacologically acceptable salt thereof according to any one of the aforementioned (1) to (16), wherein $R^5$ is a hydrogen atom or methyl group,

(19) The compound or pharmacologically acceptable salt thereof according to any one of the aforementioned (1) to (16), wherein $R^5$ is a hydrogen atom,

(20) The compounds of the following group selected from the aforementioned (1) or pharmacologically acceptable salt thereof:

ethyl 8-[N-(2-chlorophenyl)sulfamoyl]-2,3-bis(hydroxymethyl)-1,4-dioxaspiro[4.5]dec-6-ene-7-carboxylate, ethyl 8-[N-(2-chlorophenyl)sulfamoyl]-2,3-bis(1,2-dihydroxyethyl)-1,4-dioxaspiro[4.5]dec-6-ene-7-carboxylate, ethyl 8-[N-(2,4-difluorophenyl)sulfamoyl]-2,3-bis(hydroxymethyl)-1,4-dioxaspiro[4.5]dec-6-ene-7-carboxylate, ethyl 8-[N-(2,4-difluorophenyl)sulfamoyl]-2,3-bis(1,2-dihydroxyethyl)-1,4-dioxaspiro[4.5]dec-6-ene-7-carboxylate, ethyl 8-[N-(2-chloro-4-fluorophenyl)sulfamoyl]-2-hydroxymethyl-1,4-dioxaspiro[4.5]dec-6-ene-7-carboxylate, ethyl 8-[N-(2-chloro-4-fluorophenyl)sulfamoyl]-2,3-bis(hydroxymethyl)-1,4-dioxaspiro[4.5]dec-6-ene-7-carboxylate, ethyl 8-[N-(2-chloro-4-fluorophenyl)sulfamoyl]-2,3-bis(1,2-dihydroxyethyl)-1,4-dioxaspiro[4.5]dec-6-ene-7-carboxylate, ethyl 8-[N-(2-chloro-4-fluorophenyl)sulfamoyl]-2-(1,2-dihydroxyethyl)-1,4-dioxaspiro[4.5]dec-6-ene-7-carboxylate, ethyl 8-[N-(2-chloro-4-fluorophenyl)sulfamoyl]-2-(1,2,3-trihydroxypropyl)-1,4-dioxaspiro[4.5]dec-6-ene-7-carboxylate, ethyl 8-[N-(2-chloro-4-fluorophenyl)sulfamoyl]-2-(1,2,3,4-tetrahydroxybutyl)-1,4-dioxaspiro[4.5]dec-6-ene-7-carboxylate, ethyl 2,3-bis(acetylaminomethyl)-8-[N-(2-chloro-4-fluorophenyl)sulfamoyl]-1,4-dioxaspiro[4.5]dec-6-ene-7-carboxylate, ethyl 9-[N-(2-chloro-4-fluorophenyl)sulfamoyl]-3-hydroxy-1,5-dioxaspiro[5.5]undec-7-ene-8-carboxylate, ethyl 3-acetylamino-9-[N-(2-chloro-4-fluorophenyl)sulfamoyl]-1,5-dioxaspiro[5.5]undec-7-ene-8-carboxylate, ethyl 9-[N-(2-chloro-4-fluorophenyl)sulfamoyl]-3,3-bis(hydroxymethyl)-1,5-dioxaspiro[5.5]undec-7-ene-8-carboxylate, ethyl 8-[N-(2-butyl-4-fluorophenyl)sulfamoyl]-2,3-bis(hydroxymethyl)-1,4-dioxaspiro[4.5]dec-6-ene-7-carboxylate, ethyl 8-[N-(2-butyl-4-fluorophenyl)sulfamoyl]-2,3-bis(1,2-dihydroxyethyl)-1,4-dioxaspiro[4.5]dec-6-ene-7-carboxylate, ethyl 8-[N-(2-hexylphenyl)sulfamoyl]-2,3-bis(hydroxymethyl)-1,4-dioxaspiro[4.5]dec-6-ene-7-carboxylate, ethyl 8-[N-(2-hexylphenyl)sulfamoyl]-2,3-bis(1,2-dihydroxyethyl)-1,4-dioxaspiro[4.5]dec-6-ene-7-carboxylate, ethyl 8-[N-(4-fluoro-2-hexylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-hexylphenyl)sulfamoyl]-1,4-dioxaspiro[4.5]dec-6-ene-7-carboxylate, ethyl 8-[N-(2-heptylphenyl)sulfamoyl]-2,3-bis(hydroxymethyl)-1,4-dioxaspiro[4.5]dec-6-ene-7-carboxylate, ethyl 8-[N-(2-heptylphenyl)sulfamoyl]-2,3-bis(1,2-dihydroxyethyl)-1,4-dioxaspiro[4.5]dec-6-ene-7-carboxylate, ethyl 8-[N-(4-fluoro-2-heptylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-heptylphenyl)sulfamoyl]-1,4-dioxaspiro[4.5]dec-6-ene-7-carboxylate, ethyl 8-[N-(2-bromophenyl)sulfamoyl]-2,3-bis(hydroxymethyl)-1,4-dioxaspiro[4.5]dec-6-ene-7-carboxylate, ethyl 8-[N-(2-bromophenyl)sulfamoyl]-2,3-bis(1,2-dihydroxyethyl)-1,4-dioxaspiro[4.5]dec-6-ene-7-carboxylate, ethyl 8-[N-(2-chloro-6-methylphenyl)sulfamoyl]-2,3-bis(hydroxymethyl)-1,4-dioxaspiro[4.5]dec-6-ene-7-carboxylate, ethyl 8-[N-(2-chloro-6-methylphenyl)sulfamoyl]-2,3-bis(1,2-dihydroxyethyl)-1,4-dioxaspiro[4.5]dec-6-ene-7-carboxylate, ethyl 8-[N-(2-bromo-4-fluorophenyl)sulfamoyl]-2,3-bis(hydroxymethyl)-1,4-dioxaspiro[4.5]dec-6-ene-7-carboxylate, ethyl 8-[N-(2-bromo-4-fluorophenyl)sulfamoyl]-2,3-bis(1,2-dihydroxyethyl)-1,4-dioxaspiro[4.5]dec-6-ene-7-carboxylate, ethyl 2,3-bis(hydroxymethyl)-8-[N-(2-pentylphenyl)sulfamoyl]-1,4-dioxaspiro[4.5]dec-6-ene-7-carboxylate, ethyl 2,3-bis(1,2-dihydroxyethyl)-8-[N-(2-pentylphenyl)sulfamoyl]-1,4-dioxaspiro[4.5]dec-6-ene-7-carboxylate, ethyl 8-[N-(4-fluoro-2-pentylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-pentylphenyl)sulfamoyl]-1,4-dioxaspiro[4.5]dec-6-ene-7-carboxylate, ethyl 8-[N-(4-fluoro-2-octylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-octylphenyl)sulfamoyl]-1,4-dioxaspiro[4.5]dec-6-ene-7-carboxylate, ethyl 8-[N-(4-fluoro-2-propylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-propylphenyl)sulfamoyl]-1,4-dioxaspiro[4.5]dec-6-ene-7-carboxylate, and ethyl 8-[N-(2-chloro-4-fluorophenyl)-N-methylsulfamoyl]-2,3-bis(hydroxymethyl)-1,4-dioxaspiro[4.5]dec-6-ene-7-carboxylate,

(21) A medicament containing the compound or pharmacologically acceptable salt thereof selected from any one of the aforementioned (1) to (20) as an active ingredient,

(22) The medicament according to the aforementioned (21) for use in suppressing intracellular signal transduction or cell activation induced by endotoxin,

(23) The medicament according to the aforementioned (21) for use in suppressing the generation of inflammatory mediators due to intracellular signal transduction or cell activation induced by endotoxin,

(24) The medicament according to the aforementioned (21) for use as a prophylactic or therapeutic agent for a disease due to intracellular signal transduction or cell activation inducted by endotoxin,

(25) The medicament according to the aforementioned (21) for use as a prophylactic and/or therapeutic agent for a disease mediated by an inflammatory mediator, of which generation is induced by endotoxin,

(26) The medicament according to the aforementioned (21) for use as a prophylactic and/or therapeutic agent for a disease mediated by an inflammatory mediator, which is generated due to intracellular signal transduction or cell activation induced by endotoxin,

(27) The medicament according to the aforementioned (21) for use as a prophylactic and/or therapeutic agent for sepsis, and (i) a method of suppressing intracellular signal transduction induced by endotoxin and suppressing excess generation of inflammatory mediators such as TNF-α which is induced by the intracellular signal transduction, and (ii) a method of preventing and/or treating a disease mediated by intracellular signal transduction and by an inflammatory mediator which is generated due to the intracellular signal transduction, comprising administering an effective amount of the compound according to any one of the aforementioned (1) to (20) or pharmacologically acceptable salt thereof to a warm-blood animal (preferably a human).

EFFECTS OF THE INVENTION

The substituted cycloalkene derivative according to the present invention having the general formula (I) has excellent activity to suppress intracellular signal transduction or cell activation induced by endotoxin and to suppress excess generation of inflammatory mediators such as TNF-α due to the intracellular signal transduction and cell activation, and is useful as a medicament, especially as a prophylactic and/or therapeutic agent for ischemic brain disorder, arteriosclerosis, poor prognosis after coronary angioplasty, heart failure, diabetes, diabetic complication, joint inflammation, osteoporosis, osteopenia, sepsis, autoimmune disease, tissue disorder and rejection after organ transplantation, bacterial infection, virus infection, gastritis, pancreatitis, nephritis, pneumonia, hepatitis, leukemia and the like, which are induced by the intervention of the intracellular signal transduction or cell activation, and by inflammatory mediators due to the intracellular signal transduction and cell activation.

BEST MODE FOR CARRYING OUT THE INVENTION

"Halogen atom" in the definitions of $R^1$, Substituent group α, Substituent group β, Substituent group δ and Substituent group ϵ includes, for example, a fluorine atom, chlorine atom, bromine atom or iodine atom.

With respect to $R^1$, it is preferably a fluorine atom or chlorine atom, more preferably a fluorine atom.

With respect to Substituent group ϵ, it is preferably a fluorine atom, chlorine atom or bromine atom, more preferably a fluorine atom or chlorine atom.

"Alkyl group" in the definitions of the NR group which may be included in ring A, substituent of ring A, $R^1$, $R^2$, $R^5$, $R^6$, $R^7$, Substituent group β, Substituent group δ and Substituent group ϵ includes a linear or branched alkyl group.

"$C_1$-$C_6$ alkyl group" of "$C_1$-$C_6$ alkyl group which may be substituted with a group selected from Substituent group α" in the definition of the NR group which may be included in ring A; "$C_1$-$C_6$ alkyl group" of "cyclopropyl $C_1$-$C_6$ alkyl group" in the definition of a substituent of ring A; "$C_1$-$C_6$ alkyl group" of "$C_1$-$C_6$ alkyl group which may be substituted with 1 to 5 groups selected from Substituent group α" in the definition of a substituent of ring A; "$C_1$-$C_6$ alkyl group" of "$C_1$-$C_6$ alkyl group which may be substituted with a group selected from Substituent group β" in the definitions of $R^2$ and $R^5$; and "$C_1$-$C_6$ alkyl group" in the definitions of Substituent group δ, $R^6$ and $R^7$ are, for example, methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl group or the like.

Among the "$C_1$-$C_6$ alkyl groups", the one with respect to the NR group which may be included in ring A is preferably methyl.

With respect to a substituent of ring A, it is preferably a $C_1$-$C_4$ alkyl group.

With respect to $R^2$, it is preferably a $C_1$-$C_4$ alkyl group, more preferably ethyl.

With respect to $R^5$, it is preferably methyl.

With respect to $R^6$ and $R^7$, it is preferably methyl.

With respect to Substituent group δ, it is preferably a $C_1$-$C_4$ alkyl group.

$C_1$-$C_{14}$ alkyl groups of "$C_1$-$C_{14}$ alkyl group" and "cyclopropyl $C_1$-$C_{14}$ alkyl group" in the definition of Substituent group ϵ are, for example, the aforementioned "$C_1$-$C_6$ alkyl group", octyl, nonyl, decyl, dodecyl, tetradecyl or the like.

With respect to "$C_1$-$C_{14}$ alkyl group" in the definition of Substituent group ϵ, it is preferably $C_3$-$C_8$ alkyl group.

"$C_1$-$C_{20}$ alkyl group" in the definition of $R^1$ is, for example, the aforementioned "$C_1$-$C_{14}$ alkyl group", pentadecyl, hexadecyl, heptadecyl, octadecyl, nonadecyl, icosyl or the like. Preferably, it is a $C_1$-$C_6$ alkyl group, and more preferably a methyl group.

"Alkenyl group" in the definitions of the NR group which may be included in ring A, substituent of ring A, $R^1$, $R^2$, $R^5$, $R^6$, $R^7$ and Substituent group α is a linear or branched alkenyl group.

"$C_3$-$C_6$ alkenyl group" in the definition of $R^1$ is, for example, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl or 5-hexenyl, preferably a $C_3$-$C_4$ alkenyl group.

"$C_2$-$C_6$ alkenyl group" of "$C_2$-$C_6$ alkenyl group which may be substituted with a group selected from Substituent group α" in the definition of the NR group which may be included in ring A; "$C_2$-$C_6$ alkenyl group" of "$C_2$-$C_6$ alkenyl group which may be substituted with 1 to 5 groups selected from Substituent group α" in the definition of substituent of ring A; "$C_2$-$C_6$ alkenyl group" of "$C_2$-$C_6$ alkenyl group which may be substituted with a group selected from Substituent group β" in the definitions of $R^2$ and $R^5$; and "$C_2$-$C_6$ alkenyl group" in the definitions of $R^6$ and $R^7$ are, for example, vinyl or the aforementioned "$C_3$-$C_6$ alkenyl group", preferably a $C_3$-$C_4$ alkenyl group.

"Alkynyl group" in the definitions of the NR group which may be included in ring A, substituent of ring A, $R^1$, $R^2$, $R^5$, $R^6$, $R^7$ and Substituent group α is a linear or branched alkynyl group.

"$C_3$-$C_6$ alkynyl group" in the definition of $R^1$ is, for example, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl, preferably a $C_3$-$C_4$ alkyl group.

"$C_2$-$C_6$ alkynyl group" of "$C_2$-$C_6$ alkynyl group which may be substituted with a group selected from Substituent group α" in the definition of the NR group which may be included in ring A; "$C_2$-$C_6$ alkynyl group" of "$C_2$-$C_6$ alkynyl group which may be substituted with 1 to 5 groups selected from Substituent group α" in the definition of substituent of ring A; "$C_2$-$C_6$ alkynyl group" of "$C_2$-$C_6$ alkynyl group which may be substituted with a group selected from Substituent group β" in the definitions of $R^1$ and $R^5$; and "$C_2$-$C_6$ alkynyl group" in the definitions of $R^6$ and $R^7$ are, for example, ethynyl or the aforementioned "$C_3$-$C_6$ alkynyl group", preferably a $C_3$-$C_4$ alkynyl group.

"$C_3$-$C_6$ cycloalkyl group" in the definitions of Substituent group δ and Substituent group ϵ are, for example, cyclopropyl, cyclopentyl or cyclohexyl.

"3- to 7-membered cycloalkyl ring" in the definition of ring A may include an unsaturated bond, and such ring is, for example, cyclopropane, cyclobutane, cyclopentane, cyclopentene, cyclohexane, cyclohexene, cyclohexadiene, cycloheptane or cycloheptadiene.

The aforementioned "3- to 7-membered cycloalkyl ring" may form a fused ring or spiro ring with a 3- to 7-membered heterocyclyl ring or 3- to 7-membered cycloalkyl ring, and such cycloalkyl ring is, for example, 2-oxa-bicyclo[4,3,0]nonan-8-ylidene, 3-oxa-bicyclo[3,3,0]heptan-7-ylidene, 2,4-dioxa-spiro[6.6]undecan-8-ylidene, bicyclo[4,3,0]nonan-7-ylidene, spiro[6.6]undecan-8-ylidene or the like.

In addition, the aforementioned "3- to 7-membered cycloalkyl ring" may not form a fused ring or spiro ring, and may be substituted with an oxo group or a thioxo group.

With respect to the aforementioned "cycloalkyl ring", a cycloalkyl ring, fused ring which is fused to the cycloalkyl ring, or spiro ring which is spiro bound to the cycloalkyl ring may be substituted with the same or different 1 to 4 (preferably 1 or 2) groups selected from the group consisting of Substituent group α, cyclopropyl $C_1$-$C_6$ alkyl group, $C_1$-$C_6$ alkyl group which may be substituted with 1 to 5 groups selected from Substituent group α, $C_2$-$C_6$ alkenyl group which may be substituted with 1 to 5 groups selected from Substituent group α and $C_2$-$C_6$ alkynyl group which may be substituted with 1 to 5 groups selected from Substituent group α.

Preferred examples of the ring are, 3-hydroxycyclopentane, 4-hydroxycyclohexane, 3-hydroxymethylcyclopentane, 3,4-dihydroxymethylcyclopentane, 4-hydroxymethylcyclohexane, 4,4-dihydroxymethylcyclohexane, 3-(1,2-dihydroxyethyl)cyclopentane, 4-(1,2-dihydroxyethyl)cyclohexane, 3,4-bis(1,2-dihydroxyethyl)cyclopentane, 4,4-bis(1,2-dihydroxyethyl)cyclohexane, 3-(1,2,3-trihydroxypropyl)cyclopentane, 4-(1,2,3-trihydroxypropyl)cyclohexane, 3-(1,2,3,4-tetrahydroxybutyl)cyclopentane, 4-(1,2,3,4-tetrahydroxybutyl)cyclohexane, 3-ethoxycarbonylcyclopentane, 4-ethoxycarbonylcyclohexane, 4,4-diethoxycarbonylcyclchexane, 3-carbamoylcyclopentane, 4-carbamoylcyclohexane, 3-acetylaminocyclopentane, 4-acetylaminocyclohexane, 3,4-diacetylaminomethylcyclopentane, 2,3,4,5-tetrahydroxybicyclo[4,3,0]nonane (the binding position with ring B is the 8-position), 3-oxa-bicyclo[3,3,0]octane (the binding position with ring B is the 7-position), 2,4-dihydroxymethyl-3-oxa-bicyclo[3,3,0]octane (the binding position with ring B is the 7-position), and 2,4-dioxaspiro[5.5]undecane (the binding position with ring B is the 9-position).

"Cycloalkyl ring" in the definition of ring A is, among the aforementioned rings, preferably a 3- to 7-membered cycloalkyl ring which may be substituted with 1 or 2 groups selected from a group consisting of a hydroxy group, hydroxymethyl group, 1,2-dihydroxyethyl group, 1,2,3-trihydroxyethyl group, 1,2,3,4-tetrahydroxybutyl group and acetylamino group, more preferably a 3- to 5-membered saturated cycloalkyl ring which may be substituted with 1 or 2 groups selected from the group consisting of a hydroxymethyl group, 1,2-dihydroxyethyl group, 1,2,3-trihydroxypropyl group, 1,2,3,4-tetrahydroxybutyl group and acetylamino group, and particularly preferably a cyclopropyl or cyclopentyl ring which may be substituted with 1 or 2 groups selected from the group consisting of a hydroxymethyl group, 1,2-dihydroxyethyl group, 1,2,3-trihydroxypropyl group and 1,2,3,4-tetrahydroxybutyl group.

"$C_3$-$C_{10}$ cycloalkyl group" in the definition of $R^1$ is, for example, cyclopropyl, cyclobutyl, cyclopentyl, cyclohexyl, cycloheptyl or cyclooctyl.

"$C_4$-$C_{12}$ cycloalkylalkyl group" in the definition of $R^1$ is, for example, cyclopropylmethyl, cyclopentylmethyl, cyclohexylmethyl or cycloheptylmethyl, preferably a $C_4$-$C_8$ cycloalkylalkyl group, more preferably a $C_4$-$C_7$ cycloalkylalkyl group.

With respect to "3- to 7-membered heterocyclyl ring" in the definition of ring A, X and Y included in the ring, independently from each other, represent any one selected from a carbon atom, a group having the formula NR (R represents a hydrogen atom or a $C_1$-$C_6$ alkyl, $C_2$-$C_6$ alkenyl, $C_2$-$C_6$ group or $C_1$-$C_6$ alkylcarbonyl group which may be substituted with a group selected from Substituent group α), an oxygen atom, a sulfur atom, a group having the formula SO and a group having the formula $SO_2$, preferably any one selected from a carbon atom, an oxygen atom, a sulfur atom, a group having the formula SO, and a group having the formula $SO_2$. The 3- to 7-membered heterocyclyl ring may include an unsaturated bond.

Examples of such ring are, a heterocyclyl ring including a nitrogen atom such as aziridine, azetidine, pyrrolidine, pyrroline, piperidine and imidazolidine; a heterocyclyl ring including an oxygen atom such as oxirane, oxetane, tetrahydrofuran, oxolene, tetrahydropyran, dihydropyran, oxepane, 1,3-dioxclane, 1,3-dioxane and 1,3-dioxepane; a heterocyclyl ring including a sulfur atom, a group having the formula SO or a group having the formula $SO_2$ such as thiirane, thietane, thiolane, thiolene, thiane, thiepane, 1,3-dithiolane, 1,3-dithiane, 1,3-dithiepane, 1,3-dioxo-1,3-dithiolane, 1,3-dioxo-1,3-dithiane, 1,1,3,3-tetraoxo-1,3-dithiolane and 1,1,3,3-tetraoxo-1,3-dithiane; a heterocyclyl ring including an oxygen atom and a sulfur atom such as 1,3-oxathiolane, 1,3-oxathiane and 1,3-oxathiepane; a heterocyclyl ring including a nitrogen atom and an oxygen atom such as 1,3-oxapyrrolidine and 1,3-oxapyrroline; and a heterocyclyl ring including a nitrogen atom and a sulfur atom such as 1,3-thiapyrrolidine and 1,3-thiapyrroline.

Preferably, it is oxirane, tetrahydrofuran, tetrahydropyran, 1,3-dioxolane, 1,3-dioxane, 1,3-dioxepane, 1,3-dithiolane, 1,3-dithiane, 1,1,3,3-tetraoxo-1,3-dithiolane, 1,3-oxathiolane, 1,3-oxathiane or 1,3-oxathiepane.

More preferably, it is oxirane, tetrahydrofuran, 1,3-dioxolane, 1,3-dioxane, 1,3-dithiolane, 1,3-dithiane, 1,3-oxathiolane or 1,3-oxathiane.

Even more preferably, it is oxirane, 1,3-dioxolane, 1,3-dioxane or 1,3-oxathiolane.

The aforementioned "3- to 7-membered heterocyclyl ring" may form a fused ring or spiro ring with a 3- to 7-membered heterocyclyl ring or 3- to 7-membered cycloalkyl ring, preferably may form a fused ring or spiro ring with a 5- or 6-membered heterocyclyl ring (the heterocyclyl ring includes 1 or 2 oxygen and/or nitrogen atoms as hetero atom) or 5- or 6-membered cycloalkyl ring, and more preferably may form a fused ring or spiro ring with tetrahydrofuran, tetrahydropyran, pyrrolidine, piperidine, 1,3-dioxane or cyclohexyl ring.

Examples of such heterocyclyl ring are 2,4-dioxa-bicyclo[3,3,0]octane (the binding position with ring B is the 3-position), 2,4,7-trioxa-bicyclo[3,3,0]octane (the binding position with ring B is the 3-position), 7,9-dioxa-bicyclo[4,3,0]nonane (the binding position with ring B is the 8-position), 7-aza-2,4-dioxa-bicyclo[3,3,0]octane (the binding position with ring B is the 3-position), 2,4,8,10-tetraoxaspiro[5,5]undecane (the binding position with ring B is the 3-position) and the like. The binding position of these rings with ring B is the same as the aforedescribed one.

In addition, the aforementioned "3- to 7-membered heterocyclyl ring" may not form a fused ring or spiro ring, and may be substituted with an oxo group or a thioxo group.

With respect to the aforementioned "heterocyclyl ring", heterocyclyl ring, fused ring which is fused to the heterocyclyl ring or spiro ring which is spiro bound to the heterocyclyl ring may be substituted with the same or different 1 to 4 (preferably 1 or 2) substituents.

The substituent is a group selected from the group consisting of an oxo group, a thioxo group, Substituent group α, a cyclopropyl $C_1$-$C_6$ alkyl group, a $C_1$-$C_6$ alkyl group which may be substituted with 1 to 5 groups selected from Substituent group α, a $C_2$-$C_6$ alkenyl group which may be substituted with 1 to 5 groups selected from Substituent group α and a $C_2$-$C_6$ alkynyl group which may be substituted with 1 to 5 groups selected from Substituent group α.

The substituent is preferably a group selected from the group consisting of an oxo group, a thioxo group, Substituent group α, a cyclopropyl $C_1$-$C_6$ alkyl group and a $C_1$-$C_6$ alkyl group which may be substituted with 1 to 5 groups selected from Substituent group α.

More preferably, it is a group selected from the group consisting of an oxo group, a thioxo group, Substituent group α and a $C_1$-$C_6$ alkyl group which may be substituted with 1 to 4 groups selected from Substituent group α.

Even more preferably, it is 1 or 2 groups selected from the group consisting of an oxo group, a thioxo group, Substituent group α(Substituent group α is a hydroxy group and a group having the formula $NR^6R^7$, and $R^6$ and $R^7$, independently from each other, represent a hydrogen atom or $C_1$-$C_6$ alkylcarbonyl group), a methyl group, an ethyl group and a $C_1$-$C_6$ alkyl group substituted with 1 to 4 hydroxy groups.

Further preferably, it is 1 or 2 groups selected from the group consisting of Substituent group α [Substituent group α represents a hydroxy group and a group having the formula $NR^6R^7$ ($R^6$ and $R^7$, independently from each other, represent a hydrogen atom or methylcarbonyl group)], a methyl group, an ethyl group, a hydroxymethyl group, a 1,2-dihydroxyethyl group, a 1,2,3-trihydroxypropyl group and a 1,2,3,4-tetrahydroxybutyl group.

As for such examples, oxirane, oxolane, tetrahydrofuran (traditional name, oxolane according IUPAC nomenclature), tetrahydropyran (traditional name, oxane according IUPAC nomenclature), 1,3-dioxclane, 1,3-dioxane, 1,3-dioxepane, 1,3-dithiolane, 1,3-dithiane, 1,3-oxathiolane, 1,3-oxathiane, 1,3-oxathiepane, tetrahydrooxazole, tetrahydro-1,3-oxadine, tetrahydrothiazole, tetrahydro-1,3-thiazine, 1,1,3,3-tetraoxo-1,3-dithiane, 2,4,7-trioxa-bicyclo[3,3,0]octane, 2,4-dithia-7-oxa-bicyclo[3,3,0]octane, 2-thia-4,7-dioxa-bicyclo[3,3,0]octane, 2,4,8,10-tetraoxaspiro[5.5]undecane, 2,4-dithia-8,10-dioxaspiro[5.5]undecane, 2-thia-4,8,10-trioxaspiro[5.5]undecane, 2-hydroxytetrahydrofuran, 4-hydroxy-1,3-dioxolane, 4,5-dihydroxy-1,3-dioxolane, 5-hydroxy-1,3-dioxane, 5,5-dihydroxy-1,3-dioxane, 4-hydroxy-1,3-dithiolane, 4,5-dihydroxy-1,3-dithiolane, 5-hydroxy-1,3-dithiane, 5,5-dihydroxy-1,3-dithiane, 4-hydroxy-1,1,3,3-tetraoxo-1,3-dithiolane, 4,5-dihydroxy-1,1,3,3-tetraoxo-1,3-dithiolane, 4-hydroxy-1,3-oxathiolane, 5-hydroxy-1,3-oxathiane, 5,5-dihydroxy-1,3-oxathiane, 6,8-dihydroxy-2,4-dioxa-bicyclo[3,3,0]octane, 6,8-dihydroxy-2,4,7-trioxa-bicyclo[3,3,0]octane, 2,3,4,5-tetrahydroxy-7,9-dioxa-bicyclo[4,3,0]nonane, 6,8-dihydroxy-7-aza-2,4-dioxa-bicyclo[3,3,0]octane, 9-hydroxy-2,4,8,10-tetraoxaspiro[5.5]undecane, 2,3,4,5-tetrahydro-7,9-dithia-bicyclo[4,3,0]nonane, 2,3,4,5-tetrahydro-7-thia-9-oxa-bicyclo[4,3,0]nonane, 2-carboxytetrahydrofuran, 4-carboxy-1,3-dioxolane, 5-carboxy-1,3-dioxane, 4-carboxy-1,3-dithiolane, 5-carboxy-1,3-dithiane, 4-carboxy-1,1,3,3-tetraoxo-1,3-dithiolane, 4-carboxy-1,3-oxathiolane, 5-carboxy-1,3-oxathiane, 2-methoxycarbonyltetrahydrofuran, 4-methoxycarbonyl-1,3-dioxolane, 5-methoxycarbonyl-1,3-dioxane, 5,5-dimethoxycarbonyl-1,3-dioxane, 4-methoxycarbonyl-1,3-dithiolane, 5-methoxycarbonyl-1,3-dithiane, 5,5-dimethoxycarbonyl-1,3-dithiane, 4-methoxycarbonyl-1,1,3,3-tetraoxo-1,3-dithiolane, 4-methoxycarbonyl-1,3-oxathiolane, 5-methoxycarbonyl-1,3-oxathiane, 5,5-dimethoxycarbonyl-1,3-oxathiane, 6,8-dimethoxycarbonyl-2,4-dioxa-bicyclo[3,3,0]octane, 6,8-dimethoxycarbonyl-2,4,7-trioxa-bicyclo[3,3,0]octane, 6,8-dimethoxycarbonyl-7-aza-2,4-dioxa-bicyclo[3,3,0]octane, 8-methoxycarbonyl-2,4,7,9-tetraoxaspiro[5.5]undecane, 2-ethoxycarbonyltetrahydrofuran, 4-ethoxycarbonyl-1,3-dioxolane, 5-ethoxycarbonyl-1,3-dioxane, 5,5-diethoxycarbonyl-1,3-dioxane, 4-ethoxycarbonyl-1,3-dithiolane, 5-ethoxycarbonyl-1,3-dithiane, 5,5-diethoxycarbonyl-1,3-dithiane, 4-ethoxycarbonyl-1,1,3,3-tetraoxo-1,3-dithiolane, 4-ethoxycarbonyl-1,3-oxathiolane, 5-ethoxycarbonyl-1,3-oxathiane, 5,5-diethoxycarbonyl-1,3-oxathiane, 6,8-diethoxycarbonyl-2,4-dioxa-bicyclo[3,3,0]octane, 6,8-diethoxycarbonyl-2,4,7-trioxa-bicyclo[3,3,0]octane, 6,8-diethoxycarbonyl-7-aza-2,4-dioxa-bicyclo[3,3,0]octane, 8-ethoxycarbonyl-2,4,7,9-tetraoxaspiro[5.5]undecane, 2-aminotetrahydrofuran, 4-amino-1,3-dioxolane, 4,5-diamino-1,3-dioxolane, 5-amino-1,3-dioxane, 4-amino-1,3-dithiolane, 4,5-diamino-1,3-dithiolane, 5-amino-1,3-dithiane, 4-amino-1,1,3,3-tetraoxo-1,3-dithiolane, 4-amino-1,3-oxathiolane, 5-amino-1,3-oxathiane, 2-acetylaminotetrahydrofuran, 4-acetylamino-1,3-dioxolane, 4,5-bis(acetylamino)-1,3-dioxolane, 5-acetylamino-1,3-dioxane, 4-acetylamino-1,3-dithiolane, 4,5-bis(acetylamino)-1,3-dithiolane, 5-acetylamino-1,3-dithiane, 4-acetylamino-1,1,3,3-tetraoxo-1,3-dithiolane, 4-acetylamino-1,3-oxathiolane, 5-acetylamino-1,3-oxathiane, 6,8-diacetylamino-2,4-dioxa-bicyclo[3,3,0]octane, 6,8-diacetylamino-2,4,7-trioxa-bicyclo[3,3,0]octane, 6,8-diacetylamino-7-aza-2,4-dioxa-bicyclo[3,3,0]octane, 8-acetylamino-2,4,7,9-tetraoxaspiro[5.5]undecane, 2-methyltetrahydrofuran, 4-methyl-1,3-dioxclane, 4,5-dimethyl-1,3-dioxolane, 5-methyl-1,3-dioxane, 4-methyl-1,3-dithiolane, 4,5-dimethyl-1,3-dithiolane, 5-methyl-1,3-dithiane, 4-methyl-1,1,3,3-tetraoxo-1,3-dithiolane, 4-methyl-1,3-oxathiolane, 5-methyl-1,3-oxathiane, 5,5-dimethyl-1,3-dioxane, 5,5-dimethyl-1,3-dithiane, 5,5-dimethyl-1,3-oxathiane, 2-ethyltetrahydrofuran, 4-ethyl-1,3-dioxolane, 4,5-diethyl-1,3-dioxolane, 5-ethyl-1,3-dioxane, 4-ethyl-1,3-dithiolane, 4,5-diethyl-1,3-dithiolane, 5-ethyl-1,3-dithiane, 4-ethyl-1,1,3,3-tetraoxo-1,3-dithiolane, 4-ethyl-1,3-oxathiolane, S-ethyl-1,3-oxathiane, 2-hydroxymethyltetrahydrofuran, 4-hydroxymethyl-1,3-dioxolane, 5-hydroxymethyl-1,3-dioxane, 5,5-dihydroxymethyl-1,3-dioxane, 4-hydroxymethyl-1,3-dithiolane, 5-hydroxymethyl-1,3-dithiane, 5,5-dihydroxymethyl-1,3-dithiane, 4-hydroxymethyl-1,1,3,3-tetraoxo-1,3-dithiolane, 4-hydroxymethyl-1,3-oxathiolane, 5-hydroxymethyl-1,3-oxathiane, 5,5-dihydroxymethyl-1,3-oxathiane, 4,5-dihydroxymethyl-1,3-dioxolane, 4,5-dihydroxymethyl-1,3-dithiolane, 4,5-dihydroxymethyl-1,3-oxathiolane, 5,5-dihydroxymethyl-1,3-dioxane, 5,5-dihydroxymethyl-1,3-dithiane, 5,5-dihydroxymethyl-1,3-oxathiane, 6,8-dihydroxymethyl-2,4,7-trioxa-bicyclo[3,3,0]octane, 6,8-dihydroxymethyl-2,4-dithia-7-oxa-bicyclo[3,3,0]octane, 6,8-dihydroxymethyl-2-thia-4,7-dioxa-bicyclo[3,3,0]octane, 6-oxo-8-hydroxymethyl-2,4,7-trioxa-bicyclo[3,3,0]octane, 2-(1,2-dihydroxyethyl)tetrahydrofuran, 4-(1,2-dihydroxyethyl)-1,3-dioxolane, 5-(1,2-dihydroxyethyl)-1,3-dioxane, 5,5-bis(1,2-dihydroxyethyl)-1,3-dioxane, 4-(1,2-dihydroxyethyl)-1,3-dithiolane, 5-(1,2-dihydroxyethyl)-1,3-dithiane, 5,5-bis(1,2-dihydroxyethyl)-1,3-dithiane, 4-(1,2-dihydroxyethyl)-1,1,3,3-tetraoxo-1,3-dithiolane, 4-(1,2-dihydroxyethyl)-1,3-oxathiolane, 5-(1,2-dihydroxyethyl)-1,3-oxathiane, 5,5-bis(1,2-dihydroxyethyl)-1,3-oxathiane, 4,5-bis(1,2-dihydroxyethyl)-1,3-dioxolane, 4,5-bis(1,2-dihydroxyethyl)-1,3-dithiolane, 4,5-bis(1,2-dihydroxyethyl)-1,3-oxathiolane, 4,5-bis(1-hydroxyethyl)-1,3-dioxolane, 4,5-bis(1-hydroxypropyl)-1,3-dioxolane, 2-(1,2,3-trihydroxypropyl)tetrahydrofuran, 4-(1,2,3-trihydroxypropyl)-1,3-dioxolane, 5-(1,2,3-trihydroxypropyl)-1,3-dioxane, 5,5-bis(1,2,3-trihydroxypropyl)-1,3-dioxane, 4-(1,2,3-trihydroxypropyl)-1,3-dithiolane, 5-(1,2,3-trihydroxypropyl)-1,3-dithiane, 5,5-bis(1,2,3-trihydroxypropyl)-1,3-dithiane, 4-(1,2,3-trihydroxypropyl)-1,1,3,3-tetraoxo-1,3-dithiolane, 4-(1,2,3-trihydroxypropyl)-1,3-oxathiolane, 5-(1,2-dihydroxyethyl)-1,3-oxathiane, 5,5-bis(1,2,3-trihydroxypropyl)-1,3-oxathiane, 2-(1,2,3,4-tetrahydroxybutyl)tetrahydrofuran, 4-(1,2,3,4-tetrahydroxybutyl)-1,3-dioxolane, 5-(1,2,3,4-tetrahydroxybutyl)-1,3-dioxane, 5,5-bis(1,2,3,4-tetrahydroxybutyl)-1,3-dioxane, 4-(1,2,3,4-tetrahydroxybutyl)-1,3-dithiolane, 5-(1,2,3,4-tetrahydroxybutyl)-1,3-dithiane, 5,5-bis(1,2,3,4-tetrahydroxybutyl)-1,3-dithiane, 4-(1,2,3,4-tetrahydroxybutyl)-1,1,3,3-tetraoxo-1,3-dithiolane, 4-(1,2,3,4-tetrahydroxybutyl)-1,3-oxathiolane, 5-(1,2,3,4-tetrahydroxybutyl)-1,3-oxathiane, 5,5-bis(1,2,3,4-tetrahydroxybutyl)-1,3-oxathiane, 2-acetylaminomethyltetrahydrofuran, 4-acetylaminomethyl-1,3-dioxolane, 4,5-diacetylaminomethyl-1,3-dioxolane, 5-acetylaminomethyl-1,3-dioxane, 4-acetylaminomethyl-1,3-dithiolane, 4,5-diacetylaminomethyl-1,3-dithiolane, 5-acetylaminomethyl-1,3-dithiane, 4-acetylaminomethyl-1,1,3,3-tetraoxo-1,3-dithiolane, 4-acetylaminomethyl-1,3-oxathiolane, 5-acetylaminomethyl-1,3-oxathiane, 4,5-diacetylaminomethyl-1,3-dioxolane, 4,5-diacetylaminomethyl-1,3-dithiolane, 4,5-diacetylaminomethyl-1,3-oxathiolane, 2-vinyltetrahydrofuran, 4-vinyl-1,3-dioxolane, 4,5-divinyl-1,3-dioxolane, 5-vinyl-1,3-dioxane, 4-vinyl-1,3-dithiolane, 4,5-divinyl-1,3-dithiolane, 5-vinyl-1,3-dithiane, 4-vinyl-1,1,3,3-tetraoxo-1,3-dithiolane, 4-vinyl-1,3-oxathiolane, 5-vinyl-1,3-oxathiane, 2-propenyltetrahydrofuran, 4-propenyl-1,3-dioxolane, 4,5-dipropenyl-1,3-dioxolane, 5-propenyl-1,3-dioxane, 4-propenyl-1,3-dithiolane, 4,5-dipropenyl-1,3-dithiolane, 5-propenyl-1,3-dithiane, 4-propenyl-1,1,3,3-tetraoxo-1,3-dithiolane, 4-propenyl-1,3-oxathiolane, 5-propenyl-1,3-oxathiane, 2-propynyltetrahydrofuran, 4-propynyl-1,3-dioxolane, 4,5-dipropynyl-1,3-dioxolane, 5-propynyl-1,3-dioxane, 4-propynyl-1,3-dithiolane, 4,5-dipropynyl-1,3-dithiclane, 5-propynyl-1,3-dithiane, 4-propynyl-1,1,3,3-tetraoxo-1,3-dithiolane, 4-propynyl-1,3-oxathiolane and 5-propynyl-1,3-oxathiane can be mentioned.

"$C_6$-$C_{10}$ aryl group" of "$C_6$-$C_{10}$ aryl group which may be substituted with a group selected from Substituent group β" in the definition of Substituent group γ; and "$C_6$-$C_{10}$ aryl group" in the definitions of Substituent group δ and Substituent group ϵ are, for example, phenyl or naphthyl.

With respect to the "$C_6$-$C_{10}$ aryl group which may be substituted with a group selected from Substituent group β", the "$C_6$-$C_{10}$ aryl group" is substituted with a substituent selected from Substituent group β at a substitutable position, the substituent is not limited to one, and may be the same or different plural (2 to 4) substituents.

"5- or 6-membered heteroaryl group" in the definition of $R^3$ includes 1 to 3 hetero atoms selected from a nitrogen atom, an oxygen atom and a sulfur atom. As for such heteroaryl, for example, furyl, thienyl, pyrrolyl, pyrazolyl, imidazolyl, oxazolyl, isoxazolyl, thiazolyl, isothiazolyl, pyridyl, piridazinyl, pyrimidinyl and pyradinyl can be mentioned, and it is preferably furyl, thienyl, pyrrolyl, pyridyl or pyrimidinyl, more preferably pyrrolyl.

"5-membered heteroaryl group" in the definitions of Substituent group δ and Substituent group ϵ is, for example, 1,2,3-triazolyl, 1,2,4-triazolyl, tetrazolyl, thiazolyl, isothiazolyl, oxazolyl, isoxazolyl, thiadiazolyl, thienyl or furyl.

"Halogeno $C_1$-$C_6$ alkyl group" in the definition of Substituent group δ is, for example, trifluoromethyl or trifluoroethyl.

"Halogeno $C_1$-$C_{14}$ alkyl group" in the definition of Substituent group ϵ is, for example, the aforementioned "halogeno $C_1$-$C_6$ alkyl group", 4,4,4-trifluorobutyl, 5,5,5-trifluoropentyl, 6,6,6-trifluorohexyl, 7,7,7-trifluoroheptyl or 8,8,8-trifluorooctyl, preferably a halogeno $C_4$-$C_8$ alkyl group.

"$C_1$-$C_6$ alkoxy group" in the definitions of Substituent group α, Substituent group β and Substituent group δ represents a group in which an oxygen atom is bound to the aforementioned "$C_1$-$C_6$ alkyl group", for example, methoxy, ethoxy, propoxy, isopropoxy, butoxy, isobutoxy, s-butoxy, t-butoxy, pentoxy, isopentoxy, 2-methylbutoxy, 1-ethylpropoxy, 2-ethylpropoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy, preferably a $C_1$-$C_4$ alkoxy group, and more preferably $C_1$-$C_2$ alkoxy group.

"$C_1$-$C_{14}$ alkoxy group" in the definition of Substituent group ϵ represents a group in which an oxygen atom is bound to the aforementioned "$C_1$-$C_{14}$ alkyl group", for example, the aforementioned "$C_1$-$C_6$ alkoxy group", octyloxy, nonyloxy, decyloxy, dodecyloxy, tetradecyloxy or the like, preferably a $C_1$-$C_{10}$ alkoxy group, and more preferably a $C_4$-$C_8$ alkoxy group.

"Halogeno $C_1$-$C_6$ alkoxy group" in the definitions of Substituent group α and Substituent group δ represents a group in which one or two or more hydrogen atoms of the aforementioned "$C_1$-$C_6$ alkyl group" are substituted with the aforementioned "halogen atom". Preferably, it is a halogeno $C_1$-$C_4$ alkoxy group, more preferably difluoromethoxy, trifluoromethoxy or 2,2,2-trifluoroethoxy, and even more preferably trifluoromethoxy.

"Halogeno $C_1$-$C_{14}$ alkoxy group" in the definition of Substituent group ϵ represents a group in which one or two or more hydrogen atoms of the aforementioned "$C_1$-$C_{14}$ alkyl group" are substituted with the aforementioned "halogen atom". Preferably, it is a halogeno $C_1$-$C_{10}$ alkoxy group, more preferably a halogeno $C_4$-$C_8$ alkoxy group, and even more preferably 4,4,4-trifluorobutoxy, 5,5,5-trifluoropentyloxy, 6,6,6-trifluorohexyloxy, 7,7,7-trifluoroheptyloxy or 8,8,8-trifluorooctyloxy.

"$C_3$-$C_{10}$ cycloalkyloxy group" in the definition of Substituent group γ is, for example, cyclopropyloxy, cyclohexyloxy or the like.

"$C_6$-$C_{10}$ aryloxy group" in the definition of Substituent group γ is, for example, phenoxy or naphthyloxy.

"$C_7$-$C_{19}$ aralkyloxy group" in the definition of Substituent group γ is, for example, benzyloxy, 1-phenylethyloxy, 2-phenylethyloxy, benzhydryloxy or 1-naphthylmethyloxy.

"$C_1$-$C_6$ alkylthio group" in the definitions of Substituent group β and Substituent group δ represents a group in which a sulfur atom is bound to the aforementioned "$C_1$-$C_6$ alkyl group", and the sulfur atom may be oxidized. Preferably, it is a $C_1$-$C_4$ alkylthio group, for example, methylthio, ethylthio, n-propylthio, n-butylthio, methylsulfinyl or methylsulfonyl.

With respect to "$C_1$-$C_{14}$ alkylthio group" in the definition of Substituent group ϵ, the sulfur atom to which the alkyl group is bound may be oxidized, and it is for example, the aforementioned "$C_1$-$C_6$ alkylthio group", n-heptylthio, 3-methylhexylthio, n-octylthio, 2,4-dimethylhexylthio, n-octylthio, or 2,3,6-trimethylheptylthio, preferably a $C_1$-$C_{10}$ alkylthio group, and more preferably a $C_4$-$C_8$ alkylthio group.

With respect to "$C_3$-$C_{10}$ cycloalkylthio group" in the definition of Substituent group γ, the sulfur atom may be oxidized, and it is for example, cyclopropylthio, cyclohexylthio, cyclopentylsulfinyl or cyclohexylsulfonyl.

With respect to "$C_6$-$C_{10}$ arylthio group" in the definition of Substituent group γ, the sulfur atom may be oxidized, and it is for example, phenylthio, naphthylthio, phenylsulfinyl or phenylsulfonyl.

With respect to "$C_7$-$C_{19}$ aralkylthio group" in the definition of Substituent group γ, the sulfur atom may be oxidized, and it is for example, benzylthio, phenylethylthio, benzhydrylthio, benzylsulfinyl or benzylsulfonyl.

"$C_1$-$C_6$ alkanoyl group" in the definitions of $R^6$, $R^7$, Substituent group β and Substituent group δ represents a group in which a hydrogen atom or $C_1$-$C_5$ alkyl group is bound to a carbonyl group, and is for example, formyl, acetyl, propionyl, butyryl, valeryl or pyvaloyl.

"$C_1$-$C_{14}$ alkanoyl group" in the definition of Substituent group ϵ is, for example, the aforementioned "$C_1$-$C_6$ alkanoyl group", octanoyl, decanoyl, dodecanoyl or tetradecanoyl.

"$C_2$-$C_4$ alkenyl-carbonyl group" in the definition of Substituent group β is, for example, acryloyl or crotonoyl.

"$C_2$-$C_6$ alkenyl-carbonyl group" in the definitions of $R^6$ and $R^7$ is, for example, the aforementioned "$C_2$-$C_4$ alkenyl-carbonyl group", 1,3-butadienylcarbonyl or 3-methyl-2-butenylcarbonyl.

"$C_6$-$C_{10}$ aryl-carbonyl group" in the definition of Substituent group γ is, for example, benzoyl, naphthoyl or phenylacetyl.

"$C_1$-$C_6$ alkoxy-carbonyl group" in the definitions of Substituent group α and Substituent group δ represents a group in which the aforementioned "$C_1$-$C_6$ alkoxy group" is bound to a carbonyl group, and is for example, methoxycarbonyl, ethoxycarbonyl, n-propoxycarbonyl, isopropoxycarbonyl, n-butoxycarbonyl, isobutoxycarbonyl, tert-butoxycarbonyl or the like.

"$C_1$-$C_{10}$ alkoxy-carbonyl group" in the definition of Substituent group β is, for example, the aforementioned "$C_1$-$C_6$ alkoxycarbonyl group", heptyloxy, octyloxy, nonyloxy or decyloxy.

"$C_1$-$C_{14}$ alkoxy-carbonyl group" in the definition of Substituent group ϵ is, for example, the aforementioned "$C_1$-$C_{10}$ alkoxy-carbonyl group", dodecyloxycarbonyl or tetradecyloxycarbonyl, preferably a $C_1$-$C_{10}$ alkoxy-carbonyl group, and more preferably a $C_4$-$C_8$ alkoxy-carbonyl group.

"$C_3$-$C_6$ cycloalkyloxycarbonyl group" in the definition of Substituent group γ is, for example, cyclopropyloxycarbonyl, cyclopentyloxycarbonyl, cyclohexyloxycarbonyl or norbornyloxycarbonyl.

"$C_6$-$C_{10}$ aryloxy-carbonyl group" in the definition of Substituent group γ is, for example, phenoxycarbonyl or naphthyloxycarbonyl.

"$C_7$-$C_{19}$ aralkyloxy-carbonyl group" in the definition of Substituent group γ is, for example, benzyloxycarbonyl, benzhydryloxycarbonyl or 2-phenethyloxycarbonyl.

"$C_2$-$C_6$ alkanoyloxy group" in the definition of Substituent group β represents a group in which the $C_2$-$C_6$ alkanoyl group is bound to an oxygen atom, and is for example, acetoxy, propionyloxy, butyryloxy, valeryloxy or pivaloyloxy.

"$C_1$-$C_{10}$ alkoxy-carbonyloxy group" in the definition of Substituent group β is, for example, methoxycarbonyloxy, ethoxycarbonyloxy, n-propoxycarbonyloxy, isopropoxycarbonyloxy, n-butoxycarbonyloxy, tert-butoxycarbonyloxy, n-pentyloxycarbonyloxy or n-hexyloxycarbonyloxy.

"$C_6$-$C_{10}$ aryl-carbonyloxy group" in the definition of Substituent group γ is, for example, benzoyloxy, naphthyloxy or phenylacetoxy.

"Carbamoyl group which may be substituted with a group selected from a $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenyl-carbonyl group" in the definition of Substituent group α is a carbamoyl group or cyclic aminocarbonyl group which may be substituted with 1 or 2 substituents selected from $C_1$-$C_6$ alkyl groups such as methyl, ethyl, propyl and the like, $C_2$-$C_6$ alkenyl groups such as vinyl, allyl, isopropenyl and the like, $C_2$-$C_6$ alkynyl groups such as ethynyl and the like, $C_1$-$C_6$ alkanoyl groups such as acetyl and the like, and $C_2$-$C_6$ alkenyl-carbonyl groups such as acryloyl and the like, preferably, specifically for example, a carbamoyl group or cyclic aminocarbonyl group which may be substituted with 1 or 2 substituents selected from a $C_1$-$C_6$ alkyl group and a $C_1$-$C_6$ alkanoyl group, more preferably a carbamoyl group or cyclic aminocarbonyl group which is substituted with 1 or 2 $C_1$-$C_2$ alkanoyl groups. Specifically, it is carbamoyl, N-methylcarbamoyl, N-ethylcarbamoyl, N,N-dimethylcarbamoyl, N,N-diethylcarbamoyl or N-acetylcarbamoyl, preferably N-acetyl carbamoyl.

"Carbamoyl group which may be substituted with a group selected from a $C_1$-$C_4$ alkyl group, phenyl group, $C_1$-$C_7$ acyl group and $C_1$-$C_4$ alkoxyphenyl group" in the definition of Substituent group β is a carbamoyl group or cyclic aminocarbonyl group which may be substituted with 1 or 2 substituents selected from $C_1$-$C_4$ alkyl groups such as methyl, ethyl and the like, phenyl group, $C_1$-$C_7$ acyl groups such as acetyl, propionyl, benzoyl and the like, and $C_1$-$C_4$ alkoxyphenyl groups such as methoxyphenyl and the like, specifically for example, carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl, N-(p-methoxyphenyl)carbamoyl, 1-pyrrolidinylcarbonyl, piperidinocarbonyl, 1-piperadinylcarbonyl or morpholinocarbonyl.

"Thiocarbamoyl group which may be substituted with a $C_1$-$C_4$ alkyl group or phenyl group" in the definition of Substituent group β is a thiocarbamoyl group which may be substituted with 1 or 2 substituents selected from $C_1$-$C_4$ alkyl groups such as methyl, ethyl and the like, and a phenyl group, specifically for example, thiocarbamoyl, N-methylthiocarbamoyl or N-phenylthiocarbamoyl.

"Carbamoyloxy group which may be substituted with a $C_1$-$C_4$ alkyl group or phenyl group" in the definition of Substituent group β is a carbamoyloxy group which may be substituted with 1 or 2 substituents selected from $C_1$-$C_4$ alkyl groups such as methyl, ethyl and the like, and a phenyl group, specifically for example, carbamoyloxy, N-methyl carbamoyloxy, N,N-dimethyl carbamoyloxy, N-ethylcarbamoyloxy or N-phenyl carbamoyloxy.

With respect to "group having the formula $NR^6R^7$" in the definitions of Substituent group α, Substituent group δ and Substituent group ϵ, $R^6$ and $R^7$, independently from each other, represent a hydrogen atom, $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenyl-carbonyl group, or, together with the nitrogen atom to which $R^6$ and $R^7$ are bound, form a heterocyclyl group. Preferably, it is a group in which $R^6$ and $R^7$ are a hydrogen atom, $C_1$-$C_6$ alkyl group or $C_1$-$C_6$ alkanoyl group, more preferably a group in which $R^6$ and $R^7$ are a hydrogen atom, $C_1$-$C_4$ alkyl group or $C_1$-$C_4$ alkanoyl group, even more preferably a group in which $R^6$ and $R^7$ are a hydrogen atom or $C_1$-$C_2$ alkanoyl group. Specifically it is amino, methylamino, ethylamino, dimethylamino, diethylamino or acetylamino, preferably acetylamino.

"$C_1$-$C_6$ alkanoylamino group" in the definitions of Substituent group β and Substituent group δ is, for example, acetamide, propionamide, butyramide, valeroamide or pivaloamide.

"$C_1$-$C_{14}$ alkanoylamino group" in the definition of Substituent group ϵ is, for example, the aforementioned "$C_1$-$C_6$ alkanoylamino group", octanoylamino, decanoylamino, dodecanoylamino or tetradecanoylamino.

"$C_1$-$C_{10}$ alkoxy-carboxamide group" in the definition of Substituent group β is, for example, methoxycarboxamide, ethoxycarboxamide or tert-butoxycarboxamide.

"Ureido group which may be substituted with a $C_1$-$C_4$ alkyl group or phenyl group" in the definition of Substituent group β is, for example, an ureido group which may be substituted with 1 to 3 (preferably 1 or 2) substituents selected from $C_1$-$C_4$ alkyl groups such as a methyl group, ethyl group and the like, and a phenyl group, and it is for example, ureido, 1-methylureido, 3-methylureido, 3,3-dimethylureido, 1,3-dimethylureido or 3-phenylureido.

"$C_6$-$C_{10}$ aryl-carbonylamino group" in the definition of Substituent group γ is, for example, benzamide, naphthoamide or phthalimide.

"$C_6$-$C_{10}$ aryloxy-carboxamide group" in the definition of Substituent group γ is, for example, phenoxycarboxamide.

"$C_7$-$C_{19}$ aralkyloxy-carboxamide group" in the definition of Substituent group γ is, for example, benzyloxycarboxamide or benzhydryloxycarboxamide.

"$C_3$-$C_{10}$ cycloalkyloxy-carbonyloxy group" in the definition of Substituent group γ is, for example, cyclopropyloxycarbonyloxy or cyclohexyloxycarbonyloxy.

"$C_6$-$C_{10}$ aryloxy-carbonyloxy group" in the definition of Substituent group γ is, for example, phenoxycarbonyloxy or naphthyloxycarbonyloxy.

"$C_7$-$C_{19}$ aralkyloxy-carbonyloxy group" in the definition of Substituent group γ is, for example, benzyloxycarbonyloxy, 1-phenylethyloxycarbonyloxy, 2-phenylethyloxycarbonyloxy or benzhydryloxycarbonyloxy.

"Heterocyclyl group" in the definition of Substituent group γ; and "heterocyclyl group" of "heterocyclyloxy group", "heterocyclylthio group", "heterocyclylsulfinyl group", "heterocyclylsulfonyl group" and "heterocyclyloxycarbonyl group" represent a 5- to 8-membered ring (preferably 5- or 6-membered ring) group or a fused ring group thereof, which contains 1 to several (preferably 1 to 4) hetero atoms such as nitrogen atoms (may be oxidized), oxygen atoms and sulfur atoms. Examples of such "heterocyclyl group" are pyrrolyl, pyrazolyl, imidazolyl, 1,2,3-triazolyl, 1,2,4-triazolyl, tetrazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyridyl, pyridazinyl, pyrimidinyl, pyrazinyl, indolyl, pyranyl, thiopyranyl, dioxynyl, dioxolyl, quinolyl, pyrido[2,3-d]pyrimidyl, 1,5-, 1,6-, 1,7-, 1,8-, 2,6- or 2,7-naphthylidyl group, thieno[2,3-d]pyridyl, benzopyranyl, tetrahydrofuryl, tetrahydropyranyl, dioxolanyl and dioxanyl.

These heterocyclyl groups may be substituted at substitutable positions with 1 to 3 substituents selected from $C_1$-$C_4$ alkyl groups such as methyl, ethyl and the like, a hydroxy group, an oxo group and $C_1$-$C_4$ alkoxy groups such as methoxy, ethoxy and the like.

"$C_1$-$C_6$ alkyl-carbamoyl group" in the definition of Substituent group δ is, for example, methylcarbamoyl, dimethylcarbamoyl or propylcarbamoyl.

"$C_1$-$C_{14}$ alkyl-carbamoyl group" in the definition of Substituent group ϵ is, for example, the aforementioned "$C_1$-$C_6$ alkyl-carbamoyl group", octylcarbamoyl, decylcarbamoyl, dodecylcarbamoyl or tetradecylcarbamoyl, preferably a $C_1$-$C_{10}$ alkyl-carbamoyl group, and more preferably a $C_4$-$C_8$ alkyl-carbamoyl group.

"$C_1$-$C_6$ alkoxy-carbonyl $C_1$-$C_6$ alkyl-carbamoyl group" in the definition of Substituent group δ is, for example, butoxycarbonylmethylcarbamoyl or ethoxycarbonylmethylcarbamoyl.

"$C_1$-$C_{14}$ alkoxy-carbonyl $C_1$-$C_{14}$ alkyl-carbamoyl group" in the definition of Substituent group ϵ is, for example, the aforementioned "$C_1$-$C_6$ alkoxy-carbonyl $C_1$-$C_6$ alkyl-carbamoyl group" or octyloxycarbonylmethylcarbamoyl, preferably a $C_1$-$C_{10}$ alkoxy-carbonyl $C_1$-$C_{10}$ alkyl-carbamoyl group, and more preferably a $C_4$-$C_8$ alkoxy-carbonyl $C_4$-$C_8$ alkyl-carbamoyl group.

"1,3-diacylguanidino $C_1$-$C_6$ alkyl group" in the definition of Substituent group δ is, for example, 1,3-diacetylguanidinomethyl or 1,3-bis-tert-butoxycarbonylguanidinomethyl.

"1,3-diacylguanidino $C_1$-$C_{14}$ alkyl group" in the definition of Substituent group ϵ is, for example, the aforementioned "1,3-diacylguanidino $C_1$-$C_6$ alkyl group", 1,3-diacetylguanidinooctyl or 1,3-bis-tert-butoxycarbonylguanidinooctyl, preferably a 1,3-diacylguanidino $C_1$-$C_{10}$ alkyl group, and more preferably a 1,3-diacylguanidino $C_4$-$C_8$ alkyl group.

X and Y represent a group in which X and Y together with the carbon atom of ring B to which they are bound form ring A, respectively represent a hydrogen atom, or X and Y together represent a substituent of ring B (the substituent is an oxo group or a thioxo group), and preferably represent a group in which X and Y together with the carbon atom of ring B to which they are bound form ring A, or respectively represent a hydrogen atom.

In a preferred example, in the case where X and Y represent a group in which X and Y together with the carbon atom of ring B to which they are bound form ring A, ring A is a 3- to 7-membered heterocyclyl ring or 3- to 7-membered saturated cycloalkyl ring.

With respect to the heterocyclyl ring, X and Y included in the ring, independently from each other, represent any one selected from a carbon atom, a group having the formula NR (R represents a hydrogen atom, a $C_1$-$C_6$ alkyl group which may be substituted with a group selected from Substituent group α, a $C_2$-$C_6$ alkenyl group which may be substituted with a group selected from Substituent group α, a $C_2$-$C_6$ alkynyl group which may be substituted with a group selected from Substituent group α or a $C_1$-$C_6$ alkanoyl group which may be substituted with a group selected from Substituent group α), an oxygen atom, a sulfur atom, a group having the formula SO and a group having the formula $SO_2$, may form a fused ring or spiro ring with a 5- or 6-membered heterocyclyl ring (the heterocyclyl ring includes 1 or 2 oxygen and/or nitrogen atoms as hetero atom) or 5- or 6-membered cycloalkyl ring, either ring of the heterocyclyl ring, or the fused ring which is fused to the heterocyclyl ring or the spiro ring which is spiro bound to the heterocyclyl ring, may be substituted with the same or different 1 to 4 groups selected from the group consisting of an oxo group, a thioxo group, Substituent group α, a cyclopropyl $C_1$-$C_6$ alkyl group and a $C_1$-$C_6$ alkyl group which may be substituted with 1 to 5 groups selected from Substituent group α.

The 3- to 7-membered saturated cycloalkyl ring may be substituted with 1 or 2 groups selected from the group consisting of a hydroxy group, a hydroxymethyl group, a 1,2-dihydroxyethyl group, a 1,2,3-trihydroxypropyl group, a 1,2,3,4-tetrahydroxybutyl group and an acetylamino group.

Ring A is, more preferably, a 3- to 7-membered heterocyclyl ring or 3- to 5-membered cycloalkyl ring.

With respect to the heterocyclyl ring which is a more preferred example of ring A, X and Y included in the ring, independently from each other, represent any one selected from a carbon atom, an oxygen atom, a sulfur atom, a group having the formula SO and a group having the formula $SO_2$, may form a fused ring or spiro ring with a 5- or 6-membered heterocyclyl ring (the heterocyclyl ring includes 1 or 2 oxygen and/or nitrogen atoms as hetero atom) or 5- or 6-membered cycloalkyl ring, and either ring of the heterocyclyl ring, or the fused ring which is fused to the heterocyclyl ring or the spiro ring which is spiro bound to the heterocyclyl ring, may be substituted with the same or different 1 to 4 groups selected from an oxo group, a thioxo group, Substituent group α and a $C_1$-$C_6$ alkyl group which may be substituted with 1 to 4 groups selected from Substituent group α.

The 3- to 5-membered cycloalkyl ring may be substituted with 1 or 2 groups selected from the group consisting of a hydroxymethyl group, a 1,2-dihydroxyethyl group, a 1,2,3-trihydroxypropyl group, a 1,2,3,4-tetrahydroxybutyl group and an acetylamino group.

Ring A is, more preferably, the heterocyclyl ring or the undermentioned cyclopropyl or cyclopentyl ring described below.

Examples of such heterocyclyl ring are, oxirane, tetrahydrofuran, tetrahydropyrane,
1,3-dioxolane, 1,3-dioxane, 1,3-dioxepane,
1,3-dithiolane, 1,3-dithiane,
1,1,3,3-tetraoxo-1,3-dithiolane,
1,3-oxathiolane, 1,3-oxathiane or 1,3-oxathiepane, these heterocyclyl rings may form a fused ring or spiro ring with a 5- or 6-membered heterocyclyl ring (the heterocyclyl ring is tetrahydrofuran, tetrahydropyrane, pyrrolidine, piperidine or 1,3-dioxane) or cyclohexyl ring, either ring of the heterocyclyl ring, or the fused ring which is fused to the heterocyclyl ring or the spiro ring which is spiro bound to the heterocyclyl ring, may be substituted with 1 or 2 groups selected from the group consisting of an oxo group, a thioxo group, Substituent group α (Substituent group α represents a hydroxy group and a group having the formula $NR^6R^7$, and $R^6$ and $R^7$, independently from each other, represent a hydrogen atom or a $C_1$-$C_6$ alkanoyl group), a methyl group, an ethyl group and a $C_1$-$C_6$ alkyl group which is substituted with 1 to 4 hydroxy groups.

In addition, the cyclopropyl or cyclopentyl ring is a cyclopropyl or cyclopentyl ring which may be substituted with 1 or 2 groups selected from the group consisting of a hydroxymethyl group, a 1,2-dihydroxyethyl group, a 1,2,3-trihydroxypropyl group and a 1,2,3,4-tetrahydroxybutyl group.

Ring A is, further preferably for example, oxirane, tetrahydrofuran, 1,3-dioxolane, 1,3-dioxane, 1,3-dithiolane, 1,3-dithiane, 1,3-oxathiolane or 1,3-oxathiane, these heterocyclyl rings may form a fused ring or spiro ring with a 5- or 6-membered heterocyclyl ring (the heterocyclyl ring is tetrahydrofuran, tetrahydropyrane or 1,3-dioxane) or cyclohexyl ring, and either ring of the heterocyclyl ring, or the fused ring which is fused to the heterocyclyl ring or the spiro ring which is spiro bound to the heterocyclyl ring, may be substituted with 1 or 2 groups selected from the group consisting of Substituent group α [Substituent group α represents a hydroxy group and a group having the formula $NR^6R^7$ ($R^6$ and $R^7$, independently from each other, represent a hydrogen atom or acetyl group)], a methyl group, an ethyl group, a hydroxymethyl group, a 1,2-dihydroxyethyl group, a 1,2,3-trihydroxypropyl group and a 1,2,3,4-tetrahydroxybutyl group.

Ring A is, particularly preferably, oxirane, 1,3-dioxolane, 1,3-dioxane or 1,3-oxathiolane, these heterocyclyl rings may form a fused ring or spiro ring with a 5- or 6-membered heterocyclyl ring (the heterocyclyl ring is tetrahydrofuran, tetrahydropyrane or 1,3-dioxane) or cyclohexyl ring, and either ring of the heterocyclyl ring, or the fused ring which is fused to the heterocyclyl ring or the spiro ring which is spiro bound to the heterocyclyl ring may be substituted with 1 or 2 groups selected from the group consisting of Substituent group α [Substituent group α represents a hydroxy group and a group having the formula $NR^6R^7$ ($R^6$ and $R^7$, independently from each other, represent a hydrogen atom or acetyl group)], a methyl group, a hydroxymethyl group, a 1,2-dihydroxyethyl group, a 1,2,3-trihydroxypropyl group and a 1,2,3,4-tetrahydroxybutyl group.

Preferred specific examples of ring A are, cyclopropyl, 1-hydroxymethylcyclopropyl, 1,2-dihydroxymethyl cyclopropyl, cyclopentyl, 2-hydroxymethylcyclopentyl, 2,3-dihydroxymethylcyclopentyl, 2,3-bis(1,2-dihydroxyethyl)cyclopentyl, 2-(1,2-dihydroxyethyl)cyclopentyl, 2-(1,2,3-trihydroxypropyl)cyclopentyl, 2-(1,2,3,4-tetrahydroxybutyl)cyclopentyl, oxirane, tetrahydrofuran, tetrahydropyrane, 1,3-dioxolane, 1,3-dioxane, 1,3-oxathiolane, 4-hydroxymethyl-1,3-dioxolane, 4,5-dihydroxymethyl-1,3-dioxolane, 4,5-bis(1,2-dihydroxyethyl)-1,3-dioxolane, 4-(1,2-dihydroxyethyl)-1,3-dioxolane, 4-(1,2,3-trihydroxypropyl)-1,3-dioxolane, 4-(1,2,3,4-tetrahydroxybutyl)-1,3-dioxolane, 4,5-diacetylaminomethyl-1,3-dioxolane, 5-hydroxy-1,3-dioxane, 5,5-dihydroxymethyl-1,3-dioxane, 5-acetylamino-1,3-dioxane, 5,5-diethoxycarbonyl-1,3-dioxane and 2,4,7,9-tetraoxaspiro[5.5]undecane, more preferred specific examples are, 4-hydroxymethyl-1,3-dioxolane, 4,5-dihydroxymethyl-1,3-dioxolane, 4,5-bis(1,2-dihydroxyethyl)-1,3-dioxolane, 4-(1,2-dihydroxyethyl)-1,3-dioxolane, 4-(1,2,3-trihydroxypropyl)-1,3-dioxolane, 4-(1,2,3,4-tetrahydroxybutyl)-1,3-dioxolane, 4,5-diacetylaminomethyl-1,3-dioxolane, 5-hydroxy-1,3-dioxane, 5-acetylamino-1,3-dioxane and 5,5-dihydroxymethyl-1,3-dioxane.

Ring B is a 5- to 7-membered cycloalkene group. Here, l and m, which are parameters to determine the number of members of ring B, independently from each other, are an integer of 0 to 3, and l+m is 1 to 3. The l+m being 1 to 3 represents that ring B is 5- to 7-membered. Preferably, l is 0, and m is an integer of 1 to 3. More preferably, it is a cyclohexynyl group in which l is 0, and m is 1.

Among the groups defined as $R^1$, preferred is a hydroxy group, halogen atom, $C_1$-$C_6$ alkyl group or $C_1$-$C_6$ alkoxy group, more preferred is a hydroxy group, fluorine atom, chlorine atom, methyl group, ethyl group, propyl group, methoxy group or ethoxy group, further preferred is a fluorine atom or methyl group.

The number of substitutions n, which is the number of $R^1$ that are substituted to ring B, is 0 to 3, preferably 0 or 1. More preferably, n is 0.

Among the groups defined as $R^2$, preferred is a $C_1$-$C_6$ alkyl group which may be substituted with a group selected from Substituent group β, more preferred is a $C_1$-$C_6$ alkyl group, further preferred is a $C_1$-$C_4$ alkyl group, and particularly preferred is an ethyl group.

Among the groups defined as $R^3$, "5- or 6-membered heteroaryl group" of "5- or 6-membered heteroaryl group which may be substituted with a group selected from Substituent group ϵ" is particularly preferably a pyrrolyl group. That is, preferably $R^3$ is a phenyl or pyrrolyl group which may be substituted with a group selected from Substituent group ϵ. Preferably, it is a phenyl or pyrrolyl group which may be substituted with a group selected from a halogen atom, $C_1$-$C_{14}$ alkyl group and halogeno $C_1$-$C_{14}$ alkyl group, more preferably a phenyl or pyrrolyl group which may be substituted with a group selected from a fluorine atom, chlorine atom, $C_1$-$C_{10}$ alkyl group, halogeno $C_1$-$C_{10}$ alkyl group and cyclopropyl $C_1$-$C_{10}$ alkyl group, even more preferably a phenyl or pyrrolyl group which may be substituted with a group selected from a fluorine atom, chlorine atom, bromine atom, $C_3$-$C_8$ alkyl group and halogeno $C_4$-$C_8$ alkyl group, and further preferably a phenyl group which may be substituted with a group selected from a fluorine atom, chlorine atom and $C_3$-$C_8$ alkyl group.

In addition, in the case where it is substituted by a substituent, the position of substitution is preferably the 2-position or 4-position.

$R^3$ is, for example, a phenyl group, halogenophenyl group, $C_1$-$C_{14}$ alkylphenyl group, cyclopropyl $C_1$-$C_{14}$ alkylphenyl group, $C_1$-$C_{14}$ alkoxyphenyl group, $C_1$-$C_{14}$ alkoxycarbonylphenyl group, carboxylphenyl group, nitrophenyl group, cyanophenyl group, halogeno $C_1$-$C_4$ alkylphenyl group, halogeno $C_1$-$C_{14}$ alkoxyphenyl group, $C_1$-$C_{14}$ alkanoylphenyl group, phenyl group which is substituted with a 5-membered heteroaryl group, $C_1$-$C_{14}$ alkoxy-carbonyl-$C_1$-$C_{14}$ alkyl-carbamoylphenyl group, 1,3-diacylguanidino-$C_1$-$C_{14}$ alkylphenyl group, phenyl group which is substituted with a halogen and $C_1$-$C_{14}$ alkyl, phenyl group which is substituted with a halogen and $C_1$-$C_{14}$ alkoxycarbonyl, phenyl group which is substituted with a halogen and cyano, phenyl group which is substituted with a halogen and a 5-membered heteroaryl group, phenyl group which is substituted with a halogen and $C_1$-$C_{14}$ alkoxy-carbonyl-$C_1$-$C_{14}$ alkyl-carbamoyl, pyrrolyl group, halogenopyrrolyl group, $C_1$-$C_{14}$ alkylpyrrolyl group, cyclopropyl $C_1$-$C_{14}$ alkylpyrrolyl group, $C_1$-$C_{14}$ alkoxypyrrolyl group, $C_1$-$C_{14}$ alkoxycarbonylpyrrolyl group, carboxylpyrrolyl group, nitropyrrolyl group, cyanopyrrolyl group, halogeno $C_1$-$C_{14}$ alkylpyrrolyl group, halogeno $C_1$-$C_{14}$ alkoxypyrrolyl group, $C_1$-$C_{14}$ alkanoylpyrrolyl group, pyrrolyl group which is substituted with a 5-membered heteroaryl group, $C_1$-$C_{14}$ alkoxy-carbonyl-$C_1$-$C_{14}$ alkyl-carbamoylpyrrolyl group, 1,3-diacylguanidino-$C_1$-$C_{14}$ alkylpyrrolyl group, pyrrolyl group which is substituted with a halogen and $C_1$-$C_{14}$ alkyl, pyrrolyl group which is substituted with a halogen and $C_1$-$C_{14}$ alkoxycarbonyl, pyrrolyl group which is substituted with a halogen and cyano, pyrrolyl group which is substituted with a halogen and a 5-membered heteroaryl group, pyrrolyl group which is substituted with a halogen and $C_1$-$C_{14}$ alkoxy-carbonyl-$C_1$-$C_{14}$ alkyl-carbamoyl, or the like.

Among them, specific examples are preferably, phenyl, 2-fluorophenyl, 2-chlorophenyl, 2-bromophenyl, 2-iodophenyl, 3-fluorophenyl, 3-chlorophenyl, 4-fluorophenyl, 4-chlorophenyl, 2,3-difluorophenyl, 2,3-dichlorophenyl, 2,4-difluorophenyl, 2,4-dichlorophenyl, 2,5-difluorophenyl, 2,5-dichlorophenyl, 2,6-difluorophenyl, 2,6-dichlorophenyl, 3,4-difluorophenyl, 3,4-dichlorophenyl, 3,5-difluorophenyl, 3,5-dichlorophenyl, 2,4-dibromophenyl, 2,6-dibromophenyl, 4-chloro-2-fluorophenyl, 2-chloro-4-fluorophenyl, 4-bromo-2-fluorophenyl, 2-bromo-4-fluorophenyl, 3-chloro-4-fluorophenyl, 2-bromo-4-chlorophenyl, 5-chloro-2-fluorophenyl, 4-bromo-2-chlorophenyl, 2-chloro-6-fluorophenyl, 2,4-dimethoxyphenyl, 2,3,4-trifluorophenyl, 2,4,5-trifluorophenyl, 2,4,6-trifluorophenyl, 2-chloro-4,6-difluorophenyl, 2,6-dichloro-4-fluorophenyl, 2-bromo-6-chloro-4-fluorophenyl, 2-methylphenyl, 2-ethylphenyl, 2-(n-propyl)phenyl, 2-(n-butyl)phenyl, 2-(n-pentyl)phenyl, 2-(n-hexyl)phenyl, 2-(n-heptyl)phenyl, 2-(n-octyl)phenyl, 2-(n-nonyl)phenyl, 2-(n-decyl)phenyl, 2-(n-undecyl)phenyl, 2-(n-dodecyl)phenyl, 2-(n-tridecyl)phenyl, 2-(n-tetradecyl)phenyl, 2-ethynylphenyl, 2-isopropylphenyl, 2-t-butylphenyl, 2-sec-butylphenyl, 2-methoxyphenyl, 2-ethoxyphenyl, 2-difluoromethoxyphenyl, 2-methylsulfanylphenyl, 2-acetylphenyl, 2-benzylphenyl, 2-(morpholin-4-yl)phenyl, 2-[2-(pyridine-4-yl)ethyl]phenyl, 2-[2-(t-butoxycarbonylamino)ethyl]phenyl, 2-aminophenyl, 2,6-diisopropylphenyl, 2-chloro-4-methylphenyl, 4-fluoro-3-trifluoromethylphenyl, 4-fluoro-3-methoxyphenyl, 4-chloro-2-methoxycarbonylphenyl, 2-fluoro-4-methoxyphenyl, 4-chloro-2-methylphenyl, 2-fluoro-4-methylphenyl, 2-fluoro-5-methylphenyl, 2-chloro-4-methylphenyl, 2-chloro-6-methylphenyl, 4-t-butyl-2-chlorophenyl, 2-bromo-4-isopropylphenyl, 4-chloro-2-methoxy-5-methylphenyl, 4-fluoro-2-methylphenyl, 2-ethyl-4-fluorophenyl, 4-fluoro-2-(n-propyl)phenyl, 2-(n-butyl)-4-fluorophenyl, 4-fluoro-2-(n-pentyl)phenyl, 4-fluoro-2-(n-hexyl)phenyl, 4-fluoro-2-(n-heptyl)phenyl, 4-fluoro-2-(n-octyl)phenyl, 4-fluoro-2-(n-nonyl)phenyl, 2-(n-decyl)-4-fluorophenyl, 4-fluoro-2-(n-undecyl)phenyl, 2-(n-dodecyl)-4-fluorophenyl, 4-fluoro-2-(n-tridecyl)phenyl, 4-fluoro-2-(n-tetradecyl)phenyl, 2-trifluoromethylphenyl, 2-(2,2,2-trifluoroethyl)phenyl, 2-(3,3,3-trifluoropropyl)phenyl, 2-(4,4,4-trifluorobutyl)phenyl, 2-(5,5,5-trifluoropentyl)phenyl, 2-(6,6,6-trifluorohexyl)phenyl, 2-(7,7,7-trifluoroheptyl)phenyl, 2-(8,8,8-trifluorooctyl)phenyl, 2-(9,9,9-trifluorononyl)phenyl, 2-(10,10,10-trifluorodecyl)phenyl, 2-cyclopropylethylphenyl, 2-[3-cyclopropyl-(n-propyl)]phenyl, 2-[4-cyclopropyl-(n-butyl)]phenyl, 2-[5-cyclopropyl-(n-pentyl)]phenyl, 2-[6-cyclopropyl-(n-hexyl)]phenyl, 2-[7-cyclopropyl-(n-heptyl)]phenyl, 2-[8-cyclopropyl-(n-octyl)]phenyl, pyrrolyl, 2-fluoropyrrolyl, 2-chloropyrrolyl, 2-bromopyrrolyl, 2,5-difluoropyrrolyl, 2,5-dichloropyrrolyl, 2,5-dibromopyrrolyl, 2-chloro-5-fluoropyrrolyl, 2-methylpyrrolyl, 2-ethylpyrrolyl, 2-(n-propyl)pyrrolyl, 2-(n-butyl)pyrrolyl, 2-(n-pentyl)pyrrolyl, 2-(n-hexyl)pyrrolyl, 2-(n-heptyl)pyrrolyl, 2-(n-octyl)pyrrolyl, 2-(n-nonyl)pyrrolyl and 2-(n-decyl)pyrrolyl, more preferably, 2-fluorophenyl, 2-chlorophenyl, 2-bromophenyl, 2-iodo phenyl, 4-fluorophenyl, 2,4-difluorophenyl, 2,4-dichlorophenyl, 2-chloro-4-fluorophenyl, 2-bromo-4-fluorophenyl, 3-chloro-4-fluorophenyl, 2-bromo-4-chlorophenyl, 2,4-dimethoxyphenyl, 2-chloro-4,6-difluorophenyl, 2,6-dichloro-4-fluorophenyl, 2-bromo-6-chloro-4-fluorophenyl, 2-methylphenyl, 2-ethylphenyl, 2-(n-propyl)phenyl, 2-(n-butyl)phenyl, 2-(n-pentyl)phenyl, 2-(n-hexyl)phenyl, 2-(n-heptyl)phenyl, 2-(n-octyl)phenyl, 2-(n-nonyl)phenyl, 2-(n-decyl)phenyl, 2-ethynylphenyl, 2-sec-butylphenyl, 2-methoxyphenyl, 2-methylsulfanylphenyl, 2-benzylphenyl, 2-[2-(t-butoxycarbonylamino)ethyl]phenyl, 4-chloro-2-methylphenyl, 2-fluoro-5-methylphenyl, 2-chloro-4-methylphenyl, 2-chloro-6-methylphenyl, 4-chloro-2-methoxy-5-methylphenyl, 4-fluoro-2-methylphenyl, 2-ethyl-4-fluorophenyl, 4-fluoro-2-(n-propyl)phenyl, 2-(n-butyl)-4-fluorophenyl, 4-fluoro-2-(n-pentyl)phenyl, 4-fluoro-2-(n-hexyl)phenyl, 4-fluoro-2-(n-heptyl)phenyl, 4-fluoro-2-(n-octyl)phenyl, 4-fluoro-2-(n-nonyl)phenyl, 2-(n-decyl)-4-fluorophenyl, 2-(n-butyl)pyrrolyl, 2-(n-pentyl)pyrrolyl, 2-(n-hexyl)pyrrolyl, 2-(n-heptyl)pyrrolyl and 2-(n-octyl)pyrrolyl, and even more preferably, 2-chlorophenyl, 2-bromophenyl, 2,4-difluorophenyl, 2-chloro-4-fluorophenyl, 2-bromo-4-fluorophenyl, 2-(n-pentyl)phenyl, 2-(n-hexyl)phenyl, 2-(n-heptyl)phenyl, 2-chloro-6-methylphenyl, 4-fluoro-2-(n-propyl)phenyl, 2-(n-butyl)-4-fluorophenyl, 4-fluoro-2-(n-pentyl)phenyl, 4-fluoro-2-(n-hexyl)phenyl, 4-fluoro-2-(n-heptyl)phenyl and 4-fluoro-2-(n-octyl)phenyl.

With respect to the "pharmacologically acceptable salts thereof", since the compound having the general formula (I) of the present invention can be converted to a salt by reaction with an acid in the case where it has a basic group such as an amino group, or by reaction with a base in the case where it has an acidic group such as a carboxyl group, salts thereof are represented.

Salts of a basic group are preferably inorganic acid salts such as hydrohalogenic acid salts including hydrochloride, hydrobromide and hydroiodide, nitrates, perchlorates, sulfates, phosphates or the like; lower alkanesulfonic acid salts such as methanesulfonate, trifluoromethanesulfonate and ethanesulfonate, arylsulfonic acid salts such as benzene sulfonate and p-toluenesulfonate, organic acid salts such as acetate, malates, fumarates, succinates, citrates, ascorbates, tartrates, oxalates, maleates or the like; and amino acid salts such as glycine salt, lysine salt, arginine salt, ornithine salt, glutamate and aspartate, On the other hand, salts of an acidic group are preferably alkali metal salts such as sodium salt, potassium salt and lithium salt, alkaline earth metal salts such as calcium salt and magnesium salt, metal salts such as aluminum salt and iron salt; inorganic salts such as ammonium salt, amine salts including organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt and tris(hydroxymethyl)aminomethane salt; and amino acid salts such as glycine salt, lysine salt, arginine salt, ornithine salt, glutamate and aspartate.

The compounds having the general formula (I) according to the present invention or pharmacologically acceptable salts thereof have an asymmetric carbon atom in their molecules, and thus stereoisomers of R configuration and S configuration exist. Each of them, or a compound with an arbitrary ratio of these, is also included in the present invention. With respect to such stereoisomers, the compound (I) can be synthesized by using an optically resolved starting compound, or a synthesized compound (I) can be optically resolved by ordinary optical resolution or separation methods if desired.

There exist optical isomers with respect to the compound having the general formula (I) according to the present invention or pharmacologically acceptable salts thereof, and each of the optical isomers and mixtures of such isomers are also included in the present invention.

When the compound having the general formula (I) and pharmacologically acceptable salts thereof are exposed to the atmosphere or are recrystallized, they may absorb moisture, resulting in cases such as the adhesion of adsorbed water and the generation of hydrates. Such hydrated compounds and salts are also included in the present invention.

As representative compounds of the present invention, the compounds listed in the following Tables 1 to 3 can be mentioned for example, but the present invention is not limited to these compounds.

Abbreviations and "ring 1" to "ring 21" in the tables are as follows.

Ac: acetyl
Boc: butoxycarbonyl
Bn: benzyl
nBu: n-butyl
sBu: sec-butyl
tBu: tert-butyl
cBu: cyclobutylidene
ndec: n-decane
Flu: fluoren-1-yl
cPent: cyclopentylidene
cPr: cyclopropylidene
cPrl: cyclopropyl
cHept: cycloheptylidene
cHex: cyclohexylidene
dioxa: 1,3-dioxan-2-ylidene
dioxe: 1,3-dioxepan-2-ylidene
dioxo: 1,3-dioxolan-2-ylidene
dithia: 1,3-dithian-2-ylidene
dithio: 1,3-dithiolan-2-ylidene
Et: ethyl
HB: 1,2,3,4-tetrahydroxybutyl
HE: 1,2-dihydroxyethyl
nHept: n-heptyl
nHex: n-hexyl
HM: hydroxymethyl
HP: 1,2,3-trihydroxypropyl
Me: methyl
Mor: morpholino
nNon: n-nonane
O=: oxo
nOct: n-octyl
nPent: n-pentyl
Ph: phenyl
NPr: n-propyl
Pyr: pyrrolyl
Pyrd: pyridyl
S=: thioxo
oxa: 2-oxanylidene
oxathia: 1,3-oxathian-2-ylidene
oxathio: 1,3-oxathiolan-2-ylidene
oxe: 2-oxetanylidene
oxi: 2-oxiranylidene
oxo: 2-oxolanylidene
ozl: tetrahydrooxazol-2-ylidene
ozn: tetrahydro-1,3-oxadin-2-ylidene
tzl: tetrahydrothiazol-2-ylidene
tzn: tetrahydro-1,3-thiazin-2-ylidene In the Tables, "di" indicates that there are two identical substituents, and "tri" indicates that there are three identical substituents.

ring 1:
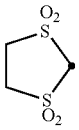
ring 2:
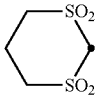
ring 3:
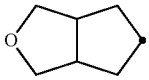
ring 4:
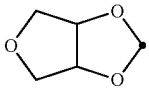
ring 5:
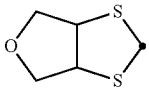
ring 6:
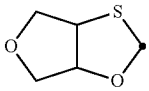
ring 7:
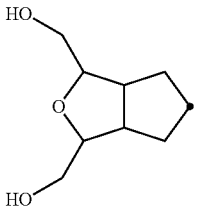
ring 8:
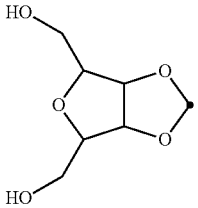
ring 9:
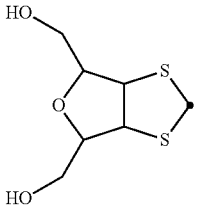
ring 10:
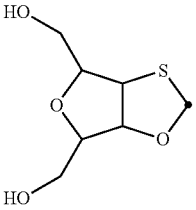
-continued
ring 11:
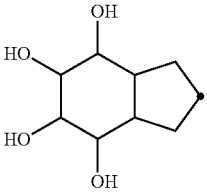
ring 12:
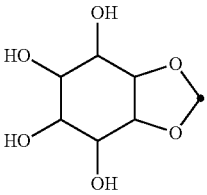
ring 13:
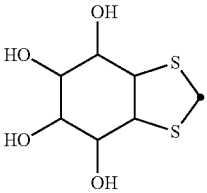
ring 14:
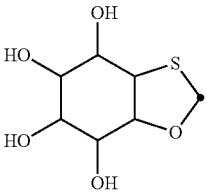
ring 15:
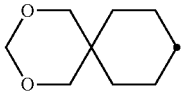
ring 16:
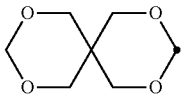
ring 17:
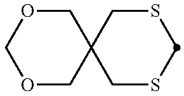
ring 18:
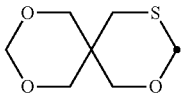
ring 19:
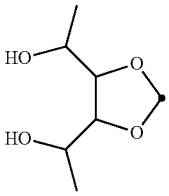

-continued ring 20:

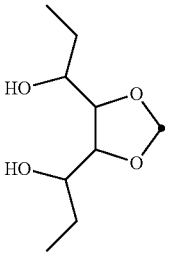

ring 21:

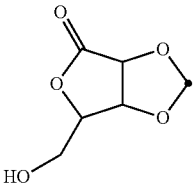

The binding position of rings 1 to 21 with ring B is the position indicated by a black dot, which is located at the right end of the aforementioned chemical structure.

The substituents represented by the abbreviations as X and Y in Table 1, are shown below.

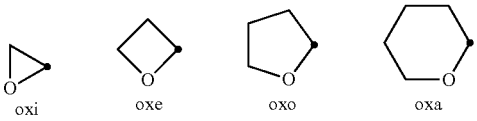

oxi oxe oxo oxa

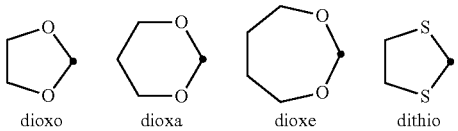

dioxo dioxa dioxe dithio

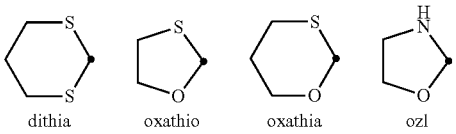

dithia oxathio oxathia ozl

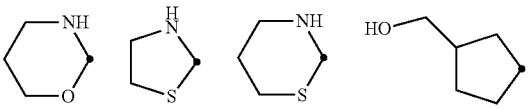

ozn tzl tzn 3-HM-cPent

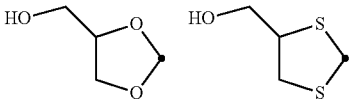

4-HM-dioxo 4-HM-dithio

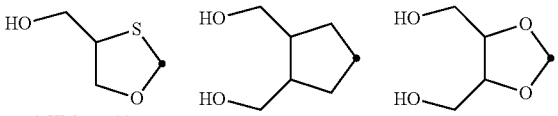

4-HM-oxathio 3,4-diHM-cPent 4,5-diHM-dioxo

-continued

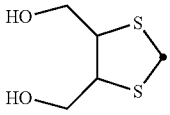

4,5-diHM-dithio

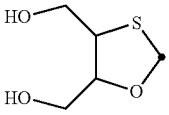

4,5-diHM-oxathio

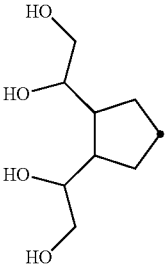

3,4-diHE-cPent

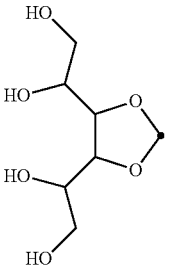

3,4-diHE-dioxo

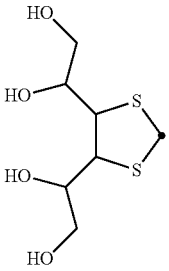

4,5-diHE-dithio

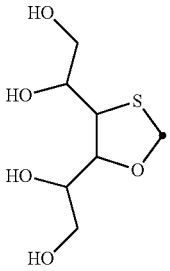

4,5-diHE-oxathio

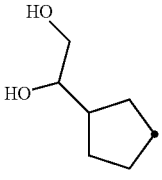

3-HE-cPent

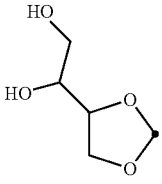

4-HE-dioxo

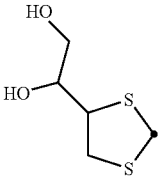

4-HE-dithio

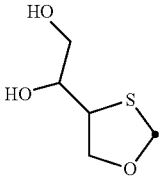

4-HE-oxathio

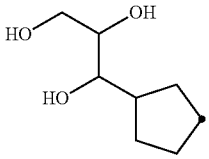

3-HP-cPent

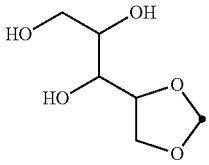

4-HP-dioxo

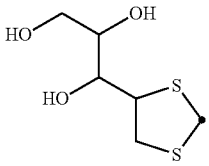

4-HP-dithio

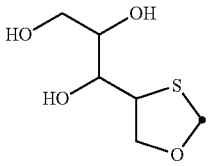

4-HP-oxathio

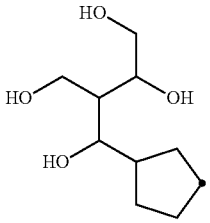

4-HB-cPent

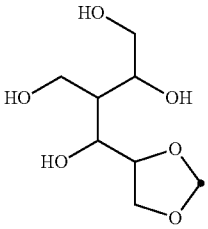

4-HB-dioxo

-continued

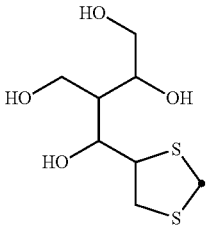

4-HB-dioxo

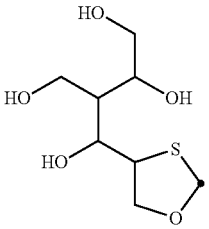

4-HB-oxathio

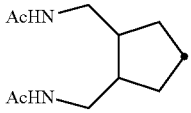

3,4-di$CH_2$NHAc-cPent

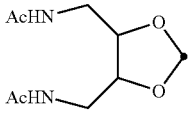

4,5-di$CH_2$NHAc-dioxo

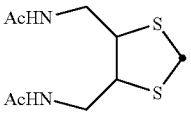

4,5-di$CH_2$NHAc-dithio

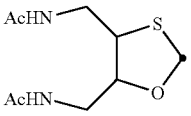

4,5-di$CH_2$NHAc-oxathio

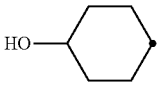

4-OH-cHex

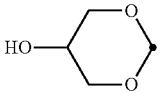

5-OH-dioxa

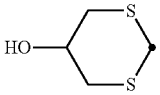

5-OH-dithia

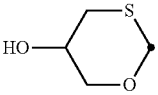

5-OH-oxathia

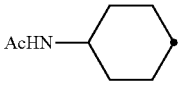

4-NHAc-cHex

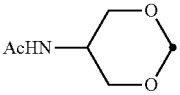

5-NHAc-dioxa

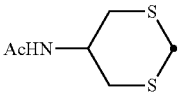

5-NHAc-dithia

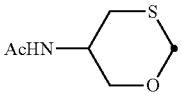

5-NHAc-oxathia

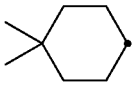

4,4-diMe-cHex

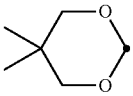

5,5-diMe-dioxa

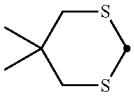

5,5-diMe-dithia

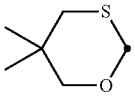

5,5-diMe-oxathia

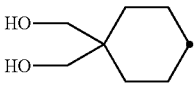

4,4-diHM-cHex

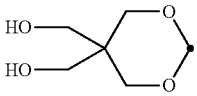

5,5-diHM-dioxa

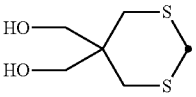

4,4-diHM-dithia

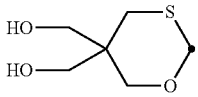

5,5-diHM-oxathia

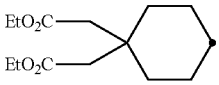

4,4-di$CO_2$Et-cHex

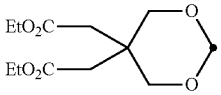

5,5-di$CO_2$Et-dioxa

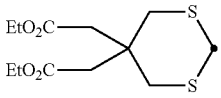

5,5-di$CO_2$Et-dithia

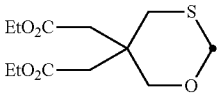

5,5-di$CO_2$Et-oxathia

TABLE 1

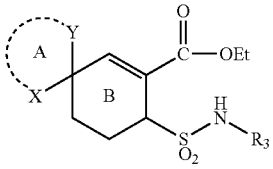

| Compound No. | X, Y | $R^3$ |
|---|---|---|
| 1-1 | O═ | Ph |
| 1-2 | S═ | Ph |
| 1-3 | cPr | Ph |
| 1-4 | cBu | Ph |
| 1-5 | cPent | Ph |
| 1-6 | cHex | Ph |
| 1-7 | cHept | Ph |
| 1-8 | oxi | Ph |
| 1-9 | oxe | Ph |
| 1-10 | oxo | Ph |
| 1-11 | oxa | Ph |
| 1-12 | dioxo | Ph |
| 1-13 | dioxa | Ph |
| 1-14 | dioxe | Ph |
| 1-15 | dithio | Ph |
| 1-16 | dithia | Ph |
| 1-17 | ring 1 | Ph |
| 1-18 | ring 2 | Ph |
| 1-19 | oxathio | Ph |
| 1-20 | oxathia | Ph |
| 1-21 | ozl | Ph |
| 1-22 | ozn | Ph |
| 1-23 | tzl | Ph |
| 1-24 | tzn | Ph |
| 1-25 | 3-HM-cPent | Ph |
| 1-26 | 4-HM-dioxo | Ph |
| 1-27 | 4-HM-dithio | Ph |
| 1-28 | 4-HM-oxathio | Ph |
| 1-29 | 3,4-diHM-cPent | Ph |
| 1-30 | 4,5-diHM-dioxo | Ph |
| 1-31 | 4,5-diHM-dithio | Ph |
| 1-32 | 4,5-diHM-oxathio | Ph |
| 1-33 | 3,4-diHE-cPent | Ph |
| 1-34 | 4,5-diHE-dioxo | Ph |
| 1-35 | 4,5-diHE-dithio | Ph |
| 1-36 | 4,5-diHE-oxathio | Ph |
| 1-37 | 3-HE-cPent | Ph |
| 1-38 | 4-HE-dioxo | Ph |
| 1-39 | 4-HE-dithio | Ph |
| 1-40 | 4-HE-oxathio | Ph |
| 1-41 | 3-HP-cPent | Ph |
| 1-42 | 4-HP-dioxo | Ph |
| 1-43 | 4-HP-dithio | Ph |
| 1-44 | 4-HP-oxathio | Ph |
| 1-45 | 3-HB-cPent | Ph |
| 1-46 | 4-HB-dioxo | Ph |
| 1-47 | 4-HB-dithio | Ph |
| 1-48 | 4-HB-oxathio | Ph |
| 1-49 | ring 3 | Ph |
| 1-50 | ring 4 | Ph |
| 1-51 | ring 5 | Ph |
| 1-52 | ring 6 | Ph |
| 1-53 | ring 7 | Ph |
| 1-54 | ring 8 | Ph |
| 1-55 | ring 9 | Ph |
| 1-56 | ring 10 | Ph |
| 1-57 | 3,4-di$CH_2$NHAc-cPent | Ph |
| 1-58 | 4,5-di$CH_2$NHAc-dioxo | Ph |
| 1-59 | 4,5-di$CH_2$NHAc-dithio | Ph |
| 1-60 | 4,5-di$CH_2$NHAc-oxathio | Ph |
| 1-61 | ring 11 | Ph |
| 1-62 | ring 12 | Ph |
| 1-63 | ring 13 | Ph |
| 1-64 | ring 14 | Ph |
| 1-65 | 4-OH-cHex | Ph |
| 1-66 | 5-OH-dioxa | Ph |
| 1-67 | 5-OH-dithia | Ph |
| 1-68 | 5-OH-oxathia | Ph |

TABLE 1-continued

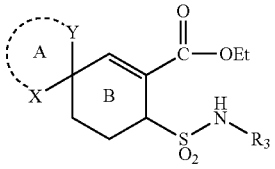

| Compound No. | X, Y | $R^3$ |
|---|---|---|
| 1-69 | 4-NHAc-cHex | Ph |
| 1-70 | 5-NHAc-dioxa | Ph |
| 1-71 | 5-NHAc-dithia | Ph |
| 1-72 | 5-NHAc-oxathia | Ph |
| 1-73 | 4,4-diMe-cHex | Ph |
| 1-74 | 5,5-diMe-dioxa | Ph |
| 1-75 | 5,5-diMe-dithia | Ph |
| 1-76 | 5,5-diMe-oxathia | Ph |
| 1-77 | 4,4-diHM-cHex | Ph |
| 1-78 | 5,5-diHM-dioxa | Ph |
| 1-79 | 5,5-diHM-dithia | Ph |
| 1-80 | 5,5-diHM-oxathia | Ph |
| 1-81 | ring 15 | Ph |
| 1-82 | ring 16 | Ph |
| 1-83 | ring 17 | Ph |
| 1-84 | ring 18 | Ph |
| 1-85 | 4,4-di$CO_2$Et-cHex | Ph |
| 1-86 | 5,5-di$CO_2$Et-dioxa | Ph |
| 1-87 | 5,5-di$CO_2$Et-dithia | Ph |
| 1-88 | 5,5-di$CO_2$Et-oxathia | h |
| 1-89 | O= | 4-F—Ph |
| 1-90 | S= | 4-F—Ph |
| 1-91 | cPr | 4-F—Ph |
| 1-92 | cBu | 4-F—Ph |
| 1-93 | cPent | 4-F—Ph |
| 1-94 | cHex | 4-F—Ph |
| 1-95 | cHept | 4-F—Ph |
| 1-96 | oxi | 4-F—Ph |
| 1-97 | oxe | 4-F—Ph |
| 1-98 | oxo | 4-F—Ph |
| 1-99 | oxa | 4-F—Ph |
| 1-100 | dioxo | 4-F—Ph |
| 1-101 | dioxa | 4-F—Ph |
| 1-102 | dioxe | 4-F—Ph |
| 1-103 | dithio | 4-F—Ph |
| 1-104 | dithia | 4-F—Ph |
| 1-105 | ring 1 | 4-F—Ph |
| 1-106 | ring 2 | 4-F—Ph |
| 1-107 | oxathio | 4-F—Ph |
| 1-108 | oxathia | 4-F—Ph |
| 1-109 | ozl | 4-F—Ph |
| 1-110 | ozn | 4-F—Ph |
| 1-111 | tzl | 4-F—Ph |
| 1-112 | tzn | 4-F—Ph |
| 1-113 | 3-HM-cPent | 4-F—Ph |
| 1-114 | 4-HM-dioxo | 4-F—Ph |
| 1-115 | 4-HM-dithio | 4-F—Ph |
| 1-116 | 4-HM-oxathio | 4-F—Ph |
| 1-117 | 3,4-diHM-cPent | 4-F—Ph |
| 1-118 | 4,5-diHM-dioxo | 4-F—Ph |
| 1-119 | 4,5-diHM-dithio | 4-F—Ph |
| 1-120 | 4,5-diHM-oxathio | 4-F—Ph |
| 1-121 | 3,4-diHE-cPent | 4-F—Ph |
| 1-122 | 4,5-diHE-diaxo | 4-F—Ph |
| 1-123 | 4,5-diHE-dithio | 4-F—Ph |
| 1-124 | 4,5-diHE-oxathio | 4-F—Ph |
| 1-125 | 3-HE-cPent | 4-F—Ph |
| 1-126 | 4-HE-dioxo | 4-F—Ph |
| 1-127 | 4-HE-dithio | 4-F—Ph |
| 1-128 | 4-HE-oxathio | 4-F—Ph |
| 1-129 | 3-HP-cPent | 4-F—Ph |
| 1-130 | 4-HP-dioxo | 4-F—Ph |
| 1-131 | 4-HP-dithio | 4-F—Ph |
| 1-132 | 4-HP-oxathio | 4-F—Ph |
| 1-133 | 3-HB-cPent | 4-F—Ph |
| 1-134 | 4-HB-dioxo | 4-F—Ph |
| 1-135 | 4-HB-dithio | 4-F—Ph |
| 1-136 | 4-HB-oxathio | 4-F—Ph |

TABLE 1-continued

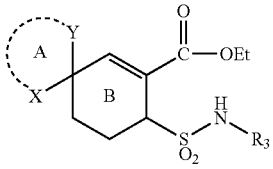

| Compound No. | X, Y | $R^3$ |
|---|---|---|
| 1-137 | ring 3 | 4-F—Ph |
| 1-138 | ring 4 | 4-F—Ph |
| 1-139 | ring 5 | 4-F—Ph |
| 1-140 | ring 6 | 4-F—Ph |
| 1-141 | ring 7 | 4-F—Ph |
| 1-142 | ring 8 | 4-F—Ph |
| 1-143 | ring 9 | 4-F—Ph |
| 1-144 | ring 10 | 4-F—Ph |
| 1-145 | 3,4-di$CH_2$NHAc-cPent | 4-F—Ph |
| 1-146 | 4,5-di$CH_2$NHAc-dioxo | 4-F—Ph |
| 1-147 | 4,5-di$CH_2$NHAc-dithio | 4-F—Ph |
| 1-148 | 4,5-di$CH_2$NHAc-oxathio | 4-F—Ph |
| 1-149 | ring 11 | 4-F—Ph |
| 1-150 | ring 12 | 4-F—Ph |
| 1-151 | ring 13 | 4-F—Ph |
| 1-152 | ring 14 | 4-F—Ph |
| 1-153 | 4-OH-cHex | 4-F—Ph |
| 1-154 | 5-OH-dioxa | 4-F—Ph |
| 1-155 | 5-OH-dithia | 4-F—Ph |
| 1-156 | 5-OH-oxathia | 4-F—Ph |
| 1-157 | 4-NHAc-cHex | 4-F—Ph |
| 1-158 | 5-NHAc-dioxa | 4-F—Ph |
| 1-159 | 5-NHAc-dithia | 4-F—Ph |
| 1-160 | 5-NHAc-oxathia | 4-F—Ph |
| 1-161 | 4,4-diMe-cHex | 4-F—Ph |
| 1-162 | 5,5-diMe-dioxa | 4-F—Ph |
| 1-163 | 5,5-diMe-dithia | 4-F—Ph |
| 1-164 | 5,5-diMe-oxathia | 4-F—Ph |
| 1-165 | 4,4-diHM-cHex | 4-F—Ph |
| 1-166 | 5,5-diHM-dioxa | 4-F—Ph |
| 1-167 | 5,5-diHM-dithia | 4-F—Ph |
| 1-168 | 5,5-diHM-oxathia | 4-F—Ph |
| 1-169 | ring 15 | 4-F—Ph |
| 1-170 | ring 16 | 4-F—Ph |
| 1-171 | ring 17 | 4-F—Ph |
| 1-172 | ring 18 | 4-F—Ph |
| 1-173 | 4,4-di$CO_2$Et-cHex | 4-F—Ph |
| 1-174 | 5,5-di$CO_2$Et-dioxa | 4-F—Ph |
| 1-175 | 5,5-di$CO_2$Et-dithia | 4-F—Ph |
| 1-176 | 5,5-di$CO_2$Et-oxathia | 4-F—Ph |
| 1-177 | O= | 2-Cl—Ph |
| 1-178 | S= | 2-Cl—Ph |
| 1-179 | cPr | 2-Cl—Ph |
| 1-180 | cBn | 2-Cl—Ph |
| 1-181 | cPent | 2-Cl—Ph |
| 1-182 | cHex | 2-Cl—Ph |
| 1-183 | cHept | 2-Cl—Ph |
| 1-184 | oxi | 2-Cl—Ph |
| 1-185 | oxe | 2-Cl—Ph |
| 1-186 | oxo | 2-Cl—Ph |
| 1-187 | oxa | 2-Cl—Ph |
| 1-188 | dioxo | 2-Cl—Ph |
| 1-189 | dioxa | 2-Cl—Ph |
| 1-190 | dioxe | 2-Cl—Ph |
| 1-191 | dithio | 2-Cl—Ph |
| 1-192 | dithia | 2-Cl—Ph |
| 1-193 | ring 1 | 2-Cl—Ph |
| 1-194 | ring 2 | 2-Cl—Ph |
| 1-195 | oxathio | 2-Cl—Ph |
| 1-196 | oxathia | 2-Cl—Ph |
| 1-197 | ozl | 2-Cl—Ph |
| 1-198 | ozn | 2-Cl—Ph |
| 1-199 | tzl | 2-Cl—Ph |
| 1-200 | tzn | 2-Cl—Ph |
| 1-201 | 3-HM-cPent | 2-Cl—Ph |
| 1-202 | 4-HM-dioxo | 2-Cl—Ph |
| 1-203 | 4-HM-dithio | 2-Cl—Ph |
| 1-204 | 4-HM-oxathio | 2-Cl—Ph |

TABLE 1-continued

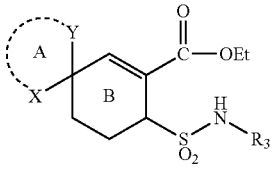

| Compound No. | X, Y | $R^3$ |
|---|---|---|
| 1-205 | 3,4-diHM-cPent | 2-Cl—Ph |
| 1-206 | 4,5-diHM-dioxo | 2-Cl—Ph |
| 1-207 | 4,5-diHM-dithio | 2-Cl—Ph |
| 1-208 | 4,5-diHM-oxathio | 2-Cl—Ph |
| 1-209 | 3,4-diHE-cPent | 2-Cl—Ph |
| 1-210 | 4,5-diHE-dioxo | 2-Cl—Ph |
| 1-211 | 4,5-diHE-dithio | 2-Cl—Ph |
| 1-212 | 4,5-diHE-oxathio | 2-Cl—Ph |
| 1-213 | 3-HE-cPent | 2-Cl—Ph |
| 1-214 | 4-HE-dioxo | 2-Cl—Ph |
| 1-215 | 4-HE-dithio | 2-Cl—Ph |
| 1-216 | 4-HE-oxathio | 2-Cl—Ph |
| 1-217 | 3-HP-cPent | 2-Cl—Ph |
| 1-218 | 4-HP-dioxo | 2-Cl—Ph |
| 1-219 | 4-HP-dithio | 2-Cl—Ph |
| 1-220 | 4-HP-oxathio | 2-Cl—Ph |
| 1-221 | 3-HB-cPent | 2-Cl—Ph |
| 1-222 | 4-HB-dioxo | 2-Cl—Ph |
| 1-223 | 4-HB-dithio | 2-Cl—Ph |
| 1-224 | 4-HB-oxathio | 2-Cl—Ph |
| 1-225 | ring 3 | 2-Cl—Ph |
| 1-226 | ring 4 | 2-Cl—Ph |
| 1-227 | ring 5 | 2-Cl—Ph |
| 1-228 | ring 6 | 2-Cl—Ph |
| 1-229 | ring 7 | 2-Cl—Ph |
| 1-230 | ring 8 | 2-Cl—Ph |
| 1-231 | ring 9 | 2-Cl—Ph |
| 1-232 | ring 10 | 2-Cl—Ph |
| 1-233 | 3,4-di$CH_2$NHAc-cPent | 2-Cl—Ph |
| 1-234 | 4,5-di$CH_2$NHAc-dioxo | 2-Cl—Ph |
| 1-235 | 4,5-di$CH_2$NHAc-dithio | 2-Cl—Ph |
| 1-236 | 4,5-di$CH_2$NHAc-oxathio | 2-Cl—Ph |
| 1-237 | ring 11 | 2-Cl—Ph |
| 1-238 | ring 12 | 2-Cl—Ph |
| 1-239 | ring 13 | 2-Cl—Ph |
| 1-240 | ring 14 | 2-Cl—Ph |
| 1-241 | 4-OH-cHex | 2-Cl—Ph |
| 1-242 | 5-OH-dioxa | 2-Cl—Ph |
| 1-243 | 5-OH-dithia | 2-Cl—Ph |
| 1-244 | 5-OH-oxathia | 2-Cl—Ph |
| 1-245 | 4-NHAc-cHex | 2-Cl—Ph |
| 1-246 | 5-NHAc-dioxa | 2-Cl—Ph |
| 1-247 | 5-NHAc-dithia | 2-Cl—Ph |
| 1-248 | 5-NHAc-oxathia | 2-Cl—Ph |
| 1-249 | 4,4-diMe-cHex | 2-Cl—Ph |
| 1-250 | 5,5-diMe-dioxa | 2-Cl—Ph |
| 1-251 | 5,5-diMe-dithia | 2-Cl—Ph |
| 1-252 | 5,5-diMe-oxathia | 2-Cl—Ph |
| 1-253 | 4,4-diHM-cHex | 2-Cl—Ph |
| 1-254 | 5,5-diHM-dioxa | 2-Cl—Ph |
| 1-255 | 5,5-diHM-dithia | 2-Cl—Ph |
| 1-256 | 5,5-diHM-oxathia | 2-Cl—Ph |
| 1-257 | ring 15 | 2-Cl—Ph |
| 1-258 | ring 16 | 2-Cl—Ph |
| 1-259 | ring 17 | 2-Cl—Ph |
| 1-260 | ring 18 | 2-Cl—Ph |
| 1-261 | 4,4-di$CO_2$Et-cHex | 2-Cl—Ph |
| 1-262 | 5,5-di$CO_2$Et-dioxa | 2-Cl—Ph |
| 1-263 | 5,5-di$CO_2$Et-dithia | 2-Cl—Ph |
| 1-264 | 5,5-di$CO_2$Et-oxathia | 2-Cl—Ph |
| 1-265 | O= | 2,4-diF—Ph |
| 1-266 | S= | 2,4-diF—Ph |
| 1-267 | cPr | 2,4-diF—Ph |
| 1-268 | cBu | 2,4-diF—Ph |
| 1-269 | cPent | 2,4-diF—Ph |
| 1-270 | cHex | 2,4-diF—Ph |
| 1-271 | cHept | 2,4-diF—Ph |
| 1-272 | oxi | 2,4-diF—Ph |

TABLE 1-continued

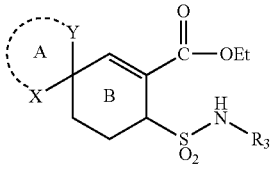

| Compound No. | X, Y | $R^3$ |
|---|---|---|
| 1-273 | oxe | 2,4-diF—Ph |
| 1-274 | oxo | 2,4-diF—Ph |
| 1-275 | oxa | 2,4-diF—Ph |
| 1-276 | dioxo | 2,4-diF—Ph |
| 1-277 | dioxa | 2,4-diF—Ph |
| 1-278 | dioxe | 2,4-diF—Ph |
| 1-279 | dithio | 2,4-diF—Ph |
| 1-280 | dithia | 2,4-diF—Ph |
| 1-281 | ring 1 | 2,4-diF—Ph |
| 1-282 | ring 2 | 2,4-diF—Ph |
| 1-283 | oxathio | 2,4-diF—Ph |
| 1-284 | oxathia | 2,4-diF—Ph |
| 1-285 | ozl | 2,4-diF—Ph |
| 1-286 | ozn | 2,4-diF—Ph |
| 1-287 | tzl | 2,4-diF—Ph |
| 1-288 | tzn | 2,4-diF—Ph |
| 1-289 | 3-HM-cPent | 2,4-diF—Ph |
| 1-290 | 4-HM-dioxo | 2,4-diF—Ph |
| 1-291 | 4-HM-dithio | 2,4-diF—Ph |
| 1-292 | 4-HM-oxathio | 2,4-diF—Ph |
| 1-293 | 3,4-diHM-cPent | 2,4-diF—Ph |
| 1-294 | 4,5-diHM-dioxo | 2,4-diF—Ph |
| 1-295 | 4,5-diHM-dithio | 2,4-diF—Ph |
| 1-296 | 4,5-diHM-oxathio | 2,4-diF—Ph |
| 1-297 | 3,4-diHE-cPent | 2,4-diF—Ph |
| 1-298 | 4,5-diHE-dioxo | 2,4-diF—Ph |
| 1-299 | 4,5-diHE-dithio | 2,4-diF—Ph |
| 1-300 | 4,5-diHE-oxathio | 2,4-diF—Ph |
| 1-301 | 3-HE-cPent | 2,4-diF—Ph |
| 1-302 | 4-HE-dioxo | 2,4-diF—Ph |
| 1-303 | 4-HE-dithio | 2,4-diF—Ph |
| 1-304 | 4-HE-oxathio | 2,4-diF—Ph |
| 1-305 | 3-HP-cPent | 2,4-diF—Ph |
| 1-306 | 4-HP-dioxo | 2,4-diF—Ph |
| 1-307 | 4-HP-dithio | 2,4-diF—Ph |
| 1-308 | 4-HP-oxathio | 2,4-diF—Ph |
| 1-309 | 3-HB-cPent | 2,4-diF—Ph |
| 1-310 | 4-HB-dioxo | 2,4-diF—Ph |
| 1-311 | 4-HB-dithio | 2,4-diF—Ph |
| 1-312 | 4-HB-oxathio | 2,4-diF—Ph |
| 1-313 | ring 3 | 2,4-diF—Ph |
| 1-314 | ring 4 | 2,4-diF—Ph |
| 1-315 | ring 5 | 2,4-diF—Ph |
| 1-316 | ring 6 | 2,4-diF—Ph |
| 1-317 | ring 7 | 2,4-diF—Ph |
| 1-318 | ring 8 | 2,4-diF—Ph |
| 1-319 | ring 9 | 2,4-diF—Ph |
| 1-320 | ring 10 | 2,4-diF—Ph |
| 1-321 | 3,4-di$CH_2$NHAc-cPent | 2,4-diF—Ph |
| 1-322 | 4,5-di$CH_2$NHAc-dioxo | 2,4-diF—Ph |
| 1-323 | 4,5-di$CH_2$NHAc-dithio | 2,4-diF—Ph |
| 1-324 | 4,5-di$CH_2$NHAc-oxathio | 2,4-diF—Ph |
| 1-325 | ring 11 | 2,4-diF—Ph |
| 1-326 | ring 12 | 2,4-diF—Ph |
| 1-327 | ring 13 | 2,4-diF—Ph |
| 1-328 | ring 14 | 2,4-diF—Ph |
| 1-329 | 4-OH-cHex | 2,4-diF—Ph |
| 1-330 | 5-OH-dioxa | 2,4-diF—Ph |
| 1-331 | 5-OH-dithia | 2,4-diF—Ph |
| 1-332 | 5-OH-oxathia | 2,4-diF—Ph |
| 1-333 | 4-NHAc-cHex | 2,4-diF—Ph |
| 1-334 | 5-NHAc-dioxa | 2,4-diF—Ph |
| 1-335 | 5-NHAc-dithia | 2,4-diF—Ph |
| 1-336 | 5-NHAc-oxathia | 2,4-diF—Ph |
| 1-337 | 4,4-diMe-cHex | 2,4-diF—Ph |
| 1-338 | 5,5-diMe-dioxa | 2,4-diF—Ph |
| 1-339 | 5,5-diMe-dithia | 2,4-diF—Ph |
| 1-340 | 5,5-diMe-oxathia | 2,4-diF—Ph |

TABLE 1-continued

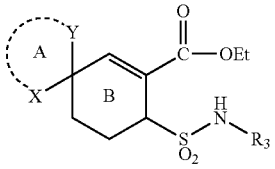

| Compound No. | X, Y | $R^3$ |
|---|---|---|
| 1-341 | 4,4-diHM-cHex | 2,4-diF—Ph |
| 1-342 | 5,5-diHM-dioxa | 2,4-diF—Ph |
| 1-343 | 5,5-diHM-dithia | 2,4-diF—Ph |
| 1-344 | 5,5-diHM-oxathia | 2,4-diF—Ph |
| 1-345 | ring 15 | 2,4-diF—Ph |
| 1-346 | ring 16 | 2,4-diF—Ph |
| 1-347 | ring 17 | 2,4-diF—Ph |
| 1-348 | ring 18 | 2,4-diF—Ph |
| 1-349 | 4,4-di$CO_2$Et-cHex | 2,4-diF—Ph |
| 1-350 | 5,5-di$CO_2$Et-dioxa | 2,4-diF—Ph |
| 1-351 | 5,5-di$CO_2$Et-dithia | 2,4-diF—Ph |
| 1-352 | 5,5-di$CO_2$Et-oxathia | 2,4-diF—Ph |
| 1-353 | O═ | 2-Cl-4-F—Ph |
| 1-354 | S═ | 2-Cl-4-F—Ph |
| 1-355 | cPr | 2-Cl-4-F—Ph |
| 1-356 | cBu | 2-Cl-4-F—Ph |
| 1-357 | cPent | 2-Cl-4-F—Ph |
| 1-358 | cHex | 2-Cl-4-F—Ph |
| 1-359 | cHept | 2-Cl-4-F—Ph |
| 1-360 | oxi | 2-Cl-4-F—Ph |
| 1-361 | oxe | 2-Cl-4-F—Ph |
| 1-362 | oxo | 2-Cl-4-F—Ph |
| 1-363 | oxa | 2-Cl-4-F—Ph |
| 1-364 | dioxo | 2-Cl-4-F—Ph |
| 1-365 | dioxa | 2-Cl-4-F—Ph |
| 1-366 | dioxe | 2-Cl-4-F—Ph |
| 1-367 | dithio | 2-Cl-4-F—Ph |
| 1-368 | dithia | 2-Cl-4-F—Ph |
| 1-369 | ring 1 | 2-Cl-4-F—Ph |
| 1-370 | ring 2 | 2-Cl-4-F—Ph |
| 1-371 | oxathio | 2-Cl-4-F—Ph |
| 1-372 | oxathia | 2-Cl-4-F—Ph |
| 1-373 | ozl | 2-Cl-4-F—Ph |
| 1-374 | ozn | 2-Cl-4-F—Ph |
| 1-375 | tzl | 2-Cl-4-F—Ph |
| 1-376 | tzn | 2-Cl-4-F—Ph |
| 1-377 | 3-HM-cPent | 2-Cl-4-F—Ph |
| 1-378 | 4-HM-dioxo | 2-Cl-4-F—Ph |
| 1-379 | 4-HM-dithio | 2-Cl-4-F—Ph |
| 1-380 | 4-HM-oxathio | 2-Cl-4-F—Ph |
| 1-381 | 3,4-diHM-cPent | 2-Cl-4-F—Ph |
| 1-382 | 4,5-diHM-dioxo | 2-Cl-4-F—Ph |
| 1-383 | 4,5-diHM-dithio | 2-Cl-4-F—Ph |
| 1-384 | 4,5-diHM-oxathio | 2-Cl-4-F—Ph |
| 1-385 | 3,4-diHE-cPent | 2-Cl-4-F—Ph |
| 1-386 | 4,5-diHE-dioxo | 2-Cl-4-F—Ph |
| 1-387 | 4,5-diHE-dithio | 2-Cl-4-F—Ph |
| 1-388 | 4,5-diHE-oxathio | 2-Cl-4-F—Ph |
| 1-389 | 3-HE-cPent | 2-Cl-4-F—Ph |
| 1-390 | 4-HE-dioxo | 2-Cl-4-F—Ph |
| 1-391 | 4-HE-dithio | 2-Cl-4-F—Ph |
| 1-392 | 4-HE-oxathio | 2-Cl-4-F—Ph |
| 1-393 | 3-HP-cPent | 2-Cl-4-F—Ph |
| 1-394 | 4-HP-dioxo | 2-Cl-4-F—Ph |
| 1-395 | 4-HP-dithio | 2-Cl-4-F—Ph |
| 1-396 | 4-HP-oxathio | 2-Cl-4-F—Ph |
| 1-397 | 3-HB-cPent | 2-Cl-4-F—Ph |
| 1-398 | 4-HB-dioxo | 2-Cl-4-F—Ph |
| 1-399 | 4-HB-dithio | 2-Cl-4-F—Ph |
| 1-400 | 4-HB-oxathio | 2-Cl-4-F—Ph |
| 1-401 | ring 3 | 2-Cl-4-F—Ph |
| 1-402 | ring 4 | 2-Cl-4-F—Ph |
| 1-403 | ring 5 | 2-Cl-4-F—Ph |
| 1-404 | ring 6 | 2-Cl-4-F—Ph |
| 1-405 | ring 7 | 2-Cl-4-F—Ph |
| 1-406 | ring 8 | 2-Cl-4-F—Ph |
| 1-407 | ring 9 | 2-Cl-4-F—Ph |
| 1-408 | ring 10 | 2-Cl-4-F—Ph |

TABLE 1-continued

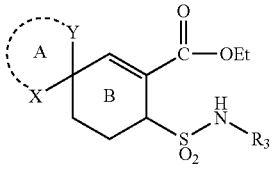

| Compound No. | X, Y | $R^3$ |
|---|---|---|
| 1-409 | 3,4-di$CH_2$NHAc-cPent | 2-Cl-4-F—Ph |
| 1-410 | 4,5-di$CH_2$NHAc-dioxo | 2-Cl-4-F—Ph |
| 1-411 | 4,5-di$CH_2$NHAc-dithio | 2-Cl-4-F—Ph |
| 1-412 | 4,5-di$CH_2$NHAc-oxathio | 2-Cl-4-F—Ph |
| 1-413 | ring 11 | 2-Cl-4-F—Ph |
| 1-414 | ring 12 | 2-Cl-4-F—Ph |
| 1-415 | ring 13 | 2-Cl-4-F—Ph |
| 1-416 | ring 14 | 2-Cl-4-F—Ph |
| 1-417 | 4-OH-cHex | 2-Cl-4-F—Ph |
| 1-418 | 5-OH-dioxa | 2-Cl-4-F—Ph |
| 1-419 | 5-OH-dithia | 2-Cl-4-F—Ph |
| 1-420 | 5-OH-oxathia | 2-Cl-4-F—Ph |
| 1-421 | 4-NHAc-cHex | 2-Cl-4-F—Ph |
| 1-422 | 5-NHAc-dioxa | 2-Cl-4-F—Ph |
| 1-423 | 5-NHAc-dithia | 2-Cl-4-F—Ph |
| 1-424 | 5-NHAc-oxathia | 2-Cl-4-F—Ph |
| 1-425 | 4,4-diMe-cHex | 2-Cl-4-F—Ph |
| 1-426 | 5,5-diMe-dioxa | 2-Cl-4-F—Ph |
| 1-427 | 5,5-diMe-dithia | 2-Cl-4-F—Ph |
| 1-428 | 5,5-diMe-oxathia | 2-Cl-4-F—Ph |
| 1-429 | 4,4-diHM-cHex | 2-Cl-4-F—Ph |
| 1-430 | 5,5-diHM-dioxa | 2-Cl-4-F—Ph |
| 1-431 | 5,5-diHM-dithia | 2-Cl-4-F—Ph |
| 1-432 | 5,5-diHM-oxathia | 2-Cl-4-F—Ph |
| 1-433 | ring 15 | 2-Cl-4-F—Ph |
| 1-434 | ring 16 | 2-Cl-4-F—Ph |
| 1-435 | ring 17 | 2-Cl-4-F—Ph |
| 1-436 | ring 18 | 2-Cl-4-F—Ph |
| 1-437 | 4,4-di$CO_2$Et-cHex | 2-Cl-4-F—Ph |
| 1-438 | 5,5-di$CO_2$Et-dioxa | 2-Cl-4-F—Ph |
| 1-439 | 5,5-di$CO_2$Et-dithia | 2-Cl-4-F—Ph |
| 1-440 | 5,5-di$CO_2$Et-oxathia | 2-Cl-4-F—Ph |
| 1-441 | O═ | 2-Cl-4-Me—Ph |
| 1-442 | S═ | 2-Cl-4-Me—Ph |
| 1-443 | cPr | 2-Cl-4-Me—Ph |
| 1-444 | cBu | 2-Cl-4-Me—Ph |
| 1-445 | cPent | 2-Cl-4-Me—Ph |
| 1-446 | cHex | 2-Cl-4-Me—Ph |
| 1-447 | cHept | 2-Cl-4-Me—Ph |
| 1-448 | oxi | 2-Cl-4-Me—Ph |
| 1-449 | oxe | 2-Cl-4-Me—Ph |
| 1-450 | oxo | 2-Cl-4-Me—Ph |
| 1-451 | oxa | 2-Cl-4-Me—Ph |
| 1-452 | dioxo | 2-Cl-4-Me—Ph |
| 1-453 | dioxa | 2-Cl-4-Me—Ph |
| 1-454 | dioxe | 2-Cl-4-Me—Ph |
| 1-455 | dithio | 2-Cl-4-Me—Ph |
| 1-456 | dithia | 2-Cl-4-Me—Ph |
| 1-457 | ring 1 | 2-Cl-4-Me—Ph |
| 1-458 | ring 2 | 2-Cl-4-Me—Ph |
| 1-459 | oxathio | 2-Cl-4-Me—Ph |
| 1-460 | oxathia | 2-Cl-4-Me—Ph |
| 1-461 | ozl | 2-Cl-4-Me—Ph |
| 1-462 | ozn | 2-Cl-4-Me—Ph |
| 1-463 | tzl | 2-Cl-4-Me—Ph |
| 1-464 | tzn | 2-Cl-4-Me—Ph |
| 1-465 | 3-HM-cPent | 2-Cl-4-Me—Ph |
| 1-466 | 4-HM-dioxo | 2-Cl-4-Me—Ph |
| 1-467 | 4-HM-dithio | 2-Cl-4-Me—Ph |
| 1-468 | 4-HM-oxathio | 2-Cl-4-Me—Ph |
| 1-469 | 3,4-diHM-cPent | 2-Cl-4-Me—Ph |
| 1-470 | 4,5-diHM-dioxo | 2-Cl-4-Me—Ph |
| 1-471 | 4,5-diHM-dithio | 2-Cl-4-Me—Ph |
| 1-472 | 4,5-diHM-oxathio | 2-Cl-4-Me—Ph |
| 1-473 | 3,4-diHE-cPent | 2-Cl-4-Me—Ph |
| 1-474 | 4,5-diHE-dioxo | 2-Cl-4-Me—Ph |
| 1-475 | 4,5-diHE-dithio | 2-Cl-4-Me—Ph |
| 1-476 | 4,5-diHE-oxathio | 2-Cl-4-Me—Ph |

TABLE 1-continued

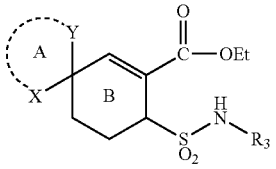

| Compound No. | X, Y | $R^3$ |
|---|---|---|
| 1-477 | 3-HE-cPent | 2-Cl-4-Me—Ph |
| 1-478 | 4-HE-dioxo | 2-Cl-4-Me—Ph |
| 1-479 | 4-HE-dithio | 2-Cl-4-Me—Ph |
| 1-480 | 4-HE-oxathio | 2-Cl-4-Me—Ph |
| 1-481 | 3-HP-cPent | 2-Cl-4-Me—Ph |
| 1-482 | 4-HP-dioxo | 2-Cl-4-Me—Ph |
| 1-483 | 4-HP-dithio | 2-Cl-4-Me—Ph |
| 1-484 | 4-HP-oxathio | 2-Cl-4-Me—Ph |
| 1-485 | 3-HB-cPent | 2-Cl-4-Me—Ph |
| 1-486 | 4-HB-dioxo | 2-Cl-4-Me—Ph |
| 1-487 | 4-HB-dithio | 2-Cl-4-Me—Ph |
| 1-488 | 4-HB-oxathio | 2-Cl-4-Me—Ph |
| 1-489 | ring 3 | 2-Cl-4-Me—Ph |
| 1-490 | ring 4 | 2-Cl-4-Me—Ph |
| 1-491 | ring 5 | 2-Cl-4-Me—Ph |
| 1-492 | ring 6 | 2-Cl-4-Me—Ph |
| 1-493 | ring 7 | 2-Cl-4-Me—Ph |
| 1-494 | ring 8 | 2-Cl-4-Me—Ph |
| 1-495 | ring 9 | 2-Cl-4-Me—Ph |
| 1-496 | ring 10 | 2-Cl-4-Me—Ph |
| 1-497 | 3,4-di$CH_2$NHAc-cPent | 2-Cl-4-Me—Ph |
| 1-498 | 4,5-di$CH_2$NHAc-dioxo | 2-Cl-4-Me—Ph |
| 1-499 | 4,5-di$CH_2$NHAc-dithio | 2-Cl-4-Me—Ph |
| 1-500 | 4,5-di$CH_2$NHAc-oxathio | 2-Cl-4-Me—Ph |
| 1-501 | ring 11 | 2-Cl-4-Me—Ph |
| 1-502 | ring 12 | 2-Cl-4-Me—Ph |
| 1-503 | ring 13 | 2-Cl-4-Me—Ph |
| 1-504 | ring 14 | 2-Cl-4-Me—Ph |
| 1-505 | 4-OH-cHex | 2-Cl-4-Me—Ph |
| 1-506 | 5-OH-dioxa | 2-Cl-4-Me—Ph |
| 1-507 | 5-OH-dithia | 2-Cl-4-Me—Ph |
| 1-508 | 5-OH-oxathia | 2-Cl-4-Me—Ph |
| 1-509 | 4-NHAc-cHex | 2-Cl-4-Me—Ph |
| 1-510 | 5-NHAc-dioxa | 2-Cl-4-Me—Ph |
| 1-511 | 5-NHAc-dithia | 2-Cl-4-Me—Ph |
| 1-512 | 5-NHAc-oxathia | 2-Cl-4-Me—Ph |
| 1-513 | 4,4-diMe-cHex | 2-Cl-4-Me—Ph |
| 1-514 | 5,5-diMe-dioxa | 2-Cl-4-Me—Ph |
| 1-515 | 5,5-diMe-dithia | 2-Cl-4-Me—Ph |
| 1-516 | 5,5-diMe-oxathia | 2-Cl-4-Me—Ph |
| 1-517 | 4,4-diHM-cHex | 2-Cl-4-Me—Ph |
| 1-518 | 5,5-diHM-dioxa | 2-Cl-4-Me—Ph |
| 1-519 | 5,5-diHM-dithia | 2-Cl-4-Me—Ph |
| 1-520 | 5,5-diHM-oxathia | 2-Cl-4-Me—Ph |
| 1-521 | ring 15 | 2-Cl-4-Me—Ph |
| 1-522 | ring 16 | 2-Cl-4-Me—Ph |
| 1-523 | ring 17 | 2-Cl-4-Me—Ph |
| 1-524 | ring 18 | 2-Cl-4-Me—Ph |
| 1-525 | 4,4-di$CO_2$Et-cHex | 2-Cl-4-Me—Ph |
| 1-526 | 5,5-di$CO_2$Et-dioxa | 2-Cl-4-Me—Ph |
| 1-527 | 5,5-di$CO_2$Et-dithia | 2-Cl-4-Me—Ph |
| 1-528 | 5,5-di$CO_2$Et-oxathia | 2-Cl-4-Me—Ph |
| 1-529 | O═ | 2-nBu—Ph |
| 1-530 | S═ | 2-nBu—Ph |
| 1-531 | cPr | 2-nBu—Ph |
| 1-532 | cBu | 2-nBu—Ph |
| 1-533 | cPent | 2-nBu—Ph |
| 1-534 | cHex | 2-nBu—Ph |
| 1-535 | cHept | 2-nBu—Ph |
| 1-536 | oxi | 2-nBu—Ph |
| 1-537 | oxe | 2-nBu—Ph |
| 1-538 | oxo | 2-nBu—Ph |
| 1-539 | oxa | 2-nBu—Ph |
| 1-540 | dioxo | 2-nBu—Ph |
| 1-541 | dioxa | 2-nBu—Ph |
| 1-542 | dioxe | 2-nBu—Ph |
| 1-543 | dithio | 2-nBu—Ph |
| 1-544 | dithia | 2-nBu—Ph |

TABLE 1-continued

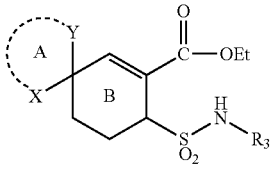

| Compound No. | X, Y | $R^3$ |
|---|---|---|
| 1-545 | ring 1 | 2-nBu—Ph |
| 1-546 | ring 2 | 2-nBu—Ph |
| 1-547 | oxathio | 2-nBu—Ph |
| 1-548 | oxathia | 2-nBu—Ph |
| 1-549 | ozl | 2-nBu—Ph |
| 1-550 | ozn | 2-nBu—Ph |
| 1-551 | tzl | 2-nBu—Ph |
| 1-552 | tzn | 2-nBu—Ph |
| 1-553 | 3-HM-cPent | 2-nBu—Ph |
| 1-554 | 4-HM-dioxo | 2-nBu—Ph |
| 1-555 | 4-HM-dithio | 2-nBu—Ph |
| 1-556 | 4-HM-oxathio | 2-nBu—Ph |
| 1-557 | 3,4-diHM-cPent | 2-nBu—Ph |
| 1-558 | 4,5-diHM-dioxo | 2-nBu—Ph |
| 1-559 | 4,5-diHM-dithio | 2-nBu—Ph |
| 1-560 | 4,5-diHM-oxathio | 2-nBu—Ph |
| 1-561 | 3,4-diHE-cPent | 2-nBu—Ph |
| 1-562 | 4,5-diHE-dioxo | 2-nBu—Ph |
| 1-563 | 4,5-diHE-dithio | 2-nBu—Ph |
| 1-564 | 4,5-diHE-oxathio | 2-nBu—Ph |
| 1-565 | 3-HE-cPent | 2-nBu—Ph |
| 1-566 | 4-HE-dioxo | 2-nBu—Ph |
| 1-567 | 4-HE-dithio | 2-nBu—Ph |
| 1-568 | 4-HE-oxathio | 2-nBu—Ph |
| 1-569 | 3-HP-cPent | 2-nBu—Ph |
| 1-570 | 4-HP-dioxo | 2-nBu—Ph |
| 1-571 | 4-HP-dithio | 2-nBu—Ph |
| 1-572 | 4-HP-oxathio | 2-nBu—Ph |
| 1-573 | 3-HB-cPent | 2-nBu—Ph |
| 1-574 | 4-HB-dioxo | 2-nBu—Ph |
| 1-575 | 4-HB-dithio | 2-nBu—Ph |
| 1-576 | 4-HB-oxathio | 2-nBu—Ph |
| 1-577 | ring 3 | 2-nBu—Ph |
| 1-578 | ring 4 | 2-nBu—Ph |
| 1-579 | ring 5 | 2-nBu—Ph |
| 1-580 | ring 6 | 2-nBu—Ph |
| 1-581 | ring 7 | 2-nBu—Ph |
| 1-582 | ring 8 | 2-nBu—Ph |
| 1-583 | ring 9 | 2-nBu—Ph |
| 1-584 | ring 10 | 2-nBu—Ph |
| 1-585 | 3,4-di$CH_2$NHAc-cPent | 2-nBu—Ph |
| 1-586 | 4,5-di$CH_2$NHAc-dioxo | 2-nBu—Ph |
| 1-587 | 4,5-di$CH_2$NHAc-dithio | 2-nBu—Ph |
| 1-588 | 4,5-di$CH_2$NHAc-oxathio | 2-nBu—Ph |
| 1-589 | ring 11 | 2-nBu—Ph |
| 1-590 | ring 12 | 2-nBu—Ph |
| 1-591 | ring 13 | 2-nBu—Ph |
| 1-592 | ring 14 | 2-nBu—Ph |
| 1-593 | 4-OH-cHex | 2-nBu—Ph |
| 1-594 | 5-OH-dioxa | 2-nBu—Ph |
| 1-595 | 5-OH-dithia | 2-nBu—Ph |
| 1-596 | 5-OH-oxathia | 2-nBu—Ph |
| 1-597 | 4-NHAc-cHex | 2-nBu—Ph |
| 1-598 | 5-NHAc-dioxa | 2-nBu—Ph |
| 1-599 | 5-NHAc-dithia | 2-nBu—Ph |
| 1-600 | 5-NHAc-oxathia | 2-nBu—Ph |
| 1-601 | 4,4-diMe-cHex | 2-nBu—Ph |
| 1-602 | 5,5-diMe-dioxa | 2-nBu—Ph |
| 1-603 | 5,5-diMe-dithia | 2-nBu—Ph |
| 1-604 | 5,5-diMe-oxathia | 2-nBu—Ph |
| 1-605 | 4,4-diHM-cHex | 2-nBu—Ph |
| 1-606 | 5,5-diHM-dioxa | 2-nBu—Ph |
| 1-607 | 5,5-diHM-dithia | 2-nBu—Ph |
| 1-608 | 5,5-diHM-oxathia | 2-nBu—Ph |
| 1-609 | ring 15 | 2-nBu—Ph |
| 1-610 | ring 16 | 2-nBu—Ph |
| 1-611 | ring 17 | 2-nBu—Ph |
| 1-612 | ring 18 | 2-nBu—Ph |

TABLE 1-continued

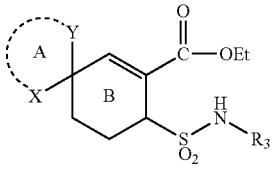

| Compound No. | X, Y | $R^3$ |
|---|---|---|
| 1-612 | 4,4-di$CO_2$Et-cHex | 2-nBu—Ph |
| 1-614 | 5,5-di$CO_2$Et-dioxa | 2-nBu—Ph |
| 1-615 | 5,5-di$CO_2$Et-dithia | 2-nBu—Ph |
| 1-616 | 5,5-di$CO_2$Et-oxathia | 2-nBu—Ph |
| 1-617 | O═ | 2-nBu-4-F—Ph |
| 1-618 | S═ | 2-nBu-4-F—Ph |
| 1-619 | cPr | 2-nBu-4-F—Ph |
| 1-620 | cBu | 2-nBu-4-F—Ph |
| 1-621 | cPent | 2-nBu-4-F—Ph |
| 1-622 | cHex | 2-nBu-4-F—Ph |
| 1-623 | cHept | 2-nBu-4-F—Ph |
| 1-624 | oxi | 2-nBu-4-F—Ph |
| 1-625 | oxe | 2-nBu-4-F—Ph |
| 1-626 | oxo | 2-nBu-4-F—Ph |
| 1-627 | oxa | 2-nBu-4-F—Ph |
| 1-628 | dioxo | 2-nBu-4-F—Ph |
| 1-629 | dioxa | 2-nBu-4-F—Ph |
| 1-630 | dioxe | 2-nBu-4-F—Ph |
| 1-631 | dithio | 2-nBu-4-F—Ph |
| 1-632 | dithia | 2-nBu-4-F—Ph |
| 1-633 | ring 1 | 2-nBu-4-F—Ph |
| 1-634 | ring 2 | 2-nBu-4-F—Ph |
| 1-635 | oxathio | 2-nBu-4-F—Ph |
| 1-636 | oxathia | 2-nBu-4-F—Ph |
| 1-637 | ozl | 2-nBu-4-F—Ph |
| 1-638 | ozn | 2-nBu-4-F—Ph |
| 1-639 | tzl | 2-nBu-4-F—Ph |
| 1-640 | tzn | 2-nBu-4-F—Ph |
| 1-641 | 3-HM-cPent | 2-nBu-4-F—Ph |
| 1-642 | 4-HM-dioxo | 2-nBu-4-F—Ph |
| 1-643 | 4-HM-dithio | 2-nBu-4-F—Ph |
| 1-644 | 4-HM-oxathio | 2-nBu-4-F—Ph |
| 1-645 | 3,4-diHM-cPent | 2-nBu-4-F—Ph |
| 1-646 | 4,5-diHM-dioxo | 2-nBu-4-F—Ph |
| 1-647 | 4,5-diHM-dithio | 2-nBu-4-F—Ph |
| 1-648 | 4,5-diHM-oxathio | 2-nBu-4-F—Ph |
| 1-649 | 3,4-diHE-cPent | 2-nBu-4-F—Ph |
| 1-650 | 4,5-diHE-dioxo | 2-nBu-4-F—Ph |
| 1-651 | 4,5-diHE-dithio | 2-nBu-4-F—Ph |
| 1-652 | 4,5-diHE-oxathio | 2-nBu-4-F—Ph |
| 1-653 | 3-HE-cPent | 2-nBu-4-F—Ph |
| 1-654 | 4-HE-dioxo | 2-nBu-4-F—Ph |
| 1-655 | 4-HE-dithio | 2-nBu-4-F—Ph |
| 1-656 | 4-HE-oxathio | 2-nBu-4-F—Ph |
| 1-657 | 3-HP-cPent | 2-nBu-4-F—Ph |
| 1-658 | 4-HP-dioxo | 2-nBu-4-F—Ph |
| 1-659 | 4-HP-dithio | 2-nBu-4-F—Ph |
| 1-660 | 4-HP-oxathio | 2-nBu-4-F—Ph |
| 1-661 | 3-HB-cPent | 2-nBu-4-F—Ph |
| 1-662 | 4-HB-dioxo | 2-nBu-4-F—Ph |
| 1-663 | 4-HB-dithio | 2-nBu-4-F—Ph |
| 1-664 | 4-HB-oxathio | 2-nBu-4-F—Ph |
| 1-665 | ring 3 | 2-nBu-4-F—Ph |
| 1-666 | ring 4 | 2-nBu-4-F—Ph |
| 1-667 | ring 5 | 2-nBu-4-F—Ph |
| 1-668 | ring 6 | 2-nBu-4-F—Ph |
| 1-669 | ring 7 | 2-nBu-4-F—Ph |
| 1-670 | ring 8 | 2-nBu-4-F—Ph |
| 1-671 | ring 9 | 2-nBu-4-F—Ph |
| 1-672 | ring 10 | 2-nBu-4-F—Ph |
| 1-673 | 3,4-di$CH_2$NHAc-cPent | 2-nBu-4-F—Ph |
| 1-674 | 4,5-di$CH_2$NHAc-dioxo | 2-nBu-4-F—Ph |
| 1-675 | 4,5-di$CH_2$NHAc-dithio | 2-nBu-4-F—Ph |
| 1-676 | 4,5-di$CH_2$NHAc-oxathio | 2-nBu-4-F—Ph |
| 1-677 | ring 11 | 2-nBu-4-F—Ph |
| 1-678 | ring 12 | 2-nBu-4-F—Ph |
| 1-679 | ring 13 | 2-nBu-4-F—Ph |
| 1-680 | ring 14 | 2-nBu-4-F—Ph |

TABLE 1-continued

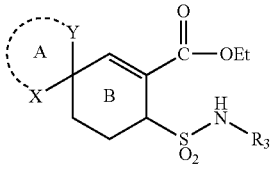

| Compound No. | X, Y | $R^3$ |
|---|---|---|
| 1-681 | 4-OH-cHex | 2-nBu-4-F—Ph |
| 1-682 | 5-OH-dioxa | 2-nBu-4-F—Ph |
| 1-683 | 5-OH-dithia | 2-nBu-4-F—Ph |
| 1-684 | 5-OH-oxathia | 2-nBu-4-F—Ph |
| 1-685 | 4-NHAc-cHex | 2-nBu-4-F—Ph |
| 1-686 | 5-NHAc-dioxa | 2-nBu-4-F—Ph |
| 1-687 | 5-NHAc-dithia | 2-nBu-4-F—Ph |
| 1-688 | 5-NHAc-oxathia | 2-nBu-4-F—Ph |
| 1-689 | 4,4-diMe-cHex | 2-nBu-4-F—Ph |
| 1-690 | 5,5-diMe-dioxa | 2-nBu-4-F—Ph |
| 1-691 | 5,5-diMe-dithia | 2-nBu-4-F—Ph |
| 1-692 | 5,5-diMe-oxathia | 2-nBu-4-F—Ph |
| 1-693 | 4,4-diHM-cHex | 2-nBu-4-F—Ph |
| 1-694 | 5,5-diHM-dioxa | 2-nBu-4-F—Ph |
| 1-695 | 5,5-diHM-dithia | 2-nBu-4-F—Ph |
| 1-696 | 5,5-diHM-oxathia | 2-nBu-4-F—Ph |
| 1-697 | ring 15 | 2-nBu-4-F—Ph |
| 1-698 | ring 16 | 2-nBu-4-F—Ph |
| 1-699 | ring 17 | 2-nBu-4-F—Ph |
| 1-700 | ring 18 | 2-nBu-4-F—Ph |
| 1-701 | 4,4-di$CO_2$Et-cHex | 2-nBu-4-F—Ph |
| 1-702 | 5,5-di$CO_2$Et-dioxa | 2-nBu-4-F—Ph |
| 1-703 | 5,5-di$CO_2$Et-dithia | 2-nBu-4-F—Ph |
| 1-704 | 5,5-di$CO_2$Et-oxathia | 2-nBu-4-F—Ph |
| 1-705 | O═ | 2-nHex—Ph |
| 1-706 | S═ | 2-nHex—Ph |
| 1-707 | cPr | 2-nHex—Ph |
| 1-708 | cBu | 2-nHex—Ph |
| 1-709 | cPent | 2-nHex—Ph |
| 1-710 | cHex | 2-nHex—Ph |
| 1-711 | cHept | 2-nHex—Ph |
| 1-712 | oxi | 2-nHex—Ph |
| 1-713 | oxe | 2-nHex—Ph |
| 1-714 | oxo | 2-nHex—Ph |
| 1-715 | oxa | 2-nHex—Ph |
| 1-716 | dioxo | 2-nHex—Ph |
| 1-717 | dioxa | 2-nHex—Ph |
| 1-718 | dioxe | 2-nHex—Ph |
| 1-719 | dithio | 2-nHex—Ph |
| 1-720 | dithia | 2-nHex—Ph |
| 1-721 | ring 1 | 2-nHex—Ph |
| 1-722 | ring 2 | 2-nHex—Ph |
| 1-723 | oxathio | 2-nHex—Ph |
| 1-724 | oxathia | 2-nHex—Ph |
| 1-725 | ozl | 2-nHex—Ph |
| 1-726 | ozn | 2-nHex—Ph |
| 1-727 | tzl | 2-nHex—Ph |
| 1-728 | tzn | 2-nHex—Ph |
| 1-729 | 3-HM-cPent | 2-nHex—Ph |
| 1-730 | 4-HM-dioxo | 2-nHex—Ph |
| 1-731 | 4-HM-dithio | 2-nHex—Ph |
| 1-732 | 4-HM-oxathio | 2-nHex—Ph |
| 1-733 | 3,4-diHM-cPent | 2-nHex—Ph |
| 1-734 | 4,5-diHM-dioxo | 2-nHex—Ph |
| 1-735 | 4,5-diHM-dithio | 2-nHex—Ph |
| 1-736 | 4,5-diHM-oxathio | 2-nHex—Ph |
| 1-737 | 3,4-diHE-cPent | 2-nHex—Ph |
| 1-738 | 4,5-diHE-dioxo | 2-nHex—Ph |
| 1-739 | 4,5-diHE-dithio | 2-nHex—Ph |
| 1-740 | 4,5-diHE-oxathio | 2-nHex—Ph |
| 1-741 | 3-HE-cPent | 2-nHex—Ph |
| 1-742 | 4-HE-dioxo | 2-nHex—Ph |
| 1-743 | 4-HE-dithio | 2-nHex—Ph |
| 1-744 | 4-HE-oxathio | 2-nHex—Ph |
| 1-745 | 3-HP-cPent | 2-nHex—Ph |
| 1-746 | 4-HP-dioxo | 2-nHex—Ph |
| 1-747 | 4-HP-dithio | 2-nHex—Ph |
| 1-748 | 4-HP-oxathio | 2-nHex—Ph |

TABLE 1-continued

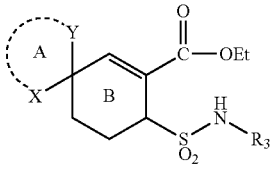

| Compound No. | X, Y | $R^3$ |
|---|---|---|
| 1-749 | 3-HB-cPent | 2-nHex—Ph |
| 1-750 | 4-HB-dioxo | 2-nHex—Ph |
| 1-751 | 4-HB-dithio | 2-nHex—Ph |
| 1-752 | 4-HB-oxathio | 2-nHex—Ph |
| 1-753 | ring 3 | 2-nHex—Ph |
| 1-754 | ring 4 | 2-nHex—Ph |
| 1-755 | ring 5 | 2-nHex—Ph |
| 1-756 | ring 6 | 2-nHex—Ph |
| 1-757 | ring 7 | 2-nHex—Ph |
| 1-758 | ring 8 | 2-nHex—Ph |
| 1-759 | ring 9 | 2-nHex—Ph |
| 1-760 | ring 10 | 2-nHex—Ph |
| 1-761 | 3,4-di$CH_2$NHAc-cPent | 2-nHex—Ph |
| 1-762 | 4,5-di$CH_2$NHAc-dioxo | 2-nHex—Ph |
| 1-763 | 4,5-di$CH_2$NHAc-dithio | 2-nHex—Ph |
| 1-764 | 4,5-di$CH_2$NHAc-oxathio | 2-nHex—Ph |
| 1-765 | ring 11 | 2-nHex—Ph |
| 1-766 | ring 12 | 2-nHex—Ph |
| 1-767 | ring 13 | 2-nHex—Ph |
| 1-768 | ring 14 | 2-nHex—Ph |
| 1-769 | 4-OH-cHex | 2-nHex—Ph |
| 1-770 | 5-OH-dioxa | 2-nHex—Ph |
| 1-771 | 5-OH-dithia | 2-nHex—Ph |
| 1-772 | 5-OH-oxathia | 2-nHex—Ph |
| 1-773 | 4-NHAc-cHex | 2-nHex—Ph |
| 1-774 | 5-NHAc-dioxa | 2-nHex—Ph |
| 1-775 | 5-NHAc-dithia | 2-nHex—Ph |
| 1-776 | 5-NHAc-oxathia | 2-nHex—Ph |
| 1-777 | 4,4-diMe-cHex | 2-nHex—Ph |
| 1-778 | 5,5-diMe-dioxa | 2-nHex—Ph |
| 1-779 | 5,5-diMe-dithia | 2-nHex—Ph |
| 1-780 | 5,5-diMe-oxathia | 2-nHex—Ph |
| 1-781 | 4,4-diHM-cHex | 2-nHex—Ph |
| 1-782 | 5,5-diHM-dioxa | 2-nHex—Ph |
| 1-783 | 5,5-diHM-dithia | 2-nHex—Ph |
| 1-784 | 5,5-diHM-oxathia | 2-nHex—Ph |
| 1-785 | ring 15 | 2-nHex—Ph |
| 1-786 | ring 16 | 2-nHex—Ph |
| 1-787 | ring 17 | 2-nHex—Ph |
| 1-788 | ring 18 | 2-nHex—Ph |
| 1-789 | 4,4-di$CO_2$Et-cHex | 2-nHex—Ph |
| 1-790 | 5,5-di$CO_2$Et-dioxa | 2-nHex—Ph |
| 1-791 | 5,5-di$CO_2$Et-dithia | 2-nHex—Ph |
| 1-792 | 5,5-di$CO_2$Et-oxathia | 2-nHex—Ph |
| 1-793 | O= | 4-F-2-nHex—Ph |
| 1-794 | S= | 4-F-2-nHex—Ph |
| 1-795 | cPr | 4-F-2-nHex—Ph |
| 1-796 | cBu | 4-F-2-nHex—Ph |
| 1-797 | cPent | 4-F-2-nHex—Ph |
| 1-798 | cHex | 4-F-2-nHex—Ph |
| 1-799 | cHept | 4-F-2-nHex—Ph |
| 1-800 | oxi | 4-F-2-nHex—Ph |
| 1-801 | oxe | 4-F-2-nHex—Ph |
| 1-802 | oxo | 4-F-2-nHex—Ph |
| 1-803 | oxa | 4-F-2-nHex—Ph |
| 1-804 | dioxo | 4-F-2-nHex—Ph |
| 1-805 | dioxa | 4-F-2-nHex—Ph |
| 1-806 | dioxe | 4-F-2-nHex—Ph |
| 1-807 | dithio | 4-F-2-nHex—Ph |
| 1-808 | dithia | 4-F-2-nHex—Ph |
| 1-809 | ring 1 | 4-F-2-nHex—Ph |
| 1-810 | ring 2 | 4-F-2-nHex—Ph |
| 1-811 | oxathio | 4-F-2-nHex—Ph |
| 1-812 | oxathia | 4-F-2-nHex—Ph |
| 1-813 | ozl | 4-F-2-nHex—Ph |
| 1-814 | ozn | 4-F-2-nHex—Ph |
| 1-815 | tzl | 4-F-2-nHex—Ph |
| 1-816 | tzn | 4-F-2-nHex—Ph |

TABLE 1-continued

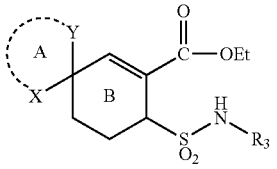

| Compound No. | X, Y | $R^3$ |
|---|---|---|
| 1-817 | 3-HM-cPent | 4-F-2-nHex—Ph |
| 1-818 | 4-HM-dioxo | 4-F-2-nHex—Ph |
| 1-819 | 4-HM-dithio | 4-F-2-nHex—Ph |
| 1-820 | 4-HM-oxathio | 4-F-2-nHex—Ph |
| 1-821 | 3,4-diHM-cPent | 4-F-2-nHex—Ph |
| 1-822 | 4,5-diHM-dioxo | 4-F-2-nHex—Ph |
| 1-823 | 4,5-diHM-dithio | 4-F-2-nHex—Ph |
| 1-824 | 4,5-diHM-oxathio | 4-F-2-nHex—Ph |
| 1-825 | 3,4-diHE-cPent | 4-F-2-nHex—Ph |
| 1-826 | 4,5-diHE-dioxo | 4-F-2-nHex—Ph |
| 1-827 | 4,5-diHE-dithio | 4-F-2-nHex—Ph |
| 1-828 | 4,5-diHE-oxathio | 4-F-2-nHex—Ph |
| 1-829 | 3-HE-cPent | 4-F-2-nHex—Ph |
| 1-830 | 4-HE-dioxo | 4-F-2-nHex—Ph |
| 1-831 | 4-HE-dithio | 4-F-2-nHex—Ph |
| 1-832 | 4-HE-oxathio | 4-F-2-nHex—Ph |
| 1-833 | 3-HP-cPent | 4-F-2-nHex—Ph |
| 1-834 | 4-HP-dioxo | 4-F-2-nHex—Ph |
| 1-835 | 4-HP-dithio | 4-F-2-nHex—Ph |
| 1-836 | 4-HP-oxathio | 4-F-2-nHex—Ph |
| 1-837 | 3-HB-cPent | 4-F-2-nHex—Ph |
| 1-838 | 4-HB-dioxo | 4-F-2-nHex—Ph |
| 1-839 | 4-HB-dithio | 4-F-2-nHex—Ph |
| 1-840 | 4-HB-oxathio | 4-F-2-nHex—Ph |
| 1-841 | ring 3 | 4-F-2-nHex—Ph |
| 1-842 | ring 4 | 4-F-2-nHex—Ph |
| 1-843 | ring 5 | 4-F-2-nHex—Ph |
| 1-844 | ring 6 | 4-F-2-nHex—Ph |
| 1-845 | ring 7 | 4-F-2-nHex—Ph |
| 1-846 | ring 8 | 4-F-2-nHex—Ph |
| 1-847 | ring 9 | 4-F-2-nHex—Ph |
| 1-848 | ring 10 | 4-F-2-nHex—Ph |
| 1-849 | 3,4-di$CH_2$NHAc-cPent | 4-F-2-nHex—Ph |
| 1-850 | 4,5-di$CH_2$NHAc-dioxo | 4-F-2-nHex—Ph |
| 1-851 | 4,5-di$CH_2$NHAc-dithio | 4-F-2-nHex—Ph |
| 1-852 | 4,5-di$CH_2$NHAc-oxathio | 4-F-2-nHex—Ph |
| 1-853 | ring 11 | 4-F-2-nHex—Ph |
| 1-854 | ring 12 | 4-F-2-nHex—Ph |
| 1-855 | ring 13 | 4-F-2-nHex—Ph |
| 1-856 | ring 14 | 4-F-2-nHex—Ph |
| 1-857 | 4-OH-cHex | 4-F-2-nHex—Ph |
| 1-858 | 5-OH-dioxa | 4-F-2-nHex—Ph |
| 1-859 | 5-OH-dithia | 4-F-2-nHex—Ph |
| 1-860 | 5-OH-oxathia | 4-F-2-nHex—Ph |
| 1-851 | 4-NHAc-cHex | 4-F-2-nHex—Ph |
| 1-852 | 5-NHAc-dioxa | 4-F-2-nHex—Ph |
| 1-863 | 5-NHAc-dithia | 4-F-2-nHex—Ph |
| 1-854 | 5-NHAc-oxathia | 4-F-2-nHex—Ph |
| 1-865 | 4,4-diMe-cHex | 4-F-2-nHex—Ph |
| 1-866 | 5,5-diMe-dioxa | 4-F-2-nHex—Ph |
| 1-857 | 5,5-diMe-dithia | 4-F-2-nHex—Ph |
| 1-868 | 5,5-diMe-oxathia | 4-F-2-nHex—Ph |
| 1-869 | 4,4-diHM-cHex | 4-F-2-nHex—Ph |
| 1-870 | 5,5-diHM-dioxa | 4-F-2-nHex—Ph |
| 1-871 | 5,5-diHM-dithia | 4-F-2-nHex—Ph |
| 1-872 | 5,5-diHM-oxathia | 4-F-2-nHex—Ph |
| 1-873 | ring 15 | 4-F-2-nHex—Ph |
| 1-874 | ring 16 | 4-F-2-nHex—Ph |
| 1-875 | ring 17 | 4-F-2-nHex—Ph |
| 1-876 | ring 18 | 4-F-2-nHex—Ph |
| 1-877 | 4,4-di$CO_2$Et-cHex | 4-F-2-nHex—Ph |
| 1-878 | 5,5-di$CO_2$Et-dioxa | 4-F-2-nHex—Ph |
| 1-879 | 5,5-di$CO_2$Et-dithia | 4-F-2-nHex—Ph |
| 1-880 | 5,5-di$CO_2$Et-oxathia | 4-F-2-nHex—Ph |
| 1-881 | O= | 2-nHept-Ph |
| 1-882 | S= | 2-nHept-Ph |
| 1-883 | cPr | 2-nHept-Ph |
| 1-884 | cBu | 2-nHept-Ph |

TABLE 1-continued

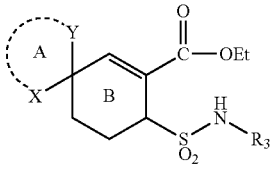

| Compound No. | X, Y | $R^3$ |
|---|---|---|
| 1-885 | cPent | 2-nHept-Ph |
| 1-886 | cHex | 2-nHept-Ph |
| 1-887 | cHept | 2-nHept-Ph |
| 1-888 | oxi | 2-nHept-Ph |
| 1-889 | oxe | 2-nHept-Ph |
| 1-890 | oxo | 2-nHept-Ph |
| 1-891 | oxa | 2-nHept-Ph |
| 1-892 | dioxo | 2-nHept-Ph |
| 1-893 | dioxa | 2-nHept-Ph |
| 1-894 | dioxe | 2-nHept-Ph |
| 1-895 | dithio | 2-nHept-Ph |
| 1-896 | dithia | 2-nHept-Ph |
| 1-897 | ring 1 | 2-nHept-Ph |
| 1-898 | ring 2 | 2-nHept-Ph |
| 1-899 | oxathio | 2-nHept-Ph |
| 1-900 | oxathia | 2-nHept-Ph |
| 1-901 | ozl | 2-nHept-Ph |
| 1-902 | ozn | 2-nHept-Ph |
| 1-903 | tzl | 2-nHept-Ph |
| 1-904 | tzn | 2-nHept-Ph |
| 1-905 | 3-HM-cPent | 2-nHept-Ph |
| 1-906 | 4-HM-dioxo | 2-nHept-Ph |
| 1-907 | 4-HM-dithio | 2-nHept-Ph |
| 1-908 | 4-HM-oxathio | 2-nHept-Ph |
| 1-909 | 3,4-diHM-cPent | 2-nHept-Ph |
| 1-910 | 4,5-diHM-dioxo | 2-nHept-Ph |
| 1-911 | 4,5-diHM-dithio | 2-nHept-Ph |
| 1-912 | 4,5-diHM-oxathio | 2-nHept-Ph |
| 1-913 | 3,4-diHE-cPent | 2-nHept-Ph |
| 1-914 | 4,5-diHE-dioxo | 2-nHept-Ph |
| 1-915 | 4,5-diHE-dithio | 2-nHept-Ph |
| 1-916 | 4,5-diHE-oxathio | 2-nHept-Ph |
| 1-917 | 3-HE-cPent | 2-nHept-Ph |
| 1-918 | 4-HE-dioxo | 2-nHept-Ph |
| 1-919 | 4-HE-dithio | 2-nHept-Ph |
| 1-920 | 4-HE-oxathio | 2-nHept-Ph |
| 1-921 | 3-HP-cPent | 2-nHept-Ph |
| 1-922 | 4-HP-dioxo | 2-nHept-Ph |
| 1-923 | 4-HP-dithio | 2-nHept-Ph |
| 1-924 | 4-HP-oxathio | 2-nHept-Ph |
| 1-925 | 3-HB-oPent | 2-nHept-Ph |
| 1-926 | 4-HB-dioxo | 2-nHept-Ph |
| 1-927 | 4-HB-dithio | 2-nHept-Ph |
| 1-928 | 4-HB-oxathio | 2-nHept-Ph |
| 1-929 | ring 3 | 2-nHept-Ph |
| 1-930 | ring 4 | 2-nHept-Ph |
| 1-931 | ring 5 | 2-nHept-Ph |
| 1-932 | ring 6 | 2-nHept-Ph |
| 1-933 | ring 7 | 2-nHept-Ph |
| 1-934 | ring 8 | 2-nHept-Ph |
| 1-935 | ring 9 | 2-nHept-Ph |
| 1-936 | ring 10 | 2-nHept-Ph |
| 1-937 | 3,4-di$CH_2$NHAc-cPent | 2-nHept-Ph |
| 1-938 | 4,5-di$CH_2$NHAc-dioxo | 2-nHept-Ph |
| 1-939 | 4,5-di$CH_2$NHAc-dithio | 2-nHept-Ph |
| 1-940 | 4,5-di$CH_2$NHAc-oxathi | 2-nHept-Ph |
| 1-941 | ring 11 | 2-nHept-Ph |
| 1-942 | ring 12 | 2-nHept-Ph |
| 1-943 | ring 13 | 2-nHept-Ph |
| 1-944 | ring 14 | 2-nHept-Ph |
| 1-945 | 4-OH-cHex | 2-nHept-Ph |
| 1-946 | 5-OH-dioxa | 2-nHept-Ph |
| 1-947 | 5-OH-dithia | 2-nHept-Ph |
| 1-948 | 5-OH-oxathia | 2-nHept-Ph |
| 1-949 | 4-NHAc-cHex | 2-nHept-Ph |
| 1-950 | 5-NHAc-dioxa | 2-nHept-Ph |
| 1-951 | 5-NHAc-dithia | 2-nHept-Ph |
| 1-952 | 5-NHAc-oxathia | 2-nHept-Ph |

TABLE 1-continued

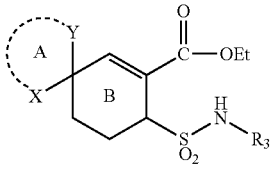

| Compound No. | X, Y | $R^3$ |
|---|---|---|
| 1-953 | 4,4-diMe-cHex | 2-nHept-Ph |
| 1-954 | 5,5-diMe-dioxa | 2-nHept-Ph |
| 1-955 | 5,5-diMe-dithia | 2-nHept-Ph |
| 1-956 | 5,5-diMe-oxathia | 2-nHept-Ph |
| 1-957 | 4,4-diHM-cHex | 2-nHept-Ph |
| 1-958 | 5,5-diHM-dioxa | 2-nHept-Ph |
| 1-959 | 5,5-diHM-dithia | 2-nHept-Ph |
| 1-960 | 5,5-diHM-oxathia | 2-nHept-Ph |
| 1-961 | ring 15 | 2-nHept-Ph |
| 1-962 | ring 16 | 2-nHept-Ph |
| 1-963 | ring 17 | 2-nHept-Ph |
| 1-964 | ring 18 | 2-nHept-Ph |
| 1-965 | 4,4-di$CO_2$Et-cHex | 2-nHept-Ph |
| 1-966 | 5,5-di$CO_2$Et-dioxa | 2-nHept-Ph |
| 1-967 | 5,5-di$CO_2$Et-dithia | 2-nHept-Ph |
| 1-968 | 5,5-di$CO_2$Et-oxathia | 2-nHept-Ph |
| 1-969 | O= | 4-F-2-nHept-Ph |
| 1-970 | S= | 4-F-2-nHept-Ph |
| 1-971 | cPr | 4-F-2-nHept-Ph |
| 1-972 | cBu | 4-F-2-nHept-Ph |
| 1-973 | cPent | 4-F-2-nHept-Ph |
| 1-974 | cHex | 4-F-2-nHept-Ph |
| 1-975 | cHept | 4-F-2-nHept-Ph |
| 1-976 | oxi | 4-F-2-nHept-Ph |
| 1-977 | oxe | 4-F-2-nHept-Ph |
| 1-978 | oxo | 4-F-2-nHept-Ph |
| 1-979 | oxa | 4-F-2-nHept-Ph |
| 1-980 | dioxo | 4-F-2-nHept-Ph |
| 1-981 | dioxa | 4-F-2-nHept-Ph |
| 1-982 | dioxe | 4-F-2-nHept-Ph |
| 1-983 | dithio | 4-F-2-nHept-Ph |
| 1-984 | dithia | 4-F-2-nHept-Ph |
| 1-985 | ring 1 | 4-F-2-nHept-Ph |
| 1-986 | ring 2 | 4-F-2-nHept-Ph |
| 1-987 | oxathio | 4-F-2-nHept-Ph |
| 1-988 | oxathia | 4-F-2-nHept-Ph |
| 1-989 | ozl | 4-F-2-nHept-Ph |
| 1-990 | ozn | 4-F-2-nHept-Ph |
| 1-991 | tzl | 4-F-2-nHept-Ph |
| 1-992 | tzn | 4-F-2-nHept-Ph |
| 1-993 | 3-HM-cPent | 4-F-2-nHept-Ph |
| 1-994 | 4-HM-dioxo | 4-F-2-nHept-Ph |
| 1-995 | 4-HM-dithio | 4-F-2-nHept-Ph |
| 1-996 | 4-HM-oxathio | 4-F-2-nHept-Ph |
| 1-997 | 3,4-diHM-cPent | 4-F-2-nHept-Ph |
| 1-998 | 4,5-diHM-dioxo | 4-F-2-nHept-Ph |
| 1-999 | 4,5-diHM-dithio | 4-F-2-nHept-Ph |
| 1-1000 | 4,5-diHM-oxathio | 4-F-2-nHept-Ph |
| 1-1001 | 3,4-diHE-cPent | 4-F-2-nHept-Ph |
| 1-1002 | 4,5-diHE-dioxo | 4-F-2-nHept-Ph |
| 1-1003 | 4,5-diHE-dithio | 4-F-2-nHept-Ph |
| 1-1004 | 4,5-diHE-oxathio | 4-F-2-nHept-Ph |
| 1-1005 | 3-HE-cPent | 4-F-2-nHept-Ph |
| 1-1006 | 4-HE-dioxo | 4-F-2-nHept-Ph |
| 1-1007 | 4-HE-dithio | 4-F-2-nHept-Ph |
| 1-1008 | 4-HE-oxathio | 4-F-2-nHept-Ph |
| 1-1009 | 3-HP-cPent | 4-F-2-nHept-Ph |
| 1-1010 | 4-HP-dioxo | 4-F-2-nHept-Ph |
| 1-1011 | 4-HP-dithio | 4-F-2-nHept-Ph |
| 1-1012 | 4-HP-oxathio | 4-F-2-nHept-Ph |
| 1-1013 | 3-HB-cPent | 4-F-2-nHept-Ph |
| 1-1014 | 4-HB-dioxo | 4-F-2-nHept-Ph |
| 1-1015 | 4-HB-dithio | 4-F-2-nHept-Ph |
| 1-1016 | 4-HB-oxathio | 4-F-2-nHept-Ph |
| 1-1017 | ring 3 | 4-F-2-nHept-Ph |
| 1-1018 | ring 4 | 4-F-2-nHept-Ph |
| 1-1019 | ring 5 | 4-F-2-nHept-Ph |
| 1-1020 | ring 6 | 4-F-2-nHept-Ph |

TABLE 1-continued

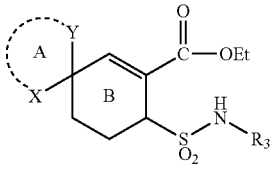

| Compound No. | X, Y | $R^3$ |
|---|---|---|
| 1-1021 | ring 7 | 4-F-2-nHept-Ph |
| 1-1022 | ring 8 | 4-F-2-nHept-Ph |
| 1-1023 | ring 9 | 4-F-2-nHept-Ph |
| 1-1024 | ring 10 | 4-F-2-nHept-Ph |
| 1-1025 | 3,4-di$CH_2$NHAc-cPent | 4-F-2-nHept-Ph |
| 1-1026 | 4,5-di$CH_2$NHAc-dioxo | 4-F-2-nHept-Ph |
| 1-1027 | 4,5-di$CH_2$NHAc-dithio | 4-F-2-nHept-Ph |
| 1-1028 | 4,5-di$CH_2$NHAc-oxathio | 4-F-2-nHept-Ph |
| 1-1029 | ring 11 | 4-F-2-nHept-Ph |
| 1-1030 | ring 12 | 4-F-2-nHept-Ph |
| 1-1031 | ring 13 | 4-F-2-nHept-Ph |
| 1-1032 | ring 14 | 4-F-2-nHept-Ph |
| 1-1033 | 4-OH-cHex | 4-F-2-nHept-Ph |
| 1-1034 | 5-OH-dioxa | 4-F-2-nHept-Ph |
| 1-1035 | 5-OH-dithia | 4-F-2-nHept-Ph |
| 1-1036 | 5-OH-oxathia | 4-F-2-nHept-Ph |
| 1-1037 | 4-NHAc-cHex | 4-F-2-nHept-Ph |
| 1-1038 | 5-NHAc-dioxa | 4-F-2-nHept-Ph |
| 1-1039 | 5-NHAc-dithia | 4-F-2-nHept-Ph |
| 1-1040 | 5-NHAc-oxathia | 4-F-2-nHept-Ph |
| 1-1041 | 4,4-diMe-cHex | 4-F-2-nHept-Ph |
| 1-1042 | 5,5-diMe-dioxa | 4-F-2-nHept-Ph |
| 1-1043 | 5,5-diMe-dithia | 4-F-2-nHept-Ph |
| 1-1044 | 5,5-diMe-oxathia | 4-F-2-nHept-Ph |
| 1-1045 | 4,4-diHM-cHex | 4-F-2-nHept-Ph |
| 1-1046 | 5,5-diHM-dioxa | 4-F-2-nHept-Ph |
| 1-1047 | 5,5-diHM-dithia | 4-F-2-nHept-Ph |
| 1-1048 | 5,5-diHM-oxathia | 4-F-2-nHept-Ph |
| 1-1049 | ring 15 | 4-F-2-nHept-Ph |
| 1-1050 | ring 16 | 4-F-2-nHept-Ph |
| 1-1051 | ring 17 | 4-F-2-nHept-Ph |
| 1-1052 | ring 18 | 4-F-2-nHept-Ph |
| 1-1053 | 4,4-di$CO_2$Et-cHex | 4-F-2-nHept-Ph |
| 1-1054 | 5,5-di$CO_2$Et-dioxa | 4-F-2-nHept-Ph |
| 1-1055 | 5,5-di$CO_2$Et-dithia | 4-F-2-nHept-Ph |
| 1-1056 | 5,5-di$CO_2$Et-oxathia | 4-F-2-nHept-Ph |
| 1-1057 | H,H | Pyr |
| 1-1058 | O= | Pyr |
| 1-1059 | S= | Pyr |
| 1-1060 | cPent | Pyr |
| 1-1061 | cHex | Pyr |
| 1-1062 | dioxo | Pyr |
| 1-1063 | dioxa | Pyr |
| 1-1064 | dithio | Pyr |
| 1-1065 | dithia | Pyr |
| 1-1066 | oxathio | Pyr |
| 1-1067 | oxathia | Pyr |
| 1-1068 | 4-HM-dioxo | Pyr |
| 1-1069 | 4,5-diHM-dioxo | Pyr |
| 1-1070 | 4,5-diHE-dioxo | Pyr |
| 1-1071 | 5-OH-dioxa | Pyr |
| 1-1072 | 5-NHAc-dioxa | Pyr |
| 1-1073 | 5,5-diHM-dioxa | Pyr |
| 1-1074 | H,H | 2-F—Pyr |
| 1-1075 | O= | 2-F—Pyr |
| 1-1076 | S= | 2-F—Pyr |
| 1-1077 | cPent | 2-F—Pyr |
| 1-1078 | cHex | 2-F—Pyr |
| 1-1079 | dioxo | 2-F—Pyr |
| 1-1080 | dioxa | 2-F—Pyr |
| 1-1081 | dithio | 2-F—Pyr |
| 1-1082 | dithia | 2-F—Pyr |
| 1-1083 | oxathia | 2-F—Pyr |
| 1-1084 | oxathia | 2-F—Pyr |
| 1-1085 | 4-HM-dioxo | 2-F—Pyr |
| 1-1086 | 4,5-diHM-dioxo | 2-F—Pyr |
| 1-1087 | 4,5-diHE-dioxo | 2-F—Pyr |
| 1-1088 | 5-OH-dioxa | 2-F—Pyr |

TABLE 1-continued

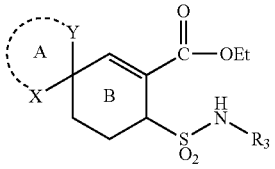

| Compound No. | X, Y | $R^3$ |
|---|---|---|
| 1-1089 | 5-NHAc-dioxa | 2-F—Pyr |
| 1-1090 | 5,5-diHM-dioxa | 2-F—Pyr |
| 1-1091 | H,H | 2-Cl—Pyr |
| 1-1092 | O= | 2-Cl—Pyr |
| 1-1093 | S= | 2-Cl—Pyr |
| 1-1094 | cPent | 2-Cl—Pyr |
| 1-1095 | cHex | 2-Cl—Pyr |
| 1-1096 | dioxo | 2-Cl—Pyr |
| 1-1097 | dioxa | 2-Cl—Pyr |
| 1-1098 | dithio | 2-Cl—Pyr |
| 1-1099 | dithia | 2-Cl—Pyr |
| 1-1100 | oxathio | 2-Cl—Pyr |
| 1-1101 | oxathia | 2-Cl—Pyr |
| 1-1102 | 4-HM-dioxo | 2-Cl—Pyr |
| 1-1103 | 4,5-diHM-dioxo | 2-Cl—Pyr |
| 1-1104 | 4,5-diHE-dioxo | 2-Cl—Pyr |
| 1-1105 | 5-OH-dioxa | 2-Cl—Pyr |
| 1-1106 | 5-NHAc-dioxa | 2-Cl—Pyr |
| 1-1107 | 5,5-diHM-dioxa | 2-Cl—Pyr |
| 1-1108 | H,H | 2-Br—Pyr |
| 1-1109 | O= | 2-Br—Pyr |
| 1-1110 | S= | 2-Br—Pyr |
| 1-1111 | cPent | 2-Br—Pyr |
| 1-1112 | cHex | 2-Br—Pyr |
| 1-1113 | dioxo | 2-Br—Pyr |
| 1-1114 | dioxa | 2-Br—Pyr |
| 1-1115 | dithio | 2-Br—Pyr |
| 1-1116 | dithia | 2-Br—Pyr |
| 1-1117 | oxathio | 2-Br—Pyr |
| 1-1118 | oxathia | 2-Br—Pyr |
| 1-1119 | 4-HM-dioxo | 2-Br—Pyr |
| 1-1120 | 4,5-diHM-dioxo | 2-Br—Pyr |
| 1-1121 | 4,5-diHE-dioxo | 2-Br—Pyr |
| 1-1122 | 5-OH-dioxa | 2-Br—Pyr |
| 1-1123 | 5-NHAc-dioxa | 2-Br—Pyr |
| 1-1124 | 5,5-diHM-dioxa | 2-Br—Pyr |
| 1-1125 | H,H | 2,5-diF—Pyr |
| 1-1126 | O= | 2,5-diF—Pyr |
| 1-1127 | S= | 2,5-diF—Pyr |
| 1-1128 | cPent | 2,5-diF—Pyr |
| 1-1129 | cHex | 2,5-diF—Pyr |
| 1-1130 | dioxo | 2,5-diF—Pyr |
| 1-1131 | dioxa | 2,5-diF—Pyr |
| 1-1132 | dithio | 2,5-diF—Pyr |
| 1-1133 | dithia | 2,5-diF—Pyr |
| 1-1134 | oxathio | 2,5-diF—Pyr |
| 1-1135 | oxathia | 2,5-diF—Pyr |
| 1-1136 | 4-HM-dioxo | 2,5-diF—Pyr |
| 1-1137 | 4,5-diHM-dioxo | 2,5-diF—Pyr |
| 1-1138 | 4,5-diHE-dioxo | 2,5-diF—Pyr |
| 1-1139 | 5-OH-dioxa | 2,5-diF—Pyr |
| 1-1140 | 5-NHAc-dioxa | 2,5-diF—Pyr |
| 1-1141 | 5,5-diHM-dioxa | 2,5-diF—Pyr |
| 1-1142 | H,H | 2,5-diCl—Pyr |
| 1-1143 | O= | 2,5-diCl—Pyr |
| 1-1144 | S= | 2,5-diCl—Pyr |
| 1-1145 | cPent | 2,5-diCl—Pyr |
| 1-1146 | cHex | 2,5-diCl—Pyr |
| 1-1147 | dioxo | 2,5-diCl—Pyr |
| 1-1148 | dioxa | 2,5-diCl—Pyr |
| 1-1149 | dithio | 2,5-diCl—Pyr |
| 1-1150 | dithia | 2,5-diCl—Pyr |
| 1-1151 | oxathio | 2,5-diCl—Pyr |
| 1-1152 | oxathia | 2,5-diCl—Pyr |
| 1-1153 | 4-HM-dioxo | 2,5-diCl—Pyr |
| 1-1154 | 4,5-diHM-dioxo | 2,5-diCl—Pyr |
| 1-1155 | 4,5-diHE-dioxo | 2,5-diCl—Pyr |
| 1-1156 | 5-OH-dioxa | 2,5-diCl—Pyr |

TABLE 1-continued

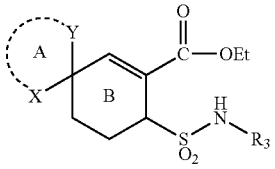

| Compound No. | X, Y | $R^3$ |
|---|---|---|
| 1-1157 | 5-NHAc-dioxa | 2,5-diCl—Pyr |
| 1-1158 | 5,5-diHM-dioxa | 2,5-diCl—Pyr |
| 1-1159 | H,H | 2,5-diBr—Pyr |
| 1-1160 | O= | 2,5-diBr—Pyr |
| 1-1161 | S= | 2,5-diBr—Pyr |
| 1-1162 | cPent | 2,5-diBr—Pyr |
| 1-1163 | cHex | 2,5-diBr—Pyr |
| 1-1164 | dioxo | 2,5-diBr—Pyr |
| 1-1165 | dioxa | 2,5-diBr—Pyr |
| 1-1166 | dithio | 2,5-diBr—Pyr |
| 1-1167 | dithia | 2,5-diBr—Pyr |
| 1-1168 | oxathio | 2,5-diBr—Pyr |
| 1-1169 | oxathia | 2,5-diBr—Pyr |
| 1-1170 | 4-HM-dioxo | 2,5-diBr—Pyr |
| 1-1171 | 4,5-diHM-dioxo | 2,5-diBr—Pyr |
| 1-1172 | 4,5-diHE-dioxo | 2,5-diBr—Pyr |
| 1-1173 | 5-OH-dioxa | 2,5-diBr—Pyr |
| 1-1174 | 5-NHAc-dioxa | 2,5-diBr—Pyr |
| 1-1175 | 5,5-diHM-dioxa | 2,5-diBr—Pyr |
| 1-1176 | H,H | 2-Me—Pyr |
| 1-1177 | O= | 2-Me—Pyr |
| 1-1178 | S= | 2-Me—Pyr |
| 1-1179 | cPent | 2-Me—Pyr |
| 1-1180 | cHex | 2-Me—Pyr |
| 1-1181 | dioxo | 2-Me—Pyr |
| 1-1182 | dioxa | 2-Me—Pyr |
| 1-1183 | dithio | 2-Me—Pyr |
| 1-1184 | dithia | 2-Me—Pyr |
| 1-1185 | oxathio | 2-Me—Pyr |
| 1-1186 | oxathia | 2-Me—Pyr |
| 1-1187 | 4-HM-dioxo | 2-Me—Pyr |
| 1-1188 | 4,5-diHM-dioxo | 2-Me—Pyr |
| 1-1189 | 4,5-diHE-dioxo | 2-Me—Pyr |
| 1-1190 | 5-OH-dioxa | 2-Me—Pyr |
| 1-1191 | 5-NHAc-dioxa | 2-Me—Pyr |
| 1-1192 | 5,5-diHM-dioxa | 2-Me—Pyr |
| 1-1193 | H,H | 2-Et—Pyr |
| 1-1194 | O= | 2-Et—Pyr |
| 1-1195 | S= | 2-Et—Pyr |
| 1-1196 | cPent | 2-Et—Pyr |
| 1-1197 | cHex | 2-Et—Pyr |
| 1-1198 | dioxo | 2-Et—Pyr |
| 1-1199 | dioxa | 2-Et—Pyr |
| 1-1200 | dithio | 2-Et—Pyr |
| 1-1201 | dithia | 2-Et—Pyr |
| 1-1202 | oxathio | 2-Et—Pyr |
| 1-1203 | oxathia | 2-Et—Pyr |
| 1-1204 | 4-HM-dioxo | 2-Et—Pyr |
| 1-1205 | 4,5-diHM-dioxo | 2-Et—Pyr |
| 1-1206 | 4,5-diHE-dioxo | 2-Et—Pyr |
| 1-1207 | 5-OH-dioxa | 2-Et—Pyr |
| 1-1208 | 5-NHAc-dioxa | 2-Et—Pyr |
| 1-1209 | 5,5-diHM-dioxa | 2-Et—Pyr |
| 1-1210 | H,H | 2-nPr—Pyr |
| 1-1211 | O= | 2-nPr—Pyr |
| 1-1212 | S= | 2-nPr—Pyr |
| 1-1213 | cPent | 2-nPr—Pyr |
| 1-1214 | cHex | 2-nPr—Pyr |
| 1-1215 | dioxo | 2-nPr—Pyr |
| 1-1216 | dioxa | 2-nPr—Pyr |
| 1-1217 | dithio | 2-nPr—Pyr |
| 1-1218 | dithia | 2-nPr—Pyr |
| 1-1219 | oxathio | 2-nPr—Pyr |
| 1-1220 | oxathia | 2-nPr—Pyr |
| 1-1221 | 4-HM-dioxo | 2-nPr—Pyr |
| 1-1222 | 4,5-diHM-dioxo | 2-nPr—Pyr |
| 1-1223 | 4,5-diHE-dioxo | 2-nPr—Pyr |
| 1-1224 | 5-OH-dioxa | 2-nPr—Pyr |

TABLE 1-continued

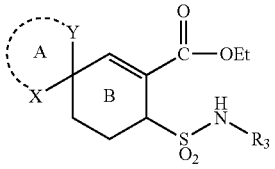

| Compound No. | X, Y | $R^3$ |
|---|---|---|
| 1-1225 | 5-NHAc-dioxa | 2-nPr—Pyr |
| 1-1226 | 5,5-diHM-dioxa | 2-nPr—Pyr |
| 1-1227 | H,H | 2-nBu—Pyr |
| 1-1228 | O= | 2-nBu—Pyr |
| 1-1229 | S= | 2-nBu—Pyr |
| 1-1230 | cPent | 2-nBu—Pyr |
| 1-1231 | cHex | 2-nBu—Pyr |
| 1-1232 | dioxo | 2-nBu—Pyr |
| 1-1233 | dioxa | 2-nBu—Pyr |
| 1-1234 | dithio | 2-nBu—Pyr |
| 1-1235 | dithia | 2-nBu—Pyr |
| 1-1236 | oxathio | 2-nBu—Pyr |
| 1-1237 | oxathia | 2-nBu—Pyr |
| 1-1238 | 4-HM-dioxo | 2-nBu—Pyr |
| 1-1239 | 4,5-diHM-dioxo | 2-nBu—Pyr |
| 1-1240 | 4,5-diHE-dioxo | 2-nBu—Pyr |
| 1-1241 | 5-OH-dioxa | 2-nBu—Pyr |
| 1-1242 | 5-NHAc-dioxa | 2-nBu—Pyr |
| 1-1243 | 5,5-diHM-dioxa | 2-nBu—Pyr |
| 1-1244 | H,H | 2-nPent-Pyr |
| 1-1245 | O= | 2-nPent-Pyr |
| 1-1246 | S= | 2-nPent-Pyr |
| 1-1247 | cPent | 2-nPent-Pyr |
| 1-1248 | cHex | 2-nPent-Pyr |
| 1-1249 | dioxo | 2-nPent-Pyr |
| 1-1250 | dioxa | 2-nPent-Pyr |
| 1-1251 | dithio | 2-nPent-Pyr |
| 1-1252 | dithia | 2-nPent-Pyr |
| 1-1253 | oxathio | 2-nPent-Pyr |
| 1-1254 | oxathia | 2-nPent-Pyr |
| 1-1255 | 4-HM-dioxo | 2-nPent-Pyr |
| 1-1256 | 4,5-diHM-dioxo | 2-nPent-Pyr |
| 1-1257 | 4,5-diHE-dioxo | 2-nPent-Pyr |
| 1-1258 | 5-OH-dioxa | 2-nPent-Pyr |
| 1-1259 | 5-NHAc-dioxa | 2-nPent-Pyr |
| 1-1260 | 5,5-diHM-dioxa | 2-nPent-Pyr |
| 1-1261 | H,H | 2-nHex—Pyr |
| 1-1262 | O= | 2-nHex—Pyr |
| 1-1263 | S= | 2-nHex—Pyr |
| 1-1264 | cPent | 2-nHex—Pyr |
| 1-1265 | cHex | 2-nHex—Pyr |
| 1-1266 | dioxo | 2-nHex—Pyr |
| 1-1267 | dioxa | 2-nHex—Pyr |
| 1-1268 | dithio | 2-nHex—Pyr |
| 1-1269 | dithia | 2-nHex—Pyr |
| 1-1270 | oxathio | 2-nHex—Pyr |
| 1-1271 | oxathia | 2-nHex—Pyr |
| 1-1272 | 4-HM-dioxo | 2-nHex—Pyr |
| 1-1273 | 4,5-diHM-dioxo | 2-nHex—Pyr |
| 1-1274 | 4,5-diHE-dioxo | 2-nHex—Pyr |
| 1-1275 | 5-OH-dioxa | 2-nHex—Pyr |
| 1-1276 | 5-NHAc-dioxa | 2-nHex—Pyr |
| 1-1277 | 5,5-diHM-dioxa | 2-nHex—Pyr |
| 1-1278 | H,H | 2-nHept-Pyr |
| 1-1279 | O= | 2-nHept-Pyr |
| 1-1280 | S= | 2-nHept-Pyr |
| 1-1281 | cPent | 2-nHept-Pyr |
| 1-1282 | cHex | 2-nHept-Pyr |
| 1-1283 | dioxo | 2-nHept-Pyr |
| 1-1284 | dioxa | 2-nHept-Pyr |
| 1-1285 | dithio | 2-nHept-Pyr |
| 1-1286 | dithia | 2-nHept-Pyr |
| 1-1287 | oxathio | 2-nHept-Pyr |
| 1-1288 | oxathia | 2-nHept-Pyr |
| 1-1289 | 4-HM-dioxo | 2-nHept-Pyr |
| 1-1290 | 4,5-diHM-dioxo | 2-nHept-Pyr |
| 1-1291 | 4,5-diHE-dioxo | 2-nHept-Pyr |
| 1-1292 | 5-OH-dioxa | 2-nHept-Pyr |

TABLE 1-continued

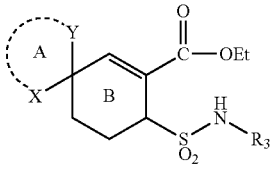

| Compound No. | X, Y | $R^3$ |
|---|---|---|
| 1-1293 | 5-NHAc-dioxa | 2-nHept-Pyr |
| 1-1294 | 5,5-diHM-dioxa | 2-nHept-Pyr |
| 1-1295 | H,H | 2-nOct-Pyr |
| 1-1296 | O═ | 2-nOct-Pyr |
| 1-1297 | S═ | 2-nOct-Pyr |
| 1-1298 | cPent | 2-nOct-Pyr |
| 1-1299 | cHex | 2-nOct-Pyr |
| 1-1300 | dioxo | 2-nOct-Pyr |
| 1-1301 | dioxa | 2-nOct-Pyr |
| 1-1302 | dithio | 2-nOct-Pyr |
| 1-1303 | dithia | 2-nOct-Pyr |
| 1-1304 | oxathio | 2-nOct-Pyr |
| 1-1305 | oxathia | 2-nOct-Pyr |
| 1-1306 | 4-HM-dioxo | 2-nOct-Pyr |
| 1-1307 | 4,5-diHM-dioxo | 2-nOct-Pyr |
| 1-1308 | 4,5-diHE-dioxo | 2-nOct-Pyr |
| 1-1309 | 5-OH-dioxa | 2-nOct-Pyr |
| 1-1310 | 5-NHAc-dioxa | 2-nOct-Pyr |
| 1-1311 | 5,5-diHM-dioxa | 2-nOct-Pyr |
| 1-1312 | H,H | 2-cPrl-Pyr |
| 1-1313 | O═ | 2-cPrl-Pyr |
| 1-1314 | S═ | 2-cPrl-Pyr |
| 1-1315 | cPent | 2-cPrl-Pyr |
| 1-1316 | cHex | 2-cPrl-Pyr |
| 1-1317 | dioxo | 2-cPrl-Pyr |
| 1-1318 | dioxa | 2-cPrl-Pyr |
| 1-1319 | dithio | 2-cPrl-Pyr |
| 1-1320 | dithia | 2-cPrl-Pyr |
| 1-1321 | oxathio | 2-cPrl-Pyr |
| 1-1322 | oxathia | 2-cPrl-Pyr |
| 1-1323 | 4-HM-dioxo | 2-cPrl-Pyr |
| 1-1324 | 4,5-diHM-dioxo | 2-cPrl-Pyr |
| 1-1325 | 4,5-diHE-dioxo | 2-cPrl-Pyr |
| 1-1326 | 5-OH-dioxa | 2-cPrl-Pyr |
| 1-1327 | 5-NHAc-dioxa | 2-cPrl-Pyr |
| 1-1328 | 5,5-diHM-dioxa | 2-cPrl-Pyr |
| 1-1329 | H,H | 2-Ph—Pyr |
| 1-1330 | O═ | 2-Ph—Pyr |
| 1-1331 | S═ | 2-Ph—Pyr |
| 1-1332 | cPent | 2-Ph—Pyr |
| 1-1333 | cHex | 2-Ph—Pyr |
| 1-1334 | dioxo | 2-Ph—Pyr |
| 1-1335 | dioxa | 2-Ph—Pyr |
| 1-1336 | dithio | 2-Ph—Pyr |
| 1-1337 | dithia | 2-Ph—Pyr |
| 1-1338 | oxathio | 2-Ph—Pyr |
| 1-1339 | oxathia | 2-Ph—Pyr |
| 1-1340 | 4-HM-dioxo | 2-Ph—Pyr |
| 1-1341 | 4,5-diHM-dioxo | 2-Ph—Pyr |
| 1-1342 | 4,5-diHE-dioxo | 2-Ph—Pyr |
| 1-1343 | 5-OH-dioxa | 2-Ph—Pyr |
| 1-1344 | 5-NHAc-dioxa | 2-Ph—Pyr |
| 1-1345 | 5,5-diHM-dioxa | 2-Ph—Pyr |
| 1-1346 | H,H | 2,5-diMe—Pyr |
| 1-1347 | O═ | 2,5-diMe—Pyr |
| 1-1348 | S═ | 2,5-diMe—Pyr |
| 1-1349 | cPent | 2,5-diMe—Pyr |
| 1-1350 | cHex | 2,5-diMe—Pyr |
| 1-1351 | dioxo | 2,5-diMe—Pyr |
| 1-1352 | dioxa | 2,5-diMe—Pyr |
| 1-1353 | dithio | 2,5-diMe—Pyr |
| 1-1354 | dithia | 2,5-diMe—Pyr |
| 1-1355 | oxathio | 2,5-diMe—Pyr |
| 1-1356 | oxathia | 2,5-diMe—Pyr |
| 1-1357 | 4-HM-dioxo | 2,5-diMe—Pyr |
| 1-1358 | 4,5-diHM-dioxo | 2,5-diMe—Pyr |
| 1-1359 | 4,5-diHE-dioxo | 2,5-diMe—Pyr |
| 1-1360 | 5-OH-dioxa | 2,5-diMe—Pyr |

TABLE 1-continued

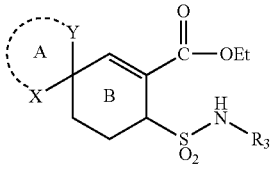

| Compound No. | X, Y | $R^3$ |
|---|---|---|
| 1-1361 | 5-NHAc-dioxa | 2,5-diMe—Pyr |
| 1-1362 | 5,5-diHM-dioxa | 2,5-diMe—Pyr |
| 1-1363 | O═ | 2-Br—Ph |
| 1-1364 | S═ | 2-Br—Ph |
| 1-1365 | cPr | 2-Br—Ph |
| 1-1366 | cBu | 2-Br—Ph |
| 1-1367 | cPent | 2-Br—Ph |
| 1-1368 | cHex | 2-Br—Ph |
| 1-1369 | cHept | 2-Br—Ph |
| 1-1370 | oxi | 2-Br—Ph |
| 1-1371 | oxe | 2-Br—Ph |
| 1-1372 | oxo | 2-Br—Ph |
| 1-1373 | oxa | 2-Br—Ph |
| 1-1374 | dioxo | 2-Br—Ph |
| 1-1375 | dioxa | 2-Br—Ph |
| 1-1376 | dioxe | 2-Br—Ph |
| 1-1377 | dithio | 2-Br—Ph |
| 1-1378 | dithia | 2-Br—Ph |
| 1-1379 | ring 1 | 2-Br—Ph |
| 1-1380 | ring 2 | 2-Br—Ph |
| 1-1381 | oxathio | 2-Br—Ph |
| 1-1382 | oxathia | 2-Br—Ph |
| 1-1383 | ozl | 2-Br—Ph |
| 1-1384 | ozn | 2-Br—Ph |
| 1-1385 | tzl | 2-Br—Ph |
| 1-1386 | tzn | 2-Br—Ph |
| 1-1387 | 3-HM-cPent | 2-Br—Ph |
| 1-1388 | 4-HM-dioxo | 2-Br—Ph |
| 1-1389 | 4-HM-dithio | 2-Br—Ph |
| 1-1390 | 4-HM-oxathio | 2-Br—Ph |
| 1-1391 | 3,4-diHM-cPent | 2-Br—Ph |
| 1-1392 | 4,5-diHM-dioxo | 2-Br—Ph |
| 1-1393 | 4,5-diHM-dithio | 2-Br—Ph |
| 1-1394 | 4,5-diHM-oxathio | 2-Br—Ph |
| 1-1395 | 3,4-diHE-cPent | 2-Br—Ph |
| 1-1396 | 4,5-diHE-dioxo | 2-Br—Ph |
| 1-1397 | 4,5-diHE-dithio | 2-Br—Ph |
| 1-1398 | 4,5-diHE-oxathio | 2-Br—Ph |
| 1-1399 | 3-HE-cPent | 2-Br—Ph |
| 1-1400 | 4-HE-dioxo | 2-Br—Ph |
| 1-1401 | 4-HE-dithio | 2-Br—Ph |
| 1-1402 | 4-HE-oxathio | 2-Br—Ph |
| 1-1403 | 3-HP-cPent | 2-Br—Ph |
| 1-1404 | 4-HP-dioxo | 2-Br—Ph |
| 1-1405 | 4-HP-dithio | 2-Br—Ph |
| 1-1406 | 4-HP-oxathio | 2-Br—Ph |
| 1-1407 | 3-HB-cPent | 2-Br—Ph |
| 1-1408 | 4-HB-dioxo | 2-Br—Ph |
| 1-1409 | 4-HB-dithio | 2-Br—Ph |
| 1-1410 | 4-HB-oxathio | 2-Br—Ph |
| 1-1411 | ring 3 | 2-Br—Ph |
| 1-1412 | ring 4 | 2-Br—Ph |
| 1-1413 | ring 5 | 2-Br—Ph |
| 1-1414 | ring 6 | 2-Br—Ph |
| 1-1415 | ring 7 | 2-Br—Ph |
| 1-1416 | ring 8 | 2-Br—Ph |
| 1-1417 | ring 9 | 2-Br—Ph |
| 1-1418 | ring 10 | 2-Br—Ph |
| 1-1419 | 3,4-di$CH_2$NHAc-cPent | 2-Br—Ph |
| 1-1420 | 4,5-di$CH_2$NHAc-dioxo | 2-Br—Ph |
| 1-1421 | 4,5-di$CH_2$NHAc-dithio | 2-Br—Ph |
| 1-1422 | 4,5-di$CH_2$NHAc-oxathio | 2-Br—Ph |
| 1-1423 | ring 11 | 2-Br—Ph |
| 1-1424 | ring 12 | 2-Br—Ph |
| 1-1425 | ring 13 | 2-Br—Ph |
| 1-1426 | ring 14 | 2-Br—Ph |
| 1-1427 | 4-OH-cHex | 2-Br—Ph |
| 1-1428 | 5-OH-dioxa | 2-Br—Ph |

TABLE 1-continued

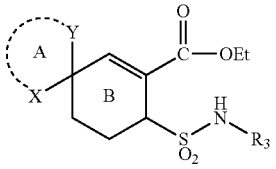

| Compound No. | X, Y | $R^3$ |
|---|---|---|
| 1-1429 | 5-OH-dithia | 2-Br—Ph |
| 1-1430 | 5-OH-oxathia | 2-Br—Ph |
| 1-1431 | 4-NHAc-cHex | 2-Br—Ph |
| 1-1432 | 5-NHAc-dioxa | 2-Br—Ph |
| 1-1433 | 5-NHAc-dithia | 2-Br—Ph |
| 1-1434 | 5-NHAc-oxathia | 2-Br—Ph |
| 1-1435 | 4,4-diMe-cHex | 2-Br—Ph |
| 1-1436 | 5,5-diMe-dioxa | 2-Br—Ph |
| 1-1437 | 5,5-diMe-dithia | 2-Br—Ph |
| 1-1438 | 5,5-diMe-oxathia | 2-Br—Ph |
| 1-1439 | 4,4-diHM-cHex | 2-Br—Ph |
| 1-1440 | 5,5-diHM-dioxa | 2-Br—Ph |
| 1-1441 | 5,5-diHM-dithia | 2-Br—Ph |
| 1-1442 | 5,5-diHM-oxathia | 2-Br—Ph |
| 1-1443 | ring 15 | 2-Br—Ph |
| 1-1444 | ring 16 | 2-Br—Ph |
| 1-1445 | ring 17 | 2-Br—Ph |
| 1-1446 | ring 18 | 2-Br—Ph |
| 1-1447 | 4,4-di$CO_2$Et-cHex | 2-Br—Ph |
| 1-1448 | 5,5-di$CO_2$Et-dioxa | 2-Br—Ph |
| 1-1449 | 5,5-di$CO_2$Et-dithia | 2-Br—Ph |
| 1-1450 | 5,5-di$CO_2$Et-oxathia | 2-Br—Ph |
| 1-1451 | O= | 2-Cl-6-Me—Ph |
| 1-1452 | S= | 2-Cl-6-Me—Ph |
| 1-1453 | cPr | 2-Cl-6-Me—Ph |
| 1-1454 | cBu | 2-Cl-6-Me—Ph |
| 1-1455 | cPent | 2-Cl-6-Me—Ph |
| 1-1456 | cHex | 2-Cl-6-Me—Ph |
| 1-1457 | cHept | 2-Cl-6-Me—Ph |
| 1-1458 | oxi | 2-Cl-6-Me—Ph |
| 1-1459 | oxe | 2-Cl-6-Me—Ph |
| 1-1460 | oxo | 2-Cl-6-Me—Ph |
| 1-1461 | oxa | 2-Cl-6-Me—Ph |
| 1-1462 | dioxo | 2-Cl-6-Me—Ph |
| 1-1463 | dioxa | 2-Cl-6-Me—Ph |
| 1-1464 | dioxe | 2-Cl-6-Me—Ph |
| 1-1465 | dithio | 2-Cl-6-Me—Ph |
| 1-1466 | dithia | 2-Cl-6-Me—Ph |
| 1-1467 | ring 1 | 2-Cl-6-Me—Ph |
| 1-1468 | ring 2 | 2-Cl-6-Me—Ph |
| 1-1469 | oxathio | 2-Cl-6-Me—Ph |
| 1-1470 | oxathia | 2-Cl-6-Me—Ph |
| 1-1471 | ozl | 2-Cl-6-Me—Ph |
| 1-1472 | ozn | 2-Cl-6-Me—Ph |
| 1-1473 | tzl | 2-Cl-6-Me—Ph |
| 1-1474 | tzn | 2-Cl-6-Me—Ph |
| 1-1475 | 3-HM-cPent | 2-Cl-6-Me—Ph |
| 1-1476 | 4-HM-dioxo | 2-Cl-6-Me—Ph |
| 1-1477 | 4-HM-dithio | 2-Cl-6-Me—Ph |
| 1-1478 | 4-HM-oxathio | 2-Cl-6-Me—Ph |
| 1-1479 | 3,4-diHM-cPent | 2-Cl-6-Me—Ph |
| 1-1480 | 4,5-diHM-dioxo | 2-Cl-6-Me—Ph |
| 1-1481 | 4,5-diHM-dithio | 2-Cl-6-Me—Ph |
| 1-1482 | 4,5-diHM-oxathio | 2-Cl-6-Me—Ph |
| 1-1483 | 3,4-diHE-cPent | 2-Cl-6-Me—Ph |
| 1-1484 | 4,5-diHE-dioxo | 2-Cl-6-Me—Ph |
| 1-1485 | 4,5-diHE-dithio | 2-Cl-6-Me—Ph |
| 1-1486 | 4,5-diHE-oxathio | 2-Cl-6-Me—Ph |
| 1-1487 | 3-HE-cPent | 2-Cl-6-Me—Ph |
| 1-1488 | 4-HE-dioxo | 2-Cl-6-Me—Ph |
| 1-1489 | 4-HE-dithio | 2-Cl-6-Me—Ph |
| 1-1490 | 4-HE-oxathio | 2-Cl-6-Me—Ph |
| 1-1491 | 3-HP-cPent | 2-Cl-6-Me—Ph |
| 1-1492 | 4-HP-dioxo | 2-Cl-6-Me—Ph |
| 1-1493 | 4-HP-dithio | 2-Cl-6-Me—Ph |
| 1-1494 | 4-HP-oxathio | 2-Cl-6-Me—Ph |
| 1-1495 | 3-HB-cPent | 2-Cl-6-Me—Ph |
| 1-1496 | 4-HB-dioxo | 2-Cl-6-Me—Ph |

TABLE 1-continued

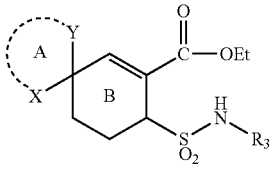

| Compound No. | X, Y | $R^3$ |
|---|---|---|
| 1-1497 | 4-HB-dithio | 2-Cl-6-Me—Ph |
| 1-1498 | 4-HB-oxathio | 2-Cl-6-Me—Ph |
| 1-1499 | ring 3 | 2-Cl-6-Me—Ph |
| 1-1500 | ring 4 | 2-Cl-6-Me—Ph |
| 1-1501 | ring 5 | 2-Cl-6-Me—Ph |
| 1-1502 | ring 6 | 2-Cl-6-Me—Ph |
| 1-1503 | ring 7 | 2-Cl-6-Me—Ph |
| 1-1504 | ring 8 | 2-Cl-6-Me—Ph |
| 1-1505 | ring 9 | 2-Cl-6-Me—Ph |
| 1-1506 | ring 10 | 2-Cl-6-Me—Ph |
| 1-1507 | 3,4-di$CH_2$NHAc-cPent | 2-Cl-6-Me—Ph |
| 1-1508 | 4,5-di$CH_2$NHAc-dioxo | 2-Cl-6-Me—Ph |
| 1-1509 | 4,5-di$CH_2$NHAc-dithio | 2-Cl-6-Me—Ph |
| 1-1510 | 4,5-di$CH_2$NHAc-oxathio | 2-Cl-6-Me—Ph |
| 1-1511 | ring 11 | 2-Cl-6-Me—Ph |
| 1-1512 | ring 12 | 2-Cl-6-Me—Ph |
| 1-1513 | ring 13 | 2-Cl-6-Me—Ph |
| 1-1514 | ring 14 | 2-Cl-6-Me—Ph |
| 1-1515 | 4-OH-cHex | 2-Cl-6-Me—Ph |
| 1-1516 | 5-OH-dioxa | 2-Cl-6-Me—Ph |
| 1-1517 | 5-OH-dithia | 2-Cl-6-Me—Ph |
| 1-1518 | 5-OH-oxathia | 2-Cl-6-Me—Ph |
| 1-1519 | 4-NHAc-cHex | 2-Cl-6-Me—Ph |
| 1-1520 | 5-NHAc-dioxa | 2-Cl-6-Me—Ph |
| 1-1521 | 5-NHAc-dithia | 2-Cl-6-Me—Ph |
| 1-1522 | 5-NHAc-oxathia | 2-Cl-6-Me—Ph |
| 1-1523 | 4,4-diMe-cHex | 2-Cl-6-Me—Ph |
| 1-1524 | 5,5-diMe-dioxa | 2-Cl-6-Me—Ph |
| 1-1525 | 5,5-diMe-dithia | 2-Cl-6-Me—Ph |
| 1-1526 | 5,5-diMe-oxathia | 2-Cl-6-Me—Ph |
| 1-1527 | 4,4-diHM-cHex | 2-Cl-6-Me—Ph |
| 1-1528 | 5,5-diHM-dioxa | 2-Cl-6-Me—Ph |
| 1-1529 | 5,5-diHM-dithia | 2-Cl-6-Me—Ph |
| 1-1530 | 5,5-diHM-oxathia | 2-Cl-6-Me—Ph |
| 1-1531 | ring 15 | 2-Cl-6-Me—Ph |
| 1-1532 | ring 16 | 2-Cl-6-Me—Ph |
| 1-1533 | ring 17 | 2-Cl-6-Me—Ph |
| 1-1534 | ring 18 | 2-Cl-6-Me—Ph |
| 1-1535 | 4,4-di$CO_2$Et-cHex | 2-Cl-6-Me—Ph |
| 1-1536 | 5,5-di$CO_2$Et-dioxa | 2-Cl-6-Me—Ph |
| 1-1537 | 5,5-di$CO_2$Et-dithia | 2-Cl-6-Me—Ph |
| 1-1538 | 5,5-di$CO_2$Et-oxathia | 2-Cl-6-Me—Ph |
| 1-1539 | O= | 2-Br-4-F—Ph |
| 1-1540 | S= | 2-Br-4-F—Ph |
| 1-1541 | cPr | 2-Br-4-F—Ph |
| 1-1542 | cBu | 2-Br-4-F—Ph |
| 1-1543 | cPent | 2-Br-4-F—Ph |
| 1-1544 | cHex | 2-Br-4-F—Ph |
| 1-1545 | cHept | 2-Br-4-F—Ph |
| 1-1546 | oxi | 2-Br-4-F—Ph |
| 1-1547 | oxe | 2-Br-4-F—Ph |
| 1-1548 | oxo | 2-Br-4-F—Ph |
| 1-1549 | oxa | 2-Br-4-F—Ph |
| 1-1550 | dioxo | 2-Br-4-F—Ph |
| 1-1551 | dioxa | 2-Br-4-F—Ph |
| 1-1552 | dioxe | 2-Br-4-F—Ph |
| 1-1553 | dithio | 2-Br-4-F—Ph |
| 1-1554 | dithia | 2-Br-4-F—Ph |
| 1-1555 | ring 1 | 2-Br-4-F—Ph |
| 1-1556 | ring 2 | 2-Br-4-F—Ph |
| 1-1557 | oxathio | 2-Br-4-F—Ph |
| 1-1558 | oxathia | 2-Br-4-F—Ph |
| 1-1559 | ozl | 2-Br-4-F—Ph |
| 1-1560 | ozn | 2-Br-4-F—Ph |
| 1-1561 | tzl | 2-Br-4-F—Ph |
| 1-1562 | tzn | 2-Br-4-F—Ph |
| 1-1563 | 3-HM-cPent | 2-Br-4-F—Ph |
| 1-1564 | 4-HM-dioxo | 2-Br-4-F—Ph |

TABLE 1-continued

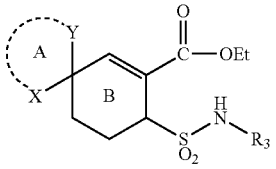

| Compound No. | X, Y | $R^3$ |
|---|---|---|
| 1-1565 | 4-HM-dithio | 2-Br-4-F—Ph |
| 1-1566 | 4-HM-oxathio | 2-Br-4-F—Ph |
| 1-1567 | 3,4-diHM-cPent | 2-Br-4-F—Ph |
| 1-1568 | 4,5-diHM-dioxo | 2-Br-4-F—Ph |
| 1-1569 | 4,5-diHM-dithio | 2-Br-4-F—Ph |
| 1-1570 | 4,5-diHM-oxathio | 2-Br-4-F—Ph |
| 1-1571 | 3,4-diHE-cPent | 2-Br-4-F—Ph |
| 1-1572 | 4,5-diHE-dioxo | 2-Br-4-F—Ph |
| 1-1573 | 4,5-diHE-dithio | 2-Br-4-F—Ph |
| 1-1574 | 4,5-diHE-oxathio | 2-Br-4-F—Ph |
| 1-1575 | 3-HE-cPent | 2-Br-4-F—Ph |
| 1-1576 | 4-HE-dioxo | 2-Br-4-F—Ph |
| 1-1577 | 4-HE-dithio | 2-Br-4-F—Ph |
| 1-1578 | 4-HE-oxathio | 2-Br-4-F—Ph |
| 1-1579 | 3-HP-cPent | 2-Br-4-F—Ph |
| 1-1580 | 4-HP-dioxo | 2-Br-4-F—Ph |
| 1-1581 | 4-HP-dithio | 2-Br-4-F—Ph |
| 1-1582 | 4-HP-oxathio | 2-Br-4-F—Ph |
| 1-1583 | 3-HB-cPent | 2-Br-4-F—Ph |
| 1-1584 | 4-HB-dioxo | 2-Br-4-F—Ph |
| 1-1585 | 4-HB-dithio | 2-Br-4-F—Ph |
| 1-1586 | 4-HB-oxathio | 2-Br-4-F—Ph |
| 1-1587 | ring 3 | 2-Br-4-F—Ph |
| 1-1588 | ring 4 | 2-Br-4-F—Ph |
| 1-1589 | ring 5 | 2-Br-4-F—Ph |
| 1-1590 | ring 6 | 2-Br-4-F—Ph |
| 1-1591 | ring 7 | 2-Br-4-F—Ph |
| 1-1592 | ring 8 | 2-Br-4-F—Ph |
| 1-1593 | ring 9 | 2-Br-4-F—Ph |
| 1-1594 | ring 10 | 2-Br-4-F—Ph |
| 1-1595 | 3,4-di$CH_2$NHAc-cPent | 2-Br-4-F—Ph |
| 1-1596 | 4,5-di$CH_2$NHAc-dioxo | 2-Br-4-F—Ph |
| 1-1597 | 4,5-di$CH_2$NHAc-dithio | 2-Br-4-F—Ph |
| 1-1598 | 4,5-di$CH_2$NHAc-oxathio | 2-Br-4-F—Ph |
| 1-1599 | ring 11 | 2-Br-4-F—Ph |
| 1-1600 | ring 12 | 2-Br-4-F—Ph |
| 1-1601 | ring 13 | 2-Br-4-F—Ph |
| 1-1602 | ring 14 | 2-Br-4-F—Ph |
| 1-1603 | 4-OH-cHex | 2-Br-4-F—Ph |
| 1-1604 | 5-OH-dioxa | 2-Br-4-F—Ph |
| 1-1605 | 5-OH-dithia | 2-Br-4-F—Ph |
| 1-1606 | 5-OH-oxathia | 2-Br-4-F—Ph |
| 1-1607 | 4-NHAc-cHex | 2-Br-4-F—Ph |
| 1-1608 | 5-NHAc-dioxa | 2-Br-4-F—Ph |
| 1-1609 | 5-NHAc-dithia | 2-Br-4-F—Ph |
| 1-1610 | 5-NHAc-oxathia | 2-Br-4-F—Ph |
| 1-1611 | 4,4-diMe-cHex | 2-Br-4-F—Ph |
| 1-1612 | 5,5-diMe-dioxa | 2-Br-4-F—Ph |
| 1-1613 | 5,5-diMe-dithia | 2-Br-4-F—Ph |
| 1-1614 | 5,5-diMe-oxathia | 2-Br-4-F—Ph |
| 1-1615 | 4,4-diHM-cHex | 2-Br-4-F—Ph |
| 1-1616 | 5,5-diHM-dioxa | 2-Br-4-F—Ph |
| 1-1617 | 5,5-diHM-dithia | 2-Br-4-F—Ph |
| 1-1618 | 5,5-diHM-oxathia | 2-Br-4-F—Ph |
| 1-1619 | ring 15 | 2-Br-4-F—Ph |
| 1-1620 | ring 16 | 2-Br-4-F—Ph |
| 1-1621 | ring 17 | 2-Br-4-F—Ph |
| 1-1622 | ring 18 | 2-Br-4-F—Ph |
| 1-1623 | 4,4-di$CO_2$Et-cHex | 2-Br-4-F—Ph |
| 1-1624 | 5,5-di$CO_2$Et-dioxa | 2-Br-4-F—Ph |
| 1-1625 | 5,5-di$CO_2$Et-dithia | 2-Br-4-F—Ph |
| 1-1626 | 5,5-di$CO_2$Et-oxathia | 2-Br-4-F—Ph |
| 1-1627 | O═ | 2-nPent-Ph |
| 1-1628 | S═ | 2-nPent-Ph |
| 1-1629 | cPr | 2-nPent-Ph |
| 1-1630 | cBu | 2-nPent-Ph |
| 1-1631 | cPent | 2-nPent-Ph |
| 1-1632 | cHex | 2-nPent-Ph |

TABLE 1-continued

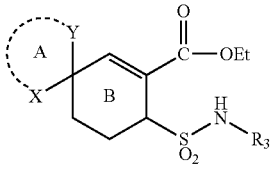

| Compound No. | X, Y | $R^3$ |
|---|---|---|
| 1-1633 | cHept | 2-nPent-Ph |
| 1-1634 | oxi | 2-nPent-Ph |
| 1-1635 | oxe | 2-nPent-Ph |
| 1-1636 | oxo | 2-nPent-Ph |
| 1-1637 | oxa | 2-nPent-Ph |
| 1-1638 | dioxo | 2-nPent-Ph |
| 1-1639 | dioxa | 2-nPent-Ph |
| 1-1640 | dioxe | 2-nPent-Ph |
| 1-1641 | dithio | 2-nPent-Ph |
| 1-1642 | dithia | 2-nPent-Ph |
| 1-1643 | ring 1 | 2-nPent-Ph |
| 1-1644 | ring 2 | 2-nPent-Ph |
| 1-1645 | oxathio | 2-nPent-Ph |
| 1-1646 | oxathia | 2-nPent-Ph |
| 1-1647 | ozl | 2-nPent-Ph |
| 1-1648 | ozn | 2-nPent-Ph |
| 1-1649 | tzl | 2-nPent-Ph |
| 1-1650 | tzn | 2-nPent-Ph |
| 1-1651 | 3-HM-cPent | 2-nPent-Ph |
| 1-1652 | 4-HM-dioxo | 2-nPent-Ph |
| 1-1653 | 4-HM-dithio | 2-nPent-Ph |
| 1-1654 | 4-HM-oxathio | 2-nPent-Ph |
| 1-1655 | 3,4-diHM-cPent | 2-nPent-Ph |
| 1-1656 | 4,5-diHM-dioxo | 2-nPent-Ph |
| 1-1657 | 4,5-diHM-dithio | 2-nPent-Ph |
| 1-1658 | 4,5-diHM-oxathio | 2-nPent-Ph |
| 1-1659 | 3,4-diHE-cPent | 2-nPent-Ph |
| 1-1660 | 4,5-diHE-dioxo | 2-nPent-Ph |
| 1-1661 | 4,5-diHE-dithio | 2-nPent-Ph |
| 1-1662 | 4,5-diHE-oxathio | 2-nPent-Ph |
| 1-1663 | 3-HE-cPent | 2-nPent-Ph |
| 1-1664 | 4-HE-dioxo | 2-nPent-Ph |
| 1-1665 | 4-HE-dithio | 2-nPent-Ph |
| 1-1666 | 4-HE-oxathio | 2-nPent-Ph |
| 1-1667 | 3-HP-cPent | 2-nPent-Ph |
| 1-1668 | 4-HP-dioxo | 2-nPent-Ph |
| 1-1669 | 4-HP-dithio | 2-nPent-Ph |
| 1-1670 | 4-HP-oxathio | 2-nPent-Ph |
| 1-1671 | 3-HB-cPent | 2-nPent-Ph |
| 1-1672 | 4-HB-dioxo | 2-nPent-Ph |
| 1-1673 | 4-HB-dithio | 2-nPent-Ph |
| 1-1674 | 4-HB-oxathio | 2-nPent-Ph |
| 1-1675 | ring 3 | 2-nPent-Ph |
| 1-1676 | ring 4 | 2-nPent-Ph |
| 1-1677 | ring 5 | 2-nPent-Ph |
| 1-1678 | ring 6 | 2-nPent-Ph |
| 1-1679 | ring 7 | 2-nPent-Ph |
| 1-1680 | ring 8 | 2-nPent-Ph |
| 1-1681 | ring 9 | 2-nPent-Ph |
| 1-1682 | ring 10 | 2-nPent-Ph |
| 1-1683 | 3,4-di$CH_2$NHAc-cPent | 2-nPent-Ph |
| 1-1684 | 4,5-di$CH_2$NHAc-dioxo | 2-nPent-Ph |
| 1-1685 | 4,5-di$CH_2$NHAc-dithio | 2-nPent-Ph |
| 1-1686 | 4,5-di$CH_2$NHAc-oxathio | 2-nPent-Ph |
| 1-1687 | ring 11 | 2-nPent-Ph |
| 1-1688 | ring 12 | 2-nPent-Ph |
| 1-1689 | ring 13 | 2-nPent-Ph |
| 1-1690 | ring 14 | 2-nPent-Ph |
| 1-1691 | 4-OH-cHex | 2-nPent-Ph |
| 1-1692 | 5-OH-dioxa | 2-nPent-Ph |
| 1-1693 | 5-OH-dithia | 2-nPent-Ph |
| 1-1694 | 5-OH-oxathia | 2-nPent-Ph |
| 1-1695 | 4-NHAc-cHex | 2-nPent-Ph |
| 1-1696 | 5-NHAc-dioxa | 2-nPent-Ph |
| 1-1697 | 5-NHAc-dithia | 2-nPent-Ph |
| 1-1698 | 5-NHAc-oxathia | 2-nPent-Ph |
| 1-1699 | 4,4-diMe-cHex | 2-nPent-Ph |
| 1-1700 | 5,5-diMe-dioxa | 2-nPent-Ph |

TABLE 1-continued

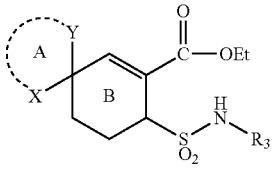

| Compound No. | X, Y | $R^3$ |
|---|---|---|
| 1-1701 | 5,5-diMe-dithia | 2-nPent-Ph |
| 1-1702 | 5,5-diMe-oxathia | 2-nPent-Ph |
| 1-1703 | 4,4-diHM-cHex | 2-nPent-Ph |
| 1-1704 | 5,5-diHM-dioxa | 2-nPent-Ph |
| 1-1705 | 5,5-diHM-dithia | 2-nPent-Ph |
| 1-1706 | 5,5-diHM-oxathia | 2-nPent-Ph |
| 1-1707 | ring 15 | 2-nPent-Ph |
| 1-1708 | ring 16 | 2-nPent-Ph |
| 1-1709 | ring 17 | 2-nPent-Ph |
| 1-1710 | ring 18 | 2-nPent-Ph |
| 1-1711 | 4,4-di$CO_2$Et-cHex | 2-nPent-Ph |
| 1-1712 | 5,5-di$CO_2$Et-dioxa | 2-nPent-Ph |
| 1-1713 | 5,5-di$CO_2$Et-dithia | 2-nPent-Ph |
| 1-1714 | 5,5-di$CO_2$Et-oxathia | 2-nPent-Ph |
| 1-1715 | O═ | 4-F-2-nPent-Ph |
| 1-1716 | S═ | 4-F-2-nPent-Ph |
| 1-1717 | cPr | 4-F-2-nPent-Ph |
| 1-1718 | cBu | 4-F-2-nPent-Ph |
| 1-1719 | cPent | 4-F-2-nPent-Ph |
| 1-1720 | cHex | 4-F-2-nPent-Ph |
| 1-1721 | cHept | 4-F-2-nPent-Ph |
| 1-1722 | oxi | 4-F-2-nPent-Ph |
| 1-1723 | oxe | 4-F-2-nPent-Ph |
| 1-1724 | oxo | 4-F-2-nPent-Ph |
| 1-1725 | oxa | 4-F-2-nPent-Ph |
| 1-1726 | dioxo | 4-F-2-nPent-Ph |
| 1-1727 | dioxa | 4-F-2-nPent-Ph |
| 1-1728 | dioxe | 4-F-2-nPent-Ph |
| 1-1729 | dithio | 4-F-2-nPent-Ph |
| 1-1730 | dithia | 4-F-2-nPent-Ph |
| 1-1731 | ring 1 | 4-F-2-nPent-Ph |
| 1-1732 | ring 2 | 4-F-2-nPent-Ph |
| 1-1733 | oxathio | 4-F-2-nPent-Ph |
| 1-1734 | oxathia | 4-F-2-nPent-Ph |
| 1-1735 | ozl | 4-F-2-nPent-Ph |
| 1-1736 | ozn | 4-F-2-nPent-Ph |
| 1-1737 | tzl | 4-F-2-nPent-Ph |
| 1-1738 | tzn | 4-F-2-nPent-Ph |
| 1-1739 | 3-HM-cPent | 4-F-2-nPent-Ph |
| 1-1740 | 4-HM-dioxo | 4-F-2-nPent-Ph |
| 1-1741 | 4-HM-dithio | 4-F-2-nPent-Ph |
| 1-1742 | 4-HM-oxathio | 4-F-2-nPent-Ph |
| 1-1743 | 3,4-diHM-cPent | 4-F-2-nPent-Ph |
| 1-1744 | 4,5-diHM-dioxo | 4-F-2-nPent-Ph |
| 1-1745 | 4,5-diHM-dithio | 4-F-2-nPent-Ph |
| 1-1746 | 4,5-diHM-oxathio | 4-F-2-nPent-Ph |
| 1-1747 | 3,4-diHE-cPent | 4-F-2-nPent-Ph |
| 1-1748 | 4,5-diHE-dioxo | 4-F-2-nPent-Ph |
| 1-1749 | 4,5-diHE-dithio | 4-F-2-nPent-Ph |
| 1-1750 | 4,5-diHE-oxathio | 4-F-2-nPent-Ph |
| 1-1751 | 3-HE-cPent | 4-F-2-nPent-Ph |
| 1-1752 | 4-HE-dioxo | 4-F-2-nPent-Ph |
| 1-1753 | 4-HE-dithio | 4-F-2-nPent-Ph |
| 1-1754 | 4-HE-oxathio | 4-F-2-nPent-Ph |
| 1-1755 | 3-HP-cPent | 4-F-2-nPent-Ph |
| 1-1756 | 4-HP-dioxo | 4-F-2-nPent-Ph |
| 1-1757 | 4-HP-dithio | 4-F-2-nPent-Ph |
| 1-1758 | 4-HP-oxathio | 4-F-2-nPent-Ph |
| 1-1759 | 3-HB-cPent | 4-F-2-nPent-Ph |
| 1-1760 | 4-HB-dioxo | 4-F-2-nPent-Ph |
| 1-1761 | 4-HB-dithio | 4-F-2-nPent-Ph |
| 1-1762 | 4-HB-oxathio | 4-F-2-nPent-Ph |
| 1-1763 | ring 3 | 4-F-2-nPent-Ph |
| 1-1764 | ring 4 | 4-F-2-nPent-Ph |
| 1-1765 | ring 5 | 4-F-2-nPent-Ph |
| 1-1766 | ring 6 | 4-F-2-nPent-Ph |
| 1-1767 | ring 7 | 4-F-2-nPent-Ph |
| 1-1768 | ring 8 | 4-F-2-nPent-Ph |

TABLE 1-continued

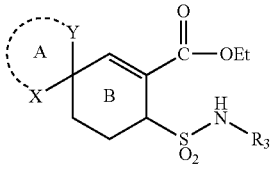

| Compound No. | X, Y | $R^3$ |
|---|---|---|
| 1-1769 | ring 9 | 4-F-2-nPent-Ph |
| 1-1770 | ring 10 | 4-F-2-nPent-Ph |
| 1-1771 | 3,4-di$CH_2$NHAc-cPent | 4-F-2-nPent-Ph |
| 1-1772 | 4,5-di$CH_2$NHAc-dioxo | 4-F-2-nPent-Ph |
| 1-1773 | 4,5-di$CH_2$NHAc-dithio | 4-F-2-nPent-Ph |
| 1-1774 | 4,5-di$CH_2$NHAc-oxathio | 4-F-2-nPent-Ph |
| 1-1775 | ring 11 | 4-F-2-nPent-Ph |
| 1-1776 | ring 12 | 4-F-2-nPent-Ph |
| 1-1777 | ring 13 | 4-F-2-nPent-Ph |
| 1-1778 | ring 14 | 4-F-2-nPent-Ph |
| 1-1779 | 4-OH-cHex | 4-F-2-nPent-Ph |
| 1-1780 | 5-OH-dioxa | 4-F-2-nPent-Ph |
| 1-1781 | 5-OH-dithia | 4-F-2-nPent-Ph |
| 1-1782 | 5-OH-oxathia | 4-F-2-nPent-Ph |
| 1-1783 | 4-NHAc-cHex | 4-F-2-nPent-Ph |
| 1-1784 | 5-NHAc-dioxa | 4-F-2-nPent-Ph |
| 1-1785 | 5-NHAc-dithia | 4-F-2-nPent-Ph |
| 1-1786 | 5-NHAc-oxathia | 4-F-2-nPent-Ph |
| 1-1787 | 4,4-diMe-cHex | 4-F-2-nPent-Ph |
| 1-1788 | 5,5-diMe-dioxa | 4-F-2-nPent-Ph |
| 1-1789 | 5,5-diMe-dithia | 4-F-2-nPent-Ph |
| 1-1790 | 5,5-diMe-oxathia | 4-F-2-nPent-Ph |
| 1-1791 | 4,4-diHM-cHex | 4-F-2-nPent-Ph |
| 1-1792 | 5,5-diHM-dioxa | 4-F-2-nPent-Ph |
| 1-1793 | 5,5-diHM-dithia | 4-F-2-nPent-Ph |
| 1-1794 | 5,5-diHM-oxathia | 4-F-2-nPent-Ph |
| 1-1795 | ring 15 | 4-F-2-nPent-Ph |
| 1-1796 | ring 16 | 4-F-2-nPent-Ph |
| 1-1797 | ring 17 | 4-F-2-nPent-Ph |
| 1-1798 | ring 18 | 4-F-2-nPent-Ph |
| 1-1799 | 4,4-di$CO_2$Et-cHex | 4-F-2-nPent-Ph |
| 1-1800 | 5,5-di$CO_2$Et-dioxa | 4-F-2-nPent-Ph |
| 1-1801 | 5,5-di$CO_2$Et-dithia | 4-F-2-nPent-Ph |
| 1-1802 | 5,5-di$CO_2$Et-oxathia | 4-F-2-nPent-Ph |
| 1-1803 | O═ | 2-nOct-Ph |
| 1-1804 | S═ | 2-nOct-Ph |
| 1-1805 | cPr | 2-nOct-Ph |
| 1-1806 | cBu | 2-nOct-Ph |
| 1-1807 | cPent | 2-nOct-Ph |
| 1-1808 | cHex | 2-nOct-Ph |
| 1-1809 | cHept | 2-nOct-Ph |
| 1-1810 | oxi | 2-nOct-Ph |
| 1-1811 | oxe | 2-nOct-Ph |
| 1-1812 | oxo | 2-nOct-Ph |
| 1-1813 | oxa | 2-nOct-Ph |
| 1-1814 | dioxo | 2-nOct-Ph |
| 1-1815 | dioxa | 2-nOct-Ph |
| 1-1816 | dioxe | 2-nOct-Ph |
| 1-1817 | dithio | 2-nOct-Ph |
| 1-1818 | dithia | 2-nOct-Ph |
| 1-1819 | ring 1 | 2-nOct-Ph |
| 1-1820 | ring 2 | 2-nOct-Ph |
| 1-1821 | oxathio | 2-nOct-Ph |
| 1-1822 | oxathia | 2-nOct-Ph |
| 1-1823 | ozl | 2-nOct-Ph |
| 1-1824 | ozn | 2-nOct-Ph |
| 1-1825 | tzl | 2-nOct-Ph |
| 1-1826 | tzn | 2-nOct-Ph |
| 1-1827 | 3-HM-cPent | 2-nOct-Ph |
| 1-1828 | 4-HM-dioxo | 2-nOct-Ph |
| 1-1829 | 4-HM-dithio | 2-nOct-Ph |
| 1-1830 | 4-HM-oxathio | 2-nOct-Ph |
| 1-1831 | 3,4-diHM-cPent | 2-nOct-Ph |
| 1-1832 | 4,5-diHM-dioxo | 2-nOct-Ph |
| 1-1833 | 4,5-diHM-dithio | 2-nOct-Ph |
| 1-1834 | 4,5-diHM-oxathio | 2-nOct-Ph |
| 1-1835 | 3,4-diHE-cPent | 2-nOct-Ph |
| 1-1836 | 4,5-diHE-dioxo | 2-nOct-Ph |

TABLE 1-continued

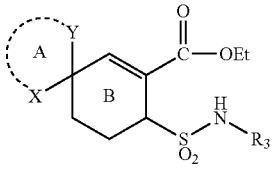

| Compound No. | X, Y | $R^3$ |
|---|---|---|
| 1-1837 | 4,5-diHE-dithio | 2-nOct-Ph |
| 1-1838 | 4,5-diHE-oxathio | 2-nOct-Ph |
| 1-1839 | 3-HE-cPent | 2-nOct-Ph |
| 1-1840 | 4-HE-dioxo | 2-nOct-Ph |
| 1-1841 | 4-HE-dithio | 2-nOct-Ph |
| 1-1842 | 4-HE-oxathio | 2-nOct-Ph |
| 1-1843 | 3-HP-cPent | 2-nOct-Ph |
| 1-1844 | 4-HP-dioxo | 2-nOct-Ph |
| 1-1845 | 4-HP-dithio | 2-nOct-Ph |
| 1-1846 | 4-HP-oxathio | 2-nOct-Ph |
| 1-1847 | 3-HB-cPent | 2-nOct-Ph |
| 1-1848 | 4-HB-dioxo | 2-nOct-Ph |
| 1-1849 | 4-HB-dithio | 2-nOct-Ph |
| 1-1850 | 4-HB-oxathio | 2-nOct-Ph |
| 1-1851 | ring 3 | 2-nOct-Ph |
| 1-1852 | ring 4 | 2-nOct-Ph |
| 1-1853 | ring 5 | 2-nOct-Ph |
| 1-1854 | ring 6 | 2-nOct-Ph |
| 1-1855 | ring 7 | 2-nOct-Ph |
| 1-1856 | ring 8 | 2-nOct-Ph |
| 1-1857 | ring 9 | 2-nOct-Ph |
| 1-1858 | ring 10 | 2-nOct-Ph |
| 1-1859 | 3,4-di$CH_2$NHAc-cPent | 2-nOct-Ph |
| 1-1860 | 4,5-di$CH_2$NHAc-dioxo | 2-nOct-Ph |
| 1-1861 | 4,5-di$CH_2$NHAc-dithio | 2-nOct-Ph |
| 1-1862 | 4,5-di$CH_2$NHAc-oxathio | 2-nOct-Ph |
| 1-1863 | ring 11 | 2-nOct-Ph |
| 1-1864 | ring 12 | 2-nOct-Ph |
| 1-1865 | ring 13 | 2-nOct-Ph |
| 1-1866 | ring 14 | 2-nOct-Ph |
| 1-1867 | 4-OH-cHex | 2-nOct-Ph |
| 1-1868 | 5-OH-dioxa | 2-nOct-Ph |
| 1-1869 | 5-OH-dithia | 2-nOct-Ph |
| 1-1870 | 5-OH-oxathia | 2-nOct-Ph |
| 1-1871 | 4-NHAc-cHex | 2-nOct-Ph |
| 1-1872 | 5-NHAc-dioxa | 2-nOct-Ph |
| 1-1873 | 5-NHAc-dithia | 2-nOct-Ph |
| 1-1874 | 5-NHAc-oxathia | 2-nOct-Ph |
| 1-1875 | 4,4-diMe-cHex | 2-nOct-Ph |
| 1-1876 | 5,5-diMe-dioxa | 2-nOct-Ph |
| 1-1877 | 5,5-diMe-dithia | 2-nOct-Ph |
| 1-1878 | 5,5-diMe-oxathia | 2-nOct-Ph |
| 1-1879 | 4,4-diHM-cHex | 2-nOct-Ph |
| 1-1880 | 5,5-diHM-dioxa | 2-nOct-Ph |
| 1-1881 | 5,5-diHM-dithia | 2-nOct-Ph |
| 1-1882 | 5,5-diHM-oxathia | 2-nOct-Ph |
| 1-1883 | ring 15 | 2-nOct-Ph |
| 1-1884 | ring 16 | 2-nOct-Ph |
| 1-1885 | ring 17 | 2-nOct-Ph |
| 1-1886 | ring 18 | 2-nOct-Ph |
| 1-1887 | 4,4-di$CO_2$Et-cHex | 2-nOct-Ph |
| 1-1888 | 5,5-di$CO_2$Et-dioxa | 2-nOct-Ph |
| 1-1889 | 5,5-di$CO_2$Et-dithia | 2-nOct-Ph |
| 1-1890 | 5,5-di$CO_2$Et-oxathia | 2-nOct-Ph |
| 1-1891 | O= | 4-F-2-nOct-Ph |
| 1-1892 | S= | 4-F-2-nOct-Ph |
| 1-1893 | cPr | 4-F-2-nOct-Ph |
| 1-1894 | cBu | 4-F-2-nOct-Ph |
| 1-1895 | cPent | 4-F-2-nOct-Ph |
| 1-1896 | cHex | 4-F-2-nOct-Ph |
| 1-1897 | cHept | 4-F-2-nOct-Ph |
| 1-1898 | oxi | 4-F-2-nOct-Ph |
| 1-1899 | oxe | 4-F-2-nOct-Ph |
| 1-1900 | oxo | 4-F-2-nOct-Ph |
| 1-1901 | oxa | 4-F-2-nOct-Ph |
| 1-1902 | diaxo | 4-F-2-nOct-Ph |
| 1-1903 | dioxa | 4-F-2-nOct-Ph |
| 1-1904 | dioxe | 4-F-2-nOct-Ph |

TABLE 1-continued

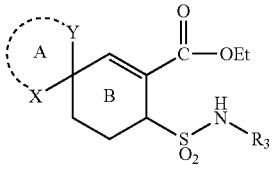

| Compound No. | X, Y | $R^3$ |
|---|---|---|
| 1-1905 | dithio | 4-F-2-nOct-Ph |
| 1-1906 | dithia | 4-F-2-nOct-Ph |
| 1-1907 | ring 1 | 4-F-2-nOct-Ph |
| 1-1908 | ring 2 | 4-F-2-nOct-Ph |
| 1-1909 | oxathio | 4-F-2-nOct-Ph |
| 1-1910 | oxathia | 4-F-2-nOct-Ph |
| 1-1911 | ozl | 4-F-2-nOct-Ph |
| 1-1912 | ozn | 4-F-2-nOct-Ph |
| 1-1913 | tzl | 4-F-2-nOct-Ph |
| 1-1914 | tzn | 4-F-2-nOct-Ph |
| 1-1915 | 3-HM-cPent | 4-F-2-nOct-Ph |
| 1-1916 | 4-HM-dioxo | 4-F-2-nOct-Ph |
| 1-1917 | 4-HM-dithio | 4-F-2-nOct-Ph |
| 1-1918 | 4-HM-oxathio | 4-F-2-nOct-Ph |
| 1-1919 | 3,4-diHM-cPent | 4-F-2-nOct-Ph |
| 1-1920 | 4,5-diHM-dioxo | 4-F-2-nOct-Ph |
| 1-1921 | 4,5-diHM-dithio | 4-F-2-nOct-Ph |
| 1-1922 | 4,5-diHM-oxathio | 4-F-2-nOct-Ph |
| 1-1923 | 3,4-diHE-cPent | 4-F-2-nOct-Ph |
| 1-1924 | 4,5-diHE-dioxo | 4-F-2-nOct-Ph |
| 1-1925 | 4,5-diHE-dithio | 4-F-2-nOct-Ph |
| 1-1926 | 4,5-diHE-oxathio | 4-F-2-nOct-Ph |
| 1-1927 | 3-HE-cPent | 4-F-2-nOct-Ph |
| 1-1928 | 4-HE-dioxo | 4-F-2-nOct-Ph |
| 1-1929 | 4-HE-dithio | 4-F-2-nOct-Ph |
| 1-1930 | 4-HE-oxathio | 4-F-2-nOct-Ph |
| 1-1931 | 3-HP-cPent | 4-F-2-nOct-Ph |
| 1-1932 | 4-HP-dioxo | 4-F-2-nOct-Ph |
| 1-1933 | 4-HP-dithio | 4-F-2-nOct-Ph |
| 1-1934 | 4-HP-oxathio | 4-F-2-nOct-Ph |
| 1-1935 | 3-HB-cPent | 4-F-2-nOct-Ph |
| 1-1936 | 4-HB-dioxo | 4-F-2-nOct-Ph |
| 1-1937 | 4-HB-dithio | 4-F-2-nOct-Ph |
| 1-1938 | 4-HB-oxathio | 4-F-2-nOct-Ph |
| 1-1939 | ring 3 | 4-F-2-nOct-Ph |
| 1-1940 | ring 4 | 4-F-2-nOct-Ph |
| 1-1941 | ring 5 | 4-F-2-nOct-Ph |
| 1-1942 | ring 6 | 4-F-2-nOct-Ph |
| 1-1943 | ring 7 | 4-F-2-nOct-Ph |
| 1-1944 | ring 8 | 4-F-2-nOct-Ph |
| 1-1945 | ring 9 | 4-F-2-nOct-Ph |
| 1-1946 | ring 10 | 4-F-2-nOct-Ph |
| 1-1947 | 3,4-di$CH_2$NHAc-cPent | 4-F-2-nOct-Ph |
| 1-1948 | 4,5-di$CH_2$NHAc-dioxo | 4-F-2-nOct-Ph |
| 1-1949 | 4,5-di$CH_2$NHAc-dithio | 4-F-2-nOct-Ph |
| 1-1950 | 4,5-di$CH_2$NHAc-oxathio | 4-F-2-nOct-Ph |
| 1-1951 | ring 11 | 4-F-2-nOct-Ph |
| 1-1952 | ring 12 | 4-F-2-nOct-Ph |
| 1-1953 | ring 13 | 4-F-2-nOct-Ph |
| 1-1954 | ring 14 | 4-F-2-nOct-Ph |
| 1-1955 | 4-OH-cHex | 4-F-2-nOct-Ph |
| 1-1956 | 5-OH-dioxa | 4-F-2-nOct-Ph |
| 1-1957 | 5-OH-dithia | 4-F-2-nOct-Ph |
| 1-1958 | 5-OH-oxathia | 4-F-2-nOct-Ph |
| 1-1959 | 4-NHAc-cHex | 4-F-2-nOct-Ph |
| 1-1960 | 5-NHAc-dioxa | 4-F-2-nOct-Ph |
| 1-1961 | 5-NHAc-dithia | 4-F-2-nOct-Ph |
| 1-1962 | 5-NHAc-oxathia | 4-F-2-nOct-Ph |
| 1-1963 | 4,4-diMe-cHex | 4-F-2-nOct-Ph |
| 1-1964 | 5,5-diMe-dioxa | 4-F-2-nOct-Ph |
| 1-1965 | 5,5-diMe-dithia | 4-F-2-nOct-Ph |
| 1-1966 | 5,5-diMe-oxathia | 4-F-2-nOct-Ph |
| 1-1967 | 4,4-diHM-cHex | 4-F-2-nOct-Ph |
| 1-1968 | 5,5-diHM-dioxa | 4-F-2-nOct-Ph |
| 1-1969 | 5,5-diHM-dithia | 4-F-2-nOct-Ph |
| 1-1970 | 5,5-diHM-oxathia | 4-F-2-nOct-Ph |
| 1-1971 | ring 15 | 4-F-2-nOct-Ph |
| 1-1972 | ring 16 | 4-F-2-nOct-Ph |

TABLE 1-continued

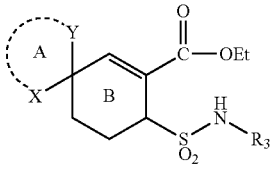

| Compound No. | X, Y | $R^3$ |
|---|---|---|
| 1-1973 | ring 17 | 4-F-2-nOct-Ph |
| 1-1974 | ring 18 | 4-F-2-nOct-Ph |
| 1-1975 | 4,4-di$CO_2$Et-cHex | 4-F-2-nOct-Ph |
| 1-1976 | 5,5-di$CO_2$Et-dioxa | 4-F-2-nOct-Ph |
| 1-1977 | 5,5-di$CO_2$Et-dithia | 4-F-2-nOct-Ph |
| 1-1978 | O═ | 2-nPr—Ph |
| 1-1979 | S═ | 2-nPr—Ph |
| 1-1980 | cPr | 2-nPr—Ph |
| 1-1981 | cBu | 2-nPr—Ph |
| 1-1982 | cPent | 2-nPr—Ph |
| 1-1983 | cHex | 2-nPr—Ph |
| 1-1984 | cHept | 2-nPr—Ph |
| 1-1985 | oxi | 2-nPr—Ph |
| 1-1986 | oxe | 2-nPr—Ph |
| 1-1987 | oxo | 2-nPr—Ph |
| 1-1988 | oxa | 2-nPr—Ph |
| 1-1989 | dioxo | 2-nPr—Ph |
| 1-1990 | dioxa | 2-nPr—Ph |
| 1-1991 | dioxe | 2-nPr—Ph |
| 1-1992 | dithio | 2-nPr—Ph |
| 1-1993 | dithia | 2-nPr—Ph |
| 1-1994 | ring 1 | 2-nPr—Ph |
| 1-1995 | ring 2 | 2-nPr—Ph |
| 1-1996 | oxathio | 2-nPr—Ph |
| 1-1997 | oxathia | 2-nPr—Ph |
| 1-1998 | ozl | 2-nPr—Ph |
| 1-1999 | ozn | 2-nPr—Ph |
| 1-2000 | tzl | 2-nPr—Ph |
| 1-2001 | tzn | 2-nPr—Ph |
| 1-2002 | 3-HM-cPent | 2-nPr—Ph |
| 1-2003 | 4-HM-dioxo | 2-nPr—Ph |
| 1-2004 | 4-HM-dithio | 2-nPr—Ph |
| 1-2005 | 4-HM-oxathio | 2-nPr—Ph |
| 1-2006 | 3,4-diHM-cPent | 2-nPr—Ph |
| 1-2007 | 4,5-diHM-dioxo | 2-nPr—Ph |
| 1-2008 | 4,5-diHM-dithio | 2-nPr—Ph |
| 1-2009 | 4,5-diHM-oxathio | 2-nPr—Ph |
| 1-2010 | 3,4-diHE-cPent | 2-nPr—Ph |
| 1-2011 | 4,5-diHE-dioxo | 2-nPr—Ph |
| 1-2012 | 4,5-diHE-dithio | 2-nPr—Ph |
| 1-2013 | 4,5-diHE-oxathio | 2-nPr—Ph |
| 1-2014 | 3-HE-cPent | 2-nPr—Ph |
| 1-2015 | 4-HE-dioxo | 2-nPr—Ph |
| 1-2016 | 4-HE-dithio | 2-nPr—Ph |
| 1-2017 | 4-HE-oxathio | 2-nPr—Ph |
| 1-2018 | 3-HP-cPent | 2-nPr—Ph |
| 1-2019 | 4-HP-dioxo | 2-nPr—Ph |
| 1-2020 | 4-HP-dithio | 2-nPr—Ph |
| 1-2021 | 4-HP-oxathio | 2-nPr—Ph |
| 1-2022 | 3-HB-cPent | 2-nPr—Ph |
| 1-2023 | 4-HB-dioxo | 2-nPr—Ph |
| 1-2024 | 4-HB-dithio | 2-nPr—Ph |
| 1-2025 | 4-HB-oxathio | 2-nPr—Ph |
| 1-2026 | ring 3 | 2-nPr—Ph |
| 1-2027 | ring 4 | 2-nPr—Ph |
| 1-2028 | ring 5 | 2-nPr—Ph |
| 1-2029 | ring 6 | 2-nPr—Ph |
| 1-2030 | ring 7 | 2-nPr—Ph |
| 1-2031 | ring 8 | 2-nPr—Ph |
| 1-2032 | ring 9 | 2-nPr—Ph |
| 1-2033 | ring 10 | 2-nPr—Ph |
| 1-2034 | 3,4-di$CH_2$NHAc-cPent | 2-nPr—Ph |
| 1-2035 | 4,5-di$CH_2$NHAc-dioxo | 2-nPr—Ph |
| 1-2036 | 4,5-di$CH_2$NHAc-dithio | 2-nPr—Ph |
| 1-2037 | 4,5-di$CH_2$NHAc-oxathio | 2-nPr—Ph |
| 1-2038 | ring 11 | 2-nPr—Ph |
| 1-2039 | ring 12 | 2-nPr—Ph |
| 1-2040 | ring 13 | 2-nPr—Ph |

TABLE 1-continued

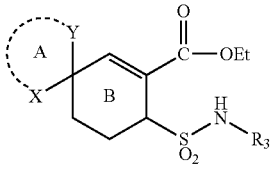

| Compound No. | X, Y | $R^3$ |
|---|---|---|
| 1-2041 | ring 14 | 2-nPr—Ph |
| 1-2042 | 4-OH-cHex | 2-nPr—Ph |
| 1-2043 | 5-OH-dioxa | 2-nPr—Ph |
| 1-2044 | 5-OH-dithia | 2-nPr—Ph |
| 1-2045 | 5-OH-oxathia | 2-nPr—Ph |
| 1-2046 | 4-NHAc-cHex | 2-nPr—Ph |
| 1-2047 | 5-NHAc-dioxa | 2-nPr—Ph |
| 1-2048 | 5-NHAc-dithia | 2-nPr—Ph |
| 1-2049 | 5-NHAc-oxathia | 2-nPr—Ph |
| 1-2050 | 4,4-diMe-cHex | 2-nPr—Ph |
| 1-2051 | 5,5-diMe-dioxa | 2-nPr—Ph |
| 1-2052 | 5,5-diMe-dithia | 2-nPr—Ph |
| 1-2053 | 5,5-diMe-oxathia | 2-nPr—Ph |
| 1-2054 | 4,4-diHM-cHex | 2-nPr—Ph |
| 1-2055 | 5,5-diHM-dioxa | 2-nPr—Ph |
| 1-2056 | 5,5-diHM-dithia | 2-nPr—Ph |
| 1-2057 | 5,5-diHM-oxathia | 2-nPr—Ph |
| 1-2058 | ring 15 | 2-nPr—Ph |
| 1-2059 | ring 16 | 2-nPr—Ph |
| 1-2060 | ring 17 | 2-nPr—Ph |
| 1-2061 | ring 18 | 2-nPr—Ph |
| 1-2062 | 4,4-di$CO_2$Et-cHex | 2-nPr—Ph |
| 1-2063 | 5,5-di$CO_2$Et-dioxa | 2-nPr—Ph |
| 1-2064 | 5,5-di$CO_2$Et-dithia | 2-nPr—Ph |
| 1-2065 | 5,5-di$CO_2$Et-oxathia | 2-nPr—Ph |
| 1-2066 | O═ | 4-F-2-nPr—Ph |
| 1-2067 | S═ | 4-F-2-nPr—Ph |
| 1-2068 | cPr | 4-F-2-nPr—Ph |
| 1-2069 | cBu | 4-F-2-nPr—Ph |
| 1-2070 | cPent | 4-F-2-nPr—Ph |
| 1-2071 | cHex | 4-F-2-nPr—Ph |
| 1-2072 | cHept | 4-F-2-nPr—Ph |
| 1-2073 | oxi | 4-F-2-nPr—Ph |
| 1-2074 | oxe | 4-F-2-nPr—Ph |
| 1-2075 | oxo | 4-F-2-nPr—Ph |
| 1-2076 | oxa | 4-F-2-nPr—Ph |
| 1-2077 | dioxo | 4-F-2-nPr—Ph |
| 1-2078 | dioxa | 4-F-2-nPr—Ph |
| 1-2079 | dioxe | 4-F-2-nPr—Ph |
| 1-2080 | dithio | 4-F-2-nPr—Ph |
| 1-2081 | dithia | 4-F-2-nPr—Ph |
| 1-2082 | ring 1 | 4-F-2-nPr—Ph |
| 1-2083 | ring 2 | 4-F-2-nPr—Ph |
| 1-2084 | oxathio | 4-F-2-nPr—Ph |
| 1-2085 | oxathia | 4-F-2-nPr—Ph |
| 1-2086 | ozl | 4-F-2-nPr—Ph |
| 1-2087 | ozn | 4-F-2-nPr—Ph |
| 1-2088 | tzl | 4-F-2-nPr—Ph |
| 1-2089 | tzn | 4-F-2-nPr—Ph |
| 1-2090 | 3-HM-cPent | 4-F-2-nPr—Ph |
| 1-2091 | 4-HM-dioxo | 4-F-2-nPr—Ph |
| 1-2092 | 4-HM-dithio | 4-F-2-nPr—Ph |
| 1-2093 | 4-HM-oxathio | 4-F-2-nPr—Ph |
| 1-2094 | 3,4-diHM-cPent | 4-F-2-nPr—Ph |
| 1-2095 | 4,5-diHM-dioxo | 4-F-2-nPr—Ph |
| 1-2096 | 4,5-diHM-dithio | 4-F-2-nPr—Ph |
| 1-2097 | 4,5-diHM-oxathio | 4-F-2-nPr—Ph |
| 1-2098 | 3,4-diHE-cPent | 4-F-2-nPr—Ph |
| 1-2099 | 4,5-diHE-dioxo | 4-F-2-nPr—Ph |
| 1-2100 | 4,5-diHE-dithio | 4-F-2-nPr—Ph |
| 1-2101 | 4,5-diHE-oxathio | 4-F-2-nPr—Ph |
| 1-2102 | 3-HE-cPent | 4-F-2-nPr—Ph |
| 1-2103 | 4-HE-dioxo | 4-F-2-nPr—Ph |
| 1-2104 | 4-HE-dithio | 4-F-2-nPr—Ph |
| 1-2105 | 4-HE-oxathio | 4-F-2-nPr—Ph |
| 1-2106 | 3-HP-cPent | 4-F-2-nPr—Ph |
| 1-2107 | 4-HP-dioxo | 4-F-2-nPr—Ph |
| 1-2108 | 4-HP-dithio | 4-F-2-nPr—Ph |

TABLE 1-continued

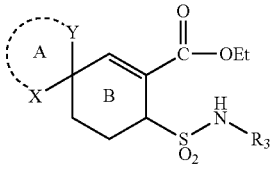

| Compound No. | X, Y | $R^3$ |
|---|---|---|
| 1-2109 | 4-HP-oxathio | 4-F-2-nPr—Ph |
| 1-2110 | 3-HB-cPent | 4-F-2-nPr—Ph |
| 1-2111 | 4-HB-dioxo | 4-F-2-nPr—Ph |
| 1-2112 | 4-HB-dithio | 4-F-2-nPr—Ph |
| 1-2113 | 4-HB-oxathio | 4-F-2-nPr—Ph |
| 1-2114 | ring 3 | 4-F-2-nPr—Ph |
| 1-2115 | ring 4 | 4-F-2-nPr—Ph |
| 1-2116 | ring 5 | 4-F-2-nPr—Ph |
| 1-2117 | ring 6 | 4-F-2-nPr—Ph |
| 1-2118 | ring 7 | 4-F-2-nPr—Ph |
| 1-2119 | ring 8 | 4-F-2-nPr—Ph |
| 1-2120 | ring 9 | 4-F-2-nPr—Ph |
| 1-2121 | ring 10 | 4-F-2-nPr—Ph |
| 1-2122 | 3,4-di$CH_2$NHAc-cPent | 4-F-2-nPr—Ph |
| 1-2123 | 4,5-di$CH_2$NHAc-dioxo | 4-F-2-nPr—Ph |
| 1-2124 | 4,5-di$CH_2$NHAc-dithio | 4-F-2-nPr—Ph |
| 1-2125 | 4,5-di$CH_2$NHAc-oxathio | 4-F-2-nPr—Ph |
| 1-2126 | ring 11 | 4-F-2-nPr—Ph |
| 1-2127 | ring 12 | 4-F-2-nPr—Ph |
| 1-2128 | ring 13 | 4-F-2-nPr—Ph |
| 1-2129 | ring 14 | 4-F-2-nPr—Ph |
| 1-2130 | 4-OH-cHex | 4-F-2-nPr—Ph |
| 1-2131 | 5-OH-dioxa | 4-F-2-nPr—Ph |
| 1-2132 | 5-OH-dithia | 4-F-2-nPr—Ph |
| 1-2133 | 5-OH-oxathia | 4-F-2-nPr—Ph |
| 1-2134 | 4-NHAc-cHex | 4-F-2-nPr—Ph |
| 1-2135 | 5-NHAc-dioxa | 4-F-2-nPr—Ph |
| 1-2136 | 5-NHAc-dithia | 4-F-2-nPr—Ph |
| 1-2137 | 5-NHAc-oxathia | 4-F-2-nPr—Ph |
| 1-2138 | 4,4-diMe-cHex | 4-F-2-nPr—Ph |
| 1-2139 | 5,5-diMe-dioxa | 4-F-2-nPr—Ph |
| 1-2140 | 5,5-diMe-dithia | 4-F-2-nPr—Ph |
| 1-2141 | 5,5-diMe-oxathia | 4-F-2-nPr—Ph |
| 1-2142 | 4,4-diHM-cHex | 4-F-2-nPr—Ph |
| 1-2143 | 5,5-diHM-dioxa | 4-F-2-nPr—Ph |
| 1-2144 | 5,5-diHM-dithia | 4-F-2-nPr—Ph |
| 1-2145 | 5,5-diHM-oxathia | 4-F-2-nPr—Ph |
| 1-2146 | ring 15 | 4-F-2-nPr—Ph |
| 1-2147 | ring 16 | 4-F-2-nPr—Ph |
| 1-2148 | ring 17 | 4-F-2-nPr—Ph |
| 1-2149 | ring 18 | 4-F-2-nPr—Ph |
| 1-2150 | 4,4-di$CO_2$Et-cHex | 4-F-2-nPr—Ph |
| 1-2151 | 5,5-di$CO_2$Et-dioxa | 4-F-2-nPr—Ph |
| 1-2152 | 5,5-di$CO_2$Et-dithia | 4-F-2-nPr—Ph |
| 1-2153 | 5,5-di$CO_2$Et-oxathia | 4-F-2-nPr—Ph |
| 1-2154 | ring 19 | 2-Cl—Ph |
| 1-2155 | ring 20 | 2-Cl—Ph |
| 1-2156 | ring 21 | 2-Cl—Ph |
| 1-2157 | ring 19 | 2-Br—Ph |
| 1-2158 | ring 20 | 2-Br—Ph |
| 1-2159 | ring 21 | 2-Br—Ph |
| 1-2160 | ring 19 | 2-Cl-6-Me—Ph |
| 1-2161 | ring 20 | 2-Cl-6-Me—Ph |
| 1-2162 | ring 21 | 2-Cl-6-Me—Ph |
| 1-2163 | ring 19 | 2-Cl-4-F—Ph |
| 1-2164 | ring 20 | 2-Cl-4-F—Ph |
| 1-2165 | ring 21 | 2-Cl-4-F—Ph |
| 1-2166 | ring 19 | 2,4-diF |
| 1-2167 | ring 20 | 2,4-diF |
| 1-2168 | ring 21 | 2,4-diF |
| 1-2169 | ring 19 | 2-Br-4-F—Ph |
| 1-2170 | ring 20 | 2-Br-4-F—Ph |
| 1-2171 | ring 21 | 2-Br-4-F—Ph |
| 1-2172 | ring 19 | 2-nBu-4-F—Ph |
| 1-2173 | ring 20 | 2-nBu-4-F—Ph |
| 1-2174 | ring 21 | 2-nBu-4-F—Ph |
| 1-2175 | ring 19 | 2-nPent-Ph |
| 1-2176 | ring 20 | 2-nPent-Ph |

TABLE 1-continued

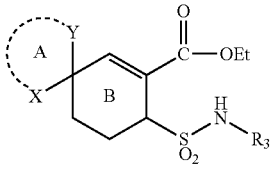

| Compound No. | X, Y | $R^3$ |
|---|---|---|
| 1-2177 | ring 21 | 2-nPent-Ph |
| 1-2178 | ring 19 | 4-F-2-nPent-Ph |
| 1-2179 | ring 20 | 4-F-2-nPent-Ph |
| 1-2180 | ring 21 | 4-F-2-nPent-Ph |
| 1-2181 | ring 19 | 2-nHex—Ph |
| 1-2182 | ring 20 | 2-nHex—Ph |
| 1-2183 | ring 21 | 2-nHex—Ph |
| 1-2184 | ring 19 | 4-F-2-nHex—Ph |
| 1-2185 | ring 20 | 4-F-2-nHex—Ph |
| 1-2186 | ring 21 | 4-F-2-nHex—Ph |
| 1-2187 | ring 19 | 2-nHept-Ph |
| 1-2188 | ring 20 | 2-nHept-Ph |
| 1-2189 | ring 21 | 2-nHept-Ph |
| 1-2190 | ring 19 | 4-F-2-nHept-Ph |
| 1-2191 | ring 20 | 4-F-2-nHept-Ph |
| 1-2192 | ring 21 | 4-F-2-nHept-Ph |
| 1-2193 | ring 19 | 2-nOct-Ph |
| 1-2194 | ring 20 | 2-nOct-Ph |
| 1-2195 | ring 21 | 2-nOct-Ph |
| 1-2196 | ring 19 | 4-F-2-nOct-Ph |
| 1-2197 | ring 20 | 4-F-2-nOct-Ph |
| 1-2198 | ring 21 | 4-F-2-nOct-Ph |
| 1-2199 | ring 19 | Ph |
| 1-2200 | ring 20 | Ph |
| 1-2201 | ring 21 | Ph |
| 1-2202 | ring 19 | 4-F—Ph |
| 1-2203 | ring 20 | 4-F—Ph |
| 1-2204 | ring 21 | 4-F—Ph |
| 1-2205 | ring 19 | 2-Cl-4-Me—Ph |
| 1-2206 | ring 20 | 2-Cl-4-Me—Ph |
| 1-2207 | ring 21 | 2-Cl-4-Me—Ph |
| 1-2208 | ring 19 | 2-nBu—Ph |
| 1-2209 | ring 20 | 2-nBu—Ph |
| 1-2210 | ring 21 | 2-nBu—Ph |
| 1-2211 | ring 19 | 2-nPr—Ph |
| 1-2212 | ring 20 | 2-nPr—Ph |
| 1-2213 | ring 21 | 2-nPr—Ph |
| 1-2214 | ring 19 | 4-F-2-nPr—Ph |
| 1-2215 | ring 20 | 4-F-2-nPr—Ph |
| 1-2216 | ring 21 | 4-F-2-nPr—Ph |
| 1-2217 | dioxo | 2-F—Ph |
| 1-2218 | 4-HM-dioxo | 2-F—Ph |
| 1-2219 | 4,5-diHM-dioxo | 2-F—Ph |
| 1-2220 | 4,5-diHE-dioxo | 2-F—Ph |
| 1-2221 | ring 19 | 2-F—Ph |
| 1-2222 | ring 20 | 2-F—Ph |
| 1-2223 | ring 21 | 2-F—Ph |
| 1-2224 | dioxo | 2-I—Ph |
| 1-2225 | 4-HM-dioxo | 2-I—Ph |
| 1-2226 | 4,5-diHM-dioxo | 2-I—Ph |
| 1-2227 | 4,5-diHE-dioxo | 2-I—Ph |
| 1-2228 | ring 19 | 2-I—Ph |
| 1-2229 | ring 20 | 2-I—Ph |
| 1-2230 | ring 21 | 2-I—Ph |
| 1-2231 | dioxo | 4-Cl—Ph |
| 1-2232 | 4-HM-dioxo | 4-Cl—Ph |
| 1-2233 | 4,5-diHM-dioxo | 4-Cl—Ph |
| 1-2234 | 4,5-diHE-dioxo | 4-Cl—Ph |
| 1-2235 | ring 19 | 4-Cl—Ph |
| 1-2236 | ring 20 | 4-Cl—Ph |
| 1-2237 | ring 21 | 4-Cl—Ph |
| 1-2238 | dioxo | 2-Me—Ph |
| 1-2239 | 4-HM-dioxo | 2-Me—Ph |
| 1-2240 | 4,5-diHM-dioxo | 2-Me—Ph |
| 1-2241 | 4,5-diHE-dioxo | 2-Me—Ph |
| 1-2242 | ring 19 | 2-Me—Ph |
| 1-2243 | ring 20 | 2-Me—Ph |
| 1-2244 | ring 21 | 2-Me—Ph |

TABLE 1-continued

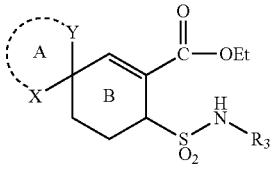

| Compound No. | X, Y | $R^3$ |
|---|---|---|
| 1-2245 | dioxo | 2-Et—Ph |
| 1-2246 | 4-HM-dioxo | 2-Et—Ph |
| 1-2247 | 4,5-diHM-dioxo | 2-Et—Ph |
| 1-2248 | 4,5-diHE-dioxo | 2-Et—Ph |
| 1-2249 | ring 19 | 2-Et—Ph |
| 1-2250 | ring 20 | 2-Et—Ph |
| 1-2251 | ring 21 | 2-Et—Ph |
| 1-2252 | dioxo | 2-C≡CH—Ph |
| 1-2253 | 4-HM-dioxo | 2-C≡CH—Ph |
| 1-2254 | 4,5-diHM-dioxo | 2-C≡CH—Ph |
| 1-2255 | 4,5-diHE-dioxo | 2-C≡CH—Ph |
| 1-2256 | ring 19 | 2-C≡CH—Ph |
| 1-2257 | ring 20 | 2-C≡CH—Ph |
| 1-2258 | ring 21 | 2-C≡CH—Ph |
| 1-2259 | dioxo | 2-iPr—Ph |
| 1-2260 | 4-HM-dioxo | 2-iPr—Ph |
| 1-2261 | 4,5-diHM-dioxo | 2-iPr—Ph |
| 1-2262 | 4,5-diHE-dioxo | 2-iPr—Ph |
| 1-2263 | ring 19 | 2-iPr—Ph |
| 1-2264 | ring 20 | 2-iPr—Ph |
| 1-2265 | ring 21 | 2-iPr—Ph |
| 1-2266 | dioxo | 2-tBu—Ph |
| 1-2267 | 4-HM-dioxo | 2-tBu—Ph |
| 1-2268 | 4,5-diHM-dioxo | 2-tBu—Ph |
| 1-2269 | 4,5-diHE-dioxo | 2-tBu—Ph |
| 1-2270 | ring 19 | 2-tBu—Ph |
| 1-2271 | ring 20 | 2-tBu—Ph |
| 1-2272 | ring 21 | 2-tBu—Ph |
| 1-2273 | dioxo | 2-sBu—Ph |
| 1-2274 | 4-HM-dioxo | 2-sBu—Ph |
| 1-2275 | 4,5-diHM-dioxo | 2-sBu—Ph |
| 1-2276 | 4,5-diHE-dioxo | 2-sBu—Ph |
| 1-2277 | ring 19 | 2-sBu—Ph |
| 1-2278 | ring 20 | 2-sBu—Ph |
| 1-2279 | ring 21 | 2-sBu—Ph |
| 1-2280 | dioxo | 2-OMe—Ph |
| 1-2281 | 4-HM-dioxo | 2-OMe—Ph |
| 1-2282 | 4,5-diHM-dioxo | 2-OMe—Ph |
| 1-2283 | 4,5-diHE-dioxo | 2-OMe—Ph |
| 1-2284 | ring 19 | 2-OMe—Ph |
| 1-2285 | ring 20 | 2-OMe—Ph |
| 1-2286 | ring 21 | 2-OMe—Ph |
| 1-2287 | dioxo | 2-OEt—Ph |
| 1-2288 | 4-HM-dioxo | 2-OEt—Ph |
| 1-2289 | 4,5-diHM-dioxo | 2-OEt—Ph |
| 1-2290 | 4,5-diHE-dioxo | 2-OEt—Ph |
| 1-2291 | ring 19 | 2-OEt—Ph |
| 1-2292 | ring 20 | 2-OEt—Ph |
| 1-2293 | ring 21 | 2-OEt—Ph |
| 1-2294 | dioxo | 2-$OCHF_2$—Ph |
| 1-2295 | 4-HM-dioxo | 2-$OCHF_2$—Ph |
| 1-2296 | 4,5-diHM-dioxo | 2-$OCHF_2$—Ph |
| 1-2297 | 4,5-diHE-dioxo | 2-$OCHF_2$—Ph |
| 1-2298 | ring 19 | 2-$OCHF_2$—Ph |
| 1-2299 | ring 20 | 2-$OCHF_2$—Ph |
| 1-2300 | ring 21 | 2-$OCHF_2$—Ph |
| 1-2301 | dioxo | 2-SMe—Ph |
| 1-2302 | 4-HM-dioxo | 2-SMe—Ph |
| 1-2303 | 4,5-diHM-dioxo | 2-SMe—Ph |
| 1-2304 | 4,5-diHE-dioxo | 2-SMe—Ph |
| 1-2305 | ring 19 | 2-SMe—Ph |
| 1-2306 | ring 20 | 2-SMe—Ph |
| 1-2307 | ring 21 | 2-SMe—Ph |
| 1-2308 | dioxo | 2-Ac—Ph |
| 1-2309 | 4-HM-dioxo | 2-Ac—Ph |
| 1-2310 | 4,5-diHM-dioxo | 2-Ac—Ph |
| 1-2311 | 4,5-diHE-dioxo | 2-Ac—Ph |
| 1-2312 | ring 19 | 2-Ac—Ph |

TABLE 1-continued

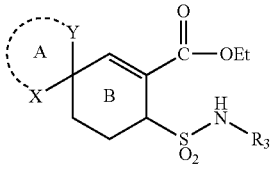

| Compound No. | X, Y | $R^3$ |
|---|---|---|
| 1-2313 | ring 20 | 2-Ac—Ph |
| 1-2314 | ring 21 | 2-Ac—Ph |
| 1-2315 | dioxo | 2-Bn—Ph |
| 1-2316 | 4-HM-dioxo | 2-Bn—Ph |
| 1-2317 | 4,5-diHM-dioxo | 2-Bn—Ph |
| 1-2318 | 4,5-diHE-dioxo | 2-Bn—Ph |
| 1-2319 | ring 19 | 2-Bn—Ph |
| 1-2320 | ring 20 | 2-Bn—Ph |
| 1-2321 | ring 21 | 2-Bn—Ph |
| 1-2322 | dioxo | 2-Mor-Ph |
| 1-2323 | 4-HM-dioxo | 2-Mor-Ph |
| 1-2324 | 4,5-diHM-dioxo | 2-Mor-Ph |
| 1-2325 | 4,5-diHE-dioxo | 2-Mor-Ph |
| 1-2326 | ring 19 | 2-Mor-Ph |
| 1-2327 | ring 20 | 2-Mor-Ph |
| 1-2328 | ring 21 | 2-Mor-Ph |
| 1-2329 | dioxo | Flu |
| 1-2330 | 4-HM-dioxo | Flu |
| 1-2331 | 4,5-diHM-dioxo | Flu |
| 1-2332 | 4,5-diHE-dioxo | Flu |
| 1-2333 | ring 19 | Flu |
| 1-2334 | ring 20 | Flu |
| 1-2335 | ring 21 | Flu |
| 1-2336 | dioxo | 2-$CH_2CH_2$Pyrd-Ph |
| 1-2337 | 4-HM-dioxo | 2-$CH_2CH_2$Pyrd-Ph |
| 1-2338 | 4,5-diHM-dioxo | 2-$CH_2CH_2$Pyrd-Ph |
| 1-2339 | 4,5-diHE-dioxo | 2-$CH_2CH_2$Pyrd-Ph |
| 1-2340 | ring 19 | 2-$CH_2CH_2$Pyrd-Ph |
| 1-2341 | ring 20 | 2-$CH_2CH_2$Pyrd-Ph |
| 1-2342 | ring 21 | 2-$CH_2CH_2$Pyrd-Ph |
| 1-2343 | dioxo | 2-$CH_2CH_2NHBoc$—Ph |
| 1-2344 | 4-HM-dioxo | 2-$CH_2CH_2NHBoc$—Ph |
| 1-2345 | 4,5-diHM-dioxo | 2-$CH_2CH_2NHBoc$—Ph |
| 1-2346 | 4,5-diHE-dioxo | 2-$CH_2CH_2NHBoc$—Ph |
| 1-2347 | ring 19 | 2-$CH_2CH_2NHBoc$—Ph |
| 1-2348 | ring 20 | 2-$CH_2CH_2NHBoc$—Ph |
| 1-2349 | ring 21 | 2-$CH_2CH_2NHBoc$—Ph |
| 1-2350 | dioxo | 2-$NH_2$—Ph |
| 1-2351 | 4-HM-dioxo | 2-$NH_2$—Ph |
| 1-2352 | 4,5-diHM-dioxo | 2-$NH_2$—Ph |
| 1-2353 | 4,5-diHE-dioxo | 2-$NH_2$—Ph |
| 1-2354 | ring 19 | 2-$NH_2$—Ph |
| 1-2355 | ring 20 | 2-$NH_2$—Ph |
| 1-2356 | ring 21 | 2-$NH_2$—Ph |
| 1-2357 | dioxo | 4-F-2-Me—Ph |
| 1-2358 | 4-HM-dioxo | 4-F-2-Me—Ph |
| 1-2359 | 4,5-diHM-dioxo | 4-F-2-Me—Ph |
| 1-2360 | 4,5-diHE-dioxo | 4-F-2-Me—Ph |
| 1-2361 | ring 19 | 4-F-2-Me—Ph |
| 1-2362 | ring 20 | 4-F-2-Me—Ph |
| 1-2363 | ring 21 | 4-F-2-Me—Ph |
| 1-2364 | dioxo | 3-Cl-4-F—Ph |
| 1-2365 | 4-HM-dioxo | 3-Cl-4-F—Ph |
| 1-2366 | 4,5-diHM-dioxo | 3-Cl-4-F—Ph |
| 1-2367 | 4,5-diHE-dioxo | 3-Cl-4-F—Ph |
| 1-2368 | ring 19 | 3-Cl-4-F—Ph |
| 1-2369 | ring 20 | 3-Cl-4-F—Ph |
| 1-2370 | ring 21 | 3-Cl-4-F—Ph |
| 1-2371 | dioxo | 4-F-3-$CF_3$—Ph |
| 1-2372 | 4-HM-dioxo | 4-F-3-$CF_3$—Ph |
| 1-2373 | 4,5-diHM-dioxo | 4-F-3-$CF_3$—Ph |
| 1-2374 | 4,5-diHE-dioxo | 4-F-3-$CF_3$—Ph |
| 1-2375 | ring 19 | 4-F-3-$CF_3$—Ph |
| 1-2376 | ring 20 | 4-F-3-$CF_3$—Ph |
| 1-2377 | ring 21 | 4-F-3-$CF_3$—Ph |
| 1-2378 | dioxo | 4-F-3-OMe—Ph |
| 1-2379 | 4-HM-dioxo | 4-F-3-OMe—Ph |
| 1-2380 | 4,5-diHM-dioxo | 4-F-3-OMe—Ph |

TABLE 1-continued

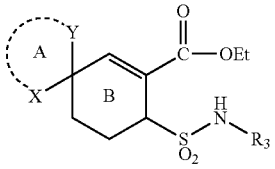

| Compound No. | X, Y | $R^3$ |
|---|---|---|
| 1-2381 | 4,5-diHE-dioxo | 4-F-3-OMe—Ph |
| 1-2382 | ring 19 | 4-F-3-OMe—Ph |
| 1-2383 | ring 20 | 4-F-3-OMe—Ph |
| 1-2384 | ring 21 | 4-F-3-OMe—Ph |
| 1-2385 | dioxo | 3,4-diF—Ph |
| 1-2386 | 4-HM-dioxo | 3,4-diF—Ph |
| 1-2387 | 4,5-diHM-dioxo | 3,4-diF—Ph |
| 1-2388 | 4,5-diHE-dioxo | 3,4-diF—Ph |
| 1-2389 | ring 19 | 3,4-diF—Ph |
| 1-2390 | ring 20 | 3,4-diF—Ph |
| 1-2391 | ring 21 | 3,4-diF—Ph |
| 1-2392 | dioxo | 2,4-diOMe—Ph |
| 1-2393 | 4-HM-dioxo | 2,4-diOMe—Ph |
| 1-2394 | 4,5-diHM-dioxo | 2,4-diOMe—Ph |
| 1-2395 | 4,5-diHE-dioxo | 2,4-diOMe—Ph |
| 1-2396 | ring 19 | 2,4-diOMe—Ph |
| 1-2397 | ring 20 | 2,4-diOMe—Ph |
| 1-2398 | ring 21 | 2,4-diOMe—Ph |
| 1-2399 | dioxo | 4-Cl-2-F—Ph |
| 1-2400 | 4-HM-dioxo | 4-Cl-2-F—Ph |
| 1-2401 | 4,5-diHM-dioxo | 4-Cl-2-F—Ph |
| 1-2402 | 4,5-diHE-dioxo | 4-Cl-2-F—Ph |
| 1-2403 | ring 19 | 4-Cl-2-F—Ph |
| 1-2404 | ring 20 | 4-Cl-2-F—Ph |
| 1-2405 | ring 21 | 4-Cl-2-F—Ph |
| 1-2406 | dioxo | 2-Br-4-Cl—Ph |
| 1-2407 | 4-HM-dioxo | 2-Br-4-Cl—Ph |
| 1-2408 | 4,5-diHM-dioxo | 2-Br-4-Cl—Ph |
| 1-2409 | 4,5-diHE-dioxo | 2-Br-4-Cl—Ph |
| 1-2410 | ring 19 | 2-Br-4-Cl—Ph |
| 1-2411 | ring 20 | 2-Br-4-Cl—Ph |
| 1-2412 | ring 21 | 2-Br-4-Cl—Ph |
| 1-2413 | dioxo | 4-Cl-2-Me—Ph |
| 1-2414 | 4-HM-dioxo | 4-Cl-2-Me—Ph |
| 1-2415 | 4,5-diHM-dioxo | 4-Cl-2-Me—Ph |
| 1-2416 | 4,5-diHE-dioxo | 4-Cl-2-Me—Ph |
| 1-2417 | ring 19 | 4-Cl-2-Me—Ph |
| 1-2418 | ring 20 | 4-Cl-2-Me—Ph |
| 1-2419 | ring 21 | 4-Cl-2-Me—Ph |
| 1-2420 | dioxo | 4-Cl-2-$CO_2$Me—Ph |
| 1-2421 | 4-HM-dioxo | 4-Cl-2-$CO_2$Me—Ph |
| 1-2422 | 4,5-diHM-dioxo | 4-Cl-2-$CO_2$Me—Ph |
| 1-2423 | 4,5-diHE-dioxo | 4-Cl-2-$CO_2$Me—Ph |
| 1-2424 | ring 19 | 4-Cl-2-$CO_2$Me—Ph |
| 1-2425 | ring 20 | 4-Cl-2-$CO_2$Me—Ph |
| 1-2426 | ring 21 | 4-Cl-2-$CO_2$Me—Ph |
| 1-2427 | dioxo | 3,4-diCl—Ph |
| 1-2428 | 4-HM-dioxo | 3,4-diCl—Ph |
| 1-2429 | 4,5-diHM-dioxo | 3,4-diCl—Ph |
| 1-2430 | 4,5-diHE-dioxo | 3,4-diCl—Ph |
| 1-2431 | ring 19 | 3,4-diCl—Ph |
| 1-2432 | ring 20 | 3,4-diCl—Ph |
| 1-2433 | ring 21 | 3,4-diCl—Ph |
| 1-2434 | dioxo | 2,5-diF—Ph |
| 1-2435 | 4-HM-dioxo | 2,5-diF—Ph |
| 1-2436 | 4,5-diHM-dioxo | 2,5-diF—Ph |
| 1-2437 | 4,5-diHE-dioxo | 2,5-diF—Ph |
| 1-2438 | ring 19 | 2,5-diF—Ph |
| 1-2439 | ring 20 | 2,5-diF—Ph |
| 1-2440 | ring 21 | 2,5-diF—Ph |
| 1-2441 | dioxo | 2,6-diF—Ph |
| 1-2442 | 4-HM-dioxo | 2,6-diF—Ph |
| 1-2443 | 4,5-diHM-dioxo | 2,6-diF—Ph |
| 1-2444 | 4,5-diHE-dioxo | 2,6-diF—Ph |
| 1-2445 | ring 19 | 2,6-diF—Ph |
| 1-2446 | ring 20 | 2,6-diF—Ph |
| 1-2447 | ring 21 | 2,6-diF—Ph |
| 1-2448 | dioxo | 2-F-4-Me—Ph |

TABLE 1-continued

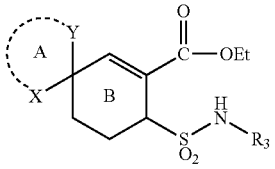

| Compound No. | X, Y | $R^3$ |
|---|---|---|
| 1-2449 | 4-HM-dioxo | 2-F-4-Me—Ph |
| 1-2450 | 4,5-diHM-dioxo | 2-F-4-Me—Ph |
| 1-2451 | 4,5-diHE-dioxo | 2-F-4-Me—Ph |
| 1-2452 | ring 19 | 2-F-4-Me—Ph |
| 1-2453 | ring 20 | 2-F-4-Me—Ph |
| 1-2454 | ring 21 | 2-F-4-Me—Ph |
| 1-2455 | dioxo | 2-F-5-Me—Ph |
| 1-2456 | 4-HM-dioxo | 2-F-5-Me—Ph |
| 1-2457 | 4,5-diHM-dioxo | 2-F-5-Me—Ph |
| 1-2458 | 4,5-diHE-dioxo | 2-F-5-Me—Ph |
| 1-2459 | ring 19 | 2-F-5-Me—Ph |
| 1-2460 | ring 20 | 2-F-5-Me—Ph |
| 1-2461 | ring 21 | 2-F-5-Me—Ph |
| 1-2462 | dioxo | 2-F-4-OMe—Ph |
| 1-2463 | 4-HM-dioxo | 2-F-4-OMe—Ph |
| 1-2464 | 4,5-diHM-dioxo | 2-F-4-OMe—Ph |
| 1-2465 | 4,5-diHE-dioxo | 2-F-4-OMe—Ph |
| 1-2466 | ring 19 | 2-F-4-OMe—Ph |
| 1-2467 | ring 20 | 2-F-4-OMe—Ph |
| 1-2468 | ring 21 | 2-F-4-OMe—Ph |
| 1-2469 | dioxo | 5-Cl-2-F—Ph |
| 1-2470 | 4-HM-dioxo | 5-Cl-2-F—Ph |
| 1-2471 | 4,5-diHM-dioxo | 5-Cl-2-F—Ph |
| 1-2472 | 4,5-diHE-dioxo | 5-Cl-2-F—Ph |
| 1-2473 | ring 19 | 5-Cl-2-F—Ph |
| 1-2474 | ring 20 | 5-Cl-2-F—Ph |
| 1-2475 | ring 21 | 5-Cl-2-F—Ph |
| 1-2476 | dioxo | 2,3,4-triF—Ph |
| 1-2477 | 4-HM-dioxo | 2,3,4-triF—Ph |
| 1-2478 | 4,5-diHM-dioxo | 2,3,4-triF—Ph |
| 1-2479 | 4,5-diHE-dioxo | 2,3,4-triF—Ph |
| 1-2480 | ring 19 | 2,3,4-triF—Ph |
| 1-2481 | ring 20 | 2,3,4-triF—Ph |
| 1-2482 | ring 21 | 2,3,4-triF—Ph |
| 1-2483 | dioxo | 2,4,5-triF—Ph |
| 1-2484 | 4-HM-dioxo | 2,4,5-triF—Ph |
| 1-2485 | 4,5-diHM-dioxo | 2,4,5-triF—Ph |
| 1-2486 | 4,5-diHE-dioxo | 2,4,5-triF—Ph |
| 1-2487 | ring 19 | 2,4,5-triF—Ph |
| 1-2488 | ring 20 | 2,4,5-triF—Ph |
| 1-2489 | ring 21 | 2,4,5-triF—Ph |
| 1-2490 | dioxo | 2,4,6-triF—Ph |
| 1-2491 | 4-HM-dioxo | 2,4,6-triF—Ph |
| 1-2492 | 4,5-diHM-dioxo | 2,4,6-triF—Ph |
| 1-2493 | 4,5-diHE-dioxo | 2,4,6-triF—Ph |
| 1-2494 | ring 19 | 2,4,6-triF—Ph |
| 1-2495 | ring 20 | 2,4,6-triF—Ph |
| 1-2496 | ring 21 | 2,4,6-triF—Ph |
| 1-2497 | dioxo | 2,4-diCl—Ph |
| 1-2498 | 4-HM-dioxo | 2,4-diCl—Ph |
| 1-2499 | 4,5-diHM-dioxo | 2,4-diCl—Ph |
| 1-2500 | 4,5-diHE-dioxo | 2,4-diCl—Ph |
| 1-2501 | ring 19 | 2,4-diCl—Ph |
| 1-2502 | ring 20 | 2,4-diCl—Ph |
| 1-2503 | ring 21 | 2,4-diCl—Ph |
| 1-2504 | dioxo | 4-Br-2-Cl—Ph |
| 1-2505 | 4-HM-dioxo | 4-Br-2-Cl—Ph |
| 1-2506 | 4,5-diHM-dioxo | 4-Br-2-Cl—Ph |
| 1-2507 | 4,5-diHE-dioxo | 4-Br-2-Cl—Ph |
| 1-2508 | ring 19 | 4-Br-2-Cl—Ph |
| 1-2509 | ring 20 | 4-Br-2-Cl—Ph |
| 1-2510 | ring 21 | 4-Br-2-Cl—Ph |
| 1-2511 | dioxo | 4-tBu-2-Cl—Ph |
| 1-2512 | 4-HM-dioxo | 4-tBu-2-Cl—Ph |
| 1-2513 | 4,5-diHM-dioxo | 4-tBu-2-Cl—Ph |
| 1-2514 | 4,5-diHE-dioxo | 4-tBu-2-Cl—Ph |
| 1-2515 | ring 19 | 4-tBu-2-Cl—Ph |
| 1-2516 | ring 20 | 4-tBu-2-Cl—Ph |

TABLE 1-continued

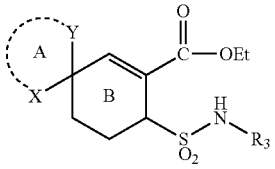

| Compound No. | X, Y | $R^3$ |
|---|---|---|
| 1-2517 | ring 21 | 4-tBu-2-Cl—Ph |
| 1-2518 | dioxo | 2-Cl-6-F—Ph |
| 1-2519 | 4-HM-dioxo | 2-Cl-6-F—Ph |
| 1-2520 | 4,5-diHM-dioxo | 2-Cl-6-F—Ph |
| 1-2521 | 4,5-diHE-dioxo | 2-Cl-6-F—Ph |
| 1-2522 | ring 19 | 2-Cl-6-F—Ph |
| 1-2523 | ring 20 | 2-Cl-6-F—Ph |
| 1-2524 | ring 21 | 2-Cl-6-F—Ph |
| 1-2525 | dioxo | 2,6-diCl—Ph |
| 1-2526 | 4-HM-dioxo | 2,6-diCl—Ph |
| 1-2527 | 4,5-diHM-dioxo | 2,6-diCl—Ph |
| 1-2528 | 4,5-diHE-dioxo | 2,6-diCl—Ph |
| 1-2529 | ring 19 | 2,6-diCl—Ph |
| 1-2530 | ring 20 | 2,6-diCl—Ph |
| 1-2531 | ring 21 | 2,6-diCl—Ph |
| 1-2532 | dioxo | 2,3-diCl—Ph |
| 1-2533 | 4-HM-dioxo | 2,3-diCl—Ph |
| 1-2534 | 4,5-diHM-dioxo | 2,3-diCl—Ph |
| 1-2535 | 4,5-diHE-dioxo | 2,3-diCl—Ph |
| 1-2536 | ring 19 | 2,3-diCl—Ph |
| 1-2537 | ring 20 | 2,3-diCl—Ph |
| 1-2538 | ring 21 | 2,3-diCl—Ph |
| 1-2539 | dioxo | 2,5-diCl—Ph |
| 1-2540 | 4-HM-dioxo | 2,5-diCl—Ph |
| 1-2541 | 4,5-diHM-dioxo | 2,5-diCl—Ph |
| 1-2542 | 4,5-diHE-dioxo | 2,5-diCl—Ph |
| 1-2543 | ring 19 | 2,5-diCl—Ph |
| 1-2544 | ring 20 | 2,5-diCl—Ph |
| 1-2545 | ring 21 | 2,5-diCl—Ph |
| 1-2546 | dioxo | 2-Cl-4,6-diF—Ph |
| 1-2547 | 4-HM-dioxo | 2-Cl-4,6-diF—Ph |
| 1-2548 | 4,5-diHM-dioxo | 2-Cl-4,6-diF—Ph |
| 1-2549 | 4,5-diHE-dioxo | 2-Cl-4,6-diF—Ph |
| 1-2550 | ring 19 | 2-Cl-4,6-diF—Ph |
| 1-2551 | ring 20 | 2-Cl-4,6-diF—Ph |
| 1-2552 | ring 21 | 2-Cl-4,6-diF—Ph |
| 1-2553 | dioxo | 2,6-diCl-4-F—Ph |
| 1-2554 | 4-HM-dioxo | 2,6-diCl-4-F—Ph |
| 1-2555 | 4,5-diHM-dioxo | 2,6-diCl-4-F—Ph |
| 1-2556 | 4,5-diHE-dioxo | 2,6-diCl-4-F—Ph |
| 1-2557 | ring 19 | 2,6-diCl-4-F—Ph |
| 1-2558 | ring 20 | 2,6-diCl-4-F—Ph |
| 1-2559 | ring 21 | 2,6-diCl-4-F—Ph |
| 1-2560 | dioxo | 2-Br-6-Cl-4-F—Ph |
| 1-2561 | 4-HM-dioxo | 2-Br-6-Cl-4-F—Ph |
| 1-2562 | 4,5-diHM-dioxo | 2-Br-6-Cl-4-F—Ph |
| 1-2563 | 4,5-diHE-dioxo | 2-Br-6-Cl-4-F—Ph |
| 1-2564 | ring 19 | 2-Br-6-Cl-4-F—Ph |
| 1-2565 | ring 20 | 2-Br-6-Cl-4-F—Ph |
| 1-2566 | ring 21 | 2-Br-6-Cl-4-F—Ph |
| 1-2567 | dioxo | 4-Cl-2-OMe-5-Me—Ph |
| 1-2568 | 4-HM-dioxo | 4-Cl-2-OMe-5-Me—Ph |
| 1-2569 | 4,5-diHM-dioxo | 4-Cl-2-OMe-5-Me—Ph |
| 1-2570 | 4,5-diHE-dioxo | 4-Cl-2-OMe-5-Me—Ph |
| 1-2571 | ring 19 | 4-Cl-2-OMe-5-Me—Ph |
| 1-2572 | ring 20 | 4-Cl-2-OMe-5-Me—Ph |
| 1-2573 | ring 21 | 4-Cl-2-OMe-5-Me—Ph |
| 1-2574 | dioxo | 2,4-diBr—Ph |
| 1-2575 | 4-HM-dioxo | 2,4-diBr—Ph |
| 1-2576 | 4,5-diHM-dioxo | 2,4-diBr—Ph |
| 1-2577 | 4,5-diHE-dioxo | 2,4-diBr—Ph |
| 1-2578 | ring 19 | 2,4-diBr—Ph |
| 1-2579 | ring 20 | 2,4-diBr—Ph |
| 1-2580 | ring 21 | 2,4-diBr—Ph |
| 1-2581 | dioxo | 2,6-diBr—Ph |
| 1-2582 | 4-HM-dioxo | 2,6-diBr—Ph |
| 1-2583 | 4,5-diHM-dioxo | 2,6-diBr—Ph |
| 1-2584 | 4,5-diHE-dioxo | 2,6-diBr—Ph |

TABLE 1-continued

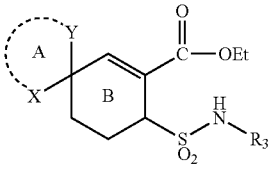

| Compound No. | X, Y | $R^3$ |
|---|---|---|
| 1-2585 | ring 19 | 2,6-diBr—Ph |
| 1-2586 | ring 20 | 2,6-diBr—Ph |
| 1-2587 | ring 21 | 2,6-diBr—Ph |
| 1-2588 | dioxo | 2-Br-4-iPr—Ph |
| 1-2589 | 4-HM-dioxo | 2-Br-4-iPr—Ph |
| 1-2590 | 4,5-diHM-dioxo | 2-Br-4-iPr—Ph |
| 1-2591 | 4,5-diHE-dioxo | 2-Br-4-iPr—Ph |
| 1-2592 | ring 19 | 2-Br-4-iPr—Ph |
| 1-2593 | ring 20 | 2-Br-4-iPr—Ph |
| 1-2594 | ring 21 | 2-Br-4-iPr—Ph |
| 1-2595 | dioxo | 2-nNon-Ph |
| 1-2596 | 4-HM-dioxo | 2-nNon-Ph |
| 1-2597 | 4,5-diHM-dioxo | 2-nNon-Ph |
| 1-2598 | 4,5-diHE-dioxo | 2-nNon-Ph |
| 1-2599 | ring 19 | 2-nNon-Ph |
| 1-2600 | ring 20 | 2-nNon-Ph |
| 1-2601 | ring 21 | 2-nNon-Ph |
| 1-2602 | dioxo | 4-F-2-nNon-Ph |
| 1-2603 | 4-HM-dioxo | 4-F-2-nNon-Ph |
| 1-2604 | 4,5-diHM-dioxo | 4-F-2-nNon-Ph |
| 1-2605 | 4,5-diHE-dioxo | 4-F-2-nNon-Ph |
| 1-2606 | ring 19 | 4-F-2-nNon-Ph |
| 1-2607 | ring 20 | 4-F-2-nNon-Ph |
| 1-2608 | ring 21 | 4-F-2-nNon-Ph |
| 1-2609 | dioxo | 2-nDec-Ph |
| 1-2610 | 4-HM-dioxo | 2-nDec-Ph |
| 1-2611 | 4,5-diHM-dioxo | 2-nDec-Ph |
| 1-2612 | 4,5-diHE-dioxo | 2-nDec-Ph |
| 1-2613 | ring 19 | 2-nDec-Ph |
| 1-2614 | ring 20 | 2-nDec-Ph |
| 1-2615 | ring 21 | 2-nDec-Ph |
| 1-2616 | dioxo | 4-F-2-nDec-Ph |
| 1-2617 | 4-HM-dioxo | 4-F-2-nDec-Ph |
| 1-2618 | 4,5-diHM-dioxo | 4-F-2-nDec-Ph |
| 1-2619 | 4,5-diHE-dioxo | 4-F-2-nDec-Ph |
| 1-2620 | ring 19 | 4-F-2-nDec-Ph |
| 1-2621 | ring 20 | 4-F-2-nDec-Ph |
| 1-2622 | ring 21 | 4-F-2-nDec-Ph |
| 1-2623 | dioxo | 2-Et-4-F—Ph |
| 1-2624 | 4-HM-dioxo | 2-Et-4-F—Ph |
| 1-2625 | 4,5-diHM-dioxo | 2-Et-4-F—Ph |
| 1-2626 | 4,5-diHE-dioxo | 2-Et-4-F—Ph |
| 1-2627 | ring 19 | 2-Et-4-F—Ph |
| 1-2628 | ring 20 | 2-Et-4-F—Ph |
| 1-2629 | ring 21 | 2-Et-4-F—Ph |

TABLE 2

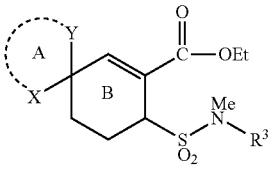

| Compound No. | X, Y | $R^3$ |
|---|---|---|
| 2-1 | dioxo | 2-Cl—Ph |
| 2-2 | 4-HM-dioxo | 2-Cl—Ph |
| 2-3 | 4,5 -diHM-dioxo | 2-Cl—Ph |
| 2-4 | 4,5 -diHE-dioxo | 2-Cl—Ph |
| 2-5 | dioxo | 2-Br—Ph |
| 2-6 | 4-HM-dioxo | 2-Br—Ph |

TABLE 2-continued

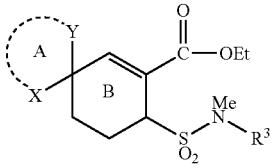

| Compound No. | X, Y | $R^3$ |
|---|---|---|
| 2-7 | 4,5 -diHM-dioxo | 2-Br—Ph |
| 2-8 | 4,5-diHE-dioxo | 2-Br—Ph |
| 2-9 | dioxo | 2-Cl-6-Me—Ph |
| 2-10 | 4-HM-dioxo | 2-Cl-6-Me—Ph |
| 2-11 | 4,5-diHM-dioxo | 2-Cl-6-Me—Ph |
| 2-12 | 4,5-diHE-dioxo | 2-Cl-6-Me—Ph |
| 2-13 | dioxo | 2-Cl-4-F—Ph |
| 2-14 | 4-HM-dioxo | 2-Cl-4-F—Ph |
| 2-15 | 4,5-diHM-dioxo | 2-Cl-4-F—Ph |
| 2-16 | 4,5-diHE-dioxo | 2-Cl-4-F—Ph |
| 2-17 | dioxo | 2,4-diF |
| 2-18 | 4-HM-dioxo | 2,4-diF |
| 2-19 | 4,5-diHM-dioxo | 2,4-diF |
| 2-20 | 4,5-diHE-dioxo | 2,4-diF |
| 2-21 | dioxo | 2-Br-4-F Ph |
| 2-22 | 4-HM-dioxo | 2-Br-4-F Ph |
| 2-23 | 4,5-diHM-dioxo | 2-Br-4-F Ph |
| 2-24 | 4,5-diHE-dioxo | 2-Br-4-F Ph |
| 2-25 | dioxo | 2-nBu-4-F Ph |
| 2-26 | 4-HM-dioxo | 2-nBu-4-F Ph |
| 2-27 | 4,5-diHM-dioxo | 2-nBu-4-F Ph |
| 2-28 | 4,5-diHE-dioxo | 2-nBu-4-F Ph |
| 2-29 | dioxo | 2-nPent-Ph |
| 2-30 | 4-HM-dioxo | 2-nPent-Ph |
| 2-31 | 4,5-diHM-dioxo | 2-nPent-Ph |
| 2-32 | 4,5-diHE-dioxo | 2-nPent-Ph |
| 2-33 | dioxo | 4-F-2-nPent-Ph |
| 2-34 | 4-HM-dioxo | 4-F-2-nPent-Ph |
| 2-35 | 4,5-diHM-dioxo | 4-F-2-nPent-Ph |
| 2-35 | 4,5-diHE-dioxo | 4-F-2-nPent-Ph |
| 2-37 | dioxo | 2-nHex—Ph |
| 2-38 | 4-HM-dioxo | 2-nHex—Ph |
| 2-39 | 4,5-diHM-dioxo | 2-nHex—Ph |
| 2-40 | 4,5-diHE-dioxo | 2-nHex—Ph |
| 2-41 | dioxo | 4-F-2-nHex Ph |
| 2-42 | 4-HM-dioxo | 4-F-2-nHex Ph |
| 2-43 | 4,5-diHM-dioxo | 4-F-2-nHex Ph |
| 2-44 | 4,5-diHE-dioxo | 4-F-2-nHex Ph |
| 2-45 | dioxo | 2-nHept-Ph |
| 2-46 | 4-HM-dioxo | 2-nHept-Ph |
| 2-47 | 4,5-diHM-dioxo | 2-nHept-Ph |
| 2-48 | 4,5-diHE-dioxo | 2-nHept-Ph |
| 2-49 | dioxo | 4-F-2-nHept-Ph |
| 2-50 | 4-HM-dioxo | 4-F-2-nHept-Ph |
| 2-51 | 4,5-diHM-dioxo | 4-F-2-nHept-Ph |
| 2-52 | 4,5-diHE-dioxo | 4-F-2-nHept-Ph |
| 2-53 | dioxo | 2-nOct-Ph |
| 2-54 | 4-HM-dioxo | 2-nOct-Ph |
| 2-55 | 4,5-diHM-dioxo | 2-nOct-Ph |
| 2-56 | 4,5-diHE-dioxo | 2-nOct-Ph |
| 2-57 | dioxo | 4-F-2-nOct-Ph |
| 2-58 | 4-HM-dioxo | 4-F-2-nOct-Ph |
| 2-59 | 4,5-diHM-dioxo | 4-F-2-nOct-Ph |
| 2-60 | 4,5-diHE-dioxo | 4-F-2-nOct-Ph |
| 2-61 | dioxo | Ph |
| 2-62 | 4-HM-dioxo | Ph |
| 2-63 | 4,5-diHM-dioxo | Ph |
| 2-64 | 4,5-diHE-dioxo | Ph |
| 2-65 | dioxo | 4-F—Ph |
| 2-66 | 4-HM-dioxo | 4-F—Ph |
| 2-67 | 4,5-diHM-dioxo | 4-F—Ph |
| 2-68 | 4,5-diHE-dioxo | 4-F—Ph |
| 2-69 | dioxo | 2-Cl-4-Me Ph |
| 2-70 | 4-HM-dioxo | 2-Cl-4-Me Ph |
| 2-71 | 4,5-diHM-dioxo | 2-Cl-4-Me Ph |
| 2-72 | 4,5-diHE-dioxo | 2-Cl-4-Me Ph |
| 2-73 | dioxo | 2-nBu—Ph |
| 2-74 | 4-HM-dioxo | 2-nBu—Ph |

TABLE 2-continued

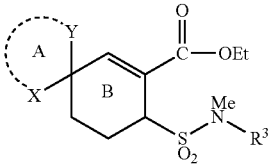

| Compound No. | X, Y | $R^3$ |
|---|---|---|
| 2-75 | 4,5-diHM-dioxo | 2-nBu—Ph |
| 2-76 | 4,5-diHE-dioxo | 2-nBu—Ph |
| 2-77 | dioxo | 2-nPr—Ph |
| 2-78 | 4-HM-dioxo | 2-nPr—Ph |
| 2-79 | 4,5-diHM-dioxo | 2-nPr—Ph |
| 2-80 | 4,5-diHE-dioxo | 2-nPr—Ph |
| 2-81 | dioxo | 4-F-2-nPr—Ph |
| 2-82 | 4-HM-dioxo | 4-F-2-nPr—Ph |
| 2-83 | 4,5-diHM-dioxo | 4-F-2-nPr—Ph |
| 2-84 | 4,5-diHE-dioxo | 4-F-2-nPr—Ph |

TABLE 3

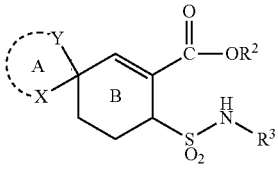

| Compound No. | X, Y | $R^2$ | $R^3$ |
|---|---|---|---|
| 3-1 | dioxo | Me | 2-Cl—Ph |
| 3-2 | 4-HM-dioxo | Me | 2-Cl—Ph |
| 3-3 | 4,5-diHM-dioxo | Me | 2-Cl—Ph |
| 3-4 | 4,5-diHE-dioxo | Me | 2-Cl—Ph |
| 3-5 | dioxo | nPr | 2-Cl—Ph |
| 3-6 | 4-HM-dioxo | nPr | 2-Cl—Ph |
| 3-7 | 4,5-diHM-dioxo | nPr | 2-Cl—Ph |
| 3-8 | 4,5-diHE-dioxo | nPr | 2-Cl—Ph |
| 3-9 | dioxo | nBu | 2-Cl—Ph |
| 3-10 | 4-HM-dioxo | nBu | 2-Cl—Ph |
| 3-11 | 4,5-diHM-dioxo | nBu | 2-Cl—Ph |
| 3-12 | 4,5-diHE-dioxo | nBu | 2-Cl—Ph |
| 3-13 | dioxo | iPr | 2-Cl—Ph |
| 3-14 | 4-HM-dioxo | iPr | 2-Cl—Ph |
| 3-15 | 4,5-diHM-dioxo | iPr | 2-Cl—Ph |
| 3-16 | 4,5-diHE-dioxo | iPr | 2-Cl—Ph |
| 3-17 | dioxo | tBu | 2-Cl—Ph |
| 3-18 | 4-HM-dioxo | tBu | 2-Cl—Ph |
| 3-19 | 4,5-diHM-dioxo | tBu | 2-Cl—Ph |
| 3-20 | 4,5-diHE-dioxo | tBu | 2-Cl—Ph |
| 3-21 | dioxo | $CH_2OAc$ | 2-Cl—Ph |
| 3-22 | 4-HM-dioxo | $CH_2OAc$ | 2-Cl—Ph |
| 3-23 | 4,5-diHM-dioxo | $CH_2OAc$ | 2-Cl—Ph |
| 3-24 | 4,5-diHE-dioxo | $CH_2OAc$ | 2-Cl—Ph |
| 3-25 | dioxo | Me | 2-Br—Ph |
| 3-26 | 4-HM-dioxo | Me | 2-Br—Ph |
| 3-27 | 4,5-diHM-dioxo | Me | 2-Br—Ph |
| 3-28 | 4,5-diHE-dioxo | Me | 2-Br—Ph |
| 3-29 | dioxo | nPr | 2-Br—Ph |
| 3-30 | 4-HM-dioxo | nPr | 2-Br—Ph |
| 3-31 | 4,5-diHM-dioxo | nPr | 2-Br—Ph |
| 3-32 | 4,5-diHE-dioxo | nPr | 2-Br—Ph |
| 3-33 | dioxo | nBu | 2-Br—Ph |
| 3-34 | 4-HM-dioxo | nBu | 2-Br—Ph |
| 3-35 | 4,5-diHM-dioxo | nBu | 2-Br—Ph |
| 3-36 | 4,5-diHE-dioxo | nBu | 2-Br—Ph |
| 3-37 | dioxo | iPr | 2-Br—Ph |
| 3-38 | 4-HM-dioxo | iPr | 2-Br—Ph |
| 3-39 | 4,5-diHM-dioxo | iPr | 2-Br—Ph |
| 3-40 | 4,5-diHE-d oxo | iPr | 2-Br—Ph |
| 3-41 | dioxo | tBu | 2-Br—Ph |

TABLE 3-continued

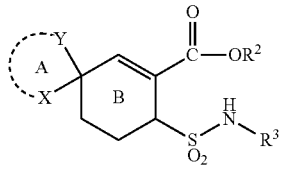

| Compound No. | X, Y | $R^2$ | $R^3$ |
|---|---|---|---|
| 3-42 | 4-HM-dioxo | tBu | 2-Br—Ph |
| 3-43 | 4,5-diHM-dioxo | tBu | 2-Br—Ph |
| 3-44 | 4,5-diHE-dioxo | tBu | 2-Br—Ph |
| 3-45 | dioxo | $CH_2OAc$ | 2-Br—Ph |
| 3-45 | 4-HM-dioxo | $CH_2OAc$ | 2-Br—Ph |
| 3-47 | 4,5-diHM-dioxo | $CH_2OAc$ | 2-Br—Ph |
| 3-48 | 4,5-diHE-dioxo | $CH_2OAc$ | 2-Br—Ph |
| 3-49 | dioxo | Me | 2-Cl-6-Me—Ph |
| 3-50 | 4-HM-dioxo | Me | 2-Cl-6-Me—Ph |
| 3-51 | 4,5-diHM-dioxo | Me | 2-Cl-6-Me—Ph |
| 3-52 | 4,5-diHE-dioxo | Me | 2-Cl-6-Me—Ph |
| 3-53 | dioxo | nPr | 2-Cl-6-Me—Ph |
| 3-54 | 4-HM-dioxo | nPr | 2-Cl-6-Me—Ph |
| 3-55 | 4,5-diHM-dioxo | nPr | 2-Cl-6-Me—Ph |
| 3-56 | 4,5-diHE-dioxo | nPr | 2-Cl-6-Me—Ph |
| 3-57 | dioxo | nBu | 2-Cl-6-Me—Ph |
| 3-58 | 4-HM-dioxo | nBu | 2-Cl-6-Me—Ph |
| 3-59 | 4,5-diHM-dioxo | nBu | 2-Cl-6-Me—Ph |
| 3-60 | 4,5-diHE-dioxo | nBu | 2-Cl-6-Me—Ph |
| 3-61 | dioxo | iPr | 2-Cl-6-Me—Ph |
| 3-62 | 4-HM-dioxo | iPr | 2-Cl-6-Me—Ph |
| 3-63 | 4,5-diHM-dioxo | iPr | 2-Cl-6-Me—Ph |
| 3-64 | 4,5-diHE-dioxo | iPr | 2-Cl-6-Me—Ph |
| 3-65 | dioxo | tBu | 2-Cl-6-Me—Ph |
| 3-66 | 4-HM-dioxo | tBu | 2-Cl-6-Me—Ph |
| 3-67 | 4,5-diHM-dioxo | tBu | 2-Cl-6-Me—Ph |
| 3-68 | 4,5-diHE-dioxo | tBu | 2-Cl-6-Me—Ph |
| 3-69 | dioxo | $CH_2OAc$ | 2-Cl-6-Me—Ph |
| 3-70 | 4-HM-dioxo | $CH_2OAc$ | 2-Cl-6-Me—Ph |
| 3-71 | 4,5-diHM-dioxo | $CH_2OAc$ | 2-Cl-6-Me—Ph |
| 3-72 | 4,5-diHE-dioxo | $CH_2OAc$ | 2-Cl-6-Me—Ph |
| 3-73 | dioxo | Me | 2-Cl-4-F—Ph |
| 3-74 | 4-HM-dioxo | Me | 2-Cl-4-F—Ph |
| 3-75 | 4,5-diHM-dioxo | Me | 2-Cl-4-F—Ph |
| 3-76 | 4,5-diHE-dioxo | Me | 2-Cl-4-F—Ph |
| 3-77 | dioxo | nPr | 2-Cl-4-F—Ph |
| 3-78 | 4-HM-dioxo | nPr | 2-Cl-4-F—Ph |
| 3-79 | 4,5-diHM-dioxo | nPr | 2-Cl-4-F—Ph |
| 3-80 | 4,5-diHE-dioxo | nPr | 2-Cl-4-F—Ph |
| 3-81 | dioxo | nBu | 2-Cl-4-F—Ph |
| 3-82 | 4-HM-dioxo | nBu | 2-Cl-4-F—Ph |
| 3-83 | 4,5-diHM-dioxo | nBu | 2-Cl-4-F—Ph |
| 3-84 | 4,5-diHE-dioxo | nBu | 2-Cl-4-F—Ph |
| 3-85 | dioxo | iPr | 2-Cl-4-F—Ph |
| 3-86 | 4-HM-dioxo | iPr | 2-Cl-4-F—Ph |
| 3-87 | 4,5-diHM-dioxo | iPr | 2-Cl-4-F—Ph |
| 3-88 | 4,5-diHE-dioxo | iPr | 2-Cl-4-F—Ph |
| 3-89 | dioxo | tBu | 2-Cl-4-F—Ph |
| 3-90 | 4-HM-dioxo | tBu | 2-Cl-4-F—Ph |
| 3-91 | 4,5-diHM-dioxo | tBu | 2-Cl-4-F—Ph |
| 3-92 | 4,5-diHE-dioxo | tBu | 2-Cl-4-F—Ph |
| 3-93 | dioxo | $CH_2OAc$ | 2-Cl-4-F—Ph |
| 3-94 | 4-HM-dioxo | $CH_2OAc$ | 2-Cl-4-F—Ph |
| 3-95 | 4,5-diHM-dioxo | $CH_2OAc$ | 2-Cl-4-F—Ph |
| 3-96 | 4,5-diHE-dioxo | $CH_2OAc$ | 2-Cl-4-F—Ph |
| 3-97 | dioxo | Me | 2,4-diF—Ph |
| 3-98 | 4-HM-dioxo | Me | 2,4-diF—Ph |
| 3-99 | 4,5-diHM-dioxo | Me | 2,4-diF—Ph |
| 3-100 | 4,5-diHE-dioxo | Me | 2,4-diF—Ph |
| 3-101 | dioxo | nPr | 2,4-diF—Ph |
| 3-102 | 4-HM-dioxo | nPr | 2,4-diF—Ph |
| 3-103 | 4,5-diHM-dioxo | nPr | 2,4-diF—Ph |
| 3-104 | 4,5-diHE-dioxo | nPr | 2,4-diF—Ph |
| 3-105 | dioxo | nBu | 2,4-diF—Ph |
| 3-106 | 4-HM-dioxo | nBu | 2,4-diF—Ph |
| 3-107 | 4,5-diHM-dioxo | nBu | 2,4-diF—Ph |
| 3-108 | 4,5-diHE-dioxo | nBu | 2,4-diF—Ph |
| 3-109 | dioxo | iPr | 2,4-diF—Ph |

TABLE 3-continued

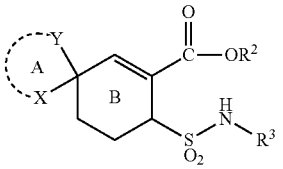

| Compound No. | X, Y | $R^2$ | $R^3$ |
|---|---|---|---|
| 3-110 | 4-HM-dioxo | iPr | 2,4-diF—Ph |
| 3-111 | 4,5-diHM-dioxo | iPr | 2,4-diF—Ph |
| 3-112 | 4,5-diHE-dioxo | iPr | 2,4-diF—Ph |
| 3-113 | dioxo | tBu | 2,4-diF—Ph |
| 3-114 | 4-HM-dioxo | tBu | 2,4-diF—Ph |
| 3-115 | 4,5-diHM-dioxo | tBu | 2,4-diF—Ph |
| 3-116 | 4,5-diHE-dioxo | tBu | 2,4-diF—Ph |
| 3-117 | dioxo | $CH_2OAc$ | 2,4-diF—Ph |
| 3-118 | 4-HM-dioxo | $CH_2OAc$ | 2,4-diF—Ph |
| 3-119 | 4,5-diHM-dioxo | $CH_2OAc$ | 2,4-diF—Ph |
| 3-120 | 4,5-diHE-dioxo | $CH_2OAc$ | 2,4-diF—Ph |
| 3-121 | dioxo | Me | 2-Br-4-F—Ph |
| 3-122 | 4-HM-dioxo | Me | 2-Br-4-F—Ph |
| 3-123 | 4,5-diHM-dioxo | Me | 2-Br-4-F—Ph |
| 3-124 | 4,5-diHE-dioxo | Me | 2-Br-4-F—Ph |
| 3-125 | dioxo | nPr | 2-Br-4-F—Ph |
| 3-126 | 4-HM-dioxo | nPr | 2-Br-4-F—Ph |
| 3-127 | 4,5-diHM-dioxo | nPr | 2-Br-4-F—Ph |
| 3-128 | 4,5-diHE-dioxo | nPr | 2-Br-4-F—Ph |
| 3-129 | dioxo | nBu | 2-Br-4-F—Ph |
| 3-130 | 4-HM-dioxo | nBu | 2-Br-4-F—Ph |
| 3-131 | 4,5-diHM-dioxo | nBu | 2-Br-4-F—Ph |
| 3-132 | 4,5-diHE-dioxo | nBu | 2-Br-4-F—Ph |
| 3-133 | dioxo | iPr | 2-Br-4-F—Ph |
| 3-134 | 4-HM-dioxo | iPr | 2-Br-4-F—Ph |
| 3-135 | 4,5-diHM-dioxo | iPr | 2-Br-4-F—Ph |
| 3-136 | 4,5-diHE-dioxo | iPr | 2-Br-4-F—Ph |
| 3-137 | dioxo | tBu | 2-Br-4-F—Ph |
| 3-138 | 4-IIM-dioxo | tBu | 2-Br-4-F—Ph |
| 3-139 | 4,5-diHM-dioxo | tBu | 2-Br-4-F—Ph |
| 3-140 | 4,5-diHE-dioxo | tBu | 2-Br-4-F—Ph |
| 3-141 | dioxo | $CH_2OAc$ | 2-Br-4-F—Ph |
| 3-142 | 4-HM-dioxo | $CH_2OAc$ | 2-Br-4-F—Ph |
| 3-143 | 4,5-diHM-dioxo | $CH_2OAc$ | 2-Br-4-F—Ph |
| 3-144 | 4,5-diHE-dioxo | $CH_2OAc$ | 2-Br-4-F—Ph |
| 3-145 | dioxo | Me | 2-nBu-4-F—Ph |
| 3-146 | 4-HM-dioxo | Me | 2-nBu-4-F—Ph |
| 3-147 | 4,5-diHM-dioxo | Me | 2-nBu-4-F—Ph |
| 3-148 | 4,5-diHE-dioxo | Me | 2-nBu-4-F—Ph |
| 3-149 | dioxo | nPr | 2-nBu-4-F—Ph |
| 3-150 | 4-HM-dioxo | nPr | 2-nBu-4-F—Ph |
| 3-151 | 4,5-diHM-dioxo | nPr | 2-nBu-4-F—Ph |
| 3-152 | 4,5-diHE-dioxo | nPr | 2-nBu-4-F—Ph |
| 3-153 | dioxo | nBu | 2-nBu-4-F—Ph |
| 3-154 | 4-HM-dioxo | nBu | 2-nBu-4-F—Ph |
| 3-155 | 4,5-diHM-dioxo | nBu | 2-nBu-4-F—Ph |
| 3-156 | 4,5-diHE-dioxo | nBu | 2-nBu-4-F—Ph |
| 3-157 | dioxo | iPr | 2-nBu-4-F—Ph |
| 3-158 | 4-HM-dioxo | iPr | 2-nBu-4-F—Ph |
| 3-159 | 4,5-diHM-dioxo | iPr | 2-nBu-4-F—Ph |
| 3-160 | 4,5-diHE-dioxo | iPr | 2-nBu-4-F—Ph |
| 3-161 | dioxo | tBu | 2-nBu-4-F—Ph |
| 3-162 | 4-HM-dioxo | tBu | 2-nBu-4-F—Ph |
| 3-163 | 4,5-diHM-dioxo | tBu | 2-nBu-4-F—Ph |
| 3-164 | 4,5-diHE-dioxo | tBu | 2-nBu-4-F—Ph |
| 3-165 | dioxo | $CH_2OAc$ | 2-nBu-4-F—Ph |
| 3-166 | 4-HM-dioxo | CH2OAo | 2-nBu-4-F—Ph |
| 3-167 | 4,5-diHM-dioxo | $CH_2OAc$ | 2-nBu-4-F—Ph |
| 3-168 | 4,5-diHE-dioxo | $CH_2OAc$ | 2-nBu-4-F—Ph |
| 3-169 | dioxo | Me | 2-nPent-Ph |
| 3-170 | 4-HM-dioxo | Me | 2-nPent-Ph |
| 3-171 | 4,5-diHM-dioxo | Me | 2-nPent-Ph |
| 3-172 | 4,5-diHE-dioxo | Me | 2-nPent-Ph |
| 3-173 | dioxo | nPr | 2-nPent-Ph |
| 3-174 | 4-HM-dioxo | nPr | 2-nPent-Ph |
| 3-175 | 4,5-diHM-dioxo | nPr | 2-nPent-Ph |
| 3-176 | 4,5-diHE-dioxo | nPr | 2-nPent-Ph |
| 3-177 | dioxo | nBu | 2-nPent-Ph |

TABLE 3-continued

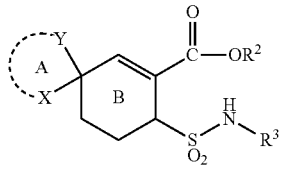

| Compound No. | X, Y | $R^2$ | $R^3$ |
|---|---|---|---|
| 3-178 | 4-HM-dioxo | nBu | 2-nPent-Ph |
| 3-179 | 4,5-diHM-dioxo | nBu | 2-nPent-Ph |
| 3-180 | 4,5-diHE-dioxo | nBu | 2-nPent-Ph |
| 3-181 | dioxo | iPr | 2-nPent-Ph |
| 3-182 | 4-HM-dioxo | iPr | 2-nPent-Ph |
| 3-183 | 4,5-diHM-dioxo | iPr | 2-nPent-Ph |
| 3-184 | 4,5-diHE-dioxo | iPr | 2-nPent-Ph |
| 3-185 | dioxo | tBu | 2-nPent-Ph |
| 3-186 | 4-HM-dioxo | tBu | 2-nPent-Ph |
| 3-187 | 4,5-diHM-dioxo | tBu | 2-nPent-Ph |
| 3-188 | 4,5-diHE-dioxo | tBu | 2-nPent-Ph |
| 3-189 | dioxo | $CH_2OAc$ | 2-nPent-Ph |
| 3-190 | 4-HM-dioxo | $CH_2OAc$ | 2-nPent-Ph |
| 3-191 | 4,5-diHM-dioxo | $CH_2OAc$ | 2-nPent-Ph |
| 3-192 | 4,5-diHE-dioxo | $CH_2OAc$ | 2-nPent-Ph |
| 3-193 | dioxo | Me | 4-F-2-nPent-Ph |
| 3-194 | 4-HM-dioxo | Me | 4-F-2-nPent-Ph |
| 3-195 | 4,5-diHM-dioxo | Me | 4-F-2-nPent-Ph |
| 3-196 | 4,5-diHE-dioxo | Me | 4-F-2-nPent-Ph |
| 3-197 | dioxo | nPr | 4-F-2-nPent-Ph |
| 3-198 | 4-HM-dioxo | nPr | 4-F-2-nPent-Ph |
| 3-199 | 4,5-diHM-dioxo | nPr | 4-F-2-nPent-Ph |
| 3-200 | 4,5-diHE-dioxo | nPr | 4-F-2-nPent-Ph |
| 3-201 | dioxo | nBu | 4-F-2-nPent-Ph |
| 3-202 | 4-HM-dioxo | nBu | 4-F-2-nPent-Ph |
| 3-203 | 4,5-diHM-dioxo | nBu | 4-F-2-nPent-Ph |
| 3-204 | 4,5-diHE-dioxo | nBu | 4-F-2-nPent-Ph |
| 3-205 | dioxo | iPr | 4-F-2-nPent-Ph |
| 3-206 | 4-HM-dioxo | iPr | 4-F-2-nPent-Ph |
| 3-207 | 4,5-diHM-dioxo | iPr | 4-F-2-nPent-Ph |
| 3-208 | 4,5-diHE-dioxo | iPr | 4-F-2-nPent-Ph |
| 3-209 | dioxo | tBu | 4-F-2-nPent-Ph |
| 3-210 | 4-HM-dioxo | tBu | 4-F-2-nPent-Ph |
| 3-211 | 4,5-diHM-dioxo | tBu | 4-F-2-nPent-Ph |
| 3-212 | 4,5-diHE-dioxo | tBu | 4-F-2-nPent-Ph |
| 3-213 | dioxo | $CH_2OAc$ | 4-F-2-nPent-Ph |
| 3-214 | 4-HM-dioxo | $CH_2OAc$ | 4-F-2-nPent-Ph |
| 3-215 | 4,5-diHM-dioxo | CH2OAo | 4-F-2-nPent-Ph |
| 3-216 | 4,5-diHE-dioxo | CH2OAo | 4-F-2-nPent-Ph |
| 3-217 | dioxo | Me | 2-nHex—Ph |
| 3-218 | 4-HM-dioxo | Me | 2-nHex—Ph |
| 3-219 | 4,5-diHM-dioxo | Me | 2-nHex—Ph |
| 3-220 | 4,5-diHE-dioxo | Me | 2-nHex—Ph |
| 3-221 | dioxo | nPr | 2-nHex—Ph |
| 3-222 | 4-HM-dioxo | nPr | 2-nHex—Ph |
| 3-223 | 4,5-diHM-dioxo | nPr | 2-nHex—Ph |
| 3-224 | 4,5-diHE-dioxo | nPr | 2-nHex—Ph |
| 3-225 | dioxo | nBu | 2-nHex—Ph |
| 3-226 | 4-HM-dioxo | nBu | 2-nHex—Ph |
| 3-227 | 4,5-diHM-dioxo | nBu | 2-nHex—Ph |
| 3-223 | 4,5-diHE-dioxo | nBu | 2-nHex—Ph |
| 3-229 | dioxo | iPr | 2-nHex—Ph |
| 3-230 | 4-HM-dioxo | iPr | 2-nHex—Ph |
| 3-231 | 4,5-diHM-dioxo | iPr | 2-nHex—Ph |
| 3-232 | 4,5-diHE-dioxo | iPr | 2-nHex—Ph |
| 3-233 | dioxo | tBu | 2-nHex—Ph |
| 3-234 | 4-HM-dioxo | tBu | 2-nHex—Ph |
| 3-235 | 4,5-diHM-dioxo | tBu | 2-nHex—Ph |
| 3-236 | 4,5-diHE-dioxo | tBu | 2-nHex—Ph |
| 3-237 | dioxo | $CH_2OAc$ | 2-nHex—Ph |
| 3-238 | 4-HM-dioxo | $CH_2OAc$ | 2-nHex—Ph |
| 3-239 | 4,5-diHM-dioxo | $CH_2OAc$ | 2-nHex—Ph |
| 3-240 | 4,5-diHE-dioxo | $CH_2OAc$ | 2-nHex—Ph |
| 3-241 | dioxo | Me | 4-F-nHex—Ph |
| 3-242 | 4-HM-dioxo | Me | 4-F-nHex—Ph |
| 3-243 | 4,5-diHM-dioxo | Me | 4-F-nHex—Ph |
| 3-244 | 4,5-diHE-dioxo | Me | 4-F-nHex—Ph |
| 3-245 | dioxo | nPr | 4-F-nHex—Ph |

TABLE 3-continued

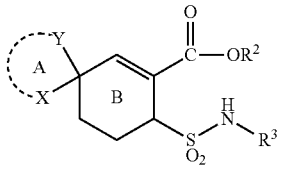

| Compound No. | X, Y | $R^2$ | $R^3$ |
|---|---|---|---|
| 3-246 | 4-HM-dioxo | nPr | 4-F-nHex—Ph |
| 3-247 | 4,5-diHM-dioxo | nPr | 4-F-nHex—Ph |
| 3-248 | 4,5-diHE-dioxo | nPr | 4-F-nHex—Ph |
| 3-249 | dioxo | nBu | 4-F-nHex—Ph |
| 3-250 | 4-HM-dioxo | nBu | 4-F-nHex—Ph |
| 3-251 | 4,5-diHM-dioxo | nBu | 4-F-nHex—Ph |
| 3-252 | 4,5-diHE-dioxo | nBu | 4-F-nHex—Ph |
| 3-253 | dioxo | iPr | 4-F-nHex—Ph |
| 3-254 | 4-HM-dioxo | iPr | 4-F-nHex—Ph |
| 3-255 | 4,5-diHM-dioxo | iPr | 4-F-nHex—Ph |
| 3-256 | 4,5-diHE-dioxo | iPr | 4-F-nHex—Ph |
| 3-257 | dioxo | tBu | 4-F-nHex—Ph |
| 3-258 | 4-HM-dioxo | tBu | 4-F-nHex—Ph |
| 3-259 | 4,5-diHM-dioxa | tBu | 4-F-nHex—Ph |
| 3-260 | 4,5-diHE-dioxo | tBu | 4-F-nHex—Ph |
| 3-261 | dioxo | $CH_2OAc$ | 4-F-nHex—Ph |
| 3-262 | 4-HM-dioxo | $CH_2OAc$ | 4-F-nHex—Ph |
| 3-263 | 4,5-diHM-dioxo | $CH_2OAc$ | 4-F-nHex—Ph |
| 3-264 | 4,5-diHE-dioxo | CH2OAC | 4-F-nHex—Ph |
| 3-265 | dioxo | Me | 2-nHept-Ph |
| 3-266 | 4-HM-dioxo | Me | 2-nHept-Ph |
| 3-267 | 4,5-diHM-dioxo | Me | 2-nHept-Ph |
| 3-268 | 4,5-diHE-dioxo | Me | 2-nHept-Ph |
| 3-269 | dioxo | nPr | 2-nHept-Ph |
| 3-270 | 4-HM-dioxo | nPr | 2-nHept-Ph |
| 3-271 | 4,5-diHM-dioxo | nPr | 2-nHept-Ph |
| 3-272 | 4,5-diHE-dioxo | nPr | 2-nHept-Ph |
| 3-273 | dioxo | nBu | 2-nHept-Ph |
| 3-274 | 4-HM-dioxo | nBu | 2-nHept-Ph |
| 3-275 | 4,5-diHM-dioxo | nBu | 2-nHept-Ph |
| 3-276 | 4,5-diHE-dioxo | nBu | 2-nHept-Ph |
| 3-277 | dioxo | iPr | 2-nHept-Ph |
| 3-278 | 4-HM-dioxo | iPr | 2-nHept-Ph |
| 3-279 | 4,5-diHM-dioxo | iPr | 2-nHept-Ph |
| 3-280 | 4,5-diHE-dioxo | iPr | 2-nHept-Ph |
| 3-281 | dioxo | tBu | 2-nHept-Ph |
| 3-282 | 4-HM-dioxo | tBu | 2-nHept-Ph |
| 3-283 | 4,5-diHM-dioxo | tBu | 2-nHept-Ph |
| 3-284 | 4,5-diHE-dioxo | tBu | 2-nHept-Ph |
| 3-285 | dioxo | $CH_2OAc$ | 2-nHept-Ph |
| 3-286 | 4-HM-dioxo | $CH_2OAc$ | 2-nHept-Ph |
| 3-287 | 4,5-diHM-dioxo | $CH_2OAc$ | 2-nHept-Ph |
| 3-288 | 4,5-diHE-dioxo | $CH_2OAc$ | 2-nHept-Ph |
| 3-289 | dioxo | Me | 4-F-2-nHept-Ph |
| 3-290 | 4-HM-dioxo | Me | 4-F-2-nHept-Ph |
| 3-291 | 4,5-diHM-dioxo | Me | 4-F-2-nHept-Ph |
| 3-292 | 4,5-diHE-dioxo | Me | 4-F-2-nHept-Ph |
| 3-293 | dioxo | nPr | 4-F-2-nHept-Ph |
| 3-294 | 4-HM-dioxo | nPr | 4-F-2-nHept-Ph |
| 3-295 | 4,5-diHM-dioxo | nPr | 4-F-2-nHept-Ph |
| 3-296 | 4,5-diHE-dioxo | nPr | 4-F-2-nHept-Ph |
| 3-297 | dioxo | nBu | 4-F-2-nHept-Ph |
| 3-298 | 4-HM-dioxo | nBu | 4-F-2-nHept-Ph |
| 3-299 | 4,5-diHM-dioxo | nBu | 4-F-2-nHept-Ph |
| 3-300 | 4,5-diHE-dioxo | nBu | 4-F-2-nHept-Ph |
| 3-301 | dioxo | iPr | 4-F-2-nHept-Ph |
| 3-302 | 4-HM-dioxo | iPr | 4-F-2-nHept-Ph |
| 3-303 | 4,5-diHM-dioxo | iPr | 4-F-2-nHept-Ph |
| 3-304 | 4,5-diHE-dioxo | iPr | 4-F-2-nHept-Ph |
| 3-305 | dioxo | tBu | 4-F-2-nHept-Ph |
| 3-306 | 4-HM-dioxo | tBu | 4-F-2-nHept-Ph |
| 3-307 | 4,5-diHM-dioxo | tBu | 4-F-2-nHept-Ph |
| 3-308 | 4,5-diHE-dioxo | tBu | 4-F-2-nHept-Ph |
| 3-309 | dioxo | $CH_2OAc$ | 4-F-2-nHept-Ph |
| 3-310 | 4-HM-dioxo | $CH_2OAc$ | 4-F-2-nHept-Ph |
| 3-311 | 4,5-diHM-dioxo | $CH_2OAc$ | 4-F-2-nHept-Ph |
| 3-312 | 4,5-diHE-dioxo | $CH_2OAc$ | 4-F-2-nHept-Ph |
| 3-313 | dioxo | Me | 2-nOct-Ph |

TABLE 3-continued

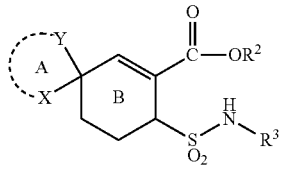

| Compound No. | X, Y | $R^2$ | $R^3$ |
|---|---|---|---|
| 3-314 | 4-HM-dioxo | Me | 2-nOct-Ph |
| 3-315 | 4,5-diHM-dioxo | Me | 2-nOct-Ph |
| 3-316 | 4,5-diHE-dioxo | Me | 2-nOct-Ph |
| 3-317 | dioxo | nPr | 2-nOct-Ph |
| 3-318 | 4-HM-dioxo | nPr | 2-nOct-Ph |
| 3-319 | 4,5-diHM-dioxo | nPr | 2-nOct-Ph |
| 3-320 | 4,5-diHE-dioxo | nPr | 2-nOct-Ph |
| 3-321 | dioxo | nBu | 2-nOct-Ph |
| 3-322 | 4-HM-dioxo | nBu | 2-nOct-Ph |
| 3-323 | 4,5-diHM-dioxo | nBu | 2-nOct-Ph |
| 3-324 | 4,5-diHE-dioxo | nBu | 2-nOct-Ph |
| 3-325 | dioxo | iPr | 2-nOct-Ph |
| 3-326 | 4-HM-dioxo | iPr | 2-nOct-Ph |
| 3-327 | 4,5-diHM-dioxo | iPr | 2-nOct-Ph |
| 3-328 | 4,5-diHE-dioxo | iPr | 2-nOct-Ph |
| 3-329 | dioxo | tBu | 2-nOct-Ph |
| 3-330 | 4-HM-dioxo | tBu | 2-nOct-Ph |
| 3-331 | 4,5-diHM-dioxo | tBu | 2-nOct-Ph |
| 3-332 | 4,5-diHE-dioxo | tBu | 2-nOct-Ph |
| 3-333 | dioxo | CH2OAo | 2-nOct-Ph |
| 3-334 | 4-HM-dioxo | $CH_2OAc$ | 2-nOct-Ph |
| 3-335 | 4,5-diHM-dioxo | $CH_2OAc$ | 2-nOct-Ph |
| 3-336 | 4,5-diHE-dioxo | $CH_2OAc$ | 2-nOct-Ph |
| 3-337 | dioxo | Me | 4-F-2-nOct-Ph |
| 3-338 | 4-HM-dioxo | Me | 4-F-2-nOct-Ph |
| 3-339 | 4,5-diHM-dioxo | Me | 4-F-2-nOct-Ph |
| 3-340 | 4,5-diHE-dioxo | Me | 4-F-2-nOct-Ph |
| 3-341 | dioxo | nPr | 4-F-2-nOct-Ph |
| 3-342 | 4-HM-dioxo | nPr | 4-F-2-nOct-Ph |
| 3-343 | 4,5-diHM-dioxo | nPr | 4-F-2-nOct-Ph |
| 3-344 | 4,5-diHE-dioxo | nPr | 4-F-2-nOct-Ph |
| 3-345 | dioxo | nBu | 4-F-2-nOct-Ph |
| 3-346 | 4-HM-dioxo | nBu | 4-F-2-nOct-Ph |
| 3-347 | 4,5-diHM-dioxo | nBu | 4-F-2-nOct-Ph |
| 3-348 | 4,5-diHE-dioxo | nBu | 4-F-2-nOct-Ph |
| 3-349 | dioxo | iPr | 4-F-2-nOct-Ph |
| 3-350 | 4-HM-dioxo | iPr | 4-F-2-nOct-Ph |
| 3-351 | 4,5-diHM-dioxo | iPr | 4-F-2-nOct-Ph |
| 3-352 | 4,5-diHE-dioxo | iPr | 4-F-2-nOct-Ph |
| 3-353 | dioxo | tBu | 4-F-2-nOct-Ph |
| 3-354 | 4-HM-dioxo | tBu | 4-F-2-nOct-Ph |
| 3-355 | 4,5-diHM-dioxo | tBu | 4-F-2-nOct-Ph |
| 3-356 | 4,5-diHE-dioxo | tBu | 4-F-2-nOct-Ph |
| 3-357 | dioxo | $CH_2OAc$ | 4-F-2-nOct-Ph |
| 3-358 | 4-HM-dioxo | $CH_2OAc$ | 4-F-2-nOct-Ph |
| 3-359 | 4,5-diHM-dioxo | $CH_2OAc$ | 4-F-2-nOct-Ph |
| 3-360 | 4,5-diHE-dioxo | $CH_2OAc$ | 4-F-2-nOct-Ph |
| 3-361 | dioxo | Me | Ph |
| 3-362 | 4-HM-dioxo | Me | Ph |
| 3-363 | 4,5-diHM-dioxo | Me | Ph |
| 3-364 | 4,5-diHE-dioxo | Me | Ph |
| 3-365 | dioxo | nPr | Ph |
| 3-366 | 4-HM-dioxo | nPr | Ph |
| 3-367 | 4,5-diHM-dioxo | nPr | Ph |
| 3-368 | 4,5-diHE-dioxo | nPr | Ph |
| 3-369 | dioxo | nBu | Ph |
| 3-370 | 4-HM-dioxo | nBu | Ph |
| 3-371 | 4,5-diHM-dioxo | nBu | Ph |
| 3-372 | 4,5-diHE-dioxo | nBu | Ph |
| 3-373 | dioxo | iPr | Ph |
| 3-374 | 4-HM-dioxo | iPr | Ph |
| 3-375 | 4,5-diHM-dioxo | iPr | Ph |
| 3-376 | 4,5-diHE-dioxo | iPr | Ph |
| 3-377 | dioxo | tBu | Ph |
| 3-378 | 4-HM-dioxo | tBu | Ph |
| 3-379 | 4,5-diHM-dioxo | tBu | Ph |
| 3-380 | 4,5-diHE-dioxo | tBu | Ph |
| 3-381 | dioxo | $CH_2OAc$ | Ph |

TABLE 3-continued

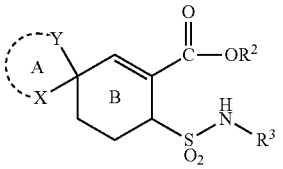

| Compound No. | X, Y | $R^2$ | $R^3$ |
|---|---|---|---|
| 3-382 | 4-HM-dioxo | $CH_2OAc$ | Ph |
| 3-383 | 4,5-diHM-dioxo | $CH_2OAc$ | Ph |
| 3-384 | 4,5-diHE-dioxo | $CH_2OAc$ | Ph |
| 3-385 | dioxo | Me | 4-F—Ph |
| 3-386 | 4-HM-dioxo | Me | 4-F—Ph |
| 3-387 | 4,5-diHM-dioxo | Me | 4-F—Ph |
| 3-388 | 4,5-diHE-dioxo | Me | 4-F—Ph |
| 3-389 | dioxo | nPr | 4-F—Ph |
| 3-390 | 4-HM-dioxo | nPr | 4-F—Ph |
| 3-391 | 4.5-diHM-dioxo | nPr | 4-F—Ph |
| 3-392 | 4,5-diHE-dioxo | nPr | 4-F—Ph |
| 3-393 | dioxo | nBu | 4-F—Ph |
| 3-394 | 4-HM-dioxo | nBu | 4-F—Ph |
| 3-395 | 4,5-diHM-dioxo | nBu | 4-F—Ph |
| 3-396 | 4,5-diHE-dioxo | nBu | 4-F—Ph |
| 3-397 | dioxo | iPr | 4-F—Ph |
| 3-398 | 4-HM-dioxo | iPr | 4-F—Ph |
| 3-399 | 4,5-diHM-dioxo | iPr | 4-F—Ph |
| 3-400 | 4,5-diHE-dioxo | iPr | 4-F—Ph |
| 3-401 | dioxo | tBu | 4-F—Ph |
| 3-402 | 4-HM-dioxo | tBu | 4-F—Ph |
| 3-403 | 4,5-diHM-dioxo | tBu | 4-F—Ph |
| 3-404 | 4,5-diHE-dioxo | tBu | 4-F—Ph |
| 3-405 | dioxo | $CH_2OAc$ | 4-F—Ph |
| 3-406 | 4-HM-dioxo | $CH_2OAc$ | 4-F—Ph |
| 3-407 | 4,5-diHM-dioxo | $CH_2OAc$ | 4-F—Ph |
| 3-408 | 4,5-diHE-dioxo | $CH_2OAc$ | 4-F—Ph |
| 3-409 | dioxo | Me | 2-Cl-4-Me—Ph |
| 3-410 | 4-HM-dioxo | Me | 2-Cl-4-Me—Ph |
| 3-411 | 4,5-diHM-dioxo | Me | 2-Cl-4-Me—Ph |
| 3-412 | 4,5-diHE-dioxo | Me | 2-Cl-4-Me—Ph |
| 3-413 | dioxo | nPr | 2-Cl-4-Me—Ph |
| 3-414 | 4-HM-dioxo | nPr | 2-Cl-4-Me—Ph |
| 3-415 | 4,5-diHM-dioxo | nPr | 2-Cl-4-Me—Ph |
| 3-416 | 4,5-diHE-dioxo | nPr | 2-Cl-4-Me—Ph |
| 3-417 | dioxo | nBu | 2-Cl-4-Me—Ph |
| 3-418 | 4-HM-dioxo | nBu | 2-Cl-4-Me—Ph |
| 3-419 | 4,5-diHM-dioxo | nBu | 2-Cl-4-Me—Ph |
| 3-420 | 4,5-diHE-dioxo | nBu | 2-Cl-4-Me—Ph |
| 3-421 | dioxo | iPr | 2-Cl-4-Me—Ph |
| 3-422 | 4-HM-dioxo | iPr | 2-Cl-4-Me—Ph |
| 3-423 | 4,5-diHM-dioxo | iPr | 2-Cl-4-Me—Ph |
| 3-424 | 4,5-diHE-dioxo | iPr | 2-Cl-4-Me—Ph |
| 3-425 | dioxo | tBu | 2-Cl-4-Me—Ph |
| 3-426 | 4-HM-dioxo | tBu | 2-Cl-4-Me—Ph |
| 3-427 | 4,5-diHM-dioxo | tBu | 2-Cl-4-Me—Ph |
| 3-428 | 4,5-diHE-dioxo | tBu | 2-Cl-4-Me—Ph |
| 3-429 | dioxo | $CH_2OAc$ | 2-Cl-4-Me—Ph |
| 3-430 | 4-HM-dioxo | $CH_2OAc$ | 2-Cl-4-Me—Ph |
| 3-431 | 4,5-diHM-dioxo | $CH_2OAc$ | 2-Cl-4-Me—Ph |
| 3-432 | 4,5-diHE-dioxo | $CH_2OAc$ | 2-Cl-4-Me—Ph |
| 3-433 | dioxo | Me | 2-nBu—Ph |
| 3-434 | 4-HM-dioxo | Me | 2-nBu—Ph |
| 3-435 | 4,5-diHM-dioxo | Me | 2-nBu—Ph |
| 3-436 | 4,5-diHE-dioxo | Me | 2-nBu—Ph |
| 3-437 | dioxo | nPr | 2-nBu—Ph |
| 3-438 | 4-HM-dioxo | nPr | 2-nBu—Ph |
| 3-439 | 4,5-diHM-dioxo | nPr | 2-nBu—Ph |
| 3-440 | 4,5-diHE-dioxo | nPr | 2-nBu—Ph |
| 3-441 | dioxo | nBu | 2-nBu—Ph |
| 3-442 | 4-HM-dioxo | nBu | 2-nBu—Ph |
| 3-443 | 4,5-diHM-dioxo | nBu | 2-nBu—Ph |
| 3-444 | 4,5-diHE-dioxo | nBu | 2-nBu—Ph |
| 3-445 | dioxo | iPr | 2-nBu—Ph |
| 3-446 | 4-HM-dioxo | iPr | 2-nBu—Ph |
| 3-447 | 4,5-diHM-dioxo | iPr | 2-nBu—Ph |
| 3-448 | 4,5-diHE-dioxo | iPr | 2-nBu—Ph |
| 3-449 | dioxo | tBu | 2-nBu—Ph |

TABLE 3-continued

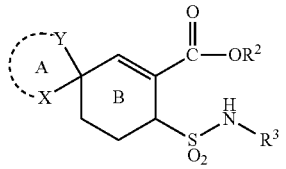

| Compound No. | X, Y | $R^2$ | $R^3$ |
|---|---|---|---|
| 3-450 | 4-HM-dioxo | tBu | 2-nBu—Ph |
| 3-451 | 4,5-diHM-dioxo | tBu | 2-nBu—Ph |
| 3-452 | 4,5-diHE-dioxo | tBu | 2-nBu—Ph |
| 3-453 | dioxo | $CH_2OAc$ | 2-nBu—Ph |
| 3-454 | 4-HM-dioxo | $CH_2OAc$ | 2-nBu—Ph |
| 3-455 | 4,5-diHM-dioxo | $CH_2OAc$ | 2-nBu—Ph |
| 3-456 | 4,5-diHE-dioxo | $CH_2OAc$ | 2-nBu—Ph |
| 3-457 | dioxo | Me | 2-nPr—Ph |
| 3-458 | 4-HM-dioxo | Me | 2-nPr—Ph |
| 3-459 | 4,5-diHM-dioxo | Me | 2-nPr—Ph |
| 3-460 | 4,5-diHE-dioxo | Me | 2-nPr—Ph |
| 3-461 | dioxo | nPr | 2-nPr—Ph |
| 3-462 | 4-HM-dioxo | nPr | 2-nPr—Ph |
| 3-463 | 4,5-diHM-dioxo | nPr | 2-nPr—Ph |
| 3-464 | 4,5-diHE-dioxo | nPr | 2-nPr—Ph |
| 3-465 | dioxo | nBu | 2-nPr—Ph |
| 3-466 | 4-HM-dioxo | nBu | 2-nPr—Ph |
| 3-467 | 4.5-diHM-dioxo | nBu | 2-nPr—Ph |
| 3-468 | 4,5-diHE-dioxo | nBu | 2-nPr—Ph |
| 3-469 | dioxo | iPr | 2-nPr—Ph |
| 3-470 | 4-HM-dioxo | iPr | 2-nPr—Ph |
| 3-471 | 4,5-diHM-dioxo | iPr | 2-nPr—Ph |
| 3-472 | 4,5-diHE-dioxo | iPr | 2-nPr—Ph |
| 3-473 | dioxo | tBu | 2-nPr—Ph |
| 3-474 | 4-HM-dioxo | tBu | 2-nPr—Ph |
| 3-475 | 4,5-diHM-dioxo | tBu | 2-nPr—Ph |
| 3-476 | 4,5-diHE-dioxo | tBu | 2-nPr—Ph |
| 3-477 | dioxo | $CH_2OAc$ | 2-nPr—Ph |
| 3-478 | 4-HM-dioxo | $CH_2OAc$ | 2-nPr—Ph |
| 3-479 | 4,5-diHM-dioxo | $CH_2OAc$ | 2-nPr—Ph |
| 3-480 | 4,5-diHE-dioxo | $CH_2OAc$ | 2-nPr—Ph |
| 3-481 | dioxo | Me | 4-F-2-nPr—Ph |
| 3-482 | 4-HM-dioxo | Me | 4-F-2-nPr—Ph |
| 3-483 | 4,5-diHM-dioxo | Me | 4-F-2-nPr—Ph |
| 3-484 | 4,5-diHE-dioxo | Me | 4-F-2-nPr—Ph |
| 3-485 | dioxo | nPr | 4-F-2-nPr—Ph |
| 3-486 | 4-HM-dioxo | nPr | 4-F-2-nPr—Ph |
| 3-487 | 4,5-diHM-dioxo | nPr | 4-F-2-nPr—Ph |
| 3-488 | 4,5-diHE-dioxo | nPr | 4-F-2-nPr—Ph |
| 3-489 | dioxo | nBu | 4-F-2-nPr—Ph |
| 3-490 | 4-HM-dioxo | nBu | 4-F-2-nPr—Ph |
| 3-491 | 4,5-diHM-dioxo | nBu | 4-F-2-nPr—Ph |
| 3-492 | 4,5-diHE-dioxo | nBu | 4-F-2-nPr—Ph |
| 3-493 | dioxo | iPr | 4-F-2-nPr—Ph |
| 3-494 | 4-HM-dioxo | iPr | 4-F-2-nPr—Ph |
| 3-495 | 4,5-diHM-dioxo | iPr | 4-F-2-nPr—Ph |
| 3-496 | 4,5-diHE-dioxo | iPr | 4-F-2-nPr—Ph |
| 3-497 | dioxo | tBu | 4-F-2-nPr—Ph |
| 3-498 | 4-HM-dioxo | tBu | 4-F-2-nPr—Ph |
| 3-499 | 4,5-diHM-dioxo | tBu | 4-F-2-nPr—Ph |
| 3-500 | 4,5-diHE-dioxo | tBu | 4-F-2-nPr—Ph |
| 3-501 | dioxo | $CH_2OAc$ | 4-F-2-nPr—Ph |
| 3-502 | 4-HM-dioxo | $CH_2OAc$ | 4-F-2-nPr—Ph |
| 3-503 | 4,5-diHM-dioxo | $CH_2OAc$ | 4-F-2-nPr—Ph |
| 3-504 | 4,5-diHE-dioxo | $CH_2OAc$ | 4-F-2-nPr—Ph |

In the compounds having the general formula (I) of the present invention, as preferred compounds exemplified compound Nos.: 1-12, 1-13, 1-19, 1-20, 1-26, 1-28, 1-30, 1-32, 1-34, 1-36, 1-38, 1-40, 1-42, 1-44, 1-46, 1-48, 1-50, 1-54, 1-58, 1-60, 1-62, 1-66, 1-68, 1-70, 1-72, 1-74, 1-78, 1-80, 1-82, 1-86, 1-100, 1-101, 1-107, 1-108, 1-114, 1-116, 1-118, 1-120, 1-122, 1-124, 1-126, 1-128, 1-130, 1-132, 1-134, 1-136, 1-138, 1-142, 1-146, 1-148, 1-150, 1-154, 1-156, 1-158, 1-160, 1-162, 1-166, 1-168, 1-170, 1-174, 1-188, 1-189, 1-195, 1-196, 1-202, 1-204, 1-206, 1-208, 1-210, 1-212, 1-214, 1-216, 1-218, 1-220, 1-222, 1-224, 1-226, 1-230, 1-234, 1-236, 1-238, 1-242, 1-244, 1-246, 1-248, 1-250, 1-254, 1-256, 1-258, 1-262, 1-276, 1-277, 1-283, 1-284, 1-290, 1-292, 1-294, 1-296, 1-298, 1-300, 1-302, 1-304, 1-306, 1-308, 1-310, 1-312, 1-314, 1-318, 1-322, 1-324, 1-326, 1-330, 1-332, 1-334, 1-336, 1-338, 1-342, 1-344, 1-346, 1-350, 1-353, 1-355, 1-360 to 1-369, 1-371, 1-372, 1-378, 1-380, 1-382, 1-384, 1-386, 1-388, 1-390, 1-392, 1-394, 1-396, 1-398, 1-400, 1-402, 1-406, 1-410, 1-412, 1-414, 1-418, 1-420, 1-422, 1-424, 1-426, 1-430, 1-432, 1-434, 1-438, 1-452, 1-453, 1-459, 1-460, 1-466, 1-468, 1-470, 1-472, 1-474, 1-476, 1-478, 1-480, 1-482, 1-484, 1-486, 1-488, 1-490, 1-494, 1-498, 1-500, 1-502, 1-506, 1-508, 1-510, 1-512, 1-514, 1-518, 1-520, 1-522, 1-526, 1-540, 1-541, 1-547, 1-548, 1-554, 1-556, 1-558, 1-560, 1-562, 1-564, 1-566, 1-568, 1-570, 1-572, 1-574, 1-576, 1-578, 1-582, 1-586, 1-588, 1-590, 1-594, 1-596, 1-598, 1-600, 1-602, 1-604, 1-606, 1-608, 1-610, 1-614, 1-628, 1-629, 1-635, 1-636, 1-642, 1-644, 1-646, 1-648, 1-650, 1-652, 1-654, 1-656, 1-658, 1-660, 1-662, 1-664, 1-666, 1-670, 1-674, 1-676, 1-678, 1-682, 1-684, 1-686, 1-688, 1-690, 1-694, 1-696, 1-698, 1-702, 1-712 to 1-720, 1-723, 1-724, 1-730, 1-732, 1-734, 1-736, 1-738, 1-740, 1-742, 1-744, 1-746, 1-748, 1-750, 1-752, 1-754, 1-758, 1-762, 1-764, 1-766, 1-770, 1-772, 1-774, 1-776, 1-778, 1-782, 1-784, 1-786, 1-790, 1-804, 1-805, 1-811, 1-812, 1-818, 1-820, 1-822, 1-824, 1-826, 1-828, 1-830, 1-832, 1-834, 1-836, 1-838, 1-840, 1-842, 1-846, 1-850, 1-852, 1-854, 1-858, 1-860, 1-862, 1-864, 1-866, 1-870, 1-872, 1-874, 1-878, 1-888 to 1-896, 1-899, 1-900, 1-906, 1-908, 1-910, 1-912, 1-914, 1-916, 1-918, 1-920, 1-922, 1-924, 1-926, 1-928, 1-930, 1-934, 1-938, 1-940, 1-942, 1-946, 1-948, 1-950, 1-952, 1-954, 1-958, 1-960, 1-962, 1-966, 1-980, 1-981, 1-987, 1-988, 1-994, 1-996, 1-998, 1-1000, 1-1002, 1-1004, 1-1006, 1-1008, 1-1010, 1-1012, 1-1014, 1-1016, 1-1018, 1-1022, 1-1026, 1-1028, 1-1030, 1-1034, 1-1036, 1-1038, 1-1040, 1-1042, 1-1046, 1-1048, 1-1050, 1-1054, 1-1057, 1-1062, 1-1063, 1-1066, 1-1067 to 1-1070, 1-1074, 1-1079, 1-1080, 1-1083, 1-1085 to 1-1087, 1-1091, 1-1096, 1-1097, 1-1100, 1-1102 to 1-1104, 1-1108, 1-1113, 1-1114, 1-1117, 1-1119 to 1-1121, 1-1125, 1-1130, 1-1131, 1-1134, 1-1136 to 1-1138, 1-1142, 1-1147, 1-1148, 1-1151, 1-1153 to 1-1155, 1-1159, 1-1164, 1-1165, 1-1168, 1-1170 to 1-1172, 1-1176, 1-1181, 1-1182, 1-1185, 1-1187 to 1-1189, 1-1193, 1-1198, 1-1199, 1-1202, 1-1204 to 1-1206, 1-1210, 1-1215, 1-1216, 1-1219, 1-1221 to 1-1223, 1-1227, 1-1232, 1-1233, 1-1236, 1-1238 to 1-1240, 1-1244, 1-1249, 1-1250, 1-1253, 1-1255 to 1-1257, 1-1261, 1-1266, 1-1267, 1-1270, 1-1272 to 1-1274, 1-1278, 1-1283, 1-1284, 1-1287, 1-1289 to 1-1291, 1-1295, 1-1300, 1-1301, 1-1304, 1-1306 to 1-1308, 1-1312, 1-1317, 1-1318, 1-1321, 1-1323 to 1-1325, 1-1329, 1-1334, 1-1335, 1-1337, 1-1340 to 1-1342, 1-1346, 1-1351, 1-1352, 1-1355, 1-1357 to 1-1359, 1-1374, 1-1375, 1-1381, 1-1382, 1-1388, 1-1390, 1-1392, 1-1394, 1-1396, 1-1398, 1-1400, 1-1402, 1-1404, 1-1406, 1-1408, 1-1410, 1-1412, 1-1416, 1-1420, 1-1422, 1-1428, 1-1430, 1-1432, 1-1434, 1-1436, 1-1440, 1-1442, 1-1444, 1-1448, 1-1462, 1-1463, 1-1469, 1-1470, 1-1476, 1-1478, 1-1480, 1-1482, 1-1484, 1-1486, 1-1488, 1-1490, 1-1492, 1-1494, 1-1496, 1-1498, 1-1500, 1-1504, 1-1508, 1-1510, 1-1516, 1-1518, 1-1520, 1-1522, 1-1524, 1-1528, 1-1530, 1-1532, 1-1536, 1-1550, 1-1551, 1-1557, 1-1558, 1-1564, 1-1566, 1-1568, 1-1570, 1-1572, 1-1574, 1-1576, 1-1578, 1-1580, 1-1582, 1-1584, 1-1586, 1-1588, 1-1592, 1-1596, 1-1598, 1-1604, 1-1606, 1-1608, 1-1610, 1-1612, 1-1616, 1-1618, 1-1620, 1-1624, 1-1638, 1-1639, 1-1645, 1-1646, 1-1652, 1-1654, 1-1656, 1-1658, 1-1660, 1-1662, 1-1664, 1-1666, 1-1668, 1-1670, 1-1672, 1-1674, 1-1676, 1-1680, 1-1684, 1-1686, 1-1692, 1-1694, 1-1696, 1-1698, 1-1700, 1-1704, 1-1706, 1-1708, 1-1712, 1-1726, 1-1727, 1-1733, 1-1734, 1-1740, 1-1742, 1-1744, 1-1746, 1-1748, 1-1750, 1-1752, 1-1754, 1-1756, 1-1758, 1-1760, 1-1762, 1-1764, 1-1768, 1-1772, 1-1774, 1-1780, 1-1782, 1-1784, 1-1786, 1-1788, 1-1792, 1-1794, 1-1796, 1-1800, 1-1814, 1-1815, 1-1821, 1-1822, 1-1828, 1-1830, 1-1832, 1-1834, 1-1836, 1-1838, 1-1840, 1-1842, 1-1844, 1-1846, 1-1848, 1-1850, 1-1852, 1-1856, 1-1860, 1-1862, 1-1868, 1-1870, 1-1872, 1-1874, 1-1876, 1-1880, 1-1882, 1-1884, 1-1888, 1-1902, 1-1903, 1-1909, 1-1910, 1-1916, 1-1918, 1-1920, 1-1922, 1-1924, 1-1926, 1-1928, 1-1930, 1-1932, 1-1934, 1-1936, 1-1938, 1-1940, 1-1944, 1-1948, 1-1950, 1-1956, 1-1958, 1-1960, 1-1962, 1-1964, 1-1968, 1-1970, 1-1972, 1-1976, 1-1989, 1-1990, 1-1996, 1-1997, 1-2003, 1-2005, 1-2007, 1-2009, 1-2011, 1-2013, 1-2015, 1-2017, 1-2019, 1-2021, 1-2023, 1-2025, 1-2027, 1-2031, 1-2035, 1-2037, 1-2043, 1-2045, 1-2047, 1-2049, 1-2051, 1-2055, 1-2057, 1-2059, 1-2063, 1-2077, 1-2078, 1-2084, 1-2085, 1-2091, 1-2093, 1-2095, 1-2097, 1-2099, 1-2101, 1-2103, 1-2105, 1-2107, 1-2109, 1-2111, 1-2113, 1-2115, 1-2119, 1-2123, 1-2125, 1-2131, 1-2133, 1-2135, 1-2137, 1-2139, 1-2143, 1-2145, 1-2147, 1-2151, 1-2154, 1-2157, 1-2160, 1-2163, 1-2166, 1-2169, 1-2172, 1-2175, 1-2178, 1-2181, 1-2184, 1-2187, 1-2190, 1-2193, 1-2196, 1-2199, 1-2202, 1-2205, 1-2208, 1-2211, 1-2214, 1-2217 to 1-2221, 1-2224 to 1-2228, 1-2231 to 1-2235, 1-2238 to 1-2242, 1-2245 to 1-2249, 1-2252 to 1-2256, 1-2259 to 1-2263, 1-2266 to 1-2270, 1-2273 to 1-2277, 1-2280 to 1-2284, 1-2287 to 1-2291, 1-2294 to 1-2298, 1-2301 to 1-2305, 1-2308 to 1-2312, 1-2315 to 1-2319, 1-2322 to 1-2326, 1-2329 to 1-2333, 1-2336 to 1-2340, 1-2343 to 1-2347, 1-2350 to 1-2354, 1-2357 to 1-2361, 1-2364 to 1-2368, 1-2371 to 1-2375, 1-2378 to 1-2382, 1-2385 to 1-2389, 1-2392 to 1-2396, 1-2399 to 1-2403, 1-2406 to 1-2410, 1-2413 to 1-2417, 1-2420 to 1-2424, 1-2427 to 1-2431, 1-2434 to 1-2438, 1-2441 to 1-2445, 1-2448 to 1-2452, 1-2455 to 1-2459, 1-2462 to 1-2466, 1-2469 to 1-2473, 1-2476 to 1-2480, 1-2483 to 1-2487, 1-2490 to 1-2494, 1-2497 to 1-2501, 1-2504 to 1-2508, 1-2511 to 1-2515, 1-2518 to 1-2522, 1-2525 to 1-2529, 1-2532 to 1-2536, 1-2539 to 1-2543, 1-2546 to 1-2550, 1-2553 to 1-2557, 1-2560 to 1-2564, 1-2567 to 1-2571, 1-2574 to 1-2578, 1-2581 to 1-2585, 1-2588 to 1-2592, 1-2595 to 1-2599, 1-2602 to 1-2606, 1-2609 to 1-2613, 1-2616 to 1-2620, 1-2623 to 1-2627, 2-3, 2-4, 2-7, 2-8, 2-11, 2-12, 2-15, 2-16, 2-19, 2-20, 2-23, 2-24, 2-27, 2-28, 2-31, 2-32, 2-35, 2-36, 2-39, 2-40, 2-43, 2-44, 2-47, 2-48, 2-51, 2-52, 2-59, 2-60, 2-83, 2-84, 3-3, 3-4, 3-7, 3-8, 3-11, 3-12, 3-15, 3-16, 3-27, 3-28, 3-31, 3-32, 3-35, 3-36, 3-39, 3-40, 3-51, 3-52, 3-55, 3-56, 3-59, 3-60, 3-63, 3-64, 3-75, 3-76, 3-79, 3-80, 3-83, 3-84, 3-87, 3-88, 3-99, 3-100, 3-103, 3-104, 3-107, 3-108, 3-111, 3-112, 3-123, 3-124, 3-127, 3-128, 3-131, 3-132, 3-135, 3-136, 3-147, 3-148, 3-151, 3-152, 3-155, 3-156, 3-159, 3-160, 3-171, 3-172, 3-175, 3-176, 3-179, 3-180, 3-183, 3-184, 3-195, 3-196, 3-199, 3-200, 3-203, 3-204, 3-207, 3-208, 3-219, 3-220, 3-223, 3-224, 3-227, 3-228, 3-231, 3-232, 3-243, 3-244, 3-247, 3-248, 3-251, 3-252, 3-255, 3-256, 3-267, 3-268, 3-271, 3-272, 3-275, 3-276, 3-279, 3-280, 3-291, 3-292, 3-295, 3-296, 3-299, 3-300, 3-303, 3-304, 3-339, 3-340, 3-343, 3-344, 3-347, 3-348, 3-351, 3-352, 3-483, 3-484, 3-487, 3-488, 3-491, 3-492, 3-495, and 3-496 can be mentioned, more preferably, exemplified compound Nos.: 1-12, 1-26, 1-30, 1-34, 1-38, 1-42, 1-46, 1-58, 1-66, 1-70, 1-78, 1-100, 1-114, 1-118, 1-122, 1-126, 1-130, 1-134, 1-146, 1-154, 1-158, 1-166, 1-188, 1-202, 1-206, 1-210, 1-214, 1-218, 1-222, 1-234, 1-242, 1-246, 1-254, 1-276, 1-290, 1-294, 1-298, 1-302, 1-306, 1-310, 1-322, 1-330, 1-334, 1-342, 1-364, 1-378, 1-382, 1-386, 1-390, 1-394, 1-398, 1-410, 1-418, 1-422, 1-430, 1-452, 1-466, 1-470, 1-474, 1-478, 1-482, 1-486, 1-498, 1-506, 1-510, 1-518, 1-540, 1-554, 1-558, 1-562, 1-566, 1-570, 1-574, 1-586, 1-594, 1-598, 1-604, 1-606, 1-628, 1-642, 1-646, 1-650, 1-654, 1-658, 1-662, 1-674, 1-682, 1-686, 1-694, 1-716, 1-730, 1-734, 1-738, 1-742, 1-746, 1-750, 1-762, 1-770, 1-774, 1-782, 1-804, 1-818, 1-822, 1-826, 1-830, 1-834, 1-838, 1-850, 1-858, 1-862, 1-870, 1-892, 1-906, 1-910, 1-914, 1-918, 1-922, 1-926, 1-938, 1-946, 1-950, 1-958, 1-980, 1-994, 1-998, 1-1002, 1-1006, 1-1010, 1-1014, 1-1026, 1-1034, 1-1038, 1-1046, 1-1227, 1-1232, 1-1239, 1-1240, 1-1244, 1-1249, 1-1256, 1-1257, 1-1261, 1-1266, 1-1273, 1-1274, 1-1278, 1-1283, 1-1290, 1-1291, 1-1295, 1-1300, 1-1307, 1-1308, 1-1374, 1-1388, 1-1392, 1-1396, 1-1400, 1-1404, 1-1408, 1-1420, 1-1428, 1-1432, 1-1440, 1-1462, 1-1476, 1-1480, 1-1484, 1-1488, 1-1492, 1-1496, 1-1508, 1-1516, 1-1520, 1-1528, 1-1550, 1-1564, 1-1568, 1-1572, 1-1576, 1-1580, 1-1584, 1-1596, 1-1604, 1-1608, 1-1616, 1-1638, 1-1652, 1-1656, 1-1660, 1-1664, 1-1668, 1-1672, 1-1684, 1-1692, 1-1696, 1-1704, 1-1726, 1-1740, 1-1744, 1-1748, 1-1752, 1-1756, 1-1760, 1-1772, 1-1780, 1-1784, 1-1792, 1-1814, 1-1828, 1-1832, 1-1836, 1-1840, 1-1844, 1-1848, 1-1860, 1-1868, 1-1872, 1-1880, 1-1902, 1-1916, 1-1920, 1-1924, 1-1928, 1-1932, 1-1936, 1-1948, 1-1956, 1-1960, 1-1968, 1-1989, 1-2003, 1-2007, 1-2011, 1-2015, 1-2019, 1-2023, 1-2035, 1-2043, 1-2047, 1-2055, 1-2077, 1-2091, 1-2095, 1-2099, 1-2103, 1-2107, 1-2111, 1-2123, 1-2131, 1-2135, 1-2143, 1-2219, 1-2220, 1-2226, 1-2227, 1-2233, 1-2234, 1-2240, 1-2241, 1-2247, 1-2248, 1-2254, 1-2255, 1-2261, 1-2262, 1-2268, 1-2269, 1-2275, 1-2276, 1-2282, 1-2283, 1-2289, 1-2290, 1-2296, 1-2297, 1-2303, 1-2304, 1-2310, 1-2311, 1-2317, 1-2318, 1-2324, 1-2325, 1-2331, 1-2332, 1-2338, 1-2339, 1-2345, 1-2346, 1-2352, 1-2353, 1-2359, 1-2360, 1-2366, 1-2367, 1-2373, 1-2374, 1-2380, 1-2381, 1-2387, 1-2388, 1-2394, 1-2395, 1-2401, 1-2402, 1-2408, 1-2409, 1-2415, 1-2416, 1-2422, 1-2423, 1-2429, 1-2430, 1-2436, 1-2437, 1-2443, 1-2444, 1-2450, 1-2451, 1-2457, 1-2458, 1-2464, 1-2465, 1-2471, 1-2472, 1-2478, 1-2479, 1-2485, 1-2486, 1-2492, 1-2493, 1-2499, 1-2500, 1-2506, 1-2507, 1-2513, 1-2514, 1-2520, 1-2521, 1-2527, 1-2528, 1-2534, 1-2535, 1-2541, 1-2542, 1-2548, 1-2549, 1-2555, 1-2556, 1-2562, 1-2563, 1-2569, 1-2570, 1-2576, 1-2577, 1-2583, 1-2584, 1-2590, 1-2591, 1-2597, 1-2598, 1-2604, 1-2605, 1-2611, 1-2612, 1-2618, 1-2619, 1-2625, 1-2626, 2-3, 2-7, 2-11, 2-15, 2-19, 2-23, 2-27, 2-31, 2-35, 2-39, 2-43, 2-47, 2-51, 2-59, 2-83, 3-7, 3-31, 3-55, 3-79, 3-103, 3-127, 3-151, 3-175, 3-199, 3-223, 3-247, 3-271, 3-295, 3-343 and 3-487can be mentioned, even more preferably, exemplified compound No. 1-206: ethyl 8-[N-(2-chlorophenyl)sulfamoyl]-2,3-bis(hydroxymethyl)-1,4-dioxaspiro[4.5]dec-6-ene-7-carboxylate, exemplified compound No. 1-210: ethyl 8-[N-(2-chlorophenyl)sulfamoyl]-2,3-bis(1,2-dihydroxyethyl)-1,4-dioxaspiro[4.5]dec-6-ene-7-carboxylate, exemplified compound No. 1-294: ethyl 8-[N-(2,4-difluorophenyl)sulfamoyl]-2,3-bis(hydroxymethyl)-1,4-dioxaspiro[4.5]dec-6-ene-7-carboxylate, exemplified compound No. 1-298: ethyl 8-[N-(2,4-difluorophenyl)sulfamoyl]-2,3-bis(1,2-dihydroxyethyl)-1,4-dioxaspiro[4.5]dec-6-ene-7-carboxylate, exemplified compound No. 1-378: ethyl 8-[N-(2-chloro-4-fluorophenyl)sulfamoyl]-2-hydroxymethyl-1,4-dioxaspiro[4.5]dec-6-ene-7-carboxylate, exemplified compound No. 1-382: ethyl 8-[N-(2-chloro-4-fluorophenyl)sulfamoyl]-2,3-bis(hydroxymethyl)-1,4-dioxaspiro[4.5]dec-6-ene-7-carboxylate, exemplified compound No. 1-386: ethyl 8-[N-(2-chloro-4-fluorophenyl)sulfamoyl]-2,3-bis(1,2-dihydroxyethyl)-1,4-dioxaspiro[4.5]dec-6-ene-7-carboxylate, exemplified compound No. 1-390: ethyl 8-[N-(2-chloro-4-fluorophenyl)sulfamoyl]-2-(1,2-dihydroxyethyl)-1,4-dioxaspiro[4.5]dec-6-ene-7-carboxylate, exemplified compound No. 1-394: ethyl 8-[N-(2-chloro-4-fluorophenyl)sulfamoyl]-2-(1,2,3-trihydroxypropyl)-1,4-dioxaspiro[4.5]dec-6-ene-7-carboxylate, exemplified compound No. 1-398: ethyl 8-[N-(2-chloro-4-fluorophenyl)sulfamoyl]-2-(1,2,3,4-tetrahydroxybutyl)-1,4-dioxaspiro[4.5]dec-6-ene-7-carboxylate, exemplified compound No. 1-410: ethyl 2,3-bis(acetylaminomethyl)-8-[N-(2-chloro-4-fluorophenyl)sulfamoyl]-1,4-dioxaspiro[4.5]dec-6-ene-7-carboxylate, exemplified compound No. 1-418: ethyl 9-[N-(2-chloro-4-fluorophenyl)sulfamoyl]-3-hydroxy-1,5-dioxaspiro[5.5]undec-7-ene-8-carboxylate, exemplified compound No. 1-422: ethyl 3-acetylamino-9-[N-(2-chloro-4-fluorophenyl)sulfamoyl]-1,5-dioxaspiro[5.5]undec-7-ene-8-carboxylate, exemplified compound No. 1-430: ethyl 9-[N-(2-chloro-4-fluorophenyl)sulfamoyl]-3,3-bis(hydroxymethyl)-1,5-dioxaspiro[5.5] undec-7-ene-8-carboxylate, exemplified compound No. 1-646: ethyl 8-[N-(2-butyl-4-fluorophenyl)sulfamoyl]-2,3-bis(hydroxymethyl)-1,4-dioxaspiro[4.5]dec-6-ene-7-carboxylate, exemplified compound No. 1-650: ethyl 8-[N-(2-butyl-4-fluorophenyl)sulfamoyl]-2,3-bis(1,2-dihydroxyethyl)-1,4-dioxaspiro[4.5]dec-6-ene-7-carboxylate, exemplified compound No. 1-734: ethyl 8-[N-(2-hexylphenyl)sulfamoyl]-2,3-bis(hydroxymethyl)-1,4-dioxaspiro[4.5]dec-6-ene-7-carboxylate, exemplified compound No. 1-738: ethyl 8-[N-(2-hexyl phenyl)sulfamoyl]-2,3-bis(1,2-dihydroxyethyl)-1,4-dioxaspiro[4.5]dec-6-ene-7-carboxylate, exemplified compound No. 1-822: ethyl 8-[N-(4-fluoro-2-hexylphenyl)sulfamoyl]-2,3-bis(hydroxymethyl)-1,4-dioxaspiro[4.5]dec-6-ene-7-carboxylate, exemplified compound No. 1-826: ethyl 2,3-bis(1,2-dihydroxyethyl)-8-[N-(4-fluoro-2-hexylphenyl)sulfamoyl]-1,4-dioxaspiro[4.5]dec-6-ene-7-carboxylate, exemplified compound No. 1-910: ethyl 8-[N-(2-heptylphenyl)sulfamoyl]-2,3-bis(hydroxymethyl)-1,4-dioxaspiro[4.5]dec-6-ene-7-carboxylate, exemplified compound No. 1-914: ethyl 8-[N-(2-heptylphenyl)sulfamoyl]-2,3-bis(1,2-dihydroxyethyl)-1,4-dioxaspiro[4.5]dec-6-ene-7-carboxylate, exemplified compound No. 1-998: ethyl 8-[N-(4-fluoro-2-heptylphenyl)sulfamoyl]-2,3-bis(hydroxymethyl)-1,4-dioxaspiro[4.5]dec-6-ene-7-carboxylate, exemplified compound No. 1-1002: ethyl 2,3-bis(1,2-dihydroxyethyl)-8-[N-(4-fluoro-2-heptylphenyl)sulfamoyl]-1,4-dioxaspiro[4.5]dec-6-ene-7-carboxylate, exemplified compound No. 1-1392: ethyl 8-[N-(2-bromophenyl)sulfamoyl]-2,3-bis(hydroxymethyl)-1,4-dioxaspiro[4.5]dec-6-ene-7-carboxylate, exemplified compound No. 1-1396: ethyl 8-[N-(2-bromophenyl)sulfamoyl]-2,3-bis(1,2-dihydroxyethyl)-1,4-dioxaspiro[4.5]dec-6-ene-7-carboxylate, exemplified compound No. 1-1480: ethyl 8-[N-(2-chloro-6-methylphenyl)sulfamoyl]-2,3-bis(hydroxymethyl)-1,4-dioxaspiro[4.5]dec-6-ene-7-carboxylate, exemplified compound No. 1-1484: ethyl 8-[N-(2-chloro-6-methylphenyl)sulfamoyl]-2,3-bis(1,2-dihydroxyethyl)-1,4-dioxaspiro[4.5]dec-6-ene-7-carboxylate, exemplified compound No. 1-1568: ethyl 8-[N-(2-bromo-4-fluorophenyl)sulfamoyl]-2,3-bis(hydroxymethyl)-1,4-dioxaspiro[4.5]dec-6-ene-7-carboxylate, exemplified compound No. 1-1572: ethyl 8-[N-(2-bromo-4-fluorophenyl)sulfamoyl]-2,3-bis(1,2-dihydroxyethyl)-1,4-dioxaspiro[4.5]dec-6-ene-7-carboxylate, exemplified compound No. 1-1656: ethyl 2,3-bis(hydroxymethyl)-8-[N-(2-pentylphenyl)sulfamoyl]-1,4-dioxaspiro[4.5]dec-6-ene-7-carboxylate, exemplified compound No. 1-1660: ethyl 2,3-bis(1,2-dihydroxyethyl)-8-[N-(2-pentylphenyl)sulfamoyl]-1,4-dioxaspiro[4.5]dec-6-ene-7-carboxylate, exemplified compound No. 1-1744: ethyl 8-[N-(4-fluoro-2-pentylphenyl)sulfamoyl]-2,3-bis(hydroxymethyl)-1,4-dioxaspiro[4.5]dec-6-ene-7-carboxylate, exemplified compound No. 1-1748: ethyl 2,3-bis(1,2-dihydroxyethyl)-8-[N-(4-fluoro-2-pentylphenyl)sulfamoyl]-1,4-dioxaspiro[4.5]dec-6-ene-7-carboxylate, exemplified compound No. 1-1920: ethyl 8-[N-(4-fluoro-2-octylphenyl)sulfamoyl]-2,3-bis(hydroxymethyl)-1,4-dioxaspiro[4.5]dec-6-ene-7-carboxylate, exemplified compound No. 1-1924: ethyl 2,3-bis(1,2-dihydroxyethyl)-8-[N-(4-fluoro-2-octylphenyl)sulfamoyl]-1,4-dioxaspiro[4.5]dec-6-ene-7-carboxylate, exemplified compound No. 1-2095: ethyl 8-[N-(4-fluoro-2-propylphenyl)sulfamoyl]-2,3-bis(hydroxymethyl)-1,4-dioxaspiro[4.5]dec-6-ene-7-carboxylate, exemplified compound No. 1-2099: ethyl 2,3-bis(1,2-dihydroxyethyl)-8-[N-(4-fluoro-2-propylphenyl)sulfamoyl]-1,4-dioxaspiro[4.5]dec-6-ene-7-carboxylate and exemplified compound No. 2-15: ethyl 8-[N-(2-chloro-4-fluorophenyl)-N-methylsulfamoyl]-2,3-bis(hydroxymethyl)-1,4-dioxaspiro[4.5]dec-6-ene-7-carboxylate can be mentioned.

The compound having the general formula (I) according to the present invention can easily be prepared in accordance with Method A to Method C shown hereafter.

Method A is a method to prepare a compound having the general formula (I), by introducing a cyclic ketal in the initial stage of the preparation.

Method B is a method to prepare a compound having the general formula (I), by introducing a cyclic ketal in the final stage of the preparation.

Method C is a method to prepare a compound having the general formula (I), by introducing $R^5$ in the final stage of the preparation.

Method A
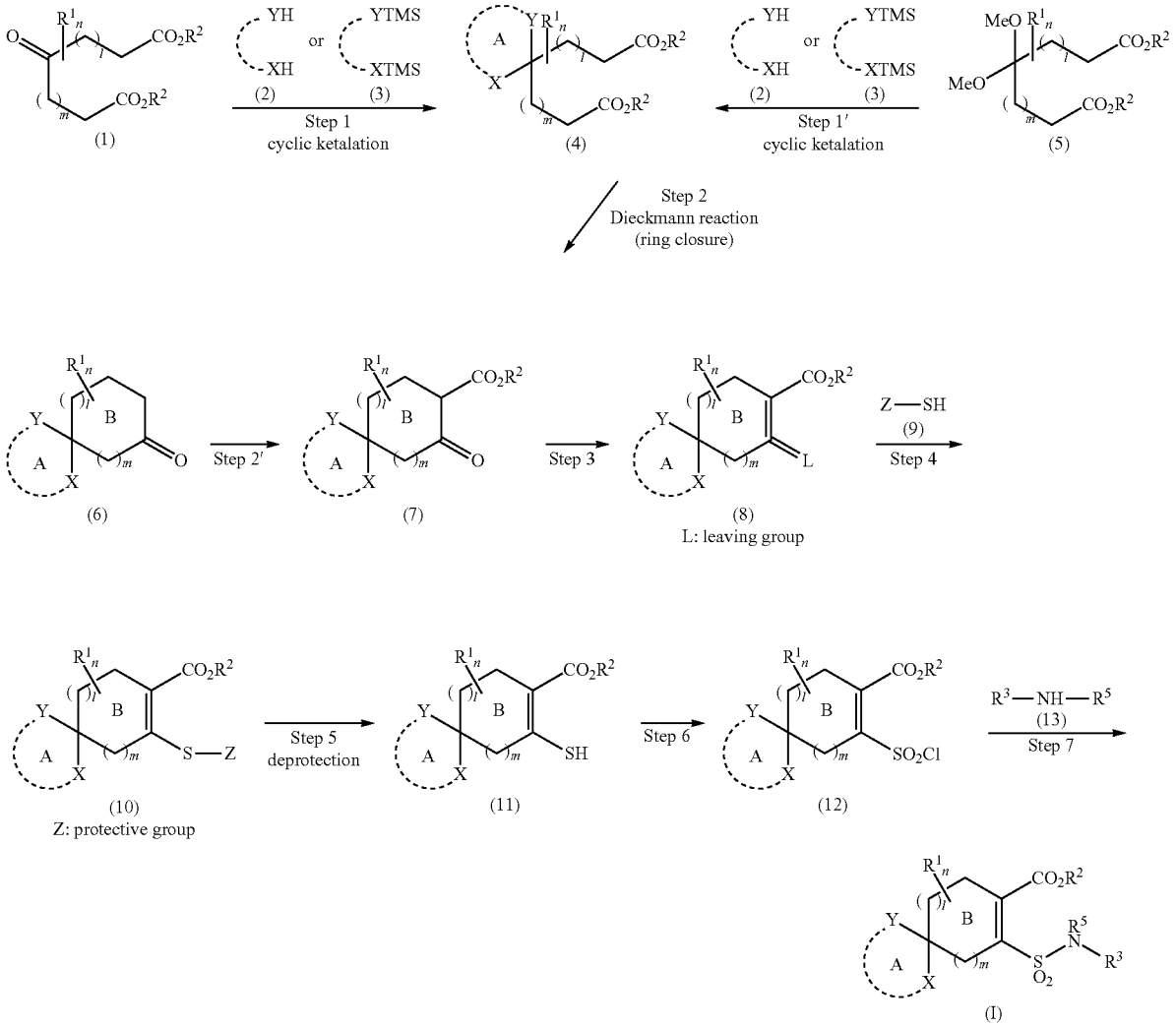
Method B
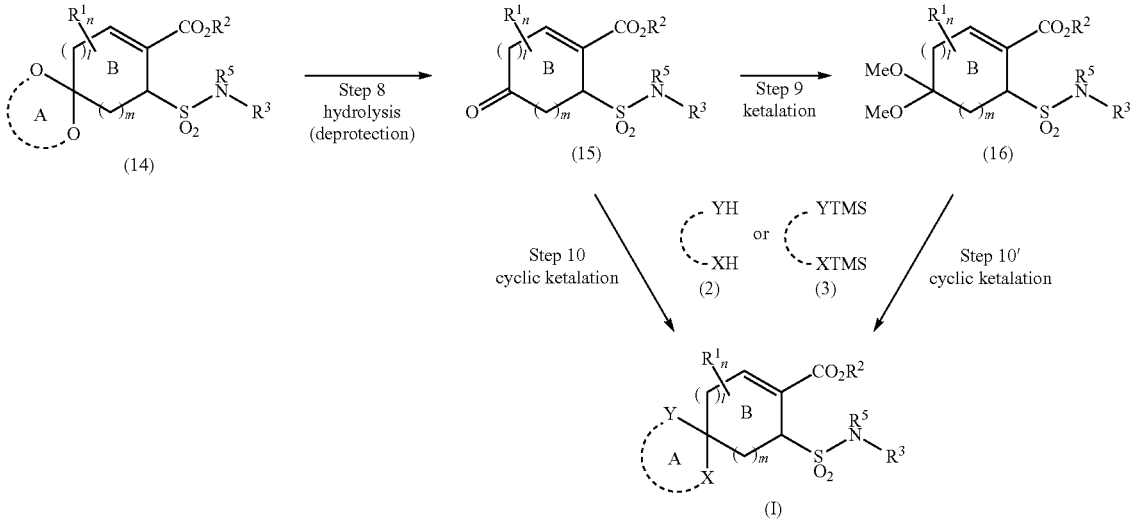

-continued

Method C

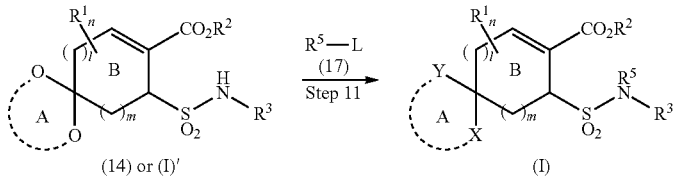

In the aforementioned Method A to Method C, ring A, ring B, X, Y, $R^1$, $R^2$, $R^3$, $R^5$, m and n have the same meanings as defined above, L represents a leaving group and Z represents a protective group.

In the reactions of Method A to Method C, in the case where the compound as the reactive substrate has a group such as an amino group, hydroxy group and/or carboxyl group, which inhibits the intended reaction, these groups may be protected with a protective group as necessary. The protective group of a group which inhibits the intended reaction is not limited so long as it is a protective group which is ordinarily used to conduct the reaction, and may be, for example, a protective w group described in "Protective Groups in Organic Synthesis, 3rd edition, T. W. Greene & P. G. M. Wuts; John Wiley & Sons, Inc."

A protective group of an amino group can be used without particular limitation so long as it is a group generally used as a protective group of an amino group, and preferably, formyl, the aforementioned $C_1$-$C_6$ alkylcarbonyl group; the aforementioned arylcarbonyl group; the aforementioned $C_1$-$C_6$ alkoxycarbonyl group; the aforementioned $C_1$-$C_6$ alkanoyl group which is substituted with halogen; aralkyl groups such as benzyl, phenethyl, 3-phenylpropyl, 4-phenylbutyl, α-naphthylmethyl, β-naphthylmethyl, diphenylmethyl, triphenylmethyl, α-naphthyldiphenylmethyl or 9-anthrylmethyl; the aforementioned aralkyloxycarbonyl group and the like can be mentioned.

A protective group of a hydroxy group can be used without particular limitation so long as it is a group generally used as a protective group of a hydroxy group, and preferably, formyl, $C_1$-$C_6$ alkylcarbonyl groups such as acetyl, arylcarbonyls such as benzoyl group; and alkoxylated alkoxymethyls such as 2-methoxyethoxymethyl can be mentioned.

A protective group of a carboxyl group can be used without particular limitation so long as it is a group generally used as a protective group of a carboxyl group, and preferably, the aforementioned $C_1$-$C_6$ alkyl group; and aralkyl groups such as benzyl, phenethyl and phenylpropyl can be mentioned.

Further, these protective groups of groups which inhibit the intended reaction may be cleaved as necessary. The cleavage reaction of these protective groups, which is the desired reaction, may be conducted in accordance with conventional procedures which are used in the field of synthetic organic chemistry (for example, the procedure described in the aforementioned Protective Groups in Organic Synthesis, 3rd edition, T. W. Greene & P. G. M. Wuts; John Wiley & Sons, Inc).

<Method A>

Step 1 of Method A is a step to react a ketone compound (1) with a compound (2) or a compound (3), which is compound (2) having its terminal substituted with a trimethylsilyl group (described as TMS in the aforementioned scheme), in an inert solvent in the presence of acid, to prepare a cyclic ketal compound (4).

This step can adopt a cyclic ketalation reaction (protection) of a ketone, which is widely used in general organic synthesis, and can be conducted in accordance with the procedure described in T. W. Greene, P. C. Wuts, Protective Groups in organic Synthesis. Third Edition, 1999, Chapter 4, pp. 293-368, John Wiley & Sons, Inc. and the like, or in accordance with similar procedures.

Here, the cyclic ketal compound (4) can also be prepared by the following procedure (Step 1' of Method A).

Step 1' of Method A is a step to react a dimethylketal compound (5) with compound (2) or compound (3), in an inert solvent in the presence of acid, to prepare a cyclic ketal compound (4). This reaction can be conducted in accordance with the same procedure as or based on the procedure of Step 1.

Step 2 of Method A is a step to allow the cyclic ketal compound (4) obtained by Step 1 or Step 1' to undergo a Dieckmann reaction, to prepare a ketoester compound (7).

This step can adopt a Dieckmann reaction which is widely used generally in organic synthesis, and can be conducted in accordance with the procedure described in Chemical Pharmaceutical Bulletin (Chem. Pharm. Bull.) Vol. 29, pp. 3238-3248 (1981) and the like, or based on that procedure.

Here, the ketoester compound (7) can also be prepared by the following procedure (Step 2' of Method A).

Step 2' of Method A is a step to react a ketone compound (6) with a dialkyl carbonate, in an inert solvent in the presence of base, to prepare a ketoester compound (7).

This step can adopt an ester group introducing reaction which is widely used generally in organic synthesis, and can be conducted in accordance with the procedure described in Canadian Journal of Chemistry (Can. J. Chem.) Vol. 70, pp. 1406-1426 (1992) and the like, or based on that procedure.

Step 3 of Method A is a step to enolate the ketoester compound (7) obtained in Step 2 or Step 2', in an inert solvent in the presence of base, to prepare a compound (8) having a leaving group L.

This step can be conducted in accordance with the procedure described in Journal of American Chemical Society (J. Am. Chem. Soc.), Vol. 120, pp. 3664-3670 (1998) and the like, or based on that procedure.

"Leaving group" in the definition of L generally represents a group which leaves as a nucleophilic residue, and for example, halogen atoms such as a fluorine atom, chlorine atom, bromine atom and iodine atom; lower alkanesulfonyloxy groups such as methanesulfonyloxy and ethanesulfonyloxy; halogeno lower alkanesulfonyloxy groups such as trifluoromethanesulfonyloxy and pentafluoroethanesulfonyloxy; and arylsulfonyloxy groups such as benzenesulfonyloxy, p-toluenesulfonyloxy and p-nitrobenzenesulfonyloxy can be mentioned. Preferably, it is a halogeno lower alkanesulfonyloxy group, particularly preferably a trifluoromethanesulfonyloxy group.

The inert solvent used is not particularly limited so long as it does not inhibit the reaction and dissolves the starting material to some degree, and for example, aromatic hydrocarbons such as benzene, toluene and xylene; halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycoldimethyl ether; amides such as formamide, N,N-dimethylformamide, N,N-dimethylacetamide, N-methyl-2-pyrrolidinone and hexamethylphosphorotriamide; or a solvent mixture of these can be mentioned. Preferably, it is a halogenated hydrocarbon, more preferably dichloromethane.

The base used includes inorganic bases such as alkali metal carbonates such as sodium carbonate, potassium carbonate and lithium carbonate; alkali metal hydrogen carbonates such as sodium hydrogen carbonate, potassium hydrogen carbonate and lithium hydrogen carbonate; alkali metal hydrides such as lithium hydride, sodium hydride and potassium hydride; alkali metal fluorides such as sodium fluoride and potassium fluoride; organic bases such as alkali metal alkoxides such as sodium methoxide, sodium ethoxide, potassium methoxide, potassium ethoxide, potassium t-butoxide and lithium methoxide; N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), preferably alkali metal hydrides or organic bases, and more preferably sodium hydride or diisopropylethylamine.

Reaction temperature varies depending on the starting compound and reaction reagent, and the reaction is conducted from −100° C. to 100° C., preferably from −78° C. to 50° C.

Reaction time varies depending on the reaction temperature, starting compound, reaction reagent or the type of solvent used, and it is generally in the range from 1 minute to 48 hours, preferably from 5 minutes to 12 hours.

Step 4 of Method A is a step to react the compound (8) having a leaving group L obtained in Step 3 with a thiol compound (9) in an inert solvent in the presence of a base, to prepare compound (10).

"Protective group" of the sulfanyl group in the definition of Z is not particularly limited so long as it is a protective group of a sulfanyl group which is widely used generally in organic synthesis, and alkanoyl groups such as formyl, acetyl, propionyl and butyryl, and arylcarbonyl groups such as benzoyl, α-naphthoyl, β-naphthoyl, pyridoyl, thienoyl and furoyl can be mentioned, for example. Preferably, it is a group which forms a pharmacologically acceptable ester, and is more preferably an acetyl group.

The inert solvent used is not particularly limited so long as it does not inhibit the reaction and dissolves the starting material to some degree, and for example, aromatic hydrocarbons such as benzene, toluene and xylene; halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycoldimethyl ether; aprotic polar solvents such as formamide, N,N-dimethylformamide, N,N-dimethylacetamide and dimethyl sulfoxide; or a solvent mixture of these can be mentioned. Preferably, it is an aprotic polar solvent, more preferably N,N-dimethylformamide.

The base used includes inorganic bases such as alkali metal carbonates, e.g. sodium carbonate, potassium carbonate and lithium carbonate; alkali metal hydrogen carbonates such as sodium hydrogen carbonate, potassium hydrogen carbonate and lithium hydrogen carbonate; alkali metal hydrides such as lithium hydride, sodium hydride and potassium hydride; alkali metal fluorides such as sodium fluoride and potassium fluoride; organic bases such as alkali metal alkoxides, e.g. sodium methoxide, sodium ethoxide, potassium methoxide, potassium ethoxide, potassium t-butoxide and lithium methoxide; N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU) can be mentioned, and is preferably an alkali metal hydride, more preferably sodium hydride or potassium hydride.

Reaction temperature varies depending on the starting compound and reaction reagent, and the reaction is conducted from −78° C. to 100° C., preferably from −20° C. to 50° C.

Reaction time varies depending on the reaction temperature, starting compound, reaction reagent or the type of solvent used, and it is generally in the range from 1 minute to 120 hours, preferably from 10 minutes to 72 hours.

Step 5 of Method A is a step to deprotect the protective group of the sulfanyl group of the compound (10) obtained in Step 4, in an inert solvent, to prepare compound (11).

This step is a deprotection step of a protective group of a sulfanyl group which is widely used in general organic synthesis, and is conducted in accordance with the procedure described in the aforementioned "Protective Groups in Organic Synthesis, 3rd edition, T. W. Greene & P. G. M. Wuts; John Wiley & Sons, Inc." and the like, or based on that procedure, and can be preferably conducted by a deprotection procedure in an inert solvent in the presence of base.

The inert solvent used is not particularly limited so long as it does not inhibit the reaction and dissolves the starting material to some degree, and for example, aromatic hydrocarbons such as benzene, toluene and xylene; halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycoldimethyl ether; alcohols such as methanol, ethanol, n-propanol, isopropanol, n-butanol, isobutanol, t-butanol, isoamyl alcohol, diethylene glycol, glycerin, octanol, cyclohexanol and 2-methoxyethanol; amides such as formamide, N,N-dimethylformamide, N,N-dimethylacetamide, N-methyl-2-pyrrolidinone and hexamethylphosphortriamide; sulfoxides such as dimethyl sulfoxide and sulfolane; or a solvent mixture of these can be mentioned, and is preferably an alcohol, and more preferably methanol or ethanol.

The base used includes alkali metal carbonates such as sodium carbonate, potassium carbonate and lithium carbonate; alkali metal hydrogen carbonates such as sodium hydrogencarbonate, potassium hydrogencarbonate and lithium hydrogencarbonate; organic bases such as alkali metal alkoxides, e.g. sodium methoxide, sodium ethoxide, potassium methoxide, potassium ethoxide, potassium t-butoxide and lithium methoxide; N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), preferably alkali metal carbonates, and more preferably potassium carbonate.

Reaction temperature varies depending on the starting compound and reaction reagent, and the reaction is conducted from −78° C. to 100° C., preferably from −20° C. to 50° C.

Reaction time varies depending on the reaction temperature, starting compound, reaction reagent or the type of solvent used, and it is generally from 1 minute to 24 hours, preferably from 5 minutes to 5 hours.

Step 6 of Method A is a step to chlorosulfonylate the thiol group of the compound (11) obtained in Step 5, in an inert solvent, to prepare compound (12).

This step can be conducted in accordance with the procedure described in Journal of Organic Chemistry (J. Org. Chem.), Vol. 16, pp. 621-625 (1951) and the like, or based on that procedure.

The inert solvent used is not particularly limited so long as it does not inhibit the reaction and dissolves the starting material to some degree, and for example, aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran, dioxane, dimethoxyethane and diethyleneglycoldimethyl ether; alcohols such as methanol, ethanol, n-propanol, isopropanol, n-butanol, isobutanol, t-butanol, isoamyl alcohol, diethylene glycol, glycerin, octanol, cyclohexanol and 2-methoxyethanol; aprotic polar solvents such as N, N-dimethylformamide, N,N-dimethylacetamide and dimethyl sulfoxide; nitrites such as acetonitrile; esters such as methyl acetate and ethyl acetate; carboxylic acids such as formic acid, acetic acid, propionic acid and trifluoroacetic acid; water; or a solvent mixture of these can be mentioned. Preferably, it is a solvent mixture of carboxylic acids and water or a solvent mixture of nitrites and water, more preferably a solvent mixture of acetic acid and water, or a solvent mixture of acetonitrile and water.

Reaction temperature varies according to the starting compound and reaction reagent, and the reaction is conducted from −78° C. to 100° C., preferably from −20° C. to 50° C.

Reaction time varies depending on the reaction temperature, starting compound, reaction reagent or the type of solvent used, and it is generally from 1 minute to 12 hours, preferably from 5 minutes to 1 hour.

Step 7 of Method A is a step to react the compound (12) obtained in Step 6 with an amine compound (13) in an inert solvent in the presence or absence of base, to prepare a compound of general formula (I).

The inert solvent used is not particularly limited so long as it does not inhibit the reaction and dissolves the starting material to some degree, and for example, aromatic hydrocarbons such as benzene, toluene and xylene; halogenated hydrocarbons such as dichloromethane, chloroform, carbon tetrachloride and dichloroethane; ethers such as diethyl ether, diisopropyl ether, tetrahydrofuran, dioxane, dimethoxyethane and diethyleneglycoldimethyl ether; aprotic polar solvents such as N,N-dimethylformamide, N,N-dimethylacetamide and dimethyl sulfoxide; nitrites such as acetonitrile; esters such as methyl acetate and ethyl acetate; or a solvent mixture of these can be mentioned. Preferably, it is an ester, more preferably ethyl acetate.

The base used includes alkali metal hydrates such as lithium hydrate, sodium hydrate and potassium hydrate; organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), preferably organic bases, and more preferably triethylamine.

Reaction temperature varies depending on the starting compound and reaction reagent, and the reaction is conducted from −78° C. to 100° C., preferably from −20° C. to 50° C.

Reaction time varies depending on the reaction temperature, starting compound, reaction reagent or the type of solvent used, and it is generally in the range from 1 minute to 120 hours, preferably from 10 minutes to 48 hours.

<Method B>

Step 8 of Method B is a step to hydrolyze the cyclic ketal compound (14) obtained in Method A in an inert solvent in the presence of acid, to prepare a ketone compound (15).

This step can adopt a deprotection reaction of a cyclic ketal compound which is widely used generally in organic synthesis, and can be conducted in accordance with the procedure described in the aforementioned T. W. Greene, O. G. Wuts, Protective Groups in Organic Synthesis. Third Edition, 1999, Chapter 4, pp. 293-368, John Wiley & Sons, Inc. and the like, or based on that procedure.

Step 9 of Method B is a step to prepare a dimethylketal compound (16) with the ketone compound (15) obtained in Step 8 in an inert solvent in the presence of acid.

This step can adopt a dimethylketalation reaction (protection) of a ketone which is widely used generally in organic synthesis, and can be conducted in accordance with the procedure described in the aforementioned T. W. Greene, 0. G. Wuts, Protective Groups in Organic Synthesis. Third Edition, 1999, Chapter 4, pp. 293-368, John Wiley & Sons, Inc. and the like, or based on that procedure.

Step 10 of Method B is a step to react the ketone compound (15) obtained in Step 8 with the compound (2) or compound (3) in an inert solvent in the presence of acid, to prepare a compound having the general formula (I).

Here, this reaction can be conducted in accordance with a similar procedure to Step 1.

Step 10' of Method B is a step to react the dimethylketal compound (16) obtained in Step 9 with the compound (2) or compound (3) in an inert solvent in the presence of acid, to prepare a compound having the general formula (I).

Here, this reaction can be conducted in accordance with a similar procedure to Step 1'.

<Method C>

Step 11 of Method C is a step, in the case where $R^5$ of the cyclic ketal compound (14) obtained in Method A or the compound having the general formula (I) obtained in Method B is a hydrogen atom, to react it with $R^5$-L (17) in an inert solvent in the presence of base, to prepare a compound having the general formula (I) which is substituted with a desired $R^5$.

$R^5$ and L represent the same meanings as described above, and "leaving group" in the definition of L represents a group which leaves as a nucleophilic residue, and for example, halogen atoms such as a fluorine atom, chlorine atom, bromine atom and iodine atom; lower-alkane sulfonyloxy groups such as methanesulfonyloxy and ethanesulfonyloxy; halogeno lower alkanesulfonyloxy groups such as trifluoromethanesulfonyloxy and pentafluoroethanesulfonyloxy; arylsulfonyloxy groups such as benzenesulfonyloxy, p-toluenesulfonyloxy and p-nitrobenzenesulfonyloxy; can be mentioned. Preferably, it is a halogen atom, particularly preferably an iodine atom.

The inert solvent used is not particularly limited so long as it does not inhibit the reaction and dissolves the starting material to some degree, and includes, for example, ketones such as acetone, methyl ethyl ketone, methyl isobutyl ketone, isophorone and cyclohexanone; ethers such as diethyl ether, diisopropyl ether, tetrahydrofuran and dioxane; aprotic polar solvents such as dimethylformamide, dimethylacetamide and dimethyl sulfoxide; nitrites such as acetonitrile; esters such as methyl acetate and ethyl acetate; aromatic hydrocarbons such as benzene, toluene and xylene; aliphatic hydrocarbons such as pentane, hexane and heptane, preferably, ethers, ketones or aprotic polar solvents, and more preferably, tetrahydrofuran, acetone or dimethylformamide.

The base used includes alkali metal carbonates such as sodium carbonate, potassium carbonate and lithium carbonate; alkali metal hydrogen carbonates such as sodium hydrogen carbonate, potassium hydrogen carbonate and lithium hydrogen carbonate; organic bases such as alkali metal alkoxides such as sodium methoxide, sodium ethoxide, potassium methoxide, potassium ethoxide, potassium t-butoxide and lithium methoxide; N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), preferably alkali metal carbonates, and more preferably potassium carbonate.

Reaction temperature varies depending on the starting compound and reaction reagent, and the reaction is conducted from −78° C. to 150° C., preferably from −20° C. to 100° C.

Reaction time varies depending on the reaction temperature, starting compound, reaction reagent or the type of solvent used, and it is generally in the range from 1 minute to 24 hours, preferably from 10 minutes to 5 hours.

After each of the aforementioned reactions is completed, the desired compound is collected from the reaction mixture in accordance with general procedures.

For example, the reaction mixture is neutralized as needed, and after filtration to remove insoluble matters in the case where insoluble matters exist, the reaction solution is extracted with an organic solvent such as ethyl acetate, which does not blend with water. Then after washing the reaction solution with water and the like, the organic layer containing the desired compound is separated and dried over anhydrous magnesium sulfate and the like, and then the solvent is evaporated to give the desired compound.

The obtained desired compound may, if necessary, be separated and purified by ordinary procedures such as recrystallization and reprecipitation, or by a procedure generally used for separation and purification of organic compounds such as appropriately combining an adsorption column chromatography method which uses silica gel, alumina or florisil of magnesium-silica type as a support; a method using a synthetic adsorbent agent such as distribution column chromatography which uses Sephadex LH-20 (produced by Pharmacia), Amberlite XAD-11 (produced by Rohm and Haas) or Diaion HP-20 (produced by Mitsubishi Chemical Corporation) as a support, a method using ion exchange chromatography, or normal phase or reverse phase column chromatography by silica gel or alkylated silica gel (preferably high performance liquid chromatography) and eluting with an appropriate eluent.

The starting compounds such as (1), (2), (3), (5), (6), (9), (13) and (17) as reactive substances of the present invention are publicly known or can easily be prepared in accordance with publicly known procedures.

The compound having the general formula (I) according to the present invention or pharmacologically acceptable salts thereof possesses excellent activity to suppress intracellular signal transduction or cell activation in various cells such as monocytes, macrophages and vascular endothelial cells, the intracellular signal transduction and cell activation being induced by endotoxin, and to suppress various cell responses induced by the intracellular signal transduction and cell activation such as an excess generation of inflammatory mediators such as TNF-α. Therefore, it is useful as a medicament, especially as a prophylactic and/or therapeutic agent for various diseases which are associated with intracellular signal transduction or cell activation induced by endotoxin, and with various cell responses (for example, excess generation of inflammatory mediators such as TNF-α) which are induced by the intracellular signal transduction and cell activation. As for such medicament, a prophylactic and/or therapeutic agent for ischemic brain disorder, arteriosclerosis, poor prognosis after coronary angioplasty, heart failure, diabetes, diabetic complication, joint inflammation, osteoporosis, osteopenia, sepsis, autoimmune disease, tissue disorder and rejection after organ transplantation, bacterial infection, virus infection, gastritis, pancreatitis, nephritis, pneumonia, hepatitis or leukemia can be mentioned.

In the case where the compound having the general formula (I) according to the present invention or the pharmacologically acceptable salts thereof is used as a prophylactic agent or a therapeutic agent for the aforementioned diseases, it can be mixed with excipients, diluents and the like that are themselves pharmacologically acceptable, and administered orally as a tablet, capsule, granules, powder or syrup, or administrated parenterally as an injection for subcutaneous injection, intramuscular injection or intravenous injection or as a suppository.

These pharmaceutical preparations are prepared in accordance with known processes by using additives including excipients (for example, organic excipients such as sugar derivatives, e.g. lactose, sucrose, glucose, mannitol or sorbitol; starch derivatives, e.g. corn starch, potato starch, α-starch or dextrin; cellulose derivatives, e.g. crystalline cellulose; gum arabic; dextran; or pullulan, and inorganic excipients such as silicate derivatives, e.g. light silicic anhydride, synthetic aluminum silicate, calcium silicate, metamagnesium aluminate; phosphates, e.g. calcium hydrogenphosphate; carbonates, e.g. calcium carbonate; salts of sulfuric acid such as calcium sulfate, can be mentioned), lubricants (for example, stearic acid, stearic acid metal salts such as calcium stearate or magnesium stearate; talc; colloid silica; waxes such as bees wax or spermaceti, boric acid; adipic acid; sulfates such as sodium sulfate; glycol; fumaric acid; sodium benzoate; DL leucine; lauryl sulfates such as sodium lauryl sulfate or magnesium lauryl sulfate; silicic acids such as silicic anhydride or silicate hydrate; and the aforementioned starch derivatives can be mentioned), binders (for example, hydroxypropyl cellulose, hydroxypropyl methyl cellulose, polyvinylpyrrolidone, macrogol and compounds similar to the aforementioned excipient can be mentioned), disintegrants (for example, cellulose derivatives such as low-substituted hydroxypropyl cellulose, carboxymethyl cellulose, calcium carboxymethyl cellulose or internally crosslinked sodium carboxymethyl cellulose; or chemically modified starches or celluloses such as carboxymethyl starch, sodium carboxymethyl starch or crosslinked polyvinylpyrrolidone can be mentioned), emulsifiers (for example, colloidal clays such as bentonite or bee gum; metal hydroxides such as magnesium hydroxide or aluminum hydroxide; anionic surfactants such as sodium lauryl sulfate or calcium stearate; cationic surfactants such as benzalkonium chloride; and nonionic surfactants such as polyoxyethylene alkyl ether, polyoxyethylene sorbitan fatty acid ester or sucrose fatty acid ester), stabilizers (for example, paraoxybenzoic acid esters such as methyl paraben or propyl paraben; alcohols such as chlorobutanol, benzyl alcohol or phenyl ethyl alcohol, benzalkonium chloride; phenols such as phenol or cresol; thimerosal; dehydroacetic acid; and sorbic acid can be mentioned) and corrigents (for example, commonly used sweeteners, acidifiers or fragrances can be mentioned) or diluents.

The amount of dosage varies according to symptoms and age, and it is desirable that the compound of the present invention is administered orally or parenterally to an adult human within a lower limit of 0.01 mg/kg (preferably 0.10 mg/kg) and an upper limit of 1000 mg/kg (preferably 100 mg/kg) per day, once a day or several times in parts depending on the symptoms.

EXAMPLES

Hereinafter, the present invention will be described in detail with reference to Examples and Test Examples, however, the scope of the present invention is not limited to these.

Example 1

Ethyl 8-[N-(2-chloro-4-fluorophenyl)sulfamoyl]-1,4-dioxaspiro[4.5]dec-6-ene-7-carboxylate (Exemplified compound No. 1-364

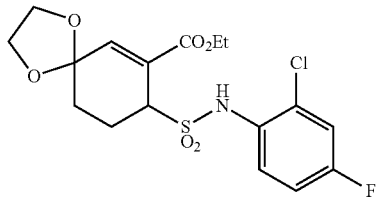

(1a) Ethyl 8-acetylsulfanyl-1,4-dioxaspiro[4.5]dec-7-ene-7-carboxylate 19.97 g (55.4 mmol) of ethyl 8-trifluoromethanesulfonyloxy-1,4-dioxaspiro[4.5]dec-7-ene-7-carboxylate [compound described as compound 6 in Tetrahedron Letter, Vol. 39, pp. 6139-6142 (1998)] was dissolved in 200 ml of dimethylformamide, and 9.50 g (83.1 mmol) of potassium thioacetate was added thereto with stirring under ice-cooling, followed by stirring at room temperature for 91 hours. To the reaction solution was added ice water and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=17:3) to give 7.15 g of the title compound as a pale brown oil (yield: 45%).

$^1$H-NMR spectrum (400 MHz, $CDCl_3$) δ ppm: 4.20 (2H, q, 7 Hz), 4.04-3.96 (4H, m), 2.73-2.66 (4H, m), 2.34 (3H, s), 1.87 (2H, t, J=6 Hz), 1.28 (3H, t, J=7 Hz).

(1b) Ethyl 8-mercapto-1,4-dioxaspiro[4.5]dec-7-ene-7-carboxylate 7.14 g (24.9 mmol) of ethyl 8-acetylsulfanyl-1,4-dioxaspiro[4.5]dec-7-ene-7-carboxylate obtained in (1a) was dissolved in 145 ml of methanol, and 2.58 g (18.7 mmol) of potassium carbonate was added thereto with stirring under ice-cooling, followed by stirring at the same temperature for 1 hour and then at room temperature for 1 hour. The reaction solution was made acidic by addition of 1N hydrochloric acid and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=9:1) to give 5.63 g of the title compound as a pale yellow oil (yield: 92%).

$^1$H-NMR spectrum (400 MHz, $CDCl_3$) δ ppm: 4.32 (1H, s), 4.21 (2H, q, 7 Hz), 4.04-3.95 (4H, m), 2.72-2.67 (2H, m), 2.59-2.57 (2H, m), 1.82 (2H, t, J=7 Hz), 1.30 (3H, t, J=7 Hz).

(1c) Ethyl 8-chlorosulfonyl-1,4-dioxaspiro[4.5]dec-7-ene-7-carboxylate

To a saturated solution prepared by blowing chlorine gas into 80 ml of solution mixture of acetonitrile-water (1:1) for 20 minutes was added a solution of 5.00 g (20.5 mmol) of ethyl 8-mercapto-1,4-dioxaspiro[4.5]dec-7-ene-7-carboxylate obtained in (1b) in 10 ml of acetonitrile with stirring under ice-cooling. Chlorine gas was further blown into the reaction solution for 10 minutes at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=2:1) to give 5.83 g of the title compound as a colorless oil (yield: 92%).

$^1$H-NMR spectrum (400 MHz, $CDCl_3$) δ ppm: 4.30 (2H, q, 7 Hz), 4.05-3.98 (4H, m), 2.91-2.86 (2H, m), 2.71-2.69 (2H, m), 1.93 (2H, t, J=7 Hz), 1.34 (3H, t, J=7 Hz).

(1d) Ethyl 8-[N-(2-chloro-4-fluorophenyl)sulfamoyl]-1,4-dioxaspiro[4.5]dec-6-ene-7-carboxylate To a solution of 197 mg (1.35 mmol) of 2-chloro-4-fluoroaniline and 0.20 ml (1.42 mmol) of triethylamine in 5 ml of ethyl acetate was added dropwise a solution of 400 mg (1.29 mmol) of ethyl 8-chlorosulfonyl-1,4-dioxaspiro[4.5]dec-7-ene-7-carboxylate obtained in (1c) in 3 ml of ethyl acetate with stirring under ice-cooling, followed by stirring at room temperature for 48 hours. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=3:1), and the resulting solid was further washed with a mixed solution of hexane-isopropyl ether (1:1) to give 325 mg of the title compound as a white powder (yield: 60%).

Melting point 117-119° C.

$^1$H-NMR spectrum (400 MHz, $CDCl_3$) δ ppm: 7.67 (1H, dd, J=9 Hz, 5 Hz), 7.16 (1H, dd, J=8 Hz, 3 Hz), 7.05-6.98 (2H, m), 6.83 (1H, s), 4.43-4.41 (1H, m), 4.26-4.01 (5H, m), 3.95-3.88 (1H, m), 2.56-2.45 (2H, m), 2.24-2.11 (1H, m), 1.88-1.80 (1H, m), 1.27 (3H, t, J=7 Hz).

Example 2

Ethyl 8-(N-phenylsulfamoyl)-1,4-dioxaspiro[4.5]dec-6-ene-7-carboxylate (Exemplified compound No. 1-12)

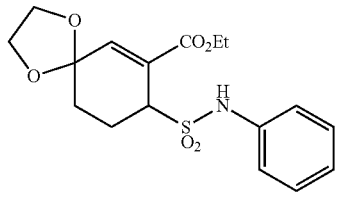

Following the process described in Example (1d), aniline was used in place of 2-chloro-4-fluoroaniline to give the title compound as an amorphous substance (yield: 81%).

$^1$H-NMR spectrum (400 MHz, $CDCl_3$) δ ppm: 7.37-7.31 (4H, m), 7.21-7.15 (1H, m), 6.95 (1H, s), 6.85-6.87 (1H, m), 4.30-4.20 (3H, m), 4.13-4.01 (3H, m), 3.94-3.88 (1H, m), 2.48-2.41 (1H, m), 2.31 (1H, td, J=14 Hz, 3 Hz), 2.10-2.00 (1H, m), 1.86-1.80 (1H, m), 1.31 (3H, t, J=7 Hz).

Example 3

Ethyl 8-[N-(2-butylphenyl)sulfamoyl]-1,4-dioxaspiro[4.5]dec-6-ene-7-carboxylate (exemplified compound No. 1-540)

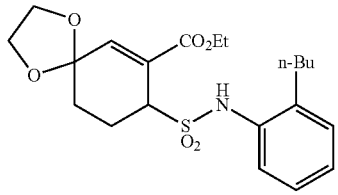

Following the process described in Example (1d), 2-butylaniline was used in place of 2-chloro-4-fluoroaniline to give the title compound as a colorless oil (56% yield).

$^1$H-NMR spectrum (400 MHz, $CDCl_3$) δ ppm: 7.55-7.52 (1H, m), 7.22-7.17 (2H, m), 7.13-7.08 (1H, m), 6.85-6.84 (1H, m), 6.63 (1H, s), 4.47-4.44 (1H, m), 4.25-4.02 (5H, m), 3.95-3.89 (1H, m), 2.71-2.62 (2H, m), 2.54-2.38 (2H, m), 2.19-2.09 (1H, m), 1.86-1.81 (1H, m), 1.62-1.53 (2H, m), 1.45-1.34 (2H, m), 1.26 (3H, t, J=7 Hz), 0.95 (3H, t, J=7 Hz).

Example 4

Ethyl 8-[N-(2-hexylphenyl)sulfamoyl]-1,4-dioxaspiro[4.5]dec-6-ene-7-carboxylate (Exemplified compound No. 1-716)

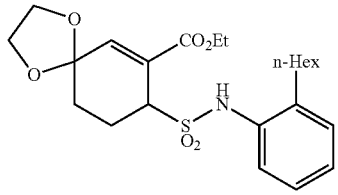

Following the process described in Example (1d), 2-hexylaniline was used in place of 2-chloro-4-fluoroaniline to give the title compound as a pale yellow oil (82% yield).

$^1$H-NMR spectrum (400 MHz, $CDCl_3$) δ ppm: 7.55-7.52 (1H, m), 7.22-7.17 (2H, m), 7.13-7.08 (1H, m), 6.85-6.84 (1H, m), 6.63 (1H, s), 4.47-4.44 (1H, m), 4.25-4.02 (5H, m), 3.95-3.89 (1H, m), 2.70-2.61 (2H, m), 2.54-2.38 (2H, m), 2.19-2.09 (1H, m), 1.86-1.81 (1H, m), 1.64-1.54 (2H, m), 1.41-1.24 (6H, m), 1.26 (3H, t, J=7 Hz), 0.91-0.85 (3H, m).

Example 5

Ethyl 8-[N-(2-heptylphenyl)sulfamoyl]-1,4-dioxaspiro[4.5]dec-6-ene-7-carboxylate (Exemplified compound No. 1-892)

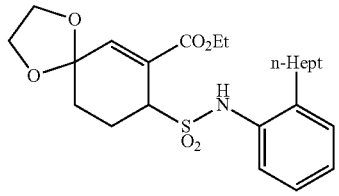

Following the process described in Example (1d), 2-heptylaniline was used in place of 2-chloro-4-fluoroaniline to give the title compound as a pale yellow oil (87% yield).

$^1$H-NMR spectrum (400 MHz, $CDCl_3$) δ ppm: 7.55-7.52 (1H, m), 7.22-7.17 (2H, m), 7.13-7.08 (1H, m), 6.85-6.84 (1H, m), 6.63 (1H, s), 4.47-4.44 (1H, m), 4.25-4.02 (5H, m), 3.95-3.89 (1H, m), 2.69-2.61 (2H, m), 2.54-2.38 (2H, m), 2.19-2.09 (1H, m), 1.86-1.81 (1H, m), 1.64-1.54 (2H, m), 1.42-1.23 (8H, m), 1.26 (3H, t, J=7 Hz), 0.88 (3H, t, J=7 Hz).

Example 6

Ethyl 8-[N-(1H-pyrrol-1-yl)sulfamoyl]-1,4-dioxaspiro[4.5]dec-6-ene-7-carboxylate (Exemplified compound No. 1-1062)

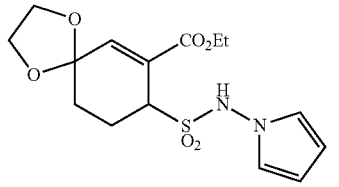

Following the process described in Example (id), 1H-pyrrol-1-ylamine was used in place of 2-chloro-4-fluoroaniline to give the title compound as a white powder (yield: 33%).

Melting point: 115-117° C.

$^1$H-NMR spectrum (400 MHz, $CDCl_3$) δ ppm: 8.05 (1H, s), 6.99 (2H, t, J=2 Hz), 6.94 (1H, s), 6.17 (2H, t, J=2 Hz), 4.55-4.51 (1H, m), 4.30 (2H, q, J=7 Hz), 4.14-4.03 (3H, m), 3.98-3.89 (1H, m), 2.51-2.44 (1H, m), 2.26-2.05 (2H, m), 1.89-1.83 (1H, m), 1.35 (3H, t, J=7 Hz).

Example 7

Ethyl 6-[N-(2-chloro-4-fluorophenyl)sulfamoyl]-3-oxo-1-cyclohexene-1-carboxylate (Exemplified compound No. 1-353)

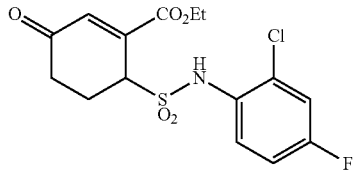

To 2.55 g (6.07 mmol) of ethyl 8-[N-(2-chloro-4-fluorophenyl)sulfamoyl]-1,4-dioxaspiro[4.5]dec-6-ene-7-carboxylate obtained in Example 1 was added 100 ml of a mixed solution of 1N hydrochloric acid-tetrahydrofuran (1:1), and the reaction solution was stirred at room temperature for 64 hours. Tetrahydrofuran was distilled off under reduced pressure, the residue was extracted by addition of ethyl acetate, and the organic layer was washed with water and dried over anhydrous magnesium sulfate, followed by concentration under reduced pressure. The residue was subjected to silica gel column chromatography (solvent; hexane:ethyl acetate=4:1), to give 2.19 g of the title compound as a pale brown powder (yield: 96%).

Melting point: 128-130° C.

$^1$H-NMR spectrum (400 MHz, $CDCl_3$) δ ppm: 7.69 (1H, dd, J=9 Hz, 5 Hz), 7.20 (1H, dd, J=8 Hz, 3 Hz), 7.09-7.03 (1H, m), 6.91 (2H, s), 4.68 (1H, dd, J=5 Hz, 2 Hz), 4.28-4.18 (2H, m), 3.21-3.09 (1H, m), 2.80-2.72 (1H, m), 2.57-2.49 (1H, m), 2.44-2.31 (1H, m), 1.28 (3H, t, J=7 Hz).

Example 8

Ethyl 9-[N-(2-chloro-4-fluorophenyl)sulfamoyl]-1,5-dioxaspiro[5.5]undec-7-ene-8-carboxylate (exemplified compound No. 1-365)

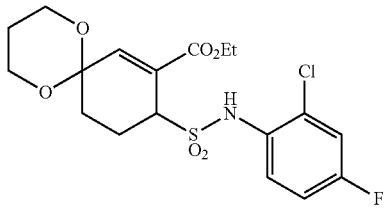

100 mg (0.27 mmol) of ethyl 6-[N-(2-chloro-4-fluorophenyl)sulfamoyl]-3-oxo-1-cyclohexene-1-carboxylate obtained in Example 7 was dissolved in 2 ml of toluene, and 0.04 ml (0.54 mmol) of propane-1,3-diol and 68 mg (0.27 mmol) of pyridinium p-toluenesulfonate were added thereto, followed by heating under reflux for 1 hour. After the reaction solution was cooled to room temperature, a saturated aqueous sodium hydrogencarbonate solution was added and extracted with ethyl acetate. The organic layer was washed with water and dried over anhydrous magnesium sulfate, followed by concentration under reduced pressure. The residue was subjected to silica gel column chromatography (solvent; hexane:ethyl acetate=2:1), and the resulting solid was further washed with hexane to give 60 mg of the title compound as a white powder (yield: 51%).

Melting point: 120-121° C.

$^1$H-NMR spectrum (400 MHz, $CDCl_3$) δ ppm: 7.65 (1H, dd, J=9 Hz, 5 Hz), 7.36 (1H, s), 7.14 (1H, dd, J=8 Hz, 3 Hz), 7.01 (1H, dd, J=7 Hz, 2 Hz), 6.98 (1H, s), 4.45-4.39 (1H, m), 4.27-4.12 (2H, m), 4.11-3.84 (4H, m), 2.46-2.06 (4H, m), 1.92-1.67 (2H, m), 1.28 (3H, t, J=7 Hz).

Example 9

Ethyl 9-[N-(2-chloro-4-fluorophenyl)sulfamoyl]-3,3-dimethyl-1,5-dioxaspiro[5.5]undec-7-ene-8-carboxylate (Exemplified compound No. 1-426)

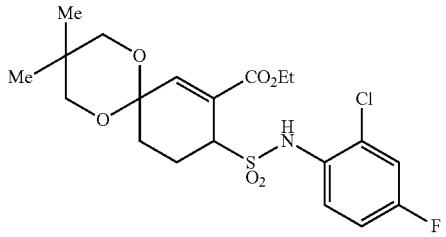

Following the process described in Example 8, 2,2-dimethylpropane-1,3-diol was used in place of propane-1,3-diol to give the title compound as a pale brown oil (yield: 64%).

$^1$H-NMR spectrum (400 MHz, $CDCl_3$) δ ppm: 7.64 (1H, dd, J=9 Hz, 5 Hz), 7.31 (1H, s), 7.13 (1H, dd, J=8 Hz, 3 Hz), 7.04-6.94 (2H, m), 4.45-4.39 (1H, m), 4.27-4.12 (2H, m), 3.69-3.46 (4H, m), 2.42-2.11 (4H, m), 1.28 (3H, t, J=7 Hz), 1.03 (3H, s), 0.97 (3H, s).

Example 10

Ethyl 8-[N-(2-chloro-4-fluorophenyl)sulfamoyl]-1,4-dithiaspiro[4.5]dec-6-ene-7-carboxylate (Exemplified compound No. 1-367)

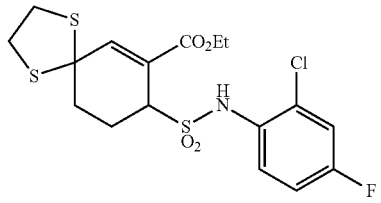

100 mg (0.27 mmol) of ethyl 6-[N-(2-chloro-4-fluorophenyl)sulfamoyl]-3-oxo-1-cyclohexene-1-carboxylate obtained in Example 7 was dissolved in 1 ml of dichloromethane and 0.034 ml (0.405 mmol) of ethane-1,2-dithiol and 0.025 ml (0.203 mmol) of boron trifluoride diethyl etherate were added thereto with stirring under ice-cooling, followed by stirring at room temperature for 1 hour. To the reaction solution was added a 1N aqueous sodium hydroxide solution and the mixture was extracted with diethyl ether. The organic layer was washed with water and dried over anhydrous magnesium sulfate, followed by concentration under reduced pressure. The resulting solid was washed with diethyl ether and then with hexane to give 325 mg of the title compound as a white powder (76% yield).

Melting point: 160-161° C.

$^1$H-NMR spectrum (400 MHz, $CDCl_3$) δ ppm: 7.65 (1H, dd, J=9 Hz, 5 Hz), 7.14 (1H, dd, J=8 Hz, 3 Hz), 7.10 (1H, s), 7.04-6.96 (2H, m), 4.40 (1H, d, J=5 Hz), 4.25-4.10 (2H, m), 3.52-3.26 (4H, m), 2.82-2.72 (1H, m), 2.58-2.50 (1H, m), 2.33-2.24 (1H, m), 2.11-1.99 (1H, m), 1.27 (3H, t, J=7 Hz).

Example 11

Ethyl 9-[N-(2-chloro-4-fluorophenyl)sulfamoyl]-1,5-dithiaspiro[5.5]undec-7-ene-8-carboxylate (Exemplified compound No. 1-368)

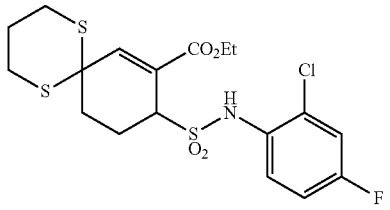

Following the process described in Example 10, propane-1,3-dithiol was used in place of ethane-1,2-dithiol to give the title compound as an amorphous substance (72% yield).

$^1$H-NMR spectrum (400 MHz, $CDCl_3$) δ ppm: 7.65 (1H, dd, J=9 Hz, 5 Hz), 7.40 (1H, s), 7.14 (1H, dd, J=8 Hz, 3 Hz), 7.03-6.96 (1H, m), 6.94 (1H, s), 4.51 (1H, d, J=5 Hz), 4.24-4.11 (2H, m), 3.17-3.07 (1H, m), 2.98-2.77 (3H, m), 2.61-2.51 (1H, m), 2.47-2.38 (1H, m), 2.36-2.27 (1H, m), 2.25-2.13 (1H, m), 2.12-1.95 (2H, m), 1.27 (3H, t, J=7 Hz).

Example 12

Ethyl 8-[N-(2-chloro-4-fluorophenyl)sulfamoyl]-1-oxa-4-thiaspiro[4.5]dec-6-ene-7-carboxylate (Exemplified compound No. 1-371)

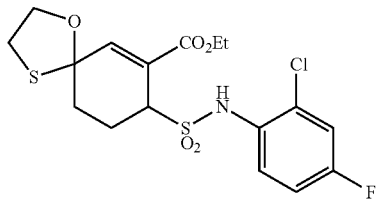

Following the process described in Example 10, 2-mercapteothanol was used in place of ethane-1,2-dithiol to give the title compound as a white powder (61% yield).

Melting point: 133-134° C.

$^1$H-NMR spectrum (400 MHz, $CDCl_3$) δ ppm: 7.65 (1H, dd, J=9 Hz, 5 Hz), 7.14 (1H, dd, J=8 Hz, 3 Hz), 7.06 (0.4H, s), 7.04-6.96 (2.6H, m), 4.46 (0.4H, dd, J=5 Hz, 3 Hz), 4.39-4.01 (4.6H, m), 3.23-3.06 (2H, m), 2.77-2.51 (1.6H, m), 2.45-2.36 (0.4H, m), 2.20-2.00 (2H, m), 1.27 (3H, t, J=7 Hz).

Example 13

Ethyl 8-[N-(2-chloro-4-fluorophenyl)sulfamoyl]-1,1,4,4-tetraoxo-1λ$^6$,4λ$^6$-dithiaspiro[4.5]dec-6-ene-7-carboxylate (Exemplified compound No. 1-369)

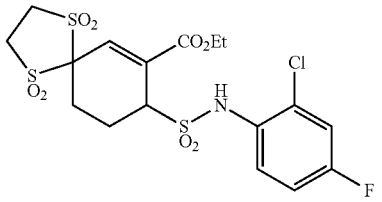

80 mg (0.18 mmol) of ethyl 8-[N-(2-chloro-4-fluorophenyl)sulfamoyl]-1,4-dithiaspiro[4.5]dec-6-ene-7-carboxylate obtained in Example 10 was dissolved in 2 ml of dichloromethane, 91 mg (1.08 mmol) of sodium hydrogencarbonate was added thereto and subsequently 239 mg (0.90 mmol) of m-chloroperbenzoic acid (65%) was added with stirring under ice-cooling, followed by stirring at room temperature for 5 hours. Water was added to the reaction solution and the mixture was extracted with ethyl acetate. The organic layer was washed with water and dried over anhydrous magnesium sulfate, followed by concentration under reduced pressure. The residue was subjected to silica gel thin layer chromatography (solvent; hexane:ethyl acetate=1:1) to give 42 mg of the title compound as a white powder (yield: 45%).

Melting point: 88-90° C.

$^1$H-NMR spectrum (400 MHz, $CDCl_3$) δ ppm: 7.65 (1H, dd, J=9 Hz, 5 Hz), 7.15 (1H, dd, J=8 Hz, 3 Hz), 7.06-6.98 (2H, m), 6.92 (1H, s), 4.57 (1H, d, J=5 Hz), 4.26-4.16 (2H, m), 3.79-3.60 (4H, m), 3.14-2.98 (1H, m), 2.69-2.60 (1H, m), 2.45-2.36 (1H, m), 2.29-2.16 (1H, m), 1.28 (3H, t, J=7 Hz).

Example 14

Ethyl 6-[N-(2-chloro-4-fluorophenyl)sulfamoyl]-1-oxaspiro[2.5]oct-4-ene-5-carboxylate (Exemplified compound No. 1-360)

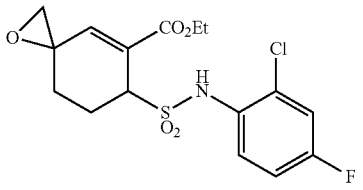

50 mg (0.133 mmol) of ethyl 6-[1-(2-chloro-4-fluorophenyl)sulfamoyl]-3-oxo-1-cyclohexene-1-carboxylate obtained in Example 7 and 0.01 ml (0.146 mmol) of dibromomethane were dissolved in 1 ml of tetrahydrofuran, and 0.18 ml (0.279 mmol) of n-butyllithium/hexane solution (1.58 M) was added dropwise thereto at −78° C., followed by stirring at room temperature for 4 hours. After the reaction solution was cooled with ice, a saturated aqueous ammonium chloride solution was added and the mixture was extracted with ethyl acetate. The organic layer was washed with water and dried over anhydrous magnesium sulfate, followed by concentration under reduced pressure. The residue was subjected to silica gel thin layer chromatography (solvent; hexane:ethyl acetate=2:1) to give 7 mg of the title compound as a yellow oil (yield: 14%).

$^1$H-NMR spectrum (400 MHz, $CDCl_3$) δ ppm: 7.68 (1H, dd, J=9 Hz, 5 Hz), 7.15 (1H, dd, J=8 Hz, 3 Hz), 7.07-6.91 (2H, m), 6.60 (1H, s), 4.50 (1H, d, J=4 Hz), 4.27-4.06 (2H, m), 2.98-2.92 (1H, m), 2.91-2.88 (1H, m), 2.83-2.70 (1H, m), 2.68-2.59 (1H, m), 2.21-2.07 (2H, m), 1.25 (3H, t, J=7 Hz).

Example 15

Ethyl (2S)-8-[N-(2-chloro-4-fluorophenyl)sulfamoyl]-2-hydroxymethyl-1,4-dioxaspiro[4.5]dec-6-ene-7-carboxylate (exemplified compound No. 1-378)

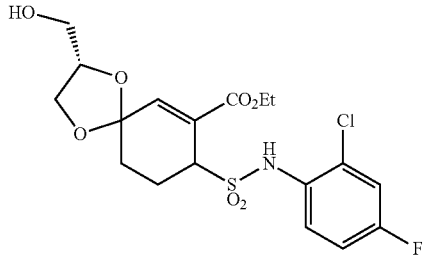

100 mg (0.27 mmol) of ethyl 6-[N-(2-chloro-4-fluorophenyl)sulfamoyl]-3-oxo-1-cyclohexene-1-carboxylate obtained in Example 7 and 69 mg (0.35 mmol) of (R)-2,3-dihydroxypropyl benzoate were dissolved in 2 ml of dichloromethane and 0.19 ml (1.05 mmol) of isopropoxytrimethylsilane and 2 μl (0.014 mmol) of trimethylsilyl trifluoromethanesulfonate were sequentially added thereto with stirring under ice-cooling, followed by stirring at the same temperature for 1 hour. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate 1:1), to give 121 mg of ethyl (2R)-2-benzoyloxymethyl-8-[N-(2-chloro-4-fluorophenyl)sulfamoyl]-1,4-dioxaspiro[4.5]dec-6-ene-7-carboxylate as a pale yellow oil (yield: 81%).

Subsequently, 121 mg (0.22 mmol) of this compound was dissolved in 2 ml of a mixture of methanol-tetrahydrofuran (1:1), and to the solution was added 0.5 ml (0.50 mmol) of 1N aqueous sodium hydroxide with stirring under ice-cooling, followed by stirring at the same temperature for 30 minutes. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=1:1) to give 41 mg of the title compound as an amorphous substance (yield: 41%).

$^1$H-NMR spectrum (400 MHz, $CDCl_3$) δ ppm: 7.64 (1H, dd, J=9 Hz, 5 Hz), 7.14 (1H, dd, J=8 Hz, 3 Hz), 7.06-6.97 (2H, m), 6.89 (0.25H, s), 6.86 (0.25H, s), 6.80 (0.25H, s), 6.78 (0.25H, s), 4.43-4.31 (1.75H, m), 4.26-4.02 (3.25H, m), 3.95-3.87 (0.75H, m), 3.85-3.77 (1H, m), 3.75-3.69 (0.25H, m), 3.68-3.59 (1H, m), 2.65-2.38 (2H, m), 2.25-2.11 (1H, m), 2.11-2.05 (0.25H, m), 2.03-1.97 (0.25H, m), 1.94-1.81 (1.5H, m), 1.26 (3H, t, J=7 Hz).

Example 16

Ethyl (2R)-8-[N-(2-chloro-4-fluorophenyl)sulfamoyl]-2-hydroxymethyl-1,4-dioxaspiro[4.5]dec-6-ene-7-carboxylate (Exemplified compound No. 1-378)

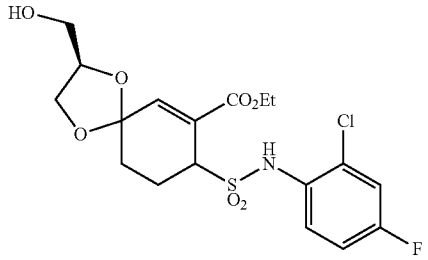

(16a) Ethyl 6-[N-(2-chloro-4-fluorophenyl)sulfamoyl]-3,3-dimethoxy-1-cyclohexene-1-carboxylate 6.1 g (16.2 mmol) of ethyl 6-[N-(2-chloro-4-fluorophenyl)sulfamoyl]-3-oxo-1-cyclohexene-1-carboxylate obtained in Example 7 was dissolved in 120 ml of methanol and 4.1 g (16.2 mmol) of pyridinium p-toluenesulfonate and 8.86 ml (81.0 mmol) of trimethoxymethane were sequentially added thereto with stirring under ice-cooling, followed by stirring overnight at room temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=2:1) to give 6.0 g of the title compound as a white powder (yield: 88%).

Melting point: 97-98° C.

$^1$H-NMR spectrum (400 MHz, $CDCl_3$) δ ppm: 7.65 (1H, dd, J=9 Hz, 5 Hz), 7.14 (1H, dd, J=8 Hz, 3 Hz), 7.07-6.97 (3H, m), 4.41 (1H, d, J=4 Hz), 4.28-4.12 (2H, m), 3.29 (3H, s), 3.23 (3H, s), 2.47-2.38 (1H, m), 2.31-2.21 (1H, m), 2.18-2.06 (1H, m), 2.01-1.93 (1H, m), 1.28 (3H, t, J=7 Hz).

(16b) Ethyl (2R)-8-[N-(2-chloro-4-fluorophenyl)sulfamoyl]-2-hydroxymethyl-1,4-dioxaspiro[4.5]dec-6-ene-7-carboxylate 342 mg (0.81 mmol) of ethyl 6-[N-(2-chloro-4-fluorophenyl)sulfamoyl]-3,3-dimethoxy-1-cyclohexen-1-carboxylate obtained in (16a) and 206 mg (1.05 mmol) of (S)-2,3-dihydroxypropyl benzoate were dissolved in 7 ml of dichloromethane, and 0.56 ml (3.15 mmol) of isopropoxytrimethylsilane and 7 μl (0.041 mmol) of trimethylsilyl trifluoromethanesulfonate were added thereto sequentially with stirring under ice-cooling, followed by stirring for 1 hour at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=1:1), to give 410 mg of ethyl (2S)-2-benzoyloxymethyl-8-[N-(2-chloro-4-fluorophenyl)sulfamoyl]-1,4-dioxaspiro[4.5]dec-6-ene-7-carboxylate as a colorless oil (yield: 91%).

Subsequently, 410 mg (0.74 mmol) of this compound was dissolved in 10 ml of a mixture of methanol-tetrahydrofuran (1:1) and 3 ml (3.0 mmol) of 1N aqueous sodium hydroxide was added thereto, followed by stirring for 15 minutes at room temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=1:1) to give 293 mg of the title compound as an amorphous substance (yield: 88%).

$^1$H-NMR spectrum (400 MHz, $CDCl_3$) δ ppm: 7.64 (1H, dd, J=9 Hz, 5 Hz), 7.14 (1H, dd, J=8 Hz, 3 Hz), 7.04-6.95 (2H, m), 6.89 (0.42H, s), 6.86 (0.02H, s), 6.80 (0.02H, s), 6.78 (0.42H, s), 4.43-4.31 (1.5H, m), 4.26-4.02 (2.5H, m), 3.96-3.89 (1H, m), 3.83-3.77 (0.5H, m), 3.75-3.69 (0.5H, m), 3.68-3.59 (1H, m), 2.65-2.41 (2H, m), 2.25-2.10 (1H, m), 1.93-1.82 (1H, m), 1.77-1.67 (0.5H, br. s), 1.58 (0.5H, br. s), 1.26 (3H, t, J=7 Hz).

Example 17

Ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate (Exemplified compound No. 1-382)

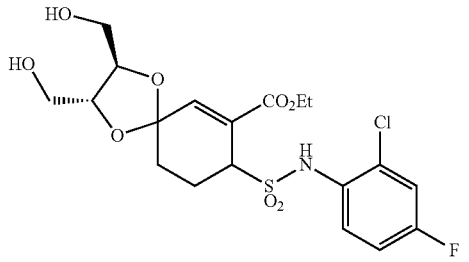

Following the process described in Example (16b), 1,4-di-O-benzoyl-D-threitol was used in place of (S)-2,3-dihydroxypropyl benzoate to give the title compound as an amorphous substance (yield: 44%).

<Alternative Procedure>

(17a) Ethyl (2R,3R)-2,3-bis(benzoyloxymethyl)-8-[N-(2-chloro-4-fluorophenyl)sulfamoyl]-1,4-dioxaspiro[4.5]dec-6-ene-7-carboxylate 1.46 g (3.08 mmol) of 1,4-di-O-benzoyl-2,3-di-O-trimethylsilyl-D-threitol obtained in Reference Example 18 was suspended in 2 ml of acetonitrile, and 0.04 ml (0.24 mmol) of trimethylsilyl trifluoromethanesulfonate and a solution of 1.00 g (2.37 mmol) of ethyl 6-[N-(2-chloro-4-fluorophenyl) sulfamoyl]-3,3-dimethoxy-1-cyclohexene-1-carboxylate obtained in Example (16a) in 5 ml of acetonitrile were sequentially added thereto with stirring under ice-cooling, followed by stirring for 1 hour at the same temperature. The reaction solution was concentrated under reduced pressure, and the residue was subjected to silica gel column chromatography (solvent; hexane:ethyl acetate=2:1) to give 1.50 g of the title compound as a pale yellow powder (yield: 92%).

$^1$H-NMR spectrum (400 MHz, $CDCl_3$) δ ppm: 8.10-8.04 (4H, m), 7.68-7.57 (3H, m), 7.49-7.44 (4H, m), 7.16 (1H, dt, J=8.0 Hz, 2.6 Hz), 7.05-7.00 (2H, m), 6.87 (1H, d, J=14.0 Hz), 4.66-4.07 (9H, m), 2.63-2.44 (2H, m), 2.25-2.19 (1H, m), 1.94 (1H, t, J=15.2 Hz), 1.19 (3H, t, J=7.0 Hz).

(17b) Ethyl (2R,3R)-8-[N-(2-chloro-4-fluorophenyl) sulfamoyl]-2,3-bis(hydroxymethyl)-1,4-dioxaspiro [4.5]dec-6-ene-7-carboxylate 1.50 g (2.18 mmol) of ethyl (2R,3R)-2,3-bis(benzoyloxymethyl)-8-[N-(2-chloro-4-fluorophenyl)sulfamoyl]-1,4-dioxaspiro[4.5]dec-6-ene-7-carboxylate obtained in (17a) was dissolved in 10 ml of a mixture of methanol-tetrahydrofuran (4:1), and 10 ml (10.0 mmol) of 1N aqueous sodium hydroxide was added thereto with stirring under ice-cooling, followed by stirring for 15 minutes at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=1:1) to give 900 mg of the title compound as a white amorphous substance (yield: 86%).

$^1$H-NMR spectrum (400 MHz, $CDCl_3$) δ ppm: 7.69-7.64 (1H, m), 7.16 (1H, dd, J=8 Hz, 3 Hz), 7.05-6.99 (2H, m), 6.91-6.90 (0.5H, m), 6.85-6.84 (0.5H, m), 4.43-4.41 (1H, m), 4.27-4.09 (3.5H, m), 4.05-4.01 (0.5H, m), 3.93-3.81 (2H, m), 3.75-3.69 (2H, m), 2.59-2.45 (2H, m), 2.23-1.50 (4H, m), 1.29-1.24 (3H, m).

Example 18

Ethyl (2S,3S)-8-[N-(2-chloro-4-fluorophenyl)sulfamoyl]-2,3-bis(hydroxymethyl)-1,4-dioxaspiro[4.5]dec-6-ene-7-carboxylate (Exemplified compound No. 1-382)

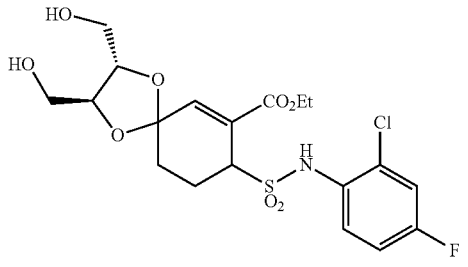

Following the process described in Example (16b), 1,4-di-O-benzoyl-L-threitol was used in place of (S)-2,3-dihydroxypropyl benzoate to give the title compound as an amorphous substance (34% yield).

<Alternative Procedure>

Following the process described in Example 17 (alternative procedure), 1,4-di-O-benzoyl-2,3-di-O-trimethylsilyl-L-threitol obtained in Reference Example 19 was used in place of 1,4-di-o-benzoyl-2,3-di-o-trimethylsilyl-D-threitol to give the title compound as an amorphous substance (yield: 73%).

$^1$H-NMR spectrum (400 MHz, $CDCl_3$) δ ppm: 7.69-7.64 (1H, m), 7.16 (1H, dd, J=8 Hz, 3 Hz), 7.05-6.99 (2H, m), 6.91-6.90 (0.5H, m), 6.85-6.84 (0.5H, m), 4.43-4.41 (1H, m)

4.27-4.09 (3.5H, m), 4.05-4.01 (0.5H, m), 3.93-3.81 (2H, m), 3.75-3.69 (2H, m), 2.59-2.45 (2H, m), 2.23-1.50 (4H, m), 1.29-1.24 (3H, m).

Example 19

Ethyl 8-[N-(2-chloro-4-fluorophenyl)sulfamoyl]-meso-2,3-bis(hydroxymethyl)-1,4-dioxaspiro[4.5]dec-6-ene-7-carboxylate (Exemplified compound No. 1-382)

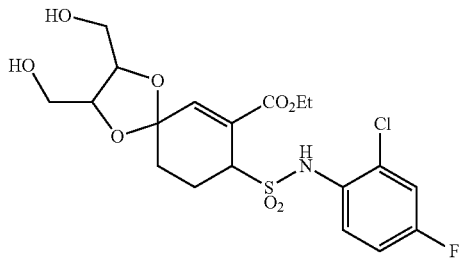

200 mg (0.47 mmol) of ethyl 6-[N-(2-chloro-4-fluorophenyl)sulfamoyl]-3,3-dimethoxy-1-cyclohexene-1-carboxylate obtained in Example (16a) and 290 mg (0.61 mmol) of 1,4-di-O-benzoyl-2,3-di-O-trimethylsilyl-meso-erythritol obtained in Reference Example 1 were dissolved in 4 ml of dichloromethane and 4 μl (0.024 mmol) of trimethylsilyl trifluoromethanesulfonate was added thereto with stirring under ice-cooling, followed by stirring for 1 hour at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=2:1) to give 171 mg of ethyl meso-2,3-bis[(benzoyloxy)methyl]-8-[N-(2-chloro-4-fluorophenyl)sulfamoyl]-1,4-dioxaspiro[4.5]dec-6-ene-7-carboxylate as an amorphous substance (yield: 53%).

Subsequently, 170 mg (0.25 mmol) of this compound was dissolved in 10 ml of a mixture of methanol-tetrahydrofuran (1:1), and 3 ml (3.0 mmol) of 1N aqueous sodium hydroxide was added thereto with stirring under ice-cooling, followed by stirring for 15 minutes at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane: ethyl acetate=1:3) to give 105 mg of the title compound as an amorphous substance (yield: 89%).

$^1$H-NMR spectrum (400 MHz, $CDCl_3$) δ ppm: 7.64 (1H, dd, J=9 Hz, 5 Hz), 7.15 (1H, dd, J=8 Hz, 3 Hz), 7.04-6.95 (2H, m), 6.93 (0.4H, s), 6.72 (0.6H, s), 4.49-4.33 (2.4H, m), 4.32-4.26 (0.6H, m), 4.25-4.07 (2H, m), 3.93-3.70 (4H, m), 2.69-2.58 (0.4H, m), 2.58-2.35 (3.6H, m), 2.24-2.09 (1H, m), 1.99-1.91 (0.6H, m), 1.90-1.83 (0.4H, m), 1.27 (3H, t, J=7 Hz).

Example 20

Ethyl (2R)-8-[N-(2-chloro-4-fluorophenyl)sulfamoyl]-2-((1R)-1,2-dihydroxyethyl)-1,4-dioxaspiro[4.5]dec-6-ene-7-carboxylate (Exemplified compound No. 1-390)

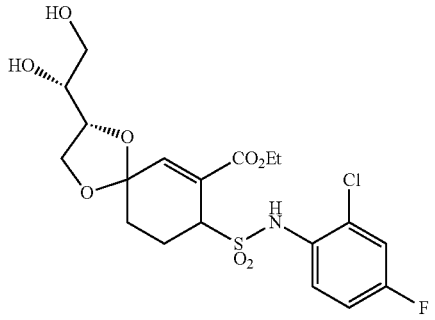

300 mg (0.71 mmol) of ethyl 6-[N-(2-chloro-4-fluorophenyl)sulfamoyl]-3,3-dimethoxy-1-cyclohexene-1-carboxylate obtained in Example (16a) and 436 mg (1.42 mmol) of (4R,5R)-2,2-dimethyl-4,5-bis[(trimethylsilyl)oxy]methyl [1.3]dioxolane were dissolved in 12 ml of dichloromethane and 26 μl (0.142 mmol) of trimethylsilyl trifluoromethanesulfonate was added thereto with stirring under ice-cooling, followed by stirring for 90 hours at room temperature. Saturated aqueous sodium hydrogencarbonate was added to the reaction solution and the mixture was extracted with dichloromethane. The organic layer was washed with water and dried over anhydrous magnesium sulfate, followed by concentration under reduced pressure. The residue was subjected to silica gel column chromatography (solvent; hexane:ethyl acetate=4:1) to give 90 mg of ethyl (2R)-8-[N-(2-chloro-4-fluorophenyl)sulfamoyl]-2-((4R)-2,2-dimethyl[1.3]dioxolan-4-yl)-1,4-dioxaspiro[4.5]dec-6-ene-7-carboxylate as an amorphous substance (yield: 24%).

Subsequently, to 85 mg (0.163 mmol) of this compound was added 4 ml of a mixture of acetic acid-water (1:1), followed by stirring overnight at room temperature. The reaction solution was neutralized with addition of saturated aqueous sodium hydrogencarbonate, and the mixture was then extracted with ethyl acetate. The organic layer was washed with water and dried over anhydrous magnesium sulfate, followed by concentration under reduced pressure. The residue was subjected to silica gel column chromatography (solvent; ethyl acetate alone) to give 46 mg of the title compound as an amorphous substance (yield: 59%).

$^1$H-NMR spectrum (400 MHz, $CDCl_3$) δ ppm: 7.69-7.64 (1H, m), 7.19-7.15 (1H, m), 7.06-6.98 (2H, m), 6.89-6.80 (1H, m), 4.43-4.41 (1H, m), 4.38-4.08 (4H, m), 4.03-3.95 (0.7H, m), 3.86 (0.3H, t, J=8 Hz), 3.77-3.63 (3H, m), 2.67-2.37 (3H, m), 2.22-1.84 (3H, m), 1.30-1.25 (3H, m).

Example 21

Ethyl (2R)-8-[N-(2-chloro-4-fluorophenyl)sulfamoyl]-2-((2R)-1,2,3-trihydroxypropyl)-1,4-dioxaspiro[4.5]dec-6-ene-7-carboxylate (Exemplified compound No. 1-394)

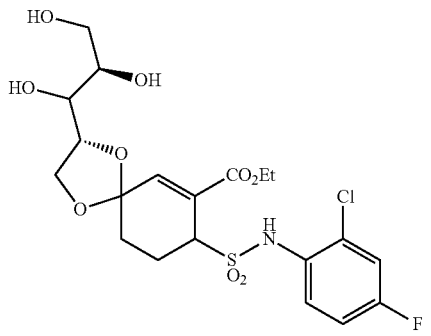

547 mg (1.07 mmol) of 1,3,4,5,7-penta-O-trimethylsilyl-D-arabitol obtained in Reference Example 2 was dissolved in 3 ml of nitromethane, to the resulting solution was added 13 μl (0.007 mmol) of trimethylsilyl trifluoromethanesulfonate and was then added 300 mg (0.71 mmol) of ethyl 6-[N-(2-chloro-4-fluorophenyl)sulfamoyl]-3,3-dimethoxy-1-cyclohexene-1-carboxylate obtained in Example (16a) with stirring under ice-cooling, followed by stirring for 1 hour at the same temperature. A saturated aqueous sodium hydrogencarbonate was added to the reaction solution and the mixture was extracted with dichloromethane. The organic layer was washed with water and dried over anhydrous magnesium sulfate, followed by concentration under reduced pressure. The residue was subjected to silica gel column chromatography (solvent; ethyl acetate alone) to give 151 mg of the title compound as an amorphous substance (yield: 42%).

$^1$H-NMR spectrum (400 MHz, $CDCl_3$) δ ppm: 7.66 (1H, dd, J=9 Hz, 5 Hz), 7.19-7.15 (1H, m), 7.10-6.99 (2H, m), 6.86 (0.5H, s), 6.82-6.80 (0.5H, m), 4.42-4.39 (1H, m), 4.28-3.65 (9H, m), 3.20-1.40 (3H, br), 2.57-2.43 (2H, m), 2.23-2.09 (1H, m), 1.92-1.82 (1H, m), 1.29-1.25 (3H, m).

Example 22

Ethyl (2R)-8-[N-(2-chloro-4-fluorophenyl)sulfamoyl]-2-((1S,2R,3R)-1,2,3,4-tetrahydroxybutyl)-1,4-dioxaspiro[4.5]dec-6-ene-7-carboxylate (Exemplified compound No. 1-398)

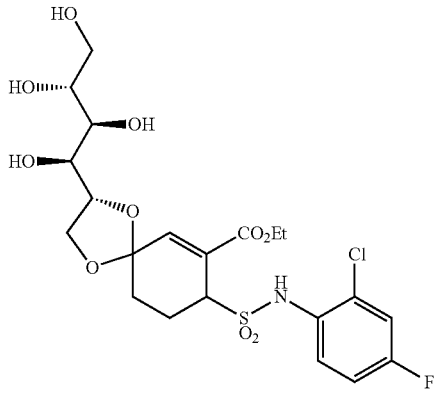

200 mg (0.47 mmol) of ethyl 6-[N-(2-chloro-4-fluorophenyl)sulfamoyl]-3,3-dimethoxy-1-cyclohexene-1-carboxylate obtained in Example (16a) and 434 mg (0.71 mmol) of 1,2,3,4,5,6-hexa-O-trimethylsilyl-D-mannitol were dissolved in 4 ml of dichloromethane, to the resulting solution were added sequentially 0.12 ml (0.47 mmol) of isopropoxytrimethylsilane and 4 μl (0.024 mmol) of trimethylsilyl trifluoromethanesulfonate with stirring under ice-cooling, followed by stirring overnight at room temperature. Saturated aqueous sodium hydrogencarbonate was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; dichloromethane: methanol=10:1) to give 130 mg of the title compound as an amorphous substance (yield: 51%).

$^1$H-NMR spectrum (400 MHz, $CDCl_3$) δ ppm: 7.62 (1H, dd, J=9 Hz, 5 Hz), 7.22-7.12 (2H, m), 7.04-6.96 (1H, m), 6.88-6.84 (0.2H, m), 6.80-6.77 (0.4H, m), 6.76 (0.4H, s), 4.41-4.31 (1H, m), 4.25-4.03 (4H, m), 3.98-3.63 (6H, m), 2.54-2.41 (2H, m), 2.22-2.08 (1H, m), 1.92-1.81 (1H, m), 1.26 (3H, t, J=7 Hz).

Example 23

Ethyl (2R,3R)-8-[N-(2-chloro-4-fluorophenyl)sulfamoyl]-2,3-bis((1R)-1,2-dihydroxyethyl)-1,4-dioxaspiro[4.5]dec-6-ene-7-carboxylate (Exemplified compound No. 1-386)

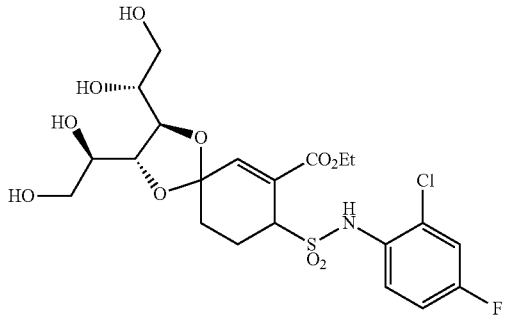

Following the process described in Example 19, 1,6-di-O-benzoyl-2,3,4,5-tetra-O-trimethylsilyl-D-mannitol obtained in Reference Example 3 was used in place of 1,4-di-O-benzoyl-2,3-di-O-trimethylsilyl-meso-erythritol to give the title compound as a white powder (yield: 11%).

Melting point: 55-56° C.

$^1$H-NMR spectrum (400 MHz, $CDCl_3$) δ ppm: 7.65 (1H, dd, J=9 Hz, 5 Hz), 7.20-7.13 (2H, m), 7.06-7.00 (1H, m), 6.80 (0.5H, s), 6.78 (0.5H, s), 4.38 (1H, d, J=5 Hz), 4.26-4.00 (5H, m), 3.98-3.88 (1.5H, m), 3.87-3.65 (5.5H, m), 2.78-2.56 (2H, m), 2.55-2.40 (2H, m), 2.23-2.09 (1H, m), 1.92-1.80 (1H, m), 1.26 (3H, t, J=7 Hz).

Example 24

Ethyl 9-[N-(2-chloro-4-fluorophenyl)sulfamoyl]-3-hydroxy-1,5-dioxaspiro[5.5]undec-7-ene-8-carboxylate (exemplified compound No. 1-418)

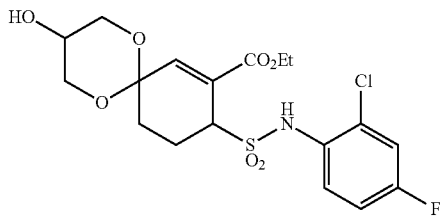

Following the process described in Example 19, 2-trimethylsilyloxy-1-trimethylsilyloxymethylethyl adamantan-1-carboxylate obtained in Reference Example 4 was used in place of 1,4-di-O-benzoyl-2,3-di-O-trimethylsilyl-meso-erythritol to give the title compound as an amorphous substance (yield: 17%).

$^1$H-NMR spectrum (400 MHz, $CDCl_3$) δ ppm: 7.69-7.64 (1H, m), 7.52-7.51 (0.5H, m), 7.18-7.15 (1H, m), 7.08-6.99 (2.5H, m), 4.45-4.42 (1H, m), 4.31-4.05 (4H, m), 3.88-3.74 (2H, m), 3.72-3.63 (1H, m), 2.78-2.52 (1H, br), 2.48-1.97 (4H, m), 1.31-1.26 (3H, m).

Example 25

Ethyl 12-[N-(2-chloro-4-fluorophenyl)sulfamoyl]-2,4,8,5-tetraoxadispiro[5.2.5.2]hexadec-10-ene-11-carboxylate (Exemplified compound No. 1-434)

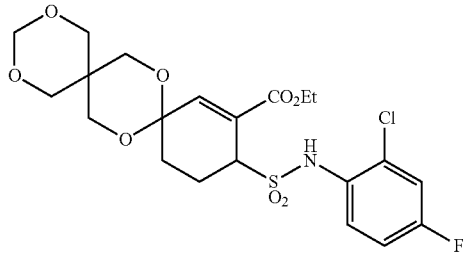

100 mg (0.266 mmol) of ethyl 6-[N-(2-chloro-4-fluorophenyl)sulfamoyl]-3-oxo-1-cyclohexene-1-carboxylate obtained in Example 7 and 156 mg (0.532 mmol) of 5,5-bis[(trimethylsilyl)oxy]methyl[1.3]dioxane were dissolved in 2 ml of dichloromethane and 10 μl (0.053 mmol) of trimethylsilyl trifluoromethanesulfonate was added thereto at −78° C., followed by stirring for 30 minutes at the same temperature and then for 2 hours at room temperature. Saturated aqueous sodium hydrogencarbonate was added to the reaction solution and the mixture was extracted with dichloromethane. The organic layer was washed with water and dried over anhydrous magnesium sulfate, followed by concentration under reduced pressure. The residue was subjected to silica gel column chromatography (solvent; hexane:ethyl acetate=2:1) and the resulting solid was further washed with isopropyl ether to give 49 mg of the title compound as a white powder (yield: 52%).

Melting point: 156-157° C.

$^1$H-NMR spectrum (400 MHz, $CDCl_3$) δ ppm: 7.66 (1H, dd, J=9 Hz, 5 Hz), 7.17 (1H, dd, J=8 Hz, 3 Hz), 7.05-6.98 (2H, m), 4.83 (1H, d, J=6 Hz), 4.78 (1H, d, J=6 Hz), 4.44-4.42 (1H, m), 4.29-4.14 (2H, m), 3.87-3.70 (8H, m), 2.44-2.38 (1H, m), 2.32-2.24 (1H, m), 2.18-2.08 (2H, m), 1.28 (3H, t, J=7 Hz).

Example 26

Ethyl 3-acetylamino-9-[N-(2-chloro-4-fluorophenyl)sulfamoyl]-1,5-dioxaspiro[5.5]undec-7-ene-8-carboxylate (Exemplified compound No. 1-422)

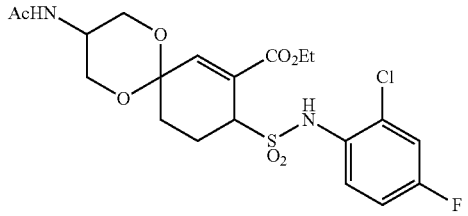

500 mg (1.19 mmol) of ethyl 6-[N-(2-chloro-4-fluorophenyl)sulfamoyl]-3,3-dimethoxy-1-cyclohexene-1-carboxylate obtained in Example (16a) and 205 mg (1.54 mmol) of N-(2-hydroxy-1-hydroxymethylethyl)acetamide were dissolved in 20 ml of dichloromethane, and 0.84 ml (4.74 mmol) of isopropoxytrimethylsilane and 43 μl (0.24 mmol) of trimethylsilyl trifluoromethanesulfonate were added sequentially with stirring under ice-cooling, followed by stirring for 30 minutes at the same temperature, and further for 66 hours at room temperature. Saturated aqueous sodium hydrogencarbonate was added to the reaction solution and the mixture was extracted with dichloromethane. The organic layer was washed with water and dried over anhydrous magnesium sulfate, followed by concentration under reduced pressure. The residue was subjected to silica gel column chromatography (solvent; ethyl acetate methanol=39:1) to give 288 mg of the title compound as an amorphous substance (yield: 50%).

$^1$H-NMR spectrum (400 MHz, $CDCl_3$) δ ppm: 7.66 (1H, dd, J=9 Hz, 5 Hz), 7.62-7.60 (0.5H, m), 7.17 (1H, dd, J=8 Hz, 3 Hz), 7.05-6.99 (2H, m), 6.93-6.91 (0.5H, m), 6.35 (1H, br.d, J=8 Hz), 4.46-4.42 (1H, m), 4.35-4.11 (4H, m), 4.03-3.95

(1H, m), 3.82-3.70 (2H, m), 2.60-2.55 (0.5H, m), 2.48-2.01 (3H, m), 2.06 (3H, s), 1.95-1.90 (0.5H, m), 1.30 (3H, t, J=7 Hz).

Example 27

Ethyl 9-[N-(2-chloro-4-fluorophenyl)sulfamoyl]-3,3-bis(hydroxymethyl)-1,5-dioxaspiro[5.5]undec-7-ene-8-carboxylate (Exemplified compound No. 1-430)

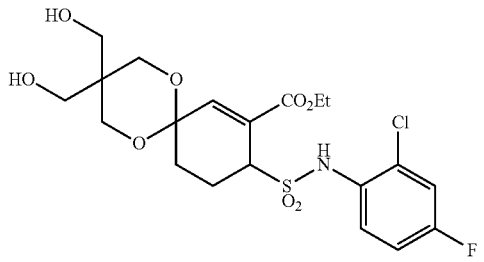

500 mg (1.19 mmol) of ethyl 6-[N-(2-chloro-4-fluorophenyl)sulfamoyl]-3,3-dimethoxy-1-cyclohexene-1-carboxylate obtained in Example (16a) and 1.0 g (2.38 mmol) of 1,3-bis[(trimethylsilyl)oxy]-2,2-bis[(trimethylsilyl)oxy]methylpropane were dissolved in 10 ml dichloromethane and 10 μl (0.06 mmol) of trimethylsilyl trifluoromethanesulfonate was added thereto with stirring under ice-cooling, followed by stirring for 2 hours at the same temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; ethyl acetate alone) to give 510 mg of the title compound as an amorphous substance (yield: 87%).

$^1$H-NMR spectrum (400 MHz, $CDCl_3$) δ ppm: 7.66 (1H, dd, J=9 Hz, 5 Hz), 7.28 (1H, s), 7.17 (1H, dd, J=8 Hz, 3 Hz), 7.11 (1H, s), 7.07-6.98 (1H, m), 4.42 (1H, d, J=4 Hz), 4.30-4.10 (2H, m), 3.92-3.68 (8H, m), 2.54-2.36 (3H, m), 2.34-2.23 (1H, m), 2.21-2.07 (2H, m), 1.28 (3H, t, J=7 Hz).

Example 28

Triethyl 9-[N-(2-chloro-4-fluorophenyl)sulfamoyl]-1,5-dioxaspiro[5.5]undec-7-ene-3,3,8-tricarboxylate (Exemplified compound No. 1-438)

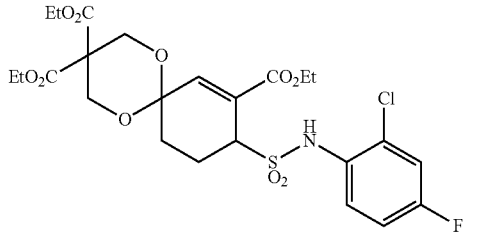

Following the process described in Example 27, diethyl 2,2-bis[(trimethylsilyl)oxy]methylmalonate obtained in Reference Example 5 was used in place of 1,3-bis[(trimethylsilyl)oxy]-2,2-bis[(trimethylsilyl)oxy]methylpropane to give the title compound as an amorphous substance (yield: 42%).

$^1$H-NMR spectrum (400 MHz, $CDCl_3$) δ ppm: 7.65 (1H, dd, J=9 Hz, 5 Hz), 7.23-7.21 (1H, m), 7.16 (1H, dd, J=8 Hz, 3 Hz), 7.04-6.99 (1H, m), 6.97 (1H, s), 4.43-4.36 (3H, m), 4.31-4.13 (8H, m), 2.44-2.37 (1H, m), 2.33-2.25 (1H, m), 2.19-2.06 (2H, m), 1.283 (3H, t, J=7 Hz), 1.280 (6H, t, J=7 Hz).

Example 29

Ethyl 6-[N-(2-chloro-4-fluorophenyl)sulfamoyl]spiro[2.5]oct-4-ene-5-carboxylate (Exemplified compound No. 1-355)

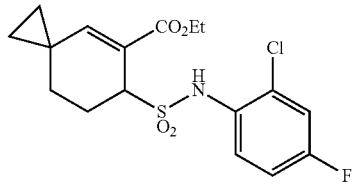

(29a) Ethyl 3-[1-(2-ethoxycarbonylethyl)cyclopropyl]propionate 24.5 ml (24.5 mmol) of 1.0 M diethyl zinc/hexane solution was added to 30 ml of dichloromethane, and then a solution of 1.89 ml (24.5 mmol) of trifluoroacetic acid in 10 ml of dichloromethane was added with stirring under ice-cooling. The reaction solution was stirred for 20 minutes at the same temperature, then a solution of 1.97 ml (24.5 mmol) of diiodomethane in 10 ml of dichloromethane was added and stirred for 20 minutes, and 1.40 g (6.13 mmol) of a solution of diethyl 4-methyleneheptanedicarboxylate (compound described in J.A.C.S. 107, 13, 3981-3997 (1985)) in 10 ml of dichloromethane was further added. After the reaction solution was stirred for 6 hours at room temperature, ice water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane: ethyl acetate=5:1) to give 1.48 g of the title compound as a brown oil (yield: 99%).

$^1$H-NMR spectrum (400 MHz, $CDCl_3$) δ ppm: 4.10 (2H, q, J=7 Hz), 3.37-2.31 (4H, m), 1.60-1.53 (4H, m), 1.25 (6H, t, J=7 Hz), 0.31 (4H, s).

(29b) Ethyl 6-hydroxyspiro[2.5]oct-5-ene-5-carboxylate 1.46 g (6.03 mmol) of ethyl 3-[1-(2-ethoxycarbonylethyl)cyclopropyl]propionate obtained in (29a) was dissolved in 60 ml of tetrahydrofuran and 1.35 g (12.1 mmol) of potassium t-butoxide was added thereto, followed by stirring for 1 hour at room temperature. The reaction solution was cooled with ice and made acidic by addition of 1N hydrochloric acid, and the mixture was extracted with ethyl acetate. The organic layer was washed with water and dried over anhydrous magnesium sulfate, followed by concentration under reduced pressure. The residue was subjected to silica gel column chromatography (solvent; ethyl acetate alone) to give 1.05 g of the title compound as a yellow oil (yield: 89%).

$^1$H-NMR spectrum (400 MHz, $CDCl_3$) δ ppm: 12.23 (0.7H, s), 4.26-4.09 (2H, m), 3.50 (0.3H, dd, J=10 Hz, 6 Hz), 2.57-2.42 (0.7H, m), 2.36 (2H, t, J=6 Hz), 2.03-1.94 (0.3H, m), 1.66-1.52 (1H, m), 1.48 (2H, t, J=6 Hz), 1.28 (3H, J=7 Hz), 0.60-0.30 (4H, m).

(29c) Ethyl 6-trifluoromethanesulfonyloxyspiro[2.5]oct-5-ene-5-carboxylate 1.05 g (5.35 mmol) of ethyl 6-hydroxyspiro[2.5]oct-5-ene-5-carboxylate obtained in (29b) was dissolved in 30 ml of dichloromethane, and 0.99 ml (5.89 mmol) of diisopropylethylamine and 1.40 ml (8.03 mmol) of trifluoromethanesulfonic anhydride were added sequentially with stirring at −78° C. After the reaction solution was stirred for 3 hours at the same temperature, it was warmed to room temperature. The reaction solution was poured into saturated aqueous sodium hydrogencarbonate and the mixture was extracted with ethyl acetate. The organic layer was washed with water and dried over anhydrous magnesium sulfate, followed by concentration under reduced pressure. The residue was subjected to silica gel column chromatography (solvent; ethyl acetate alone) to give 1.56 g of the title compound as a brown oil (yield: 89%).

$^1$H-NMR spectrum (400 MHz, $CDCl_3$) δ ppm: 4.26 (2H, q, J=7 Hz), 2.57-2.46 (2H, m), 2.35-2.29 (2H, m), 1.60-1.53 (2H, m), 1.32 (3H, t, J=7 Hz), 0.49-0.40 (4H, m).

(29d) Ethyl 6-mercaptospiro[2.5]oct-5-ene-5-carboxylate

Following the process described in Example (1a), ethyl 6-trifluoromethanesulfonyloxyspiro[2.5]oct-5-ene-5-carboxylate obtained in (29c) was used in place of ethyl 8-trifluoromethanesulfonyloxy-1,4-dioxaspiro[4.5]dec-7-ene-7-carboxylate to give ethyl 6-acetylsulfanylspiro[2.5]oct-5-ene-5-carboxylate as a pale yellow oil (yield: 58%).

Subsequently, 700 mg (2.75 mmol) of this compound was dissolved in 14 ml of ethanol, and 2.75 ml (11 mmol) of 4N hydrogen chloride/dioxane solution was added thereto with stirring under ice-cooling, followed by stirring for 4 hours at room temperature. The reaction solution was concentrated under reduced pressure, and the residue was subjected to silica gel column chromatography (solvent; hexane:ethyl acetate=10:1), to give 300 mg of the title compound as a pale yellow oil (yield: 51%).

$^1$H-NMR spectrum (400 MHz, $CDCl_3$) δ ppm: 4.19 (2H, q, J=7 Hz), 4.12 (1H, s), 2.57 (2H, t, J=6 Hz), 2.22-2.18 (2H, m), 1.46 (2H, t, J=6 Hz), 1.29 (3H, t, J=7 Hz), 0.40-0.33 (4H, m).

(29e) Ethyl 6-(chlorosulfonyl)spiro[2.5]oct-5-ene-5-carboxylate 7 ml of acetic acid was added to 651 mg (4.23 mmol) of sodium perborate tetrahydrate, the mixture was heated to 50° C., and a solution of 300 mg (1.41 mmol) of ethyl 6-mercaptospiro[2.5]oct-5-ene-5-carboxylate obtained in (29d) in 3 ml of acetic acid was added thereto, followed by stirring for 2 hours at the same temperature and further for 3 hours at 80° C. The reaction solution was cooled to room temperature and concentrated under reduced pressure. 5 ml of thionyl chloride was added to the residue, and the mixture was heated under reflux for 2 hours. The reaction solution was cooled to room temperature again and concentrated under reduced pressure. Ice water was added to the residue and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=5:1 to give 195 mg of the title compound as a colorless oil (yield: 50%).

$^1$H-NMR spectrum (400 MHz, $CDCl_3$) δ ppm: 4.28 (2H, q, J=7 Hz), 2.77-2.69 (2H, m), 2.43-2.38 (2H, m), 1.62 (2H, t, J=6 Hz), 1.33 (3H, t, J=7 Hz), 0.52-0.46 (4H, m).

(29f) Ethyl 6-[N-(2-chloro-4-fluorophenyl)sulfamoyl]spiro[2.5]oct-4-ene-5-carboxylate Following the process described in Example (1d), ethyl 6-(chlorosulfonyl)spiro[2.5]oct-5-ene-5-carboxylate obtained in (29e) was used in place of ethyl 8-chlorosulfonyl-1,4-dioxaspiro[4.5]dec-7-ene-7-carboxylate to give the title compound as a white powder (yield: 17%).

Melting point: 125-126° C.

$^1$H-NMR spectrum (400 MHz, $CDCl_3$) δ ppm: 7.69 (1H, dd, J=9 Hz, 5 Hz), 7.13 (1H, dd, J=8 Hz, 3 Hz), 7.03-6.96 (2H, m), 6.58 (1H, s), 4.53 (1H, d, J=5 Hz), 4.20-4.04 (2H, m), 2.62-2.50 (2H, m), 1.98-1.85 (1H, m), 1.23 (3H, t, J=7 Hz), 1.22-1.13 (1H, m), 1.09-0.99 (2H, m), 0.93-0.80 (2H, m).

Example 30

Ethyl 8-[N-(2-chloro-4-fluorophenyl)sulfamoyl]-1-oxaspiro[4.5]dec-6-ene-7-carboxylate (low polarity diastereomer), (high polarity diastereomer) (Exemplified compound No. 1-362)

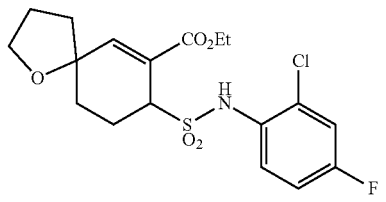

(30a) 7-(1,3-Dioxan-2-yl)-5-[2-(1,3-dioxan-2-yl)ethyl]heptane-1,5-diol 430 mg (5 mmol) of γ-butyrolactone was dissolved in 10 ml of tetrahydrofuran, and 22 ml (11 mmol) of 0.5 M (1,3-dioxan-2-ylethyl)magnesium bromide/tetrahydrofuran solution was added thereto with stirring under ice-cooling, followed by stirring for 3 hours at 50° C. After the reaction solution was cooled with ice, saturated aqueous ammonium chloride was added and the mixture was extracted with ethyl acetate. The organic layer was washed with water and dried over anhydrous magnesium sulfate, followed by concentration under reduced pressure. The residue was subjected to silica gel column chromatography (solvent; ethyl acetate: ethanol=10:1) to give 880 mg of the title compound as a colorless oil (yield: 55%).

$^1$H-NMR spectrum (400 MHz, $CDCl_3$) δ ppm:

4.51 (2H, t, J=5 Hz), 4.08 (4H, dd, J=10 Hz, 4 Hz), 3.79-3.70 (4H, m), 3.61 (2H, t, J=6 Hz), 2.13-2.00 (2H, m), 1.68-1.56 (12H, m), 1.55-1.49 (2H, m), 1.37-1.29 (2H, m).

(30b) 2-(2-{2-[2-(1,3-dioxan-2-yl)ethyl]tetrahydrofuran-2-yl}ethyl)-1,3-dioxane 2.60 g (8.17 mmol) of 7-(1,3-dioxan-2-yl)-5-[2-(1,3-dioxan-2-yl)ethyl]heptane-1,5-diol obtained in (30a) was dissolved in 45 ml of pyridine, and a solution of 1.64 g (8.58 mmol) of p-toluenesulfonyl chloride in 15 ml of pyridine was added thereto with stirring under ice-cooling, followed by stirring for 1 hour at the same temperature and further for 3 hours at room temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=1:1) to give 1.31 g of the title compound as a colorless oil (yield: 53%)

$^1$H-NMR spectrum (400 MHz, $CDCl_3$) δ ppm:

4.50 (2H, t, J=5 Hz), 4.09 (2H, dd, J=11 Hz, 5 Hz), 3.83-3.68 (6H, m), 2.15-1.99 (2H, m), 1.92-1.82 (2H, m), 1.73-1.48 (12H, m), 1.38-1.29 (2H, m).

(30c) Ethyl 3-[2-(2-ethoxycarbonylethyl)tetrahydrofuran-2-yl]propionate 1.31 g (43.6 mmol) of 2-(2-{(2-[2-(1,3-dioxan-2-yl)ethyl] tetrahydrofuran-2-yl}ethyl)-1,3-dioxane obtained in (30b) was dissolved in 15 ml of acetone, and 16.3 ml (43.6 mmol) of Jones reagent was added thereto with stirring under ice-cooling, followed by stirring for 3 hours at room temperature. The reaction solution was cooled with ice, and then the reaction was terminated by addition of isopropyl alcohol. Water was added to the reaction solution and the mixture was extracted with ethyl acetate. The organic layer was washed with water and dried over anhydrous magnesium sulfate, followed by concentration under reduced pressure. The residue was dissolved in 15 ml of ethanol, and 0.76 ml (10.5 mmol) of thionyl chloride was added, followed by stirring overnight at room temperature. The reaction solution was concentrated under reduced pressure, and the residue was subjected to silica gel column chromatography (solvent; hexane:ethyl acetate=1:1) to give 610 mg of the title compound as a yellow oil (yield: 51%).

$^1$H-NMR spectrum (400 MHz, $CDCl_3$) δ ppm:

4.13 (4H, q, J=7 Hz), 3.78 (2H, t, J=7 Hz), 2.37-2.31 (4H, m), 1.95-1.87 (2H, m), 1.86-1.79 (4H, m) 1.71 (2H, t, J=7 Hz), 1.26 (6H, t, J=7 Hz).

(30d) Ethyl 8-oxo-1-oxaspiro[4.5]decane-7-carboxylate 610 mg (2.24 mmol) of ethyl 3-[2-(2-ethoxycarbonylethyl) tetrahydrofuran-2-yl]propionate obtained in (30c) was dissolved in 18 ml of tetrahydrofuran, and 503 mg (4.48 mmol) of potassium t-butoxide was added thereto, followed by heating under reflux for 1 hour. After the reaction solution was cooled with ice, the reaction solution was made acidic by addition of 1N hydrochloric acid, and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=2:1) to give 340 mg of the title compound as a colorless oil (yield: 67%).

$^1$H-NMR spectrum (400 MHz, $CDCl_3$) δ ppm:

12.24 (1H, s), 4.26-4.12 (2H, m), 3.96-3.79 (2H, m), 2.63-2.47 (1H, m), 2.43-2.12 (3H, m), 2.05-1.86 (2H, m), 1.86-1.60 (4H, m), 1.30 (3H, t, J=7 Hz).

(30e) Ethyl 8-trifluoromethanesulfonyloxy-1-oxaspiro[4.5]dec-7-ene-7-carboxylate To a suspension of 72 mg of 55% sodium hydride (1.65 mmol)/3 ml of dichloromethane, was added a solution of 340 mg (1.50 mmol) of ethyl 8-oxo-1-oxaspiro[4.5]decane-7-carboxylate obtained in (29d) in 4 ml of dichloromethane with stirring under ice-cooling, followed by stirring for 1 hour at the same temperature. Subsequently, the reaction solution was cooled to −78° C., and 0.28 ml (1.65 mmol) of trifluoromethanesulfonic anhydride was added thereto. The mixture was stirred for 1 hour at the same temperature, and then warmed to room temperature. After ice water was added to the reaction solution to terminate the reaction, the mixture was extracted with ethyl acetate. The organic layer was washed with water and dried over anhydrous magnesium sulfate, followed by concentration under reduced pressure. The residue was subjected to silica gel column chromatography (solvent; ethyl acetate alone) to give 480 mg of the title compound as a pale yellow oil (yield: 89%).

$^1$H-NMR spectrum (400 MHz, $CDCl_3$) δ ppm:

4.26 (2H, q, J=7 Hz), 3.92-3.81 (2H, m), 2.74-2.63 (1H, m), 2.62-2.48 (2H, m), 2.45-2.34 (1H, m), 2.04-1.68 (6H, m), 1.32 (3H, t, J=7 Hz).

(30f) Ethyl 8-acetylthio-1-oxaspiro[4.5]dec-7-ene-7-carboxylate

Following the process described in Example (1a), ethyl 8-trifluoromethanesulfonyloxy-1-oxaspiro[4.5]dec-7-ene-7-carboxylate obtained in (30e) was used in place of ethyl 8-trifluoromethanesulfonyloxy-1,4-dioxaspiro[4.5]dec-7-ene-7-carboxylate to give the title compound as a yellow oil (yield: 32%).

$^1$H-NMR spectrum (400 MHz, $CDCl_3$) δ ppm:

4.18 (2H, q, J=7 Hz), 3.91-3.83 (2H, m), 2.65-2.60 (1H, m), 2.60-2.51 (2H, m), 2.40-2.35 (1H, m), 2.32 (2.6H, s), 2.29 (0.4H, s), 2.00-1.93 (2H, m), 1.87-1.67 (4H, m), 1.28 (3H, t, J=7 Hz).

(30g) Ethyl 8-mercapto-1-oxaspiro[4.5]dec-7-ene-7-carboxylate 120 mg (0.42 mmol) of ethyl 8-acetylthio-1-oxaspiro[4.5] dec-7-ene-7-carboxylate obtained in (30f) was dissolved in 3 ml of ethanol, and 1 ml (4 mmol) of 4N hydrogen chloride/dioxane solution was added thereto, followed by stirring for 4 hours at room temperature. The reaction solution was concentrated under reduced pressure and the residue was subjected to silica gel column chromatography (solvent; hexane: ethyl acetate=3:1) to give 100 mg of the title compound as a pale yellow oil (98% yield).

$^1$H-NMR spectrum (400 MHz, $CDCl_3$) δ ppm:

4.24-4.16 (2H, m), 4.12 (1H, s), 3.91-3.80 (2H, m), 2.84-2.71 (1H, m), 2.52-2.34 (3H, m), 2.01-1.90 (2H, m), 1.82-1.58 (4H, m), 1.23 (3H, t, J=7 Hz).

(30h) Ethyl 8-chlorosulfonyl-1-oxaspiro[4.5]dec-7-ene-7-carboxylate 100 mg (0.41 mmol) of ethyl 8-mercapto-1-oxaspiro[4.5] dec-7-ene-7-carboxylate obtained in (30f) was dissolved in 4 ml of solution mixture of acetic acid and water (acetic acid: water=1:1), and chlorine gas was blown into the reaction solution with stirring under ice-cooling for 15 minutes. Ice water was added to the reaction solution and the mixture was extracted with ethyl acetate. The organic layer was washed with water and dried over anhydrous sodium sulfate, followed by concentration under reduced pressure. The residue was subjected to silica gel column chromatography (solvent; hexane:ethyl acetate=3:1) to give 108 mg of the title compound as a colorless oil (yield: 85%).

$^1$H-NMR spectrum (400 MHz, $CDCl_3$) δ ppm:

4.28 (2H, q, J=7 Hz), 3.88 (2H, t, J=7 Hz), 2.92-2.81 (1H, m), 2.77-2.66 (1H, m), 1.58 (2H, m), 2.06-1.89 (3H, m), 1.80 (2H, t, 7 Hz), 1.77-1.67 (1H, m), 1.34 (3H, t, J=7 Hz).

(30i) Ethyl 8-[N-(2-chloro-4-fluorophenyl)sulfamoyl]-1-oxaspiro[4.5]dec-6-ene-7-carboxylate (low polarity diastereomer), (high polarity diastereomer)

To a solution of 57 mg (0.39 mmol) of 2-chloro-4-fluoroaniline and 0.05 ml (0.39 mmol) of triethylamine in 1 ml of ethyl acetate, was added dropwise a solution of 108 mg (0.35 mmol) of ethyl 8-chlorosulfonyl-1-oxaspiro[4.5]dec-7-ene-7-carboxylate obtained in (29h) in 2 ml of ethyl acetate with stirring under ice-cooling, followed by stirring overnight at room temperature. Water was added to the reaction solution and the mixture was extracted with ethyl acetate. The organic layer was washed with water and dried over anhydrous magnesium sulfate, followed by concentration under reduced pressure. The residue was subjected to silica gel thin layer chromatography (solvent; hexane:ethyl acetate=3:1) to give 12 mg of low polarity diastereomer of the title compound as a white powder and 20 mg of high polarity diastereomer of the title compound as an amorphous substance (yield: 8%, 14%).

(Low Polarity Diastereomer)

Melting point: 112-114° C.

$^1$H-NMR spectrum (400 MHz, $CDCl_3$) δ ppm:

7.65 (1H, dd, J=9 Hz, 5 Hz), 7.14 (1H, dd, J=8 Hz, 3 Hz), 7.04-6.97 (1H, m), 6.95 (1H, s), 6.90 (1H, s), 4.45 (1H, dd, J=6 Hz, 2 Hz), 4.22-4.10 (2H, m), 3.96-3.88 (1H, m), 3.86-3.79 (1H, m), 2.41-2.33 (1H, m), 2.29-2.18 (1H, m), 2.13-2.01 (4H, m), 1.94-1.79 (2H, m), 1.25 (3H, t, J=7 Hz).

(High Polarity Diastereomer)

$^1$H-NMR spectrum (400 MHz, $CDCl_3$) δ ppm:

7.66 (1H, dd, J=9 Hz, 5 Hz), 7.13 (1H, dd, J=8 Hz, 3 Hz), 7.04-6.96 (2H, m), 6.95 (1H, s), 4.36 (1H, d, J=5 Hz), 4.22-4.10 (2H, m), 4.03-3.96 (1H, m), 3.93-3.85 (1H, m), 2.56-2.48 (1H, m), 2.40-2.29 (1H, m), 2.06-1.63 (6H, m), 1.26 (3H, t, J=7 Hz).

Example 31

Ethyl 6-[N-(1H-pyrrol-1-yl)sulfamoyl]-1-cyclohexene-1-carboxylate (Exemplified compound No. 1-1057)

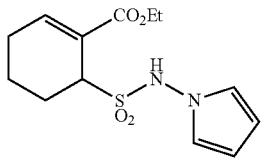

To a solution of 1.0 g (12.18 mmol) of 1H-pyrrol-1-ylamine and 1.8 ml (13.40 mmol) of triethylamine in 60 ml of ethyl acetate was added dropwise a solution of 3.6 g (12.18 mmol) of ethyl 2-chlorosulfonyl-1-cyclohexene-1-carboxylate (compound disclosed in the specification of Japanese Patent Application (Kokai) No. 2000-178246) in 12 ml of ethyl acetate with stirring under ice-cooling, followed by stirring overnight at room temperature. Water was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=3:1) and the resulting solid was further washed with isopropyl ether to give 1.9 g of the title compound as a white powder (yield: 52%).

Melting point: 85-86° C.

$^1$H-NMR spectrum (400 MHz, $CDCl_3$) δ ppm:

8.15 (1H, s), 7.44-7.42 (1H, m), 7.02 (2H, t, J=2 Hz), 6.17 (2H, t, J=2 Hz), 4.57-4.56 (1H, m), 4.29 (2H, q, J=7 Hz), 2.52-2.46 (2H, m), 2.32-2.23 (1H, m), 1.93-1.66 (3H, m), 1.34 (3H, t, J=7 Hz).

Example 32

Ethyl 6-[N-(2-methyl-1H-pyrrol-1-yl)sulfamoyl]-1-cyclohexene-1-carboxylate (Exemplified compound No. 1-1176)

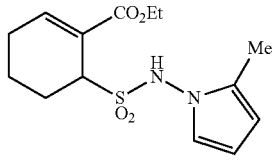

Following the process described in Example 31, 2-methyl-1H-pyrrol-1-ylamine was used in place of 1H-pyrrol-1-ylamine to give the title compound as a white powder (yield: 32%).

Melting point: 100-101° C.

$^1$H-NMR spectrum (400 MHz, $CDCl_3$) δ ppm:

7.95 (1H, s), 7.43-7.39 (1H, m), 7.03-6.99 (1H, m), 6.07 (1H, t, J=4 Hz), 5.88-5.84 (1H, m), 4.60-4.55 (1H, m), 4.26 (2H, q, J=7 Hz), 2.56-2.43 (2H, m), 2.34-2.20 (1H, m), 2.29 (3H, s), 1.95-1.66 (3H, m), 1.33 (3H, t, J=7 Hz).

Example 33

Ethyl 6-[N-(2-ethyl-1H-pyrrol-1-yl)sulfamoyl]-1-cyclohexene-1-carboxylate (Exemplified compound No. 1-1193)

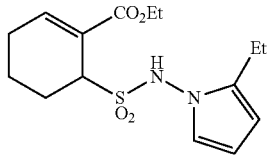

Following the process described in Example 31, 2-ethyl-1H-pyrrol-1-ylamine was used in place of 1H-pyrrol-1-ylamine to give the title compound as a white powder (yield: 51%).

Melting point: 77-78° C.

$^1$H-NMR spectrum (400 MHz, $CDCl_3$) δ ppm:

7.97 (1H, s), 7.46-7.41 (1H, m), 7.04-7.01 (1H, m), 6.13 (1H, t, J=4 Hz), 5.92-5.87 (1H, m), 4.62-4.57 (1H, m), 4.28

(2H, q, J=7 Hz), 2.79-2.64 (2H, m), 2.58-2.42 (2H, m), 2.35-2.21 (1H, m), 1.95-1.65 (3H, m), 1.33 (3H, t, J=7 Hz), 1.24 (3H, t, J=8 Hz).

Example 34

Ethyl 6-[N-(2-propyl-1H-pyrrol-1-yl)sulfamoyl]-1-cyclohexene-1-carboxylate (Exemplified compound No. 1-1210)

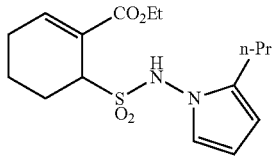

Following the process described in Example 31, 2-propyl-1H-pyrrol-1-ylamine was used in place of 1H-pyrrol-1-ylamine to give the title compound as a white powder (yield: 31%).

Melting point: 66-68° C.

$^1$H-NMR spectrum (400 MHz, $CDCl_3$) δ ppm:

7.97 (1H, s), 7.46-7.41 (1H, m), 7.04-7.01 (1H, m), 6.12 (1H, t, J=3 Hz), 5.92-5.87 (1H, m), 4.62-4.57 (1H, m), 4.27 (2H, q, J=7 Hz), 2.73-2.62 (2H, m), 2.57-2.43 (2H, m), 2.34-2.21 (1H, m) 1.95-1.63 (5H, m), 1.33 (3H, t, J=7 Hz), 0.99 (3H, t, J=7 Hz).

Example 35

Ethyl 6-[N-(2-butyl-1H-pyrrol-1-yl)sulfamoyl]-1-cyclohexene-1-carboxylate (Exemplified compound No. 1-1227)

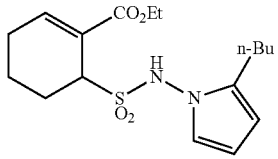

Following the process described in Example 31, 2-butyl-1H-pyrrol-1-ylamine was used in place of 1H-pyrrol-1-ylamine to give the title compound as a white powder (yield: 26%).

Melting point: 49-50° C.

$^1$H-NMR spectrum (400 MHz, $CDCl_3$) δ ppm:

7.94 (1H, s), 7.43-7.39 (1H, m), 7.01-6.98 (1H, m), 6.11-6.08 (1H, m), 5.89-5.85 (1H, m), 4.60-4.55 (1H, m), 4.26 (2H, q, J=7 Hz), 2.71-2.65 (2H, m), 2.56-2.43 (2H, m), 2.33-2.20 (1H, m) 1.94-1.57 (5H, m), 1.45-1.35 (2H, m), 1.32 (3H, t, J=7 Hz), 0.93 (3H, t, J=7 Hz).

Example 36

Ethyl 6-[N-(2-pentyl-1H-pyrrol-1-yl)sulfamoyl]-1-cyclohexene-1-carboxylate (Exemplified compound No. 1-1244)

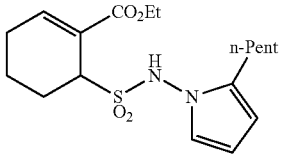

Following the process described in Example 31, 2-pentyl-1H-pyrrol-1-ylamine obtained in Reference Example 6 was used in place of 1H-pyrrol-1-ylamine to give the title compound as a white powder (yield: 33%).

Melting point: 60-61° C.

$^1$H-NMR spectrum (400 MHz, $CDCl_3$) δ ppm:

7.96 (1H, s), 7.46-7.41 (1H, m), 7.04-7.00 (1H, m), 6.12 (1H, t, J=3 Hz), 5.92-5.86 (1H, m), 4.62-4.56 (1H, m), 4.28 (2H, q, J=7 Hz), 2.72-2.65 (2H, m), 2.57-2.44 (2H, m), 2.34-2.21 (1H, m), 1.95-1.59 (5H, m), 1.42-1.29 (4H, m), 1.34 (3H, t, J=7 Hz), 0.89 (3H, t, J=7 Hz).

Example 37

Ethyl 6-[N-(2-hexyl-1H-pyrrol-1-yl)sulfamoyl]-1-cyclohexene-1-carboxylate (Exemplified compound No. 1-1261)

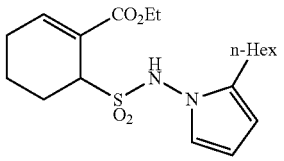

Following the process described in Example 31, 2-hexyl-1H-pyrrol-1-ylamine obtained in Reference Example 7 was used in place of 1H-pyrrol-1-ylamine to give the title compound as a yellow oil (yield: 46%).

$^1$H-NMR spectrum (400 MHz, $CDCl_3$) δ ppm:

7.93 (1H, s), 7.43-7.39 (1H, m), 7.01-6.98 (1H, m), 6.12-6.08 (1H, m), 5.89-5.85 (1H, m), 4.60-4.55 (1H, m), 4.27 (2H, q, J=' Hz), 2.71-2.64 (2H, m), 2.56-2.43 (2H, m), 2.33-2.21 (1H, m), 1.91-1.58 (5H, m), 1.42-1.27 (6H, m), 1.33 (3H, t, J=7 Hz), 0.88 (3H, t, J=7 Hz).

Example 38

Ethyl 6-[N-(2-heptyl-1H-pyrrol-1-yl)sulfamoyl]-1-cyclohexene-1-carboxylate (Exemplified compound No. 1-1278)

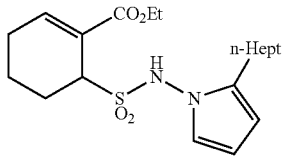

Following the process described in Example 31, 2-heptyl-1H-pyrrol-1-ylamine obtained in Reference Example 8 was used in place of 1H-pyrrol-1-ylamine to give the title compound as a colorless oil (yield: 13%).

$^1$H-NMR spectrum (400 MHz, $CDCl_3$) δ ppm:

7.97 (1H, s), 7.46-7.41 (1H, m), 7.04-7.01 (1H, m), 6.11 (1H, t, J=3 Hz), 5.96-5.86 (1H, m), 4.62-4.56 (1H, m), 4.28 (2H, q, J=7 Hz), 2.72-2.62 (2H, m), 2.58-2.43 (2H, m), 2.35-2.21 (1H, m), 1.94-1.59 (5H, m), 1.41-1.22 (8H, m), 1.33 (3H, t, J=7 Hz), 0.88 (3H, t, J=7 Hz).

Example 39

Ethyl 6-[N-(2-octyl-1H-pyrrol-1-yl)sulfamoyl]-1-cyclohexene-1-carboxylate (Exemplified compound No. 1-1295)

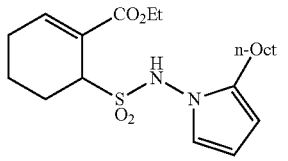

Following the process described in Example 31, 2-octyl-1H-pyrrol-1-ylamine obtained in Reference Example 8 was used in place of 1H-pyrrol-1-ylamine to give the title compound as a pale yellow oil (yield: 18%).

$^1$H-NMR spectrum (400 MHz, $CDCl_3$) δ ppm:

7.96 (1H, s), 7.46-7.41 (1H, m), 7.04-7.00 (1H, m), 6.11 (1H, t, J=4 Hz), 5.91-5.86 (1H, m), 4.61-4.57 (1H, m), 4.28 (2H, q, J=7 Hz), 2.71-2.64 (2H, m), 2.57-2.44 (2H, m), 2.34-2.20 (1H, m), 1.95-1.58 (5H, m), 1.42-1.19 (10H, m), 1.33 (3H, t, J=7 Hz), 0.88 (3H, t, J=7 Hz).

Example 40

Ethyl 6-[N-(2-cyclopropyl-1H-pyrrol-1-yl)sulfamoyl]-1-cyclohexene-1-carboxylate (Exemplified compound No. 1-1312)

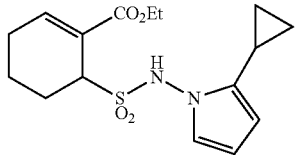

Following the process described in Example 31, 2-cyclopropyl-1H-pyrrol-1-ylamine obtained in Reference Example 10 was used in place of 1H-pyrrol-1-ylamine to give the title compound as a pale pink powder (yield: 42%).

Melting point: 95-96° C.

$^1$H-NMR spectrum (400 MHz, $CDCl_3$) δ ppm:

7.87 (1H, s), 7.41-7.37 (1H, m), 6.98-6.95 (1H, m), 6.05-6.02 (1H, m), 5.69-5.66 (1H, m), 4.66-4.61 (1H, m), 4.25 (2H, q, J=7 Hz), 2.60-2.43 (2H, m), 2.34-2.20 (1H, m), 2.05-1.87 (2H, m), 1.82-1.68 (2H, m), 1.31 (3H, t, J=7 Hz), 0.94-0.82 (2H, m), 0.73-0.65 (1H, m), 0.59-0.51 (1H, m).

Example 41

Ethyl 6-[N-(2-phenyl-1H-pyrrol-1-yl)sulfamoyl]-1-cyclohexene-1-carboxylate (Exemplified compound No. 1-1329)

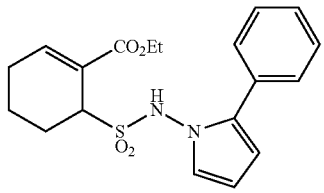

Following the process described in Example 31, 2-phenyl-1H-pyrrol-1-ylamine was used in place of 1H-pyrrol-1-ylamine to give the title compound as a pale yellow powder (yield: 21%).

Melting point: 160-161° C.

$^1$H-NMR spectrum (400 MHz, $CDCl_3$) δ ppm:

7.99 (1H, s), 7.57 (2H, d, J=8 Hz), 7.39 (2H, t, J=8 Hz), 7.33-7.27 (2H, m), 7.14-7.11 (1H, m), 6.32-6.28 (1H, m), 6.25 (1H, t, J=4 Hz), 4.22 (2H, q, J=7 Hz), 4.18-4.14 (1H, m), 2.44-2.32 (1H, m), 2.24-2.07 (2H, m), 1.91-1.75 (1H, m), 1.67-1.51 (1H, m), 1.40-1.29 (1H, m), 1.28 (3H, t, J=7 Hz).

Example 42

Ethyl 6-[N-(2,5-dimethyl-1H-pyrrol-1-yl)sulfamoyl]-1-cyclohexene-1-carboxylate (Exemplified compound No. 1-1346)

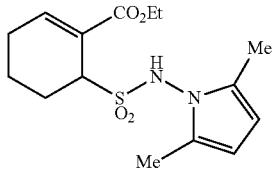

Following the process described in Example 31, 2,5-dimethyl-1H-pyrrol-1-ylamine was used in place of 1H-pyrrol-1-ylamine to give the title compound as a white powder (yield: 29%).

Melting point: 96-97° C.

$^1$H-NMR spectrum (400 MHz, $CDCl_3$) δ ppm:

7.88 (1H, s), 7.40-7.35 (1H, m), 5.75 (2H, s), 4.58-4.52 (1H, m), 4.24 (2H, q, 7 Hz), 2.69-2.61 (1H, m), 2.53-2.42 (1H, m), 2.33-2.19 (1H, m), 2.26 (6H, s), 2.02-1.91 (1H, m), 1.86-1.73 (2H, m), 1.30 (3H, t, J=7 Hz).

Example 43

Ethyl 6-[N-(2-chloro-1H-pyrrol-1-yl)sulfamoyl]-1-cyclohexene-1-carboxylate (Exemplified compound No. 1-1091)

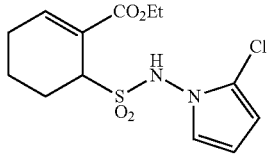

150 mg (0.503 mmol) of ethyl 6-[N-(1H-pyrrol-1-yl)sulfamoyl]-1-cyclohexene-1-carboxylate obtained in Example 31 was dissolved in 3 ml of tetrahydrofuran, and 70 mg (0.528 mmol) of N-chlorosuccinimide was added thereto with stirring under ice-cooling, followed by stirring overnight at room temperature. Water was added to the reaction solution and the mixture was extracted with ethyl acetate. The organic layer was washed with water and dried over anhydrous magnesium sulfate, followed by concentration under reduced pressure. The residue was subjected to silica gel thin layer chromatography (solvent; hexane:ethyl acetate=2:1) and the resulting solid was further washed with isopropyl ether to give 50 mg of the title compound as a white powder (yield: 30%).

Melting point: 60-61° C.

$^1$H-NMR spectrum (400 MHz, $CDCl_3$) δ ppm:

7.91 (1H, s), 7.43-7.37 (1H, m), 7.04 (1H, dd, J=4 Hz, 2 Hz), 6.14 (1H, t, J=4 Hz), 6.10 (1H, dd, J=4 Hz, 2 Hz), 4.65-4.61 (1H, m), 4.26 (2H, q, J=7 Hz), 2.61-2.44 (2H, m), 2.33-2.21 (1H, m), 2.05-1.90 (1H, m), 1.83-1.71 (2H, m), 1.30 (3H, t, J=7 Hz).

Example 44

Ethyl 6-[N-(2-bromo-1H-pyrrol-1-yl)sulfamoyl]-1-cyclohexene-1-carboxylate (exemplified compound No. 1-1108)

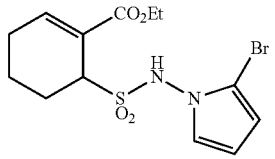

Following the process described in Example 43, N-bromosuccinimide was used in place of N-chlorosuccinimide to give the title compound as a white powder (yield: 50%).

$^1$H-NMR spectrum (400 MHz, $CDCl_3$) δ ppm:

7.85 (1H, s), 7.42-7.38 (1H, m), 7.15 (1H, dd, J=4 Hz, 2 Hz), 6.22-6.17 (2H, m), 4.67-4.62 (1H, m), 4.25 (2H, q, J=7 Hz), 2.60-2.44 (2H, m), 2.33-2.20 (1H, m), 2.05-1.92 (1H, m), 1.83-1.70 (2H, m), 1.30 (3H, t, J=7 Hz).

Example 45

Ethyl 6-[N-(2,5-dichloro-1H-pyrrol-1-yl)sulfamoyl]-1-cyclohexene-1-carboxylate (Exemplified compound No. 1-1142)

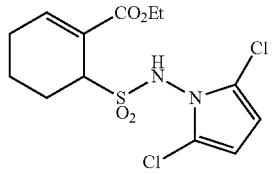

Following the process described in Example 42, 2.1 equivalent of N-chlorosuccinimide was used relative to ethyl 6-[N-(1H-pyrrol-1-yl)sulfamoyl]-1-cyclohexene-1-carboxylate obtained in Example 31 to give the title compound as a pale yellow oil (yield: 25%).

Melting point: 144-145° C.

$^1$H-NMR spectrum (400 MHz, $CDCl_3$) δ ppm:

8.08 (1H, s), 7.39-7.33 (1H, m), 6.07 (2H, s), 4.89-4.83 (1H, m), 4.24 (2H, q, J=7 Hz), 2.67-2.58 (1H, m), 2.52-2.42 (1H, m), 2.31-2.19 (1H, m), 2.03-1.88 (1H, m), 1.87-1.72 (2H, m), 1.29 (3H, t, J=7 Hz).

Example 46

Ethyl 6-[N-(2,5-dibromo-1H-pyrrol-1-yl)sulfamoyl]-1-cyclohexene-1-carboxylate (Exemplified compound No. 1-1159)

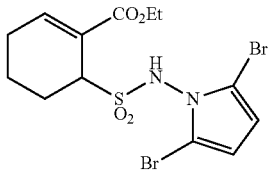

Following the process described in Example 44, 2.1 equivalent of N-bromosuccinimide was used relative to ethyl 6-[N-(1H-pyrrol-1-yl)sulfamoyl]-1-cyclohexene-1-carboxylate obtained in Example 31 to give the title compound as a white powder (yield: 3%).

Melting point: 123-124° C.

$^1$H-NMR spectrum (400 MHz, $CDCl_3$) δ ppm:

8.05 (1H, s), 7.40-7.35 (1H, m), 6.24 (2H, s), 5.02-4.95 (1H, m), 4.25 (2H, q, J=7 Hz), 2.69-2.60 (1H, m), 2.53-2.42 (1H, m), 2.33-2.19 (1H, m), 2.02-1.90 (1H, m), 1.87-1.72 (2H, m), 1.29 (3H, t, J=7 Hz).

Example 47 t-Butyl 8-[N-(2-chloro-4-fluorophenyl)sulfamoyl]-1,4-dioxaspiro[4.5]dec-6-ene-7-carboxylate (Exemplified compound No. 3-89)

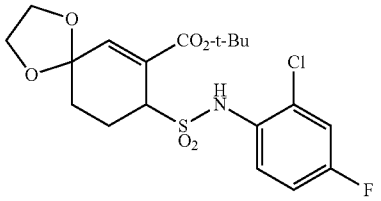

(47a) 8-[N-(2-Chloro-4-fluorophenyl)sulfamoyl]-1,4-dioxaspiro[4.5]dec-6-ene-7-carboxylic acid 1.8 g (4.29 mmol) of ethyl 8-[N-(2-chloro-4-fluorophenyl)sulfamoyl]-1,4-dioxaspiro[4.5]dec-6-ene-7-carboxylate obtained in Example 1 was dissolved in 60 ml of a water-tetrahydrofuran (1:1) solution, and 900 mg (21.45 mmol) of lithium hydroxide was added thereto, followed by stirring for 7 hours at 50° C. The reaction solution was cooled with ice, it was then made acidic by addition of 1N hydrochloric acid, and the mixture was extracted with ethyl acetate. The organic layer was washed with water and dried over anhydrous magnesium sulfate, followed by concentration under reduced pressure. The residue was washed with hexane to give 1.43 g of the title compound as a pale brown powder (yield: 85%).

$^1$H-NMR spectrum (400 MHz, $CDCl_3$) δ ppm:

7.68 (1H, dd, J=9 Hz, 5 Hz), 7.16 (1H, dd, J=8 Hz, 3 Hz), 7.04-6.93 (3H, m), 4.36 (1H, d, J=5 Hz), 4.16-4.02 (3H, m), 3.97-3.88 (1H, m), 2.57-2.45 (3H, m), 2.25-2.13 (1H, m), 1.90-1.82 (1H, m).

(47b) t-Butyl 8-[N-(2-chloro-4-fluorophenyl)sulfamoyl]-1,4-dioxaspiro[4.5]dec-6-ene-7-carboxylate 100 mg (0.26 mmol) of 8-[N-(2-chloro-4-fluorophenyl)sulfamoyl]-1,4-dioxaspiro[4.5]dec-6-ene-7-carboxylic acid obtained in (47a) was dissolved in 2 ml of toluene, and 1 ml of N,N-dimethylformamide di-t-butyl acetal was added thereto, followed by stirring for 3 hours at 100° C. After the reaction solution was cooled to room temperature, water was added and the mixture was extracted with ethyl acetate. The organic layer was washed with water and dried over anhydrous magnesium sulfate, followed by concentration under reduced pressure. The residue was subjected to silica gel thin layer chromatography (solvent; dichloromethane:methanol=1:50) to give 52 mg of the title compound as a white amorphous substance (yield: 45%).

$^1$H-NMR spectrum (400 MHz, $CDCl_3$) δ ppm:

7.64 (1H, dd, J=9 Hz, 5 Hz), 7.15 (1H, dd, J=8 Hz, 3 Hz), 7.05-6.98 (2H, m), 6.71 (1H, s), 4.42-4.38 (1H, m), 4.13-4.01 (3H, m), 3.95-3.88 (1H, m), 2.51-2.40 (2H, m), 2.21-2.10 (1H, m), 1.86-1.79 (1H, m), 1.46 (9H, s).

Following the process described in Example (47b), various corresponding acetals were used in place of N,N-dimethylformamide di-t-butyl acetal to synthesize the compounds of Examples 48 to 51.

Example 48

Methyl 8-[N-(2-chloro-4-fluorophenyl)sulfamoyl]-1,4-dioxaspiro[4.5]dec-6-ene-7-carboxylate (Exemplified compound No. 3-73)

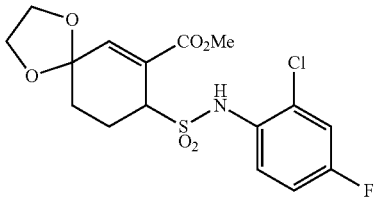

White powder (yield: 50%)

$^1$H-NMR spectrum (400 MHz, $CDCl_3$) δ ppm:

7.67 (1H, dd, J=9 Hz, 5 Hz), 7.16 (1H, dd, J=8 Hz, 3 Hz), 7.06-6.99 (1H, m), 6.98 (1H, s), 6.84 (1H, s), 4.43-4.38 (1H, m), 4.15-3.99 (3H, m), 3.95-3.88 (1H, m), 3.73 (3H, s), 2.56-2.43 (2H, m), 2.24-2.12 (1H, m), 1.88-1.79 (1H, m).

Example 49

Propyl 8-[N-(2-chloro-4-fluorophenyl)sulfamoyl]-1,4-dioxaspiro[4.5]dec-6-ene-7-carboxylate (Exemplified compound No. 3-77)

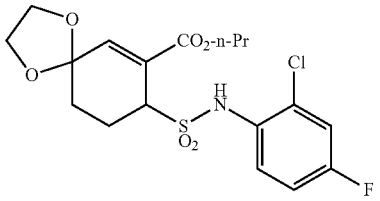

White amorphous substance (yield: 18%)

$^1$H-NMR spectrum (400 MHz, $CDCl_3$) δ ppm:

7.67 (1H, dd, J=9 Hz, 5 Hz), 7.16 (1H, dd, J=8 Hz, 3 Hz), 7.05-6.97 (2H, m), 6.81 (1H, s), 4.42 (1H, d, J=5 Hz), 4.16-3.99 (5H, m), 3.95-3.88 (1H, m), 2.55-2.44 (2H, m), 2.24-2.11 (1H, m), 1.88-1.81 (1H, m), 1.71-1.60 (2H, m), 0.94 (3H, t, J=7 Hz).

Example 50

Butyl 8-[N-(2-chloro-4-fluorophenyl)sulfamoyl]-1,4-dioxaspiro[4.5]dec-6-ene-7-carboxylate (Exemplified compound No. 3-81)

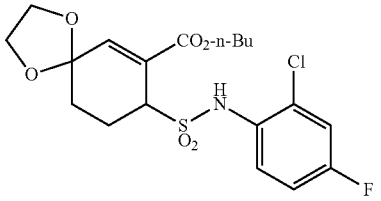

White powder (yield: 26%)

$^1$H-NMR spectrum (400 MHz, $CDCl_3$) δ ppm:

7.66 (1H, dd, J=9 Hz, 5 Hz), 7.16 (1H, dd, J=8 Hz, 3 Hz), 7.05-6.96 (2H, m), 6.80 (1H, s), 4.42 (1H, d, J=5 Hz), 4.20-4.00 (5H, m), 3.95-3.87 (1H, m), 2.55-2.44 (2H, m), 2.24-2.11 (1H, m), 1.88-1.80 (1H, m), 1.66-1.57 (2H, m), 1.43-1.32 (2H, m), 0.93 (3H, t, J=7 Hz).

Example 51

Isopropyl 8-[N-(2-chloro-4-fluorophenyl)sulfamoyl]-1,4-dioxaspiro[4.5]dec-6-ene-7-carboxylate (Exemplified compound No. 3-85)

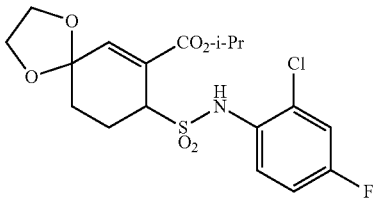

White powder (yield: 21%)

$^1$H-NMR spectrum (400 MHz, $CDCl_3$) δ ppm:

7.66 (1H, dd, J=9 Hz, 5 Hz), 7.16 (1H, dd, J=8 Hz, 3 Hz), 7.06-6.98 (2H, m), 6.78 (1H, s), 5.11-4.99 (1H, m), 4.42 (1H, d, J=5 Hz), 4.15-3.99 (3H, m), 3.95-3.88 (1H, m), 2.55-2.43 (2H, m), 2.24-2.11 (1H, m), 1.99-1.79 (1H, m), 1.26 (3H, d, J=2 Hz), 1.24 (3H, d, J=2 Hz).

Example 52

Acetoxymethyl 8-[N-(2-chloro-4-fluorophenyl)sulfamoyl]-1,4-dioxaspiro[4.5]dec-6-ene-7-carboxylate (Exemplified compound No. 3-93)

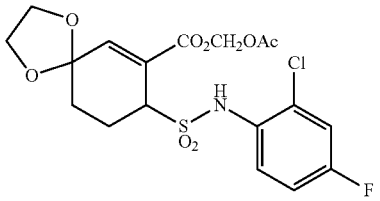

1 g (2.55 mmol) of 8-[N-(2-chloro-4-fluorophenyl)sulfamoyl]-1,4-dioxaspiro[4.5]dec-6-ene-7-carboxylic acid obtained in Example 47a was dissolved in 20 ml of acetonitrile, and 0.50 ml (5.10 mmol) of bromomethyl acetate, 499 mg (1.53 mmol) of cesium carbonate and 471 mg (1.28 mmol) of tetrabutylammonium iodide were added thereto, followed by stirring for 1 hour at room temperature. 0.1 N hydrochloric acid was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; dichloromethane:methanol=49:1) to give 833 mg of the title compound as an amorphous substance (yield: 70%).

$^1$H-NMR spectrum (400 MHz, $CDCl_3$) δ ppm:

7.67 (1H, dd, J=9 Hz, 5 Hz), 7.18 (1H, dd, J=8 Hz, 3 Hz), 7.08-7.02 (1H, m), 7.01 (1H, s), 6.92 (1H, s), 5.80 (2H, s), 4.41 (1H, dd, J=6 Hz, 2 Hz), 4.15-4.01 (3H, m), 3.94-3.88 (1H, m), 2.48 (1H, td, J=14 Hz, 4 Hz), 2.44-2.37 (1H, m), 2.22-2.14 (1H, m), 2.12 (3H, s), 1.85-1.79 (1H, m).

Following the process described in Example (1d), various corresponding anilines were used in place of 2-chloro-4-fluoroaniline to synthesize the compounds of Examples 53 to 121.

Example 53

Ethyl 8-[N-(2-fluorophenyl)sulfamoyl]-1,4-dioxaspiro[4.5]dec-6-ene-7-carboxylate (Exemplified compound No. 1-2217)

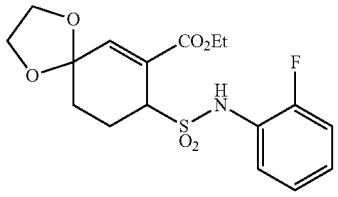

Oil (yield: 61%)

$^1$H-NMR spectrum (400 MHz, $CDC_3$) δ ppm:

7.67-7.62 (1H, m), 7.17-7.09 (3H, m), 6.96 (1H, d, J=3 Hz), 6.83 (1H, t, J=1 Hz), 4.43-4.40 (1H, m), 4.24-4.01 (5H, m), 3.95-3.89 (1H, m), 2.55-2.41 (2H, m), 2.21-2.10 (1H, m), 1.89-1.81 (1H, m), 1.27 (3H, t, J=7 Hz).

Example 54

Ethyl 8-[N-(2-chlorophenyl)sulfamoyl]-1,4-dioxaspiro[4.5]dec-6-ene-7-carboxylate (Exemplified compound No. 1-188)

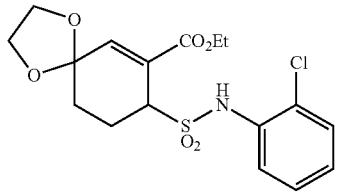

Pale brown powder (yield: 69%)

Melting point: 157-160° C.

$^1$H-NMR spectrum (400 MHz, $CDCl_3$) δ ppm:

7.70 (1H, dd, J=8 Hz, 1 Hz), 7.39 (1H, dd, J=8 Hz, 2 Hz), 7.31-7.26 (1H, m), 7.10-7.05 (2H, m), 6.83 (1H, t, J=1 Hz), 4.49-4.46 (1H, m), 4.24-4.02 (5H, m), 3.95-3.89 (1H, m), 2.60-2.48 (2H, m), 2.24-2.13 (1H, m), 1.88-1.81 (1H, m), 1.24 (3H, t, J=7 Hz).

Example 55

Ethyl 8-[N-(2-bromophenyl)sulfamoyl]-1,4-dioxaspiro[4.5]dec-6-ene-7-carboxylate (Exemplified compound No. 1-1374)

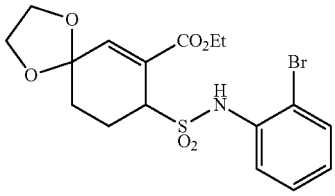

Oil (yield: 59%)

$^1$H-NMR spectrum (400 MHz, $CDCl_3$) δ ppm:

7.70 (1H, dd, J=8 Hz, 1 Hz), 7.55 (1H, dd, J=8 Hz, 2 Hz), 7.36-7.30 (1H, m), 7.04-6.98 (2H, m), 6.83 (1H, t, J=1 Hz), 4.50-4.47 (1H, m), 4.23-4.01 (5H, m), 3.95-3.88 (1H, m), 2.62-2.49 (2H, m), 2.24-2.13 (1H, m), 1.88-1.81 (1H, m), 1.24 (3H, t, J=7 Hz).

Example 56

Ethyl 8-[N-(2-iodophenyl)sulfamoyl]-1,4-dioxaspiro[4.5]dec-6-ene-7-carboxylate (Exemplified compound No. 1-2224)

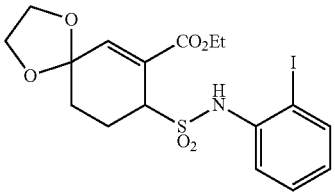

Amorphous substance (yield: 53%)

$^1$H-NMR spectrum (400 MHz, $CDCl_3$) δ ppm:

7.79 (1H, dd, J=8 Hz, 1 Hz), 7.67 (1H, dd, J=8 Hz, 1 Hz), 7.38-7.33 (1H, m), 6.88-6.82 (3H, m), 4.49 (1H, d, J=5 Hz), 4.24-4.01 (5H, m), 3.95-3.88 (1H, m), 2.63-2.49 (2H, m), 2.24-2.13 (1H, m), 1.88-1.81 (1H, m), 1.24 (3H, t, J=7 Hz).

Example 57

Ethyl 8-[N-(4-fluorophenyl)sulfamoyl]-1,4-dioxaspiro[4.5]dec-6-ene-7-carboxylate (Exemplified compound No. 1-100)

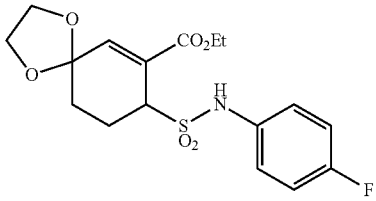

White powder (yield: 87%)

Melting point: 141-146° C.

$^1$H-NMR spectrum (400 MHz, $CDCl_3$) δ ppm:

7.38-7.33 (2H, m), 7.07-7.01 (3H, m), 6.87 (1H, t, J=1 Hz), 4.30-4.21 (3H, m), 4.14-4.01 (3H, m), 3.95-3.89 (1H, m), 2.45-2.38 (1H, m), 2.27 (1H, td, J=14 Hz, 3 Hz), 2.09-1.99 (1H, m), 1.87-1.80 (1H, m), 1.33 (3H, t, J=7 Hz).

Example 58

Ethyl 8-[N-(4-chlorophenyl)sulfamoyl]-1,4-dioxaspiro[4.5]dec-6-ene-7-carboxylate (Exemplified compound No. 1-2231)

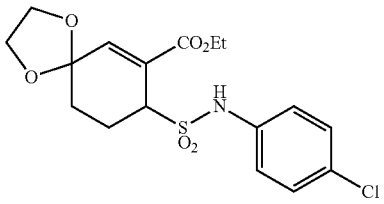

White powder (yield: 81%)

Melting point: 153-156° C.

$^1$H-NMR spectrum (400 MHz, $CDCl_3$) δ ppm:

7.31 (4H, s), 7.03 (1H, s), 6.87 (1H, t, J=1 Hz), 4.29-4.19 (3H, m), 4.14-4.02 (3H, m), 3.95-3.89 (1H, m), 2.47-2.40 (1H, m), 2.27 (1H, td, J=14 Hz, 3 Hz), 2.10-2.00 (1H, m), 1.88-1.81 (1H, m), 1.32 (3H, t, J=7 Hz).

Example 59

Ethyl 8-[N-(2-methylphenyl)sulfamoyl]-1,4-dioxaspiro[4.5]dec-6-ene-7-carboxylate (Exemplified compound No. 1-2238)

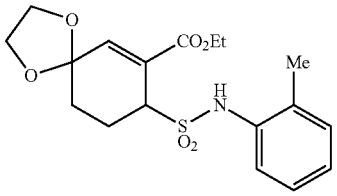

White powder (yield: 75%)

Melting point: 101-104° C.

$^1$H-NMR spectrum (400 MHz, $CDCl_3$) δ ppm:

7.56-7.53 (1H, m), 7.23-7.18 (2H, m), 7.11-7.06 (1H, m), 6.85 (1H, t, J=1 Hz), 6.62 (1H, s), 4.44 (1H, dd, J=6 Hz, 2 Hz), 4.25-4.01 (5H, m), 3.95-3.89 (1H, m), 2.55-2.48 (1H, m), 2.42 (1H, td, J=14 Hz, 4 Hz), 2.34 (3H, s), 2.19-2.09 (1H, m), 1.88-1.81 (1H, m), 1.26 (3H, t, J=7 Hz).

Example 60

Ethyl 8-[N-(2-ethylphenyl)sulfamoyl]-1,4-dioxaspiro[4.5]dec-6-ene-7-carboxylate (Exemplified compound No. 1-2245)

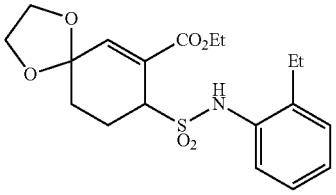

White powder (yield: 66%)

Melting point: 83-87° C.

$^1$H-NMR spectrum (500 MHz, $CDCl_3$) δ ppm:

7.54 (1H, dd, J=8 Hz, 1 Hz), 7.25-7.19 (2H, m), 7.14 (1H, td, J=7 Hz, 1 Hz), 6.85 (1H, s), 6.63 (1H, s), 4.47 (1H, dd, J=6 Hz, 2 Hz), 4.25-4.02 (5H, m), 2.75-2.66 (2H, m), 2.54-2.48 (1H, m), 2.43 (1H, td, J=14 Hz, 4 Hz), 2.19-2.11 (1H, m), 1.87-1.81 (1H, m), 1.28-1.23 (6H, m).

Example 61

Ethyl 8-[N-(2-propylphenyl)sulfamoyl]-1,4-dioxaspiro[4.5]dec-6-ene-7-carboxylate (Exemplified compound No. 1-1989)

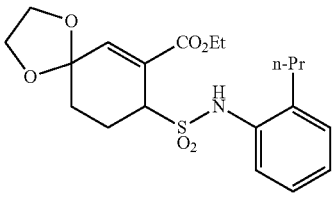

Oil (53% yield)

$^1$H-NMR spectrum (400 MHz, $CDCl_3$) δ ppm:

7.55-7.52 (1H, m), 7.23-7.18 (2H, m), 7.14-7.09 (1H, m), 6.85 (1H, t, J=1 Hz), 6.64 (1H, s), 4.48-4.44 (1H, m), 4.24-4.02 (5H, m), 3.95-3.89 (1H, m), 2.67-2.62 (2H, m), 2.54-

2.39 (2H, m), 2.20-2.10 (1H, m), 1.87-1.81 (1H, m), 1.69-1.58 (2H, m), 1.26 (3H, t, J=7 Hz), 0.99 (3H, t, J=7 Hz).

Example 62

Ethyl 8-[N-(2-ethynylphenyl)sulfamoyl]-1,4-dioxaspiro[4.5]dec-6-ene-7-carboxylate (Exemplified compound No. 1-2252)

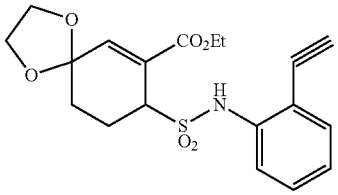

Oil (yield: 19%)

$^1$H-NMR spectrum (400 MHz, $CDCl_3$) δ ppm:

7.66 (1H, dd, J=8 Hz, 1 Hz), 7.47 (1H, dd, J=8 Hz, 2 Hz), 7.37 (1H, td, J=8 Hz, 2 Hz), 7.21 (1H, s), 7.07 (1H, td, J=8 Hz, 1 Hz), 6.82 (1H, t, J=1 Hz), 4.52-4.49 (1H, m), 4.22-4.01 (5H, m), 3.95-3.88 (1H, m), 3.49 (1H, s), 2.65-2.50 (2H, m), 2.24-2.13 (1H, m), 1.88-1.81 (1H, m), 1.22 (3H, t, J=7 Hz).

Example 63

Ethyl 8-[N-(2-isopropylphenyl)sulfamoyl]-1,4-dioxaspiro[4.5]dec-6-ene-7-carboxylate (Exemplified compound No. 1-2259)

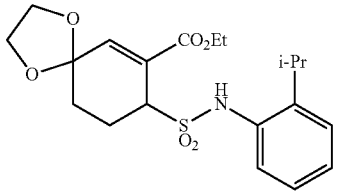

Pale brown powder (yield: 65%)

Melting point: 115-118° C.

$^1$H-NMR spectrum (500 MHz, $CDCl_3$) δ ppm:

7.53-7.49 (1H, m), 7.34-7.30 (1H, m), 7.23-7.17 (2H, m), 6.86 (1H, s), 6.69 (1H, s), 4.47 (1H, dd, J=6 Hz, 2 Hz), 4.27-4.02 (5H, m), 3.95-3.89 (1H, m), 3.33-3.24 (1H, m), 2.53-2.47 (1H, m), 2.42 (1H, td, J=14 Hz, 3 Hz), 2.18-2.10 (1H, m), 1.86-1.81 (1H, m), 1.29-1.21 (9H, m).

Example 64

Ethyl 8-[N-(2-t-butylphenyl)sulfamoyl]-1,4-dioxaspiro[4.5]dec-6-ene-7-carboxylate (Exemplified compound No. 1-2266)

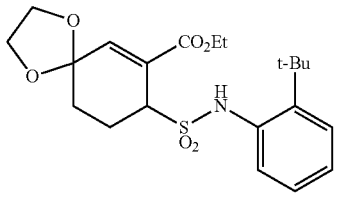

White powder (yield: 53%)

Melting point: 117-120° C.

$^1$H-NMR spectrum (400 MHz, $CDCl_3$) δ ppm:

7.45 (1H, dd, J=8 Hz, 1 Hz), 7.38 (1H, dd, J=8 Hz, 2 Hz), 7.23 (1H, td, J=8 Hz, 2 Hz), 7.12-7.07 (1H, m), 6.86 (1H, t, J=1 Hz), 6.64 (1H, s), 4.64-4.61 (1H, m), 4.24-4.03 (5H, m), 3.97-3.90 (1H, m), 2.65-2.53 (2H, m), 2.28-2.18 (1H, m), 1.90-1.83 (1H, m), 1.45 (9H, s), 1.23 (3H, t, J=7 Hz).

Example 65

Ethyl 8-[N-(2-sec-butylphenyl)sulfamoyl]-1,4-dioxaspiro[4.5]dec-6-ene-7-carboxylate (Exemplified compound No. 1-2273)

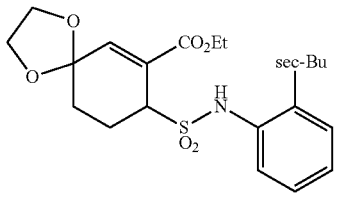

Oil (71% yield)

$^1$H-NMR spectrum (400 MHz, $CDCl_3$) δ ppm:

7.54-7.49 (1H, m), 7.29-7.16 (3H, m), 6.86 (1H, dt, J=5 Hz, 1 Hz), 6.68 (1H, d, J=10 Hz), 4.47-4.44 (1H, m), 4.27-4.02 (5H, m) 3.95-3.89 (1H, m), 3.12-2.95 (1H, m), 2.53-2.35 (2H, m), 2.19-2.07 (1H, m), 1.86-1.80 (1H, m), 1.70-1.55 (2H, m), 1.31-1.19 (6H, m), 0.91-0.80 (3H, m).

Example 66

Ethyl 8-[N-(2-methoxyphenyl)sulfamoyl]-1,4-dioxaspiro[4.5]dec-6-ene-7-carboxylate (Exemplified compound No. 1-2280)

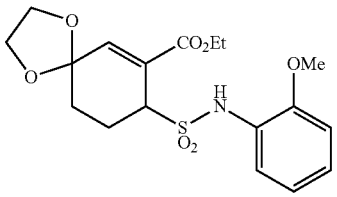

White powder (yield: 70%)

$^1$H-NMR spectrum (400 MHz, $CDCl_3$) δ ppm:

7.57 (1H, dd, J=8 Hz, 2 Hz), 7.11-7.05 (2H, m), 6.96 (1H, td, J=8 Hz, 1 Hz), 6.89 (1H, dd, J=8 Hz, 1 Hz), 6.79 (1H, t, J=1 Hz), 4.44 (1H, d, J=4 Hz), 4.21-4.00 (5H, m), 3.94-3.84 (4H, m), 2.58 (1H, td, J=14 Hz, 4 Hz), 2.50-2.43 (1H, m), 2.18-2.08 (1H, m), 1.84-1.77 (1H, m), 1.23 (3H, t, J=7 Hz).

Example 67

Ethyl 8-[N-(2-ethoxyphenyl)sulfamoyl]-1,4-dioxaspiro[4.5]dec-6-ene-7-carboxylate (Exemplified compound No. 1-2287)

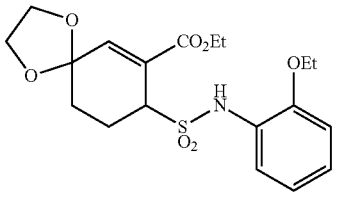

White powder (yield: 60%)

Melting point: 129-134° C.

$^1$H-NMR spectrum (400 MHz, $CDCl_3$) δ ppm:

7.58 (1H, dd, J=8 Hz, 2 Hz), 7.12 (1H, s), 7.06 (1H, td, J=8 Hz, 2 Hz), 6.95 (1H, td, J=8 Hz, 2 Hz), 6.87 (1H, dd, J=8 Hz, 1 Hz), 6.79 (1H, t, J=1 Hz), 4.45-4.42 (1H, m), 4.20-4.00 (7H, m), 3.94-3.87 (1H, m), 2.57 (1H, td, J=14 Hz, 4 Hz), 2.50-2.44 (1H, m), 2.18-2.08 (1H, m), 1.85-1.78 (1H, m), 1.45 (3H, t, J=7 Hz), 1.23 (3H, t, J=7 Hz)

Example 68

Ethyl 8-[N-(2-difluoromethoxyphenyl)sulfamoyl]-1,4-dioxaspiro[4.5]dec-6-ene-7-carboxylate (Exemplified compound No. 1-2294)

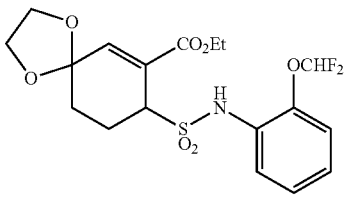

White powder (yield: 48%)

Melting point: 85-88° C.

$^1$H-NMR spectrum (400 MHz, $CDCl_3$) δ ppm:

7.69 (1H, dd, J=8 Hz, 2 Hz), 7.25-7.08 (4H, m), 6.84 (1H, s), 6.57 (1H, dd, J=74 Hz, 73 Hz), 4.44-4.41 (1H, m), 4.21-4.02 (5H, m), 3.95-3.89 (1H, m), 2.57-2.44 (2H, m), 2.21-2.10 (1H, m), 1.90-1.82 (1H, m), 1.26 (3H, t, J=7 Hz).

Example 69

Ethyl 8-[N-(2-methylsulfanylphenyl)sulfamoyl]-1,4-dioxaspiro[4.5]dec-6-ene-7-carboxylate (Exemplified compound No. 1-2301)

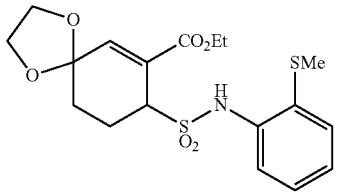

White powder (yield: 56%)

Melting point: 93-95° C.

$^1$H-NMR spectrum (400 MHz, $CDCl_3$) δ ppm:

7.70 (1H, s), 7.63 (1H, dd, J=8 Hz, 1 Hz), 7.51 (1H, dd, J=8 Hz, 2 Hz), 7.33-7.28 (1H, m), 7.08 (1H, td, J=8 Hz, 1 Hz), 6.82 (1H, q, J=1 Hz), 4.50 (1H, d, J=4 Hz), 4.21-4.01 (5H, m), 3.95-3.88 (1H, m), 2.65-2.50 (2H, m), 2.38 (3H, s), 2.23-2.12 (1H, m), 1.88-1.81 (1H, m), 1.25-1.21 (3H, m).

Example 70

Ethyl 8-[N-(2-acetylphenyl)sulfamoyl]-1,4-dioxaspiro[4.5]dec-6-ene-7-carboxylate (Exemplified compound No. 1-2308)

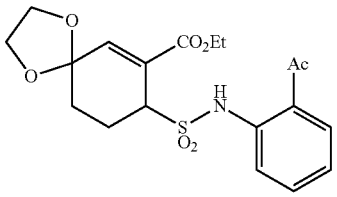

Oil (yield: 25%)

$^1$H-NMR spectrum (400 MHz, $CDCl_3$) δ ppm:

11.46 (1H, s), 7.91 (1H, dd, J=8 Hz, 1 Hz), 7.85 (1H, dd, J=8 Hz, 1 Hz), 7.59-7.54 (1H, m), 7.15-7.10 (1H, m), 6.80 (1H, t, J=1 Hz), 4.50-4.47 (1H, m), 4.16-4.00 (5H, m), 3.94-3.88 (1H, m), 2.68-2.59 (4H, m), 2.56-2.49 (1H, m), 2.20-2.09 (1H, m), 1.87-1.80 (1H, m), 1.25 (3H, t, J=7 Hz).

Example 71

Ethyl 8-[N-(2-benzylphenyl)sulfamoyl]-1,4-dioxaspiro[4.5]dec-6-ene-7-carboxylate (Exemplified compound No. 1-2315)

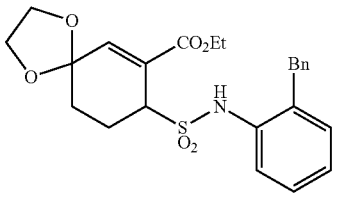

White powder (yield: 73%)

Melting point: 127-129° C.

$^1$H-NMR spectrum (500 MHz, $CDCl_3$) δ ppm:

7.58 (1H, dd, J=8 Hz, 1 Hz), 7.32-7.13 (8H, m), 6.80 (1H, s), 6.50 (1H, s), 4.36 (1H, dd, J=6 Hz, 2 Hz), 4.23-4.00 (7H, m), 3.93-3.87 (1H, m), 2.36 (1H, td, J=14 Hz, 4 Hz), 2.19-2.13 (1H, m), 2.03-1.94 (1H, m), 1.76-1.70 (1H, m), 1.26 (3H, t, J=7 Hz).

Example 72

Ethyl 8-{N-[2-(morpholin-4-yl)phenyl]sulfamoyl}-1,4-dioxaspiro[4.5]dec-6-ene-7-carboxylate (Exemplified compound No. 1-2322)

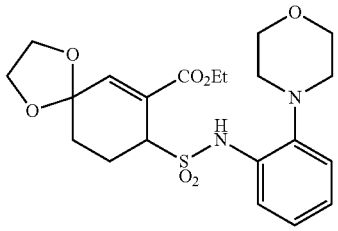

White powder (yield: 71%)

Melting point: 118-121° C.

$^1$H-NMR spectrum (400 MHz, $CDCl_3$) δ ppm:

8.10 (1H, s), 7.58 (1H, dd, J=8 Hz, 2 Hz), 7.23 (1H, dd, J=8 Hz, 2 Hz), 7.20-7.15 (1H, m), 7.07 (1H, td, J=8 Hz, 2 Hz), 6.82 (1H, t, 1 Hz), 4.47-4.44 (1H, m), 4.15-4.00 (5H, m), 3.95-3.85 (5H, m), 2.92-2.83 (4H, m), 2.59-2.50 (2H, m), 2.24-2.12 (1H, m), 1.90-1.82 (1H, m), 1.23 (3H, t, J=7 Hz).

Example 73

Ethyl 8-[N-(9H-fluoren-1-yl)sulfamoyl]-1,4-dioxaspiro[4.5]dec-6-ene-7-carboxylate (Exemplified compound No. 1-2329)

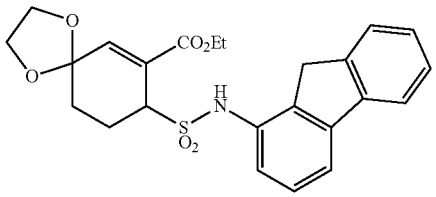

Pale brown powder (yield: 60%)

Melting point: 156-160° C.

$^1$H-NMR spectrum (500 MHz, $CDCl_3$) δ ppm:

7.78 (1H, d, J=7 Hz), 7.62 (1H, d, J=8 Hz), 7.58 (1H, d, J=7 Hz), 7.54 (1H, d, J=8 Hz), 7.42-7.37 (2H, m), 7.34 (1H, td, J=7 Hz, 1 Hz), 6.92 (1H, s), 6.86 (1H, s), 4.45 (1H, dd, J=6 Hz, 2 Hz), 4.22-4.00 (5H, m), 3.96 (2H, s), 3.94-3.89 (1H, m), 2.56-2.50 (1H, m), 2.37 (1H, td, J=14 Hz, 3 Hz), 2.17-2.08 (1H, m), 1.88-1.82 (1H, m), 1.26 (3H, t, J=7 Hz).

Example 74

Ethyl 8-(N-{2-[2-(pyridin-4-yl)ethyl] phenyl}sulfamoyl)-1,4-dioxaspiro[4.5]dec-6-ene-7-carboxylate (Exemplified compound No. 1-2336)

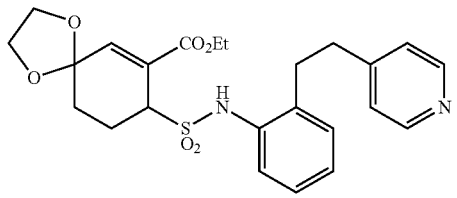

White powder (yield: 26%)

Melting point: 77-80° C.

$^1$H-NMR spectrum (500 MHz, $CDCl_3$) δ ppm:

8.50-8.47 (2H, m), 7.54-7.52 (1H, m), 7.26-7.22 (1H, m), 7.19-7.13 (4H, m), 6.89 (1H, t, J=1 Hz), 6.80 (1H, s), 4.43 (1H, dd, J=6 Hz, 3 Hz), 4.25-4.18 (2H, m), 4.14-4.03 (3H, m), 3.96-3.90 (1H, m), 3.15-3.00 (2H, m), 2.99-2.89 (2H, m), 2.54-2.48 (1H, m), 2.33 (1H, td, J=14 Hz, 3 Hz), 2.17-2.09 (1H, m), 1.88-1.82 (1H, m), 1.29 (3H, t, J=7 Hz).

Example 75

Ethyl 8-(N-{2-[2-(t-butoxycarbonylamino) ethyl] phenyl}sulfamoyl)-1,4-dioxaspiro[4.5]dec-6-ene-7-carboxylate (Exemplified compound No. 1-2343)

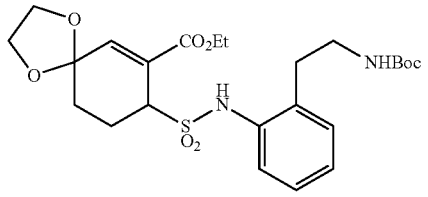

Amorphous substance (yield: 65%)

$^1$H-NMR spectrum (500 MHz, $CDCl_3$) δ ppm:

8.00 (1H, s), 7.62 (1H, d, J=8 Hz), 7.24 (1H, td, J=8 Hz, 2 Hz), 7.17 (1H, d, J=7 Hz), 7.10 (1H, t, J=7 Hz), 6.83 (1H, s), 4.90 (1H, brs), 4.46 (1H, d, J=5 Hz), 4.23-4.01 (5H, m), 3.94-3.88 (1H, m), 3.27 (2H, q, J=7 Hz), 2.96-2.83 (2H, m), 2.59-2.52 (2H, m), 2.18-2.09 (1H, m), 1.83-1.78 (1H, m), 1.48-1.41 (9H, m), 1.27 (3H, t, J=7 Hz).

Example 76

Ethyl 8-[N-(2-aminophenyl)sulfamoyl]-1,4-dioxaspiro[4.5]dec-6-ene-7-carboxylate (Exemplified compound No. 1-2350)

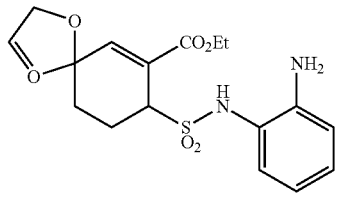

Oil (yield: 13%)

$^1$H-NMR spectrum (400 MHz, $CDCl_3$) δ ppm:

7.39 (1H, dd, J=8 Hz, 2 Hz), 7.11-7.06 (1H, m), 6.89 (1H, t, J=1 Hz), 6.79-6.73 (2H, m), 4.46 (1H, dd, J=6 Hz, 3 Hz), 4.31-3.86 (3H, m), 4.28 (2H, q, J=7 Hz), 4.11-4.02 (3H, m), 3.95-3.89 (1H, m), 2.48-2.41 (1H, m), 2.24 (1H, td, J=14 Hz, 3 Hz), 2.13-2.03 (1H, m), 1.86-1.79 (1H, m), 1.32 (3H, t, J=7 Hz).

Example 77

Ethyl 8-[N-(2,4-difluorophenyl)sulfamoyl]-1,4-dioxaspiro[4.5]dec-6-ene-7-carboxylate (Exemplified compound No. 1-276)

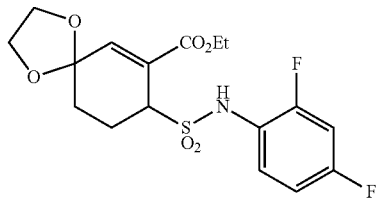

White powder (yield: 74%)

Melting point: 128-131° C.

$^1$H-NMR spectrum (400 MHz, $CDCl_3$) δ ppm:

7.64-7.57 (1H, m), 6.97 (1H, brs), 6.93-6.86 (2H, m), 6.84 (1H, t, J=1 Hz), 4.36 (1H, dd, J=6 Hz, 2 Hz), 4.28-4.02 (5H, m), 3.95-3.90 (1H, m), 2.53-2.46 (1H, m), 2.40 (1H, td, J=1-4 Hz, 4 Hz), 2.21-2.10 (1H, m), 1.88-1.81 (1H, m), 1.29 (3H, t, J=7 Hz).

Example 78

Ethyl 8-[N-(2-bromo-4-fluorophenyl)sulfamoyl]-1,4-dioxaspiro[4.5]dec-6-ene-7-carboxylate (Exemplified compound No. 1-1550)

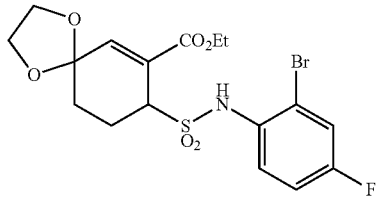

Pale yellow powder (yield: 48%)

Melting point: 106-111° C.

$^1$H-NMR spectrum (400 MHz, $CDCl_3$) δ ppm:

7.68 (1H, dd, J=9 Hz, 5 Hz), 7.32 (1H, dd, J=8 Hz, 3 Hz), 7.10-7.04 (1H, m), 6.94 (1H, s), 6.82 (1H, t, J=1 Hz), 4.46-4.43 (1H, m), 4.26-4.01 (5H, m), 3.95-3.89 (1H, m), 2.57-2.47 (2H, m), 2.24-2.13 (1H, m), 1.87-1.81 (1H, m), 1.26 (3H, t, J=7 Hz).

Example 79

Ethyl 8-[N-(4-fluoro-2-methylphenyl)sulfamoyl]-1,4-dioxaspiro[4.5]dec-6-ene-7-carboxylate (Exemplified compound No. 1-2357)

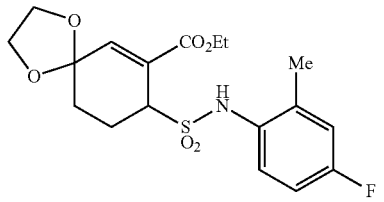

White powder (yield: 79%)

Melting point: 103-105° C.

$^1$H-NMR spectrum (400 MHz, $CDCl_3$) δ ppm:

7.49 (1H, dd, J=9 Hz, 5 Hz), 6.96-6.85 (3H, m), 6.64 (1H, brs), 4.39 (1H, dd, J=6 Hz, 3 Hz), 4.27-4.18 (2H, m), 4.14-4.02 (3H, m), 3.96-3.89 (1H, m), 2.52-2.45 (1H, m), 2.40-2.31 (4H, m), 2.18-2.08 (1H, m), 1.87-1.80 (1H, m), 1.29 (3H, t, J=7 Hz).

Example 80

Ethyl 8-[N-(3-chloro-4-fluorophenyl)sulfamoyl]-1,4-dioxaspiro[4.5]dec-6-ene-7-carboxylate (Exemplified compound No. 1-2364)

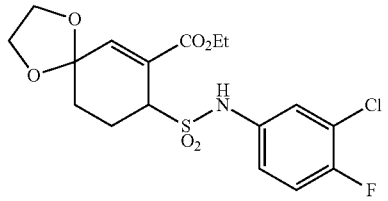

Pale brown powder (yield: 81%)

Melting point: 111-118° C.

$^1$H-NMR spectrum (400 MHz, $CDCl_3$) δ ppm:

7.47 (1H, dd, J=6 Hz, 3 Hz), 7.29-7.25 (1H, m), 7.15-7.09 (2H, m), 6.88 (1H, s), 4.28 (2H, q, J=7 Hz), 4.21-4.18 (1H, m), 4.14-4.02 (3H, m), 3.96-3.89 (1H, m), 2.49-2.41 (1H, m), 2.25 (1H, td, J=14 Hz, 3 Hz), 2.12-2.01 (1H, m), 1.89-1.82 (1H, m), 1.34 (3H, t, J=7 Hz).

Example 81

Ethyl 8-[N-(4-fluoro-3-trifluoromethylphenyl)sulfamoyl]-1,4-dioxaspiro[4.5]dec-6-ene-7-carboxylate (Exemplified compound No. 1-2371)

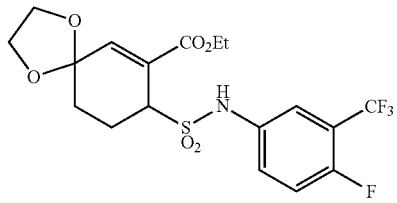

White powder (yield: 78%)

Melting point: 109-111° C.

$^1$H-NMR spectrum (400 MHz, $CDCl_3$) δ ppm:

7.64-7.57 (2H, m), 7.27-7.17 (2H, m), 6.89 (1H, s), 4.28 (2H, q, J=7 Hz), 4.19-4.16 (1H, m), 4.14-4.03 (3H, m), 3.96-

3.89 (1H, m), 2.49-2.42 (1H, m), 2.26 (1H, td, J=14 Hz, 3 Hz), 2.13-2.03 (1H, m), 1.89-1.83 (1H, m), 1.34 (3H, t, J=7 Hz).

Example 82

Ethyl 8-[N-(4-fluoro-3-methoxy phenyl)sulfamoyl]-1,4-dioxaspiro[4,5]dec-6-ene-7-carboxylate (Exemplified compound No. 1-2378)

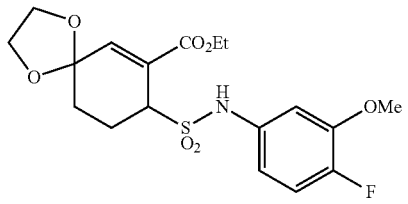

Oil (yield: 72%)

$^1$H-NMR spectrum (400 MHz, $CDCl_3$) δ ppm:

7.09 (1H, dd, J=7 Hz, 2 Hz), 7.03 (1H, dd, J=11 Hz, 9 Hz), 6.96 (1H, brs), 6.88-6.83 (2H, m), 4.30-4.23 (3H, m), 4.14-4.02 (3H, m), 3.95-3.89 (4H, m), 2.46-2.38 (1H, m), 2.27 (1H, td, J=14 Hz, 3 Hz), 2.10-2.00 (1H, m), 1.88-1.81 (1H, m), 1.33 (3H, t, J=7 Hz).

Example 83

Ethyl 8-[N-(3,4-difluorophenyl)sulfamoyl]-1,4-dioxaspiro[4.5]dec-6-ene-7-carboxylate (Exemplified compound No. 1-2385)

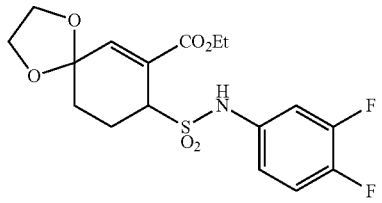

Pale brown powder (yield: 94%)

Melting point: 118-121° C.

$^1$H-NMR spectrum (400 MHz, $CDCl_3$) δ ppm:

7.33-7.26 (1H, m), 7.18-7.06 (3H, m), 6.89 (1H, s), 4.28 (2H, q, J=7 Hz), 4.19 (1H, dd, J=5 Hz, 3 Hz), 4.14-4.02 (3H, m), 3.96-3.89 (1H, m), 2.48-2.41 (1H, m), 2.25 (1H, td, J=14 Hz, 3 Hz), 2.11-2.01 (1H, m), 1.89-1.82 (1H, m), 1.34 (3H, t, J=7 Hz).

Example 84

Ethyl 8-[N-(2,4-dimethoxyphenyl)sulfamoyl]-1,4-dioxaspiro[4.5]dec-6-ene-7-carboxylate (Exemplified compound No. 1-2392)

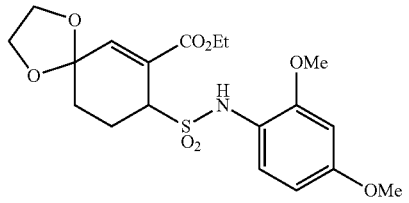

White powder (yield: 49%)

Melting point: 118-121° C.

$^1$H-NMR spectrum (400 MHz, $CDCl_3$) δ ppm:

7.47-7.45 (1H, m), 6.78 (2H, d, J=9.8 Hz), 6.50-6.47 (2H, m), 4.38 (1H, d, J=4.7 Hz), 4.21-3.80 (12H, m), 2.54 (1H, dt, J=14.2 Hz, 7.2 Hz), 2.45-2.38 (1H, m), 2.14-2.08 (1H, m), 1.81-1.76 (1H, m), 1.25 (3H, t, J=7.0 Hz).

Example 85

Ethyl 8-[N-(2-butyl-4-fluorophenyl)sulfamoyl]-1,4-dioxaspiro[4.5]dec-6-ene-7-carboxylate (Exemplified compound No. 1-628)

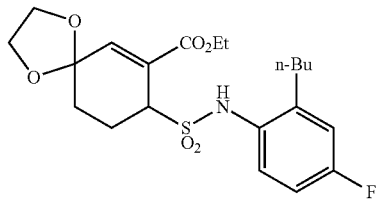

Brown oil (yield: 82%)

$^1$H-NMR spectrum (400 MHz, $CDCl_3$) δ ppm:

7.49 (1H, dd, J=9 Hz, 5 Hz), 6.94 (1H, dd, J=10 Hz, 3 Hz), 6.92-6.86 (2H, m), 6.60 (1H, s), 4.41 (1H, dd, J=6 Hz, 2 Hz), 4.28-4.18 (2H, m), 4.14-4.02 (3H, m), 3.96-3.89 (1H, m), 2.75-2.63 (2H, m), 2.52-2.45 (1H, m), 2.37 (1H, dt, J=14 Hz,

3 Hz), 2.18-2.08 (1H, m), 1.87-1.80 (1H, m), 1.63-1.52 (2H, m), 1.44-1.35 (2H, m), 1.29 (3H, t, J=7 Hz), 0.95 (3H, t, J=8 Hz).

Example 86

Ethyl 8-[N-(4-fluoro-2-pentylphenyl)sulfamoyl]-1,4-dioxaspiro[4.5]dec-6-ene-7-carboxylate (Exemplified compound No. 1-1726)

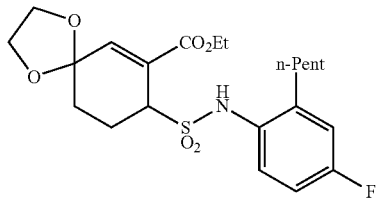

Brown oil (yield: 78%)

$^1$H-NMR spectrum (400 MHz, $CDCl_3$) δ ppm:

7.49 (1H, dd, J=9 Hz, 5 Hz), 6.94 (1H, dd, J=10 Hz, 3 Hz), 6.92-6.85 (2H, m), 6.61 (1H, s), 4.40 (1H, dd, J=6 Hz, 2 Hz), 4.27-4.18 (2H, m), 4.14-4.02 (3H, m), 3.95-3.90 (1H, m), 2.76-2.61 (2H, m), 2.52-2.45 (1H, m), 2.37 (1H, dt, J=14 Hz, 3 Hz), 2.18-2.09 (1H, m), 1.87-1.81 (1H, m), 1.65-1.52 (2H, m), 1.39-1.32 (4H, m), 1.30 (3H, t, J=7 Hz), 0.90 (3H, t, J=7 Hz).

Example 87

Ethyl 8-[N-(4-fluoro-2-hexylphenyl)sulfamoyl]-1,4-dioxaspiro[4.5]dec-6-ene-7-carboxylate (Exemplified compound No. 1-804)

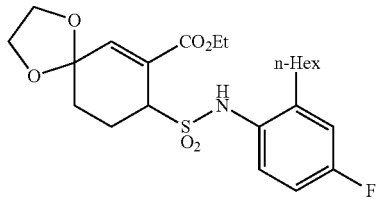

Pale brown oil (yield: 58%)

$^1$H-NMR spectrum (400 MHz, $CDCl_3$) δ ppm:

7.49 (1H, dd, J=9 Hz, 5 Hz), 6.96-6.85 (3H, m), 6.61 (1H, s), 4.40 (1H, dd, J=6 Hz, 2 Hz), 4.28-4.18 (2H, m), 4.14-4.02 (3H, m), 3.95-3.89 (1H, m), 2.76-2.61 (2H, m), 2.52-2.45 (1H, m), 2.37 (1H, td, J=14 Hz, 3 Hz), 2.18-2.08 (1H, m), 1.87-1.81 (1H, m), 1.63-1.52 (2H, m), 1.42-1.25 (9H, m), 0.91-0.85 (3H, m).

Example 88

Ethyl 8-[N-(4-fluoro-2-heptylphenyl)sulfamoyl]-1,4-dioxaspiro[4.5]dec-6-ene-7-carboxylate (Exemplified compound No. 1-980)

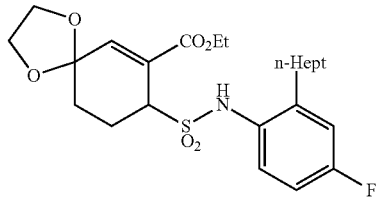

Pale yellow oil (yield: 85%)

$^1$H-NMR spectrum (400 MHz, $CDCl_3$) δ ppm:

7.49 (1H, dd, J=9 Hz, 5 Hz), 6.96-6.87 (3H, m), 6.63 (1H, s), 4.41 (1H, dd, J=6 Hz, 2 Hz), 4.27-4.19 (2H, m), 4.14-3.91 (4H, m), 2.76-2.62 (2H, m), 2.52-2.46 (1H, m), 2.37 (1H, dt, J=14 Hz, 3 Hz), 2.18-2.09 (1H, m), 1.84 (1H, dt, J=13 Hz, 4 Hz), 1.62-1.55 (2H, m), 1.40-1.24 (11H, m), 0.88 (3H, t, J=7 Hz).

Example 89

Ethyl 8-[N-(4-fluoro-2-octylphenyl)sulfamoyl]-1,4-dioxaspiro[4.5]dec-6-ene-7-carboxylate (Exemplified compound No. 1-1902)

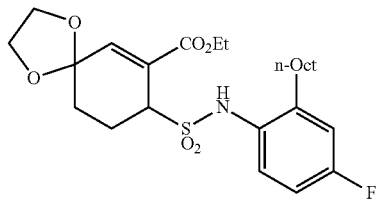

Pale yellow oil (yield: 72%)

$^1$H-NMR spectrum (400 MHz, $CDCl_3$) δ ppm:

7.49 (1H, dd, J=9 Hz, 5 Hz), 6.96-6.87 (3H, m), 6.62 (1H, s), 4.40 (1H, dd, J=6 Hz, 2 Hz), 4.27-4.19 (2H, m), 4.15-3.90 (4H, m), 2.74-2.62 (2H, m), 2.52-2.46 (1H, m), 2.37 (1H, dt,

J=14 Hz, 3 Hz), 2.18-2.10 (1H, m), 1.86-1.81 (1H, m), 1.63-1.53 (2H, m), 1.40-1.24 (13H, m), 0.88 (3H, t, J=7 Hz).

Example 90

Ethyl 8-[N-(4-fluoro-2-nonylphenyl)sulfamoyl]-1,4-dioxaspiro[4.5]dec-6-ene-7-carboxylate (Exemplified compound No. 1-2602)

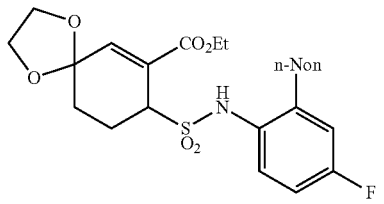

Pale orange oil (yield: 82%)

$^1$H-NMR spectrum (500 MHz, $CDCl_3$) δ ppm:

7.49 (1H, dd, J=9 Hz, 5 Hz), 6.94 (1H, dd, J=9 Hz, 3 Hz), 6.92-6.85 (2H, m), 6.62 (1H, s), 4.40 (1H, dd, J=6 Hz, 2 Hz), 4.28-4.17 (2H, m), 4.15-4.03 (3H, m), 3.95-3.90 (1H, m), 2.75-2.62 (2H, m), 2.52-2.45 (1H, m), 2.37 (1H, td, J=14 Hz, 3 Hz), 2.18-2.09 (1H, m), 1.86-1.81 (1H, m), 1.63-1.53 (2H, m), 1.39-1.22 (15H, m), 0.88 (3H, t, J=7 Hz).

Example 91

Ethyl 8-[N-(2-decyl-4-fluorophenyl)sulfamoyl]-1,4-dioxaspiro[4.5]dec-6-ene-7-carboxylate (Exemplified compound No. 1-2616)

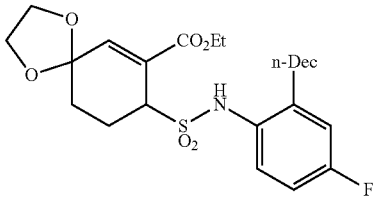

Pale yellow oil (yield: 83%)

$^1$H-NMR spectrum (500 MHz, $CDCl_3$) δ ppm:

7.49 (1H, dd, J=9 Hz, 5 Hz), 6.94 (1H, dd, J=9 Hz, 3 Hz), 6.92-6.85 (2H, m), 6.62 (1H, s), 4.40 (1H, dd, J=5 Hz, 3 Hz), 4.28-4.17 (2H, m), 4.15-4.03 (3H, m), 3.95-3.90 (1H, m), 2.75-2.62 (2H, m), 2.51-2.45 (1H, m), 2.37 (1H, td, J=14 Hz, 3 Hz), 2.18-2.09 (1H, m), 1.86-1.81 (1H, m), 1.63-1.53 (2H, m), 1.39-1.22 (17H, m), 0.88 (3H, t, J=7 Hz).

Example 92

Ethyl 8-[N-(4-chloro-2-fluorophenyl)sulfamoyl]-1,4-dioxaspiro[4.5]dec-6-ene-7-carboxylate (Exemplified compound No. 1-2399)

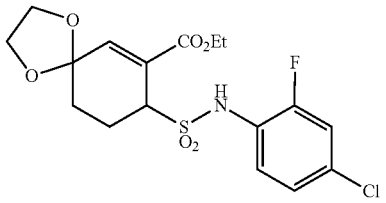

White powder (yield: 65%)

Melting point: 130-133° C.

$^1$H-NMR spectrum (400 MHz, $CDCl_3$) δ ppm:

7.62-7.56 (1H, m), 7.18-7.11 (2H, m), 7.02 (1H, s), 6.84 (1H, t, J=1 Hz), 4.37 (1H, dd, J=6 Hz, 2 Hz), 4.25-4.02 (5H, m), 3.96-3.89 (1H, m), 2.55-2.48 (1H, m), 2.42 (1H, td, J=14 Hz, 4 Hz), 2.21-2.11 (1H, m), 1.88-1.82 (1H, m), 1.29 (3H, t, J=7 Hz).

Example 93

Ethyl 8-[N-(2-bromo-4-chlorophenyl)sulfamoyl]-1,4-dioxaspiro[4.5]dec-6-ene-7-carboxylate (Exemplified compound No. 1-2406)

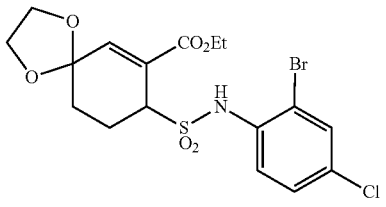

Pale brown powder (yield: 51%)

Melting point: 100-110° C.

$^1$H-NMR spectrum (400 MHz, $CDCl_3$) δ ppm:

7.64 (1H, d, J=9 Hz), 7.56 (1H, d, J=3 Hz), 7.31 (1H, dd, J=9 Hz, 3 Hz), 7.02 (1H, s), 6.83 (1H, t, J=1 Hz), 4.47-4.43

(1H, m), 4.23-4.02 (5H, m), 3.95-3.89 (1H, m), 2.58-2.48 (2H, m), 2.24-2.14 (1H, m), 1.89-1.82 (1H, m), 1.26 (3H, t, J=7 Hz).

Example 94

Ethyl 8-[N-(4-chloro-2-methylphenyl)sulfamoyl]-1,4-dioxaspiro[4.5]dec-6-ene-7-carboxylate (Exemplified compound No. 1-2413)

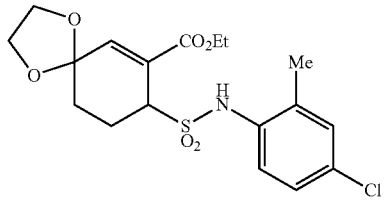

White powder (yield: 74%)

Melting point: 123-126° C.

$^1$H-NMR spectrum (400 MHz, $CDCl_3$) δ ppm:

7.49 (1H, d, J=9 Hz), 4.21-4.15 (2H, m), 6.86 (1H, t, J=1 Hz), 6.65 (1H, s), 4.38 (1H, dd, J=6 Hz, 3 Hz), 4.24-4.15 (2H, m), 4.14-4.02 (3H, m), 3.96-3.89 (1H, m), 2.54-2.47 (1H, m), 2.41-2.32 (4H, m), 2.19-2.09 (1H, m), 1.88-1.82 (1H, m), 1.29 (3H, t, J=7 Hz).

Example 95

Ethyl 8-[N-(4-chloro-2-methoxycarbonylphenyl)sulfamoyl]-1,4-dioxaspiro[4.5]dec-6-ene-7-carboxylate (Exemplified compound No. 1-2420)

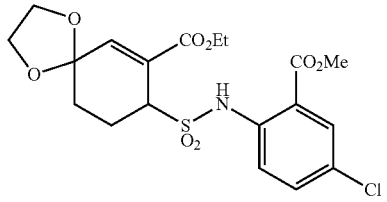

White powder (yield: 46%)

Melting point: 131-134° C.

$^1$H-NMR spectrum (400 MHz, $CDCl_3$) δ ppm:

10.48 (1H, s), 8.00 (1H, d, J=3 Hz), 7.79 (1H, d, J=9 Hz), 7.50 (1H, dd, J=9 Hz, 3 Hz), 6.80 (1H, t, J=1 Hz), 4.47 (1H, dd, J=6 Hz, 2 Hz), 4.14-4.01 (5H, m), 3.95-3.88 (4H, m), 2.66-2.50 (2H, m), 2.22-2.11 (1H, m), 1.88-1.81 (1H, m), 1.25 (3H, t, J=7 Hz).

Example 96

Ethyl 8-[N-(3,4-dichlorophenyl)sulfamoyl]-1,4-dioxaspiro[4.5]dec-6-ene-7-carboxylate (Exemplified compound No. 1-2427)

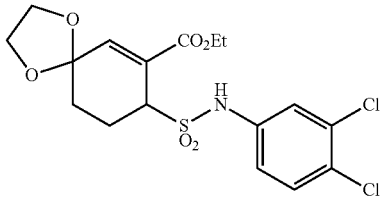

White powder (yield: 66%)

Melting point: 163-164° C.

$^1$H-NMR spectrum (400 MHz, $CDCl_3$) δ ppm:

7.49 (1H, d, J=2 Hz), 7.41 (1H, d, J=9 Hz), 7.23 (1H, dd, J=9 Hz, 3 Hz), 7.16 (1H, s), 6.88 (1H, t, J=1 Hz), 4.27 (2H, q, J=7 Hz), 4.21 (1H, q, J=3 Hz), 4.14-4.02 (3H, m), 3.96-3.88 (1H, m), 2.50-2.43 (1H, m), 2.27 (1H, td, J=14 Hz, 3 Hz), 2.13-2.03 (1H, m), 1.89-1.82 (1H, m), 1.33 (3H, t, J=7 Hz).

Example 97

Ethyl 8-[N-(2,5-difluorophenyl)sulfamoyl]-1,4-dioxaspiro[4.5]dec-6-ene-7-carboxylate (Exemplified compound No. 1-2434)

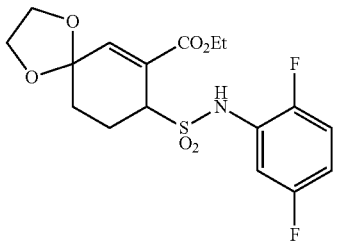

Pale brown powder (yield: 61%)

Melting point: 125-128° C.

$^1$H-NMR spectrum (500 MHz, $CDCl_3$) δ ppm:

7.45-7.41 (1H, m), 7.09-7.00 (2H, m), 6.86 (1H, s), 6.80-6.74 (1H, m), 4.41 (1H, dd, J=6 Hz, 2 Hz), 4.26-4.02 (5H, m), 3.95-3.90 (1H, m), 2.58-2.52 (1H, m), 2.44 (1H, td, J=14 Hz, 3 Hz), 2.23-2.14 (1H, m), 1.89-1.84 (1H, m), 1.28 (3H, t, J=7 Hz).

Example 98

Ethyl 8-[N-(2,6-difluorophenyl)sulfamoyl]-1,4-dioxaspiro[4.5]dec-6-ene-7-carboxylate (Exemplified compound No. 1-2441)

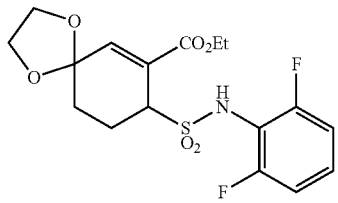

White powder (yield: 56%)

Melting point: 129-131° C.

$^1$H-NMR spectrum (500 MHz, $CDCl_3$) δ ppm:

7.25-7.18 (1H, m), 7.01-6.95 (2H, m), 6.89-6.87 (2H, m), 4.64 (1H, dd, J=5 Hz, 2 Hz), 4.31-4.21 (2H, m), 4.15-4.03 (3H, m), 3.96-3.91 (1H, m), 2.63-2.57 (1H, m), 2.36 (1H, td, J=14 Hz, 3 Hz), 2.26-2.17 (1H, m), 1.87-1.82 (1H, m), 1.29 (3H, t, J=7 Hz).

Example 99

Ethyl 8-[N-(2-fluoro-4-methylphenyl)sulfamoyl]-1,4-dioxaspiro[4.5]dec-6-ene-7-carboxylate (Exemplified compound No. 1-2448)

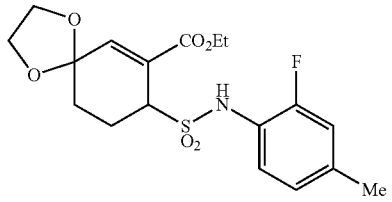

White powder (yield: 69%)

Melting point: 136-138° C.

$^1$H-NMR spectrum (500 MHz, $CDCl_3$) δ ppm:

7.49 (1H, t, J=9 Hz), 6.95-6.92 (2H, m), 6.86 (1H, d, J=2 Hz), 6.83 (1H, s), 4.40-4.37 (1H, m), 4.26-4.15 (2H, m), 4.13-4.01 (3H, m), 3.94-3.89 (1H, m), 2.51-2.40 (2H, m), 2.32 (3H, s), 2.18-2.09 (1H, m), 1.86-1.81 (1H, m), 1.27 (3H, t, J=7 Hz).

Example 100

Ethyl 8-[N-(2-fluoro-5-methylphenyl)sulfamoyl]-1,4-dioxaspiro[4.5]dec-6-ene-7-carboxylate (Exemplified compound No. 1-2455)

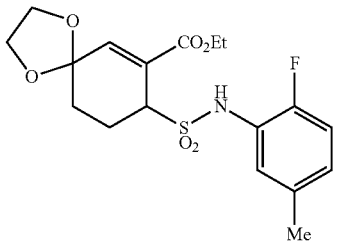

Oil (yield: 63%)

$^1$H-NMR spectrum (500 MHz, $CDCl_3$) δ ppm:

7.43 (1H, dd, J=8 Hz, 2 Hz), 6.98 (1H, dd, J=10 Hz, 8 Hz), 6.91-6.87 (2H, m), 6.83 (1H, t, J=1 Hz), 4.42 (1H, dd, J=6 Hz, 2 Hz), 4.26-4.02 (5H, m), 3.95-3.89 (1H, m), 2.54-2.42 (2H, m), 2.20-2.12 (1H, m), 1.87-1.82 (1H, m), 1.27 (3H, t, J=7 Hz).

Example 101

Ethyl 8-[N-(2-fluoro-4-methoxyphenyl)sulfamoyl]-1,4-dioxaspiro[4.5]dec-6-ene-7-carboxylate (Exemplified compound No. 1-2462)

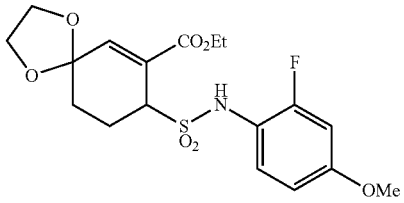

Pale brown powder (yield: 57%)

Melting point: 167-169° C.

$^1$H-NMR spectrum (400 MHz, $CDCl_3$) δ ppm:

7.50 (1H, t, J=9 Hz), 6.82 (1H, t, J=1 Hz), 6.79 (1H, brs), 6.71-6.67 (2H, m), 4.38-4.35 (1H, m), 4.28-4.19 (2H, m), 4.14-4.01 (3H, m), 3.95-3.88 (1H, m), 3.79 (3H, s), 2.49-2.36 (2H, m), 2.18-2.08 (1H, m), 1.86-1.79 (1H, m), 1.29 (3H, t, J=7 Hz).

Example 102

Ethyl 8-[N-(5-chloro-2-fluorophenyl)sulfamoyl]-1,4-dioxaspiro[4.5]dec-6-ene-7-carboxylate (Exemplified compound No. 1-2469)

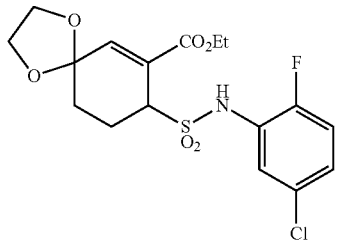

White powder (yield: 55%)

Melting point: 88-90° C.

$^1$H-NMR spectrum (500 MHz, $CDCl_3$) δ ppm:

7.68-7.65 (1H, m), 7.07-7.01 (3H, m), 6.86 (1H, s), 4.40 (1H, dd, J=6 Hz, 2 Hz), 4.27-4.15 (2H, m), 4.14-4.03 (3H, m), 3.96-3.90 (1H, m), 2.58-2.52 (1H, m), 2.43 (1H, td, J=14 Hz, 3 Hz), 2.23-2.15 (1H, m), 1.89-1.84 (1H, m), 1.29 (3H, t, J=7 Hz).

Example 103

Ethyl 8-[N-(2,3,4-trifluorophenyl)sulfamoyl]-1,4-dioxaspiro[4.5]dec-6-ene-7-carboxylate (Exemplified compound No. 1-2476)

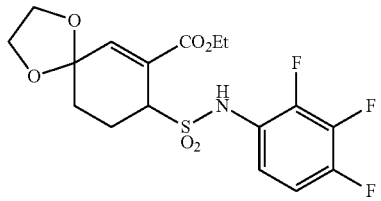

White powder (yield: 71%)

Melting point: 149-152° C.

$^1$H-NMR spectrum (400 MHz, $CDCl_3$) δ ppm:

7.41-7.34 (1H, m), 7.14 (1H, brs), 7.02-6.93 (1H, m), 6.85 (1H, t, J=1 Hz), 4.36 (1H, dd, J=6 Hz, 2 Hz), 4.28-4.20 (2H, m), 4.14-4.02 (3H, m), 3.96-3.90 (1H, m), 2.55-2.46 (1H, m), 2.38 (1H, td, J=14 Hz, 4 Hz), 2.22-2.12 (1H, m), 1.89-1.82 (1H, m), 1.31 (3H, t, J=7 Hz).

Example 104

Ethyl 8-[N-(2,4,5-trifluorophenyl)sulfamoyl]-1,4-dioxaspiro[4.5]dec-6-ene-7-carboxylate (Exemplified compound No. 1-2483)

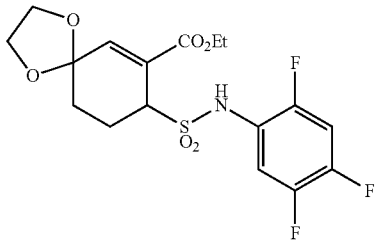

White powder (yield: 72%)

Melting point: 104-107° C.

$^1$H-NMR spectrum (400 MHz, $CDCl_3$) δ ppm:

7.60-7.52 (1H, m), 7.05-6.97 (2H, m), 6.86 (1H, t, J=1 Hz), 4.35 (1H, dd, J=6 Hz, 2 Hz), 4.28-4.19 (2H, m), 4.15-4.02 (3H, m), 3.96-3.90 (1H, m), 2.56-2.49 (1H, m), 2.38 (1H, td, J=14 Hz, 4 Hz), 2.23-2.12 (1H, m), 1.90-1.83 (1H, m), 1.30 (3H, t, J=7 Hz).

Example 105

Ethyl 8-[N-(2,4,6-trifluorophenyl)sulfamoyl]-1,4-dioxaspiro[4.5]dec-6-ene-7-carboxylate (Exemplified compound No. 1-2490)

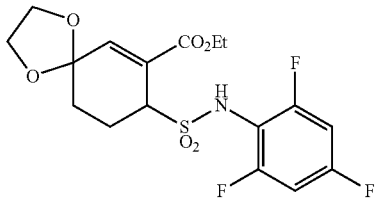

White powder (yield: 61%)

Melting point: 131-133° C.

$^1$H-NMR spectrum (400 MHz, $CDCl_3$) δ ppm:

6.91 (1H, s), 6.88 (1H, t, J=1 Hz), 6.80-6.72 (2H, m), 4.55 (1H, dd, J=6 Hz, 3 Hz), 4.31-4.23 (2H, m), 4.14-4.03 (3H, m), 3.96-3.90 (1H, m), 2.62-2.55 (1H, m), 2.32 (1H, td, J=14 Hz, 3 Hz), 2.25-2.15 (1H, m), 1.88-1.81 (1H, m), 1.31 (3H, t, J=7 Hz).

Example 106

Ethyl 8-[N-(2,4-dichlorophenyl)sulfamoyl]-1,4-dioxaspiro[4.5]dec-6-ene-7-carboxylate (Exemplified compound No. 1-2497)

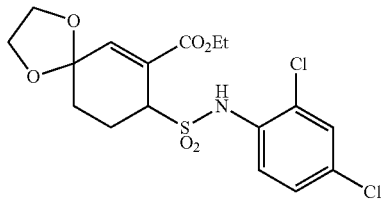

Pale brown powder (yield: 67%)

Melting point: 109-111° C.

$^1$H-NMR spectrum (400 MHz, $CDCl_3$) δ ppm:

7.65 (1H, d, J=9 Hz), 7.41 (1H, d, J=2 Hz), 7.28-7.24 (1H, m), 7.07 (1H, s), 6.83 (1H, s), 4.46-4.42 (1H, m), 4.24-4.02 (5H, m), 3.98-3.89 (1H, m), 2.56-2.46 (2H, m), 2.24-2.13 (1H, m), 1.89-1.82 (1H, m), 1.26 (3H, t, J=7 Hz).

Example 107

Ethyl 8-[N-(4-bromo-2-chlorophenyl)sulfamoyl]-1,4-dioxaspiro[4.5]dec-6-ene-7-carboxylate (Exemplified compound No. 1-2504)

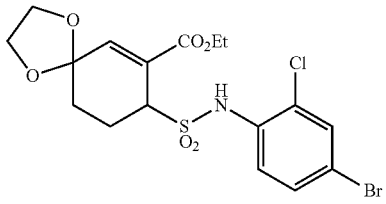

White powder (yield: 74%)

Melting point: 102-107° C.

$^1$H-NMR spectrum (500 MHz, $CDCl_3$) δ ppm:

7.59 (1H, d, J=9 Hz), 7.55 (1H, d, J=2 Hz), 7.40 (1H, dd, J=9 Hz, 2 Hz), 7.08 (1H, s), 6.83 (1H, s), 4.44 (1H, d, J=5 Hz), 4.23-4.02 (5H, m), 3.95-3.89 (1H, m), 2.55-2.47 (2H, m), 2.23-2.14 (1H, m), 1.89-1.83 (1H, m), 1.26 (3H, t, J=7 Hz).

Example 108

Ethyl 8-[N-(2-chloro-4-methylphenyl)sulfamoyl]-1,4-dioxaspiro[4.5]dec-6-ene-7-carboxylate (Exemplified compound No. 1-452)

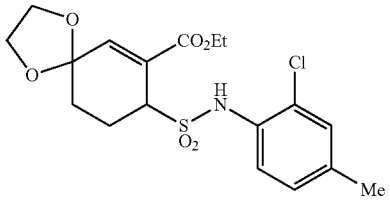

Pale brown powder (yield: 69%)

Melting point: 130-135° C.

$^1$H-NMR spectrum (400 MHz, $CDCl_3$) δ ppm:

7.57 (1H, d, J=9 Hz), 7.20 (1H, d, J=2 Hz), 7.10-7.06 (1H, m), 6.97 (1H, s), 6.81 (1H, d, J=1 Hz), 4.44 (1H, d, J=5 Hz), 4.25-4.00 (5H, m), 3.95-3.87 (1H, m), 2.59-2.45 (2H, m), 2.31 (3H, s), 2.22-2.10 (1H, m), 1.87-1.79 (1H, m), 1.25 (3H, t, J=7 Hz).

Example 109

Ethyl 8-[N-(4-t-butyl-2-chlorophenyl)sulfamoyl]-1,4-dioxaspiro[4.5]dec-6-ene-7-carboxylate (Exemplified compound No. 1-2511)

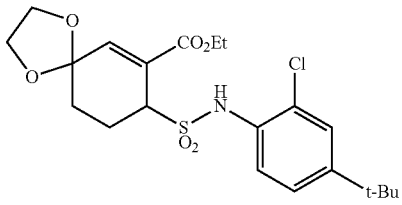

Amorphous substance (yield: 49%)

$^1$H-NMR spectrum (400 MHz, $CDCl_3$) δ ppm:

7.61 (1H, d, J=9 Hz), 7.38 (1H, d, J=2 Hz), 7.29 (1H, dd, J=9 Hz, 2 Hz), 7.00 (1H, s), 6.82 (1H, s), 4.46 (1H, d, J=4 Hz), 4.23-4.01 (5H, m), 3.95-3.88 (1H, m), 2.59-2.47 (2H, m), 2.23-2.12 (1H, m), 1.87-1.80 (1H, m), 1.29 (9H, s), 1.25-1.21 (3H, m).

Example 110

Ethyl 8-[N-(2-chloro-6-fluorophenyl)sulfamoyl]-1,4-dioxaspiro[4.5]dec-6-ene-7-carboxylate (Exemplified compound No. 1-2518)

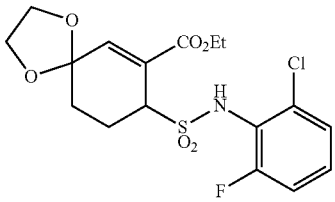

Amorphous substance (yield: 62%)

$^1$H-NMR spectrum (400 MHz, $CDCl_3$) δ ppm:

7.27-7.24 (1H, m), 7.21-7.15 (1H, m), 7.12-7.06 (1H, m), 6.98 (1H, s), 6.86 (1H, s), 4.77-4.74 (1H, m), 4.30-4.21 (2H, m), 4.15-4.03 (3H, m), 3.96-3.90 (1H, m), 2.67-2.60 (1H, m), 2.38 (1H, td, J=14 Hz, 3 Hz), 2.28-2.17 (1H, m), 1.88-1.81 (1H, m), 1.29 (3H, t, J=7 Hz).

Example 111

Ethyl 8-[N-(2,6-dichlorophenyl)sulfamoyl]-1,4-dioxaspiro[4.5]dec-6-ene-7-carboxylate (Exemplified compound No. 1-2525)

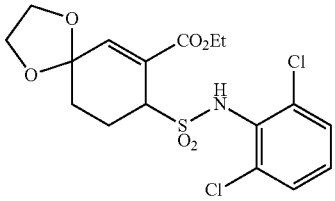

Amorphous substance (yield: 24%)

$^1$H-NMR spectrum (500 MHz, $CDCl_3$) δ ppm:

7.39 (1H, s), 7.38 (1H, s), 7.27 (1H, s), 7.17 (1H, t, J=8 Hz), 6.87 (1H, s), 4.88 (1H, dd, J=5 Hz, 3 Hz), 4.29 (2H, q, J=7 Hz), 4.15-4.03 (3H, m), 3.96-3.91 (1H, m), 2.68-2.62 (1H, m), 2.31 (1H, td, J=14 Hz, 3 Hz), 2.26-2.18 (1H, m), 1.88-1.82 (1H, m), 1.31 (3H, t, J=7 Hz).

Example 112

Ethyl 8-[N-(2-chloro-6-methylphenyl) sulfamoyl]-1,4-dioxaspiro[4.5]dec-6-ene-7-carboxylate (Exemplified compound No. 1-1462)

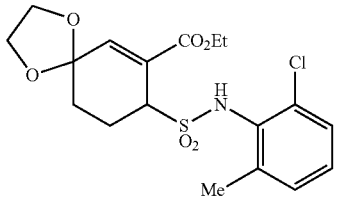

Amorphous substance (yield: 55%)

$^1$H-NMR spectrum (400 MHz, $CDCl_3$) δ ppm:

7.29-7.23 (1H, m), 7.20-7.09 (3H, m), 6.84 (1H, t, J=1 Hz), 4.80-4.77 (1H, m), 4.30-4.20 (2H, m), 4.13-4.00 (3H, m), 3.95-3.89 (1H, m), 2.58-2.46 (4H, m), 2.33 (1H, td, J=14 Hz, 3 Hz), 2.25-2.14 (1H, m), 1.85-1.78 (1H, m), 1.28 (3H, t, J=7 Hz).

Example 113

Ethyl 8-[N-(2,3-dichlorophenyl)sulfamoyl]-1,4-dioxaspiro[4.5]dec-6-ene-7-carboxylate (Exemplified compound No. 1-2532)

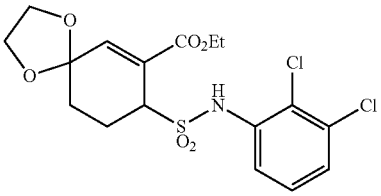

Amorphous substance (yield: 70%)

$^1$H-NMR spectrum (400 MHz, $CDCl_3$) δ ppm:

7.56-7.61 (1H, m), 7.26-7.19 (3H, m), 5.83 (1H, s), 4.46 (1H, d, J=5 Hz), 4.22-4.01 (5H, m), 3.95-3.89 (1H, m), 2.57-2.48 (2H, m), 2.25-2.14 (1H, m), 1.89-1.82 (1H, m), 1.25 (3H, t, J=7 Hz).

Example 114

Ethyl 8-[N-(2,5-dichlorophenyl)sulfamoyl]-1,4-dioxaspiro[4.5]dec-6-ene-7-carboxylate (Exemplified compound No. 1-2539)

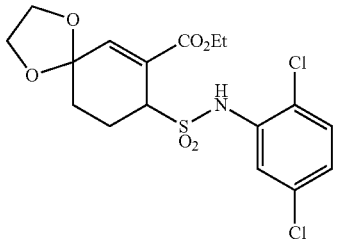

White powder (yield: 78%)

Melting point: 120-124° C.

$^1$H-NMR spectrum (500 MHz, $CDCl_3$) δ ppm:

7.72 (1H, d, J=2 Hz), 7.31 (1H, d, J=9 Hz), 7.11 (1H, s), 7.05 (1H, dd, J=9 Hz, 2 Hz), 6.86 (1H, s), 4.46 (1H, dd, J=6 Hz, 2 Hz), 4.25-4.03 (5H, m), 3.95-3.90 (1H, m), 2.58-2.48 (2H, m), 2.26-2.17 (1H, m), 1.90-1.84 (1H, m), 1.26 (3H, t, J=7 Hz).

Example 115

Ethyl 8-[N-(2-chloro-4,6-difluorophenyl)sulfamoyl]-1,4-dioxaspiro[4.5]dec-6-ene-7-carboxylate (Exemplified compound No. 1-2546)

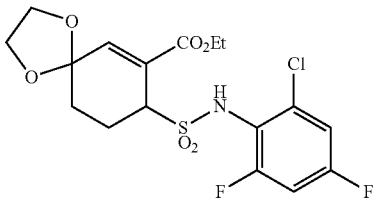

Oil (yield: 29%)

$^1$H-NMR spectrum (400 MHz, $CDCl_3$) δ ppm:

7.07-7.03 (1H, m), 6.99 (1H, s), 6.91-6.83 (2H, m), 4.67 (1H, dd, J=5 Hz, 3 Hz), 4.31-4.23 (2H, m), 4.14-4.03 (3H, m), 3.97-3.90 (1H, m), 2.65-2.57 (1H, m), 2.34 (1H, td, J=14 Hz, 3 Hz), 2.27-2.17 (1H, m), 1.88-1.81 (1H, m), 1.31 (3H, t, J=7 Hz).

Example 116

Ethyl 8-[N-(2,6-dichloro-4-fluorophenyl)sulfamoyl]-1,4-dioxaspiro[4.5]dec-6-ene-7-carboxylate (Exemplified compound No. 1-2553)

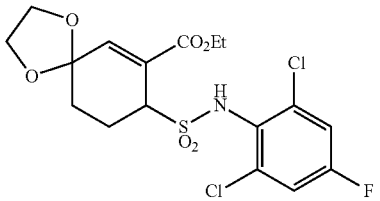

Amorphous substance (yield: 39%)

$^1$H-NMR spectrum (400 MHz, $CDCl_3$) δ ppm:

7.22 (1H, s), 7.17 (2H, d, J=7 Hz), 6.88 (1H, t, J=1 Hz), 4.84-4.81 (1H, m), 4.29 (2H, q, J=7 Hz), 4.14-4.03 (3H, m), 3.97-3.90 (1H, m), 2.67-2.60 (1H, m), 2.34-2.17 (2H, m), 1.88-1.81 (1H, m), 1.33 (3H, t, J=7 Hz).

Example 117

Ethyl 8-[N-(2-bromo-6-chloro-4-fluorophenyl)sulfamoyl]-1,4-dioxaspiro[4.5]dec-6-ene-7-carboxylate (Exemplified compound No. 1-2560)

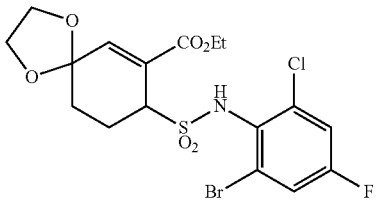

Amorphous substance (yield: 46%)

$^1$H-NMR spectrum (400 MHz, $CDCl_3$) δ ppm:

7.35 (1H, dd, J=7.5 Hz, 2.8 Hz), 7.24-7.21 (2H, m), 7.24 (1H, s), 4.90 (1H, d, J=5.1 Hz), 4.30 (2H, q, J=7.2 Hz), 4.14-3.92 (4H, m), 2.67-2.62 (1H, m), 2.33-2.18 (2H, m), 1.88-1.84 (1H, m), 1.33 (3H, t, J=6.6 Hz).

Example 118

Ethyl 8-[N-(4-chloro-2-methoxy-5-methylphenyl) sulfamoyl]-1,4-dioxaspiro[4.5]dec-6-ene-7-carboxylate (Exemplified compound No. 1-2567)

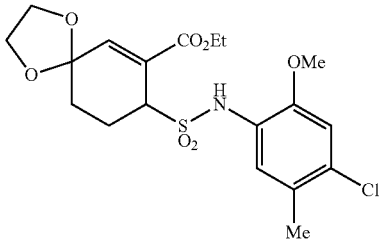

White powder (yield: 54%)

$^1$H-NMR spectrum (400 MHz, $CDCl_3$) δ ppm:

7.43 (1H, s), 6.96 (1H, s), 6.87 (1H, s), 6.78 (1H, t, J=1 Hz), 4.41 (1H, dd, J=6 Hz, 2 Hz), 4.20-4.00 (5H, m), 3.94-3.88 (1H, m), 3.85 (3H, s), 2.58-2.43 (2H, m), 2.31 (3H, s), 2.20-2.08 (1H, m), 1.85-1.78 (1H, m), 1.25 (3H, t, J=7 Hz).

Example 119

Ethyl 8-[N-(2,4-dibromophenyl)sulfamoyl]-1,4-dioxaspiro[4.5]dec-6-ene-7-carboxylate (Exemplified compound No. 1-2574)

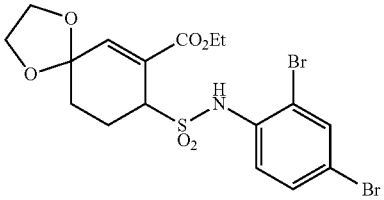

Oil (yield: 56%)

$^1$H-NMR spectrum (500 MHz, $CDCl_3$) δ ppm:

7.70 (1H, d, J=2 Hz), 7.59 (1H, d, J=9 Hz), 7.44 (1H, dd, J=9 Hz, 2 Hz), 7.02 (1H, s), 6.83 (1H, s), 4.47-4.44 (1H, m), 4.23-4.02 (5H, m), 3.95-3.90 (1H, m), 2.57-2.49 (2H, m), 2.23-2.15 (1H, m), 1.88-1.83 (1H, m), 1.26 (3H, t, J=7 Hz).

Example 120

Ethyl 8-[N-(2,6-dibromophenyl)sulfamoyl]-1,4-dioxaspiro[4.5]dec-6-ene-7-carboxylate (Exemplified compound No. 1-2581)

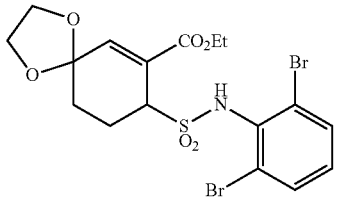

Amorphous substance (yield: 41%)

$^1$H-NMR spectrum (500 MHz, $CDCl_3$) δ ppm:

7.61 (2H, d, J=8 Hz), 7.26 (1H, brs), 7.02 (1H, t, J=8 Hz), 6.88 (1H, s), 5.02-5.00 (1H, m), 4.29 (2H, q, J=7 Hz), 4.15-3.91 (4H, m), 2.70-2.64 (1H, m), 2.33-2.19 (2H, m), 1.87-1.83 (1H, m), 1.32 (3H, t, J=7 Hz).

Example 121

Ethyl 8-[N-(2-bromo-4-isopropylphenyl)sulfamoyl]-1,4-dioxaspiro[4.5]dec-6-ene-7-carboxylate (Exemplified compound No. 1-2588)

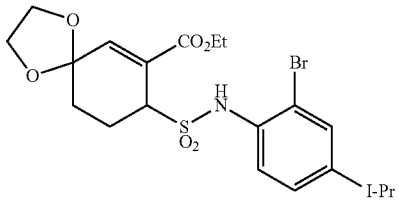

White powder (yield: 51%)

Melting point: 130-134° C.

$^1$H-NMR spectrum (500 MHz, $CDCl_3$) δ ppm:

7.60 (1H, d, J=8 Hz), 7.40 (1H, d, J=2 Hz), 7.18 (1H, dd, J=8 Hz, 2 Hz), 6.94 (1H, s), 6.82 (1H, s), 4.48-4.46 (1H, m), 4.24-4.01 (5H, m), 3.94-3.88 (1H, m), 2.89-2.83 (1H, m), 2.60-2.47 (2H, m), 2.22-2.13 (1H, m), 1.86-1.81 (1H, m), 1.25-1.21 (9H, m).

Example 122

Ethyl 8-[N-(2-chloro-4-fluorophenyl)sulfamoyl]-1,4-dioxaspiro[4.5]dec-6-ene-7-carboxylate (low polarity compound, first peak), (high polarity compound, second peak) (Exemplified compound No. 1-364)

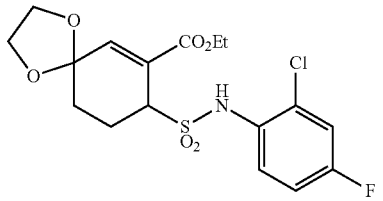

Ethyl 8-[N-(2-chloro-4-fluorophenyl)sulfamoyl]-1,4-dioxaspiro[4.5]dec-6-ene-7-carboxylate obtained in Example 1 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white powder. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd. inner diameter 0.46 cm, length 25 cm) |
| Mobile phase | hexane:2-propanol = 1:1 |
| Flow rate | 1.0 ml/min |
| Temperature | 40° C. |
| Detection | 254 nm (UV) |
| Retention time | low polarity compound (first peak): 6.1 minutes<br>high polarity compound (second peak): 10.5 minutes |

(Low Polarity Compound, First Peak)

Melting point: 116-117° C.

$^1$H-NMR spectrum (400 MHz, $CDCl_3$) δ ppm:

7.68 (1H, dd, J=9.2 Hz, 5.3 Hz), 7.17 (1H, dd, J=7.8 Hz, 2.7 Hz), 7.05-7.00 (2H, m), 6.83 (1H, s), 4.43 (1H, d, J=5.4 Hz), 4.26-3.90 (6H, m), 2.55-2.47 (2H, m), 4.15-2.47 (1H, m), 4.02-2.13 (1H, m), 1.27 (3H, t, J=7.0 Hz).

(High Polarity Compound, Second Peak)

Melting point: 116-117° C.

$^1$H-NMR spectrum (400 MHz, $CDCl_3$) δ ppm:

7.68 (1H, dd, J=9.0 Hz, 5.5 Hz), 7.17 (1H, dd, J=8.0 Hz, 2.9 Hz), 7.06-7.00 (2H, m), 6.84 (1H, s), 4.43 (1H, d, J=5.4 Hz), 4.26-3.90 (6H, m), 2.55-2.47 (2H, m), 1.13-2.23 (1H, m), 1.87-1.83 (1H, m), 1.27 (3H, t, J=6.6 Hz).

Example 123

Ethyl 9-[N-(2-chloro-4-fluorophenyl)sulfamoyl]-1,4-dioxaspiro[4.5]dec-7-ene-8-carboxylate

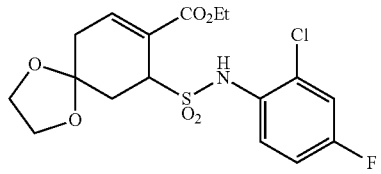

(123a) Ethyl 7-trifluoromethanesulfonyloxy-1,4-dioxaspiro[4.5]dec-7-ene-8-carboxylate Following the process described in Example (30e), ethyl 7-oxo-1,4-dioxaspiro[4.5]decane-8-carboxylate [compound disclosed as Compound 292c in US Patent application No. US2004/259914 A1] was used in place of ethyl 8-oxo-1-oxaspiro[4.5]decane-7-carboxylate to give the title compound as a white powder (yield: 96%).

$^1$H-NMR spectrum (400 MHz, $CDCl_3$) δ ppm:

4.28 (2H, q, J=7 Hz), 4.04-3.96 (4H, m), 2.65-2.61 (4H, m), 1.82-1.78 (2H, m), 1.32 (3H, t, J=7 Hz).

(123b) Ethyl 7-acetylsulfanyl-1,4-dioxaspiro[4.5]dec-7-ene-8-carboxylate

Following the process described in Example (1a), ethyl 7-trifluoromethanesulfonyloxy-1,4-dioxaspiro[4.5]dec-7-ene-8-carboxylate obtained in (123a) was used in place of ethyl 8-trifluoromethanesulfonyloxy-1,4-dioxaspiro[4.5]dec-7-ene-7-carboxylate to obtain the title compound as a pale brown oil (yield: 83%).

$^1$H-NMR spectrum (400 MHz, $CDCl_3$) δ ppm:

4.21 (2H, q, 7 Hz), 4.04-3.96 (4H, m), 2.72-2.65 (4H, m), 2.32 (3H, s), 1.85 (2H, t, J=7 Hz), 1.29 (3H, t, J=7 Hz).

(123c) Ethyl 7-mercapto-1,4-dioxaspiro[4.5]dec-7-ene-8-carboxylate

Following the process described in Example (1b), ethyl 7-acetylsulfanyl-1,4-dioxaspiro[4.5]dec-7-ene-8-carboxylate obtained in (123b) was used in place of ethyl 8-acetylsulfanyl-1,4-dioxaspiro[4.5]dec-7-ene-7-carboxylate to give the title compound as a pale brown powder (yield: 85%).

$^1$H-NMR spectrum (400 MHz, $CDCl_3$) δ ppm:

4.22 (2H, q, 7 Hz), 4.20 (1H, s), 4.02-3.95 (4H, m), 2.69-2.66 (2H, m), 2.61-2.56 (2H, m), 1.82-1.78 (2H, m), 1.30 (3H, t, J=7 Hz).

(123d) Ethyl 7-chlorosulfonyl-1,4-dioxaspiro[4.5]dec-7-ene-8-carboxylate

Following the process described in Example (1c), ethyl 7-mercapto-1,4-dioxaspiro[4.5]dec-7-ene-8-carboxylate obtained in (123c) was used in place of ethyl 8-mercapto-1,4-dioxaspiro[4.5]dec-7-ene-7-carboxylate to give the title compound as a colorless oil (yield: 62%).

$^1$H-NMR spectrum (400 MHz, $CDCl_3$) δ ppm:

4.31 (2H, q, 7 Hz), 4.09-4.00 (4H, m), 2.82-2.73 (4H, m), 1.86 (2H, t, J=7 Hz), 1.35 (3H, t, J=7 Hz).

(123e) Ethyl 9-[N-(2-chloro-4-fluorophenyl)sulfamoyl]-1,4-dioxaspiro[4.5]dec-7-ene-8-carboxylate Following the process described in Example (1d), ethyl 7-chlorosulfonyl-1,4-dioxaspiro[4.5]dec-7-ene-8-carboxylate obtained in (123d) was used in place of ethyl 8-chlorosulfonyl-1,4-dioxaspiro[4.5]dec-7-ene-7-carboxylate to give the title compound as a white powder (yield: 61%).

Melting point: 120-122° C.

$^1$H-NMR spectrum (400 MHz, $CDCl_3$) δ ppm:

7.81 (1H, s), 7.66 (1H, dd, J=9 Hz, 5 Hz), 7.14-7.10 (2H, m), 6.98-6.92 (1H, m), 4.71-4.67 (1H, m), 4.22-3.96 (6H, m), 2.75-2.56 (3H, m), 2.08-2.02 (1H, m), 1.24 (3H, t, J=7 Hz).

Example 124

Ethyl 2-bromoethyl-8-[N-(2-chloro-4-fluorophenyl)sulfamoyl]-1,4-dioxaspiro[4.5]dec-6-ene-7-carboxylate

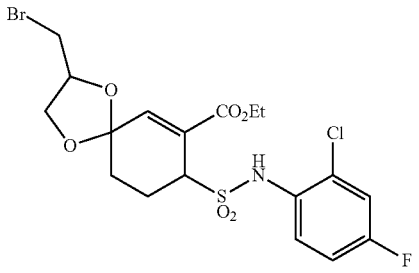

Following the process described in Example (17a), 1-bromo-2,3-bis[(trimethylsilyl)oxy]propane was used in place of 1,4-di-O-benzoyl-2,3-di-O-trimethylsilyl-D-threitol to give the title compound as a white amorphous substance (yield: 100%).

$^1$H-NMR spectrum (400 MHz, $CDCl_3$) δ ppm:

7.67 (1H, dd, J=9.2 and 5.3 Hz), 7.17 (1H, dd, J=7.8 and 2.8 Hz), 7.05-6.99 (2H, m), 6.86-6.77 (1H, m), 4.53-3.84 (6H, m), 3.53-3.31 (2H, m), 2.66-2.41 (2H, m), 2.24-2.12 (1H, m), 1.89-1.86 (1H, m), 1.28-1.24 (3H, m).

Example 125

Ethyl (2S)-8-[N-(2-chloro-4-fluorophenyl)sulfamoyl]-2-methoxycarbonylmethyl-1,4-dioxaspiro[4.5]dec-6-ene-7-carboxylate

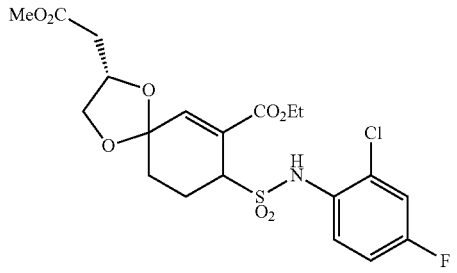

Following the process described in Example (17a), methyl (S)-3,4-bis[(trimethylsilyl)oxy]butyrate obtained in Reference Example 20 was used in place of 1,4-di-O-benzoyl-2,3-di-O-trimethylsilyl-D-threitol to give the title compound as a colorless oil (yield: 96%).

$^1$H-NMR spectrum (400 MHz, $CDCl_3$) δ ppm:

7.67 (1H, dd, J=9.0 Hz, 5.4 Hz), 7.16 (1H, dd, J=7.9 Hz, 2.8 Hz), 7.05-6.98 (2H, m), 6.88-6.76 (1H, m), 4.63-4.58 (1H, m), 4.47-4.41 (1H, m), 4.32-4.10 (3H, m), 3.84-3.59 (4H, m), 2.85-2.39 (4H, m), 2.21-2.16 (1H, m), 1.89-1.80 (1H, m), 1.29-1.24 (3H, m).

Example 126

Ethyl 3-[N-(2-chloro-4-fluorophenyl)sulfamoyl]-7,12-dioxaspiro[5.6]dodec-1-ene-2-carboxylate (Exemplified compound No. 1-366)

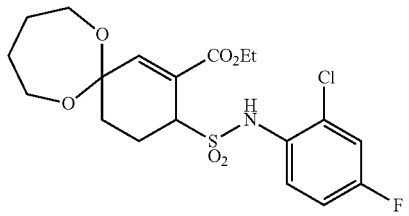

34 mg (0.61 mmol) of 1,4-butanediol was dissolved in 5 ml of dichloromethane, 0.32 ml (1.83 mmol) of isopropoxytrimethylsilane, and 200 mg (0.47 mmol) of ethyl 6-[N-(2-chloro-4-fluorophenyl)sulfamoyl]-3,3-dimethoxy-1-cyclohexene-1-carboxylate obtained in Example (16a) and 4 μl (0.024 mmol) of trimethylsilyl trifluoromethanesulfonate were sequentially added thereto with stirring under ice-cooling, followed by stirring for 2 hours at the same temperature. Saturated aqueous sodium hydrogencarbonate was added to the reaction solution and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=3:1), and the resulting solid was further washed with hexane to give 6 mg of the title compound as a white powder (yield: 3%).

Melting point: 142-144° C.

$^1$H-NMR spectrum (400 MHz, $CDCl_3$) δ ppm:

7.68 (1H, dd, J=9 Hz, 5 Hz), 7.16 (1H, dd, J=8 Hz, 3 Hz), 7.04 (1H, s), 7.03-6.98 (2H, m), 4.44-4.40 (1H, m), 4.27-4.11 (2H, m), 3.91-3.62 (4H, m), 2.46-2.38 (1H, m), 2.31-2.21 (1H, m), 2.17-1.94 (2H, m), 1.71-1.58 (4H, m), 1.27 (3H, t, J=7 Hz).

Example 127

Ethyl 4-[N-(2-chloro-4-fluorophenyl)sulfamoyl]-3a', 4',6',6a'-tetrahydrospiro[cyclohex-2-ene-1,2'-furo[3.4-d][1.3]dioxol]-3-carboxylate (Exemplified compound No. 1-402)

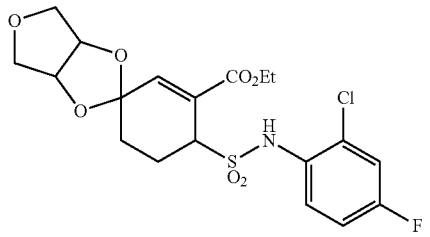

Following the process described in Example 21, 1,4-anhydro-2,3-di-O-trimethylsilyl-meso-erythritol obtained in Reference Example 21 was used in place of 1,3,4,5,7-penta-O-trimethylsilyl-D-arabitol to give the title compound as a white powder (yield: 56%).

Melting point: 227-228° C.

$^1$H-NMR spectrum (400 MHz, $CDCl_3$+$CD_3OD$) δ ppm:

7.61 (1H, dd, J=9 Hz, 5 Hz), 7.17 (1H, dd, J=8 Hz, 3 Hz), 7.07-6.97 (1H, m), 6.91 (1H, s), 4.93 (1H, dd, J=6 Hz, 4 Hz), 4.81 (1H, dd, J=6 Hz, 4 Hz), 4.39 (1H, d, J=5 Hz), 4.26-4.05 (3H, m), 4.01 (1H, d, J=11 Hz), 3.51-3.41 (2H, m), 2.54-2.34 (2H, m), 2.20-2.07 (1H, m), 1.90-1.79 (1H, m), 1.25 (3H, t, J=7 Hz).

Example 128

Ethyl 8-[N-(2-chloro-4-fluorophenyl)sulfamoyl]-2,2, 3,3-tetramethyl-1,4-dioxaspiro[4.5]dec-6-ene-7-carboxylate

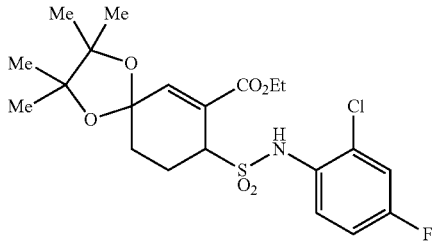

Following the process described in Example (17a), 2,3-dimethyl-2,3-bis[(trimethylsilyl)oxy]butane was used in place of 1,4-di-O-benzoyl-2,3-di-O-trimethylsilyl-D-threitol to give the title compound as a pale yellow oil (yield: 10%).

$^1$H-NMR spectrum (400 MHz, $CDCl_3$) δ ppm:

7.66 (1H, dd, J=8.8 Hz, 5.6 Hz), 7.16 (1H, dd, J=7.8 Hz, 2.7 Hz), 7.04-7.03 (1H, m), 6.89 (1H, s), 4.37 (1H, d, J=4.0 Hz), 4.25-4.10 (2H, m), 2.51-2.43 (2H, m), 2.24-2.14 (1H, m), 1.94-1.89 (1H, m), 1.31-1.23 (15H, m).

Example 129

Ethyl 8-[N-(2-chloro-4-fluorophenyl)sulfamoyl]-2,2, 3-triethyl-1,4-dioxaspiro[4.5]dec-6-ene-7-carboxylate

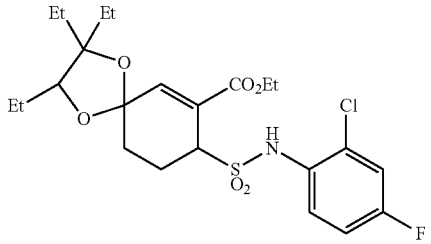

Following the process described in Example (17a), 3-ethyl-3,4-bis[(trimethylsilyl)oxy]hexane obtained in Reference Example 22 was used in place of 1,4-di-O-benzoyl-2,3-di-O-trimethylsilyl-D-threitol to give the title compound as a white powder (yield: 88%).

Melting point: 124-126° C.

$^1$H-NMR spectrum (400 MHz, $CDCl_3$) δ ppm:

7.69-7.66 (1H, m), 7.17-7.15 (1H, m), 7.04-7.00 (2H, m), 6.88-6.69 (1H, m), 4.40-4.39 (1H, m), 4.28-4.10 (2H, m), 3.90-3.68 (1H, m), 2.54-2.31 (2H, m), 2.25-2.12 (1H, m), 1.85-1.37 (7H, m), 1.29-1.24 (3H, m), 1.08-0.84 (9H, m).

Example 130

Ethyl (3R)-8-[N-(2-chloro-4-fluorophenyl)sulfamoyl]-2,2,3-triphenyl-1,4-dioxaspiro[4.5]dec-6-ene-7-carboxylate

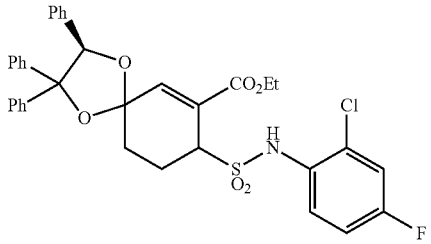

Following the process described in Example (17a), (R)-1, 2-bis[(trimethylsilyl)oxy]-1,1,2-triphenylethane obtained in Reference Example 23 was used in place of 1,4-di-O-benzoyl-2,3-di-O-trimethylsilyl-D-threitol to give the title compound as a colorless oil (yield: 30%).

$^1$H-NMR spectrum (400 MHz, $CDCl_3$) δ ppm:

7.22-6.91 (20H, m), 5.99-5.76 (1H, m), 4.54-4.32 (1H, m), 4.34-4.08 (2H, m), 2.87-1.97 (4H, m), 1.36-1.14 (3H, m).

Example 131

Ethyl (2R,3R)-8-[N-(2-chlorophenyl)sulfamoyl]-2,3-bis(hydroxymethyl)-1,4-dioxaspiro[4.5]dec-6-ene-7-carboxylate (Exemplified compound No. 1-206)

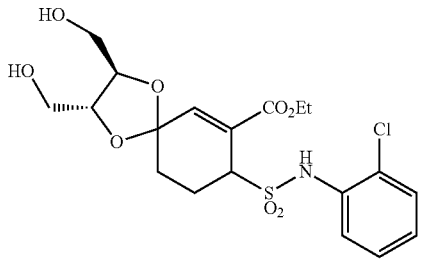

Following the process described in Examples 7, (16a) and 17 (alternative procedure), ethyl 8-[N-(2-chlorophenyl)sulfamoyl]-1,4-dioxaspiro[4.5]dec-6-ene-7-carboxylate obtained in Example 54 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 31%).

$^1$H-NMR spectrum (400 MHz, $CDCl_3$) δ ppm:

7.71-7.67 (1H, m), 7.41-7.38 (1H, m), 7.32-7.26 (1H, m), 7.14-7.06 (2H, m), 6.90 (0.5H, t, J=1 Hz), 6.84 (0.5H, t, J=1 Hz), 4.47 (1H, dd, J=6 Hz, 2 Hz), 4.26-4.07 (3.5H, m), 4.05-4.00 (0.5H, m), 3.94-3.80 (2H, m), 3.77-3.67 (2H, m), 2.64-2.47 (2H, m), 2.27-1.87 (4H, m), 1.27-1.22 (3H, m).

Example 132

Ethyl (2R,3R)-8-[N-(2-bromophenyl)sulfamoyl]-2,3-bis(hydroxymethyl)-1,4-dioxaspiro[4.5]dec-6-ene-7-carboxylate (Exemplified compound No. 1-1392)

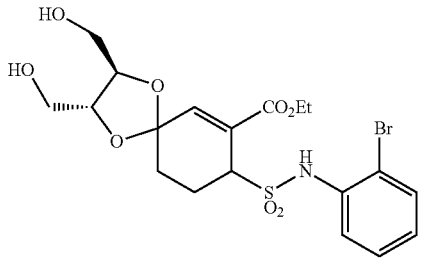

Following the process described in Examples 7, (16a) and 17 (alternative procedure), ethyl 8-[N-(2-bromophenyl)sulfamoyl]-1,4-dioxaspiro[4.5]dec-6-ene-7-carboxylate obtained in Example 55 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 28%)

$^1$H-NMR spectrum (500 MHz, $CDCl_3$) δ ppm:

7.71-7.67 (1H, m), 7.56 (1H, d, J=8 Hz), 7.35-7.31 (1H, m), 7.07-6.98 (2H, m), 6.90 (0.5H, s), 6.84 (0.5H, s), 4.48 (1H, d, J=5 Hz), 4.25-4.08 (3.5H, m), 4.06-4.01 (0.5H, m), 3.94-3.80 (2H, m), 3.76-3.68 (2H, m), 2.65-2.48 (2H, m), 2.23-1.87 (4H, m), 1.27-1.22 (3H, m).

Example 133

Ethyl (2R,3R)-2,3-bis(hydroxymethyl)-8-[N-(2-iodophenyl)sulfamoyl]-1,4-dioxaspiro[4.5]dec-6-ene-7-carboxylate (Exemplified compound No. 1-2226)

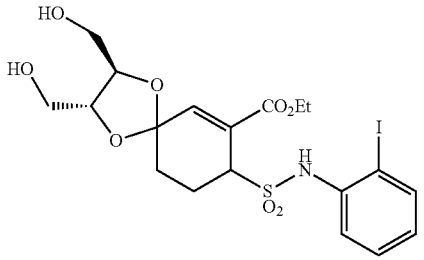

Following the process described in Examples 7, (16a) and 17 (alternative procedure), ethyl 8-[N-(2-iodophenyl)sulfamoyl]-1,4-dioxaspiro[4.5]dec-6-ene-7-carboxylate obtained in Example 56 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 26%).

$^1$H-NMR spectrum (500 MHz, $CDCl_3$) δ ppm:

7.80 (1H, d, J=8 Hz), 7.68-7.63 (1H, m), 7.38-7.33 (1H, m), 6.90-6.83 (3H, m), 4.50-4.46 (1H, m), 4.27-4.09 (3.5H, m), 4.06-4.02 (0.5H, m), 3.94-3.80 (2H, m), 3.77-3.68 (2H, m), 3.53 (1H, brs), 2.66-2.56 (1H, m), 2.55-2.49 (1H, m), 2.24-2.14 (1H, m), 2.00-1.85 (2H, m), 1.27-1.23 (3H, m).

Example 134

Ethyl (2R,3R)-8-[N-(2-hexylphenyl)sulfamoyl]-2,3-bis (hydroxymethyl)-1,4-dioxaspiro[4.5]dec-6-ene-7-carboxylate (Exemplified compound No. 1-734)

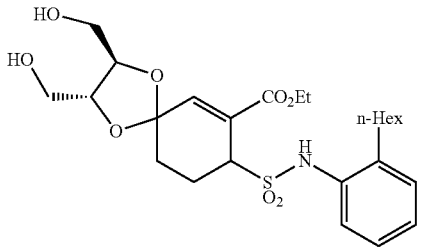

Following the process described in Examples 7, (16a) and 17 (alternative procedure), ethyl 8-[N-(2-hexylphenyl)sulfamoyl]-1,4-dioxaspiro[4.5]dec-6-ene-7-carboxylate obtained in Example 4 was used in place of ethyl 8-[N-(2-chloro-4-fluorophenyl)sulfamoyl]-1,4-dioxaspiro[4.5]dec-6-ene-7-carboxylate to give the title compound as a colorless oil (yield: 28%).

$^1$H-NMR spectrum (400 MHz, $CDCl_3$) δ ppm:

7.54-7.50 (1H, m), 7.23-7.17 (2H, m), 7.15-7.09 (1H, m), 6.94-6.91 (0.5H, m), 6.88-6.85 (0.5H, m), 6.70 (0.5H, s), 6.65 (0.5H, s), 4.48-4.43 (1H, m), 4.28-4.08 (3.5H, m), 4.06-4.00 (0.5H, m), 3.93-3.80 (2H, m), 3.76-3.68 (2H, m), 2.70-2.61

(2H, m), 2.55-2.41 (2H, m), 2.21-2.07 (1H, m), 1.96-1.75 (3H, m), 1.64-1.52 (2H, m), 1.42-1.23 (9H, m), 0.91-0.85 (3H, m).

Example 135

Ethyl (2R,3R)-8-[N-(2-heptylphenyl)sulfamoyl]-2,3-bis(hydroxymethyl)-1,4-dioxaspiro[4.5]dec-6-ene-7-carboxylate (Exemplified compound No. 1-910)

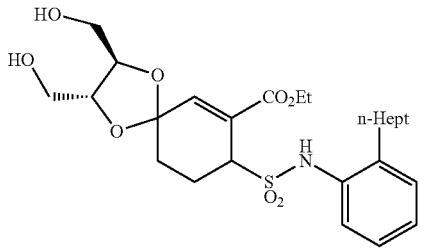

Following the process described in Examples 7, (16a) and 17 (alternative procedure), ethyl 8-[N-(2-heptylphenyl)sulfamoyl]-1,4-dioxaspiro[4.5]dec-6-ene-7-carboxylate obtained in Example 5 was used in place of ethyl 8-[N-(2-chloro-4-fluorophenyl)sulfamoyl]-1,4-dioxaspiro[4.5]dec-6-ene-7-carboxylate to give the title compound as a colorless oil (yield: 33%).

$^1$H-NMR spectrum (400 MHz, $CDCl_3$) δ ppm:

7.54-7.50 (1H, m), 7.23-7.18 (2H, m), 7.14-7.09 (1H, m), 6.94-6.91 (0.5H, m), 6.88-6.85 (0.5H, m), 6.70 (0.5H, s), 6.65 (0.5H, s), 4.47-4.43 (1H, m), 4.28-4.08 (3.5H, m), 4.06-4.00 (0.5H, m), 3.93-3.80 (2H, m), 3.76-3.68 (2H, m), 2.70-2.61 (2H, m), 2.54-2.41 (2H, m), 2.20-2.08 (1H, m), 1.96-1.74 (3H, m), 1.64-1.53 (2H, m), 1.41-1.22 (11H, m), 0.88 (3H, t, J=7 Hz).

Example 136

Ethyl (2R,3R)-8-[N-(2-chloro-4-methylphenyl)sulfamoyl]-2,3-bis(hydroxymethyl)-1,4-dioxaspiro[4.5]dec-6-ene-7-carboxylate (Exemplified compound No. 1-470)

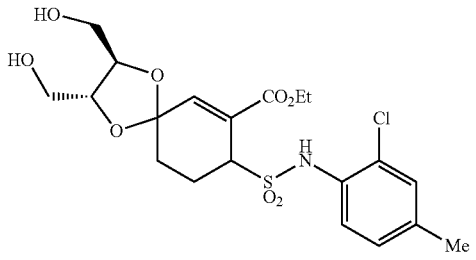

Following the process described in Examples 7, (16a) and 17 (alternative procedure), ethyl 8-[N-(2-chloro-4-methylphenyl)sulfamoyl]-1,4-dioxaspiro[4.5]dec-6-ene-7-carboxylate obtained in Example 108 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 50%).

$^1$H-NMR spectrum (400 MHz, $CDCl_3$) δ ppm:

7.56 (1H, dd, J=8 Hz, 2 Hz), 7.23-7.21 (1H, m), 7.11-7.07 (1H, m), 7.01 (1H, brs), 6.90 (0.5H, t, J=1 Hz), 6.84-6.82 (0.5H, m), 4.44 (1H, dd, J=6 Hz, 2 Hz), 4.27-4.08 (3.5H, m), 4.05-4.00 (0.5H, m), 3.93-3.80 (2H, m), 3.77-3.68 (2H, m), 2.63-2.44 (2H, m), 2.31 (3H, s), 2.22-1.62 (4H, m), 1.29-1.23 (3H, m).

Example 137

Ethyl (2R,3R)-8-[N-(2,4-dichlorophenyl)sulfamoyl]-2,3-bis(hydroxymethyl)-1,4-dioxaspiro[4.5]dec-6-ene-7-carboxylate (Exemplified compound No. 1-2499)

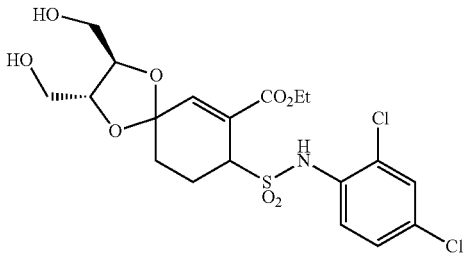

Following the process described in Examples 7, (16a) and 17 (alternative procedure), ethyl 8-[N-(2,4-dichlorophenyl)sulfamoyl]-1,4-dioxaspiro[4.5]dec-6-ene-7-carboxylate obtained in Example 106 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 22%).

$^1$H-NMR spectrum (400 MHz, $CDCl_3$) δ ppm:

7.64 (1H, dd, J=9 Hz, 2 Hz), 7.41 (1H, d, J=2 Hz), 7.28-7.25 (1H, m), 7.07 (1H, brs), 6.91 (0.5H, t, J=1 Hz), 6.85 (0.5H, t, J=1 Hz), 4.43 (1H, dd, J=6 Hz, 2 Hz), 4.26-4.09 (3.5H, m), 4.07-4.02 (0.5H, m), 3.94-3.81 (2H, m), 3.77-3.68 (2H, m), 2.60-2.47 (2H, m), 2.24-1.85 (4H, m), 1.29-1.24 (3H, m).

Example 138

Ethyl (2R,3R)-8-[N-(2-bromo-4-chlorophenyl)sulfamoyl]-2,3-bis(hydroxymethyl)-1,4-dioxaspiro[4.5]dec-6-ene-7-carboxylate (Exemplified compound No. 1-2408)

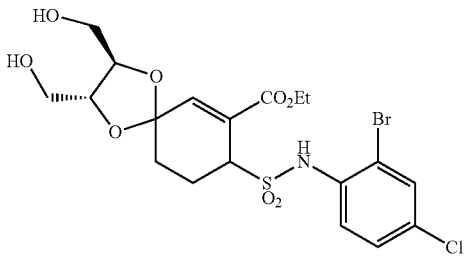

Following the process described in Examples 7, (16a) and 17 (alternative procedure), ethyl 8-[N-(2-bromo-4-chlorophenyl)sulfamoyl]-1,4-dioxaspiro[4.5]dec-6-ene-7-carboxylate obtained in Example 93 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 10%).

$^1$H-NMR spectrum (500 MHz, $CDCl_3$) δ ppm:

7.64 (1H, dd, J=9 Hz, 3 Hz), 7.57 (1H, d, J=2 Hz), 7.31 (1H, dd, J=9 Hz, 2 Hz), 7.01 (1H, brs), 6.91 (0.5H, s), 6.85 (0.5H, s), 4.45 (1H, d, J=4 Hz), 4.26-4.10 (3.5H, m), 4.06-4.02 (0.5H, m), 3.94-3.82 (2H, m), 3.77-3.69 (2H, m), 2.61-2.48 (2H, m), 2.24-2.15 (1H, m), 2.02-1.85 (3H, m), 1.29-1.24 (3H, m).

Example 139

Ethyl (2R,3R)-8-[N-(2-chloro-6-methylphenyl)sulfamoyl]-2,3-bis(hydroxymethyl)-1,4-dioxaspiro[4.5]dec-6-ene-7-carboxylate (Exemplified compound No. 1-1480)

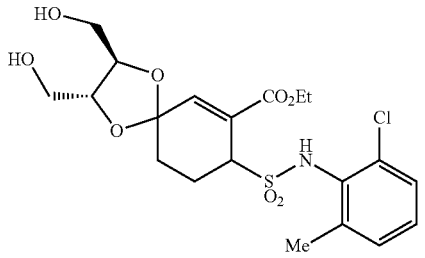

Following the process described in Examples 7, (16a) and 17 (alternative procedure), ethyl 8-[N-(2-chloro-6-methylphenyl)sulfamoyl]-1,4-dioxaspiro[4.5]dec-6-ene-7-carboxylate obtained in Example 112 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 45%).

$^1$H-NMR spectrum (500 MHz, $CDCl_3$) δ ppm:

7.28 (1H, dd, J=8 Hz, 1 Hz), 7.23-7.07 (3H, m), 6.93-6.91 (0.5H, m), 6.86-6.85 (0.5H, m), 4.80-4.76 (1H, m), 4.30-4.17 (3H, m), 4.11-4.07 (0.5H, m), 4.04-4.00 (0.5H, m), 3.92-3.81 (2H, m), 3.75-3.69 (2H, m), 2.59-2.48 (3H, m), 2.42-2.33 (1H, m), 2.26-2.15 (1H, m), 2.07 (1H, brs), 1.94-1.85 (1H, m), 1.63 (1H, brs), 1.29-1.24 (3H, m).

Example 140

Ethyl (2R,3R)-8-[N-(3-chloro-4-fluorophenyl)sulfamoyl]-2,3-bis(hydroxymethyl)-1,4-dioxaspiro[4.5]dec-6-ene-7-carboxylate (Exemplified compound No. 1-2366)

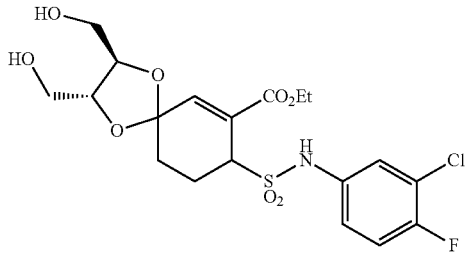

Following the process described in Examples 7, (16a) and 17 (alternative procedure), ethyl 8-[N-(3-chloro-4-fluorophenyl)sulfamoyl]-1,4-dioxaspiro[4.5]dec-6-ene-7-carboxylate obtained in Example 80 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 47%).

$^1$H-NMR spectrum (400 MHz, $CDCl_3$) δ ppm:

7.47 (1H, dd, J=6 Hz, 3 Hz), 7.29-7.25 (1H, m), 7.17-7.06 (2H, m), 6.97 (0.5H, t, J=1 Hz), 6.93-6.92 (0.5H, m), 4.33-4.09 (4.5H, m), 4.06-4.02 (0.5H, m), 3.94-3.82 (2H, m), 3.77-3.68 (2H, m), 2.48-2.40 (1H, m), 2.34-2.24 (1H, m), 2.12-2.01 (2H, m), 1.97-1.89 (2H, m), 1.35 (3H, t, J=7 Hz).

Example 141

Ethyl (2R,3R)-8-[N-(2-chloro-4,6-difluorophenyl)sulfamoyl]-2,3-bis(hydroxymethyl)-1,4-dioxaspiro[4.5]dec-6-ene-7-carboxylate (Exemplified compound No. 1-2548)

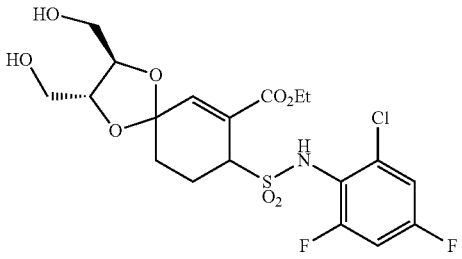

Following the process described in Examples 7, (16a) and 17 (alternative procedure), ethyl 8-[N-(2-chloro-4,6-difluorophenyl)sulfamoyl]-1,4-dioxaspiro[4.5]dec-6-ene-7-carboxylate obtained in Example 115 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 35%).

$^1$H-NMR spectrum (500 MHz, $CDCl_3$) δ ppm:

7.07-6.85 (4H, m), 4.67 (1H, dd, J=10 Hz, 6 Hz), 4.32-4.19 (3H, m), 4.14-4.02 (1H, m), 3.93-3.82 (2H, m), 3.76-3.70 (2H, m), 2.66-2.55 (1H, m), 2.43-2.34 (1H, m), 2.28-2.17 (1H, m), 2.06-1.88 (3H, m), 1.33-1.29 (3H, m).

Example 142

Ethyl (2R,3R)-8-[N-(2,6-dichloro-4-fluorophenyl)sulfamoyl]-2,3-bis(hydroxymethyl)-1,4-dioxaspiro[4.5]dec-6-ene-7-carboxylate (Exemplified compound No. 1-2555)

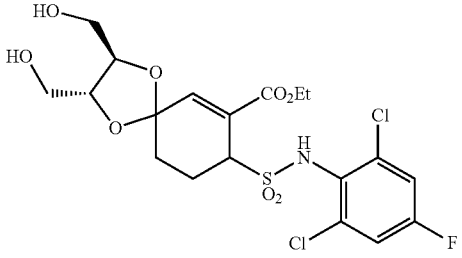

Following the process described in Examples 7, (16a) and 17 (alternative procedure), ethyl 8-[N-(2,6-dichloro-4-fluorophenyl)sulfamoyl]-1,4-dioxaspiro[4.5]dec-6-ene-7-carboxylate obtained in Example 116 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 25%).

$^1$H-NMR spectrum (400 MHz, $CDCl_3$) δ ppm:

7.26-7.05 (3H, m), 6.97-6.95 (0.5H, m), 6.90-6.89 (0.5H, m), 4.85-4.80 (1H, m), 4.33-4.19 (3H, m), 4.13-4.08 (0.5H, m), 4.06-4.02 (0.5H, m), 3.93-3.82 (2H, m), 3.76-3.70 (2H, m), 2.72-2.56 (1H, m), 2.39-2.20 (2H, m), 2.05-1.59 (3H, m), 1.35-1.30 (3H, m).

Example 143

Ethyl (2R,3R)-8-[N-(2-bromo-6-chloro-4-fluorophenyl)sulfamoyl]-2,3-bis(hydroxymethyl)-1,4-dioxaspiro[4.5]dec-6-ene-7-carboxylate (Exemplified compound No. 1-2562)

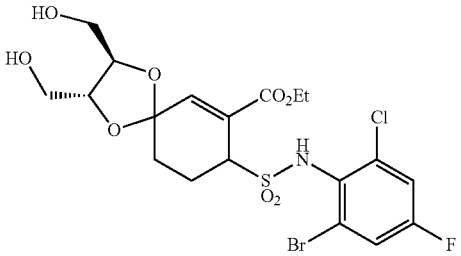

Following the process described in Examples 7, (16a) and 17 (alternative procedure), ethyl 8-[N-(2-bromo-6-chloro-4-fluorophenyl)sulfamoyl]-1,4-dioxaspiro[4.5]dec-6-ene-7-carboxylate obtained in Example 117 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 29%).

$^1$H-NMR spectrum (500 MHz, $CDCl_3$) δ ppm:

7.36-7.31 (1H, m), 7.23-7.19 (1H, m), 7.16 (1H, brs), 6.95 (0.5H, s), 6.90-6.88 (0.5H, m), 4.91-4.85 (1H, m), 4.33-4.17 (3H, m), 4.15-4.00 (1H, m), 3.94-3.80 (2H, m), 3.76-3.70 (2H, m), 3.55 (1H, brs), 2.70-2.57 (1H, m), 2.38-2.16 (2H, m), 1.96-1.87 (2H, m), 1.35-1.30 (3H, m).

Example 144

Ethyl (2R,3R)-8-[N-(2,4-difluorophenyl)sulfamoyl]-2,3-bis(hydroxymethyl)-1,4-dioxaspiro[4.5]dec-6-ene-7-carboxylate (Exemplified compound No. 1-294)

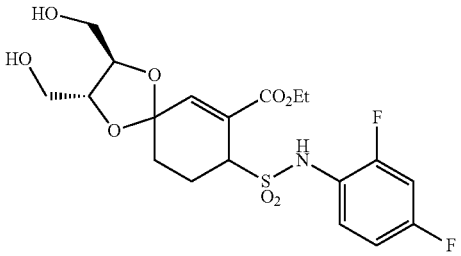

Following the process described in Examples 7, (16a) and 17 (alternative procedure), ethyl 8-[N-(2,4-difluorophenyl)sulfamoyl]-1,4-dioxaspiro[4.5]dec-6-ene-7-carboxylate obtained in Example 77 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 35%).

$^1$H-NMR spectrum (400 MHz, $CDCl_3$) δ ppm:

7.63-7.56 (1H, m), 7.07 (1H, brs), 6.94-6.85 (3H, m), 4.38-4.34 (1H, m), 4.30-4.08 (3.5H, m), 4.06-4.00 (0.5H, m), 3.93-3.81 (2H, m), 3.78-3.68 (2H, m), 2.53-2.40 (2H, m), 2.38-1.87 (4H, m), 1.31-1.27 (3H, m).

Example 145

Ethyl (2S,3S)-8-[N-(2,4-difluorophenyl)sulfamoyl]-2,3-bis(hydroxymethyl)-1,4-dioxaspiro[4.5]dec-6-ene-7-carboxylate (Exemplified compound No. 1-294)

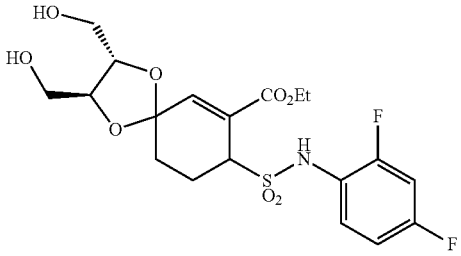

Following the process described in Examples 7, (16a) and 18 (alternative procedure), ethyl 8-[N-(2,4-difluorophenyl)sulfamoyl]-1,4-dioxaspiro[4.5]dec-6-ene-7-carboxylate obtained in Example 77 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 58%).

$^1$H-NMR spectrum (400 MHz, $CDCl_3$) δ ppm:

7.62-7.57 (1H, m), 6.93-6.86 (3H, m), 4.37-4.34 (1H, m), 4.29-4.18 (3H, m), 4.13-4.09 (0.5H, m), 4.06-4.01 (0.5H, m), 3.94-3.82 (2H, m), 3.76-3.69 (2H, m), 2.53-2.39 (2H, m), 2.21-1.50 (4H, m), 1.32-1.27 (3H, m).

Example 146

Ethyl (2R,3R)-8-[N-(2-bromo-4-fluorophenyl)sulfamoyl]-2,3-bis(hydroxymethyl)-1,4-dioxaspiro[4.5]dec-6-ene-7-carboxylate (Exemplified compound No. 1-1568)

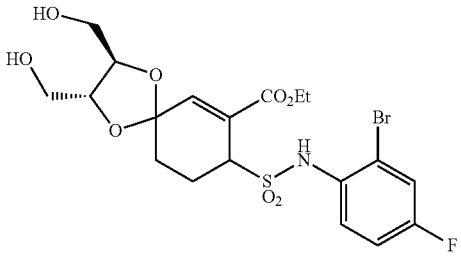

Following the process described in Examples 7, (16a) and 17 (alternative procedure), ethyl 8-[N-(2-bromo-4-fluorophenyl)sulfamoyl]-1,4-dioxaspiro[4.5]dec-6-ene-7-carboxylate obtained in Example 78 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 33%).

$^1$H-NMR spectrum (500 MHz, $CDCl_3$) δ ppm:

7.69-7.64 (1H, m), 7.33 (1H, dd, J=7 Hz, 3 Hz), 7.10-7.05 (1H, m), 6.93 (1H, brs), 6.93 (0.5H, s), 6.84 (0.5H, s), 4.44 (1H, d, J=4 Hz), 4.27-4.09 (3.5H, m), 4.06-4.01 (0.5H, m), 3.94-3.80 (2H, m), 3.77-3.68 (2H, m), 3.54 (1H, brs), 2.61-2.46 (2H, m), 2.23-2.14 (1H, m), 2.02-1.85 (2H, m), 1.29-1.24 (3H, m).

Example 147

Ethyl (2S,3S)-8-[N-(2-bromo-4-fluorophenyl)sulfamoyl]-2,3-bis(hydroxymethyl)-1,4-dioxaspiro[4.5]dec-6-ene-7-carboxylate (Exemplified compound No. 1-1568)

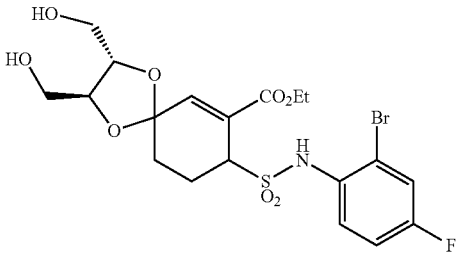

Following the process described in Examples 7, (16a) and 18 (alternative procedure), ethyl 8-[N-(2-bromo-4-fluorophenyl)sulfamoyl]-1,4-dioxaspiro[4.5]dec-6-ene-7-carboxylate obtained in Example 78 was used in place of ethyl 8-[N-(2-chloro-4-fluorophenyl)sulfamoyl]-1,4-dioxaspiro[4.5]dec-6-ene-7-carboxylate to give the title compound as a white amorphous substance (yield: 49%).

$^1$H-NMR spectrum (400 MHz, $CDCl_3$) δ ppm:

7.69-7.65 (1H, m), 7.33 (1H, dd, J=8 Hz, 3 Hz), 7.10-7.06 (1H, m), 6.99 (1H, brs), 6.91 (0.5H, s), 6.83 (0.5H, s), 4.44 (1H, d, J=4 Hz), 4.24-3.73 (8H, m), 2.61-2.48 (2H, m), 2.61-2.48 (1H, m), 1.96-1.87 (1H, m), 1.26 (3H, t, J=6 Hz).

Example 148

Ethyl (2R,3R)-8-[N-(2-butyl-4-fluorophenyl)sulfamoyl]-2,3-bis(hydroxymethyl)-1,4-dioxaspiro[4.5]dec-6-ene-7-carboxylate (Exemplified compound No. 1-646)

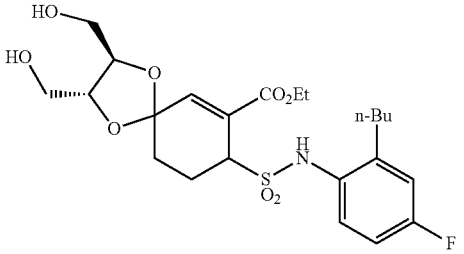

Following the process described in Examples 7, (16a) and 17 (alternative procedure), ethyl 8-[N-(2-butyl-4-fluorophenyl)sulfamoyl]-1,4-dioxaspiro[4.5]dec-6-ene-7-carboxylate obtained in Example 85 was used in place of ethyl 8-[N-(2-chloro-4-fluorophenyl)sulfamoyl]-1,4-dioxaspiro[4.5]dec-6-ene-7-carboxylate to give the title compound as a pale red amorphous substance (yield: 40%).

$^1$H-NMR spectrum (400 MHz, $CDCl_3$) δ ppm:

7.51-7.45 (1H, m), 6.97-6.85 (3H, m), 6.65 (0.5H, s), 6.59 (0.5H, s), 4.43-4.36 (1H, m), 4.29-4.16 (3H, m), 4.13-4.08 (0.5H, m), 4.07-4.01 (0.5H, m), 3.95-3.80 (2H, m), 3.77-3.68 (2H, m), 2.78-2.62 (2H, m), 2.53-2.35 (2H, m), 2.19-1.84 (4H, m), 1.65-1.49 (2H, m), 1.44-1.35 (2H, m), 1.33-1.27 (3H, m), 0.95 (3H, t, J=7 Hz).

Example 149

Ethyl (2S,3S)-8-[N-(2-butyl-4-fluorophenyl)sulfamoyl]-2,3-bis(hydroxymethyl)-1,4-dioxaspiro[4.5]dec-6-ene-7-carboxylate (Exemplified compound No. 1-646)

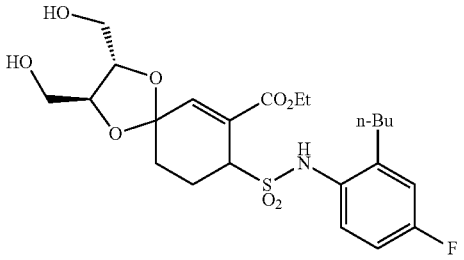

Following the process described in Examples 7, (16a) and 18 (alternative procedure), ethyl 8-[N-(2-butyl-4-fluorophenyl)sulfamoyl]-1,4-dioxaspiro[4.5]dec-6-ene-7-carboxylate obtained in Example 85 was used in place of ethyl 8-[N-(2-chloro-4-fluorophenyl)sulfamoyl]-1,4-dioxaspiro[4.5]dec-6-ene-7-carboxylate to give the title compound as a pale red amorphous substance (yield: 14%).

$^1$H-NMR spectrum (400 MHz, $CDCl_3$) δ ppm:

7.50-7.44 (1H, m), 6.98-6.86 (3H, m), 6.73 (0.4H, s), 6.68 (0.6H, s), 4.43-4.37 (1H, m), 4.26-4.16 (3H, m), 4.11-4.07 (0.4H, m), 4.05-3.99 (0.6H, m), 3.90-3.80 (2H, m), 3.78-3.68 (2H, m), 2.77-2.62 (2H, m), 2.53-2.23 (3H, m), 2.20-2.07 (2H, m), 1.96-1.86 (1H, m), 1.63-1.53 (2H, m), 1.44-1.34 (2H, m), 1.32-1.26 (3H, m), 0.95 (3H, t, J=7 Hz).

Example 150

Ethyl (2R,3R)-8-[N-(4-fluoro-2-pentylphenyl)sulfamoyl]-2,3-bis(hydroxymethyl)-1,4-dioxaspiro[4.5]dec-6-ene-7-carboxylate (Exemplified compound No. 1-1744)

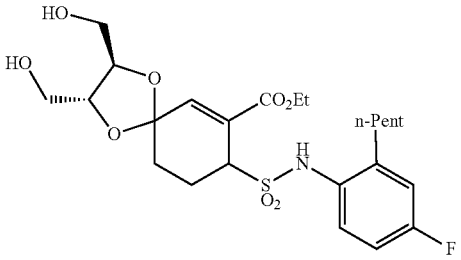

Following the process described in Examples 7, (16a) and 17 (alternative procedure), ethyl 8-[N-(4-fluoro-2-pentylphenyl)sulfamoyl]-1,4-dioxaspiro[4.5]dec-6-ene-7-carboxylate obtained in Example 86 was used in place of ethyl 8-[N-(2-chloro-4-fluorophenyl)sulfamoyl]-1,4-dioxaspiro[4.5]dec-6-ene-7-carboxylate to give the title compound as a pale red amorphous substance (yield: 33%).

$^1$H-NMR spectrum (400 MHz, $CDCl_3$) δ ppm:

7.50-7.43 (1H, m), 6.97-6.85 (3H, m), 6.67 (0.5H, s), 6.61 (0.5H, s), 4.42-4.37 (1H, m), 4.30-4.17 (3H, m), 4.12-4.08 (0.5H, m), 4.05-4.01 (0.5H, m), 3.93-3.82 (2H, m), 3.76-3.68 (2H, m), 2.77-2.61 (2H, m), 2.53-2.35 (2H, m), 2.19-1.80 (4H, m), 1.66-1.50 (2H, m), 1.40-1.22 (7H, m), 0.95-0.87 (3H, m).

Example 151

Ethyl (2S,3S)-8-[N-(4-fluoro-2-pentylphenyl)sulfamoyl]-2,3-bis(hydroxymethyl)-1,4-dioxaspiro[4.5]dec-6-ene-7-carboxylate (Exemplified compound No. 1-1744)

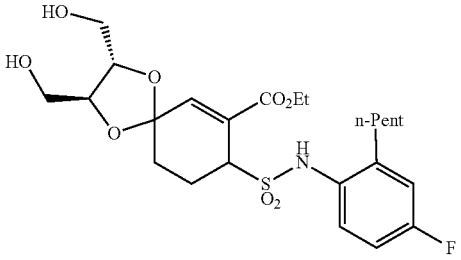

Following the process described in Examples 7, (16a) and 18 (alternative procedure), ethyl 8-[N-(4-fluoro-2-pentylphenyl)sulfamoyl]-1,4-dioxaspiro[4.5]dec-6-ene-7-carboxylate obtained in Example 86 was used in place of ethyl 8-[N-(2-chloro-4-fluorophenyl)sulfamoyl]-1,4-dioxaspiro[4.5]dec-6-ene-7-carboxylate to give the title compound as a pale red amorphous substance (yield: 30%).

$^1$H-NMR spectrum (400 MHz, $CDCl_3$) δ ppm:

7.50-7.42 (1H, m), 6.97-6.84 (3H, m), 6.77 (0.5H, s), 6.72 (0.5H, s), 4.42-4.36 (1H, m), 4.30-4.14 (3H, m), 4.12-4.05 (0.5H, m), 4.04-3.98 (0.5H, m), 3.91-3.77 (2H, m), 3.76-3.67 (2H, m), 2.76-2.59 (2H, m), 2.53-2.20 (4H, m), 2.20-2.06 (1H, m), 1.97-1.84 (1H, m), 1.66-1.52 (2H, m), 1.41-1.22 (7H, m), 0.95-0.88 (3H, m).

Example 152

Ethyl (2R,3R)-8-[N-(4-fluoro-2-hexylphenyl)sulfamoyl]-2,3-bis(hydroxymethyl)-1,4-dioxaspiro[4.5]dec-6-ene-7-carboxylate (Exemplified compound No. 1-822)

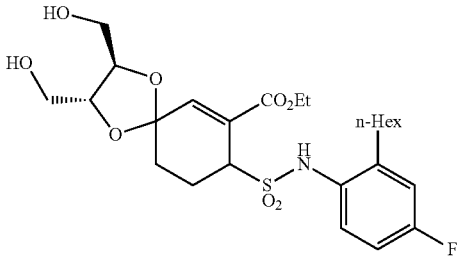

Following the process described in Examples 7, (16a) and 17 (alternative procedure), ethyl 8-[N-(4-fluoro-2-hexylphenyl)sulfamoyl]-1,4-dioxaspiro[4.5]dec-6-ene-7-carboxylate obtained in Example 87 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 54%).

$^1$H-NMR spectrum (400 MHz, $CDCl_3$) δ ppm:

7.50-7.45 (1H, m), 6.96-6.86 (3H, m), 6.67 (0.5H, s), 6.61 (0.5H, s), 4.41-4.37 (1H, m), 4.30-4.16 (3H, m), 4.13-4.08 (0.5H, m), 4.06-4.01 (0.5H, m), 3.93-3.81 (2H, m), 3.76-3.69 (2H, m), 2.76-2.61 (2H, m), 2.52-2.36 (2H, m), 2.20-1.50 (6H, m), 1.41-1.26 (9H, m), 0.91-0.85 (3H, m).

Example 153

Ethyl (2S,3S)-8-E[N-(4-fluoro-2-hexylphenyl)sulfamoyl]-2,3-bis(hydroxymethyl)-1,4-dioxaspiro[4.5]dec-6-ene-7-carboxylate (Exemplified compound No. 1-822)

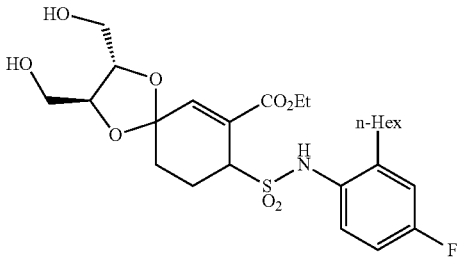

Following the process described in Examples 7, (16a) and 18 (alternative procedure), ethyl 8-[N-(4-fluoro-2-hexylphenyl)sulfamoyl]-1,4-dioxaspiro[4.5]dec-6-ene-7-carboxylate obtained in Example 87 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 54%).

$^1$H-NMR spectrum (400 MHz, $CDCl_3$) δ ppm:

7.50-7.44 (1H, m), 6.96-6.86 (3H, m), 6.70-6.67 (0.5H, m), 6.64-6.61 (0.5H, m), 4.41-4.37 (1H, m), 4.29-4.15 (3H, m), 4.12-4.07 (0.5H, m), 4.05-4.00 (0.5H, m), 3.93-3.80 (2H, m), 3.76-3.68 (2H, m), 2.76-2.61 (2H, m), 2.52-2.35 (2H, m), 2.31-1.51 (6H, m), 1.40-1.26 (9H, m), 0.91-0.86 (3H, m).

Example 154

Ethyl (2R,3R)-8-[N-(4-fluoro-2-heptylphenyl)sulfamoyl]-2,3-bis(hydroxymethyl)-1,4-dioxaspiro[4.5]dec-6-ene-7-carboxylate (Exemplified compound No. 1-998)

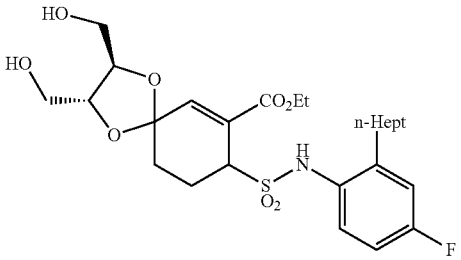

Following the process described in Example 7, (16a) and 17 (alternative procedure), ethyl 8-[N-(4-fluoro-2-heptylphenyl)sulfamoyl]-1,4-dioxaspiro[4.5]dec-6-ene-7-carboxylate obtained in Example 88 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 41%).

$^1$H-NMR spectrum (400 MHz, $CDCl_3$) δ ppm:

7.49 (1H, m), 6.96-6.87 (3H, m), 6.68 (0.5H, s), 6.61 (0.5H, s), 4.41-4.40 (1H, m), 4.30-3.71 (8H, m), 2.72-2.65 (2H, m), 2.48-2.39 (2H, m), 2.14-2.10 (2H, m), 1.95-1.87 (2H, m), 1.37-1.22 (11H, m), 0.88 (3H, t, J=7 Hz).

Example 155

Ethyl (2S,3S)-8-[N-(4-fluoro-2-heptylphenyl)sulfamoyl]-2,3-bis(hydroxymethyl)-1,4-dioxaspiro[4.5]dec-6-ene-7-carboxylate (Exemplified compound No. 1-998)

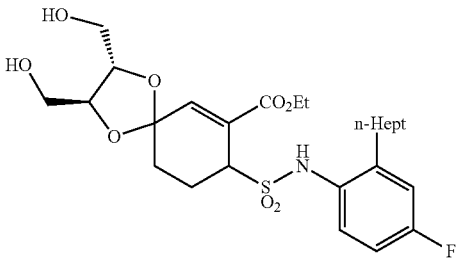

Following the process described in Examples 7, (16a) and 18 (alternative procedure), ethyl 8-[N-(4-fluoro-2-heptylphenyl)sulfamoyl]-1,4-dioxaspiro[4.5]dec-6-ene-7-carboxylate obtained in Example 88 was used in place of ethyl 8-[N-(2-chloro-4-fluorophenyl)sulfamoyl]-1,4-dioxaspiro[4.5]dec-6-ene-7-carboxylate to give the title compound as a white amorphous substance (yield: 70%).

$^1$H-NMR spectrum (400 MHz, $CDCl_3$) δ ppm:

7.50, 7.48 (1H, m), 6.97-6.88 (3H, m), 6.70 (0.5H, s), 6.70 (0.5H, s), 4.41-4.39 (1H, m), 4.28-3.71 (8H, m), 2.75-2.63 (2H, m), 2.51-2.37 (2H, m), 2.19-2.10 (2H, m), 1.95-1.88 (2H, m), 1.35-1.23 (11H, m), 0.88 (3H, t, J=7 Hz).

Example 156

Ethyl (2R,3R)-8-[N-(4-fluoro-2-octylphenyl)sulfamoyl]-2,3-bis(hydroxymethyl)-1,4-dioxaspiro[4.5]dec-6-ene-7-carboxylate (Exemplified compound No. 1-1920)

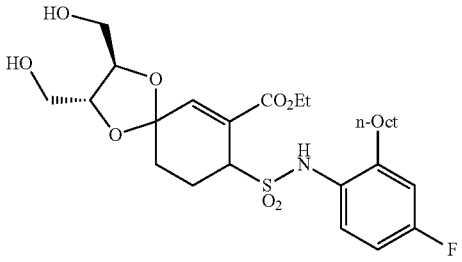

Following the process described in Examples 7, (16a) and 17 (alternative procedure), ethyl 8-[N-(4-fluoro-2-octylphenyl)sulfamoyl]-1,4-dioxaspiro[4.5]dec-6-ene-7-carboxylate obtained in Example 89 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 47%).

$^1$H-NMR spectrum (400 MHz, $CDCl_3$) δ ppm:

7.51-7.47 (1H, m), 6.97-6.88 (3H, m), 6.71 (0.5H, s), 6.64 (0.5H, s), 4.41-4.39 (1H, m), 4.28-3.72 (8H, m), 2.76-2.62 (2H, m), 2.51-2.37 (2H, m), 2.18-1.89 (4H, m), 1.37-1.27 (13H, m), 0.88 (3H, t, J=7 Hz).

Example 157

Ethyl (2S,3S)-8-[N-(4-fluoro-2-octylphenyl)sulfamoyl]-2,3-bis(hydroxymethyl)-1,4-dioxaspiro[4.5]dec-6-ene-7-carboxylate (Exemplified compound No. 1-1920)

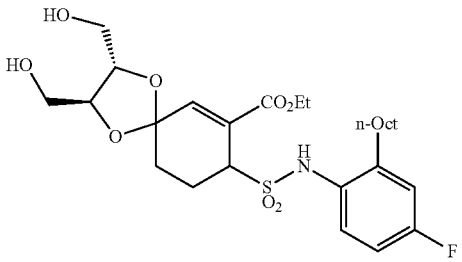

Following the process described in Examples 7, (16a) and 18 (alternative procedure), ethyl 8-[N-(4-fluoro-2-octylphenyl)sulfamoyl]-1,4-dioxaspiro[4.5]dec-6-ene-7-carboxylate obtained in Example 89 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 51%).

$^1$H-NMR spectrum (400 MHz, $CDCl_3$) δ ppm:

7.49 (1H, dd, J=9 Hz, 5 Hz), 6.97-6.88 (3H, m), 6.69 (0.5H, s), 6.63 (0.5H, s), 4.41-4.39 (1H, m), 4.31-3.70 (8H, m), 2.72-2.66 (2H, m), 2.52-2.37 (2H, m), 2.19-1.88 (4H, m), 1.37-1.27 (13H, m), 0.88 (3H, t, J=7 Hz).

Example 158

Ethyl (2R,3R)-8-[1N-(4-fluoro-2-nonylphenyl)sulfamoyl]-2,3-bis(hydroxymethyl)-1,4-dioxaspiro[4.5]dec-6-ene-7-carboxylate (Exemplified compound No. 1-2604)

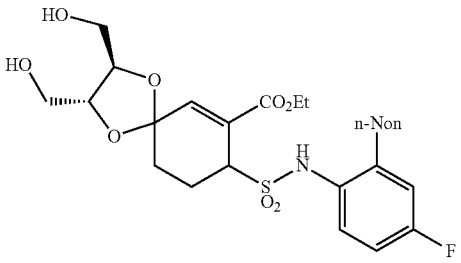

Following the process described in Examples 7, (16a) and 17 (alternative procedure), ethyl 8-[N-(4-fluoro-2-nonylphenyl)sulfamoyl]-1,4-dioxaspiro[4.5]dec-6-ene-7-carboxylate obtained in Example 90 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 48%). This compound was separable into two optical isomers in accordance with the following HPLC conditions.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.43 minutes<br>high polarity compound (second peak): 4.73 minutes |

$^1$H-NMR spectrum (400 MHz, $CDCl_3$) δ ppm:

7.50-7.45 (1H, m), 6.97-6.86 (3H, m), 6.66 (0.5H, s), 6.60 (0.5H, s), 4.42-4.37 (1H, m), 4.28-4.18 (3H, m), 4.13-4.08 (0.5H, m), 4.06-4.01 (0.5H, m), 3.95-3.81 (2H, m), 3.76-3.69 (2H, m), 2.77-2.61 (2H, m), 2.53-2.35 (2H, m), 2.19-1.99 (2H, m), 1.96-1.86 (2H, m), 1.64-1.52 (2H, m), 1.40-1.18 (15H, m), 0.91-0.85 (3H, m).

Example 159

Ethyl (2S,3S)-8-[N-(4-fluoro-2-nonylphenyl)sulfamoyl]-2,3-bis(hydroxymethyl)-1,4-dioxaspiro[4.5]dec-6-ene-7-carboxylate (Exemplified compound No. 1-2604)

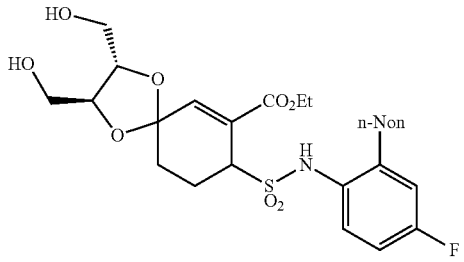

Following the process described in Examples 7, (16a) and 18 (alternative procedure), ethyl 8-[N-(4-fluoro-2-nonylphenyl)sulfamoyl]-1,4-dioxaspiro[4.5]dec-6-ene-7-carboxylate obtained in Example 90 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 54%). This compound was separable into two optical isomers in accordance with the following HPLC conditions.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 6.7 minutes<br>high polarity compound (second peak): 10.1 minutes |

$^1$H-NMR spectrum (400 MHz, $CDCl_3$) δ ppm:

7.50-7.45 (1H, m), 6.97-6.86 (3H, m), 6.71 (0.5H, s), 6.65 (0.5H, s), 4.42-4.37 (1H, m), 4.30-4.16 (3H, m), 4.13-4.08 (0.5H, m), 4.05-4.00 (0.5H, m), 3.93-3.80 (2H, m), 3.77-3.69

(2H, m), 2.76-2.61 (2H, m), 2.52-2.01 (5H, m), 1.95-1.86 (1H, m), 1.64-1.52 (2H, m), 1.41-1.22 (15H, m), 0.88 (3H, t, J=7 Hz).

Example 160

Ethyl (2R,3R)-8-[N-(2-decyl-4-fluorophenyl)sulfamoyl]-2,3-bis(hydroxymethyl)-1,4-dioxaspiro[4.5]dec-6-ene-7-carboxylate (Exemplified compound No. 1-2618)

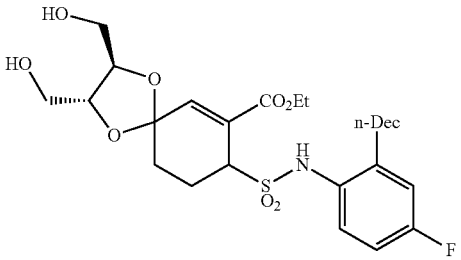

Following the process described in Examples 7, (16a) and 17 (alternative procedure), ethyl 8-[N-(2-decyl-4-fluorophenyl)sulfamoyl]-1,4-dioxaspiro[4.5]dec-6-ene-7-carboxylate obtained in Example 91 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 35%). This compound was separable into two optical isomers in accordance with the following HPLC conditions.

| HPLC conditions | |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.30 minutes<br>high polarity compound (second peak): 4.55 minutes |

$^1$H-NMR spectrum (400 MHz, $CDCl_3$) δ ppm:

7.51-7.45 (1H, m), 6.97-6.86 (3H, m), 6.67 (0.5H, s), 6.61 (0.5H, s), 4.42-4.36 (1H, m), 4.30-4.17 (3H, m), 4.13-4.08 (0.5H, m), 4.06-4.01 (0.5H, m), 3.94-3.80 (2H, m), 3.76-3.69 (2H, m), 2.76-2.61 (2H, m), 2.53-2.35 (2H, m), 2.19-2.00 (2H, m), 1.99-1.86 (2H, m), 1.65-1.51 (2H, m), 1.40-1.18 (17H, m), 0.91-0.85 (3H, m).

Example 161

Ethyl (2S,3S)-8-[N-(2-decyl-4-fluorophenyl)sulfamoyl]-2,3-bis(hydroxymethyl)-1,4-dioxaspiro[4.5]dec-6-ene-7-carboxylate (Exemplified compound No. 1-2618)

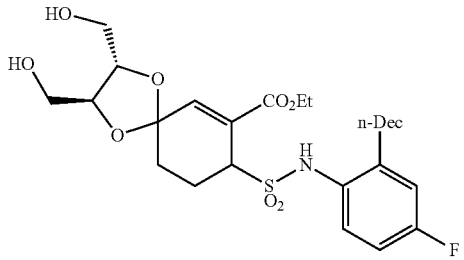

Following the process described in Examples 7, (16a) and 18 (alternative procedure), ethyl 8-[N-(2-decyl-4-fluorophenyl)sulfamoyl]-1,4-dioxaspiro[4.5]dec-6-ene-7-carboxylate obtained in Example 91 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 56%). This compound was separable into two optical isomers in accordance with the following HPLC conditions.

| HPLC conditions | |
|---|---|
| Column | CHIRALPAK AD-H (produced by Daicel Chemical Industries, Ltd. inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 6.4 minutes<br>high polarity compound (second peak): 9.1 minutes |

$^1$H-NMR spectrum (500 MHz, $CDCl_3$) δ ppm:

7.50-7.45 (1H, m), 6.97-6.87 (3H, m), 6.70 (0.5H, s), 6.64 (0.5H, s), 4.42-4.38 (1H, m), 4.30-4.17 (3H, m), 4.12-4.08 (0.5H, m), 4.05-4.01 (0.5H, m), 3.93-3.81 (2H, m), 3.78-3.69 (2H, m), 2.76-2.62 (2H, m), 2.52-2.37 (2H, m), 2.33-2.09

(2H, m), 2.06-1.87 (2H, m), 1.63-1.52 (2H, m), 1.40-1.22 (17H, m), 0.88 (3H, t, J=7 Hz).

Example 162

Ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-382)

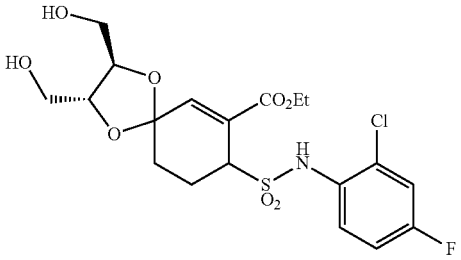

Ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate obtained in Example 17 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 12.0 minutes<br>high polarity compound (second peak): 16.5 minutes |

(Low Polarity Compound, First Peak)

Optical rotation $[\alpha]_D$+86.7 (c=2.0, MeOH)

$^1$H-NMR spectrum (400 MHz, $CDCl_3$) δ ppm:

7.67 (1H, dd, J=9 Hz, 5 Hz), 7.17 (1H, dd, J=8 Hz, 3 Hz), 7.07-6.98 (2H, m), 6.91 (1H, s), 4.42 (1H, dd, J=6 Hz, 2 Hz), 4.28-4.08 (4H, m), 3.91 (1H, dd, J=12 Hz, 4 Hz), 3.84 (1H, dd, J=12 Hz, 4 HZ), 3.77-3.68 (2H, m), 2.60-2.43 (2H, m), 2.26-2.11 (1H, m), 1.99-1.87 (1H, m), 1.58 (2H, bs), 1.27 (3H, t, J=7 Hz).

(High Polarity Compound, Second Peak)

$^1$H-NMR spectrum (400 MHz, $CDCl_3$) δ ppm:

7.66 (1H, dd, J=9 Hz, 5 Hz), 7.17 (1H, dd, J=8 Hz, 3 Hz), 7.07-6.98 (2H, m), 6.84 (1H, s), 4.42 (1H, d, J=5 Hz), 4.28-4.08 (3H, m), 4.07-4.01 (1H, m), 3.93-3.82 (2H, m), 3.77-3.68 (2H, m), 2.61-2.46 (2H, m), 2.24-2.11 (1H, m), 1.95-1.87 (1H, m), 1.57 (2H, bs), 1.27 (3H, t, J=7 Hz).

Example 163

Ethyl (2S,3S)-8-[N-(2-chloro-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-382)

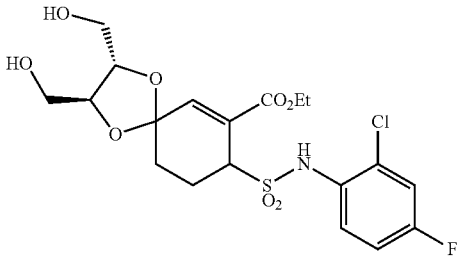

Ethyl (2S,3S)-8-[N-(2-chloro-4-fluorophenyl)sulfamoyl]-2,3-bis(hydroxymethyl)-1,4-dioxaspiro[4.5]dec-6-ene-7-carboxylate obtained in Example 18 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 11.4 minutes<br>high polarity compound (second peak): 27.4 minutes |

(Low Polarity Compound, First Peak)

$^1$H-NMR spectrum (400 MHz, $CDCl_3$) δ ppm:

7.66 (1H, dd, J=9 Hz, 5 Hz), 7.17 (1H, dd, J=8 Hz, 3 Hz), 7.06-7.00 (1H, m), 6.98 (1H, s), 6.84 (1H, s), 4.42 (1H, d, J=5 Hz), 4.27-4.09 (3H, m), 4.07-4.00 (1H, m), 3.93-3.83 (2H, m), 3.76-3.68 (2H, m), 2.60-2.47 (2H, m), 2.24-2.12 (1H, m), 1.95-1.60 (3H, m), 1.27 (3H, t, J=7 Hz).

(High Polarity Compound, Second Peak)

$^1$H-NMR spectrum (400 MHz, $CDCl_3$) δ ppm:

7.67 (1H, dd, J=9 Hz, 5 Hz), 7.17 (1H, dd, J=8 Hz, 3 Hz), 7.06-6.99 (2H, m), 6.90 (1H, s), 4.44-4.41 (1H, m), 4.27-4.09 (4H, m), 3.91 (1H, dd, J=12 Hz, 4 Hz), 3.84 (1H, dd, J=12 Hz,

4 HZ), 3.77-3.68 (2H, m), 2.60-2.45 (2H, m), 2.24-2.12 (1H, m), 2.00-1.65 (3H, m), 1.27 (3H, t, J=7 Hz).

Example 164

Ethyl (2R,3R)-8-[N-(2,4-difluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-294)

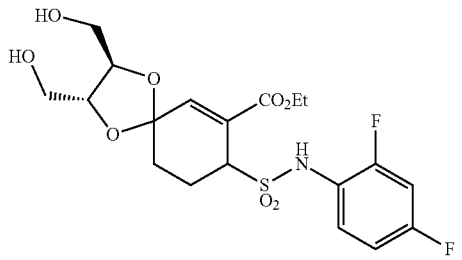

Ethyl (2R,3R)-8-[N-(2,4-difluorophenyl)sulfamoyl]-2,3-bis(hydroxymethyl)-1,4-dioxaspiro[4.5]dec-6-ene-7-carboxylate obtained in Example 144 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 13.7 minutes<br>high polarity compound (second peak): 15.9 minutes |

(Low Polarity Compound, First Peak)

$^1$H-NMR spectrum (500 MHz, $CDCl_3$) δ ppm:

7.62-7.57 (1H, m), 6.93-6.87 (3H, m), 4.36 (1H, q, J=3 Hz), 4.28-4.18 (3H, m), 4.15-4.09 (1H, m), 3.91 (1H, dd, J=12 Hz, 4 Hz), 3.84 (1H, dd, J=12 Hz, 4 Hz), 3.75-3.70 (2H, m), 2.51-2.40 (2H, m), 2.20-2.12 (1H, m), 1.96-1.90 (1H, m), 1.61 (2H, brs), 1.29 (3H, t, J=7 Hz).

(High Polarity Compound, Second Peak)

$^1$H-NMR spectrum (500 MHz, $CDCl_3$) δ ppm:

7.62-7.57 (1H, m), 6.97 (1H, brs), 6.93-6.86 (3H, m), 4.37-4.35 (1H, m), 4.29-4.17 (3H, m), 4.06-4.02 (1H, m), 3.91-3.84 (2H, m), 3.76-3.69 (2H, m), 2.53-2.41 (2H, m), 2.20-2.11 (1H, m), 2.05 (1H, brs), 1.94-1.88 (2H, m), 1.29 (3H, t, J=7 Hz).

Example 165

Ethyl (2S,3S)-8-[N-(2,4-difluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-294)

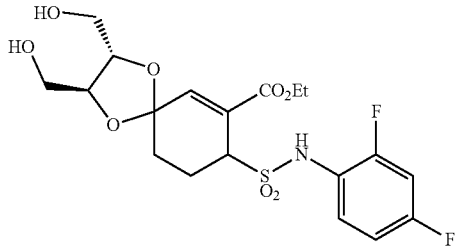

Ethyl (2S,3S)-8-[N-(2,4-difluorophenyl)sulfamoyl]-2,3-bis(hydroxymethyl)-1,4-dioxaspiro[4.5]dec-6-ene-7-carboxylate obtained in Example 145 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 6.9 minutes<br>high polarity compound (second peak): 10.7 minutes |

(Low Polarity Compound, First Peak)

$^1$H-NMR spectrum (500 MHz, $CDCl_3$) δ ppm:

7.62-7.57 (1H, m), 6.93-6.86 (3H, m), 4.36 (1H, d, J=4 Hz), 4.29-4.18 (3H, m), 4.06-4.01 (1H, m), 3.91-3.84 (2H, m), 3.75-3.70 (2H, m), 2.52-2.42 (2H, m), 2.19-1.50 (4H, m), 1.29 (3H, t, J=7 Hz).

(High Polarity Compound, Second Peak)

$^1$H-NMR spectrum (500 MHz, $CDCl_3$) δ ppm:

7.62-7.57 (1H, m), 6.93-6.87 (3H, m), 4.36 (1H, dd, J=6 Hz, 3 Hz), 4.29-4.18 (3H, m), 4.13-4.09 (1H, m), 3.91 (1H, dd, J=12 Hz, 4 Hz), 3.84 (1H, dd, J=12 Hz, 4 Hz), 3.75-3.70 (2H, m), 2.51-2.40 (2H, m), 2.20-1.50 (4H, m), 1.29 (3H, t, J=7 Hz).

Example 166

Ethyl (2R,3R)-8-[N-(2-bromo-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-1568)

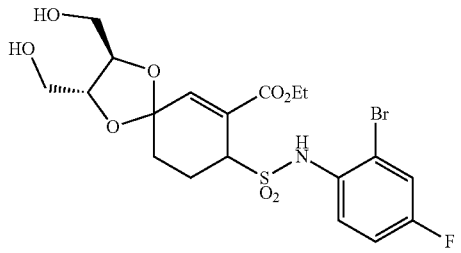

Ethyl (2R,3R)-8-[N-(2-bromo-4-fluorophenyl)sulfamoyl]-2,3-bis(hydroxymethyl)-1,4-dioxaspiro[4.5]dec-6-ene-7-carboxylate obtained in Example 146 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 6.8 minutes<br>high polarity compound (second peak): 8.8 minutes |

(Low Polarity Compound, First Peak)

$^1$H-NMR spectrum (400 MHz, $CDCl_3$) δ ppm:

7.68 (1H, dd, J=9.2 Hz, 5.2 Hz), 7.34 (1H, dd, J=7.6 Hz, 2.9 Hz), 7.11-7.06 (1H, m), 6.91 (1H, s), 4.44 (1H, dd, J=5.8 Hz, 2.0 Hz), 4.28-4.10 (4H, m), 3.93-3.70 (4H, m), 2.60-2.47 (2H, m), 2.24-2.14 (1H, m), 1.97-1.92 (1H, m), 1.27 (3H, t, J=7.0 Hz).

(High Polarity Compound, Second Peak)

$^1$H-NMR spectrum (400 MHz, $CDCl_3$) δ ppm:

7.67 (1H, dd, J=9.2 Hz, 5.3 Hz), 7.34 (1H, dd, J=7.6 Hz, 2.9 Hz), 7.11-7.06 (1H, m), 6.85 (1H, s), 4.44 (1H, d, J=5.0 Hz), 4.27-4.02 (4H, m), 3.92-3.84 (2H, m), 3.76-3.70 (2H, m), 2.61-2.48 (2H, m), 2.23-2.15 (1H, m), 1.92-1.88 (1H, m), 1.27 (3H, t, J=7.2 Hz).

Example 167

Ethyl (2S,3S)-8-[N-(2-bromo-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-1568)

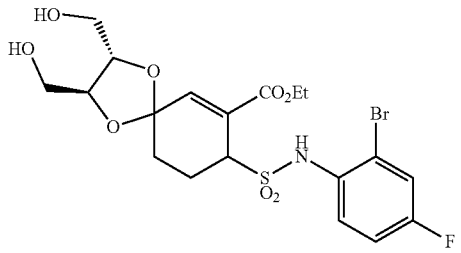

Ethyl (2S,3S)-8-[N-(2-bromo-4-fluorophenyl)sulfamoyl]-2,3-bis(hydroxymethyl)-1,4-dioxaspiro[4.5]dec-6-ene-7-carboxylate obtained in Example 147 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd.<br>inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 6.7 minutes<br>high polarity compound (second peak): 13.2 minutes |

(Low Polarity Compound, First Peak)

$^1$H-NMR spectrum (400 MHz, $CDCl_3$) δ ppm:

7.67 (1H, dd, J=9 Hz, 5 Hz), 7.33 (1H, dd, J=8 Hz, 3 Hz), 7.10-7.06 (1H, m), 6.84 (1H, s), 4.44 (1H, d, J=5 Hz), 4.24-3.70 (8H, m), 2.61-2.48 (2H, m), 2.24-1.87 (2H, m), 1.26 (3H, t, J=7 Hz).

(High Polarity Compound, Second Peak)

$^1$H-NMR spectrum (400 MHz, $CDCl_3$) δ ppm:

7.67 (1H, dd, J=9 Hz, 5 Hz), 7.33 (1H, dd, J=8 Hz, 3 Hz), 7.10-7.05 (1H, m), 6.91 (1H, s), 4.44 (1H, d, J=6 Hz), 4.27-3.69 (8H, m), 2.59-2.48 (2H, m), 2.23-1.91 (2H, m), 1.26 (3H, t, J=7 Hz).

Example 168

Ethyl (2R,3R)-8-[N-(2-butyl-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-646)

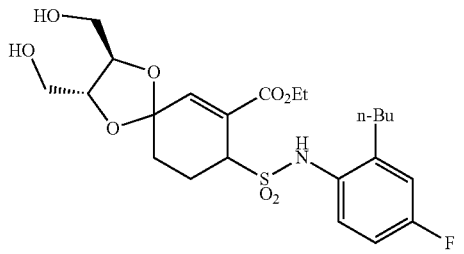

Ethyl (2R,3R)-8-[N-(2-butyl-4-fluorophenyl)sulfamoyl]-2,3-bis(hydroxymethyl)-1,4-dioxaspiro[4.5]dec-6-ene-7-carboxylate obtained in Example 148 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a pale red amorphous substance and a white powder. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 5.02 minutes<br>high polarity compound (second peak): 5.24 minutes |

(Low Polarity Compound, First Peak)

$^1$H-NMR spectrum (400 MHz, $CDCl_3$) δ ppm:

7.49 (1H, dd, J=9 Hz, 5 Hz), 6.98-6.93 (2H, m), 6.90 (1H, dt, J=8 Hz, 3 Hz), 6.67 (1H, s), 4.40 (1H, dd, J=6 Hz, 3 Hz), 4.29-4.19 (3H, m), 4.13-4.08 (1H, m), 3.92 (1H, dd, J=12 Hz, 4 Hz), 3.85 (1H, dd, 12 Hz, 4 Hz), 3.76-3.69 (2H, m), 2.78-2.62 (2H, m), 2.53-2.35 (2H, m), 2.19-1.80 (4H, m), 1.65-1.49 (2H, m), 1.44-1.34 (2H, m), 1.31 (3H, t, J=7 Hz), 0.95 (3H, t, J=7 Hz).

(High Polarity Compound, Second Peak)

$^1$H-NMR spectrum (400 MHz, $CDCl_3$) δ ppm:

7.48 (1H, dd, J=9 Hz, 5 Hz), 6.95 (1H, dd, J=9 Hz, 3 Hz), 6.93-6.86 (2H, m), 6.62 (1H, s), 4.41 (1H, d, J=4 Hz), 4.28-4.17 (3H, m), 4.05-4.01 (1H, m), 3.91-3.83 (2H, m), 3.77-3.69 (2H, m), 2.77-2.62 (2H, m), 2.53-2.35 (2H, m), 2.18-1.76 (4H, m), 1.65-1.50 (2H, m), 1.44-1.35 (2H, m), 1.30 (3H, t, J=7 Hz), 0.95 (3H, t, J=7 Hz).

Example 169

Ethyl (2S,3S)-8-[N-(2-butyl-4-fluorophenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-646)

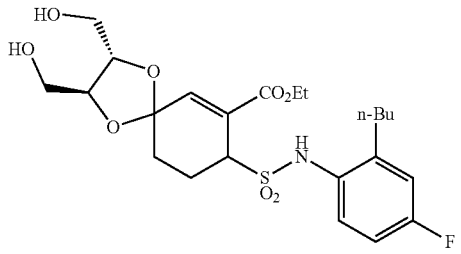

Ethyl (2S,3S)-8-[N-(2-butyl-4-fluorophenyl)sulfamoyl]-2,3-bis(hydroxymethyl)-1,4-dioxaspiro[4.5]dec-6-ene-7-carboxylate obtained in Example 149 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white powder and a pale red amorphous substance. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 5.08 minutes<br>high polarity compound (second peak): 5.58 minutes |

(Low Polarity Compound, First Peak)

$^1$H-NMR spectrum (400 MHz, $CDCl_3$) δ ppm:

7.47 (1H, dd, J=9 Hz, 5 Hz), 6.95 (1H, dd, J=9 Hz, 3 Hz), 6.93-6.86 (2H, m), 6.61 (1H, s), 4.41 (1H, d, J=4 Hz), 4.26-4.16 (3H, m), 4.05-3.99 (1H, m), 3.90-3.80 (2H, m), 3.78-3.68 (2H, m), 2.77-2.62 (2H, m), 2.53-2.39 (2H, m), 2.33-2.05 (2H, m), 1.96-1.86 (1H, m), 1.80-1.65 (1H, m), 1.63-1.52 (2H, m), 1.44-1.35 (2H, m), 1.29 (3H, t, J=7 Hz), 0.95 (3H, t, J=7 Hz).

(High Polarity Compound, Second Peak)

$^1$H-NMR spectrum (400 MHz, $CDCl_3$) δ ppm:

7.48 (1H, dd, J=9 Hz, 5 Hz), 6.99-6.86 (3H, m), 6.70 (1H, s), 4.40 (1H, dd, J=6 Hz, 3 Hz), 4.29-4.17 (3H, m), 4.13-4.07 (1H, m), 3.90 (1H, dd, J=12 Hz, 4 Hz), 3.84 (1H, dd, 12 Hz, 4 Hz), 3.76-3.69 (2H, m), 2.77-2.62 (2H, m), 2.53-2.23 (3H, m), 2.20-2.00 (2H, m), 1.96-1.86 (1H, m), 1.63-1.52 (2H, m), 1.44-1.34 (2H, m), 1.30 (3H, t, J=7 Hz), 0.95 (3H, t, J=7 Hz).

Example 170

Ethyl (2R,3R)-8-[N-(4-fluoro-2-pentylphenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-1744)

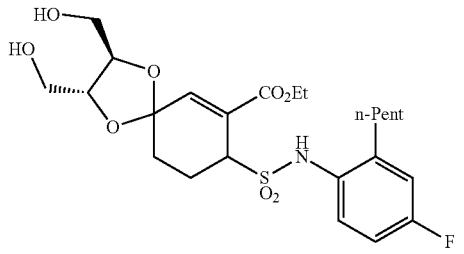

Ethyl (2R,3R)-8-[N-(4-fluoro-2-pentylphenyl)sulfamoyl]-2,3-bis(hydroxymethyl)-1,4-dioxaspiro[4.5]dec-6-ene-7-carboxylate obtained in Example 150 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a pale red amorphous substance and a white powder. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.83 minutes<br>high polarity compound (second peak): 5.01 minutes |

(Low Polarity Compound, First Peak)

$^1$H-NMR spectrum (400 MHz, $CDCl_3$) δ ppm:

7.48 (1H, dd, J=9 Hz, 5 Hz), 6.97-6.92 (2H, m), 6.90 (1H, dt, J=8 Hz, 3 Hz), 6.66 (1H, s), 4.40 (1H, dd, J=6 Hz, 3 Hz), 4.28-4.18 (3H, m), 4.14-4.07 (1H, m), 3.92 (1H, dd, J=12 Hz, 4 Hz), 3.85 (1H, dd, 12 Hz, 4 Hz), 3.76-3.69 (2H, m), 2.76-2.61 (2H, m), 2.50-2.35 (2H, m), 2.19-2.08 (1H, m), 1.97-1.87 (1H, m), 1.81-1.49 (4H, m), 1.40-1.32 (4H, m), 1.30 (3H, t, J=7 Hz), 0.90 (3H, t, J=7 Hz).

(High Polarity Compound, Second Peak)

$^1$H-NMR spectrum (400 MHz, $CDCl_3$) δ ppm:

7.48 (1H, dd, J=9 Hz, 5 Hz), 6.95 (1H, dd, J=9 Hz, 3 Hz), 6.93-6.86 (2H, m), 6.60 (1H, s), 4.41 (1H, d, J=5 Hz), 4.29-4.17 (3H, m), 4.07-4.01 (1H, m), 3.93-3.84 (2H, m), 3.76-3.69 (2H, m), 2.76-2.61 (2H, m), 2.54-2.36 (2H, m), 2.19-2.07 (1H, m), 2.06-1.70 (3H, m), 1.66-1.50 (2H, m), 1.40-1.32 (4H, m), 1.30 (3H, t, J=7 Hz), 0.90 (3H, t, J=7 Hz).

Example 171

Ethyl (2S,3S)-8-[N-(4-fluoro-2-pentylphenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-1744)

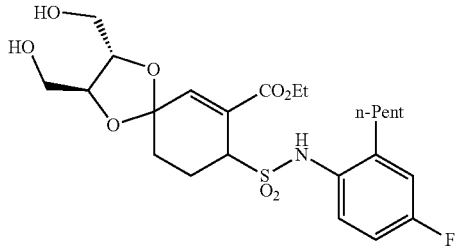

Ethyl (2S,3S)-8-[N-(4-fluoro-2-pentylphenyl)sulfamoyl]-2,3-bis(hydroxymethyl)-1,4-dioxaspiro[4.5]dec-6-ene-7-carboxylate obtained in Example 151 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white powder and a pale red amorphous substance. According to the result of HPLC analysis of the two optical isomers obtained under the conditions below, their optical purity were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.90 minutes<br>high polarity compound (second peak): 6.18 minutes |

(Low Polarity Compound, First Peak)

$^1$H-NMR spectrum (400 MHz, $CDCl_3$) δ ppm:

7.48 (1H, dd, J=9 Hz, 5 Hz), 6.97-6.85 (3H, m), 6.59 (1H, s), 4.40 (1H, d, J=5 Hz), 4.29-4.17 (3H, m), 4.06-4.00 (1H, m), 3.91-3.83 (2H, m), 3.76-3.69 (2H, m), 2.76-2.59 (2H, m), 2.53-2.36 (2H, m), 2.20-2.06 (1H, m), 1.94-1.85 (1H, m), 1.80-1.50 (4H, m), 1.41-1.22 (7H, m), 0.91 (3H, t, J=7 Hz).

(High Polarity Compound, Second Peak)

$^1$H-NMR spectrum (400 MHz, $CDCl_3$) δ ppm:

7.47 (1H, dd, J=9 Hz, 5 Hz), 6.97-6.92 (2H, m), 6.89 (1H, dt, J=8 Hz, 3 Hz), 6.73 (1H, s), 4.40 (1H, dd, J=6 Hz, 3 Hz), 4.28-4.17 (3H, m), 4.12-4.05 (1H, m), 3.89 (1H, dd, J=12 Hz, 4 Hz), 3.82 (1H, dd, 12 Hz, 4 Hz), 3.76-3.69 (2H, m), 2.76-2.61 (2H, m), 2.51-2.35 (2H, m), 2.26-2.01 (2H, m), 1.97-1.68 (2H, m), 1.66-1.54 (2H, m), 1.41-1.31 (4H, m), 1.29 (3H, t, J=7 Hz), 0.90 (3H, t, J=7 Hz).

Example 172

Ethyl (2R,3R)-8-[N-(4-fluoro-2-hexylphenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-822)

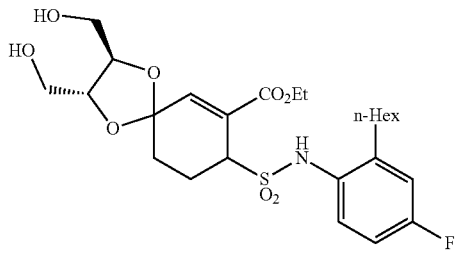

Ethyl (2R,3R)-8-[N-(4-fluoro-2-hexylphenyl)sulfamoyl]-2,3-bis(hydroxymethyl)-1,4-dioxaspiro[4.5]dec-6-ene-7-carboxylate obtained in Example 152 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 9:1 |
| Flow rate | 1.0 ml/min |
| Temperature | 40° C. |
| Detection | 254 nm (UV) |
| Retention time | low polarity compound (first peak): 25.2 minutes<br>high polarity compound (second peak): 29.3 minutes |

(Low Polarity Compound, First Peak)

$^1$H-NMR spectrum (400 MHz, $CDCl_3$) δ ppm:

7.48 (1H, dd, J=9 Hz, 5 Hz), 6.97-6.87 (3H, m), 6.66 (1H, s), 4.41-4.37 (1H, m), 4.29-4.19 (3H, m), 4.13-4.09 (1H, m), 3.95-3.88 (1H, m), 3.87-3.81 (1H, m), 3.77-3.69 (2H, m), 2.77-2.62 (2H, m), 2.51-2.36 (2H, m), 2.19-2.09 (2H, m), 1.95-1.89 (2H, m), 1.63-1.52 (2H, m), 1.40-1.28 (9H, m), 0.91-0.86 (3H, m).

(High Polarity Compound, Second Peak)

$^1$H-NMR spectrum (400 MHz, $CDCl_3$) δ ppm:

7.47 (1H, dd, J=9 Hz, 5 Hz), 6.96-6.86 (3H, m), 6.63 (1H, s), 4.42-4.39 (1H, m), 4.30-4.16 (3H, m), 4.06-4.01 (1H, m), 3.91-3.83 (2H, m), 3.77-3.69 (2H, m), 2.76-2.61 (2H, m), 2.53-2.37 (2H, m), 2.18-2.08 (2H, m), 2.03-1.98 (1H, m), 1.93-1.86 (1H, m), 1.63-1.52 (2H, m), 1.41-1.26 (9H, m), 0.91-0.86 (3H, m).

Example 173

Ethyl (2S,3S)-8-[N-(4-fluoro-2-hexylphenyl)sulfamoyl]-2,3-bis(hydroxymethyl)-1,4-dioxaspiro[4.5]dec-6-ene-7-carboxylate (low polarity compound, first peak), (high polarity compound, second peak) (Exemplified compound No. 1-822)

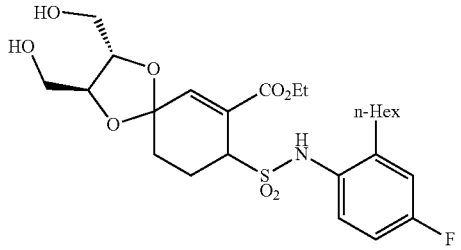

Ethyl (2S,3S)-8-[N-(4-fluoro-2-hexylphenyl)sulfamoyl]-2,3-bis(hydroxymethyl)-1,4-dioxaspiro[4.5]dec-6-ene-7-carboxylate obtained in Example 153 was subjected to high performance liquid chromatography (column; CHIRALPAK AD-H, size; inner diameter 2 cm, length 25 cm, solvent; hexane:2-propanol) to separate and purity two optical isomers, and low polarity compound (first peak) and high polarity compound (second peak) were respectively obtained as an amorphous substance. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 7.6 minutes<br>high polarity compound (second peak): 10.6 minutes |

(Low Polarity Compound, First Peak)

$^1$H-NMR spectrum (500 MHz, $CDCl_3$) δ ppm:

7.48 (1H, dd, J=9 Hz, 5 Hz), 6.95 (1H, dd, J=9 Hz, 3 Hz), 6.92-6.87 (2H, m), 6.61 (1H, s), 4.40 (1H, d, J=4 Hz), 4.29-4.17 (3H, m), 4.06-4.02 (1H, m), 3.91-3.84 (2H, m), 3.76-3.70 (2H, m), 2.75-2.62 (2H, m), 2.52-2.46 (1H, m), 2.42 (1H, td, J=14 Hz, 3 Hz), 2.17-2.09 (1H, m), 2.05 (1H, dd, J=8 Hz, 5 Hz), 1.96-1.87 (2H, m), 1.64-1.53 (2H, m), 1.40-1.27 (9H, m), 0.91-0.87 (3H, m).

(High Polarity Compound, Second Peak)

$^1$H-NMR spectrum (500 MHz, $CDCl_3$) δ ppm:

7.48 (1H, dd, J=9 Hz, 5 Hz), 6.96-6.93 (2H, m), 6.90 (1H, td, J=8 Hz, 3 Hz), 6.67 (1H, m), 4.39 (1H, dd, J=6 Hz, 4 Hz), 4.30-4.19 (3H, m), 4.13-4.09 (1H, m), 3.91 (1H, dt, J=12 Hz, 4 Hz), 3.84 (1H, dt, J=12 Hz, 4 Hz), 3.76-3.69 (2H, m), 2.76-2.63 (2H, m), 2.50-2.44 (1H, m), 2.40 (1H, td, J=13 Hz, 3 Hz), 2.18-2.10 (2H, m), 1.95-1.89 (2H, m), 1.63-1.53 (2H, m), 1.40-1.28 (9H, m), 0.91-0.87 (3H, m).

Example 174

Ethyl (2R,3R)-8-[N-(4-fluoro-2-heptylphenyl)sulfamoyl]-2,3-bis(hydroxymethyl)-1,4-dioxaspiro[4.5]dec-6-ene-7-carboxylate (Low Polarity Compound, First Peak), (High Polarity Compound, Second Peak) (Exemplified Compound No. 1-998)

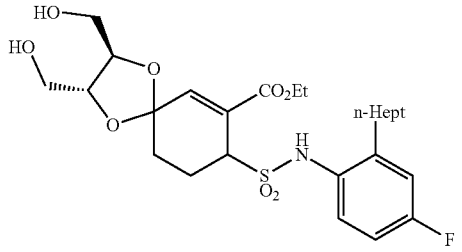

Ethyl (2R,3R)-8-[N-(4-fluoro-2-heptylphenyl)sulfamoyl]-2,3-bis(hydroxymethyl)-1,4-dioxaspiro[4.5]dec-6-ene-7-carboxylate obtained in Example 154 was subjected to high performance liquid chromatography (column; CHIRALPAK AD-H, size; inner diameter 2 cm, length 25 cm, solvent; hexane:2-propanol) to separate and purify the two optical isomers, and low polarity compound (first peak) and high polarity compound (second peak) were respectively obtained as a white amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd. inner diameter 0.46 cm, length 25 cm) |
| Mobile phase | hexane:2-propanol = 9:1 |
| Flow rate | 1.0 ml/min |
| Temperature | 40° C. |
| Detection | 254 nm (UV) |
| Retention time | low polarity compound (first peak): 23.9 minutes<br>high polarity compound (second peak): 27.4 minutes |

(Low Polarity Compound, First Peak)

$^1$H-NMR spectrum (400 MHz, $CDCl_3$) δ ppm:

7.48 (1H, dd, J=8 Hz, 5 Hz), 6.96-6.88 (3H, m), 6.67 (1H, s), 4.40-4.38 (1H, m), 4.27-3.69 (8H, m), 2.72-2.62 (2H, m), 2.49-1.89 (6H, m), 1.34-1.25 (11H, m), 0.88 (3H, t, J=7 Hz).

(High Polarity Compound, Second Peak)

$^1$H-NMR spectrum (400 MHz, $CDCl_3$) δ ppm:

7.47 (1H, dd, J=9 Hz, 5 Hz), 6.96-6.87 (3H, m), 6.64 (1H, brs), 4.40 (1H, d, J=4 Hz), 4.29-3.71 (8H, m), 2.75-2.61 (2H, m), 2.51-2.37 (2H, m), 2.17-1.86 (4H, m), 1.42-1.22 (11H, m), 0.88 (3H, t, J=7 Hz).

Example 175

Ethyl (2S,3S)-8-[N-(4-fluoro-2-heptylphenyl)sulfamoyl]-2,3-bis(hydroxymethyl)-1,4-dioxaspiro[4.5]dec-6-ene-7-carboxylate (Low Polarity Compound, First Peak), (High Polarity Compound, Second Peak) (Exemplified Compound No. 1-998)

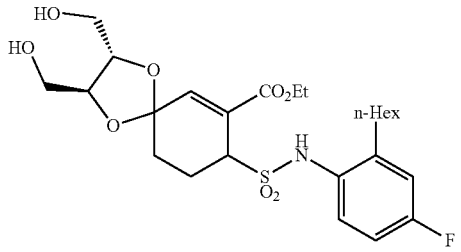

Ethyl (2S,3S)-8-[N-(4-fluoro-2-heptylphenyl)sulfamoyl]-2,3-bis(hydroxymethyl)-1,4-dioxaspiro[4.5]dec-6-ene-7-carboxylate obtained in Example 155 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white powder and a white amorphous substance. According to the result of HPLC analysis of the two optical isomers obtained under the conditions below, their optical purities were respectively >99% ee.

| HPLC conditions | |
|---|---|
| column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.8 minutes<br>high polarity compound (second peak): 6.3 minutes |

(Low Polarity Compound, First Peak)

$^1$H-NMR spectrum (400 MHz, $CDCl_3$) δ ppm:

7.48 (1H, dd, J=9 Hz, 5 Hz), 6.97-6.88 (3H, m), 6.64 (1H, s), 4.41 (1H, d, J=4 Hz), 4.27-3.72 (8H, m), 2.75-2.62 (2H, m), 2.51-2.38 (2H, m), 2.18-1.38 (4H, m), 1.38-1.28 (11H, m), 0.88 (3H, t, J=7 Hz).

(High Polarity Compound, Second Peak)

$^1$H-NMR spectrum (400 MHz, $CDCl_3$) δ ppm:

7.49 (1H, dd, J=9 Hz, 5 Hz), 6.97-6.88 (3H, m), 6.69 (1H, s), 4.41-4.39 (1H, m), 4.29-3.71 (8H, m), 2.77-2.62 (2H, m), 2.49-1.90 (6H, m), 1.38-1.29 (11H, m), 0.89 (3H, t, J=7 Hz).

Example 176

Ethyl (2R,3R)-8-[N-(4-fluoro-2-octylphenyl)sulfamoyl]-2,3-bis(hydroxymethyl)-1,4-dioxaspiro[4.5]dec-6-ene-7-carboxylate (Low Polarity Compound, First Peak), (High Polarity Compound, Second Peak) (Exemplified Compound No. 1-1920)

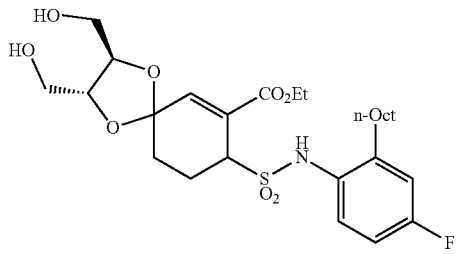

Ethyl (2R,3R)-8-[N-(4-fluoro-2-octylphenyl)sulfamoyl]-2,3-bis(hydroxymethyl)-1,4-dioxaspiro[4.5]dec-6-ene-7-carboxylate obtained in Example 156 was subjected to high performance liquid chromatography (column; CHIPALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white amorphous substance. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 9:1 |
| Flow rate | 1.0 ml/min |
| Temperature | 40° C. |
| Detection | 254 nm (UV) |
| Retention time | low polarity compound (first peak): 22.9 minutes<br>high polarity compound (second peak): 25.8 minutes |

(Low Polarity Compound, First Peak)

$^1$H-NMR spectrum (400 MHz, $CDCl_3$) δ ppm:

7.48 (1H, dd, J=9 Hz, 5 Hz), 6.96-6.88 (3H, m), 6.68 (1H, s), 6.68-4.40 (1H, m), 4.28-3.70 (8H, m), 4.28-3.70 (2H, m), 2.52-1.89 (6H, m), 1.36-1.19 (13H, m), 0.88 (3H, t, J=7 Hz).

(High Polarity Compound, Second Peak)

$^1$H-NMR spectrum (400 MHz, $CDCl_3$) δ ppm:

7.46 (1H, dd, J=9 Hz, 5 Hz), 6.95-6.87 (3H, m), 4.40 (1H, d, J=5 Hz), 4.28-3.71 (8H, m), 2.73-2.60 (2H, m), 2.50-1.87 (6H, m), 1.31-1.25 (13H, m), 0.89 (3H, t, J=7 Hz).

Example 177

Ethyl (2S,3S)-8-[N-(4-fluoro-2-octylphenyl)sulfamoyl]-2,3-bis(hydroxymethyl)-1,4-dioxaspiro[4.5]dec-6-ene-7-carboxylate (Low Polarity Compound, First Peak), (High Polarity Compound, Second Peak) (Exemplified Compound No. 1-1920)

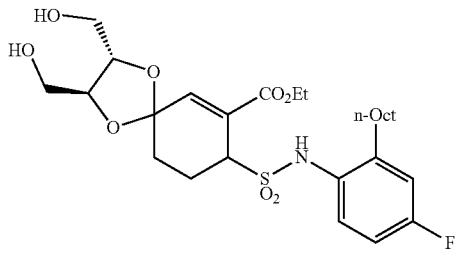

Ethyl (2S,3S)-8-[N-(4-fluoro-2-octylphenyl)sulfamoyl]-2,3-bis(hydroxymethyl)-1,4-dioxaspiro[4.5]dec-6-ene-7-carboxylate obtained in Example 157 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white powder and a colorless oil. According to the result of HPLC analysis of the two optical isomers obtained under the conditions below, their optical purities were respectively >99% ee.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 4.7 minutes<br>high polarity compound (second peak): 6.1 minutes |

(Low Polarity Compound, First Peak)

$^1$H-NMR spectrum (400 MHz, $CDCl_3$) δ ppm:

7.48 (1H, dd, J=9 Hz, 5 Hz), 6.97-6.88 (3H, m), 6.63 (1H, s), 4.41 (1H, d, J=5 Hz), 4.28-3.71 (8H, m), 2.75-2.62 (2H, m), 2.51-1.88 (6H, m), 1.38-1.27 (13H, m), 0.88 (3H, t, J=7 Hz).

(High Polarity Compound, Second Peak)

$^1$H-NMR spectrum (400 MHz, $CDCl_3$) δ ppm:

7.49 (1H, dd, J=9 Hz, 6 Hz), 6.97-6.88 (3H, m), 6.97-6.88 (1H, m), 4.41-4.38 (1H, m), 4.31-3.71 (8H, m), 2.77-2.63 (2H, m), 2.50-1.90 (6H, m), 2.50-1.90 (13H, m), 0.88 (3H, t, J=7 Hz).

Example 178

Ethyl (2R,3R)-8-[N-(2-chloro-4-fluorophenyl)sulfamoyl]-2,3-bis(methoxymethyl)-1,4-dioxaspiro[4.5]dec-6-ene-7-carboxylate

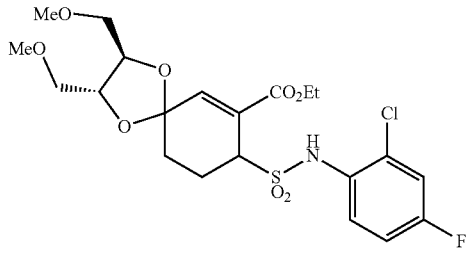

Following the process described in Example (17a), 1,4-di-O-methyl-2,3-di-O-trimethylsilyl-D-threitol was used in place of 1,4-di-O-benzoyl-2,3-di-O-trimethylsilyl-D-threitol to give the title compound as a colorless oil (yield: 89%).

$^1$H-NMR spectrum (400 MHz, $CDCl_3$) δ ppm:

7.68-7.64 (1H, m), 7.16 (1H, dd, J=8.1 Hz, 3.0 Hz), 7.17-7.16 (3H, m), 4.39 (1H, d, J=3.5 Hz), 4.24-3.98 (4H, m), 3.43-3.42 (4H, m), 3.43 (1.5H, s), 3.42 (1.5H, s), 3.39 (1.5H, s), 3.38 (1.5H, s), 2.57-2.45 (2H, m), 2.57-2.45 (1H, m), 1.96-1.86 (1H, m), 1.27 (3H, dt, J=6.9 Hz, 2.1 Hz).

Example 179

Ethyl (2S,3S)-8-[N-(2-chloro-4-fluorophenyl)sulfamoyl]-2,3-bis(methoxymethyl)-1,4-dioxaspiro[4.5]dec-6-ene-7-carboxylate

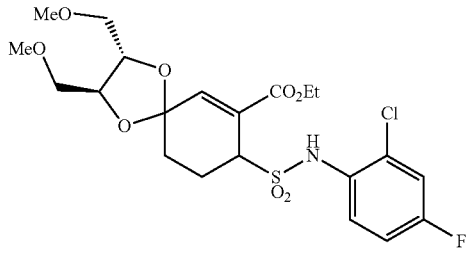

Following the process described in Example (17a), 1,4-di-O-methyl-2,3-di-O-trimethylsilyl-L-threitol was used in place of 1,4-di-o-benzoyl-2,3-di-O-trimethylsilyl-D-threitol to give the title compound as a colorless oil (91% yield).

$^1$H-NMR spectrum (400 MHz, $CDCl_3$) δ ppm:

7.68-7.64 (1H, m), 7.16 (1H, dd, J=7.8 and 2.4 Hz), 7.04-7.00 (2H, m), 6.89 (1H, s), 4.40-4.39 (1H, m), 4.23-3.97 (4H, m), 3.62-3.47 (4H, m), 3.43 (1.5H, s), 3.41 (1.5H, s), 3.39 (1.5H, s), 3.38 (1.5H, s), 2.58-2.45 (2H, m), 2.26-2.16 (1H, m), 1.96-1.86 (1H, m), 1.26 (3H, dt, J=7.0 and 3.5 Hz).

Example 180

Ethyl (2S,3S)-2,3-bis(benzyloxymethyl)-8-[N-(2-chloro-4-fluorophenyl)sulfamoyl]-1,4-dioxaspiro[4.5]dec-6-ene-7-carboxylate

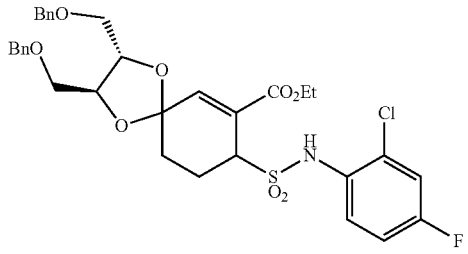

Following the process described in Example (17a), 1,4-di-O-benzyl-2,3-di-o-trimethylsilyl-L-threitol was used in place of 1,4-di-O-benzoyl-2,3-di-O-trimethylsilyl-D-threitol to give the title compound as a colorless oil (yield: 94%).

$^1$H-NMR spectrum (400 MHz, $CDCl_3$) δ ppm:

7.69-7.64 (1H, m), 7.37-7.26 (10H, m), 7.16 (1H, dd, J=7.8 Hz, 2.8 Hz), 7.04-6.90 (3H, m), 4.64-4.51 (4H, m), 4.40 (1H, t, J=4.5 Hz), 4.30-4.05 (4H, m), 3.68-3.57 (4H, m), 2.58-2.45 (2H, m), 2.25-2.17 (1H, m), 1.96-1.86 (1H, m), 1.21 (3H, dt, J=7.0 Hz, 3.5 Hz).

Example 181

Ethyl (2R,3R)-2,3-bis(acetoxymethyl)-8-[N-(2-chloro-4-fluorophenyl)sulfamoyl]-1,4-dioxaspiro[4.5]dec-6-ene-7-carboxylate

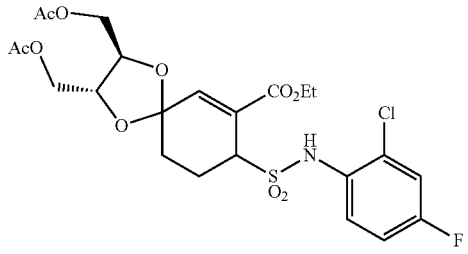

Following the process described in Example (17a), 1,4-di-O-acetyl-2,3-di-O-trimethylsilyl-D-threitol obtained in Reference Example 24 was used in place of 1,4-di-O-benzoyl-2,3-di-O-trimethylsilyl-D-threitol to give the title compound as a white amorphous substance (50% yield).

$^1$H-NMR spectrum (400 MHz, $CDCl_3$) δ ppm:

7.67 (1H, dd, J=9.2 Hz, 5.3 Hz), 7.17 (1H, dd, J=7.9 Hz, 2.8 Hz), 7.05-7.00 (2H, m), 6.90-6.76 (1H, m), 4.41 (1H, d, J=4.7 Hz), 4.37-4.37 (8H, m), 2.60-2.46 (2H, m), 2.23-2.04 (8H, m), 1.26 (3H, t, J=7.0 Hz).

Example 182

Ethyl (2S,3S)-2,3-bis(acetylaminomethyl)-8-[N-(2-chloro-4-fluorophenyl)sulfamoyl]-1,4-dioxaspiro[4.5]dec-6-ene-7-carboxylate (Exemplified compound No. 1-410)

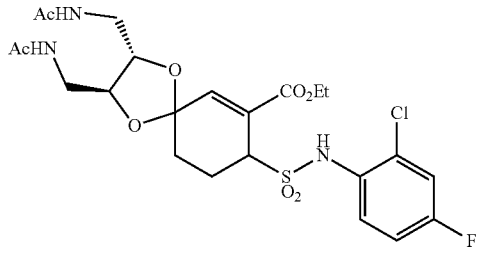

218 mg (1.07 mmol) of N-(4-acetylamino-2R,3R-dihydroxybutyl)acetamide and 0.57 ml (3.20 mmol) of isopropoxytrimethylsilane were dissolved in 3 ml of nitromethane, and 13 μl (0.071 mmol) of trimethylsilyl trifluoromethanesulfonate and 300 mg (0.711 mmol) of ethyl 6-[N-(2-chloro-4-fluorophenyl)sulfamoyl]-3,3-dimethoxy-1-cyclohexene-1-carboxylate obtained in Example (16a) were sequentially added thereto with stirring under ice-cooling, followed by stirring for 3 hours at the same temperature and then for 116 hours at room temperature. To the reaction solution was added saturated aqueous sodium hydrogencarbonate and the mixture was extracted with ethyl acetate. The organic layer was washed with water and dried over anhydrous magnesium sulfate, followed by concentration under reduced pressure. The residue was subjected to silica gel column chromatography (solvent; ethyl acetate methanol=9:1) to give 203 mg of the title compound as an amorphous substance (yield: 51%).

$^1$H-NMR spectrum (400 MHz, $CDCl_3$) δ ppm:

7.68-7.63 (1H, m), 7.20-7.15 (1H, m), 7.08-7.00 (2H, m), 6.78-6.73 (1H, m), 6.46-6.38 (1H, m), 6.34-6.26 (1H, m), 4.42-4.39 (1H, m), 4.29-4.14 (2H, m), 3.96-3.85 (1.5H, m), 3.75-3.69 (0.5H, m), 3.61-3.42 (4H, m), 2.55-2.43 (2H, m), 2.21-2.01 (7H, m), 1.90-1.78 (1H, m), 1.31-1.25 (3H, m).

Example 183

Ethyl (2R,3R)-8-[N-(2-chloro-4-fluorophenyl)sulfamoyl]-2,3-bis((R)-1-hydroxyethyl)-1,4-dioxaspiro[4.5]dec-6-ene-7-carboxylate (Exemplified compound No. 1-2163)

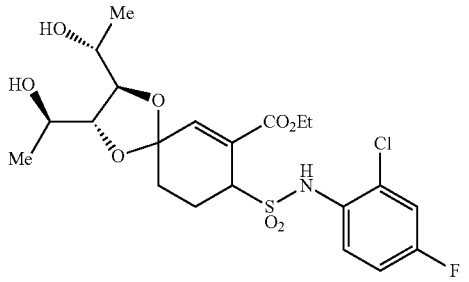

Following the process described in Example 17 (alternative procedure), (1R,2R,3R,4R)-4-benzoyloxy-1-methyl-2,3-bis[(trimethylsilyl)oxy]pentyl benzoate obtained in Reference Example 25 was used in place of 1,4-di-O-benzoyl-2,3-di-O-trimethylsilyl-D-threitol to give the title compound as a white amorphous substance (yield: 33%).

$^1$H-NMR spectrum (400 MHz, $CDCl_3$) δ ppm:

7.66 (1H, dd, J=9.0 and 5.0 Hz), 7.17 (1H, dd, J=7.8 and 2.7 Hz), 7.09 (1H, d, J=9.0 Hz), 7.05-7.00 (1H, m), 6.80 (0.5H, s), 6.76 (0.5H, s), 4.39 (1H, d, J=5.4 Hz), 4.27-4.09 (2H, m), 3.88-3.56 (4H, m), 2.50-2.42 (2H, m), 2.19-2.11 (1H, m), 1.85-1.79 (1H, m), 1.33 (3H, t, J=5.3 Hz), 1.27 (6H, t, J=7.0 Hz).

Example 184

Ethyl (2R,3R)-8-[N-(2-chloro-4-fluorophenyl)sulfamoyl]-2,3-bis((R)-1-hydroxypropyl)-1,4-dioxaspiro[4.5]dec-6-ene-7-carboxylate (Exemplified compound No. 1-2164)

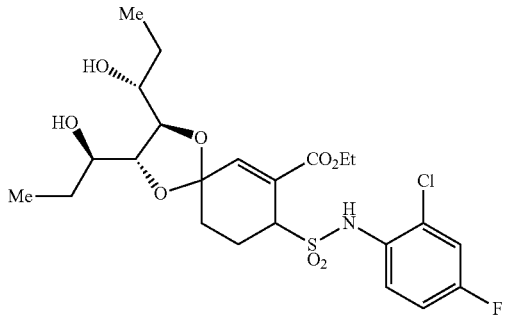

Following the process described in Example 17 (alternative procedure), (1R,2R,3R,4R)-4-benzoyloxy-1-ethyl-2,3-bis[(trimethylsilyl)oxy]hexyl benzoate obtained in Reference Example 26 was used in place of 1,4-di-O-benzoyl-2,3-di-O-trimethylsilyl-D-threitol to give the title compound as a white amorphous substance (yield: 21%).

$^1$H-NMR spectrum (400 MHz, $CDCl_3$) δ ppm:

7.68 (1H, dd, J=9.2 Hz, 5.2 Hz), 7.18 (1H, dd, J=7.4 Hz, 2.4 Hz), 7.06-7.01 (2H, m), 6.81 (0.5H, s), 6.78 (0.5H, s), 4.40 (1H, d, J=5.1 Hz), 4.29-4.12 (2H, m), 3.88-3.55 (4H, m), 3.03 (1H, brs), 2.92 (1H, brs), 2.51-2.41 (2H, m), 2.21-2.13 (2H, m), 1.90-1.73 (1H, m), 1.55-1.43 (3H, m), 1.29 (3H, t, J=7.2 Hz), 1.05-0.97 (6H, m).

Example 185

Ethyl (3a'R,6a'R,6'R)-4-[N-(2-chloro-4-fluorophenyl)sulfamoyl]-6'-hydroxymethyl-4'-oxo-3a',4',6',6a'-tetrahydrospiro[cyclohex-2-ene-1,2'-furo[3.4-d][1.3]dioxol]-3-carboxylate (Exemplified compound No. 1-2165)

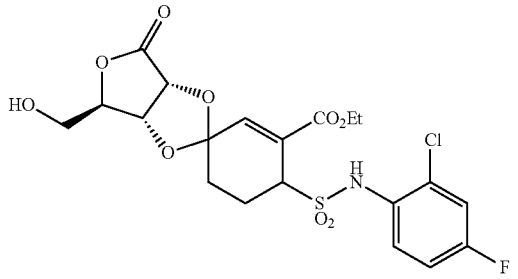

Following the process described in Example (17a), (3R,4R,5R)-3,4-bis[(trimethylsilyl)oxy]-5-[(trimethylsilyl)oxy]methyldihydrofuran-2-one was used in place of 1,4-di-O-benzoyl-2,3-di-O-trimethylsilyl-D-threitol to give the title compound as a white amorphous substance (yield: 25%).

$^1$H-NMR spectrum (400 MHz, $CDCl_3$) δ ppm:

7.69-7.64 (1H, m), 7.20-7.16 (1H, m), 7.06-6.96 (2H, m), 6.82-6.68 (1H, m), 5.04-4.62 (3H, m), 4.44-4.40 (1H, m), 4.26-4.14 (2H, m), 4.05-3.98 (1H, m), 3.90-3.81 (1H, m), 2.74-2.46 (2H, m), 2.24-2.12 (1H, m), 1.97-1.83 (2H, m), 1.30-1.26 (3H, m).

Example 186

Ethyl (2R,3R)-8-[N-(2-chloro-4-fluorophenyl)sulfamoyl]-2,3-bis((1R)-1,2-dihydroxyethyl)-1,4-dioxaspiro[4.5]dec-6-ene-7-carboxylate (low polarity compound, first peak), (high polarity compound, second peak) (Exemplified compound No. 1-386)

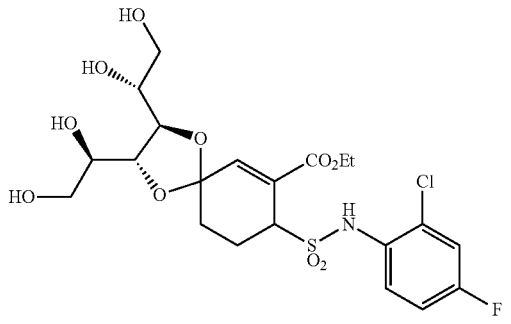

Ethyl (2R,3R)-8-[N-(2-chloro-4-fluorophenyl)sulfamoyl]-2,3-bis((1R)-1,2-dihydroxyethyl)-1,4-dioxaspiro[4.5]dec-6-ene-7-carboxylate obtained in Example 23 was subjected to high performance liquid chromatography (column; CHIRALPAK AD-H, size; inner diameter 2 cm, length 25 cm, solvent; hexane:2-propanol) to separate and purify two optical isomers, and low polarity compound (first peak) and high polarity compound (second peak) were respectively obtained as a white amorphous substance. According to the result of HPLC analysis of the two optical isomers obtained under the conditions below, their optical purities were respectively >99% ee.

| HPLC conditions | |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 7.3 minutes<br>high polarity compound (second peak): 9.9 minutes |

(Low Polarity Compound, First Peak)

$^1$H-NMR spectrum (400 MHz, $CDCl_3$) δ ppm:

7.65 (1H, dd, J=9 Hz, 5 Hz), 7.21 (1H, bs), 7.17 (1H, dd, J=8 Hz, 3 Hz), 7.06-6.99 (1H, m), 6.80 (1H, s), 4.38 (1H, d, J=5 Hz), 4.27-4.12 (4H, m), 4.08 (2H, d, J=7 Hz), 3.95-3.88 (1H, m), 3.87-3.64 (5H, m), 2.98-2.68 (2H, m), 2.54-2.42 (2H, m), 2.22-2.08 (1H, m), 1.91-1.82 (1H, m), 1.25 (3H, t, J=7 Hz).

(High Polarity Compound, Second Peak)

$^1$H-NMR spectrum (400 MHz, $CDCl_3$) δ ppm:

7.63 (1H, dd, J=9 Hz, 5 Hz), 7.15 (1H, bs), 7.12 (1H, dd, J=8 Hz, 3 Hz), 7.05-6.97 (1H, m), 6.76 (1H, s), 4.37 (1H, d, J=6 Hz), 4.27-4.01 (5H, m), 3.97-3.86 (2H, m), 3.85-3.45 (5H, m), 2.77-2.57 (2H, m), 2.52-2.41 (2H, m), 2.21-2.08 (1H, m), 1.89-1.80 (1H, m), 1.26 (3H, t, J=7 Hz).

Example 187

Ethyl-(2R,3R)-8-[N-(2-chloro-4-fluorophenyl)-N-methylsulfamoyl]-2,3-bis(hydroxymethyl)-1,4-dioxaspiro[4.5]dec-6-ene-7-carboxylate (Exemplified Compound No. 2-15)

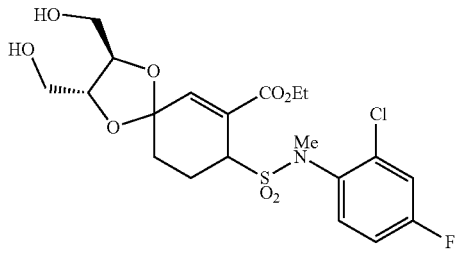

235 mg (0.49 mmol) of ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate obtained in Example 17 was dissolved in 1.5 ml of acetone, and 84 mg (0.59 mmol) of methyl iodide and 138 mg (1.00 mmol) of potassium carbonate were added sequentially, followed by stirring for 3 hours at 50° C. After the reaction solution was filtered, the filtrate was concentrated under reduced pressure, and the residue was subjected to silica gel column chromatography (solvent; hexane ethyl acetate=1:3) to give 175 mg of the title compound as a white amorphous substance (yield: 73%).

$^1$H-NMR spectrum (400 MHz, $CDCl_3$) δ ppm:

7.57 (1H, brs), 7.22 (1H, dd, J=8 Hz, 3 Hz), 7.05-7.00 (1H, m), 6.87 (0.5H, s), 6.79 (0.5H, s), 4.58 (1H, brs), 4.28-3.73 (8H, m), 3.25 (3H, s), 2.60-1.80 (6H, m), 1.26 (3H, t, J=7 Hz).

Example 188

Ethyl 8-[N-(4-fluoro-2-propylphenyl)sulfamoyl]-1,4-dioxaspiro[4.5]dec-6-ene-7-carboxylate (Exemplified compound No. 1-2077)

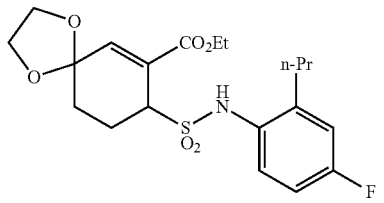

Following the process described in Example (id), 4-fluoro-2-propylphenylamine obtained in Reference Example 27 was used in place of 2-chloro-4-fluoroaniline to give the title compound as an oil (yield: 84%).

$^1$H-NMR spectrum (400 MHz, $CDCl_3$) δ ppm:

8.09-8.07 (4H, m), 7.59-7.55 (2H, m), 7.47-7.43 (4H, m), 7.47-7.43 (2H, m), 3.96 (2H, s), 2.00-1.79 (4H, m), 1.02 (6H, t, J=7 Hz), 0.07 (18H, s).

Example 189

Ethyl (2S,3S)-8-[N-(4-fluoro-2-propylphenyl)sulfamoyl]-2,3-bis(hydroxymethyl)-1,4-dioxaspiro[4.5]dec-6-ene-7-carboxylate (Exemplified Compound No. 1-2095)

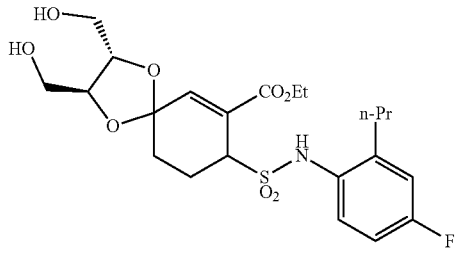

Following the process described in Examples 7, (16a) and 18 (alternative procedure), ethyl 8-[N-(4-fluoro-2-propylphenyl)sulfamoyl]-1,4-dioxaspiro[4.5]dec-6-ene-7-carboxylate obtained in Example 188 was used in place of ethyl 8-[N-(2-chloro-4-fluorophenyl)sulfamoyl]-1,4-dioxaspiro[4.5]dec-6-ene-7-carboxylate to give the title compound as a white amorphous substance (38% yield). This compound was separable into two optical isomers in accordance with the following HPLC conditions.

| | HPLC conditions |
|---|---|
| Column | CHIRALPAK AD-H (produced by Da cel Chemical Industries, Ltd. inner diameter 0.46 cm, length 25 cm) |

-continued

| | HPLC conditions |
|---|---|
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 9.6 minutes<br>high polarity compound (second peak): 14.1 minutes |

$^1$H-NMR spectrum (400 MHz, $CDCl_3$) δ ppm:

7.51-7.47 (1H, m), 6.97-6.88 (3H, m), 6.70 (0.5H, s), 6.64 (0.5H, s), 4.42-4.39 (1H, m), 4.28-3.72 (8H, m), 2.75-2.61 (2H, m), 2.52-2.37 (2H, m), 2.19-1.87 (4H, m), 1.68-1.57 (2H, m), 1.32-1.28 (3H, m), 0.99 (3H, t, J=8 Hz).

Example 190

Ethyl (2R,3R)-2,3-bis((1R)-1,2-dihydroxyethyl)-8-[N-(4-fluoro-2-pentylphenyl)sulfamoyl]-1,4-dioxaspiro[4.5]dec-6-ene-7-carboxylate (Exemplified Compound No. 1-1748)

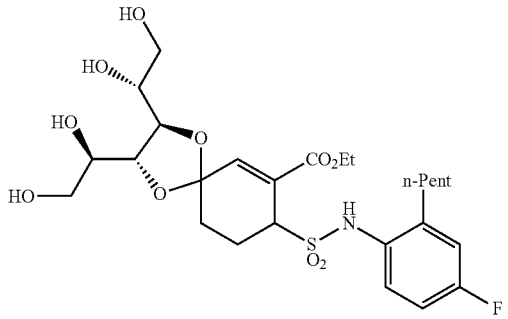

Following the process described in Examples 7, (16a) and 23, ethyl 8-[N-(4-fluoro-2-pentylphenyl)sulfamoyl]-1,4-dioxaspiro[4.5]dec-6-ene-7-carboxylate obtained in Example 86 was used in place of ethyl 8-[N-(2-chloro-4-fluorophenyl)sulfamoyl]-1,4-dioxaspiro[4.5]dec-6-ene-7-carboxylate to give the title compound as a white powder (yield: 33%). This compound was separable into two optical isomers in accordance with the following HPLC conditions.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 7:3 |
| Flow rate | 1.0 ml/min |
| Temperature | 40° C. |
| Detection | 254 nm (UV) |
| Retention time | low polarity compound (first peak): 5.29 minutes<br>high polarity compound (second peak): 5.82 minutes |

$^1$H-NMR spectrum (400 MHz, $CDCl_3$) δ ppm:

7.49-7.44 (1H, m), 6.97-6.86 (2H, m), 6.84 (0.5H, m), 6.82 (0.5H, m), 6.73 (0.5H, s), 6.69 (0.5H, s), 4.41-4.36 (1H, m), 4.27-4.17 (2H, m), 4.12-4.01 (1.5H, m), 3.97-3.88 (1.5H, m), 3.88-3.67 (5H, m), 2.77-2.60 (2H, m), 2.50-2.30 (2H, m), 2.20-1.40 (8H, m), 1.39-1.25 (7H, m), 0.93-0.86 (3H, m).

Example 191

Ethyl (2S,3S)-8-[N-(4-fluoro-2-methylphenyl)sulfamoyl]-2,3-bis(hydroxymethyl)-1,4-dioxaspiro[4.5]dec-6-ene-7-carboxylate (Exemplified Compound No. 1-2359)

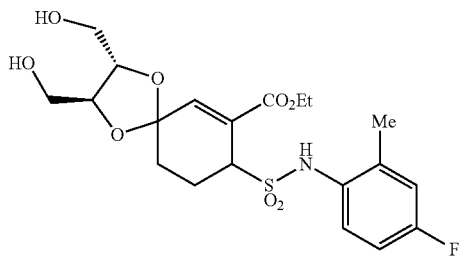

Following the process described in Examples 7, (16a) and 18 (alternative procedure), ethyl 8-[N-(4-fluoro-2-methylphenyl)sulfamoyl]-1,4-dioxaspiro[4.5]dec-6-ene-7-carboxylate obtained in Example 79 was used in place of ethyl 8-[N-(2-chloro-4-fluorophenyl)sulfamoyl]-1,4-dioxaspiro[4.5]dec-6-ene-7-carboxylate to give the title compound as an amorphous substance (yield: 49%). This compound was separable into two optical isomers in accordance with the following HPLC conditions.

| | HPLC conditions |
|---|---|
| Column | CHIRALPAK AD-H (produced by Daicel Chemical Industries, Ltd. inner diameter 0.46 cm, length 25 cm) |
| Mobile phase | hexane:2-propanol = 4:1 |
| Flow rate | 1.0 ml/min |
| Temperature | 40° C. |
| Detection | 254 nm (UV) |
| Retention time | low polarity compound (first peak): 13.5 minutes<br>high polarity compound (second peak): 19.6 minutes |

$^1$H-NMR spectrum (400 MHz, $CDCl_3$) δ ppm:

7.49 (1H, dd, J=8.8 Hz, 5.3 Hz), 6.96-6.88 (3H, m), 6.70 (0.5H, brs), 6.64 (0.5H, brs), 4.40-4.37 (1H, m), 4.28-3.70 (8H, m), 2.51-2.32 (5H, m), 2.21-1.87 (2H, m), 1.31-1.27 (3H, m).

REFERENCE EXAMPLES

Reference Example 1

1,4-Di-O-benzoyl-2,3-di-O-trimethylsilyl-meso-erythritol 300 mg (0.90 mmol) of 1,4-di-O-benzoyl-meso-erythritol (compound described in J. Am. Chem. Soc., 82, 2585 (1960)), 0.28 ml (1.98 mmol) of triethylamine and 11 mg (0.09 mmol) of 4-dimethylaminopyridine were dissolved in 6 ml of dichloromethane, and 0.24 ml (1.89 mmol) of trimethylsilyl chloride was added thereto with stirring under ice-cooling, followed by stirring for 2 hours at the same temperature. To the reaction solution was added saturated aqueous sodium hydrogencarbonate and the mixture was extracted with ethyl acetate. The organic layer was washed with water and dried over anhydrous sodium sulfate, followed by concentration under reduced pressure. The residue was subjected to silica gel column chromatography (solvent; ethyl acetate alone) to give 418 mg of the title compound as a white powder (yield: 98%).

$^1$H-NMR spectrum (400 MHz, $CDCl_3$) δ ppm:

8.04 (4H, d, J=7 Hz), 7.55 (2H, t, J=7 Hz), 7.43 (4H, t, J=7 Hz), 4.53 (2H, dd, J=12 Hz, J=3 Hz), 4.36 (2H, dd, J=12 Hz, 5 Hz), 4.13-4.08 (2H, m) 0.13 (18H, s)

Reference Example 2

1,3,4,5,7-Penta-O-trimethylsilyl-D-arabitol

Following the process described in Reference Example 1, D-arabitol was used in place of 1,4-di-o-benzoyl-meso-erythritol to give the title compound as a colorless oil (yield: 26%).

$^1$H-NMR spectrum (400 MHz, $CDCl_3$) δ ppm:

3.84-3.80 (1H, m), 3.76-3.68 (3H, m), 3.63-3.54 (2H, m), 3.49 (1H, dd, J=10 Hz, J=7 Hz), 0.14-0.09 (45H, m).

Reference Example 3

1,6-Di-O-benzoyl-2,3,4,5-tetra-O-trimethylsilyl-D-mannitol

Following the process described in Reference Example 1, 1,6-di-O-benzoyl-D-mannitol was used in place of 1,4-di-O-benzoyl-meso-erythritol to give the title compound as a pale brown oil (yield: 98%).

$^1$H-NMR spectrum (400 MHz, $CDCl_3$) δ ppm:

8.05 (4H, d, J=7 Hz), 7.55 (2H, t, J=7 Hz), 7.43 (4H, t, J=7 Hz), 4.59 (2H, dd, J=12 Hz, 2 Hz), 4.38-4.31 (2H, m), 4.24-4.20 (2H, m), 3.83 (2H, br.s), 0.17 (18H, s), 0.11 (18H, s).

Reference Example 4

2-Trimethylsilyloxy-1-trimethylsilyloxymethylethyl adamantane-1-carboxylate (4a) 2-Phenyl[1.3]dioxan-5-ol adamantane-1-carboxylate 1.00 g (5.55 mmol) of 2-phenyl[1.3]dioxan-5-ol, 1.16 ml (8.32 mmol) of triethylamine and 68 mg (0.56 mmol) of 4-dimethylaminopyridine were dissolved in 20 ml of dichloromethane, and 1.28 g (6.10 mmol) of 1-adamantanecarbonyl chloride was added thereto with stirring under ice-cooling, followed by stirring for 30 minutes at the same temperature, and then further for 15 hours at room temperature. Dichloromethane was distilled off under reduced pressure, and to the residue was added aqueous sodium hydrogencarbonate and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=9:1) to give 1.52 g of the title compound as a pale yellow powder (yield: 80%).

$^1$H-NMR spectrum (400 MHz, $CDCl_3$) δ ppm:

7.52-7.48 (2H, m), 7.42-7.33 (3H, m), 5.54 (1H, s), 4.68-4.66 (1H, m), 4.26-4.22 (2H, m), 4.18-4.13 (2H, m), 2.07-2.01 (3H, m), 2.01-1.97 (6H, m), 1.77-1.69 (6H, m).

(4b) 2-Hydroxy-1-hydroxymethylethyl adamantane-1-carboxylate 400 mg (1.17 mmol) of 2-phenyl[1.3]dioxan-5-yl adamantane-1-carboxylate obtained in (4a) was dissolved in 8 ml of ethyl acetate and 400 mg of 20% palladium hydroxide-carbon (water content: 50%) was added thereto, followed by stirring for 4 hours under hydrogen atmosphere at room temperature. After the catalyst was filtered, the filtrate was concentrated under reduced pressure to give 294 mg of the title compound as a white powder (yield: 99%).

$^1$H-NMR spectrum (400 MHz, $CDCl_3$) δ ppm:

4.90-4.85 (1H, m), 3.84-3.76 (4H, m), 2.16-2.00 (5H, m), 1.94-1.87 (6H, m), 1.78-1.67 (6H, m).

(4c) 2-Trimethylsilyloxy-1-trimethylsilyloxymethylethyl adamantane-1-carboxylate Following the process described in Reference Example 1, 2-hydroxy-1-hydroxymethylethyl adamantane-1-carboxylate obtained in (4b) was used in place of 1,4-di-O-benzoyl-meso-erythritol to give the title compound as a colorless oil (yield: 70%).

$^1$H-NMR spectrum (400 MHz, $CDCl_3$) δ ppm:

4.85-4.79 (1H, m), 3.72-3.61 (4H, m), 2.04-1.97 (3H, m), 1.92-1.83 (6H, m), 1.76-1.65 (6H, m), 0.11 (18H, s).

Reference Example 5

Diethyl 2,2-bis[(trimethylsilyl)oxy]methylmalonate

Following the process described in Reference Example 1, diethyl 2,2-bis(hydroxymethyl)malonate was used in place of 1,4-di-O-benzoyl-meso-erythritol to give the title compound as a colorless oil (yield: 75%).

$^1$H-NMR spectrum (400 MHz, $CDCl_3$) δ ppm:

4.17 (4H, q, J=7 Hz), 4.04 (4H, s), 1.23 (6H, t, J=7 Hz), 0.07 (18H, s).

Reference Example 6

2-Pentyl-1H-pyrrol-1-ylamine (6a) (2E)-4-Oxo-2-nonenal 2.0 g (14.47 mmol) of 2-pentylfuran was dissolved in 60 ml of dichloromethane, and 3.84 g (14.47 mmol) of 65% m-chloroperbenzoic acid was added dropwise thereto with stirring under ice-cooling, followed by stirring for 1 hour at the same temperature. To the reaction solution was added saturated aqueous sodium carbonate and the mixture was extracted with dichloromethane. The organic layer was washed with water, dried over anhydrous magnesium sulfate, and was then concentrated under reduced pressure to give 1.62 g of the title compound as a yellow oil (yield: 73%).

$^1$H-NMR spectrum (400 MHz, $CDCl_3$) δ ppm:

10.23 (1H, d, J=7 Hz), 6.95 (1H, d, J=12 Hz), 6.18 (1H, dd, J=12 Hz, 7 Hz), 2.26 (2H, t, J=7 Hz), 1.73-1.61 (2H, m), 1.40-1.26 (4H, m), 0.91 (3H, t, J=6 Hz).

(6b) 4-Oxononanal 1.62 g (10.5 mmol) of (2E)-4-oxo-2-nonenal obtained in (6a) was dissolved in 30 ml of ethyl acetate, and 160 mg of 10% palladium-carbon (water content: 50%) was added thereto, followed by restirring for 2 hours under hydrogen atmosphere at room temperature. After the catalyst was filtered, the filtrate was concentrated under reduced pressure to give 1.50 g of the title compound as a pale yellow oil (91% yield).

$^1$H-NMR spectrum (400 MHz, $CDCl_3$) δ ppm:

9.81 (1H, s), 2.81-2.67 (4H, m), 2.47 (2H, t, J=7 HZ), 1.67-1.53 (2H, m), 1.38-1.21 (4H, m), 0.89 (3H, t, J=7 Hz).

(6c) Benzyl 2-pentyl-1H-pyrrol-1-ylcarbamate 1.50 g (9.60 mmol) of 4-oxononanal obtained in (6b) was dissolved in 45 ml of ethanol-acetic acid (2:1) solution mixture, and 1.60 g (9.60 mmol) of benzyl hydrazinecarboxylate was added thereto, followed by stirring for 1 hour at 80° C. The reaction solution was concentrated under reduced pressure, and the residue was subjected to silica gel column chromatography (solvent; hexane:ethyl acetate=2:1) to give 2.12 g of the title compound as a yellow oil (77% yield).

$^1$H-NMR spectrum (400 MHz, $CDCl_3$) δ ppm:

7.36 (5H, bs), 7.21 (1H, ds), 6.63-6.59 (1H, m), 6.07 (1H, t, J=4 Hz), 5.89-5.84 (1H, m), 5.22 (2H, ds), 2.46-2.36 (2H, m), 1.63-1.49 (2H, m), 1.37-1.22 (4H, m), 0.88 (3H, t, J=7 Hz).

(6d) 2-Pentyl-1H-pyrrole-1-amine 1.0 g (3.49 mmol) of benzyl 2-pentyl-1H-pyrrol-1-ylcarbamate obtained in (6c) was dissolved in 20 ml of ethanol, and 100 mg of 10% palladium-carbon (water content: 50%) was added thereto, followed by stirring for 2 hours under hydrogen atmosphere at room temperature. After the catalyst was filtered, the filtrate was concentrated under reduced pressure. The residue was subjected to silica gel column chromatography (solvent; hexane:ethyl acetate=2:1) to give 430 mg of the title compound as a yellow oil (yield: 81%).

$^1$H-NMR spectrum (400 MHz, $CDCl_3$) δ ppm:

6.68 (1H, m), 5.97 (1H, t, J=3 Hz), 5.82-5.77 (1H, m), 4.52 (2H, s), 2.58 (2H, t, J=8 Hz), 1.69-1.57 (2H, m), 1.44-1.31 (4H, m), 0.91 (3H, t, J=7 Hz).

Reference Example 7

2-Hexyl-1H-pyrrol-1-ylamine

Following the procedure described in Reference Example 6, 2-hexylfuran was used as the starting material in place of 2-pentylfuran to give the title compound as a yellow oil (yield: 29%).

$^1$H-NMR spectrum (400 MHz, $CDCl_3$) δ ppm:

6.67-6.63 (1H, m), 5.99-5.94 (1H, m), 5.81-5.77 (1H, m), 4.52 (2H, br.s), 2.62-2.55 (2H, m), 1.67-1.56 (2H, m), 1.44-1.21 (6H, m), 0.89 (3H, t, J=7 Hz).

Reference Example 8

2-Heptyl-1H-pyrrol-1-ylamine

Following the procedure described in Reference Example 6, 2-heptylfuran was used as the starting material in place of 2-pentylfuran to give the title compound as a pale yellow solid (yield: 59%).

$^1$H-NMR spectrum (400 MHz, $CDCl_3$) δ ppm:

6.67-6.63 (1H, m), 5.99-5.94 (1H, m), 5.81-5.77 (1H, m), 4.52 (2H, br.s), 2.62-2.55 (2H, m), 1.67-1.53 (2H, m), 1.44-1.21 (8H, m), 0.89 (3H, t, J=7 Hz).

Reference Example 9

2-Octyl-1H-pyrrol-1-ylamine

Following the procedure described in Reference Example 6, 2-octylfuran was used as the starting material in place of 2-pentylfuran to give the title compound as a yellow oil (yield: 11%).

$^1$H-NMR spectrum (400 MHz, $CDCl_3$) δ ppm:

6.65-6.61 (1H, m), 5.97-5.93 (1H, m), 5.78-5.75 (1H, m), 4.51 (2H, br.s), 2.60-2.55 (2H, m), 1.66-1.54 (2H, m), 1.42-1.21 (10H, m), 0.88 (3H, t, J=7 Hz).

Reference Example 10

2-Cyclopropyl-1H-pyrrol-1-ylamine (10a) 4-Cyclopropyl-4-oxobutanal 230 mg (1.79 mmol) of 1-cyclopropyl-4-hydroxy-1-butanone was dissolved in 7 ml of dichloromethane, and 580 mg (2.69 mmol) of pyridinium chlorochromate was added thereto, followed by stirring for 1 hour at room temperature. To the reaction solution was added diethyl ether, the mixture was filtered using Celite, and the filtrate was concentrated under reduced pressure. The residue was subjected to silica gel column chromatography (solvent; diethyl ether alone) to give 176 mg of the title compound as a pale yellow oil (yield: 78%).

$^1$H-NMR spectrum (400 MHz, $CDCl_3$) δ ppm:

9.78 (1H, s), 2.91 (2H, t, J=7 Hz), 2.78-2.71 (2H, m), 2.01-1.93 (1H, m), 1.08-1.01 (2H, m), 0.96-0.88 (2H, m).

(10b) 2-Cyclopropyl-1H-pyrrol-1-ylamine

Following the procedures described in Reference Examples (6c) and (6d), 4-cyclopropyl-4-oxobutanal obtained in (10a) was used in place of 4-oxononanal to give the title compound as a pale yellow oil (yield: 45%).

$^1$H-NMR spectrum (400 MHz, $CDCl_3$) δ ppm:

6.70-6.64 (1H, m), 5.94-5.88 (1H, m), 5.71-5.64 (1H, m), 4.69 (2H, br.s), 1.83-1.72 (1H, m), 0.91-0.83 (2H, m), 0.64-0.57 (2H, m).

Reference Example 11

4-Fluoro-2-heptylphenylamine (11a) 4-Fluoro-2-(hept-1-enyl)-1-nitrobenzene 3.0 g (7.0 mmol) of hexyltriphenylphosphonium bromide was suspended in 30 ml of tetrahydrofuran, and 4.5 ml (7.0 mmol) of n-butyl lithium/hexane solution (1.56 M) was added dropwise thereto at −10° C. After the reaction solution was stirred for 10 minutes at the same temperature, 846 mg (5.0 mmol) of 4-fluoro-2-nitrobenzaldehyde was added, and the reaction solution was further stirred for 1 hour. To the reaction solution was added 1N aqueous potassium hydrogensulfate and the mixture was extracted with ethyl acetate. The organic layer was washed sequentially with saturated aqueous sodium hydrogencarbonate and water and dried over anhydrous magnesium sulfate, followed by concentration under reduced pressure. The residue was subjected to silica gel column chromatography (solvent; hexane:ethyl acetate=19:1) to give 917 mg of the title compound as a pale yellow oil (yield: 77%).

$^1$H-NMR spectrum (400 MHz, $CDCl_3$) δ ppm:

8.09 (1.7H, dd, J=9 Hz, 5 Hz), 7.97 (1H, dd, J=9 Hz, 5 Hz), 7.26-6.99 (5.4H, m), 6.89 (1H, d, J=16 Hz), 6.69 (1.7H, d, J=11 Hz), 6.26 (1H, dt, J=16 Hz, 7 Hz), 5.87 (1.7H, dt, J=12 Hz, 8 Hz), 2.28 (2H, q, J=7 Hz), 2.10 (3.4H, q, J=7 Hz), 1.52-1.23 (16.2H, m), 0.91 (3H, m), 0.86 (5.1H, m).

(11b) 4-Fluoro-2-heptylphenylamine 910 mg (3.8 mmol) of 4-fluoro-2-(hept-1-enyl)-1-nitrobenzene obtained in (11a) was dissolved in 5 ml of ethanol, and 100 mg of 10% palladium-carbon (water content: 50%) was added thereto, followed by stirring for 2 hours under hydrogen atmosphere at room temperature. After the catalyst was filtered, the filtrate was concentrated under reduced pressure, and the residue was subjected to silica gel column chromatography (solvent; hexane:ethyl acetate=9:1) to give 730 mg of the title compound as a pale yellow oil (yield: 91%).

$^1$H-NMR spectrum (400 MHz, $CDCl_3$) δ ppm:

6.80-6.71 (2H, m), 6.61 (1H, dd, J=9 Hz, 5 Hz), 3.47 (2H, brs), 2.45 (2H, t, J=7 Hz), 1.64-1.58 (2H, m), 1.42-1.24 (8H, m), 0.89 (3H, t, J=6 Hz).

Reference Example 12

2-Butyl-4-fluorophenylamine

Following the procedure described in Reference Example 11, propyltriphenylphosphonium bromide was used in place of hexyltriphenylphosphonium bromide to give the title compound as a brown oil (yield: 78%).

$^1$H-NMR spectrum (400 MHz, $CDCl_3$) δ ppm:

6.80-6.69 (2H, m), 6.60 (1H, dd, J=9 Hz, 5 Hz), 3.51 (2H, bs), 2.46 (2H, t, J=8 Hz), 1.63-1.56 (2H, m), 1.45-1.37 (2H, m), 0.96 (3H, t, J=7 Hz).

Reference Example 13

4-Fluoro-2-pentylphenylamine

Following the procedure described in Reference Example 11, butyltriphenylphosphonium bromide was used in place of hexyltriphenylphosphonium bromide to give the title compound as a yellow oil (yield: 78%).

$^1$H-NMR spectrum (400 MHz, $CDCl_3$) δ ppm:

6.80-6.69 (2H, m), 6.60 (1H, dd, J=9 Hz, 5 Hz), 3.50 (2H, bs), 2.45 (2H, t, J=8 Hz), 1.64-1.58 (2H, m), 1.45-1.36 (4H, m), 0.91 (3H, t, J=7 Hz).

Reference Example 14

4-Fluoro-2-hexylphenylamine

Following the procedure described in Reference Example 11, pentyltriphenylphosphonium bromide was used in place of hexyltriphenylphosphonium bromide to give the title compound as a pale brown oil (yield: 63%).

$^1$H-NMR spectrum (400 MHz, $CDCl_3$) δ ppm:

6.81-6.71 (2H, m), 6.66 (1H, dd, J=9 Hz, 5 Hz), 4.19 (2H, brs), 2.48 (2H, t, J=8 Hz), 1.65-1.57 (2H, m), 1.43-1.25 (6H, m), 0.92-0.85 (3H, m).

Reference Example 15

4-Fluoro-2-octylphenylamine

Following the procedure described in Reference Example 11, heptyltriphenylphosphonium bromide was used in place of hexyltriphenylphosphonium bromide to give the title compound as a pale yellow oil (yield: 65%)

$^1$H-NMR spectrum (400 MHz, $CDCl_3$) δ ppm:

6.80-6.71 (2H, m), 6.61 (1H, dd, J=9 Hz, 5 Hz), 2.45 (2H, t, J=7 Hz), 1.64-1.56 (2H, m), 1.38-1.22 (10H, m), 0.88 (3H, t, J=7 Hz).

Reference Example 16

4-Fluoro-2-nonylphenylamine

Following the procedure described in Reference Example 11, octyltriphenylphosphonium bromide was used in place of hexyltriphenylphosphonium bromide to give the title compound as a pale brown oil (yield: 97%).

$^1$H-NMR spectrum (500 MHz, $CDCl_3$) δ ppm:

6.77 (1H, dd, J=10 Hz, 3 Hz), 6.72 (1H, td, J=8 Hz, 3 Hz), 6.59 (1H, dd, J=9 Hz, 5 Hz), 3.46 (2H, brs), 2.45 (2H, t, J=8 Hz), 1.64-1.56 (2H, m), 1.44-1.21 (12H, m), 0.88 (3H, t, J=7 Hz).

Reference Example 17

2-Decyl-4-fluorophenylamine

Following the procedure described in Reference Example 11, nonyltriphenylphosphonium bromide was used in place of hexyltriphenylphosphonium bromide to give the title compound as a pale brown oil (yield: 67%).

$^1$H-NMR spectrum (500 MHz, $CDCl_3$) δ ppm:

6.77 (1H, dd, J=10 Hz, 3 Hz), 6.73 (1H, dd, J=8 Hz, 3 Hz), 6.60 (1H, dd, J=9 Hz, 5 Hz), 3.47 (2H, brs), 2.45 (2H, t, J=8 Hz), 1.64-1.56 (2H, m), 1.43-1.21 (14H, m), 0.88 (3H, t, J=7 Hz).

Reference Example 18

1,4-Di-O-benzoyl-2,3-di-o-trimethylsilyl-D-threitol 17.48 g (52.9 mmol) of 1,4-di-C-benzoyl-D-threitol and 10.8 g (159 mmol) of imidazol were dissolved in 250 ml of dichloromethane, and 12.6 g (116 mmol) of chlorotrimethylsilane was added thereto with stirring under ice-cooling, followed by stirring for 1 hour at room temperature. The reaction solution was directly subjected to silica gel column chromatography (solvent; hexane:ethyl acetate=20:1-5:1) to give 24.59 g of f the title compound as a white powder (yield: 98%).

$^1$H-NMR spectrum (400 MHz, $CDCl_3$) δ ppm:

8.04 (4H, dd, J=8 Hz, J=1 Hz), 7.57-7.52 (2H, m), 7.46-7.40 (4H, m), 4.50 (2H, dd, J=11 Hz, J=4 Hz), 4.48-4.33 (2H, m), 4.13-4.08 (2H, m), 0.14 (18H, s).

Reference Example 19

1,4-Di-O-benzoyl-2,3-di-O-trimethylsilyl-L-threitol

Following the process described in Reference Example 18, 1,4-di-O-benzoyl-L-threitol was used in place of 1,4-di-o-benzoyl-D-threitol to give the title compound as a white powder (yield: 98%).

$^1$H-NMR spectrum (400 MHz, $CDCl_3$) δ ppm:

8.04 (4H, dd, J=8 Hz, J=1 Hz), 7.57-7.52 (2H, m), 7.46-7.40 (4H, m), 4.50 (2H, dd, J=11 Hz, J=4 Hz), 4.48-4.33 (2H, m), 4.13-4.08 (2H, m), 0.14 (18H, s)

Reference Example 20

Methyl (S)-3,4-bis[(trimethylsilyl)oxy]butyrate

Following the process described in Reference Example 18, methyl (S)-3,4-dihydroxybutyrate was used in place of 1,4-di-O-benzoyl-D-threitol to give the title compound as an oil (yield: 62%).

$^1$H-NMR spectrum (400 MHz, $CDCl_3$) δ ppm:

4.18-4.12 (1H, m), 3.67 (3H, s), 3.52 (1H, dd, J=10 Hz, 6 Hz), 3.40 (1H, dd, J=10 Hz, 6 Hz), 2.59 (1H, dd, J=15 Hz, 5 Hz), 2.37 (1H, dd, J=15 Hz, 7 Hz), 0.10 (18H, s).

Reference Example 21

1,4-Anhydro-2,3-di-O-trimethylsilyl-meso-erythritol

Following the process described in Reference Example 1, 1,4-anhydroerythritol was used in place of 1,4-di-o-benzoyl-meso-erythritol to give the title compound as a colorless oil (yield: 21%).

$^1$H-NMR spectrum (400 MHz, $CDCl_3$) δ ppm:

4.15-4.10 (2H, m), 3.92-3.85 (2H, m), 3.68-3.62 (2H, m), 0.14 (18H, s).

Reference Example 22

3-Ethyl-3,4-bis[(trimethylsilyl)oxy]hexane (22a) 3-Ethylhexane-3,4-diol 590 mg (5.0 mmol) of dimethyloxalate was dissolved in 20 ml of tetrahydrofuran, and 22 ml (22 mmol) of 1.0 M ethyl magnesium bromide/tetrahydrofuran solution was added thereto with stirring under ice-cooling, followed by stirring for 2 hours at the same temperature. The reaction solution was made acidic by addition of 1N hydrochloric acid and the mixture was extracted with ethyl acetate. The organic layer was washed with water and dried over anhydrous magnesium sulfate, followed by concentration under reduced pressure. The residue was subjected to silica gel column chromatography (solvent; hexane:ethyl acetate=3:1) to give 276 mg of the title compound as an oil (yield: 38%).

$^1$H-NMR spectrum (400 MHz, $CDCl_3$) δ ppm:

3.45-3.41 (1H, m), 1.87 (1H, d, J=6 Hz), 1.75 (1H, s), 1.70-1.31 (6H, m), 1.04 (3H, t, J=7 Hz), 0.89 (3H, t, J=8 Hz), 0.89 (3H, t, J=8 Hz).

(22b) 3-Ethyl-3,4-bis[(trimethylsilyl)oxy]hexane 270 mg (1.85 mmol) of 3-ethylhexane-3,4-diol obtained in (22a) was dissolved in 5 ml of pyridine, and 597 mg (3.7 mmol) of 1,1,1,3,3,3-hexamethylsilazane and 1.20 g (11 mmol) of chlorotrimethylsilane were added sequentially, followed by stirring for 2 hours at the same temperature and further overnight at room temperature. To the reaction solution was added water and the mixture was extracted with ethyl acetate. The organic layer was washed with water and dried over anhydrous sodium sulfate, followed by concentration under reduced pressure. The residue was subjected to silica gel column chromatography (solvent; hexane:ethyl acetate=9:1) to give 469 mg of the title compound as an oil (yield: 88%).

$^1$H-NMR spectrum (400 MHz, $CDCl_3$) δ ppm:

3.38 (1H, dd, J=9.0 Hz, 3.0 Hz), 1.68-1.33 (6H, m), 0.90 (3H, t, J=6.0 Hz), 0.92-0.90 (6H, m), 0.11-0.08 (18H, m).

Reference Example 23

(R)-1,2-Bis[(trimethylsilyl)oxy]-1,1,2-triphenylethane

Following the process described in Reference Example 18, (R)-1,1,2-triphenyl-1,2-ethanediol was used in place of 1,4-di-O-benzoyl-D-threitol to give the title compound as a powder (yield: 99%).

$^1$H-NMR spectrum (400 MHz, $CDCl_3$) δ ppm:

7.28-7.18 (15H, m), 5.51 (1H, s), −0.05 (9H, s), −0.16 (9H, s).

Reference Example 24

1,4-Di-O-acetyl-2,3-di-O-trimethylsilyl-D-threitol

Following the process described in Reference Example 18, 1,4-di-O-acetyl-D-threitol was used in place of 1,4-di-O-benzoyl-D-threitol to give the title compound as an oil (yield: 96%).

$^1$H-NMR spectrum (400 MHz, $CDCl_3$) δ ppm:

4.20 (2H, dd, J=11 Hz, 4 Hz), 4.01 (2H, dd, J=11 Hz, 7 Hz), 3.88-3.84 (2H, m), 2.06 (6H, s), 0.13 (18H, s).

Reference Example 25

(1R,2R,3R,4R)-4-Benzoyloxy-1-methyl-2,3-bis[(trimethylsilyl)oxy]pentyl benzoate

Following the process described in Reference Example 18, (1R,2S,3S,4R)-4-benzoyloxy-2,3-dihydroxy-1-methylpentyl benzoate was used in place of 1,4-di-O-benzoyl-D-threitol to give the title compound as an oil (yield: 86%).

$^1$H-NMR spectrum (400 MHz, $CDCl_3$) δ ppm:

8.06-8.04 (4H, m), 7.57-7.54 (2H, m), 7.46-7.42 (4H, m), 5.31-5.25 (2H, m), 3.98-3.97 (2H, m), 1.41 (6H, d, J=6 Hz), 0.12 (18H, s).

Reference Example 26

(1R,2R,3R,4R)-4-Benzoyloxy-1-ethyl-2,3-bis[(trimethylsilyl)oxy]hexyl benzoate

Following the process described in Reference Example 18, (1R,2S,3S,4R)-4-benzoyloxy-1-ethyl-2,3-dihydroxyhexyl benzoate was used in place of 1,4-di-O-benzoyl-D-threitol to give the title compound as an oil (yield: 82%).

$^1$H-NMR spectrum (400 MHz, $CDCl_3$) δ ppm:

8.09-8.07 (4H, m), 7.59-7.55 (2H, m), 7.47-7.43 (4H, m), 7.47-7.43 (2H, m), 3.96 (2H, s), 2.00-1.79 (4H, m), 1.02 (6H, t, J=7 Hz), 0.07 (18H, s).

Reference Example 27

4-Fluoro-2-propylphenylamine

Following the process described in Reference Example 11, ethyltriphenylphosphonium bromide was used in place of hexyltriphenylphosphonium bromide to give the title compound as a pale yellow oil (yield: 17%).

$^1$H-NMR spectrum (400 MHz, $CDCl_3$) δ ppm:

6.80-6.59 (3H, m), 3.48 (2H, brs), 2.45 (2H, t, J=7 Hz), 1.70-1.58 (2H, m), 1.01 (3H, t, J=8 Hz).

Test Examples

Test Example 1

Suppression Effect Against Endotoxin Stimulated TNF-α Production in Cells (In Vitro)

The suppression rate of the compound according to the present invention against TNF-α production when human monocyte cell line U937 was stimulated by endotoxin, was measured. Specifically, to RPMI1640 medium containing 10% (volume %) of heat-inactivated new born calf serum, was added 12-O-tetradecanoylphorbol 13-acetate so that its final concentration became 30 ng/ml. U937 cells were suspended with the medium and plated to a 96 well culture plate (Sumilon) so that number of cells/volume was $2\times10^4$/0.1 ml, and were then cultured for 3 days at 37° C. in a carbon dioxide incubator with 5% $CO_2$ and 100% humidity. After completion of incubation, the culture supernatant was removed. The compound according to the present invention was added to each of the wells in various concentrations, and lipopolysaccharide (LPS) (E. coli 0111:B4, Sigma) was also added so that its final concentration was 30 ng/ml. After incubating the culture plate in the carbon dioxide incubator again for 4.5 hours, the culture supernatant was collected. By using a 384 half well black plate (Greiner) and HTRF quantitative kit of CIS Bio International, the concentration of TNF-α in the culture supernatant was measured as time-resolved fluorescence with Discovery (Packard). From the measured value in the absence of LPS (X), measured value in the absence of the compound according to the present invention (Y) and measured value in the presence of the compound according to the present invention (Z), the suppression rate of TNF-α production was obtained by the following calculation formula [I].

$$\text{Suppression rate of TNF-}\alpha\text{ production (\%)}=\{1-(Z-X)/(Y-X)\}\times100 \quad [I]$$

In the present test, the compound according to the present invention showed an excellent suppression effect against endotoxin stimulated TNF-α production in cells.

Test Example 2

Suppression Effect Against Elevated TNF-α Concentration in Blood (In Vivo)

The suppression effect of the compound according to the present invention against elevated TNF-α concentration in blood was evaluated. The test for TNF-α concentration elevation in blood was conducted in accordance with the process of Parant et al, which is described in Journal of Leukocyte Biology, Vol. 47, p. 164 (1990).

In the test, 3 to 4 male Sprague Dawley rats (8-9 weeks old) were used for each group.

4 hours before the administration of LPS, muramyl dipeptide dissolved in a physiological saline solution (1 mg/ml) was administered to the tail vein at a rate of 1 ml/kg. 0.5 hours before the administration of LPS, the rats were anaesthetized with pentobarbital (40 mg/kg), and the compound according to the present invention dissolved in 5% dimethyl acetamide/95% polyethylene glycol 400 solution was administered to the right femoral vein at a rate of 1 ml/kg. The control group was administered with 5% dimethyl acetamide/95% polyethylene glycol 400 solution at a rate of 1 ml/kg. LPS dissolved in a physiological saline solution (3 μg/ml) was administered to the left femoral vein at a rate of 1 ml/kg. 2 hours after the administration of LPS, blood was collected using 3.8% (w/v) sodium citrate solution as an anticoagulant, and blood plasma was separated by centrifuge (10,000 g, 5 minutes, 4° C.). TNF-α concentration in the blood plasma was measured using a TNF-α quantitative kit (Bio Source International, Inc.). From the TNF-α concentration in the blood of control group (X) and the TNF-α concentration in the blood of the group administered with the compound according to the present invention (Y), the TNF-α elevation suppression rate was calculated using the following calculation formula [II].

$$\text{TNF-}\alpha\text{ elevation suppression rate (\%)}=\{1-Y/X\}\times 100 \quad [II]$$

In the present test, the compound according to the present invention showed excellent suppression effects against elevated TNF-α concentration in blood.

The invention claimed is:

1. A compound represented by the general formula (I):

(I)

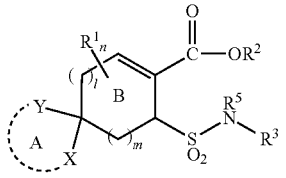

{wherein

X and Y represent a group in which X and Y together with the carbon atom of ring B to which they are bound form ring A, *or* X and Y together represent a substituent of ring B[, or X and Y each represents a hydrogen atom];

(1) in the case where X and Y represent a group in which X and Y together with the carbon atom of ring B to which they are bound form ring A:

ring A represents a 3- to 7-membered heterocyclyl ring (in the heterocyclyl ring, X and Y, independently from each other, represent any one selected from a carbon atom, a group having the formula NR (R represents a hydrogen atom or a $C_1$-$C_6$ alkyl, $C_2$-$C_6$ alkenyl, $C_2$-$C_6$ alkynyl or $C_1$-$C_6$ alkanoyl group which may be substituted with one or more groups selected from Substituent group α), an oxygen atom, a sulfur atom, a group having the formula SO and a group having the formula $SO_2$, the heterocyclyl ring may include an unsaturated bond, may form a fused ring or spiro ring with a 3- to 7-membered heterocyclyl ring or 3- to 7-membered cycloalkyl ring, and ring A, including the fused ring or spiro ring, may be substituted with the same or different 1 to 4 groups selected from the group consisting of an oxo group, a thioxo group, Substituent group α, a cyclopropyl $C_1$-$C_6$ alkyl group, a $C_1$-$C_6$ alkyl group which may be substituted with 1 to 5 groups selected from Substituent group α, a $C_2$-$C_6$ alkenyl group which may be substituted with 1 to 5 groups selected from Substituent group α, and a $C_2$-$C_6$ alkynyl group which may be substituted with 1 to 5 groups selected from Substituent group α) or a 3- to 7-membered cycloalkyl ring (the cycloalkyl ring may include an unsaturated bond, may form a fused ring or spiro ring with a 3- to 7-membered heterocyclyl ring or 3- to 7-membered cycloalkyl ring, and ring A, including the fused ring or spiro ring, may be substituted with the same or different 1 to 4 groups selected from the group consisting of Substituent group α, a cyclopropyl $C_1$-$C_6$ alkyl group, a $C_1$-$C_6$ alkyl group which may be substituted with 1 to 5 groups selected from Substituent group α, a $C_2$-$C_6$ alkenyl group which may be substituted with 1 to 5 groups selected from Substituent group α, and a $C_2$-$C_6$ alkynyl group which may be substituted with 1 to 5 groups selected from Substituent group α);

(2) in the case where X and Y together represent a substituent of ring B:

X and Y represent an oxo group or a thioxo group;

l and m, independently from each other, represent an integer of 0 to 3, and l+m is 1 to 3;

$R^1$ represents an aliphatic hydrocarbon group which may be substituted with one or more groups selected from Substituent group β and Substituent group γ (wherein the aliphatic hydrocarbon group represents a $C_1$-$C_{20}$ alkyl group, $C_3$-$C_{10}$cycloalkyl group, $C_4$-$C_{12}$ cycloalkylalkyl group, $C_3$-$C_6$ alkenyl group or $C_3$-$C_6$ alkynyl group), a phenyl group which may be substituted with one or more groups selected from Substituent group δ, a group having the formula $OR^4$ ($R^4$ represents a hydrogen atom or an aliphatic hydrocarbon group which may be substituted with one or more groups selected from Substituent group β and Substituent group γ, the aliphatic hydrocarbon group has the same meaning as defined above) or a halogen atom;

n represents an integer of 0 to 3;

$R^2$ represents a hydrogen atom, a $C_1$-$C_6$ alkyl group which may be substituted with one or more groups selected from Substituent group β, a $C_2$-$C_6$ alkenyl group which may be substituted with one or more groups selected from Substituent group β, or a $C_2$-$C_6$ alkynyl group which may be substituted with one or more groups selected from Substituent group β;

$R^3$ represents a phenyl group which may be substituted with one or more groups selected from Substituent group ϵ, or a 5- or 6-membered heteroaryl group which may be substituted with one or more groups selected from Substituent group ϵ (the heteroaryl group includes 1 to 3 hetero atoms selected from a nitrogen atom, oxygen atom and sulfur atom);

$R^5$ represents a hydrogen atom, a $C_1$-$C_6$ alkyl group which may be substituted with one or more groups selected from Substituent group β, a $C_2$-$C_6$ alkenyl group which may be substituted with one or more groups selected from Substituent group β, or a $C_2$-$C_6$ alkynyl group which may be substituted with one or more groups selected from Substituent group β;

provided that in the case where $R^3$ is a phenyl group which may be substituted with one or more groups selected from Substituent group ϵ, X and Y represent the aforementioned (1) or (2);

Substituent group α represents a hydroxy group, halogen atom, $C_1$-$C_6$ alkoxy group, halogeno $C_1$-$C_6$ alkoxy group, carboxy group, $C_1$-$C_6$ alkoxycarbonyl group;

carbamoyl group which may be substituted with one or more groups selected from a $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenyl-carbonyl group;

and a group having the formula $NR^6R^7$, and $R^6$ and $R^7$, independently from each other, represent a hydrogen atom, $C_1$-$C_6$ alkyl group, $C_2$-$C_6$ alkenyl group, $C_2$-$C_6$ alkynyl group, $C_1$-$C_6$ alkanoyl group or $C_2$-$C_6$ alkenyl-carbonyl group, or together with the nitrogen atom to which they are bound form a heterocyclyl group;

Substituent group β represents an oxo group, hydroxy group, cyclopropyl group, $C_1$-$C_6$ alkoxy group, $C_1$-$C_6$ alkylthio group, nitro group, halogen atom, cyano group, carboxy group, $C_1$-$C_{10}$ alkoxy-carbonyl group, $C_1$-$C_6$ alkanoyl group, $C_2$-$C_4$ alkenyl-carbonyl group, $C_2$-$C_6$ alkanoyloxy group, $C_2$-$C_4$ alkenyl-carbonyloxy group;

carbamoyl group which may be substituted with one or more groups selected from a $C_1$-$C_4$ alkyl group, phenyl group, $C_1$-$C_7$ acyl group and $C_1$-$C_4$ alkoxy-phenyl group;

thiocarbamoyl group which may be substituted with a $C_1$-$C_4$ alkyl group or phenyl group;

carbamoyloxy group which may be substituted with a $C_1$-$C_4$ alkyl group or phenyl group;

$C_1$-$C_6$ alkanoylamino group, $C_1$-$C_{10}$ alkoxy-carboxamide group, $C_1$-$C_{10}$ alkoxy-carbonyloxy group, and ureido group which may be substituted with a $C_1$-$C_4$ alkyl group or phenyl group;

Substituent group γ represents a heterocyclic group, $C_3$-$C_{10}$ cycloalkyloxy group, $C_6$-$C_{10}$ aryloxy group, $C_7$-$C_{19}$ aralkyloxy group, heterocyclyloxy group, $C_3$-$C_{10}$ cycloalkylthio group, $C_6$-$C_{10}$ arylthio group, $C_7$-$C_{19}$ aralkylthio group, heterocyclylthio group, heterocyclylsulfinyl group, heterocyclylsulfonyl group, $C_3$-$C_6$ cycloalkyloxy-carbonyl group, $C_6$-$C_{10}$ aryloxy-carbonyl group, $C_7$-$C_{19}$ aralkyloxy-carbonyl group, heterocyclyloxycarbonyl group, $C_6$-$C_{10}$aryl-carbonyl group, $C_6$-$C_{10}$ aryl-carbonyloxy group, $C_6$-$C_{10}$ aryl-carbonylamino group, $C_6$-$C_{10}$ aryloxy-carboxamide group, $C_7$-$C_{19}$ aralkyloxy-carboxamide group, $C_6$-$C_{10}$ aryloxy-carbonyloxy group, $C_7$-$C_{19}$ aralkyloxy-carbonyloxy group, $C_3$-$C_{10}$ cycloalkyloxy-carbonyloxy group and $C_6$-$C_{10}$ aryl group which may be substituted with one or more groups selected from Substituent group β;

Substituent group δ represents a hydroxy group, nitro group, cyano group, halogen atom, $C_1$-$C_6$ alkyl group, halogeno $C_1$-$C_6$ alkyl group, $C_1$-$C_6$ alkoxy group, halogeno $C_1$-$C_6$ alkoxy group, carboxy group, $C_1$-$C_6$ alkanoyl group, $C_1$-$C_6$ alkoxy-carbonyl group, $C_1$-$C_6$ alkanoylamino group, $C_1$-$C_6$ alkylthio group, carbamoyl group, $C_1$-$C_6$ alkyl-carbamoyl group, $C_1$-$C_6$ alkoxy-carbonyl $C_1$-$C_6$ alkyl-carbamoyl group, 1,3-diacylguanidino $C_1$-$C_6$ alkyl group, a group having the formula $NR^6R^7$ ($R^6$ and $R^7$ are the same as $R^6$ and $R^7$ of Substituent group α), $C_3$-$C_6$ cycloalkyl group, $C_6$-$C_{10}$ aryl group and 5-membered heteroaryl group; and Substituent group ϵ represents a hydroxy group, nitro group, cyano group, halogen atom, $C_1$-$C_{14}$ alkyl group, cyclopropyl $C_1$-$C_{14}$ alkyl group, halogeno $C_1$-$C_{14}$ alkyl group, $C_1$-$C_{14}$ alkoxy group, halogeno $C_1$-$C_{14}$ alkoxy group, carboxy group, $C_1$-$C_{14}$ alkanoyl group, $C_1$-$C_{14}$ alkoxy-carbonyl group, $C_1$-$C_{14}$ alkanoylamino group, $C_1$-$C_{14}$ alkylthio group, carbamoyl group, $C_1$-$C_{14}$ alkyl-carbamoyl group, $C_1$-$C_{14}$ alkoxy-carbonyl $C_1$-$C_{14}$ alkyl-carbamoyl group, 1,3-diacylguanidino $C_1$-$C_{14}$ alkyl group, group having the formula $NR^6R^7$ ($R^6$ and $R^7$ are the same as $R^6$ and $R^7$ of Substituent group α), $C_3$-$C_6$ cycloalkyl group, $C_6$-$C_{10}$ aryl group and 5-membered heteroaryl group} or a pharmacologically acceptable salt thereof.

2. The compound or pharmacologically acceptable salt thereof according to claim 1, wherein 1 is 0 and m is an integer of 1 to 3.

3. The compound or pharmacologically acceptable salt thereof according to claim 1, wherein 1 is 0 and m is 2.

4. The compound or pharmacologically acceptable salt thereof according to claim 1, wherein X and Y together with the carbon atom of ring B form ring A, and ring A is a 3- to 7-membered heterocyclyl ring (in the heterocyclyl ring, X and Y, independently from each other, represent any one selected from a carbon atom, a group having the formula NR (R represents a hydrogen atom or a $C_1$-$C_6$ alkyl, $C_2$-$C_6$ alkenyl, $C_2$-$C_6$ alkynyl or $C_1$-$C_6$ alkanoyl group which may be substituted with one or more groups selected from Substituent group α), an oxygen atom, a sulfur atom, a group having the formula SO and a group having the formula $SO_2$, the heterocyclyl ring may form a fused ring or Spiro ring with a 5- or 6-membered heterocyclyl ring (the heterocyclyl ring includes 1 or 2 oxygen and/or nitrogen atoms as hetero atoms) or 5- to 6-membered cycloalkyl ring, and ring A, including the fused ring or Spiro ring, may be substituted with the same or different 1 to 4 groups selected from the group consisting of an oxo group, a thioxo group, Substituent group α, a cyclopropyl $C_1$-$C_6$ alkyl group and a $C_1$-$C_6$ alkyl group which may be substituted with 1 to 5 groups selected from Substituent group α) or a 3- to 7-membered saturated cycloalkyl ring (the 3- to 7-membered saturated cycloalkyl ring may be substituted with 1 or 2 groups selected from the group consisting of a hydroxy group, hydroxymethyl group, 1,2-dihydroxyethyl group, 1,2,3-trihydroxypropyl group, 1,2,3,4-tetrahydroxybutyl group and acetylamino group).

5. The compound or pharmacologically acceptable salt thereof according to claim 1, wherein X and Y represent a group in which X and Y together with the carbon atom of ring B form ring A, and ring A is a 3- to 7-membered heterocyclyl ring (in the heterocyclyl ring, X and Y, independently from each other, represent any one selected from a carbon atom, an oxygen atom, sulfur atom, a group having the formula SO and a group having the formula $SO_2$, the heterocyclyl ring may form a fused ring or Spiro ring with a 5- or 6-membered heterocyclyl ring (the heterocyclyl ring includes 1 or 2 oxygen and/or nitrogen atoms as hetero atoms) or 5- or 6-membered cycloalkyl ring, and ring A, including the fused ring or Spiro ring, may be substituted with the same or different 1 to 4 groups selected from the group consisting of an oxo group, a thioxo group, Substituent group α and a $C_1$-$C_6$ alkyl group which may be substituted with 1 to 4 groups selected from Substituent group α) or a 3- to 5-membered saturated cycloalkyl ring (the 3- to 5-membered saturated cycloalkyl ring may be substituted with 1 or 2 groups selected from the group consisting of a hydroxymethyl group, 1,2-dihydroxyethyl group, 1,2,3-trihydroxypropyl group, 1,2,3,4-tetrahydroxybutyl group and acetylamino group).

6. The compound or pharmacologically acceptable salt thereof according to claim 1, wherein X and Y represent a group in which X and Y together with the carbon atom of ring B form ring A, and ring A is a 3- to 7-membered heterocyclyl ring (the 3- to 7-membered heterocyclyl ring is oxirane, oxolane, tetrahydrofuran, tetrahydropyran, 1,3-dioxolane, 1,3-dioxane, 1,3-dioxepane, 1,3-dithiolane, 1,3-dithiane, 1,1,3,3-tetraoxo-1,3-dithiolane, 1,3-oxathiolane, 1,3-oxathiane or 1,3-oxathiepane, these heterocyclyl rings may form a fused ring or spiro ring with a 5- or 6-membered heterocyclyl ring (the 5- or 6-membered heterocyclyl ring is tetrahydrofuran, tetrahydropyran, pyrrolidine, piperidine or 1,3-dioxane) or cyclohexyl ring, and ring A, including the fused ring and spiro ring, may be substituted with 1 or 2 groups selected from the group consisting of an oxo group, a thioxo group, Substituent group α (Substituent group α represents a hydroxy group and a group having the formula $NR^6R^7$, and R6 and $R^7$, independently from each other, represent a hydrogen atom or $C_1$-$C_6$ alkanoyl group), a methyl group, an ethyl group and a $C_1$-$C_6$ alkyl group which is substituted with 1 to 4 hydroxy groups), or a cyclopropyl or cyclopentyl ring (the cyclopropyl or cyclopentyl ring may be substituted with 1 or 2 groups selected from the group consisting of a hydroxymethyl group, 1,2-dihydroxyethyl group, 1,2,3-trihydroxypropyl group, and a 1,2,3,4-tetrahydroxybutyl group).

7. The compound or pharmacologically acceptable salt thereof according to claim 1, wherein X and Y represent a group in which X and Y together with the carbon atom of ring B form ring A, and ring A is a 3- to 6-membered heterocyclyl ring {the heterocyclyl ring is oxirane, tetrahydrofuran, 1,3-dioxolane, 1,3-dioxane, 1,3-dithiolane, 1,3-dithiane, 1,3-oxathiolane, or 1,3-oxathiane, these heterocyclyl rings may form a fused ring or Spiro ring with a 5- or 6-membered heterocyclyl ring (the 5- or 6-membered heterocyclyl ring is tetrahydrofuran, tetrahydropyran or 1,3-dioxane) or cyclohexyl ring, and ring A, including the fused ring or spiro ring, may be substituted with 1 or 2 groups selected from the group consisting of Substituent group α (Substituent group α represents a hydroxy group and a group having the formula $NR^6R^7$ ($R^6$ and $R^7$, independently from each other, represent a hydrogen atom or acetyl group), a methyl group, an ethyl group, a hydroxymethyl group, a 1,2-dihydroxyethyl group, a 1,2,3-trihydroxypropyl group and a 1,2,3,4-tetrahydroxybutyl group}.

8. The compound or pharmacologically acceptable salt thereof according to claim 1, wherein n is 0 or 1, and $R^1$ is a hydroxy group, halogen atom, $C_1$-$C_6$ alkyl group or $C_1$-$C_6$ alkoxy group.

9. The compound or pharmacologically acceptable salt thereof according to claim 1, wherein n is 0 or 1, and $R^1$ is a fluorine atom or methyl group.

10. The compound or pharmacologically acceptable salt thereof according to claim 1, wherein n is 0.

11. The compound or pharmacologically acceptable salt thereof according to claim 1, wherein $R^2$ is a $C_1$-$C_6$ alkyl group.

12. The compound or pharmacologically acceptable salt thereof according to claim 1, wherein $R^2$ is a $C_1$-$C_4$ alkyl group.

13. The compound or pharmacologically acceptable salt thereof according to claim 1, wherein $R^2$ is an ethyl group.

14. The compound or pharmacologically acceptable salt thereof according to claim 1, wherein $R^3$ is a phenyl group which may be substituted with one or more groups selected from Substituent group ϵ, or a pyrrolyl group which may be substituted with one or more groups selected from Substituent group ϵ, and Substituent group ϵ is a halogen atom, $C_1$-$C_{14}$ alkyl group and halogeno $C_1$-$C_{14}$ alkyl group.

15. The compound or pharmacologically acceptable salt thereof according to claim 1, wherein $R^3$ is a phenyl group which may be substituted with one or more groups selected from Substituent group ϵ, or a pyrrolyl group which may be substituted with one or more groups selected from Substituent group ϵ, and Substituent group ϵ is a fluorine atom, chlorine atom, bromine atom, $C_3$-$C_8$ alkyl group and halogeno $C_4$-$C_8$ alkyl group.

16. The compound or pharmacologically acceptable salt thereof according to claim 1, wherein $R^3$ is a phenyl group which may be substituted with one or more groups selected from Substituent group ϵ, and Substituent group ϵ is a fluorine atom, chlorine atom and $C_3$-$C_8$ alkyl group.

17. The compound or pharmacologically acceptable salt thereof according to claim 1, wherein $R^5$ is a hydrogen atom or $C_1$-$C_6$ alkyl group.

18. The compound or pharmacologically acceptable salt thereof according to claim 1, wherein $R^5$ is a hydrogen atom or methyl group.

19. The compound or pharmacologically acceptable salt thereof according to claim 1, wherein $R^5$ is a hydrogen atom.

20. The compounds of the following group selected from claim 1 or pharmacologically acceptable salt thereof:

ethyl 8-[N-(2-chloropheny)sulfamoyl]-2,3-bis(hydroxymethyl)-1,4-dioxaspiro[4.5]dec-6-ene-7-carboxylate, ethyl 8-[N-(2-chloropheny)sulfamoyl]-2,3-bis(1,2-dihydroxyethyl)-1,4-dioxaspiro[4.5]dec-6-ene-7-carboxylate, ethyl 8-[N-(2,4-difluorophenyl)sulfamoyl]-2,3-bis(hydroxymethyl)-1,4-dioxaspiro[4.5]dec-6-ene-7-carboxylate, ethyl 8-[N-(2,4-difluorophenyl)sulfamoyl]-2,3-bis(1,2-dihydroxyethyl)-1,4-dioxaspiro[4.5]dec-6-ene-7-carboxylate, ethyl 8-[N-(2-chloro-4-fluorophenyl)sulfamoyl]-2-hydroxymethyl-1,4-dioxaspiro[4.5]dec-6-ene-7-carboxylate, ethyl 8-[N-(2-chloro-4-fluorophenyl)sulfamoyl]-2,3-bis(hydroxymethyl)-1,4-dioxaspiro[4.5]dec-6-ene-7-carboxylate, ethyl 8-[N-(2-chloro-4-fluoropheny)sulfamoyl]-2,3-bis(1,2-dihydroxyethyl)-1,4-dioxaspiro[4.5]dec-6-ene-7-carboxylate, ethyl 8-[N-(2-chloro-4-fluoropheny)sulfamoyl]-2-(1,2-dihydroxyethyl)-1,4-dioxaspiro[4.5]dec-6-ene-7-carboxylate, ethyl 8-[N-(2-chloro-4-fluorophenyl)sulfamoyl]-2-(1,2,3-trihydroxypropyl)-1,4-dioxaspiro[4.5]dec-6-ene-7-carboxylate, ethyl 8-[N-(2-chloro-4-fluorophenyl)sulfamoyl]-2-(1,2,3,4-tetrahydroxybutyl)-1,4-dioxaspiro[4.5]dec-6-ene-7-carboxylate, ethyl 2,3-bis(acetylaminomethyl)-8-[N-(2-chloro-4-fluorophenyl)sulfamoyl]-1,4-dioxaspiro[4.5]dec-6-ene-7-carboxylate, ethyl 9-[N-(2-chloro-4-fluorophenyl)sulfamoyl]-3-hydroxy-1,5-dioxaspiro[5.5]undec-7-ene-8-carboxylate, ethyl 3-acetylamino-9-[N-(2-chloro-4-fluorophenyl)sulfamoyl]-1,5-dioxaspiro[5.5]undec-7-ene-8-carboxylate, ethyl 9-[N-(2-chloro-4-fluorophenyl)sulfamoyl]-3,3-bis(hydroxymethyl)-1,5-dioxaspiro[5.5]undec-7-ene-8-carboxylate, ethyl 8-[N-(2-butyl-4-fluorophenyl)sulfamoyl]-2,3-bis(hydroxymethyl)-1,4-dioxaspiro[4.5]dec-6-ene-7-carboxylate, ethyl 8-[N-(2-butyl-4-fluoropheny)sulfamoyl]-2,3-bis(1,2-dihydroxyethyl)-1,4-dioxaspiro[4.5]dec-6-ene-7-carboxylate, ethyl 8-[N-(2-hexylphenyl)sulfamoyl]-2,3-bis(hydroxymethyl)-1,4-dioxaspiro[4.5]dec-6-ene-7-carboxylate, ethyl 8-[N-(2-hexylphenyl)sulfamoyl]-2,3-bis(1,2-dihydroxyethyl)-1,4-dioxaspiro[4.5]dec-6-ene-7-carboxylate, ethyl 8-[N-(4-fluoro-2-hexylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-hexylphenyl)sulfamoyl]-1,4-dioxaspiro[4.5]dec-6-ene-7-carboxylate, ethyl 8-[N-(2-heptylphenyl)sulfamoyl]-2,3-bis(hydroxymethyl)-1,4-dioxaspiro[4.5]dec-6-ene-7-carboxylate, ethyl 8-[N-(2-heptylphenyl)sulfamoyl]-2,3-bis(1,2-dihydroxyethyl)-1,4-dioxaspiro[4.5]dec-6-ene-7-carboxylate, ethyl 8-[N-(4-fluoro-2-heptylphenyl)sulfamoyl]-2,3-bis(hydroxymethyl)-1,4-dioxaspiro[4.5]dec-6-ene-7-carboxylate, ethyl 2,3-bis(1,2-dihydroxyethyl)-8-[N-(4-fluoro-2-heptylphenyl)sulfamoyl]-1,4-dioxaspiro[4.5]dec-6-ene-7-carboxylate, ethyl 8-[N-(2-bromophenyl)sulfamoyl]-2,3-bis(hydroxymethyl)-1,4-dioxaspiro[4.5]dec-6-ene-7-carboxylate, ethyl 8-[N-(2-bromophenyl)sulfamoyl]-2,3-bis(1,2-dihydroxyethyl)-1,4-dioxaspiro[4.5]dec-6-ene-7-carboxylate, ethyl 8-[N-(2-chloro-6-methylphenyl)sulfamoyl]-2,3-bis(hydroxymethyl)-1,4-dioxaspiro [4.5]dec-6-ene-7-carboxylate, ethyl 8-[N-(2-chloro-6-methylphenyl)sulfamoyl]-2,3-bis(1,2-dihydroxyethyl)-1,4-dioxaspiro [4.5]dec-6-ene-7-carboxylate, ethyl 8-[N-(2-bromo-4-fluorophenyl)sulfamoyl]-2,3-bis(hydroxymethyl)-1,4-dioxaspiro [4.5]dec-6-ene-7-carboxylate, ethyl 8-[N-(2-bromo-4-fluorophenyl)sulfamoyl]-2,3-bis(1,2-dihydroxyethyl)-1,4-dioxaspiro [4.5]dec-6-ene-7-carboxylate, ethyl 2,3-bis(hydroxymethyl)-8-[N-(2-pentylphenyl)sulfamoyl]-1,4-dioxaspiro[4.5]dec-6-ene-7-carboxylate, ethyl 2,3-bis(1,2-dihydroxyethyl)-8-[N-(2-pentylphenyl)sulfamoyl]-1,4-dioxaspiro [4.5]dec-6-ene-7-carboxylate, ethyl 8-[N-(4-fluoro-2-pentylphenyl)sulfamoyl]-2,3-bis(hydroxymethyl)-1,4-dioxaspiro [4.5]dec-6-ene-7-carboxylate, ethyl 2,3-bis(1,2-dihydroxyethyl)-8-[N-(4-fluoro-2-pentylphenyl)sulfamoyl]-1,4-dioxaspiro [4.5]dec-6-ene-7-carboxylate, ethyl 8-[N-(4-fluoro-2-octylphenyl)sulfamoyl]-2,3-bis(hydroxymethyl)-1,4-dioxaspiro [4.5]dec-6-ene-7-carboxylate, ethyl 2,3-bis(1,2-dihydroxyethyl)-8-[N-(4-fluoro-2-octylphenyl)sulfamoyl]-1,4-dioxaspiro [4.5]dec-6-ene-7-carboxylate, ethyl 8-[N-(4-fluoro-2-propylphenyl)sulfamoyl]-2,3-bis(hydroxymethyl)-1,4-dioxaspiro [4.5]dec-6-ene-7-carboxylate, ethyl 2,3-bis(1,2-dihydroxyethyl)-8-[N-(4-fluoro-2-propylphenyl)sulfamoyl]-1,4-dioxaspiro [4.5]dec-6-ene-7-carboxylate, and ethyl 8-[N-(2-chloro-4-fluorophenyl)-N-methylsulfamoyl]-2,3-bis(hydroxymethyl)-1,4-dioxaspiro[4.5]dec-6-ene-7-carboxylate.

21. A pharmaceutical composition or pharmacologically acceptable salt thereof comprising any of the compounds according to claim 1, and a pharmaceutically acceptable excipient.

22. A method for suppressing intracellular signal transduction or cell activation induced by, endotoxin comprising the administration of an effective amount of the pharmaceutical composition or pharmaceutically acceptable salt thereof according to claim 21.

23. A method for suppressing the generation of inflammatory mediators due to intracellular signal transduction or cell activation induced by endotoxin comprising the administration of an effective amount of the pharmaceutical composition or pharmaceutically acceptable salt thereof according to claim 21.

24. A method for treatment of sepsis comprising the administration of an effective amount of the pharmaceutical composition or pharmaceutically acceptable salt thereof according to claim 21.

25. The compounds of the following group selected from claim 1 or pharmacologically acceptable salt thereof:

ethyl 8-[N-(2-chloro-4-fluorophenyl)sulfamoyl]-2,3-bis(hydroxymethyl)-1,4-dioxaspiro[4.5]dec-6-ene-7-carboxylate, ethyl 8-[N-(2-chloro-4-fluorophenyl)sulfamoyl]-2,3-bis(1,2-dihydroxyethyl)-1,4-dioxaspiro[4.5]dec-6-ene-7-carboxylate, ethyl 8-[N-(2-butyl-4-fluorophenyl)sulfamoyl]-2,3-bis(hydroxymethyl)-1,4-dioxaspiro[4.5]dec-6-ene-7-carboxylate, ethyl 8-[N-(2-butyl-4-fluorophenyl)sulfamoyl]-2,3-bis(1,2-dihydroxyethyl)-1,4-dioxaspiro[4.5]dec-6-ene-7-carboxylate, ethyl 8-[N-(4-fluoro-2-hexylphenyl)sulfamoyl]-2,3-bis(hydroxymethyl)-1,4-dioxaspiro[4.5]dec-6-ene-7-carboxylate, ethyl 8-[N-(2-bromo-4-fluorophenyl)sulfamoyl]-2,3-bis(hydroxymethyl)-1,4-dioxaspiro[4.5]dec-6-ene-7-carboxylate, ethyl 8-[N-(4-fluoro-2-pentylphenyl)sulfamoyl]-2,3-bis(hydroxymethyl)-1,4-dioxaspiro[4.5]dec-6-ene-7-carboxylate, and ethyl 2,3-bis(1,2-dihydroxyethyl)-8[N-(4-fluoro-2-pentylphenyl)sulfamoyl]-1,4-dioxaspiro[4.5]dec-6-ene-7-carboxylate.

26. The following compound selected from claim 1 or pharmacologically acceptable salt thereof: ethyl 8-[N-(2-chloro-4-fluorophenyl)sulfamoyl]-2,3-bis(hydroxymethyl)-1,4-dioxaspiro[4.5]dec-6-ene-7-carboxylate.

27. The following compound selected from claim 1 or pharmacologically acceptable salt thereof: ethyl 8-[N-(2-chloro-4-fluorophenyl)sulfamoyl]-2,3-bis(1,2-dihydroxyethyl)-1,4-dioxaspiro[4.5]dec-6-ene-7-carboxylate.

28. The following compound selected from claim 1 or pharmacologically acceptable salt thereof: ethyl 8-[N-(2-butyl-4-fluorophenyl)sulfamoyl]-2,3-bis(hydroxymethyl) -1,4-dioxaspiro[4.5]dec-6-ene-7-carboxylate.

29. The following compound selected from claim 1 or pharmacologically acceptable salt thereof: ethyl 8-[N-(2-butyl-4-fluorophenyl)sulfamoyl]-2,3-bis(1,2-dihydroxyethyl)-1,4-dioxaspiro[4.5]dec-6-ene-7-carboxylate.

30. The following compound selected from claim 1 or pharmacologically acceptable salt thereof: ethyl 8-[N-(4-fluoro-2-hexylphenyl)sulfamoyl]-2,3-bis(hydroxymethyl)-1,4-dioxaspiro[4.5]dec-6-ene-7-carboxylate.

31. The following compound selected from claim 1 or pharmacologically acceptable salt thereof: ethyl 8-[N-(2-bromo-4-fluorophenyl)sulfamoyl]-2,3-bis(hydroxymethyl) -1,4-dioxaspiro[4.5]dec-6-ene-7-carboxylate

32. The following compound selected from claim 1 or pharmacologically acceptable salt thereof: ethyl 8-[N-(4-fluoro-2-pentylphenyl)sulfamoyl]-2,3-bis(hydroxymethyl) -1,4-dioxaspiro[4.5]dec-6-ene-7-carboxylate.

33. The following compound selected from claim 1 or pharmacologically acceptable salt thereof: ethyl 2,3-bis(1,2-dihydroxyethyl)-8-[N-(4-fluoro-2-pentylphenyl)sulfamoyl]-1,4-dioxaspiro[4.5]dec-6-ene-7-carboxylate.

34. A pharmaceutically acceptable salt of ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate.

35. A potassium salt of ethyl (2R,3R)-8-[N-(2-chloro-4-fluorophenyl)sulfamoyl]-2,3-bis(hydroxymethyl)-1,4-dioxaspiro[4.5]dec-6-ene-7-carboxylate.

36. A pharmaceutical composition comprising the compound according to claim 34, and a pharmaceutically acceptable excipient.

37. A method for treating sepsis comprising administering a pharmaceutical composition comprising the compound according to claim 34, and a pharmaceutically acceptable excipient.

38. A pharmaceutical composition comprising the compound according to claim 35, and a pharmaceutically acceptable excipient.

39. A method of treating sepsis comprising administering a pharmaceutical composition comprising the compound according to claim 35, and a pharmaceutically acceptable excipient.

40. A pharmaceutically acceptable salt of ethyl (2R,3R,8R)-8-[N-(2-chloro-4-fluorophenyl)sulfamoyl]-2,3-bis(hydroxymethyl)-1,4dioxaspiro[4.5]dec-6-ene-7-carboxylate.

41. Potassium (2-chloro-4-fluorophenyl){[(2R,3R,8R)-7-(ethoxycarbonyl)-2,3-bis(hydroxymethyl)-1,4-dioxaspiro[4.5]dec-6-en-8-yl] sulfonyl}azanide.

42. A pharmaceutical composition comprising the compound according to claim 40, and a pharmaceutically acceptable excipient.

43. A method for treating sepsis comprising administering a pharmaceutical composition comprising the compound according to claim 40, and a pharmaceutically acceptable excipient.

44. A pharmaceutical composition comprising the compound according to claim 41, and a pharmaceutically acceptable excipient.

45. A method for treating sepsis comprising administering a pharmaceutical composition comprising the compound according to claim 41, and a pharmaceutically acceptable excipient.

* * * * *

UNITED STATES PATENT AND TRADEMARK OFFICE

CERTIFICATE OF CORRECTION

PATENT NO. : RE43,858 E
APPLICATION NO. : 13/224745
DATED : December 11, 2012
INVENTOR(S) : Tomio Kimura et al.

It is certified that error appears in the above-identified patent and that said Letters Patent is hereby corrected as shown below:

In the Claims:

In column 230, at line 47, delete "ethyl 8-[N-(2-chloropheny)sulfamoyl]-2,3-bis(hy-"
and insert -- ethyl 8-[N-(2-chlorophenyl)sulfamoyl]-2,3-bis(hy- --.

In column 230, at line 50, delete "ethyl 8-[N-(2-chloropheny)sulfamoyl]-2,3-bis(1,2-dihy-"
and insert -- ethyl 8-[N-(2-chlorophenyl)sulfamoyl]-2,3-bis(1,2-dihy- --.

In column 230, at line 65, delete "ethyl 8-[N-(2-chloro-4-fluoropheny)sulfamoyl]-2,3-bis(1,"
and insert -- ethyl 8-[N-(2-chloro-4-fluorophenyl)sulfamoyl]-2,3-bis(1, --.

In column 231, at line 1, delete "ethyl 8-[N-(2-chloro-4-fluoropheny)sulfamoyl]-2-(1,2-di-"
and insert -- ethyl 8-[N-(2-chloro-4-fluorophenyl)sulfamoyl]-2-(1,2-di- --.

In column 231, at line 24, delete "ethyl 8-[N-(2-butyl-4-fluoropheny)sulfamoyl]-2,3-bis(1,"
and insert -- ethyl 8-[N-(2-butyl-4-fluorophenyl)sulfamoyl]-2,3-bis(1, --.

In column 233, at line 4, delete "ethyl 2,3-bis(1,2-dihydroxyethyl)-8[N-(4-fluoro-2-pen-"
and insert -- ethyl 2,3-bis(1,2-dihydroxyethyl)-8-[N-(4-fluoro-2-pen- --.

In column 233, at line 29, delete "-1,4-dioxaspiro[4.5]dec-6-ene-7-carboxylate"
and insert -- -1.4-dioxaspiro[4.5]dec-6-ene-7-carboxylate. --.

Signed and Sealed this
Twenty-first Day of May, 2013

Teresa Stanek Rea

Teresa Stanek Rea
*Acting Director of the United States Patent and Trademark Office*